(12) United States Patent
Sharma et al.

(10) Patent No.: US 10,842,557 B2
(45) Date of Patent: *Nov. 24, 2020

(54) VAPOR ABLATION SYSTEM WITH A CATHETER HAVING MORE THAN ONE POSITIONING ELEMENT AND CONFIGURED TO TREAT DUODENAL TISSUE

(71) Applicant: Santa Anna Tech LLC, Santa Ana, CA (US)

(72) Inventors: Virender K. Sharma, Paradise Valley, AZ (US); Harry Jabs, Oakland, CA (US)

(73) Assignee: Santa Anna Tech LLC, Santa Ana, CA (US)

(*) Notice: Subject to any disclaimer, the term of this patent is extended or adjusted under 35 U.S.C. 154(b) by 953 days.

This patent is subject to a terminal disclaimer.

(21) Appl. No.: 15/386,476

(22) Filed: Dec. 21, 2016

(65) Prior Publication Data

US 2017/0165002 A1     Jun. 15, 2017

Related U.S. Application Data

(63) Continuation of application No. 14/594,444, filed on Jan. 12, 2015, now Pat. No. 9,561,068, which is a
(Continued)

(51) Int. Cl.
*A61B 18/04* (2006.01)
*A61B 18/14* (2006.01)
(Continued)

(52) U.S. Cl.
CPC ........ *A61B 18/1492* (2013.01); *A61B 5/1076* (2013.01); *A61B 5/6853* (2013.01);
(Continued)

(58) Field of Classification Search
CPC .......... A61B 2018/00273; A61B 2018/00279; A61B 2018/00285; A61B 5/6839;
(Continued)

(56) References Cited

U.S. PATENT DOCUMENTS

| 408,899 A | 8/1889 | Small |
|---|---|---|
| 697,181 A | 4/1902 | Smith |

(Continued)

FOREIGN PATENT DOCUMENTS

| CN | 2757751 Y | 2/2006 |
|---|---|---|
| CN | 1803113 A | 7/2006 |

(Continued)

OTHER PUBLICATIONS

Office Action dated Dec. 13, 2017 for U.S. Appl. No. 14/062,054; (pp. 1-15).

(Continued)

*Primary Examiner* — Jaymi E Della
(74) *Attorney, Agent, or Firm* — Novel IP

(57) ABSTRACT

Ablation catheters and systems include multiple inline chambers for containing and heating an ablative agent. The heating chamber includes one or more channels to increase the contact surface area of the ablative agent with the walls of the heating chamber to provide more efficient heating. Induction heating is used to heat a chamber and vaporize a fluid within by wrapping a coil about a ferromagnetic chamber and providing an alternating current to the coil. A magnetic field is created in the area surrounding the chamber which induces electric current flow in the chamber, heating the chamber and vaporizing the fluid inside. Positioning elements help maintain the device in the proper position with respect to the target tissue and also prevent the passage of ablative agent to normal tissues.

55 Claims, 136 Drawing Sheets

Related U.S. Application Data continuation-in-part of application No. 14/158,687, filed on Jan. 17, 2014, now Pat. No. 9,561,067, and a continuation-in-part of application No. 13/486,980, filed on Jun. 1, 2012, now Pat. No. 9,561,066, and a continuation-in-part of application No. 12/573,939, filed on Oct. 6, 2009, now abandoned.

(60) Provisional application No. 61/753,831, filed on Jan. 17, 2013, provisional application No. 61/493,344, filed on Jun. 3, 2011, provisional application No. 61/102,885, filed on Oct. 6, 2008.

(51) Int. Cl.
*A61B 17/24* (2006.01)
*A61B 5/00* (2006.01)
*A61B 5/107* (2006.01)
*A61B 17/34* (2006.01)
*A61B 18/08* (2006.01)
A61B 17/00 (2006.01)
A61B 17/42 (2006.01)
A61B 18/00 (2006.01)
A61B 5/03 (2006.01)
A61B 90/00 (2016.01)

(52) U.S. Cl.
CPC .......... *A61B 17/24* (2013.01); *A61B 17/3415* (2013.01); *A61B 18/04* (2013.01); *A61B 18/082* (2013.01); *A61B 5/03* (2013.01); *A61B 2017/00084* (2013.01); *A61B 2017/00274* (2013.01); *A61B 2017/00809* (2013.01); *A61B 2017/00818* (2013.01); *A61B 2017/4216* (2013.01); *A61B 2018/0022* (2013.01); *A61B 2018/00285* (2013.01); *A61B 2018/00482* (2013.01); *A61B 2018/00488* (2013.01); *A61B 2018/00494* (2013.01); *A61B 2018/00541* (2013.01); *A61B 2018/00547* (2013.01); *A61B 2018/00559* (2013.01); *A61B 2018/00577* (2013.01); *A61B 2018/00642* (2013.01); *A61B 2018/00744* (2013.01); *A61B 2018/00791* (2013.01); *A61B 2018/00821* (2013.01); *A61B 2018/048* (2013.01); *A61B 2090/064* (2016.02); *A61M 2205/3368* (2013.01)

(58) Field of Classification Search
CPC ........ A61B 5/6882; A61B 2018/00005; A61B 2018/00011; A61B 2018/00029; A61B 2018/044; A61B 2018/046; A61B 18/04
See application file for complete search history.

(56) References Cited

U.S. PATENT DOCUMENTS

| | | |
|---|---|---|
| 1,719,750 A | 7/1929 | Bridge |
| 3,818,913 A | 6/1974 | Wallach |
| 3,880,168 A | 4/1975 | Berman |
| 3,924,628 A | 12/1975 | Droegemueller |
| 3,930,505 A | 1/1976 | Wallach |
| 3,938,502 A | 2/1976 | Bom |
| 4,024,866 A | 5/1977 | Wallach |
| 4,083,077 A | 4/1978 | Knight |
| 4,672,962 A | 6/1987 | Hershenson |
| 4,672,963 A | 6/1987 | Barken |
| 4,682,596 A | 7/1987 | Bales |
| 4,701,587 A | 10/1987 | Carter |
| 4,748,979 A | 6/1988 | Hershenson |
| 4,773,410 A | 9/1988 | Blackmer |
| 4,793,352 A | 12/1988 | Eichenlaub |
| 4,828,544 A | 5/1989 | Lane |
| 4,872,920 A | 10/1989 | Flynn |
| 4,898,574 A | 2/1990 | Uchiyama |
| 4,915,113 A | 4/1990 | Holman |
| 4,950,266 A | 8/1990 | Sinofsky |
| 4,950,267 A | 8/1990 | Ishihara |
| 4,976,711 A | 12/1990 | Parins |
| 4,985,027 A | 1/1991 | Dressel |
| 5,006,119 A | 4/1991 | Acker |
| 5,011,566 A | 4/1991 | Hoffman |
| 5,045,056 A | 9/1991 | Behl |
| 5,084,043 A | 1/1992 | Hertzmann |
| 5,084,044 A | 1/1992 | Quint |
| 5,102,410 A | 4/1992 | Dressel |
| 5,112,328 A | 5/1992 | Taboada |
| 5,122,138 A | 6/1992 | Manwaring |
| 5,158,536 A | 10/1992 | Sekins |
| 5,190,539 A | 3/1993 | Fletcher |
| 5,217,459 A | 6/1993 | Kamerling |
| 5,217,465 A | 6/1993 | Steppe |
| 5,222,938 A | 6/1993 | Behl |
| 5,263,951 A | 11/1993 | Spears |
| 5,277,696 A | 1/1994 | Hagen |
| 5,298,298 A | 3/1994 | Hoffman |
| 5,312,399 A | 5/1994 | Hakky |
| 5,318,014 A | 6/1994 | Carter |
| 5,330,518 A | 7/1994 | Neilson |
| 5,331,947 A | 7/1994 | Shturman |
| 5,334,190 A | 8/1994 | Seiler |
| 5,344,397 A | 9/1994 | Heaven |
| 5,348,551 A | 9/1994 | Spears |
| 5,352,512 A | 10/1994 | Hoffman |
| 5,366,490 A | 11/1994 | Edwards |
| 5,370,609 A | 12/1994 | Drasler |
| 5,370,675 A | 12/1994 | Edwards |
| 5,385,544 A | 1/1995 | Edwards |
| 5,405,376 A | 4/1995 | Mulier |
| 5,409,453 A | 4/1995 | Lundquist |
| 5,417,686 A | 5/1995 | Peterson |
| 5,421,819 A | 6/1995 | Edwards |
| 5,424,620 A | 6/1995 | Cheon |
| 5,425,731 A | 6/1995 | Daniel |
| 5,425,931 A | 6/1995 | Arai |
| 5,433,708 A | 7/1995 | Nichols |
| 5,433,739 A | 7/1995 | Sluijter |
| 5,435,805 A | 7/1995 | Edwards |
| 5,437,629 A | 8/1995 | Goldrath |
| 5,443,470 A | 8/1995 | Stern |
| 5,449,380 A | 9/1995 | Chin |
| 5,451,208 A | 9/1995 | Goldrath |
| 5,462,521 A | 10/1995 | Brucker |
| 5,470,308 A | 11/1995 | Edwards |
| 5,470,309 A | 11/1995 | Edwards |
| 5,484,400 A | 1/1996 | Edwards |
| 5,500,012 A | 3/1996 | Brucker |
| 5,503,638 A | 4/1996 | Cooper |
| 5,524,620 A | 6/1996 | Rosenschein |
| 5,529,076 A | 6/1996 | Schachar |
| 5,531,676 A | 7/1996 | Edwards |
| 5,540,658 A | 7/1996 | Evans |
| 5,542,915 A | 8/1996 | Edwards |
| 5,542,916 A | 8/1996 | Hirsch |
| 5,542,928 A | 8/1996 | Evans |
| 5,545,171 A | 8/1996 | Sharkey |
| 5,549,628 A | 8/1996 | Cooper |
| 5,549,644 A | 8/1996 | Lundquist |
| 5,554,110 A | 9/1996 | Edwards |
| 5,554,172 A | 9/1996 | Horner |
| 5,556,377 A | 9/1996 | Rosen |
| 5,558,673 A | 9/1996 | Edwards |
| 5,562,608 A | 10/1996 | Sekins |
| 5,575,803 A | 11/1996 | Cooper |
| 5,584,872 A | 12/1996 | LaFontaine |
| 5,588,960 A | 12/1996 | Edwards |
| 5,591,125 A | 1/1997 | Edwards |
| 5,591,157 A | 1/1997 | Hennings |
| 5,591,162 A | 1/1997 | Fletcher |
| 5,599,294 A | 2/1997 | Edwards |
| 5,601,591 A | 2/1997 | Edwards |
| 5,609,151 A | 3/1997 | Mulier |
| 5,616,120 A | 4/1997 | Andrew |

(56) References Cited

U.S. PATENT DOCUMENTS

| | | |
|---|---|---|
| 5,620,440 A | 4/1997 | Heckele |
| 5,624,392 A | 4/1997 | Saab |
| 5,630,794 A | 5/1997 | Lax |
| 5,667,488 A | 9/1997 | Lundquist |
| 5,669,907 A | 9/1997 | Platt, Jr. |
| 5,672,153 A | 9/1997 | Lax |
| 5,672,290 A | 9/1997 | Levy |
| 5,674,191 A | 10/1997 | Edwards |
| 5,681,282 A | 10/1997 | Eggers |
| 5,683,366 A | 11/1997 | Eggers |
| 5,695,507 A | 12/1997 | Auth |
| 5,697,281 A | 12/1997 | Eggers |
| 5,697,536 A | 12/1997 | Eggers |
| 5,697,882 A | 12/1997 | Eggers |
| 5,697,909 A | 12/1997 | Eggers |
| 5,700,262 A | 12/1997 | Acosta |
| 5,707,352 A | 1/1998 | Sekins |
| 5,720,718 A | 2/1998 | Rosen |
| 5,720,719 A | 2/1998 | Edwards |
| 5,730,719 A | 3/1998 | Edwards |
| 5,735,811 A | 4/1998 | Brisken |
| 5,741,247 A | 4/1998 | Rizoiu |
| 5,741,248 A | 4/1998 | Stern |
| 5,743,870 A | 4/1998 | Edwards |
| 5,752,965 A | 5/1998 | Francis |
| 5,755,753 A | 5/1998 | Knowlton |
| 5,769,880 A | 6/1998 | Truckai |
| 5,782,914 A | 7/1998 | Schankereli |
| 5,785,521 A | 7/1998 | Rizoiu |
| 5,797,903 A | 8/1998 | Swanson |
| 5,800,379 A | 9/1998 | Edwards |
| 5,800,482 A | 9/1998 | Pomeranz |
| 5,800,493 A | 9/1998 | Stevens |
| 5,810,764 A | 9/1998 | Eggers |
| 5,820,580 A | 10/1998 | Edwards |
| 5,824,703 A | 10/1998 | Clark, Jr. |
| 5,827,268 A | 10/1998 | Laufer |
| 5,830,179 A | 11/1998 | Mikus |
| 5,836,906 A | 11/1998 | Edwards |
| 5,843,019 A | 12/1998 | Eggers |
| 5,843,073 A | 12/1998 | Sinofsky |
| 5,849,011 A | 12/1998 | Jones |
| 5,861,005 A | 1/1999 | Kontos |
| 5,871,469 A | 2/1999 | Eggers |
| 5,871,481 A | 2/1999 | Kannenberg |
| 5,873,855 A | 2/1999 | Eggers |
| 5,873,877 A | 2/1999 | McGaffigan |
| 5,879,329 A | 3/1999 | Ginsburg |
| 5,885,243 A | 3/1999 | Capetan |
| 5,888,198 A | 3/1999 | Eggers |
| 5,891,095 A | 4/1999 | Eggers |
| 5,891,134 A | 4/1999 | Goble |
| 5,891,457 A | 4/1999 | Neuwirth |
| 5,897,553 A | 4/1999 | Muller |
| 5,902,272 A | 5/1999 | Eggers |
| 5,913,856 A | 6/1999 | Chia |
| 5,938,660 A | 8/1999 | Swartz |
| 5,944,686 A | 8/1999 | Patterson |
| 5,944,715 A | 8/1999 | Goble |
| 5,954,714 A | 9/1999 | Saadat |
| 5,957,919 A | 9/1999 | Laufer |
| 5,957,922 A | 9/1999 | Imran |
| 5,964,752 A | 10/1999 | Stone |
| 5,964,756 A | 10/1999 | McGaffigan |
| 5,968,037 A | 10/1999 | Rizoiu |
| 5,976,123 A | 11/1999 | Baumgardner |
| 5,980,504 A | 11/1999 | Sharkey |
| 5,980,516 A | 11/1999 | Mulier |
| 5,986,662 A | 11/1999 | Argiro |
| 5,989,212 A | 11/1999 | Sussman |
| 5,989,238 A | 11/1999 | Ginsburg |
| 5,989,249 A | 11/1999 | Kirwan, Jr. |
| 5,989,445 A | 11/1999 | Wise |
| 5,997,499 A | 12/1999 | Sussman |
| 6,015,406 A | 1/2000 | Goble |
| 6,016,809 A | 1/2000 | Mulier |
| 6,017,361 A | 1/2000 | Mikus |
| 6,024,733 A | 2/2000 | Eggers |
| 6,027,501 A | 2/2000 | Goble |
| 6,032,077 A | 2/2000 | Pomeranz |
| 6,032,674 A | 3/2000 | Eggers |
| 6,036,713 A | 3/2000 | Kieturakis |
| 6,045,532 A | 4/2000 | Eggers |
| 6,045,549 A | 4/2000 | Smethers |
| 6,047,700 A | 4/2000 | Eggers |
| 6,053,172 A | 4/2000 | Hovda |
| 6,053,909 A | 4/2000 | Shadduck |
| 6,056,746 A | 5/2000 | Goble |
| 6,059,011 A | 5/2000 | Giolo |
| 6,063,079 A | 5/2000 | Hovda |
| 6,063,081 A | 5/2000 | Mulier |
| 6,066,132 A | 5/2000 | Chen |
| 6,066,134 A | 5/2000 | Eggers |
| 6,074,358 A | 6/2000 | Andrew |
| 6,077,257 A | 6/2000 | Edwards |
| 6,080,128 A | 6/2000 | Sussman |
| 6,080,151 A | 6/2000 | Swartz |
| 6,083,255 A | 7/2000 | Laufer |
| 6,086,585 A | 7/2000 | Hovda |
| 6,095,149 A | 8/2000 | Sharkey |
| 6,099,251 A | 8/2000 | LaFleur |
| 6,102,046 A | 8/2000 | Weinstein |
| 6,102,885 A | 8/2000 | Bass |
| 6,105,581 A | 8/2000 | Eggers |
| 6,106,516 A | 8/2000 | Massengill |
| 6,109,268 A | 8/2000 | Thapliyal |
| 6,110,162 A | 8/2000 | Sussman |
| 6,112,123 A | 8/2000 | Kelleher |
| 6,113,593 A | 9/2000 | Tu |
| 6,113,597 A | 9/2000 | Eggers |
| 6,113,722 A | 9/2000 | Hoffman |
| 6,117,109 A | 9/2000 | Eggers |
| 6,126,682 A | 10/2000 | Sharkey |
| 6,130,671 A | 10/2000 | Argiro |
| 6,139,538 A | 10/2000 | Houghton |
| 6,139,571 A | 10/2000 | Fuller |
| 6,149,620 A | 11/2000 | Baker |
| 6,156,036 A | 12/2000 | Sussman |
| 6,159,194 A | 12/2000 | Eggers |
| 6,159,208 A | 12/2000 | Hovda |
| 6,162,232 A | 12/2000 | Shadduck |
| 6,168,594 B1 | 1/2001 | LaFontaine |
| 6,174,308 B1 | 1/2001 | Goble |
| 6,179,805 B1 | 1/2001 | Sussman |
| 6,179,824 B1 | 1/2001 | Eggers |
| 6,179,836 B1 | 1/2001 | Eggers |
| 6,183,469 B1 | 2/2001 | Thapliyal |
| 6,190,381 B1 | 2/2001 | Olsen |
| 6,194,066 B1 | 2/2001 | Hoffman |
| 6,196,989 B1 | 3/2001 | Padget |
| 6,200,333 B1 | 3/2001 | Laufer |
| 6,203,542 B1 | 3/2001 | Ellsberry |
| 6,206,847 B1 | 3/2001 | Edwards |
| 6,206,848 B1 | 3/2001 | Sussman |
| 6,210,402 B1 | 4/2001 | Olsen |
| 6,210,404 B1 | 4/2001 | Shadduck |
| 6,210,405 B1 | 4/2001 | Goble |
| 6,219,059 B1 | 4/2001 | Argiro |
| 6,224,592 B1 | 5/2001 | Eggers |
| 6,228,078 B1 | 5/2001 | Eggers |
| 6,228,081 B1 | 5/2001 | Goble |
| 6,228,082 B1 | 5/2001 | Baker |
| 6,231,567 B1 | 5/2001 | Rizoiu |
| 6,234,178 B1 | 5/2001 | Goble |
| 6,235,020 B1 | 5/2001 | Cheng |
| 6,235,025 B1 | 5/2001 | Swartz |
| 6,238,389 B1 | 5/2001 | Paddock |
| 6,238,391 B1 | 5/2001 | Olsen |
| 6,241,702 B1 | 6/2001 | Lundquist |
| 6,254,597 B1 | 7/2001 | Rizoiu |
| 6,254,600 B1 | 7/2001 | Willink |
| 6,258,087 B1 | 7/2001 | Edwards |
| 6,261,286 B1 | 7/2001 | Goble |
| 6,261,311 B1 | 7/2001 | Sharkey |

(56) References Cited

U.S. PATENT DOCUMENTS

| | | | |
|---|---|---|---|
| 6,264,650 | B1 | 7/2001 | Hovda |
| 6,264,651 | B1 | 7/2001 | Underwood |
| 6,264,652 | B1 | 7/2001 | Eggers |
| 6,264,654 | B1 | 7/2001 | Swartz |
| 6,277,112 | B1 | 8/2001 | Underwood |
| 6,277,114 | B1 | 8/2001 | Bullivant |
| 6,277,130 | B1 | 8/2001 | Shadduck |
| 6,283,961 | B1 | 9/2001 | Underwood |
| 6,283,989 | B1 | 9/2001 | Laufer |
| 6,287,274 | B1 | 9/2001 | Sussman |
| 6,287,320 | B1 | 9/2001 | Slepian |
| 6,290,715 | B1 | 9/2001 | Sharkey |
| 6,293,942 | B1 | 9/2001 | Goble |
| 6,296,636 | B1 | 10/2001 | Cheng |
| 6,296,638 | B1 | 10/2001 | Davison |
| 6,299,620 | B1 | 10/2001 | Shadduck |
| 6,299,633 | B1 | 10/2001 | Laufer |
| 6,300,150 | B1 | 10/2001 | Venkatasubramanian |
| 6,306,129 | B1 | 10/2001 | Little |
| 6,306,134 | B1 | 10/2001 | Goble |
| 6,309,387 | B1 | 10/2001 | Eggers |
| 6,312,408 | B1 | 11/2001 | Eggers |
| 6,312,474 | B1 | 11/2001 | Francis |
| 6,315,755 | B1 | 11/2001 | Sussman |
| 6,319,222 | B1 | 11/2001 | Andrew |
| 6,322,549 | B1 | 11/2001 | Eggers |
| 6,327,505 | B1 | 12/2001 | Medhkour |
| 6,331,171 | B1 | 12/2001 | Cohen |
| 6,355,032 | B1 | 3/2002 | Hovda |
| 6,358,248 | B1 | 3/2002 | Muller |
| 6,363,937 | B1 | 4/2002 | Hovda |
| 6,364,877 | B1 | 4/2002 | Goble |
| 6,375,635 | B1 | 4/2002 | Moutafis |
| 6,379,350 | B1 | 4/2002 | Sharkey |
| 6,379,351 | B1 | 4/2002 | Thapliyal |
| 6,391,025 | B1 | 5/2002 | Weinstein |
| 6,394,949 | B1 | 5/2002 | Crowley |
| 6,394,996 | B1 | 5/2002 | Lawrence |
| 6,398,759 | B1 | 6/2002 | Sussman |
| 6,398,775 | B1 | 6/2002 | Perkins |
| 6,409,723 | B1 | 6/2002 | Edwards |
| 6,416,507 | B1 | 7/2002 | Eggers |
| 6,416,508 | B1 | 7/2002 | Eggers |
| 6,416,509 | B1 | 7/2002 | Goble |
| 6,419,673 | B1 | 7/2002 | Edwards |
| 6,423,027 | B1 | 7/2002 | Gonon |
| 6,432,103 | B1 | 8/2002 | Ellsberry |
| 6,440,127 | B2 | 8/2002 | McGovern |
| 6,458,231 | B1 | 10/2002 | Wapner |
| 6,461,296 | B1 | 10/2002 | Desai |
| 6,461,350 | B1 | 10/2002 | Underwood |
| 6,461,354 | B1 | 10/2002 | Olsen |
| 6,464,694 | B1 | 10/2002 | Massengill |
| 6,464,695 | B2 | 10/2002 | Hovda |
| 6,468,270 | B1 | 10/2002 | Hovda |
| 6,468,274 | B1 | 10/2002 | Alleyne |
| 6,468,313 | B1 | 10/2002 | Claeson |
| 6,482,201 | B1 | 11/2002 | Olsen |
| 6,482,202 | B1 | 11/2002 | Goble |
| 6,488,673 | B1 | 12/2002 | Laufer |
| 6,488,680 | B1 | 12/2002 | Francischelli |
| 6,491,710 | B2 | 12/2002 | Satake |
| 6,493,589 | B1 | 12/2002 | Medhkour |
| 6,500,173 | B2 | 12/2002 | Underwood |
| 6,508,816 | B2 | 1/2003 | Shadduck |
| 6,510,854 | B2 | 1/2003 | Goble |
| 6,517,568 | B1 | 2/2003 | Sharkey |
| 6,522,930 | B1 | 2/2003 | Schaer |
| 6,527,761 | B1 | 3/2003 | Soltesz |
| 6,527,766 | B1 | 3/2003 | Bair |
| 6,528,771 | B1 | 3/2003 | Matsen |
| 6,540,741 | B1 | 4/2003 | Underwood |
| 6,544,211 | B1 | 4/2003 | Andrew |
| 6,544,248 | B1 | 4/2003 | Bass |
| 6,544,261 | B2 | 4/2003 | Ellsberry |
| 6,547,810 | B1 | 4/2003 | Sharkey |
| 6,551,271 | B2 | 4/2003 | Nguyen |
| 6,551,274 | B2 | 4/2003 | Heiner |
| 6,551,300 | B1 | 4/2003 | McGaffigan |
| 6,557,559 | B1 | 5/2003 | Eggers |
| 6,558,314 | B1 | 5/2003 | Adelman |
| 6,558,379 | B1 | 5/2003 | Batchelor |
| 6,566,636 | B1 | 5/2003 | Bentley |
| 6,569,146 | B1 | 5/2003 | Werner |
| 6,575,929 | B2 | 6/2003 | Sussman |
| 6,575,932 | B1 | 6/2003 | OBrien |
| 6,575,968 | B1 | 6/2003 | Eggers |
| 6,579,270 | B2 | 6/2003 | Sussman |
| 6,582,423 | B1 | 6/2003 | Thapliyal |
| 6,585,639 | B1 | 7/2003 | Kotmel |
| 6,585,732 | B2 | 7/2003 | Mulier |
| 6,588,613 | B1 | 7/2003 | Pechenik |
| 6,589,201 | B1 | 7/2003 | Sussman |
| 6,589,204 | B1 | 7/2003 | Sussman |
| 6,589,237 | B2 | 7/2003 | Woloszko |
| 6,592,594 | B2 | 7/2003 | Rimbaugh |
| 6,595,989 | B1 | 7/2003 | Schaer |
| 6,595,990 | B1 | 7/2003 | Weinstein |
| 6,599,311 | B1 | 7/2003 | Biggs |
| 6,602,248 | B1 | 8/2003 | Sharps |
| 6,605,087 | B2 | 8/2003 | Swartz |
| 6,607,529 | B1 | 8/2003 | Jones |
| 6,610,043 | B1 | 8/2003 | Ingenito |
| 6,620,130 | B1 | 9/2003 | Ginsburg |
| 6,620,155 | B1 | 9/2003 | Underwood |
| 6,623,444 | B2 | 9/2003 | Babaev |
| 6,629,974 | B2 | 10/2003 | Penny |
| 6,632,193 | B1 | 10/2003 | Davison |
| 6,632,220 | B1 | 10/2003 | Eggers |
| 6,634,363 | B1 | 10/2003 | Danek |
| 6,647,300 | B1 | 11/2003 | Balasubramanian |
| 6,648,847 | B2 | 11/2003 | Sussman |
| 6,652,594 | B2 | 11/2003 | Francis |
| 6,653,525 | B2 | 11/2003 | Ingenito |
| 6,659,106 | B1 | 12/2003 | Hovda |
| 6,669,685 | B1 | 12/2003 | Rizoiu |
| 6,669,694 | B2 | 12/2003 | Shadduck |
| 6,673,071 | B2 | 1/2004 | VanDusseldorp |
| 6,676,628 | B2 | 1/2004 | Sussman |
| 6,676,629 | B2 | 1/2004 | Andrew |
| 6,679,264 | B1 | 1/2004 | Deem |
| 6,679,879 | B2 | 1/2004 | Shadduck |
| 6,682,520 | B2 | 1/2004 | Ingenito |
| 6,692,494 | B1 | 2/2004 | Cooper |
| 6,695,839 | B2 | 2/2004 | Sharkey |
| 6,699,244 | B2 | 3/2004 | Carranza |
| 6,708,056 | B2 | 3/2004 | Duchon |
| 6,712,811 | B2 | 3/2004 | Underwood |
| 6,712,812 | B2 | 3/2004 | Roschak |
| 6,716,252 | B2 | 4/2004 | Lazarovitz |
| 6,719,738 | B2 | 4/2004 | Mehier |
| 6,719,754 | B2 | 4/2004 | Underwood |
| 6,719,755 | B2 | 4/2004 | Sliwa, Jr. |
| 6,723,064 | B2 | 4/2004 | Babaev |
| 6,726,684 | B1 | 4/2004 | Woloszko |
| 6,726,696 | B1 | 4/2004 | Houser |
| 6,726,708 | B2 | 4/2004 | Lasheras |
| 6,730,079 | B2 | 5/2004 | Lovewell |
| 6,734,405 | B2 | 5/2004 | Centanni |
| 6,740,082 | B2 | 5/2004 | Shadduck |
| 6,746,447 | B2 | 6/2004 | Davison |
| 6,749,604 | B1 | 6/2004 | Eggers |
| 6,755,794 | B2 | 6/2004 | Soukup |
| 6,758,846 | B2 | 7/2004 | Goble |
| 6,760,616 | B2 | 7/2004 | Hoey |
| 6,763,836 | B2 | 7/2004 | Tasto |
| 6,764,487 | B2 | 7/2004 | Mulier |
| 6,766,202 | B2 | 7/2004 | Underwood |
| 6,770,070 | B1 | 8/2004 | Balbierz |
| 6,770,071 | B2 | 8/2004 | Woloszko |
| 6,772,012 | B2 | 8/2004 | Ricart |
| 6,773,431 | B2 | 8/2004 | Eggers |
| 6,776,765 | B2 | 8/2004 | Soukup |
| 6,776,780 | B2 | 8/2004 | Mulier |

(56) References Cited

U.S. PATENT DOCUMENTS

| | | |
|---|---|---|
| 6,780,178 B2 | 8/2004 | Palanker |
| 6,780,180 B1 | 8/2004 | Goble |
| 6,805,130 B2 | 10/2004 | Tasto |
| 6,813,520 B2 | 11/2004 | Truckai |
| 6,827,718 B2 | 12/2004 | Hutchins |
| 6,832,996 B2 | 12/2004 | Woloszko |
| 6,837,884 B2 | 1/2005 | Woloszko |
| 6,837,886 B2 | 1/2005 | Collins |
| 6,837,887 B2 | 1/2005 | Woloszko |
| 6,837,888 B2 | 1/2005 | Ciarrocca |
| 6,852,108 B2 | 2/2005 | Barry |
| 6,860,847 B2 | 3/2005 | Alferness |
| 6,860,868 B1 | 3/2005 | Sussman |
| 6,875,194 B2 | 4/2005 | MacKool |
| 6,893,438 B2 | 5/2005 | Hall |
| 6,896,672 B1 | 5/2005 | Eggers |
| 6,896,674 B1 | 5/2005 | Woloszko |
| 6,896,675 B2 | 5/2005 | Leung |
| 6,901,927 B2 | 6/2005 | Deem |
| 6,904,909 B2 | 6/2005 | Andreas |
| 6,905,475 B2 | 6/2005 | Hauschild |
| 6,905,496 B1 | 6/2005 | Ellman |
| 6,907,881 B2 | 6/2005 | Suki |
| 6,911,028 B2 | 6/2005 | Shadduck |
| 6,915,806 B2 | 7/2005 | Pacek |
| 6,916,318 B2 | 7/2005 | Francischelli |
| 6,918,903 B2 | 7/2005 | Bass |
| 6,921,385 B2 | 7/2005 | Clements |
| 6,929,640 B1 | 8/2005 | Underwood |
| 6,929,642 B2 | 8/2005 | Xiao |
| 6,949,096 B2 | 9/2005 | Davison |
| 6,949,098 B2 | 9/2005 | Mulier |
| 6,952,615 B2 | 10/2005 | Satake |
| 6,955,674 B2 | 10/2005 | Eick |
| 6,955,675 B2 | 10/2005 | Jain |
| 6,960,182 B2 | 11/2005 | Moutafis |
| 6,960,203 B2 | 11/2005 | Xiao |
| 6,960,204 B2 | 11/2005 | Eggers |
| 6,969,376 B2 | 11/2005 | Takagi |
| 6,972,014 B2 | 12/2005 | Eum |
| 6,986,769 B2 | 1/2006 | Nelson |
| 6,991,028 B2 | 1/2006 | Comeaux |
| 6,991,631 B2 | 1/2006 | Woloszko |
| 7,004,940 B2 | 2/2006 | Ryan |
| 7,004,941 B2 | 2/2006 | Tvinnereim |
| 7,014,652 B2 | 3/2006 | Cioanta |
| 7,022,088 B2 | 4/2006 | Keast |
| 7,025,762 B2 | 4/2006 | Johnston |
| 7,031,504 B1 | 4/2006 | Argiro |
| 7,083,612 B2 | 8/2006 | Littrup |
| 7,087,040 B2 | 8/2006 | McGuckin, Jr. |
| 7,089,064 B2 | 8/2006 | Manker |
| 7,094,215 B2 | 8/2006 | Davison |
| 7,101,367 B2 | 9/2006 | Xiao |
| 7,104,986 B2 | 9/2006 | Hovda |
| 7,105,007 B2 | 9/2006 | Hibler |
| 7,112,198 B2 | 9/2006 | Satake |
| 7,113,838 B2 | 9/2006 | Funk |
| RE39,358 E | 10/2006 | Goble |
| 7,128,748 B2 | 10/2006 | Mooradian |
| 7,130,697 B2 | 10/2006 | Chornenky |
| 7,131,969 B1 | 11/2006 | Hovda |
| 7,136,064 B2 | 11/2006 | Zuiderveld |
| 7,144,402 B2 | 12/2006 | Kuester, III |
| 7,144,588 B2 | 12/2006 | Oray |
| 7,153,301 B2 | 12/2006 | Swartz |
| 7,166,105 B2 | 1/2007 | Mulier |
| 7,169,143 B2 | 1/2007 | Eggers |
| 7,179,255 B2 | 2/2007 | Lettice |
| 7,186,234 B2 | 3/2007 | Dahla |
| 7,192,400 B2 | 3/2007 | Campbell |
| 7,192,428 B2 | 3/2007 | Eggers |
| 7,201,750 B1 | 4/2007 | Eggers |
| 7,217,268 B2 | 5/2007 | Eggers |
| 7,225,040 B2 | 5/2007 | Eller |
| 7,233,820 B2 | 6/2007 | Gilboa |
| 7,235,070 B2 | 6/2007 | Vanney |
| 7,237,555 B2 | 7/2007 | Kochamba |
| 7,241,293 B2 | 7/2007 | Davison |
| 7,261,709 B2 | 8/2007 | Swoyer |
| 7,261,710 B2 | 8/2007 | Elmouelhi |
| 7,270,658 B2 | 9/2007 | Woloszko |
| 7,270,659 B2 | 9/2007 | Ricart |
| 7,270,661 B2 | 9/2007 | Dahla |
| 7,276,063 B2 | 10/2007 | Davison |
| 7,280,881 B2 | 10/2007 | Eller |
| 7,297,143 B2 | 11/2007 | Woloszko |
| 7,297,145 B2 | 11/2007 | Woloszko |
| 7,320,325 B2 | 1/2008 | Duchon |
| 7,335,195 B2 | 2/2008 | Mehier |
| 7,335,197 B2 | 2/2008 | Sage |
| 7,340,307 B2 | 3/2008 | Maguire |
| 7,347,859 B2 | 3/2008 | Garabedian |
| 7,364,579 B2 | 4/2008 | Mulier |
| 7,410,486 B2 | 8/2008 | Fuimaono |
| 7,419,500 B2 | 9/2008 | Marko |
| 7,422,588 B2 | 9/2008 | Mulier |
| 7,429,262 B2 | 9/2008 | Woloszko |
| 7,435,250 B2 | 10/2008 | Francischelli |
| 7,470,228 B2 | 12/2008 | Connors |
| 7,470,272 B2 | 12/2008 | Mulier |
| 7,503,904 B2 | 3/2009 | Choi |
| 7,512,445 B2 | 3/2009 | Truckai |
| 7,549,987 B2 | 6/2009 | Shadduck |
| 7,559,367 B2 | 7/2009 | Vinegar |
| 7,585,295 B2 | 9/2009 | Ben-Nun |
| 7,597,147 B2 | 10/2009 | Vitek |
| 7,674,259 B2 | 3/2010 | Shadduck |
| 7,678,111 B2 | 3/2010 | Mulier |
| 7,727,228 B2 | 6/2010 | Abboud |
| 7,753,871 B2 | 7/2010 | Mehier |
| 7,794,460 B2 | 9/2010 | Mulier |
| 7,831,133 B2 | 11/2010 | Vinegar |
| 7,892,229 B2 | 2/2011 | Shadduck |
| 7,913,698 B2 | 3/2011 | Barry |
| 7,993,323 B2 | 8/2011 | Barry |
| 8,014,711 B2 | 9/2011 | Ito |
| 8,016,823 B2 | 9/2011 | Shadduck |
| 8,145,113 B2 | 3/2012 | Murakami |
| 8,147,532 B2 | 4/2012 | Barry |
| 8,187,269 B2 | 5/2012 | Shadduck |
| 8,224,165 B2 | 7/2012 | Vinegar |
| 8,226,637 B2 | 7/2012 | Satake |
| 8,229,588 B2 | 7/2012 | Tsen |
| 8,231,617 B2 | 7/2012 | Satake |
| 8,251,985 B2 | 8/2012 | Hoey |
| 8,272,383 B2 | 9/2012 | Hoey |
| 8,273,079 B2 | 9/2012 | Hoey |
| 8,313,485 B2 | 11/2012 | Shadduck |
| 8,322,335 B2 | 12/2012 | Barry |
| 8,355,623 B2 | 1/2013 | Vinegar |
| 8,372,065 B2 | 2/2013 | Hoey |
| 8,388,611 B2 | 3/2013 | Shadduck |
| 8,419,723 B2 | 4/2013 | Shadduck |
| 8,437,870 B2 | 5/2013 | Tsai |
| 8,444,636 B2 | 5/2013 | Shadduck |
| 8,512,326 B2 | 8/2013 | Shadduck |
| 8,521,074 B2 | 8/2013 | Murakami |
| 8,574,226 B2 | 11/2013 | Shadduck |
| 8,579,888 B2 | 11/2013 | Hoey |
| 8,579,892 B2 | 11/2013 | Hoey |
| 8,579,893 B2 | 11/2013 | Hoey |
| 8,585,645 B2 | 11/2013 | Barry |
| 8,585,692 B2 | 11/2013 | Shadduck |
| 8,632,530 B2 | 1/2014 | Hoey |
| 8,647,339 B2 | 2/2014 | Satake |
| 8,721,632 B2 | 5/2014 | Hoey |
| 8,734,380 B2 | 5/2014 | Barry |
| 8,758,341 B2 | 6/2014 | Shadduck |
| 8,761,626 B2 | 6/2014 | Seo |
| 8,801,702 B2 | 8/2014 | Hoey |
| 8,805,466 B2 | 8/2014 | Salahieh |
| 8,858,549 B2 | 10/2014 | Shadduck |
| 8,900,223 B2 | 12/2014 | Shadduck |

(56) References Cited

U.S. PATENT DOCUMENTS

| | | | |
|---|---|---|---|
| 8,911,430 B2 | 12/2014 | Hoey |
| 9,113,858 B2 | 8/2015 | Barry |
| 9,113,944 B2 | 8/2015 | Shadduck |
| 9,125,667 B2 | 9/2015 | Stone |
| 9,161,801 B2 | 10/2015 | Hoey |
| 9,179,973 B2 | 11/2015 | Nabutovsky |
| 9,198,708 B2 | 12/2015 | Hoey |
| 9,204,889 B2 | 12/2015 | Shadduck |
| 9,345,507 B2 | 5/2016 | Hoey |
| 9,387,310 B2 | 7/2016 | Satake |
| 9,433,457 B2 | 9/2016 | Shadduck |
| 9,468,487 B2 | 10/2016 | Shadduck |
| 9,526,555 B2 | 12/2016 | Hoey |
| 9,615,875 B2 | 4/2017 | Shadduck |
| 9,757,535 B2 | 9/2017 | Rajagopalan |
| 9,844,641 B2 | 12/2017 | Rajagopalan |
| 9,907,599 B2 | 3/2018 | Hoey |
| 9,974,607 B2 | 5/2018 | Stone |
| 10,299,857 B2 | 5/2019 | Rajagopalan |
| 2001/0020167 A1 | 9/2001 | Woloszko |
| 2001/0029370 A1 | 10/2001 | Hodva |
| 2001/0037106 A1 | 11/2001 | Shadduck |
| 2002/0013601 A1 | 1/2002 | Nobles |
| 2002/0019627 A1 | 2/2002 | Maguire |
| 2002/0049438 A1 | 4/2002 | Sharkey |
| 2002/0077516 A1 | 6/2002 | Flanigan |
| 2002/0078956 A1 | 6/2002 | Sharpe |
| 2002/0082667 A1* | 6/2002 | Shadduck ............... A61B 18/04 607/96 |
| 2002/0095152 A1 | 7/2002 | Ciarrocca |
| 2002/0111386 A1 | 8/2002 | Sekins |
| 2002/0133147 A1 | 9/2002 | Marchitto |
| 2002/0156470 A1* | 10/2002 | Shadduck ........... A61B 18/1485 606/41 |
| 2002/0161326 A1 | 10/2002 | Sussman |
| 2002/0177846 A1* | 11/2002 | Mulier ................... A61B 18/04 606/27 |
| 2002/0193789 A1 | 12/2002 | Underwood |
| 2003/0028189 A1 | 2/2003 | Woloszko |
| 2003/0040742 A1 | 2/2003 | Underwood |
| 2003/0069575 A1 | 4/2003 | Chin |
| 2003/0088145 A1 | 5/2003 | Scott |
| 2003/0088246 A1 | 5/2003 | Swartz |
| 2003/0097126 A1 | 5/2003 | Woloszko |
| 2003/0099279 A1 | 5/2003 | Venkatasubramanian |
| 2003/0109869 A1 | 6/2003 | Shadduck |
| 2003/0130655 A1 | 7/2003 | Woloszko |
| 2003/0130738 A1 | 7/2003 | Hovda |
| 2003/0144654 A1 | 7/2003 | Hilal |
| 2003/0158545 A1 | 8/2003 | Hovda |
| 2003/0163178 A1 | 8/2003 | Davison |
| 2003/0181922 A1 | 9/2003 | Alferness |
| 2003/0204138 A1 | 10/2003 | Choi |
| 2003/0212394 A1 | 11/2003 | Pearson |
| 2003/0212395 A1 | 11/2003 | Woloszko |
| 2003/0216729 A1 | 11/2003 | Marchitto |
| 2003/0225364 A1 | 12/2003 | Kraft |
| 2004/0006333 A1 | 1/2004 | Arnold |
| 2004/0024398 A1 | 2/2004 | Hovda |
| 2004/0024399 A1 | 2/2004 | Sharps |
| 2004/0031494 A1 | 2/2004 | Danek |
| 2004/0037986 A1 | 2/2004 | Houston |
| 2004/0038868 A1 | 2/2004 | Ingenito |
| 2004/0047855 A1 | 3/2004 | Ingenito |
| 2004/0049180 A1 | 3/2004 | Sharps |
| 2004/0054366 A1 | 3/2004 | Davison |
| 2004/0055606 A1 | 3/2004 | Hendricksen |
| 2004/0059313 A1 | 3/2004 | Tachibana |
| 2004/0068256 A1 | 4/2004 | Rizoiu |
| 2004/0068306 A1 | 4/2004 | Shadduck |
| 2004/0087937 A1 | 5/2004 | Eggers |
| 2004/0116922 A1 | 6/2004 | Hovda |
| 2004/0193150 A1 | 9/2004 | Sharkey |
| 2004/0199226 A1 | 10/2004 | Shadduck |
| 2004/0230188 A1 | 11/2004 | Cioanta |
| 2004/0230190 A1 | 11/2004 | Dahla |
| 2004/0230316 A1 | 11/2004 | Cioanta |
| 2004/0254532 A1 | 12/2004 | Mehier |
| 2005/0004634 A1 | 1/2005 | Ricart |
| 2005/0010205 A1 | 1/2005 | Hovda |
| 2005/0015047 A1 | 1/2005 | Shah |
| 2005/0095168 A1 | 5/2005 | Centanni |
| 2005/0119650 A1 | 6/2005 | Sanders |
| 2005/0166925 A1 | 8/2005 | Wilson |
| 2005/0171582 A1 | 8/2005 | Matlock |
| 2005/0177147 A1 | 8/2005 | Vancelette |
| 2005/0187543 A1 | 8/2005 | Underwood |
| 2005/0215991 A1 | 9/2005 | Altman |
| 2005/0222485 A1 | 10/2005 | Shaw |
| 2005/0228423 A1 | 10/2005 | Khashayar |
| 2005/0228424 A1 | 10/2005 | Khashayar |
| 2005/0240171 A1 | 10/2005 | Forrest |
| 2005/0267468 A1 | 12/2005 | Truckai |
| 2005/0283143 A1 | 12/2005 | Rizoiu |
| 2006/0004400 A1 | 1/2006 | McGurk |
| 2006/0036237 A1 | 2/2006 | Davison |
| 2006/0041277 A1* | 2/2006 | Deem ................... A61N 1/0551 607/3 |
| 2006/0047291 A1 | 3/2006 | Barry |
| 2006/0085054 A1 | 4/2006 | Zikorus |
| 2006/0095032 A1* | 5/2006 | Jackson ............... A61B 5/0538 606/41 |
| 2006/0100619 A1 | 5/2006 | McClurken |
| 2006/0130830 A1 | 6/2006 | Barry |
| 2006/0135955 A1* | 6/2006 | Shadduck .............. A61B 18/04 606/27 |
| 2006/0161233 A1 | 7/2006 | Barry |
| 2006/0178670 A1 | 8/2006 | Woloszko |
| 2006/0200076 A1 | 9/2006 | Gonzalez |
| 2006/0200191 A1 | 9/2006 | Zadno-Azizi |
| 2006/0224154 A1 | 10/2006 | Shadduck |
| 2006/0276871 A1 | 12/2006 | Lamson |
| 2007/0032785 A1 | 2/2007 | Diederich |
| 2007/0036417 A1 | 2/2007 | Argiro |
| 2007/0049920 A1 | 3/2007 | McClurken |
| 2007/0083085 A1 | 4/2007 | Birnkrant |
| 2007/0091087 A1 | 4/2007 | Zuiderveld |
| 2007/0142846 A1 | 6/2007 | Catanese |
| 2007/0179496 A1 | 8/2007 | Swoyer |
| 2007/0225744 A1 | 9/2007 | Nobles |
| 2007/0225750 A1* | 9/2007 | Ren ........................ A61F 2/013 606/200 |
| 2007/0239197 A1 | 10/2007 | Dubey |
| 2007/0265687 A1 | 11/2007 | Deem |
| 2008/0021484 A1 | 1/2008 | Catanese |
| 2008/0021485 A1 | 1/2008 | Catanese |
| 2008/0033232 A1 | 2/2008 | Catanese |
| 2008/0033458 A1 | 2/2008 | McLean |
| 2008/0033488 A1 | 2/2008 | Catanese |
| 2008/0033493 A1 | 2/2008 | Deckman |
| 2008/0039833 A1 | 2/2008 | Catanese |
| 2008/0039872 A1 | 2/2008 | Catanese |
| 2008/0039874 A1 | 2/2008 | Catanese |
| 2008/0039875 A1 | 2/2008 | Catanese |
| 2008/0039876 A1 | 2/2008 | Catanese |
| 2008/0039893 A1 | 2/2008 | McLean |
| 2008/0039894 A1 | 2/2008 | Catanese |
| 2008/0046045 A1 | 2/2008 | Yon |
| 2008/0103566 A1 | 5/2008 | Mehier |
| 2008/0110457 A1 | 5/2008 | Barry |
| 2008/0114297 A1 | 5/2008 | Barry |
| 2008/0132826 A1 | 6/2008 | Shadduck |
| 2008/0183036 A1 | 7/2008 | Saadat |
| 2008/0208187 A1 | 8/2008 | Bhushan |
| 2008/0208189 A1 | 8/2008 | Van Wyk |
| 2008/0249399 A1 | 10/2008 | Appling |
| 2008/0275440 A1 | 11/2008 | Kratoska |
| 2008/0281267 A1 | 11/2008 | Mehier |
| 2008/0300571 A1 | 12/2008 | Lepivert |
| 2009/0018553 A1 | 1/2009 | McLean |
| 2009/0054868 A1 | 2/2009 | Sharkey |
| 2009/0054869 A1 | 2/2009 | Sharkey |
| 2009/0054870 A1 | 2/2009 | Sharkey |
| 2009/0054871 A1 | 2/2009 | Sharkey |

(56) References Cited

U.S. PATENT DOCUMENTS

| | | | |
|---|---|---|---|
| 2009/0082837 A1 | 3/2009 | Gellman | |
| 2009/0105702 A1 | 4/2009 | Shadduck | |
| 2009/0105703 A1 | 4/2009 | Shadduck | |
| 2009/0125009 A1 | 5/2009 | Zikorus | |
| 2009/0125010 A1 | 5/2009 | Sharkey | |
| 2009/0149846 A1 | 6/2009 | Hoey | |
| 2009/0216220 A1* | 8/2009 | Hoey | A61B 18/082 606/27 |
| 2009/0221998 A1 | 9/2009 | Epstein | |
| 2009/0227998 A1 | 9/2009 | Aljuri | |
| 2009/0277457 A1 | 11/2009 | Hoey | |
| 2009/0301483 A1 | 12/2009 | Barry | |
| 2009/0306640 A1 | 12/2009 | Glaze | |
| 2009/0312753 A1 | 12/2009 | Shadduck | |
| 2010/0016757 A1 | 1/2010 | Greenburg | |
| 2010/0049031 A1 | 2/2010 | Fruland | |
| 2010/0076416 A1* | 3/2010 | Hoey | A61B 18/18 606/2 |
| 2010/0094270 A1 | 4/2010 | Sharma | |
| 2010/0114082 A1 | 5/2010 | Sharma | |
| 2010/0114083 A1 | 5/2010 | Sharma | |
| 2010/0145254 A1 | 6/2010 | Shadduck | |
| 2010/0145325 A1 | 6/2010 | Hoey | |
| 2010/0145326 A1 | 6/2010 | Hoey | |
| 2010/0160905 A1 | 6/2010 | Shadduck | |
| 2010/0179416 A1 | 7/2010 | Hoey | |
| 2010/0179528 A1 | 7/2010 | Shadduck | |
| 2010/0204688 A1 | 8/2010 | Hoey | |
| 2010/0262133 A1 | 10/2010 | Hoey | |
| 2010/0274260 A1 | 10/2010 | DArpiany | |
| 2010/0286679 A1 | 11/2010 | Hoey | |
| 2010/0292767 A1 | 11/2010 | Hoey | |
| 2010/0298948 A1 | 11/2010 | Hoey | |
| 2011/0077628 A1 | 3/2011 | Hoey | |
| 2011/0118717 A1 | 5/2011 | Shadduck | |
| 2011/0160648 A1 | 6/2011 | Hoey | |
| 2011/0172654 A1 | 7/2011 | Barry | |
| 2011/0238144 A1 | 9/2011 | Hoey | |
| 2011/0264090 A1 | 10/2011 | Shadduck | |
| 2011/0276046 A1* | 11/2011 | Heimbecher | A61B 18/1492 606/35 |
| 2012/0065632 A1 | 3/2012 | Shadduck | |
| 2012/0078078 A1 | 3/2012 | MacAdam | |
| 2012/0101413 A1 | 4/2012 | Beetel | |
| 2012/0116376 A1 | 5/2012 | Hoey | |
| 2012/0232409 A1 | 9/2012 | Stahmann | |
| 2012/0259271 A1 | 10/2012 | Shadduck | |
| 2012/0323167 A1 | 12/2012 | Hoey | |
| 2013/0006231 A1 | 1/2013 | Sharma | |
| 2013/0074847 A1 | 3/2013 | Hoey | |
| 2013/0079772 A1 | 3/2013 | Shadduck | |
| 2013/0116683 A1 | 5/2013 | Shadduck | |
| 2013/0172867 A1 | 7/2013 | Shadduck | |
| 2013/0237978 A1 | 9/2013 | Shadduck | |
| 2013/0267939 A1 | 10/2013 | Barry | |
| 2013/0296837 A1 | 11/2013 | Burnett | |
| 2013/0345670 A1* | 12/2013 | Rajagopalan | A61N 7/022 604/506 |
| 2014/0025057 A1 | 1/2014 | Hoey | |
| 2014/0031805 A1 | 1/2014 | Shadduck | |
| 2014/0107637 A1 | 4/2014 | Hoey | |
| 2014/0114306 A1 | 4/2014 | Harada | |
| 2014/0200569 A1 | 7/2014 | Shadduck | |
| 2014/0200570 A1 | 7/2014 | Hoey | |
| 2014/0276713 A1 | 9/2014 | Hoey | |
| 2014/0288543 A1 | 9/2014 | Hoey | |
| 2014/0324037 A1 | 10/2014 | Hoey | |
| 2014/0357956 A1 | 12/2014 | Salahieh | |
| 2014/0371736 A1 | 12/2014 | Levin | |
| 2015/0025515 A1 | 1/2015 | Hoey | |
| 2015/0025516 A1 | 1/2015 | Hoey | |
| 2015/0080883 A1 | 3/2015 | Haverkost | |
| 2015/0126990 A1 | 5/2015 | Sharma | |
| 2015/0265329 A1 | 9/2015 | Lalonde | |

FOREIGN PATENT DOCUMENTS

| | | |
|---|---|---|
| CN | 102238920 | 9/2011 |
| EP | 1602338 B1 | 12/2005 |
| EP | 2341859 | 7/2011 |
| FR | 2655548 | 6/1991 |
| WO | 1992010142 | 6/1992 |
| WO | 1995028198 A1 | 10/1995 |
| WO | 9902096 A | 1/1999 |
| WO | 1999053853 | 10/1999 |
| WO | 2000029055 | 5/2000 |
| WO | 2001024715 | 4/2001 |
| WO | 2002069821 | 9/2002 |
| WO | 2003070302 | 8/2003 |
| WO | 2003086498 | 10/2003 |
| WO | 2005025635 | 3/2005 |
| WO | 2005102175 | 11/2005 |
| WO | 2006003665 | 1/2006 |
| WO | 2006004482 | 1/2006 |
| WO | 2006019728 A2 | 2/2006 |
| WO | 2006055695 | 5/2006 |
| WO | 2006108974 | 10/2006 |
| WO | 2009009398 | 1/2009 |
| WO | 2009074844 A1 | 6/2009 |
| WO | 2010042461 | 4/2010 |
| WO | 2010042461 A1 | 4/2010 |
| WO | 2012167213 | 12/2012 |
| WO | 2012167213 A2 | 12/2012 |
| WO | 2013086461 A1 | 6/2013 |
| WO | 2013152119 A1 | 10/2013 |
| WO | 2014113724 | 7/2014 |
| WO | 2014113724 A2 | 7/2014 |
| WO | 2017201504 A1 | 11/2017 |

OTHER PUBLICATIONS

Extended European Search Report for EP14740240.8, dated Jul. 28, 2016.

International Search Report for PCT/US2016/012840, dated Aug. 18, 2016.

Office Action dated Mar. 4, 2015 for U.S. Appl. No. 14/594,444.

"Understanding Microprocessors, Advantages of 32-bit CPUs and DSPs." Stevens. Stevens Water Monitoring Systems, Inc., May 12, 2008. Web. Feb. 4, 2013. <http://web.archive.org/web/20080512144927/http://www.stevenswater.com/articles/cpu.aspx>.

International Search Report for PCT/US2009/059609, dated Mar. 5, 2010.

International Search Report for PCT/US2012/040639, dated Dec. 18, 2012.

Hai; Photoselective Vaporization Prostatectomy: A Palliative Treatment Option for Men with Urinary Obstruction Secondary to Prostate Cancer; PCRI Prost. Cancer Rsrch. Inst. Reprint. from PCRI Insights Nov. 2005, vol. 8(4); pp. 4.

Van De Velde; Vapo-cauterization of the uterus; Amer. J. Med. Sci.; vol. CXVII; 1899.

Blacker; Vaporization of the uterus; J. Obstet. & Gyn.; pp. 488-511; 1901.

Microsulis America, Inc.; Instructions for Use, Microsulis Microwave Endometrial Ablation (MEA) System; Microsulis Americas, Inc.—MEA System Instructions for Use; Dec. 2002; 62795/09/038 Issue 1; pp. 16-35; Microsulis Americas.

Sharma et al; Barrett's Oesophagus, A randomised controlled trial of ablation of Barrett's oesophagus with multipolar electrocoagulation versus argon plasma coagulation in combination with acid suppression: long term results; Gut; 2006; 55:1233-1239; doi: 10.1136/gut.2005.086777.

Sharma et al; Balloon-based, cicrumferential, endoscopic radiofrequency ablation of Barrett's esophagus: 1-year follow-up of 100 patients (with video); Gastrointestinal Endoscopy; 2007; vol. 65, No. 2; 0016-5/$32.00 doi:10.1016/j.gie.2006.09.033; pp. 185-195.

Sanfilippo et al; Update: Options in Endometrial Ablation; Supplement to OBG Management; Dec. 2009; pp. S1-S24; Dowden Health Media.

(56) References Cited

OTHER PUBLICATIONS

United States FDA; Summary of Safety and Effectiveness Data: Cryogen, Inc.: Her Option Uterine Cryoablation Therapy System; PMA P000032; Sep. 14, 2001; pp. 1-22.
American Medical Systems, Inc.; her option office cryoablation therapy Resource Guide; 2007; pp. 1-29; American Medical Systems, Inc.. 10700 Bren Road West, Minnetonka, MN 55343 USA.
Boston Scientific; HTA System Endometrial Ablation System; 2006; BVU 1090 Rev. A 10M 9/06-9/08; Boston Scientific Corporation, One Boston Scientific Place, Natick, MA 01760-1537.
Ethicon Women's Health & Urology; Instructions for Use, Gynecare Thermachoice III Uterine Balloon Therapy System, Thermal Balloon Ablation Silicone Catheter and Syringe (Single-Use); Mar. 26, 2008; pp. 1-156; TCIII_389630.R06_Main.indd; Gynecare, a division of Ethicon, Inc. a Johnson & Johnson company, Sommerville, NJ, 08876-0151 USA.
Johnston et al.; Cryoablation of Barrett's esophagus: a pilot study; Gastrointestinal Endoscopy; 2005; pp. 842-848; vol. 62, No. 6, 0016-5107/$30.00 doi:10.1016/j.gie.2005.05.008; American Society for Gastrointestinal Endoscopy.
Carter; Endometrial Ablation: More Choices, More Options; The Female Patient; 2005; pp. 35-40; 30(12).
Thibeau; AW-06995-001; Text, Manual, Novasure, V1, EN, US; Aug. 26, 2011; pp. 1-23; Hologic, Inc.
Neuwirth et al.; The endometrial ablator: a new instrument; Obst. & Gyn.; vol. 83; No. 5; part 1; pp. 792-796; 1994.
Prior et al.; Treatment of mennorrhagia by radiofrequency heating; Int. J. Hyperthermia; vol. 7; No. 2; pp. 213-220; 1991.
International Search Report for PCT/US2014/012131, dated Jul. 30, 2014.
Office Action dated Feb. 20, 2015 for U.S. Appl. No. 13/486,980.
European Search Report, 12793307, Sharma, Virender K., dated Sep. 22, 2014.
Notice of Allowance dated Jan. 7, 2015 for U.S. Appl. No. 12/793,307.
Office Action dated Dec. 26, 2014 for U.S. Appl. No. 12/573,946.
Office Action dated Jul. 20, 2015 for U.S. Appl. No. 14/594,444.
Notice of Allowance dated Oct. 3, 2016 for U.S. Appl. No. 14/594,444.
Office Action dated Jun. 13, 2016 for U.S. Appl. No. 14/158,687.
First Office Action for EP09819726.2, dated Oct. 28, 2015.
First Office Action for Chinese Patent Application No. CN201280027522.X, dated Sep. 2, 2015.
Office Action dated Dec. 3, 2015 for U.S. Appl. No. 12/573,946.
Office Action dated Sep. 10, 2015 for U.S. Appl. No. 13/486,980.
Notice of Allowance dated May 23, 2016 for U.S. Appl. No. 12/573,946.
Office Action dated Sep. 19, 2016 for U.S. Appl. 14/062,054.
Office Action dated Sep. 27, 2016 for U.S. Appl. No. 14/158,687.
Office Action dated Nov. 4, 2016 for U.S. Appl. No. 13/486,980.
Office Action dated Mar. 7, 2017 for U.S. Appl. No. 14/062,054.
Notice of Allowance dated Apr. 5, 2017 for U.S. Appl. No. 12/573,946.
European Search Report for EP12793307, dated Apr. 10, 2017.
Office Action for CN2015100881831, dated Apr. 6, 2017.
European Search Report for EP16205336, dated Feb. 10, 2017.
International Search Report for PCT/US2017/033693, dated Oct. 2, 2017.
Office Action dated May 24, 2018 for U.S. Appl. No. 15/144,768 (pp. 1-23).
Office Action for Indian Patent Applicatin No. 2960/CHENP/2011, dated May 24, 2018.
Supplemetary European Search Report for EP16737670.6, dated Jun. 12, 2018.
Examination Report for EP16737670.6, dated Jul. 20, 2018.

* cited by examiner

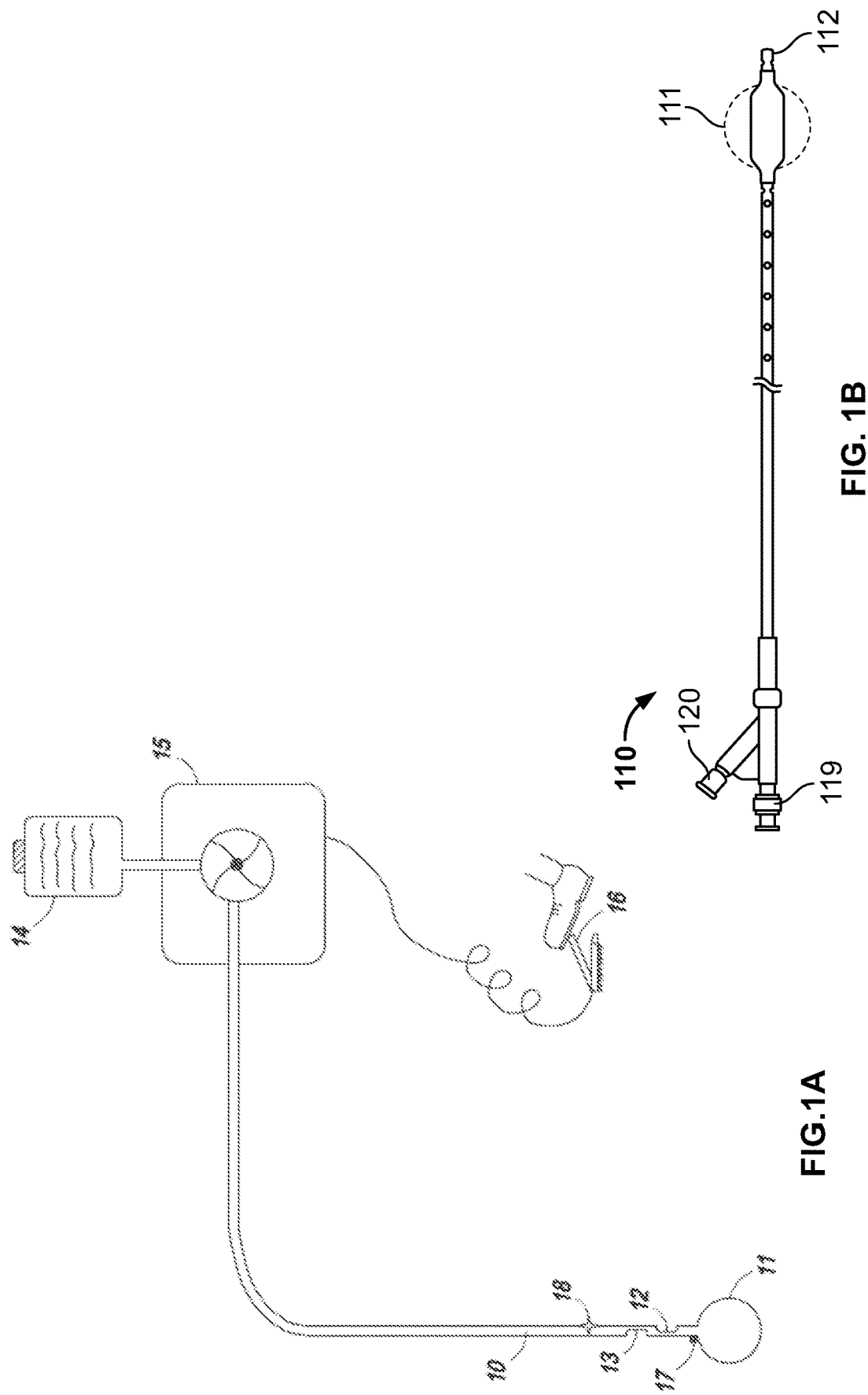

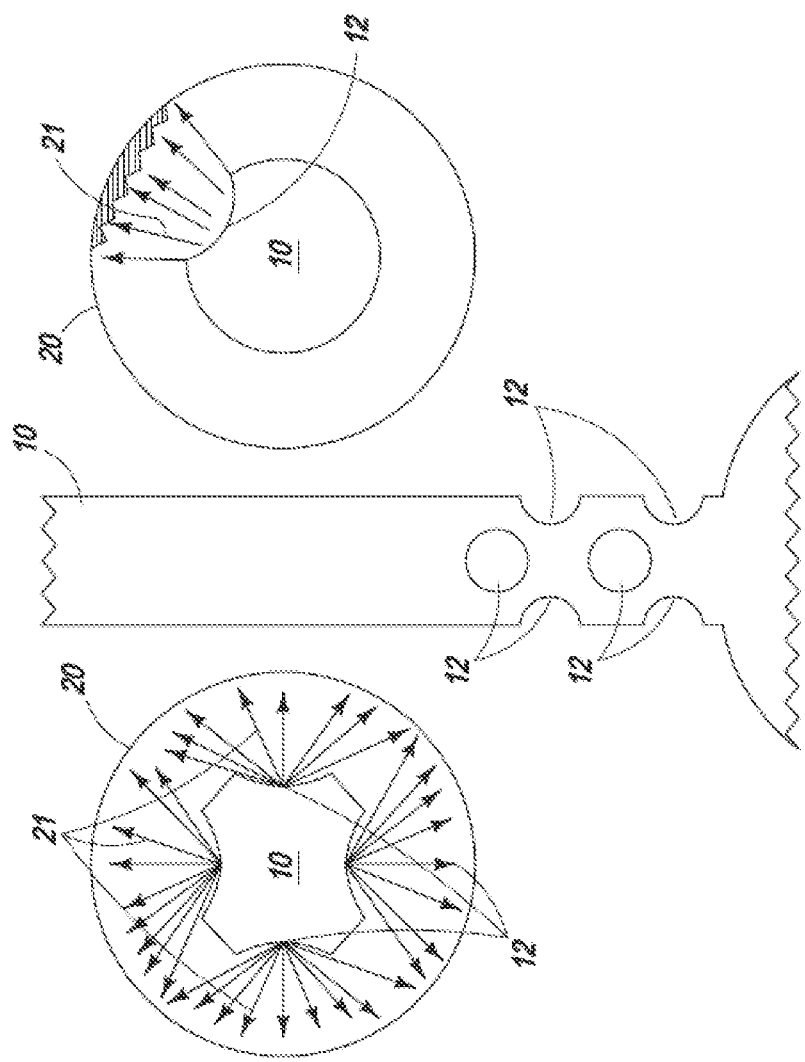

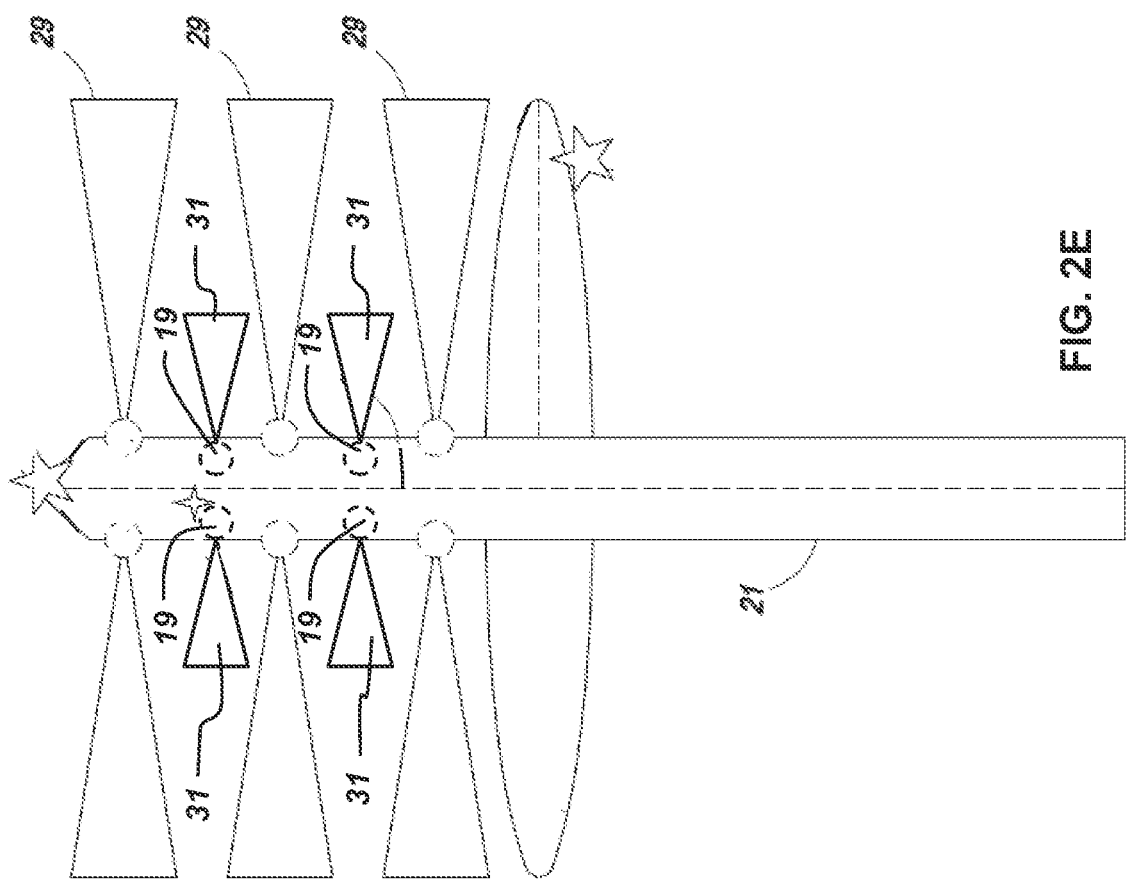

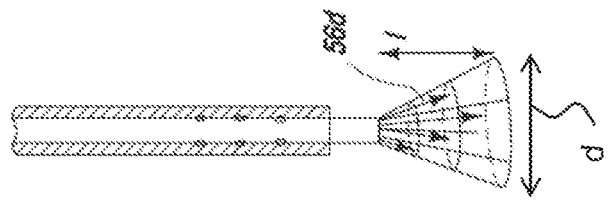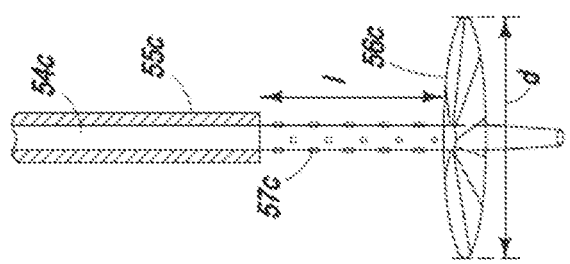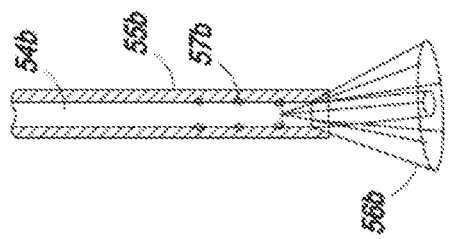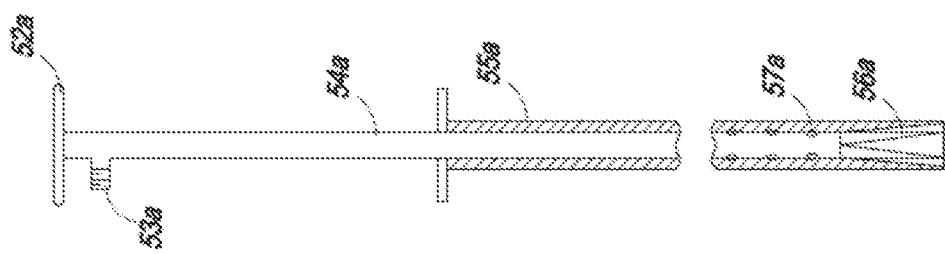

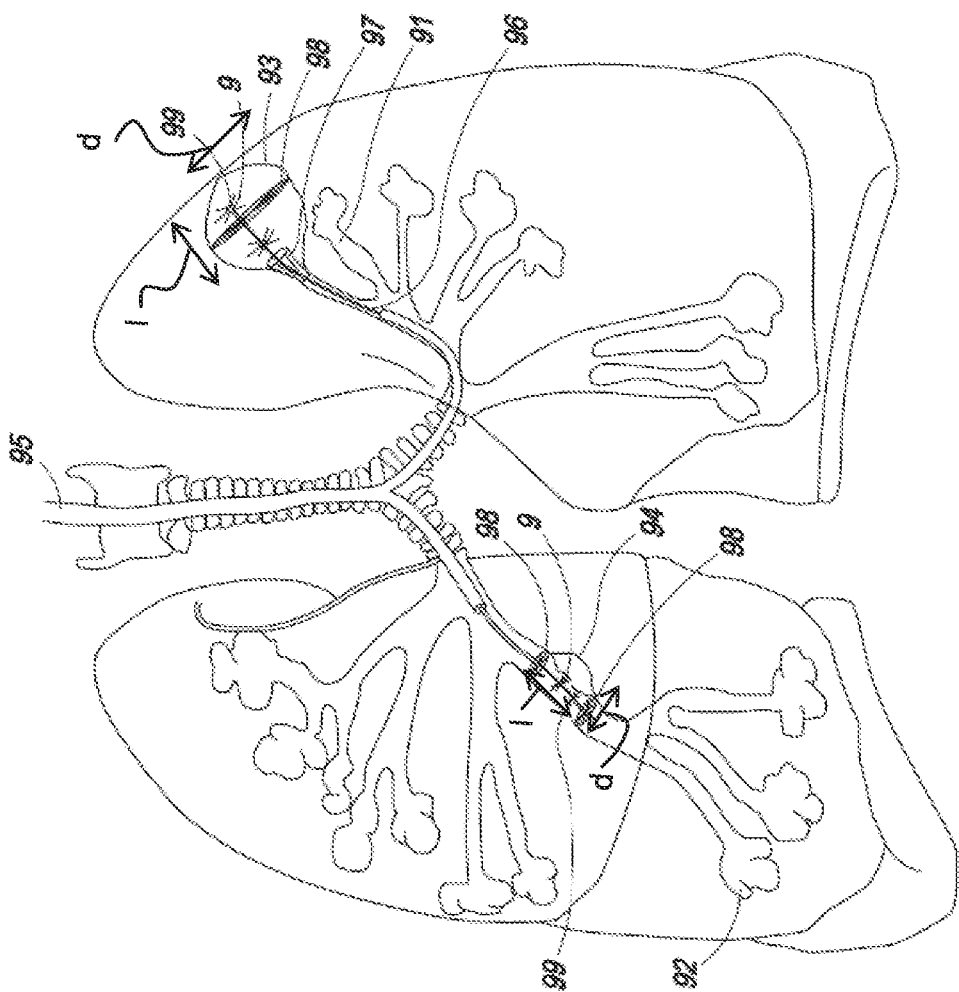

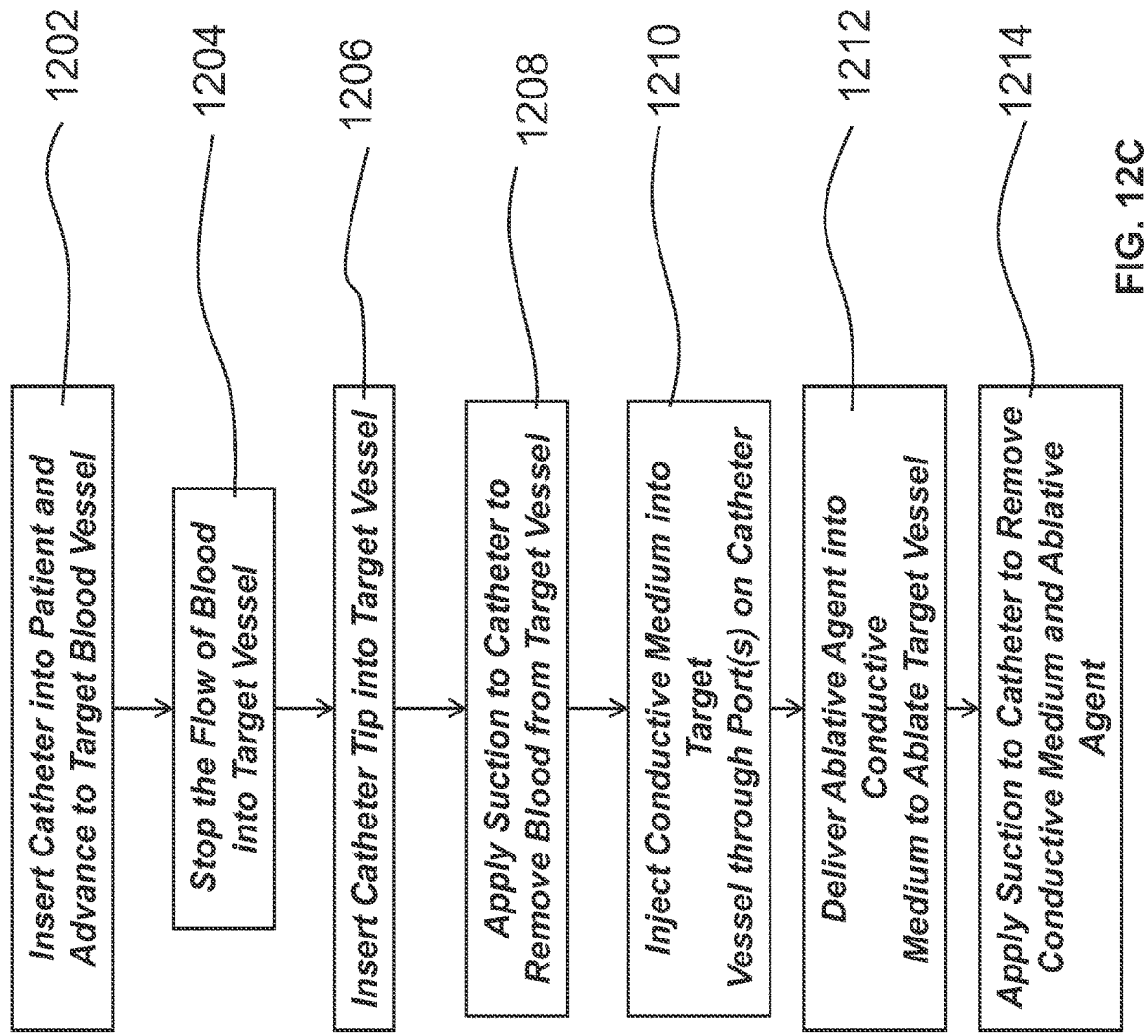

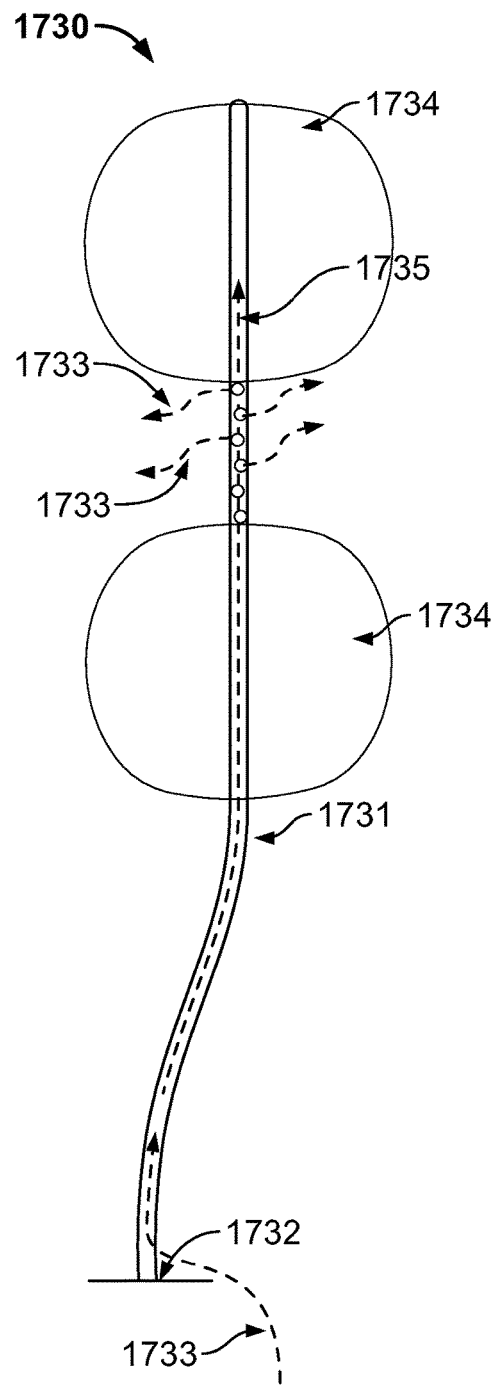
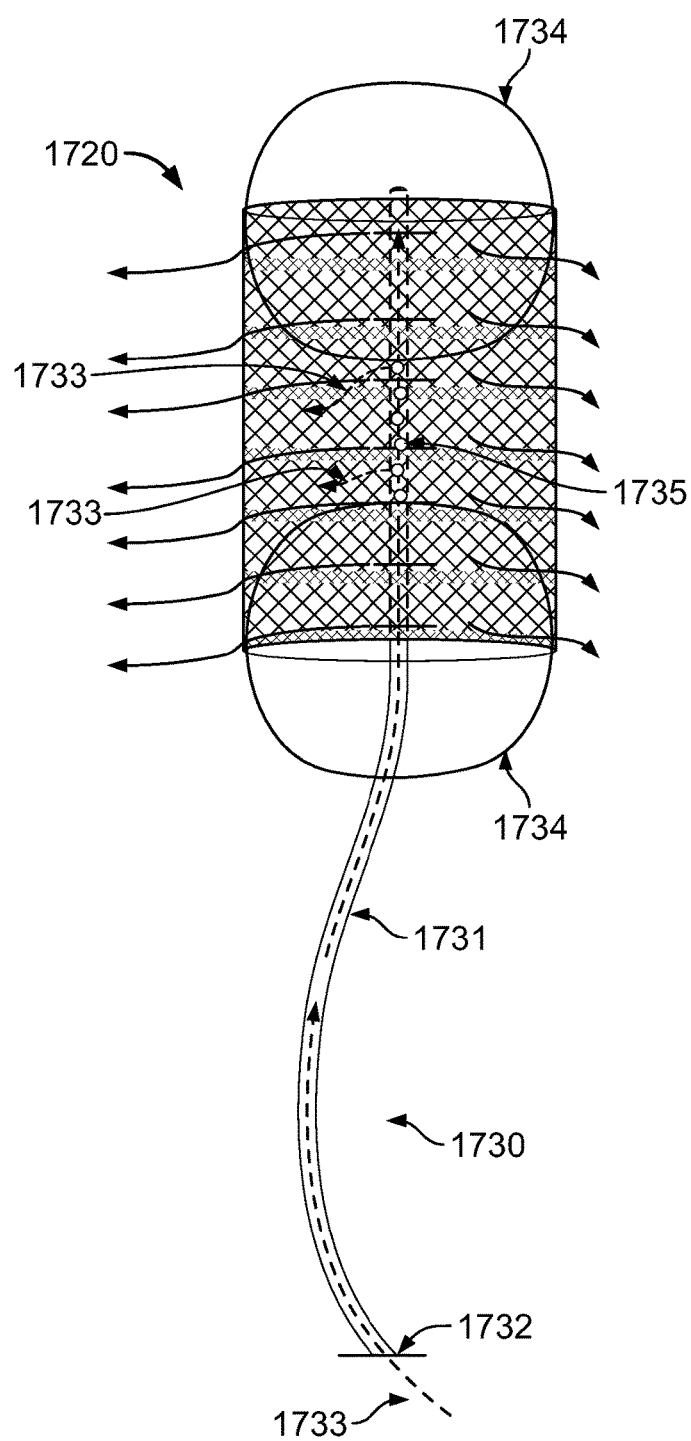
FIG. 17B
FIG. 17C

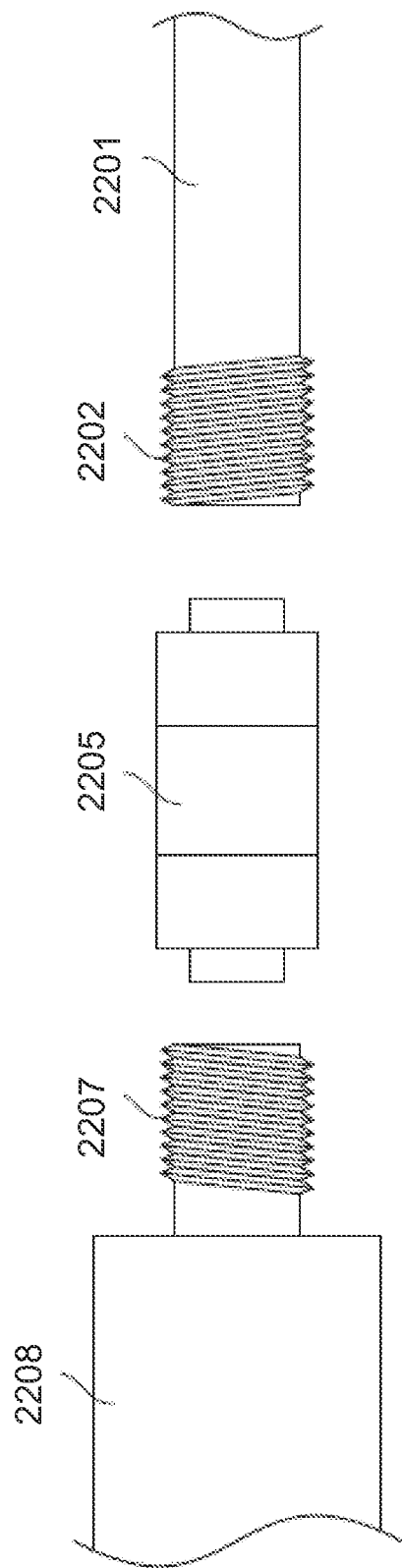
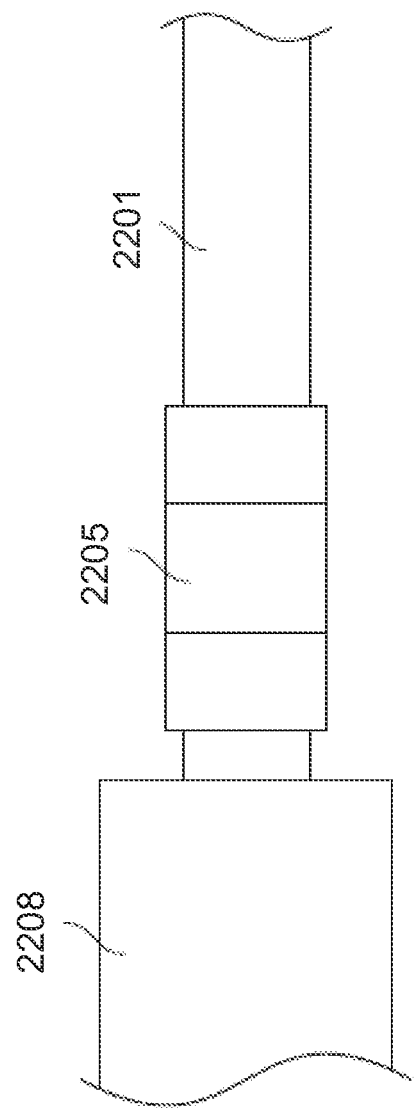
FIG. 22A
FIG. 22B

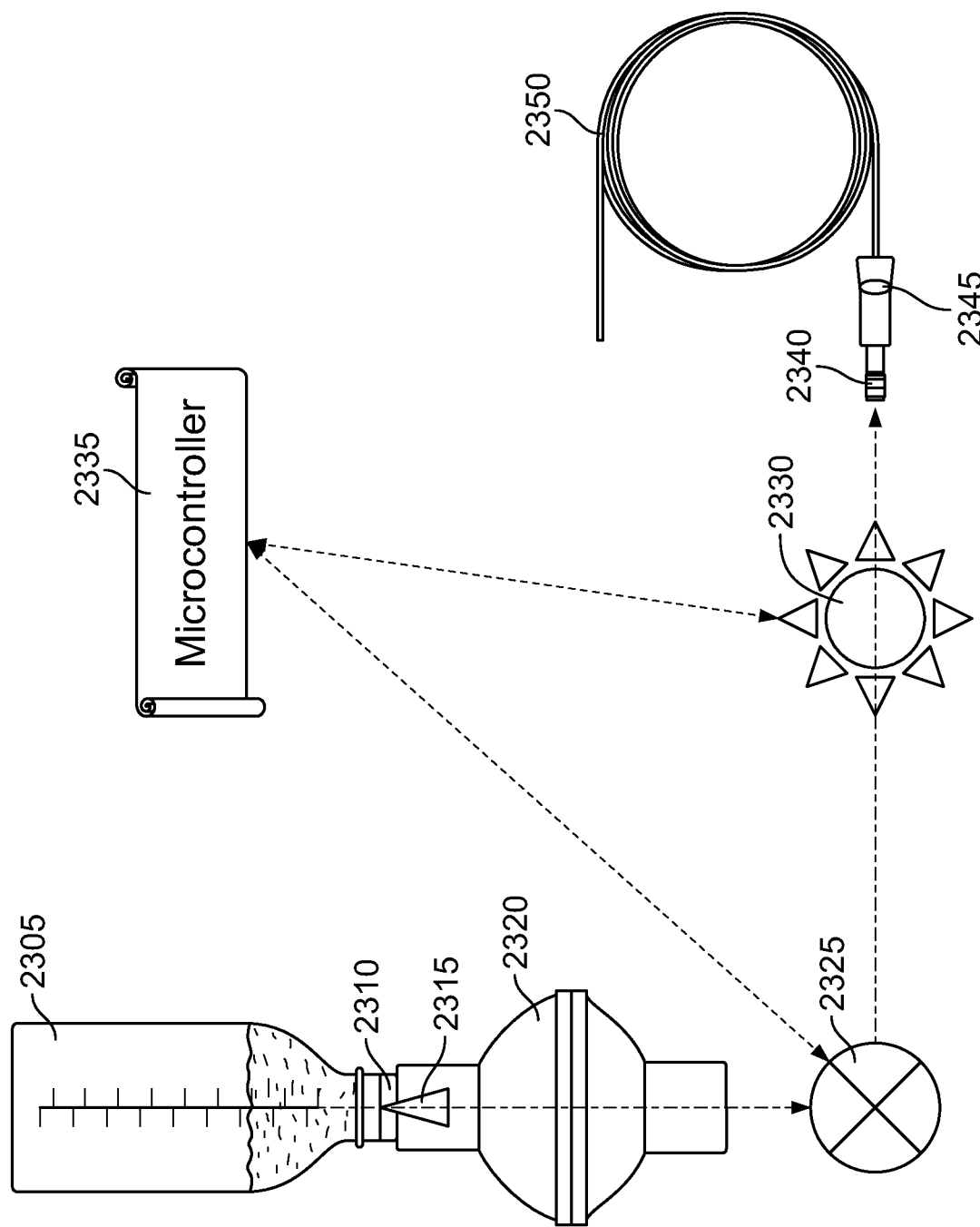

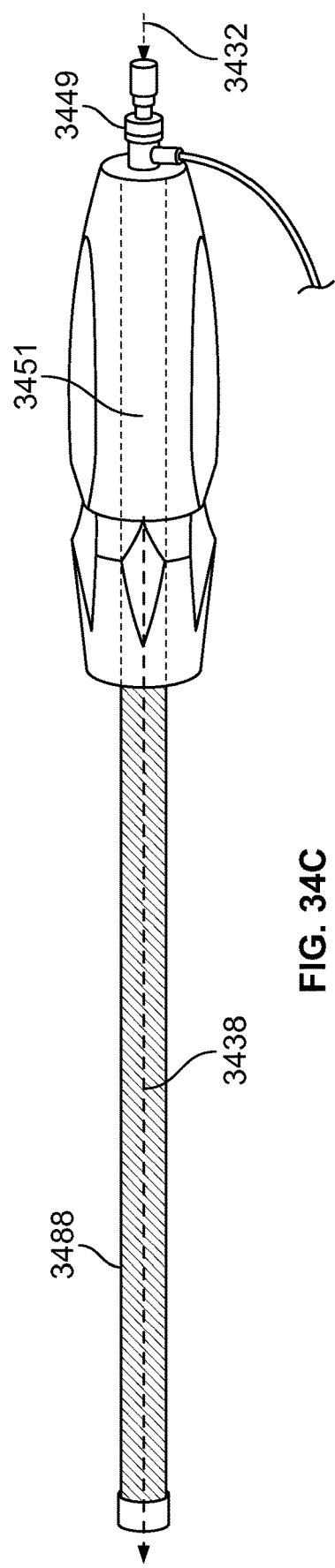
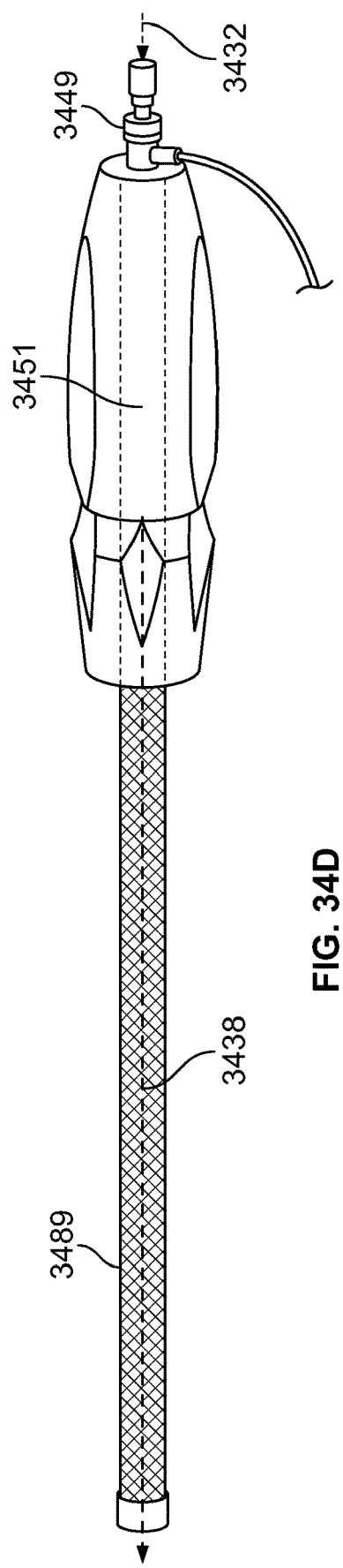

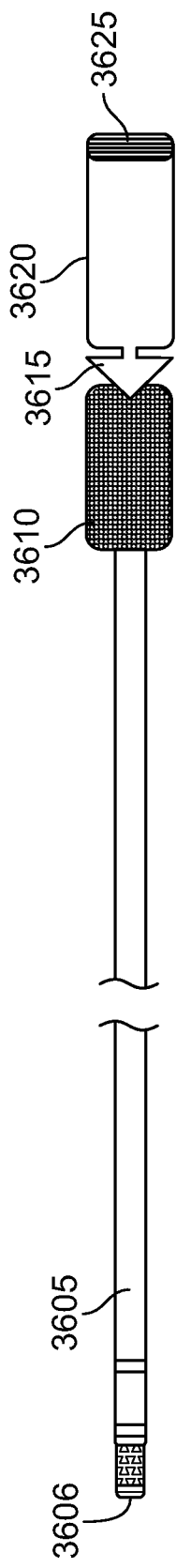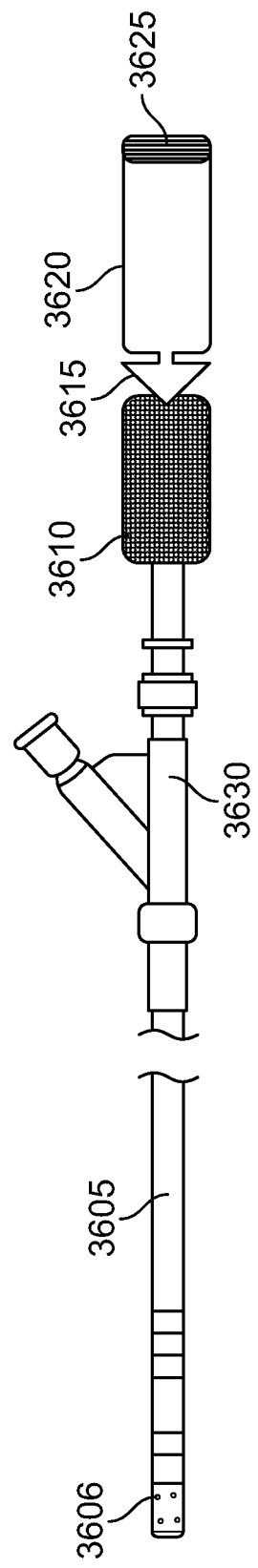
FIG. 36A
FIG. 36B

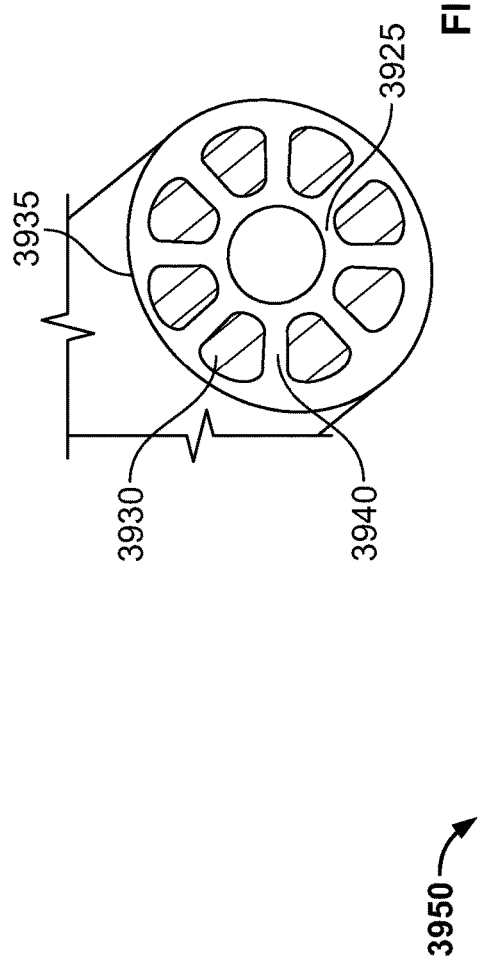
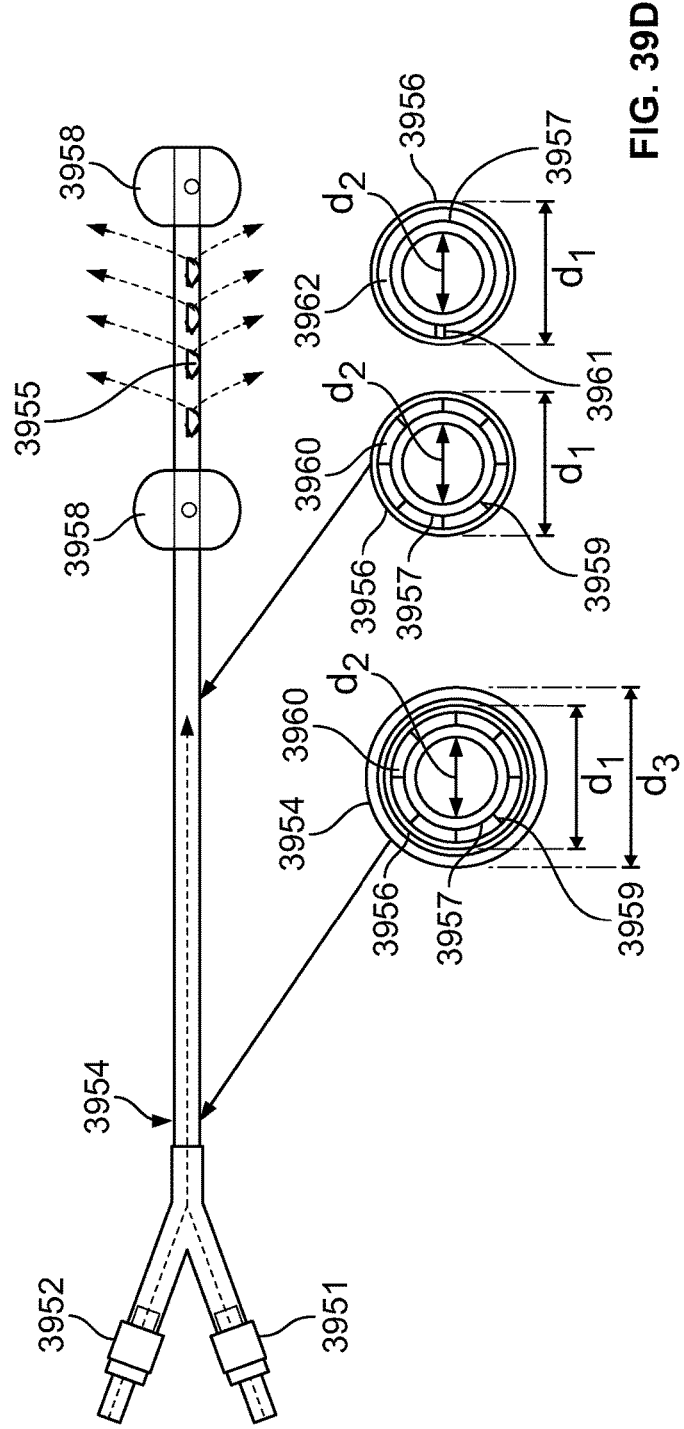

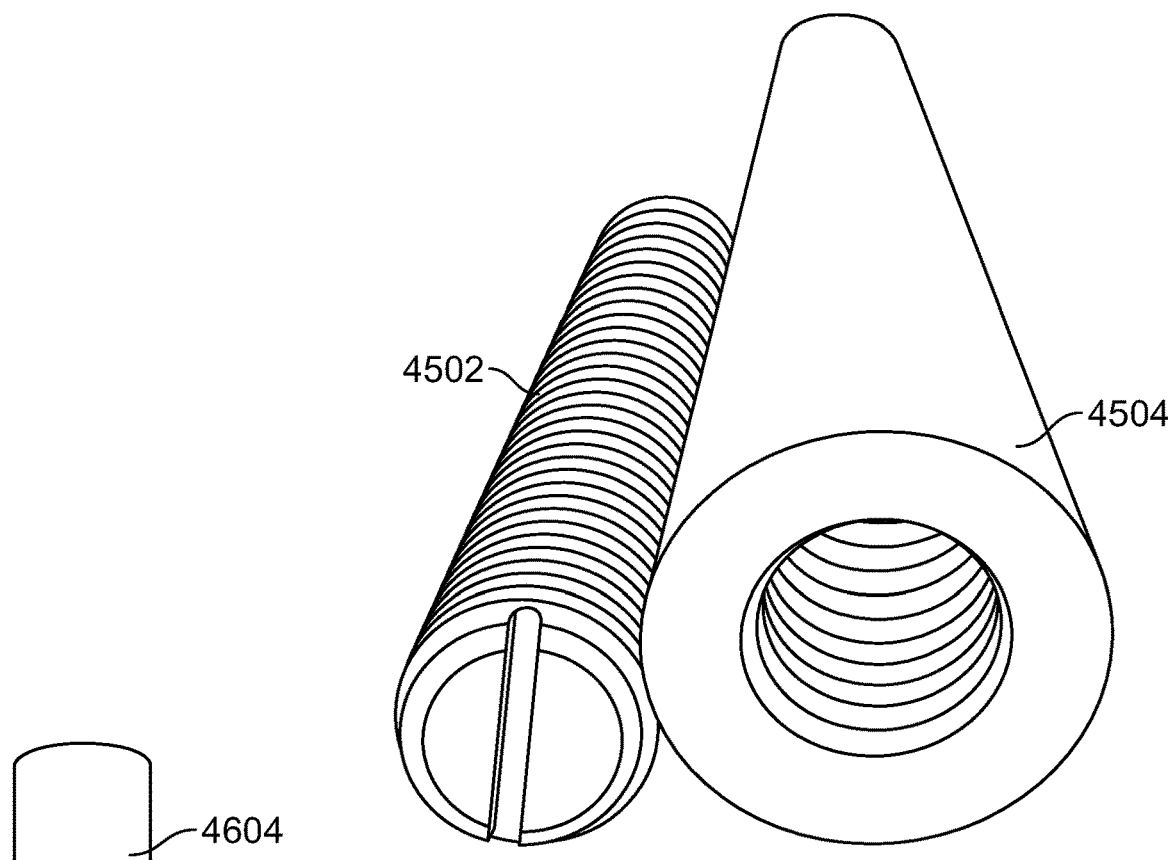
FIG. 45
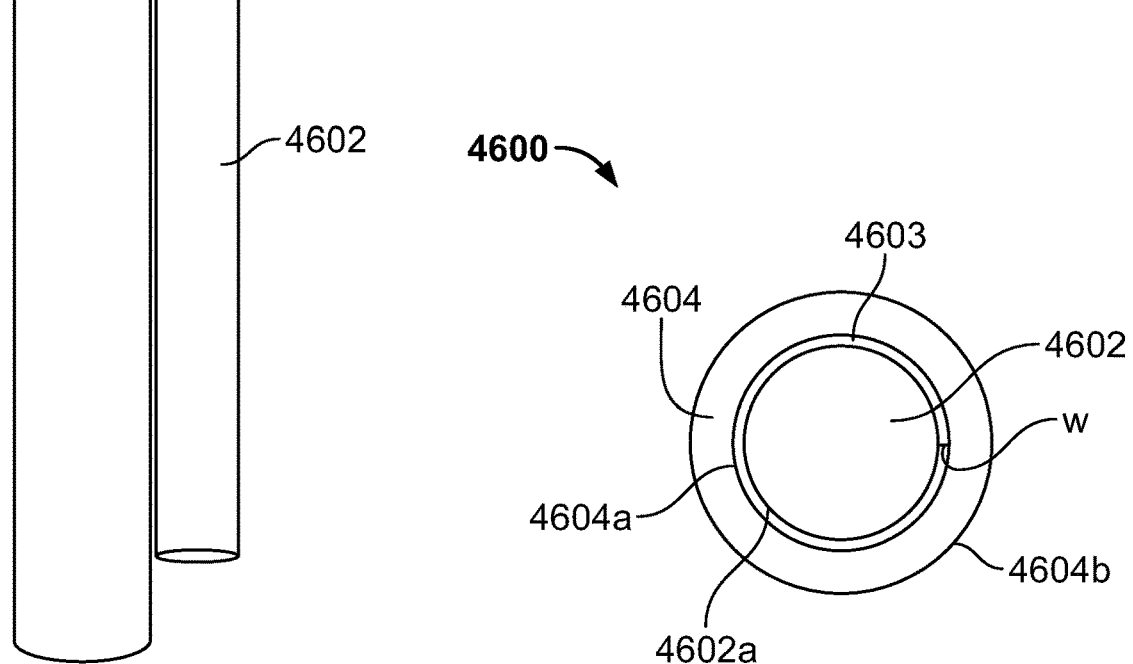
FIG. 46A  FIG. 46B

4935
Electrical Energy is Provided to Induction Coil to Pre-heat Heating Chamber Core to a Pre-determined Temperature Suitable for Treatment 4936
Thermocouple Continuously Senses Temperature of Heating Chamber Core 4937
Once Core Temperature Reaches Pre-determined Temperature Suitable for Treatment, System Permits User to Begin Steam Generation 4938
Steam Generation Commences When Water is Introduced Into Heating Chamber by a Pump 4939
Generated Steam is Delivered for Ablation Treatment 4940
Energy Delivery Ceases if Sensed Core Temperature Rises Above Pre-determined Temperature Suitable for Treatment and Resumes When it Falls Below Said Temperature

FIG. 49H

VAPOR ABLATION SYSTEM WITH A CATHETER HAVING MORE THAN ONE POSITIONING ELEMENT AND CONFIGURED TO TREAT DUODENAL TISSUE

CROSS-REFERENCE

The present application is a continuation application of U.S. patent application Ser. No. 14/594,444, entitled "Method and Apparatus for Tissue Ablation" and filed on Jan. 12, 2015, which is a continuation-in-part application of U.S. patent application Ser. No. 14/158,687 ("'687 application"), of the same title and filed on Jan. 17, 2014, which relies on U.S. Provisional Patent Application No. 61/753,831, of the same title and filed on Jan. 17, 2013, for priority.

The '687 application is also a continuation-in-part application of U.S. patent application Ser. No. 13/486,980 ("'980 application"), entitled "Method and Apparatus for Tissue Ablation" and filed on Jun. 1, 2012, which relies on U.S. Provisional Patent Application No. 61/493,344, of the same title and filed on Jun. 3, 2011, for priority.

The '980 application is also a continuation-in-part application of U.S. patent application Ser. No. 12/573,939, entitled "Method and Apparatus for Tissue Ablation" and filed on Oct. 6, 2009, which relies on U.S. Provisional Patent Application No. 61/102,885, of the same title and filed on Oct. 6, 2008, for priority.

The aforementioned applications are herein incorporated by reference in their entirety.

FIELD

The present specification relates to medical apparatuses and procedures for ablating tissue. More particularly, the present specification relates to devices and methods for the ablation of tissue in hollow and solid organs using positioning attachments and/or components capable of creating steam and conducting steam to the target tissue.

BACKGROUND

Ablation, as it pertains to the present specification, relates to the removal or destruction of a body tissue, usually by surgery or introduction of a noxious substance. Ablation is commonly used to eliminate diseased or unwanted tissues, such as, but not limited to, cysts, polyps, tumors, hemorrhoids, and other similar lesions.

Colon polyps affect almost 25% of the population over the age of 50. While most polyps are detected on colonoscopy and easily removed using a snare, flat sessile polyps are hard to remove using the snare technique and carry a high risk of complications, such as bleeding and perforation. Recently, with improvement in imaging techniques, more flat polyps are being detected. Endoscopically unresectable polyps require surgical removal. Most colon cancer arises from colon polyps and, safe and complete resection of these polyps is imperative for the prevention of colon cancer.

Barrett's esophagus is a precancerous condition effecting 10-14% of the US population with gastro esophageal reflux disease (GERD) and is the proven precursor lesion of esophageal adenocarcinoma, the fastest rising cancer in developed nations. The incidence of the cancer has risen over 6 fold in the last 2 decades and the mortality rate has risen by 7 fold. The 5-year mortality rate from esophageal cancer is 85%. Ablation of Barrett's epithelium has shown to prevent its progression to esophageal cancer.

Benign Prostatic Hyperplasia (BPH) is a non-cancerous condition of the prostate defined by an increase in the number of prostatic stromal and epithelial cells, resulting in an overall increase in the size of the prostate. The increase in size can constrict the prostatic urethra, resulting in urinary problems such as an increase in urinary frequency, urinary hesitancy, urinary retention, dysuria, and an increase in the occurrence of urinary tract infections (UTI's). Approximately 50% of men show histological evidence of BPH by age 50, which rises to 75% by age 80. About half of these men have symptoms. Although BPH does not lead to cancer, it can have a significant impact on urinary health and quality of life. Therapies aimed at alleviating the symptoms associated with BPH include those involved with reducing prostate size, such as transurethral microwave thermotherapy and transurethral needle ablation, which uses RF energy. When such less invasive therapies are ineffective, surgery, such as transurethral resection of the prostate, often becomes necessary.

Prostate cancer is diagnosed in approximately 8% of men between the ages of 50 and 70 and tends to occur in men as they grow older. Men experiencing symptoms with prostate cancer often exhibit symptoms similar to those encountered with BPH and can also suffer from sexual problems caused by the disease. Typically, men diagnosed with prostate cancer when the cancer is at an early stage have a very good prognosis. Therapy ranges from active surveillance to surgery and radiation and chemotherapy depending on the severity of the disease and the age of the patient.

Dysfunctional uterine bleeding (DUB), or menorrhagia, affects 30% of women in reproductive age. The associated symptoms have considerable impact on a woman's health and quality of life. The condition is typically treated with endometrial ablation or a hysterectomy. The rates of surgical intervention in these women are high. Almost 30% of women in the US will undergo hysterectomy by the age of 60, with menorrhagia or DUB being the cause for surgery in 50-70% of these women. Endometrial ablation techniques have been FDA approved for women with abnormal uterine bleeding and with intramural fibroids less than 2 cm in size. The presence of submucosal uterine fibroids and a large uterus size have been shown to decrease the efficacy of standard endometrial ablation. Of the five FDA approved global ablation devices, only microwave ablation has been approved for use where the submucosal fibroids are less than 3 cm in size and are not occluding the endometrial cavity and, additionally, for large uteri up to 14 cm in width.

The known ablation treatments for Barrett's esophagus include laser treatment, ultrasonic ablation, photodynamic therapy (PDT) using photo-sensitizer drugs, multipolar electrocoagulation, such as by use of a bicap probe, argon plasma coagulation (APC), radiofrequency ablation, and cryoablation. The treatments are delivered with the aid of an endoscope wherein devices are passed through the channel of the endoscope or alongside the endoscope.

Conventional techniques have inherent limitations, however, and have not found widespread clinical applications. First, most of the hand held ablation devices (bicap probe, APC, cryoablation) are point and shoot devices that create small foci of ablation. This ablation mechanism is operator dependent, cumbersome, and time consuming. Second, because the target tissue is moving due to patient movement, respiration movement, normal peristalsis, and vascular pulsations, the depth of ablation of the target tissue is inconsistent and results in a non-uniform ablation. Superficial ablation results in incomplete ablation with residual neoplastic tissue left behind. Deeper ablation results in complications such as bleeding, stricture formation, and perforation. All of these limitations and complications have been reported with conventional devices.

For example, radiofrequency ablation uses a rigid bipolar balloon based electrode and radiofrequency thermal energy. The thermal energy is delivered by direct contact of the electrode with the diseased Barrett's epithelium allowing for a relatively uniform, large area ablation. However, the rigid electrode does not accommodate for variations in esophageal size and is ineffective in ablating esophageal tissue in a tortuous esophagus, proximal esophageal lesions as an esophagus narrows toward the top, and esophageal tissue at the gastroesophageal junction due to changes in the esophageal diameter. Nodular disease in Barrett's esophagus also cannot be treated using the rigid bipolar RF electrode. Due to its size and rigidity, the electrode cannot be passed through the scope. In addition, sticking of sloughed tissue to the electrode impedes delivery of radiofrequency energy, resulting in incomplete ablation. The electrode size is limited to 3 cm, thus requiring repeat applications to treat larger lengths of Barrett's esophagus.

Photodynamic therapy (PDT) is a two part procedure that involves injecting a photo-sensitizer that is absorbed and retained by the neoplastic and pre-neoplastic tissue. The tissue is then exposed to a selected wavelength of light which activates the photo-sensitizer and results in tissue destruction. PDT is associated with complications such as stricture formation and photo-sensitivity which has limited its use to the most advanced stages of the disease. In addition, patchy uptake of the photosensitizer results in incomplete ablation and residual neoplastic tissue.

Cryoablation of the esophageal tissues via direct contact with liquid nitrogen has been studied in both animal models and humans and has been used to treat Barrett's esophagus and early esophageal cancer. A spray catheter that directly sprays liquid $N_2$ or $CO_2$ (cryoablation) or argon (APC) to ablate Barrett's tissue in the esophagus has been described. These techniques suffer the shortcoming of the traditional hand-held devices. Treatment using this probe is cumbersome and requires operator control under direct endoscopic visualization. Continuous movement in the esophagus due to respiration or cardiac or aortic pulsations or movement causes an uneven distribution of the ablative agent and results in non-uniform and/or incomplete ablation. Close or direct contact of the catheter to the surface epithelium may cause deeper tissue injury, resulting in perforation, bleeding, or stricture formation. Too distant a placement of the catheter due to esophageal movement will result in incomplete Barrett's epithelium ablation, requiring multiple treatment sessions or buried lesions with a continued risk of esophageal cancer. Expansion of cryogenic gas in the esophagus results in uncontrolled retching which may result in esophageal tear or perforation requiring continued suctioning of cryogen.

Colon polyps are usually resected using snare resection with or without the use of monopolar cautery. Flat polyps or residual polyps after snare resection have been treated with argon plasma coagulation or laser treatment. Both these treatments have the previously mentioned limitations. Hence, most large flat polyps undergo surgical resection due to the high risk of bleeding, perforation, and residual disease using traditional endoscopic resection or ablation techniques.

Most of the conventional balloon catheters traditionally used for tissue ablation either heat or cool the balloon itself or a heating element such as radio frequency (RF) coils mounted on the balloon. This requires direct contact of the balloon catheter with the ablated surface. When the balloon catheter is deflated, the epithelium sticks to the catheter and sloughs off, thereby causing bleeding. Blood can interfere with the delivery of energy, i.e. energy sink. In addition, reapplication of energy will result in deeper burn in the area where superficial lining has sloughed. Further, balloon catheters cannot be employed for treatment in non-cylindrical organs, such as the uterus or sinuses, and also do not provide non-circumferential or focal ablation in a hollow organ. Additionally, if used with cryogens as ablative agents, which expand exponentially upon being heated, balloon catheters may result in a closed cavity and trap the escape of cryogen, resulting in complications such as perforations and tears.

Metal stents have been used for palliation of malignant obstruction. However, tumor ingrowth continues to be a significant problem affecting stent longevity. Covered stents provide a good solution for in-growth, however, tumor compression can lead to stent blockage and dysfunction. Traditional coverings on the stents, such as silicone, have poor thermal conductivity and do not allow for successful thermal therapy after the stent has been deployed.

Accordingly, there is a need in the art for improved devices and methods for delivering ablative agents to a tissue surface, for providing a consistent, controlled, and uniform ablation of the target tissue, and for minimizing the adverse side effects of introducing ablative agents into a patient. What is also needed is a stent that provides the ability to deliver ablative therapy to an inoperable tumor post deployment.

SUMMARY

The present specification is directed toward a device to perform ablation of endometrial tissue, comprising a catheter having a shaft through which an ablative agent can travel, a first positioning element attached to said catheter shaft at a first position, wherein said first positioning element is configured to center said catheter in a center of a cervix, and an optional second positioning element attached to said catheter shaft at a second position, wherein the shaft comprises a plurality of ports through which said ablative agent can be released out of said shaft and wherein said ports are located between said first position and second position.

Optionally, the first positioning element is conical. The first positioning element comprises an insulated membrane which can be configured to prevent an escape of thermal energy through the cervix. The second positioning element is disc shaped. The second positioning element has a dimension which can be used to determine a uterine cavity size. The second positioning element has a dimension which can be used to calculate an amount of thermal energy needed to ablate the endometrial tissue. The device also includes at least one temperature sensor, which can be used to control delivery of the ablative agent, such as steam.

Optionally, the second positioning element is separated from endometrial tissue to be ablated by a distance of greater than 0.1 mm. The first positioning element is a covered wire mesh. The first positioning element is comprises a circular body with a diameter between 0.1 mm and 10 cm. The second positioning element is oval and wherein said oval has a long axis between 0.1 mm and 10 cm and a short axis between 0.1 mm and 5 cm.

In another embodiment, the present specification is directed toward a device to perform ablation of endometrial tissue, comprising a catheter having a hollow shaft through which steam can be delivered, a first positioning element attached to said catheter shaft at a first position, wherein said first positioning element is conical and configured to center said catheter in a center of a cervix, an optional second positioning element attached to said catheter shaft at a second position, wherein the second positioning element is disc shaped, a plurality of ports integrally formed in said catheter shaft, wherein steam can be released out of said ports and directed toward endometrial tissue and wherein said ports are located between said first position and second position; and at least one temperature sensor.

Optionally, the second positioning element has a dimension, which can be used to determine a uterine cavity size. The second positioning element has a dimension, which can be used to calculate an amount of thermal energy needed to ablate the endometrial tissue. The temperature sensors are used to control delivery of said ablative agent. The first positioning element comprises wire mesh. The second positioning element has a disc shape that is oval and wherein said oval has a long axis between 0.1 mm and 10 cm and a short axis between 0.1 mm and 5 cm.

In another embodiment, the catheter has a first shaft with a first lumen and a first positioning element which is used to position the catheter in a patient's cervix. Distal to the first positioning element, the catheter shaft bifurcates into a separate second shaft and a separate third shaft. The second shaft includes a second lumen and a second positioning element and the third shaft includes a third lumen and a third positioning element. The second and third positioning elements are configured to position the second and third shafts respectively, in an intramural portion or an isthmus of a patient's fallopian tube, partially or completely blocking the opening of each fallopian tube. Each of the two bifurcated catheter shafts can be controlled individually in a coaxial fashion. Each of the bifurcated shafts has one or more openings for the ablative agent to pass from the lumen of the respective shaft to the surrounding tissue. Each of the positioning elements is used to occlude the respective openings. In one embodiment, the bifurcated catheter shaft length is used to measure the distance from the cervix to the opening of fallopian tube which in turn is used to calculate the amount of ablative agent needed to ablate the desired tissue.

The prior art describes the need to provide an expansion mechanism to open a collapsed hollow organ to provide uniform ablation. This is routinely performed using balloons, shaped meshes or other structures. It is desirable to provide a method for ablation not requiring an expansion mechanism. The present specification is also directed toward a method of providing vapor to a hollow organ where the vapor heats the air in the hollow organ, thus expanding the organ for uniform delivery of ablative energy. The vapor is released at a predetermined temperature and pressure to cause adequate expansion of the desired tissue without over expanding the hollow organ and causing a tear or perforation.

The prior art also describes the need for an occlusive mechanism to prevent the flow of ablative energy out of the target tissue region. It is desirable to provide a method for ablation which does not require the use of an occlusive agent to prevent the flow of energy beyond the targeted tissue to prevent damage to healthy tissue. The present specification is also directed toward a method of providing vapor to a hollow organ wherein the vapor does not escape substantially beyond the target tissue to be ablated. The vapor is released at a predetermined temperature and pressure to cause localization of vapor in the desired tissue and condensation of the vapor in the desired tissue without escape of the vapor substantially beyond the targeted tissue, thus preventing significant damage to normal tissue.

The present specification is also directed toward a vapor ablation device for ablation of endometrial tissue comprising a catheter designed to be inserted through a cervical os and into an endometrial cavity, wherein the catheter is connected to a vapor generator for generation of vapor and includes at least one port positioned in the endometrial cavity to deliver the vapor into the endometrial cavity. The vapor is delivered through the port and heats and expands the air in the endometrial cavity to maintain the endometrial cavity pressure below 200 mm Hg and ideally below 50 mm of Hg. In one embodiment, an optional pressure sensor measures the pressure and maintains the intracavitary pressure at the desired therapeutic level, wherein the endometrial cavity is optimally expanded to allow for uniform distribution of ablative energy without the risk of significant leakage of the ablative energy beyond the endometrial cavity and damage to the adjacent normal tissue.

The present specification is also directed toward a device to perform ablation of tissue in a hollow organ, comprising a catheter having a shaft through which an ablative agent can travel; a first positioning element attached to said catheter shaft at a first position, wherein said first positioning element is configured to position said catheter at a predefined distance from the tissue to be ablated; and wherein the shaft comprises one or more port through which said ablative agent can be released out of said shaft.

Optionally, the device further comprises a second positioning element attached to said catheter shaft at a position different from said first positioning element. The first positioning element is at least one of a conical shape, disc shape, or a free form shape conformed to the shape of the hollow organ. The second positioning element has predefined dimensions and wherein said predefined dimensions are used to determine the dimensions of the hollow organ to be ablated. The first positioning element comprises an insulated membrane. The insulated membrane is configured to prevent an escape of thermal energy. The second positioning element is at least one of a conical shape, disc shape, or a free form shape conformed to the shape of the hollow organ. The second positioning element has predefined dimensions and wherein said predefined dimensions are used to determine the dimensions of the hollow organ to be ablated. The second positioning element has a predefined dimension and wherein said predefined dimension is used to calculate an amount of thermal energy needed to ablate the tissue. The device further comprises at least one temperature sensor. The temperature sensor is used to control delivery of said ablative agent. The ablative agent is steam. The first positioning element is a covered wire mesh. The first positioning element comprises a circular body with a diameter between 0.01 mm and 10 cm. The first positioning element is oval and wherein said oval has a long axis between 0.01 mm and 10 cm and a short axis between 0.01 mm and 9 cm.

In another embodiment, the present specification is directed to a device to perform ablation of tissue in a hollow organ, comprising a catheter having a hollow shaft through which steam can be delivered; a first positioning element attached to said catheter shaft at a first position, wherein said first positioning element is configured to position said catheter at a predefined distance from the surface of the hollow organ; a second positioning element attached to said catheter shaft at a second position, wherein the second positioning element is shaped to position said catheter at a predefined distance from the surface of the hollow organ; a plurality of ports integrally formed in said catheter shaft, wherein steam can be released out of said ports and directed toward tissue to be ablated and wherein said ports are located between said first position and second position; and at least one temperature sensor.

Optionally, the first positioning element has a predefined dimension and wherein said dimension is used to determine the size of the hollow organ. The second positioning element has a predefined dimension and wherein said dimension is used to calculate an amount of thermal energy needed to ablate the tissue. The temperature sensor is used to control delivery of said ablative agent. The first positioning element comprises wire mesh. The second positioning element has a disc shape that is oval and wherein said oval has a long axis between 0.01 mm and 10 cm and a short axis between 0.01 mm and 9 cm.

In another embodiment, the present specification is directed to a device to perform ablation of the gastrointestinal tissue, comprising a catheter having a shaft through which an ablative agent can travel; a first positioning element attached to said catheter shaft at a first position, wherein said first positioning element is configured to position the catheter at a fixed distance from the gastrointestinal tissue to be ablated, and wherein said first positioning element is separated from an ablation region by a distance of between 0 mm and 5 cm, and an input port at a second position and in fluid communication with said catheter shaft in order to receive said ablative agent wherein the shaft comprises one or more ports through which said ablative agent can be released out of said shaft.

Optionally, the first positioning element is at least one of an inflatable balloon, wire mesh disc or cone. By introducing said ablative agent into said ablation region, the device creates a gastrointestinal pressure equal to or less than 5 atm. The ablative agent has a temperature between −100 degrees Celsius and 200 degrees Celsius. The catheter further comprises a temperature sensor. The catheter further comprises a pressure sensor. The first positioning element is configured to abut a gastroesophageal junction when placed in a gastric cardia. The ports are located between said first position and second position. The diameter of the positioning element is between 0.01 mm and 100 mm. The ablative agent is steam. The first positioning element comprises a circular body with a diameter between 0.01 mm and 10 cm.

In another embodiment, the present specification is directed toward a device to perform ablation of esophageal tissue, comprising a catheter having a hollow shaft through which steam can be transported; a first positioning element attached to said catheter shaft at a first position, wherein said first positioning element is configured to abut a gastroesophageal junction when placed in a gastric cardia; and an input port at a second position and in fluid communication with said catheter shaft in order to receive said steam wherein the shaft comprises a plurality of ports through which said steam can be released out of said shaft and wherein said ports are located between said first position and second position. The device further comprises a temperature sensor wherein said temperature sensor is used to control the release of said steam. The first positioning element comprises at least one of a wire mesh disc, a wire mesh cone, or an inflatable balloon. The first positioning element is separated from an ablation region by a distance of between 0 mm and 1 cm. The diameter of the first positioning element is between 1 mm and 100 mm.

In another embodiment, the present specification is directed to a device to perform ablation of gastrointestinal tissue, comprising a catheter having a hollow shaft through which steam can be transported; a first positioning element attached to said catheter shaft at a first position, wherein said first positioning element is configured to abut the gastrointestinal tissue; and an input port at a second position and in fluid communication with said catheter shaft in order to receive said steam wherein the shaft comprises one or more ports through which said steam can be released out of said shaft onto the gastrointestinal tissue.

Optionally, the device further comprises a temperature sensor wherein said temperature sensor is used to control the release of said steam. The first positioning element comprises at least one of a wire mesh disc and a wire mesh cone. The diameter of the first positioning element is 0.1 mm to 50 mm. The device is used to perform non-circumferential ablation.

In another embodiment, the present specification is directed to a device to perform ablation of endometrial tissue, comprising a catheter having a shaft through which an ablative agent can travel; a first positioning element attached to said catheter shaft at a first position, wherein said first positioning element is configured to center said catheter in a center of a cervix; and a shaft comprises a plurality of ports through which said ablative agent can be released out of said shaft.

Optionally, the device further comprises a second positioning element attached to said catheter shaft at a second position. The first positioning element is conical. The first positioning element comprises an insulated membrane. The insulated membrane is configured to prevent an escape of thermal energy through the cervix. The second positioning element is disc shaped. The second positioning element has a predefined dimension and wherein said dimension is used to determine a uterine cavity size. The second positioning element has a predefined dimension and wherein said dimension is used to calculate an amount of thermal energy needed to ablate the endometrial tissue. The device further comprises at least one temperature sensor wherein said temperature sensor is used to control delivery of said ablative agent. The ablative agent is steam. The first positioning element is a covered wire mesh. The first positioning element comprises a circular body with a diameter between 0.01 mm and 10 cm. The second positioning element is oval and wherein said oval has a long axis between 0.01 mm and 10 cm and a short axis between 0.01 mm and 5 cm. When deployed, the positioning elements also serve to open up the uterine cavity.

In another embodiment, the present specification is directed toward a device to perform ablation of endometrial tissue, comprising a catheter having a hollow shaft through which steam can be delivered; a first positioning element attached to said catheter shaft at a first position, wherein said first positioning element is conical and configured to center said catheter in a center of a cervix; a second positioning element attached to said catheter shaft at a second position, wherein the second positioning element is elliptical shaped; a plurality of ports integrally formed in said catheter shaft, wherein steam can be released out of said ports and directed toward endometrial tissue and wherein said ports are located between said first position and second position; and at least one temperature sensor.

Optionally, the second positioning element has a predefined dimension and wherein said dimension is used to determine a uterine cavity size. The second positioning element has a diameter and wherein said diameter is used to calculate an amount of thermal energy needed to ablate the endometrial tissue. The temperature sensors are used to control delivery of said ablative agent. The first positioning element comprises wire mesh. The second positioning element has a disc shape that is oval and wherein said oval has a long axis between 0.01 mm and 10 cm and a short axis between 0.01 mm and 5 cm.

Optionally, the second positioning element can use one or more sources of infrared, electromagnetic, acoustic or radiofrequency energy to measure the dimensions of the hollow cavity. The energy is emitted from the sensor and is reflected back to the detector in the sensor. The reflected data is used to determine the dimension of the hollow cavity.

In one embodiment, the present specification discloses a device to be used in conjunction with a tissue ablation system, comprising: a handle with a pressure-resistant port on its distal end, a flow channel through which an ablative agent can travel, and one or more connection ports on its proximal end for the inlet of said ablative agent and for an RF feed; an insulated catheter that attaches to said pressure-resistant port of said snare handle, containing a shaft through which an ablative agent can travel and one or more ports along its length for the release of said ablative agent; and one or more positioning elements attached to said catheter shaft at one or more separate positions, wherein said positioning element(s) is configured to position said catheter at a pre-defined distance from the tissue to be ablated.

Optionally, the handle has one pressure-resistant port for the attachment of both an ablative agent inlet and an RF feed. The handle has one separate pressure-resistant port for the attachment of an ablative agent inlet and one separate port for the attachment of an RF feed or an electrical feed.

In another embodiment, the present specification discloses a device to be used in conjunction with a tissue ablation system, comprising: a handle with a pressure-resistant port on its distal end, a flow channel passing through said handle which is continuous with a pre-attached cord through which an ablative agent can travel, and a connection port on its proximal end for an RF feed or an electrical field; an insulated catheter that attaches to said pressure-resistant port of said handle, containing a shaft through which an ablative agent can travel and one or more ports along its length for the release of said ablative agent; and one or more positioning elements attached to said catheter shaft at one or more separate positions, wherein said positioning element(s) is configured to position said catheter at a predefined distance from the tissue to be ablated. Optionally, the distal end of said catheter is designed to puncture the target.

In another embodiment, the present specification discloses a device to be used in conjunction with a tissue ablation system, comprising: an esophageal probe with a pressure-resistant port on its distal end, a flow channel through which an ablative agent can travel, and one or more connection ports on its proximal end for the inlet of said ablative agent and for an RF feed or an electrical feed; an insulated catheter that attaches to said pressure-resistant port of said esophageal probe, containing a shaft through which an ablative agent can travel and one or more ports along its length for the release of said ablative agent; and one or more inflatable positioning balloons at either end of said catheter positioned beyond said one or more ports, wherein said positioning balloons are configured to position said catheter at a predefined distance from the tissue to be ablated.

Optionally, the catheter is dual lumen, wherein a first lumen facilitates the transfer of ablative agent and a second lumen contains an electrode for RF ablation. The catheter has differential insulation along its length.

The present specification is also directed toward a tissue ablation device, comprising: a liquid reservoir, wherein said reservoir includes an outlet connector that can resist at least 1 atm of pressure for the attachment of a reusable cord; a heating component comprising: a length of coiled tubing contained within a heating element, wherein activation of said heating element causes said coiled tubing to increase from a first temperature to a second temperature and wherein said increase causes a conversion of liquid within said coiled tubing to vapor; and an inlet connected to said coiled tubing; an outlet connected to said coiled tubing; and at least one pressure-resistant connection attached to the inlet and/or outlet; a cord connecting the outlet of said reservoir to the inlet of the heating component; a single use cord connecting a pressure-resistant inlet port of a vapor based ablation device to the outlet of said heating component.

In one embodiment, the liquid reservoir is integrated within an operating room equipment generator. In one embodiment, the liquid is water and the vapor is steam.

In one embodiment, the pressure-resistant connections are luer lock connections. In one embodiment, the coiled tubing is copper.

In one embodiment, the tissue ablation device further comprises a foot pedal, wherein only when said foot pedal is pressed, vapor is generated and passed into said single use cord. In another embodiment, only when pressure is removed from said foot pedal, vapor is generated and passed into said single use cord.

In another embodiment, the present specification discloses a vapor ablation system used for supplying vapor to an ablation device, comprising; a single use sterile fluid container with attached compressible tubing used to connect the fluid source to a heating unit in the handle of a vapor ablation catheter. The tubing passes through a pump that delivers the fluid into the heating unit at a predetermined speed. There is present a mechanism such as a unidirectional valve between the fluid container and the heating unit to prevent the backflow of vapor from the heating unit. The heating unit is connected to the ablation catheter to deliver the vapor from the heating unit to the ablation site. The flow of vapor is controlled by a microprocessor. The microprocessor uses a pre-programmed algorithm in an open-loop system or uses information from one or more sensors incorporated in the ablation system in a closed-loop system or both to control delivery of vapor.

In one embodiment, the handle of the ablation device is made of a thermally insulating material to prevent thermal injury to the operator. The heating unit is enclosed in the handle. The handle locks into the channel of an endoscope after the catheter is passed through the channel of the endoscope. The operator can than manipulate the catheter by holding the insulated handle or by manipulating the catheter proximal to the insulating handle.

The present specification is also directed toward a vapor ablation system comprising: a container with a sterile liquid therein; a pump in fluid communication with said container; a first filter disposed between and in fluid communication with said container and said pump; a heating component in fluid communication with said pump; a valve disposed between and in fluid communication with said pump and heating container; a catheter in fluid communication with said heating component, said catheter comprising at least one opening at its operational end; and, a microprocessor in operable communication with said pump and said heating component, wherein said microprocessor controls the pump to control a flow rate of the liquid from said container, through said first filter, through said pump, and into said heating component, wherein said liquid is converted into vapor via the transfer of heat from said heating component to said fluid, wherein said conversion of said fluid into said vapor results is a volume expansion and a rise in pressure where said rise in pressure forces said vapor into said catheter and out said at least one opening, and wherein a temperature of said heating component is controlled by said microprocessor.

In one embodiment, the vapor ablation system further comprises at least one sensor on said catheter, wherein information obtained by said sensor is transmitted to said microprocessor, and wherein said information is used by said microprocessor to regulate said pump and said heating component and thereby regulate vapor flow. In one embodiment, the at least one sensor includes one or more of a temperature sensor, flow sensor, or pressure sensor.

In one embodiment, the vapor ablation system further comprises a screw cap on said liquid container and a puncture needle on said first filter, wherein said screw cap is punctured by said puncture needle to provide fluid communication between said container and said first filter.

In one embodiment, the liquid container and catheter are disposable and configured for a single use.

In one embodiment, the fluid container, first filter, pump, heating component, and catheter are connected by sterile tubing and the connections between said pump and said heating component and said heating component and said catheter are pressure resistant.

The present specification is also directed toward a tissue ablation system comprising: a catheter with a proximal end and a distal end and a lumen therebetween, said catheter comprising: a handle proximate the proximal end of said catheter and housing a fluid heating chamber and a heating element enveloping said chamber, a wire extending distally from said heating element and leading to a controller; an insulating sheath extending and covering the length of said catheter and disposed between said handle and said heating element at said distal end of said catheter; and, at least one opening proximate the distal end of said catheter for the passage of vapor; and, a controller operably connected to said heating element via said wire, wherein said controller is capable of modulating energy supplied to said heating element and further wherein said controller is capable of adjusting a flow rate of liquid supplied to said catheter; wherein liquid is supplied to said heating chamber and then converted to vapor within said heating chamber by a transfer of heat from said heating element to said chamber, wherein said conversion of said liquid to vapor results in a volume expansion and a rise in pressure within said catheter, and wherein said rise in pressure pushes said vapor through said catheter and out said at least one opening.

In one embodiment, the tissue ablation system further comprises a pressure resistant fitting attached to the fluid supply and a one-way valve in said pressure resistant fitting to prevent a backflow of vapor into the fluid supply.

In one embodiment, the tissue ablation system further comprises at least one sensor on said catheter, wherein information obtained by said sensor is transmitted to said microprocessor, and wherein said information is used by said microprocessor to regulate said pump and said heating component and thereby regulate vapor flow.

In one embodiment, the tissue ablation system further comprises a metal frame within said catheter, wherein said metal frame is in thermal contact with said heating chamber and conducts heat to said catheter lumen, thereby preventing condensation of said vapor. In various embodiments, the metal frame comprises a metal skeleton with outwardly extending fins at regularly spaced intervals, a metal spiral, or a metal mesh and the metal frame comprises at least one of copper, stainless steel, or another ferric material.

In one embodiment, the heating element comprises a heating block, wherein said heating block is supplied power by said controller.

In various embodiments, the heating element uses one of magnetic induction, microwave, high intensity focused ultrasound, or infrared energy to heat said heating chamber and the fluid therein.

The present specification also discloses an ablation catheter for use with a hollow tissue or organ, comprising: a distal end having at least one opening for the injection of a conductive medium into said hollow tissue or organ and at least one opening for the delivery of an ablative agent into said hollow tissue or organ; a proximal end configured to receive said conductive medium and said ablative agent from a source; and, a shaft, having at least one lumen therewithin, between said distal end and said proximal end.

In one embodiment, the ablation catheter for use with a hollow tissue or organ further comprises at least one positioning element for positioning said catheter proximate target tissue to be ablated. In one embodiment, the ablation catheter further comprises at least one occlusive element to occlude blood flow in said hollow tissue or organ.

The present specification also discloses a method of treating a disorder of a prostate, the method comprising: introducing an ablation catheter into the prostate; and, delivering an ablative agent into the prostate and ablating prostate tissue without ablating the prostatic urethra. In one embodiment, the ablative agent is vapor. In one embodiment, the catheter is introduced transurethraly. In another embodiment, the catheter is introduced transrectally.

The present specification also discloses an ablation catheter for use in treating a disorder of the prostate, said catheter comprising: one or more needles for piercing the prostatic tissue and delivering an ablative agent into the prostate; and, one or more positioning elements to position said needles at a predefined distance in the prostate. In one embodiment, the ablation catheter further comprises a mechanism to cool a prostatic urethra or a rectal wall.

The present specification also discloses a method for treating benign prostatic hyperplasia of a prostate of a patient comprising the steps of: inserting a plurality of vapor delivery needles through a urethral wall of the patient in a plurality of locations into a prostate lobe; and, delivering water vapor through the needles into the prostate at each location to ablate the prostatic tissue.

The present specification also discloses a method of providing ablation to a patient's endometrium comprising the steps of: inserting an ablation catheter, said catheter comprising a lumen and vapor delivery ports, through a cervix and a cervical canal into the endometrial cavity; and, delivering an ablative agent through said ablation catheter lumen and said delivery ports and into the endometrial cavity to create endometrial ablation. In one embodiment, the method of providing ablation to a patient's endometrium further comprises the step of measuring at least one dimension of the endometrial cavity and using said dimension to determine the delivery of ablative agent. In one embodiment, the method of providing ablation to a patient's endometrium further comprises the step of using a positioning element to position said catheter in the center of the endometrial cavity. In one embodiment, the positioning element includes an expansion mechanism in contact with endometrial tissue to move said endometrial tissue surfaces away from the vapor delivery ports of the catheter. In one embodiment, the method of providing ablation to a patient's endometrium further comprises the step of using an occlusive element to occlude the cervical os to prevent leakage of the ablative agent through the os. In one embodiment, the ablative agent heats and expands the air in the endometrial cavity, expanding the endometrial cavity to allow for more uniform delivery of ablative agent. As the endometrial cavity is expanded, the pressure therein is maintained at a level such that the ablative agent does not escape the endometrial cavity.

The present specification also discloses a method of providing ablative therapy to a patient's endometrium comprising the steps of: inserting a coaxial vapor ablation catheter, comprising an inner catheter and an outer catheter, through the cervical os and into the cervical canal to occlude the cervical canal; advancing the inner catheter of the coaxial vapor ablation catheter into the endometrial cavity; and, delivering vapor through vapor delivery ports on the inner catheter into the endometrial cavity to ablate the endometrial tissue. The inner catheter is advanced to the fundus of the uterus, thus measuring the uterine cavity length. The length of inner catheter needed, in-turn determines the number of vapor delivery ports that are exposed to deliver the ablative agent, thus controlling the amount of ablative agent to be delivered.

The present specification also discloses a method for hemorrhoid ablation comprising the steps of: inserting an ablation device, said device comprising a port for engaging a hemorrhoid, at least one port for delivery of an ablative agent, and a mechanism to create suction, into a patient's anal canal; engaging the targeted hemorrhoid by suctioning the hemorrhoid into the ablation device; and, delivering the ablative agent to the hemorrhoid to ablate the hemorrhoid. In one embodiment, the method further comprises the step of compressing the engaged hemorrhoid prior to delivering the ablative agent.

The present specification also discloses a method of ablating a tissue or organ, comprising the steps of: inserting a catheter into said target tissue or organ; using the catheter to remove contents of said target tissue or organ via suction; using the catheter to replace said removed contents with a conductive medium; introducing an ablative agent to said conductive medium, and changing the temperature of said conductive medium to ablate said tissue or organ.

The present specification also discloses a method of ablating a hollow tissue or organ, comprising the steps of: inserting a catheter into a hollow tissue or organ of a patient, said catheter having a stent coupled to its distal end; advancing said catheter and stent to target tissue; deploying said stent, wherein said deployment involves releasing said stent from said distal end of said catheter, further wherein said deployment causes said stent to expand such that it comes into physical contact with, and is held in place by, the internal surface of said hollow tissue or organ; and, delivering ablative agent through said catheter and into the lumen of said stent, wherein ablative energy from said ablative agent is transferred from said lumen through said stent and into the surrounding tissue to ablate said tissue. In one embodiment, the stent is optionally covered by a thermally permeable membrane which allows for the ablative energy to pass from inside of the stent to the surrounding tissue while preventing leakage of a significant amount of fluid from inside the stent into the surrounding tissue. In one embodiment, the membrane also prevents ingrowth of tumor tissue into the stent.

The present specification also discloses a stent for use with an ablation catheter, said stent comprising: a compressible, cylindrical hollow body with a lumen therewithin, said body being comprised of a thermally conductive material, wherein said body is transformable between a first, compressed configuration for delivery and a second, expanded configuration for deployment; one or more openings for the passage of thermal energy from said lumen of said stent to the exterior of said stent; one or more flaps covering said openings to prevent the ingrowth of tissue surrounding said stent into the lumen of said stent; and, at least one coupling means to couple said stent to said ablation catheter for delivery and/or retrieval. In one embodiment, the deployment of the stent and delivery of ablative energy can be performed in separate steps and at separate times. For example, the ablation can be performed at a future time after the placement of the stent to shrink the growth of an expanding tumor. Multiple serial ablations can be performed through the same stent over time.

The present specification also discloses an ablation catheter assembly comprising: a catheter having an elongate body with a lumen within, a proximal end, and a distal end; a first inline chamber having an elongate body with a lumen within, a proximal end, and a distal end, wherein said distal end of said first inline chamber is connected to said proximal end of said catheter and said lumen of said first inline chamber is in fluid communication with said lumen of said catheter, further wherein said first inline chamber is composed of a ferromagnetic or thermally conducting material; a second inline chamber having an elongate body with a lumen within, a proximal end, and a distal end, wherein said distal end of said second inline chamber is connected to said proximal end of said first inline chamber and said lumen of said second inline chamber is in fluid communication with said lumen of said first inline chamber, further wherein said second inline chamber is configured to contain a fluid; an optional one way valve positioned at the connection between said first inline chamber and said second inline chamber, said valve allowing flow of fluid from said second inline chamber into said first inline chamber but not in the reverse direction; and, a piston within and proximate said proximal end of said second inline chamber; wherein said proximal end of said second inline chamber is connected to an external pump and said pump engages said piston to push a fluid from said second inline chamber into said first inline chamber where an external heating element heats said first inline chamber and the transfer of said heat to said fluid causes vaporization of said fluid, further wherein said vaporized fluid passes through said elongate body and out said distal end of said catheter.

Optionally, in one embodiment, the ablation catheter assembly further comprises a thermally insulated handle on said catheter body. In one embodiment, the pump is a syringe pump. In one embodiment, the pump is controlled by a microprocessor to deliver ablative vapor at a predetermined rate. Optionally, a peristaltic pump or any other pump known in the field can be used to push fluid from the second inline chamber to the first inline chamber at a rate that is controllable by a microprocessor. In one embodiment, the ablation catheter assembly further comprises at least one sensor on said catheter, wherein information from said sensor is relayed to said microprocessor and the delivery rate of ablative vapor is based upon said information.

In one embodiment, a membrane is positioned between the first inline chamber and the second inline chamber which functions to prevent flow of the fluid from the second inline chamber into the first inline chamber until therapy is ready to be delivered. As pressure is applied to the fluid in the second inline chamber by action of the piston, said pressure is transmitted to the membrane, resulting in rupture of the membrane. The fluid is then allowed to flow from the second inline chamber into the first inline chamber.

In another embodiment, a valve is positioned between the first inline chamber and the second inline chamber which functions to prevent flow of the fluid from the second inline chamber into the first inline chamber until therapy is ready to be delivered. As pressure is applied to the fluid in the second inline chamber by action of the piston, said pressure is transmitted to the valve, resulting in opening of the valve. The fluid is then allowed to flow from the second inline chamber into the first inline chamber.

In another embodiment, a heat sensitive plug is positioned between the first inline chamber and the second inline chamber which functions to prevent flow of the fluid from the second inline chamber into the first inline chamber until therapy is ready to be delivered. As the temperature in the first inline chamber rises above a predetermined level, the plug melts and the fluid is allowed to flow from the second inline chamber into the first inline chamber.

In another embodiment, a shape-memory metal member is positioned between the first inline chamber and the second inline chamber which functions to prevent flow of the fluid from the second inline chamber into the first inline chamber until therapy is ready to be delivered. As the temperature in the first inline chamber rises above a predetermined level, the shape-memory metal member changes in shape to provide a pathway such that fluid is allowed to flow from the second inline chamber into the first inline chamber.

In one embodiment, the heating element is any one of a resistive heater, an RF heater, a microwave heater and an electromagnetic heater. In one embodiment, the fluid is water. In one embodiment, the first inline chamber comprises a plurality of channels within to increase the contact surface area of said fluid with said first inline chamber. In various embodiments, the channels comprise any one of metal tubes, metal beads, and metal filings.

In one embodiment, the elongate body of said catheter includes an outer surface and an inner surface and said inner surface includes a groove pattern to decrease the resistance to flow of said fluid within said catheter.

Optionally, in one embodiment, the catheter comprises a first inner wall and a second outer wall and an insulating layer between said first wall and said second wall. In one embodiment, said first inner wall and said second outer wall are connected by a plurality of spokes. In one embodiment, the insulating layer is filled with air. In another embodiment, the insulating layer is filled with a fluid. In another embodiment, the insulating layer is made of any thermally insulating material.

The present specification also discloses a system for heating a fluid, said system comprising: a chamber for containing said fluid, said chamber defining an enclosed three dimensional space and having a proximal end and a distal end, wherein said proximal end includes an inlet port for delivery of said fluid and said distal end includes an outlet port, further wherein said chamber is composed of an electrically non-conducting and thermally insulating material and an induction heating element made of a ferromagnetic material positioned within said chamber; and, an induction coil positioned around said chamber, said induction heating element capable of absorbing the energy of a magnetic field induced by an alternating current; wherein, when the alternating current is supplied to said induction coil, a magnetic field is created in the area surrounding said chamber and said magnetic field induces electric current flow within the ferromagnetic material of said chamber, further wherein said magnetic field induces magnetization of said ferromagnetic material which undergoes a magnetic hysteresis, resulting in hysteresis loss and subsequent further heating of said ferromagnetic material, further wherein said electric current flow results in the resistive heating of said chamber and said heat is transferred to said fluid, converting said fluid into vapor which exits said chamber through said outlet port.

In various embodiments, the ferromagnetic material comprises any one of, or alloys of, iron, nickel, stainless steel, manganese, silicon, carbon and copper. In various embodiments, the ferromagnetic material is a curie material with a curie temperature between 60° C. and 250° C.

In one embodiment, the induction coil comprises a metal wire coil looped about said chamber. In one embodiment, the coil is looped about a length of said chamber such that said coil is in physical contact with said chamber. In other embodiments, the coil is looped about a length of said chamber spaced away from said chamber with a layer of air or insulating material between said coil and said chamber.

The present specification also discloses a method for heating a fluid, said method comprising the steps of: providing a chamber for containing said fluid, said chamber defining an enclosed three dimensional space and having a proximal end and a distal end, wherein said proximal end includes an inlet port for delivery of said fluid and said distal end includes an outlet port, further wherein said chamber is composed of an electrically non-conducting and thermally insulating material and an induction heating element made of a ferromagnetic material positioned within said chamber; surrounding said chamber with an induction coil; filling said container with said fluid; providing an alternating current to said induction coil such that a magnetic field is created in the area surrounding said chamber and said magnetic field induces electric current flow within the ferromagnetic material of said chamber, further wherein said magnetic field induces magnetization of said ferromagnetic material which undergoes a magnetic hysteresis, resulting in hysteresis loss and subsequent further heating of said ferromagnetic material, further wherein said electric current flow results in the resistive heating of said chamber and said heat is transferred to said fluid, converting said fluid into vapor which exits said chamber through said outlet port. Optionally, the chamber is insulated to prevent heat losses from the chamber or thermal injury to an operator from the heated chamber.

The present specification also discloses a system for heating a fluid, said system comprising: a chamber for containing said fluid, said chamber defining an enclosed three dimensional space and having a proximal end and a distal end, wherein said proximal end includes an inlet port for delivery of said fluid and said distal end includes an outlet port, further wherein said chamber is composed of an electrically non-conducting and thermally insulating material and an induction heating element made of a Curie point material positioned within said chamber; and, an induction coil positioned around said chamber, said induction coil capable of receiving high frequency energy; wherein, when high frequency energy is supplied to said induction coil, a magnetic field is created in the area surrounding said chamber and said magnetic field induces electric current flow within the Curie material of said chamber, further wherein said magnetic field induces magnetization of said ferromagnetic material which undergoes a magnetic hysteresis, resulting in hysteresis loss and subsequent further heating of said ferromagnetic material, further wherein said electric current flow results in the resistive heating of said chamber and said heat is transferred to said fluid, converting said fluid into vapor which exits said chamber through said outlet port, further wherein when said Curie point material is heated to its Curie temperature, it temporarily loses its ferromagnetic properties, ceases to absorb energy through magnetic hysteresis loss and the temperature drops below its Curie temperature, has its ferromagnetic properties restored and once again undergoes hysteresis and generates heat, and continues in a cyclical process as long as said high frequency energy is supplied to said induction coil. Optionally, the chamber is insulated to prevent heat losses from the chamber or thermal injury to an operator from the heated chamber.

The present specification also discloses a vapor ablation system comprising: a chamber for containing a fluid, said chamber defining an enclosed three dimensional space and having a proximal end and a distal end, wherein said proximal end includes an inlet port for delivery of said fluid and said distal end includes an outlet port, further wherein said chamber is composed of an electrically non-conducting and thermally insulating material and an induction heating element made of a Curie point material positioned within said chamber; a catheter connected to said outlet port of said chamber; a fluid supply source connected to said inlet port of said chamber; and, an induction coil positioned around said chamber, said induction coil capable of receiving high frequency energy; wherein, when high frequency energy is supplied to said induction coil, a magnetic field is created in the area surrounding said chamber and further wherein said magnetic field induces magnetization of said ferromagnetic material which undergoes a magnetic hysteresis, resulting in hysteresis loss and subsequent further heating of said ferromagnetic material and said magnetic field induces electric current flow within the Curie material of said chamber, further wherein said electric current flow results in the resistive heating of said chamber and said heat is transferred to said fluid, converting said fluid into vapor which exits said chamber through said outlet port and enters said catheter for vapor delivery, further wherein when said Curie point material is heated to its Curie temperature, it temporarily loses its ferromagnetic properties and energy absorption through magnetic hysteresis loss ceases, the temperature drops below its Curie temperature and its ferromagnetic properties are restored and it once again undergoes hysteresis and generates heat, and continues in a cyclical process as long as said high frequency energy is supplied to said induction coil.

The Curie point material may have a Curie temperature ranging from 60 to 500 degrees Celsius. Optionally, the Curie point material is a nickel/iron alloy comprising at least 25% nickel.

The Curie point material may further comprise any one or combination of copper, chromium, manganese, and silicon.

Optionally, the fluid is water and said vapor is steam.

The vapor ablation system may further comprise a fluid pump. Optionally, the fluid pump is a syringe pump.

The vapor ablation system may further comprise a microcontroller to control the delivery of said vapor. Optionally, the vapor ablation system further comprises a touchscreen user interface enabling control of system parameters including power, vapor flow rate, and pressure. Optionally, the vapor ablation system further comprises a multi-function foot pedal. Optionally, the vapor ablation system further comprises at least one sensor wherein information from said sensor is relayed to said microcontroller and a delivery rate of said vapor is based upon said information. The sensor may include any one or combination of a temperature sensor, pressure sensor, or impedance tuner. Optionally, the vapor ablation system further comprises at least one alarm wherein said alarm is issued when information from said at least one sensor falls outside of a predetermined threshold value.

The chamber may be tightly packed with ball bearings balls composed of said Curie point material and said fluid physically contacts said ball bearings balls during heat transfer.

The chamber may be single use and disposable.

Optionally, the chamber has a clam shell shape and said fluid does not physically contact said Curie point material.

Optionally, the chamber is reusable.

The chamber and catheter may be thermally insulated.

The present specification also discloses a method for heating a fluid, said method comprising the steps of: providing a chamber for containing said fluid, said chamber defining an enclosed three dimensional space and having a proximal end and a distal end, wherein said proximal end includes an inlet port for delivery of said fluid and said distal end includes an outlet port, further wherein said chamber is composed of an electrically non-conducting and thermally insulating material and an induction heating element made of a Curie point material positioned within said chamber; surrounding said chamber with an induction coil; providing high frequency energy to said induction coil such that a magnetic field is created in the area surrounding said chamber and said magnetic field induces magnetization of said ferromagnetic material which undergoes magnetic hysteresis resulting in hysteresis loss and subsequent heating of said ferromagnetic material and additionally induces electric current flow within the Curie point material of said chamber, inducing eddy currents and resulting in the generation of additional heat within said chamber; filling said container with said fluid, wherein said heat is transferred to said fluid, converting said fluid into vapor which exits said chamber through said outlet port; continuing to supply said high frequency energy such that said Curie point material is heated to its Curie temperature, temporarily loses its ferromagnetic properties, whereupon the energy absorption through hysteresis loss ceases, the temperature drops below its Curie temperature whereupon the Curie point material's ferromagnetic properties are restored and it once again undergoes hysteresis and generates heat, and continues in a cyclical process as long as said high frequency energy is supplied to said induction coil.

The present specification also discloses a vapor generation system comprising: a vaporizer for vaporizing a liquid to form a vapor, the vaporizer including: a means for generating a changing magnetic field; a non-ferromagnetic chamber having an inlet and an outlet and capable of withstanding a pressure of at least 5 psi, said means for generating a changing magnetic field positioned about said chamber; and a ferromagnetic member contained within said non-ferromagnetic chamber creating a passage defined by the space between an outer surface of the ferromagnetic member and an inner surface of the chamber, said ferromagnetic member comprising a thermal mass and a surface area being defined around the member and the non-ferromagnetic chamber, wherein said ferromagnetic member becomes inductively heated by the changing magnetic field to a temperature sufficient to convert liquid flowing through the passage to vapor and an inner surface of the chamber is non-inductively heated by the member to a temperature sufficient to allow said conversion of said liquid to vapor while a temperature of an outer surface of the chamber is actively maintained below 100° C., and a catheter connected to the outlet of the chamber for supplying the vapor formed within the passage to a defined region in the body.

Optionally, the outer surface of the chamber is actively cooled to maintain a temperature of the outer surface to be at least 20° C. less than a temperature of the inner surface of the chamber.

Optionally, a surface area to volume ratio of the ferromagnetic member is equal to or greater than $2(D_1+L)/D_2 \times L$ where $D_1$ is the shortest cross-sectional dimension of the member, $D_2$ is the longest cross-sectional dimension of the member and L is the length of the member.

The passage may have a width equal to or less than 25 mm.

Optionally, the non-ferromagnetic chamber is composed of thermoplastic or ceramic.

Optionally, the ceramic is a machinable glass ceramic such as MACOR®.

The means for generating a magnetic field may be an inductive coil. Optionally, the inductive coil is separated from said outer surface of said chamber by at least 0.1 mm. Optionally, a cooling agent is passed between said coil and said outer surface of said chamber to maintain a temperature of said outer surface at less than 100° C. Optionally, a temperature of the outer surface of the chamber is maintained to be at least 20° C. less than a temperature of the inner surface of the chamber.

The present specification also discloses a vapor generation catheter comprising: a liquid source; a vaporizer in fluid connection with said liquid source for vaporizing the liquid to form a vapor, the vaporizer comprising: a means for generating a changing magnetic field, a thermally insulating chamber having an inlet and an outlet and capable of withstanding a pressure greater than 5 psi, said means for generating a changing magnetic field positioned about said chamber; a ferromagnetic member contained within said chamber creating a passage defined by the space between an outer surface of the ferromagnetic member and an inner surface of the chamber, wherein said ferromagnetic member is inductively heated by the changing magnetic field and said chamber is non-inductively heated by the member, said ferromagnetic member and chamber collectively supplying sufficient heat to a liquid in said passage to convert the liquid into vapor; and a resistive valve at the outlet of the chamber that opens at a pressure of less than 5 psi; and a catheter in fluid connection with the resistive valve for supplying the vapor to the targeted tissue.

Optionally, the liquid is non-ionized water or a solution of a metal salt and water.

The present specification also discloses a method of ablating a tissue, the method comprising: passing a liquid through a passage in a thermally insulating chamber containing a ferromagnetic member within at a flow rate between 0.1 ml/min to 100 ml/min, wherein said passage is defined by the space between an outer surface of the ferromagnetic member and an inner surface of the thermally insulating chamber and a distance between the two surfaces is equal to or less than 25 mm; inductively heating the ferromagnetic member to a predefined temperature equal to or greater than 100° C.; and non-inductively heating the chamber wherein the temperature of an outer surface of the chamber is maintained at less than 100° C.; wherein the inductively heated ferromagnetic member and non-inductively heated chamber vaporize the liquid within the passage, causing an increase in a pressure inside the passage to greater than 1 psi but less than 100 psi such that created vapor flows out of the passage through a catheter to a defined area for ablation.

Optionally, the ferromagnetic member comprises a Curie point material.

Optionally, the chamber includes a pressure sensor which senses the pressure in the chamber and said method further comprises the step of shutting down said inductive heating when a predefined pressure is reached. Optionally, the pressure sensor is in line with the path of the fluid and senses the pressure in the path of the fluid and said method further comprises the step of shutting down said inductive heating when a predefined pressure is reached.

Optionally, the chamber includes a temperature sensor which senses the temperature of the outer surface of the chamber and said method further comprises the step of shutting down said inductive heating when a predefined temperature is reached.

Optionally, the chamber includes a system to actively cool down said outer surface of the chamber and said method further comprises the step of activating said system to maintain a temperature of said outer surface at less than 100° C. Optionally, a temperature of the outer surface of the chamber is maintained to be at least 20° C. less than a temperature of the inner surface of the chamber.

Optionally, the chamber includes a valve at an outlet of said passage and said valve opens at a pressure equal to or less than 5 psi.

Optionally, the chamber includes a valve at an inlet of said passage which allows backflow of a liquid at a pressure greater than 5 psi.

The present specification also discloses a steam-based ablation system comprising: a disposable fluid circuit comprising: a water reservoir containing water; a water heating chamber having a length, wherein the water heating chamber comprises a non-ferromagnetic material having a lumen extending therethrough and a ferromagnetic material positioned within said lumen and wherein the ferromagnetic material is separated from the non-ferromagnetic material, across the length of the water heating chamber, by a space; a catheter comprising a proximal end and a distal end, wherein the distal end comprises one or more ports; and a contiguous fluid channel connecting said water reservoir, said water heating chamber, and the proximal end of said catheter; an induction chamber adapted to receive said water heating chamber, wherein said induction chamber comprises a plurality of coils for receiving an electrical current and for generating a magnetic field; an induction circuit for delivering said electrical current to said induction chamber; and a pump or motor for applying a force to said water in the water reservoir in order to move the water from the water reservoir and into the water heating chamber.

Optionally, the system further comprises mechanisms to keep the water in the reservoir separate from the water heating chamber until therapy is initiated. These mechanisms may include one of a pressure sensitive membrane that bursts when a certain amount of pressure is applied, a thermally sensitive plug that dissolves when a certain temperature is exceeded, or a valve with a valve stem actuated by pressure (against a spring) or temperature (shape-memory metal or bi-metal).

The induction circuit may generate a sinusoidal wave form and comprise a switching circuit having a resonant tank circuit.

Optionally, the non-ferromagnetic material is electrically insulating. Optionally, during operation, a lumen surface of the non-ferromagnetic material is configured to be heated to a temperature greater than 100 degrees Celsius. Optionally, during operation, an external surface of the non-ferromagnetic material is configured to be heated to a temperature no greater than 100 degrees Celsius. Optionally, during operation, an external surface of the non-ferromagnetic material is configured to be heated to a temperature at least 20° C. below a temperature of an inner surface of the non-ferromagnetic material. Optionally, during operation, an external surface of the non-ferromagnetic material is configured to be cooled to a temperature at least 20° C. below a temperature of an inner surface of the non-ferromagnetic material. Optionally, during operation, the system is programmed to shut down heating when an external surface of the non-ferromagnetic material is heated to a temperature greater than 100 degrees Celsius.

The induction chamber may comprise a cylindrical volume around which said plurality of coils are positioned and a lumen positioned within said cylindrical volume adapted to receive said water heating chamber.

Optionally, said water is at least one of ionized water, non-ionized water, sterile water, or a solution of metal salt and water.

The electrical current may have a frequency of between 100 Hz and 100 kHz.

Optionally, during operation, the water heating chamber and induction chamber are magnetically coupled wherein a conversion of magnetic energy into heat within the water heating chamber has an efficiency of greater than 40%.

The non-ferromagnetic material may be a cylinder and the ferromagnetic material may be a metal rod.

The ferromagnetic material may comprise any one of, or alloys of, iron, nickel, stainless steel, manganese, silicon, carbon, copper, electrically conducting material, electrically insulating material, or a Curie material having a Curie temperature between 60° C. and 500° C.

Optionally, the disposable fluid circuit does not comprise any input ports or openings for receiving fluid from an external source into said disposable fluid circuit. Optionally, the disposable fluid circuit does not comprise any other ports or openings, other than the one or more ports in the catheter, for receiving or expelling fluid external to said disposable fluid circuit.

The fluid channel may comprise flexible tubing wherein the water reservoir is a pliable plastic bag or a syringe.

Optionally, prior to use, a portion of the fluid channel positioned between the water reservoir and the water heating chamber is blocked by a barrier, thereby blocking water from passively flowing from the water reservoir to the water heating chamber. Optionally, during use, said barrier is adapted to be breached by an increase in water pressure to permit water to flow from the water reservoir to the water heating chamber. Optionally, during use, said barrier is adapted to be breached by an increase in the temperature to permit water to flow from the water reservoir to the water heating chamber.

Optionally, the steam-based ablation system further comprises a check valve or a fracture diaphragm positioned in the contiguous fluid channel between the water reservoir and the water heating chamber to prevent water from entering said water heating chamber until force is applied to said water.

Optionally, a temperature of an external surface of said water heating chamber does not increase by more than 500 percent of its pre-operation external surface temperature during five minutes or less of continuous operation. Continuous operation may be defined as operation during which a temperature of the ferromagnetic material is maintained at a level greater than 100° C.

Optionally, during operation, a temperature of an external surface of said water heating chamber does not exceed 120 degrees Celsius. Optionally, during operation, a temperature of an external surface of said water heating chamber does not exceed 150 degrees Celsius. Optionally, during operation, a temperature profile of the water heating chamber is measured to identify a maximum temperature and a location of said maximum temperature in said heating chamber.

The steam-based ablation system may further comprise a thermocouple wherein said thermocouple is positioned proximate said location of said maximum temperature.

The present specification also discloses a steam-based ablation system comprising: a disposable fluid circuit comprising: a water reservoir containing water; a water heating chamber having a length, wherein the water heating chamber comprises a volume of non-ferromagnetic material having a lumen extending therethrough and a ferromagnetic cylindrical rod, having a thermal capacity of 0.05 cal/K to 1 Mcal/K, positioned within said lumen; a catheter comprising a proximal end and a distal end, wherein the distal end comprises one or more ports; and a contiguous fluid channel connecting said water reservoir, said water heating chamber, and the proximal end of said catheter; an induction chamber adapted to receive said water heating chamber, wherein said induction chamber comprises a plurality of coils for receiving an electrical current and for generating a magnetic field; and an induction circuit for delivering said electrical current to said induction chamber.

The steam-based ablation system may further comprise a pump for applying a force to said water in the water reservoir in order to move the water from the water reservoir, through the water heating chamber, and into the catheter.

The steam-based ablation system may further comprise a motor for applying a force to said water in the water reservoir in order to move the water from the water reservoir, through the water heating chamber, and into the catheter.

The water reservoir may be elevated relative to the water heating chamber wherein water in said water reservoir is gravity fed into the water heating chamber.

Optionally, the water reservoir comprises a bladder tank.

The induction chamber may comprise a cylindrical volume around which said plurality of coils are positioned and a lumen positioned within said cylindrical volume adapted to receive said water heating chamber.

Optionally, the disposable fluid circuit does not comprise any ports or openings, other than the one or more ports in the catheter, for expelling water out from the disposable fluid circuit or for receiving water from an external source.

The present specification also discloses a steam-based ablation system comprising: a disposable fluid circuit comprising: a pliable plastic bag containing water; a water heating chamber having a length, wherein the water heating chamber comprises a volume of non-ferromagnetic material having a lumen extending therethrough and a ferromagnetic cylindrical rod positioned within said lumen; a catheter comprising a proximal end and a distal end, wherein the distal end comprises one or more ports; and flexible tubing connecting said water reservoir, said water heating chamber, and the proximal end of said catheter, wherein the disposable fluid circuit does not comprise any ports or openings, other than the one or more ports in the catheter, for expelling water or vapor out from the disposable fluid circuit or for receiving water from an external source; an induction chamber adapted to receive said water heating chamber, wherein said induction chamber comprises a plurality of coils for receiving an electrical current and for generating a magnetic field; and an induction circuit for delivering said electrical current to said induction chamber.

Optionally, the steam-based ablation system further comprises a handle attached to said catheter for manipulating said catheter. Heating provided by said water heating chamber does not occur in the handle. Optionally, the steam-based ablation system further comprises an additional mechanism in a handle or along a length of said catheter distal to the handle to secondarily heat the vapor.

Optionally, prior to use, a portion of an internal lumen of the flexible tubing positioned between the water reservoir and the water heating chamber is blocked by a barrier, thereby blocking water from passively flowing from the water reservoir to the water heating chamber.

Optionally, the induction chamber comprises a volume around which said plurality of coils are positioned and a lumen positioned within said volume adapted to receive said water heating chamber.

Optionally, the non-ferromagnetic material is a cylinder, the ferromagnetic material is a metal rod, and the ferromagnetic material comprises any one of, or alloys of, iron, nickel, stainless steel, manganese, silicon, carbon, copper, electrically conducting material, electrically insulating material, or a Curie material having a Curie temperature between 60° C. and 500° C.

The present specification also discloses a vapor ablation system including a catheter component comprising: a water reservoir; a heating chamber; and a catheter; and a generator component comprising: an induction coil and a microprocessor, wherein said catheter component is operationally connected to said generator component such that said induction coil can be positioned proximate said heating chamber for inductive heating of water within said heating chamber. Optionally, the catheter component is a single-use component while the generator component is a multiple-use component.

The aforementioned and other embodiments of the present invention shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings, wherein:

FIG. 1A illustrates an ablation device, in accordance with an embodiment of the present specification;

FIG. 1B illustrates another embodiment of a catheter for use with the ablation device of FIG. 1A;

FIG. 2A illustrates a longitudinal section of an ablation device with ports distributed thereon;

FIG. 2B illustrates a cross section of a port on the ablation device, in accordance with an embodiment of the present specification;

FIG. 2C illustrates a cross section of a port on the ablation device, in accordance with another embodiment of the present specification;

FIG. 2E illustrates a catheter of the ablation device, in accordance with another embodiment of the present specification;

FIG. 5A illustrates the ablation device with a coaxial catheter design, in accordance with an embodiment of the present specification;

FIG. 5B illustrates a partially deployed positioning device, in accordance with an embodiment of the present specification;

FIG. 5C illustrates a completely deployed positioning device, in accordance with an embodiment of the present specification;

FIG. 5D illustrates the ablation device with a conical positioning element, in accordance with an embodiment of the present specification;

FIG. 5E illustrates the ablation device with a disc shaped positioning element, in accordance with an embodiment of the present specification;

FIG. 9A illustrates bronchial and bullous ablation being performed in a pulmonary system by using the ablation device, in accordance with an embodiment of the present specification;

FIG. 12C is a flow chart listing the steps involved in a blood vessel ablation process using an ablation catheter, in accordance with one embodiment of the present specification;

FIG. 17B illustrates a catheter used to deploy, and provide an ablative agent to, the stent of FIG. 17A;

FIG. 17C illustrates the stent of FIG. 17A working in conjunction with the catheter of FIG. 17B;

FIG. 22A illustrates the unassembled interface connection between the ablation device and the single use cord of the heating coil vapor delivery system of FIG. 20, in accordance with an embodiment of the present specification;

FIG. 22B illustrates the assembled interface connection between the ablation device and the single use cord of the heating coil vapor delivery system of FIG. 20, in accordance with an embodiment of the present specification;

FIG. 23 illustrates a vapor ablation system using a heater or heat exchange unit for supplying vapor to the ablation device, in accordance with another embodiment of the present specification;

FIG. 34C is a longitudinal view cross sectional diagram illustrating another embodiment of a catheter with a metal spiral used with induction heating in the vapor ablation system of the present specification;

FIG. 34D is a longitudinal view cross sectional diagram illustrating another embodiment of a catheter with a mesh used with induction heating in the vapor ablation system of the present specification;

FIG. 36A illustrates a catheter assembly having an inline chamber for heat transfer in accordance with one embodiment of the present specification;

FIG. 36B illustrates the catheter assembly of FIG. 36A including an optional handle;

FIG. 39C illustrates a cross-sectional view of a double layered catheter in accordance with another embodiment of the present specification FIG. 39D illustrates a catheter having the double layer configuration depicted in FIG. 39B;

FIG. 40A is an illustration of a vapor ablation system using induction heating in accordance with one embodiment of the present specification;

FIG. 40B is a graph illustrating the behavior, in relation to the ideal gas law, of a plurality of gases as they are heated to high temperatures;

FIG. 40C is an illustration of one embodiment of a catheter for use with the vapor ablation systems of the present specification;

FIG. 40D is a flowchart listing the steps of a method of using the ablation catheter of FIG. 40C, in accordance with one embodiment of the present specification;

FIG. 40E is a flowchart listing the steps of a method of using the ablation catheter of FIG. 40C, in accordance with another embodiment of the present specification;

FIG. 40F is an illustration of one embodiment of a positioning element of an ablation catheter, depicting a plurality of thermally conducting elements attached thereto;

FIG. 40G is an illustration of one embodiment of a positioning element of an ablation catheter, depicting a plurality of hollow thermally conducting elements attached thereto;

FIG. 40H is an illustration of an ablation catheter having a plurality of thermally conducting elements within a positioning element, in accordance with one embodiment of the present specification;

FIG. 40I is an illustration of an ablation catheter having a thermally conducting element attached to an outer surface of a positioning element;

FIG. 40J is a flowchart listing the steps of a method of using a vapor ablation system in accordance with one embodiment of the present specification;

FIG. 40K is a flowchart listing the steps of a method of using a vapor ablation system in accordance with another embodiment of the present specification;

Figure 41A:
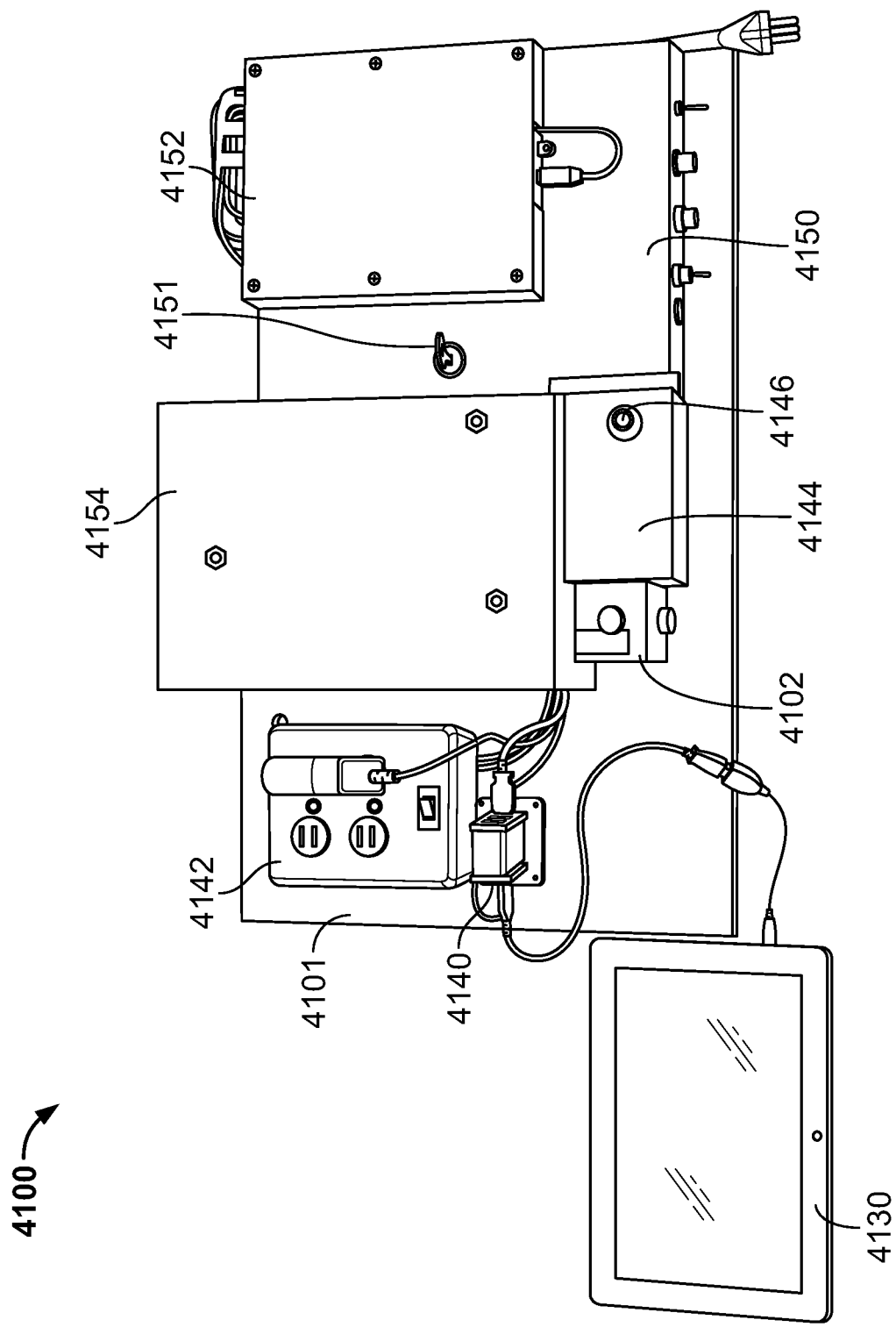
Figure 41B:
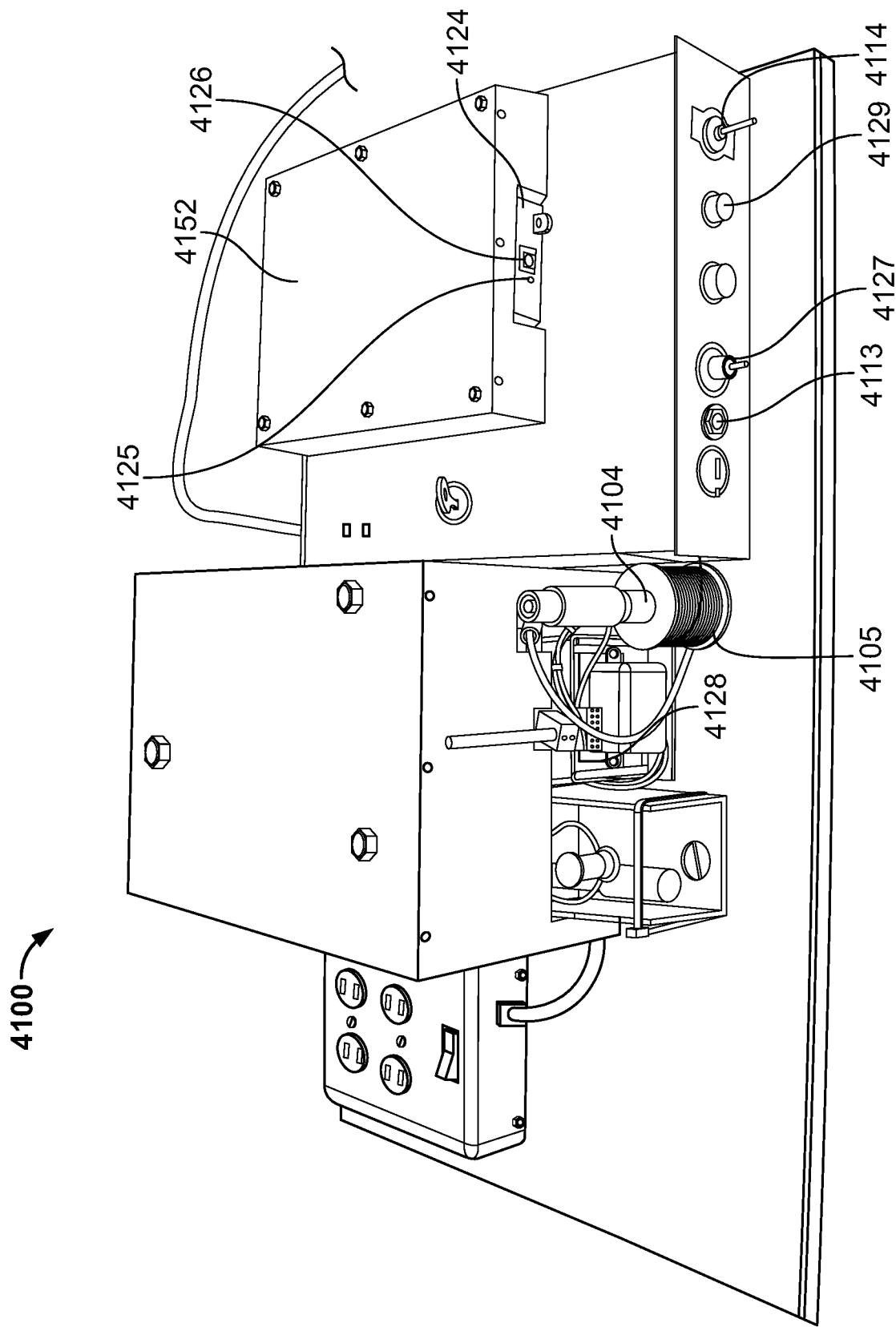
Figure 41C:
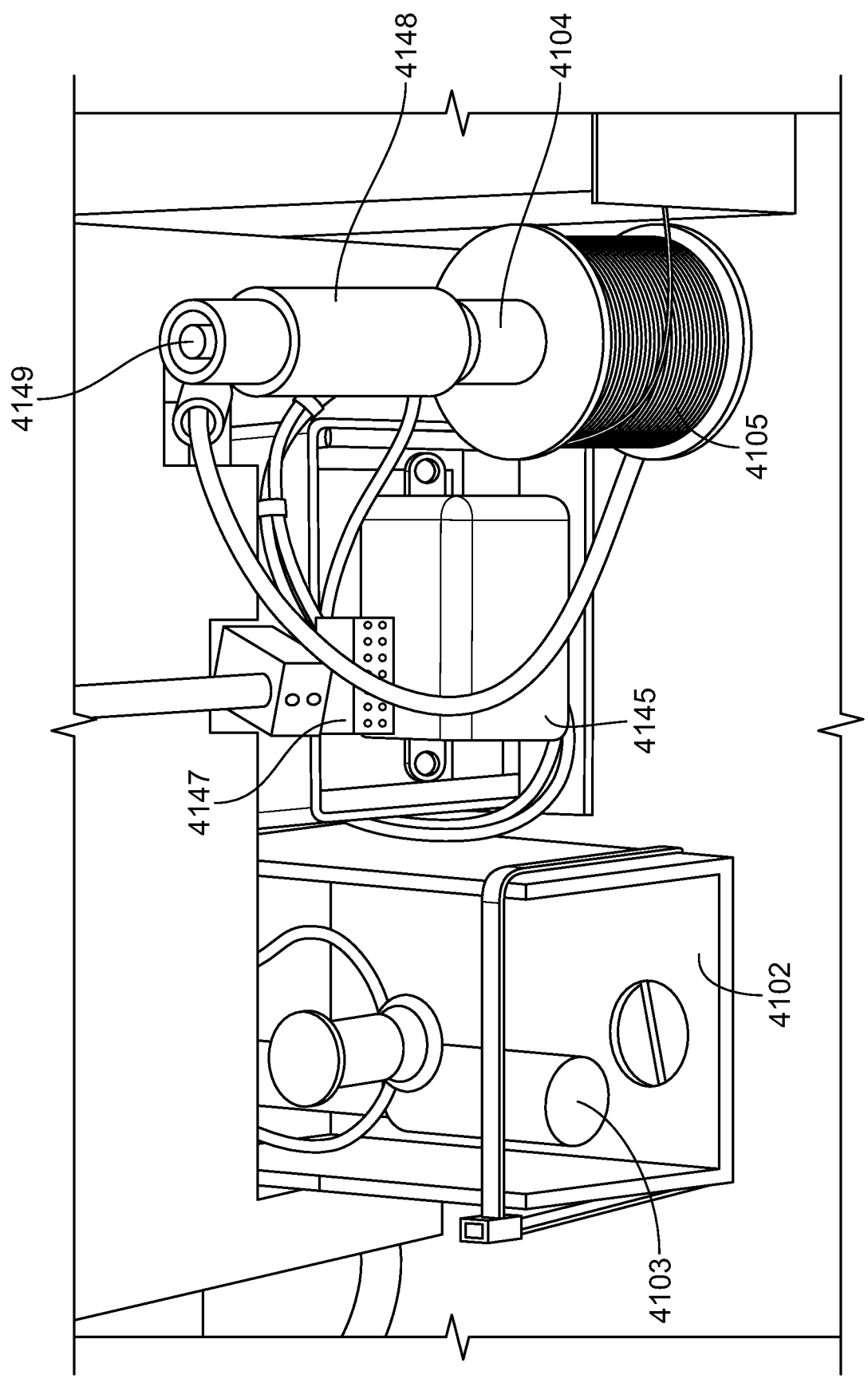
Figure 41D:
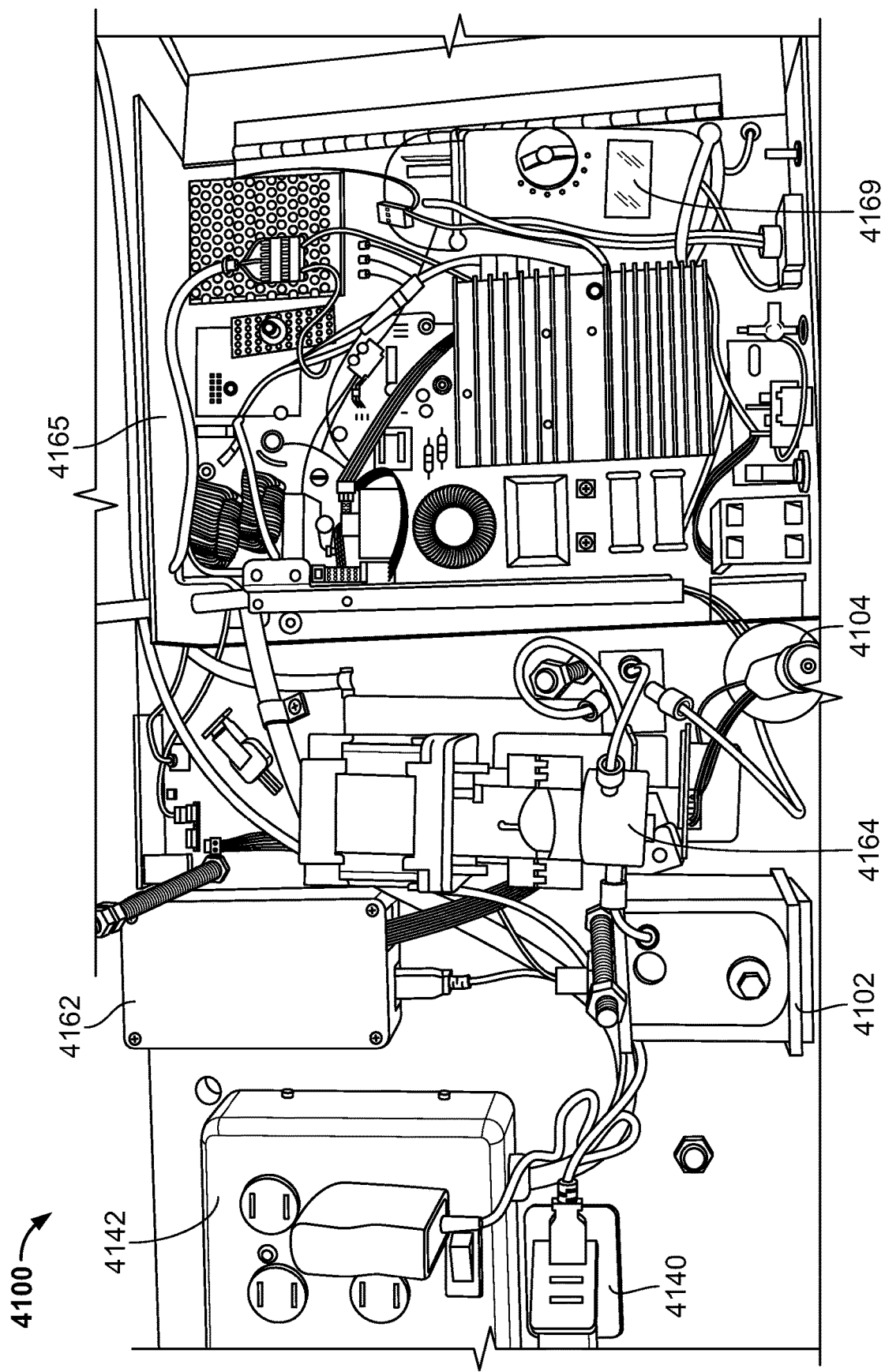
Figure 41E:
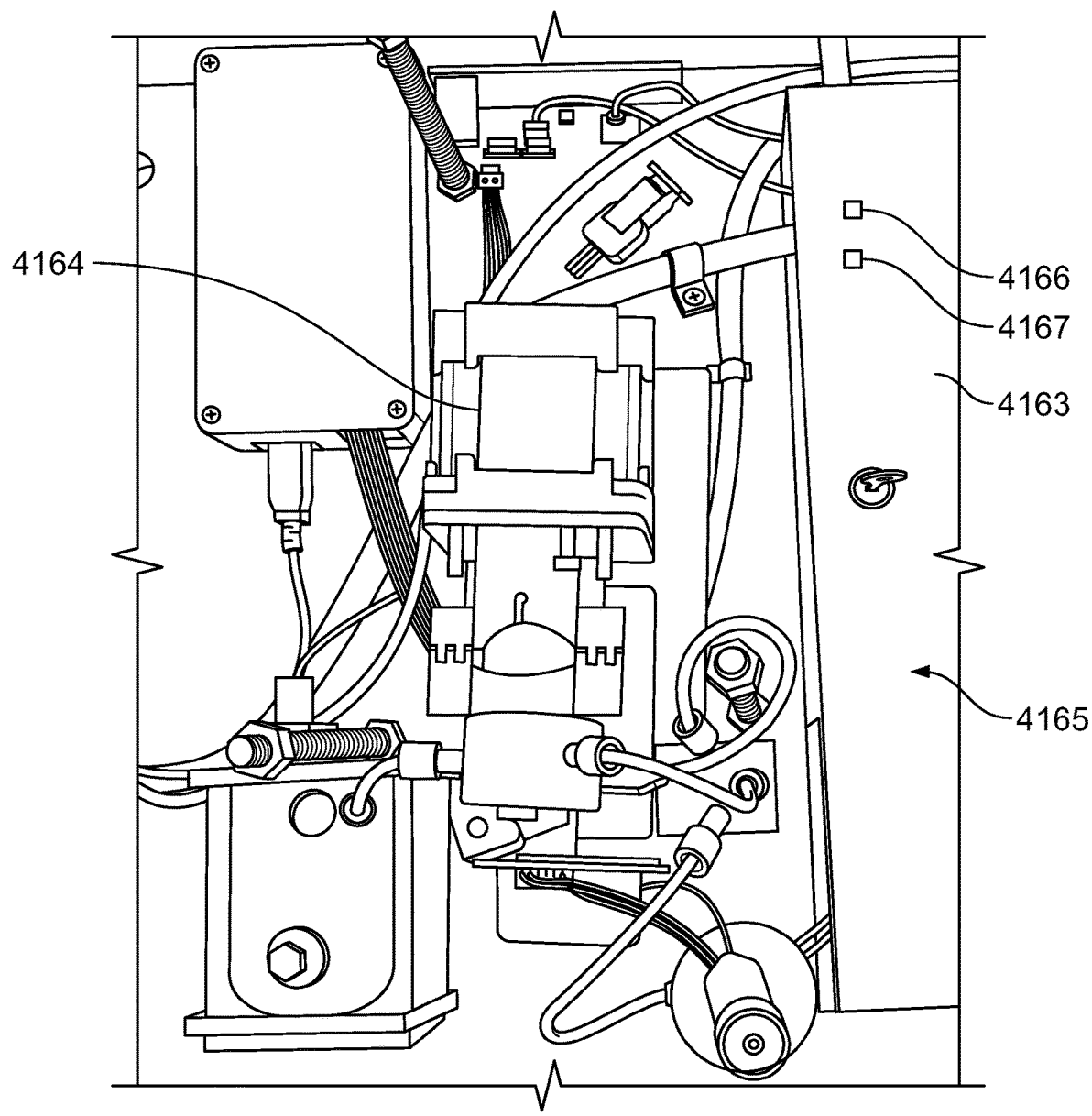
Figure 41F:
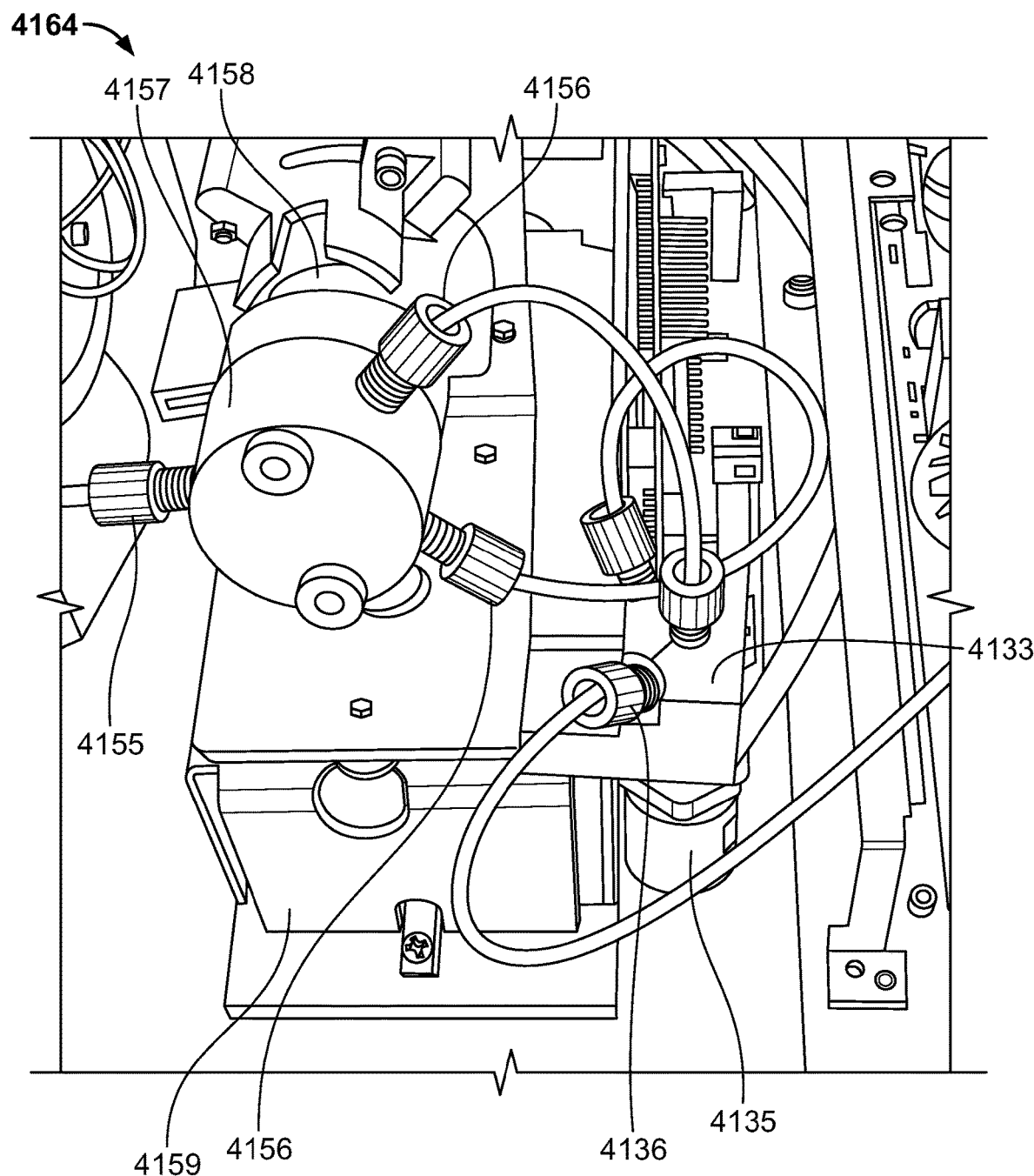
Figure 41G:
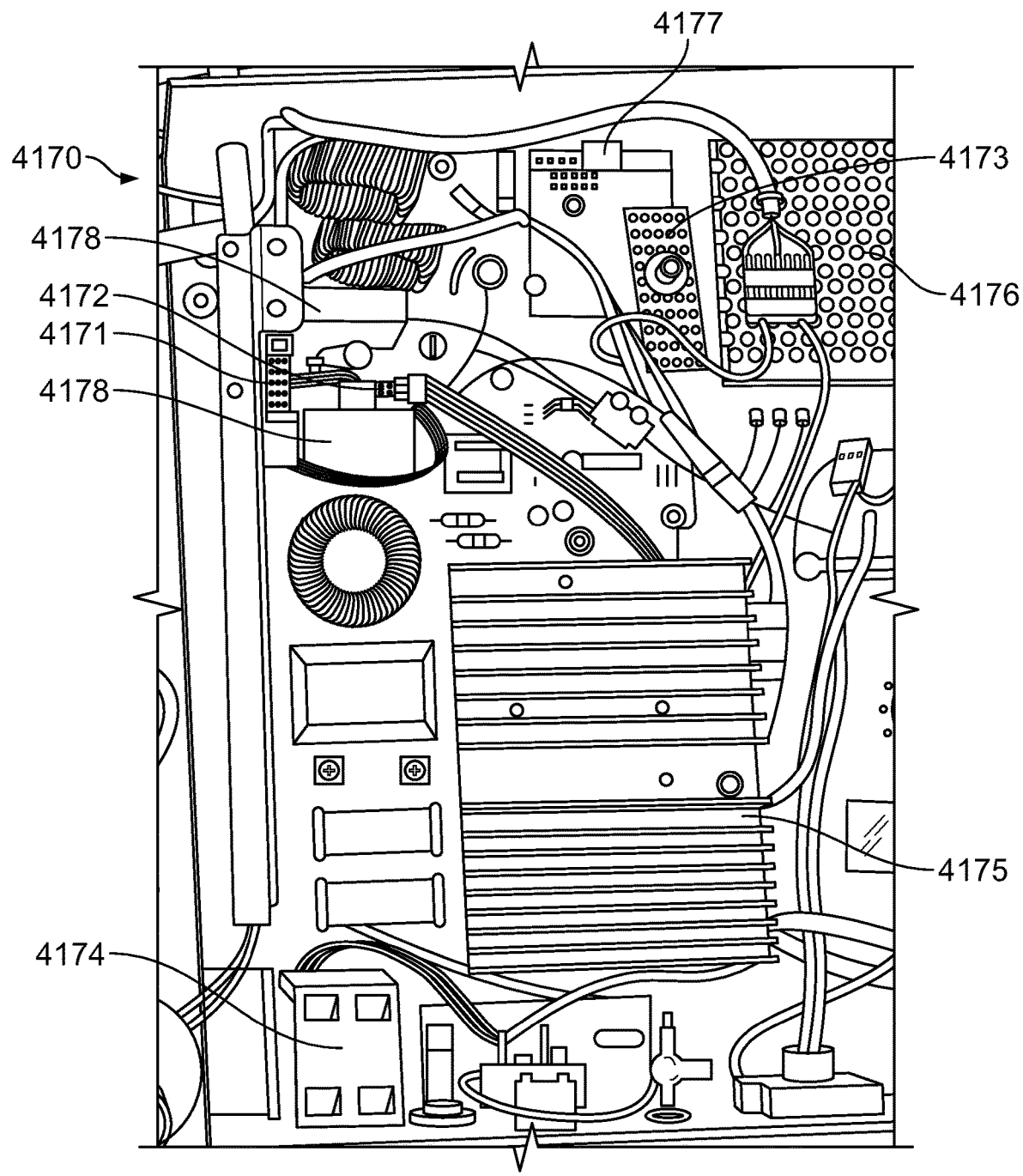
Figure 41H:
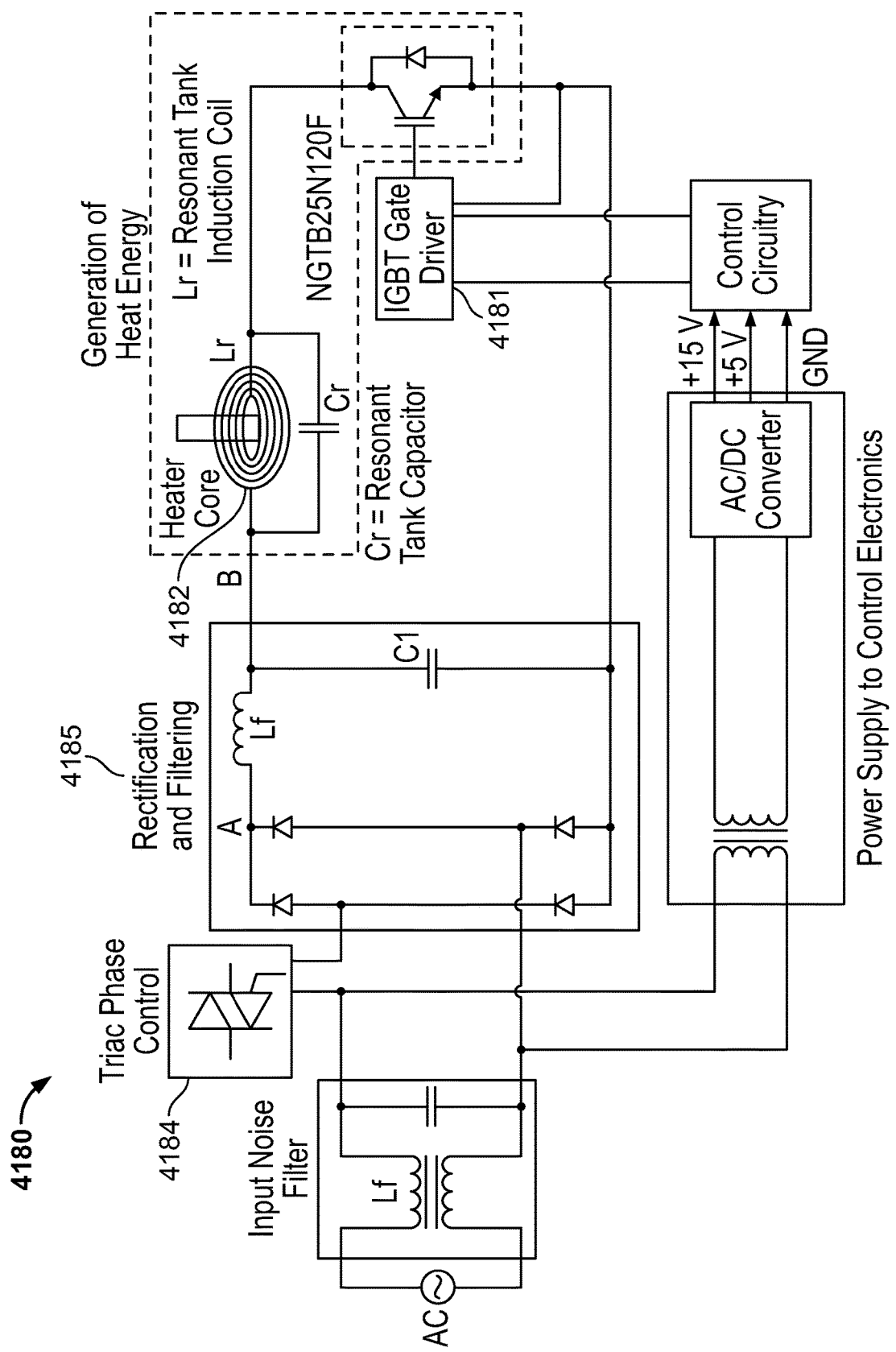
Figure 41I:
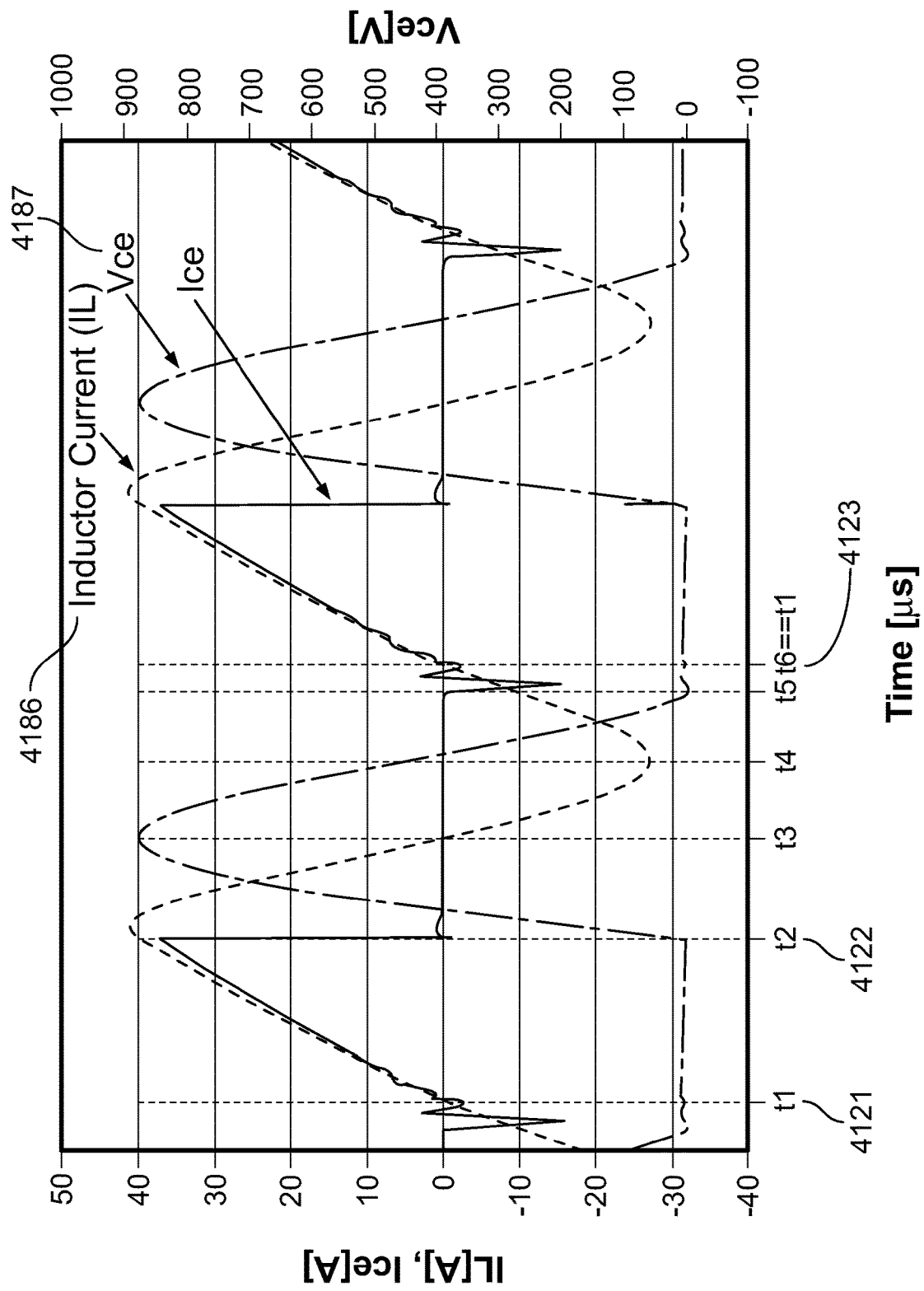
Figure 41J:
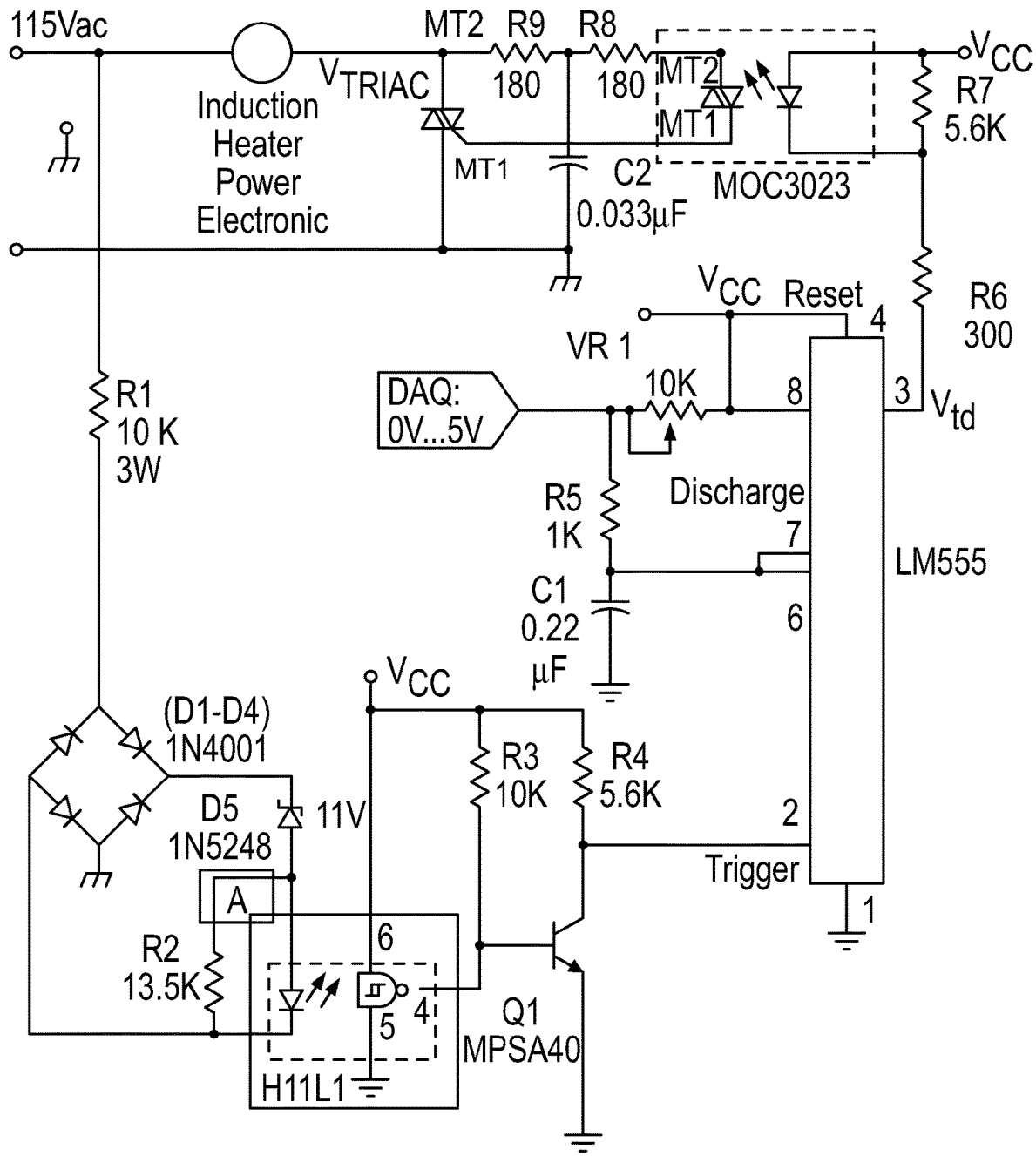
Figure 42:
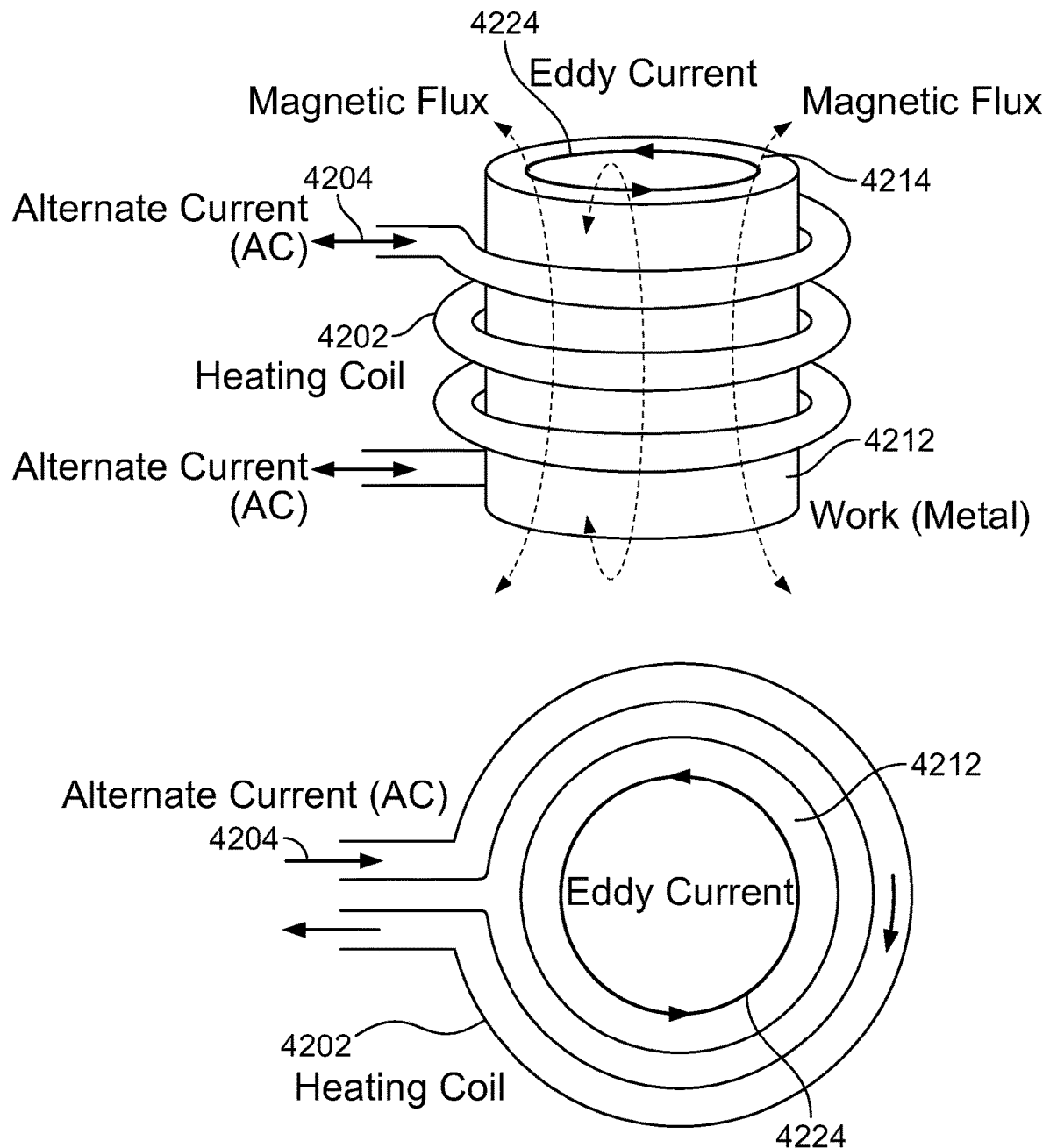
Figure 43:
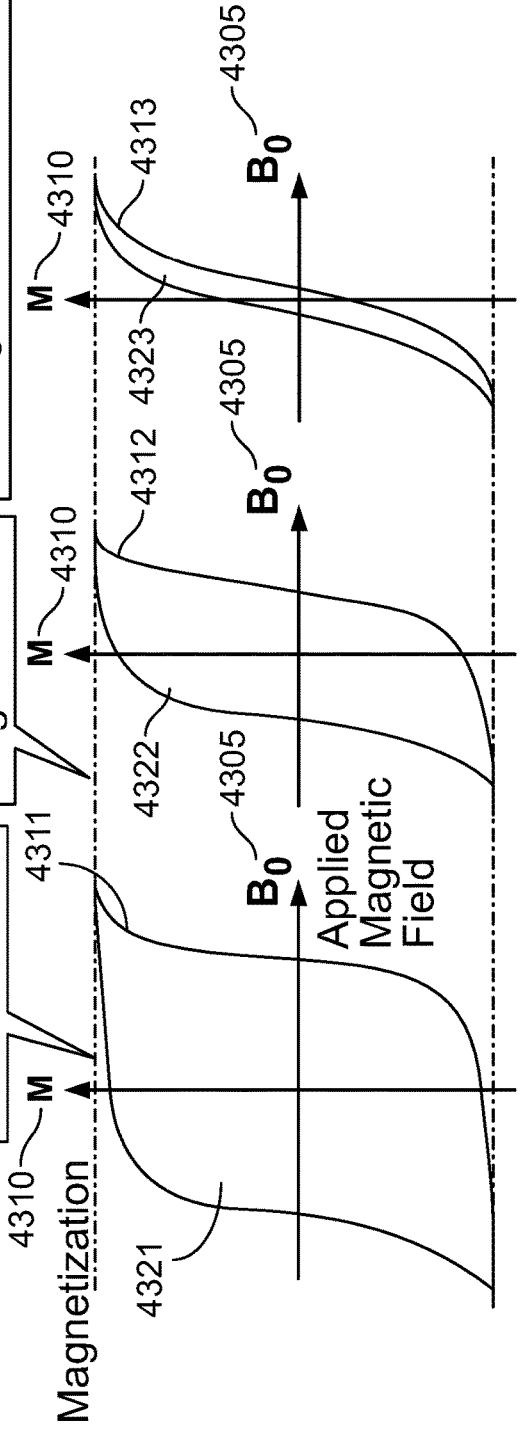
Figure 44:
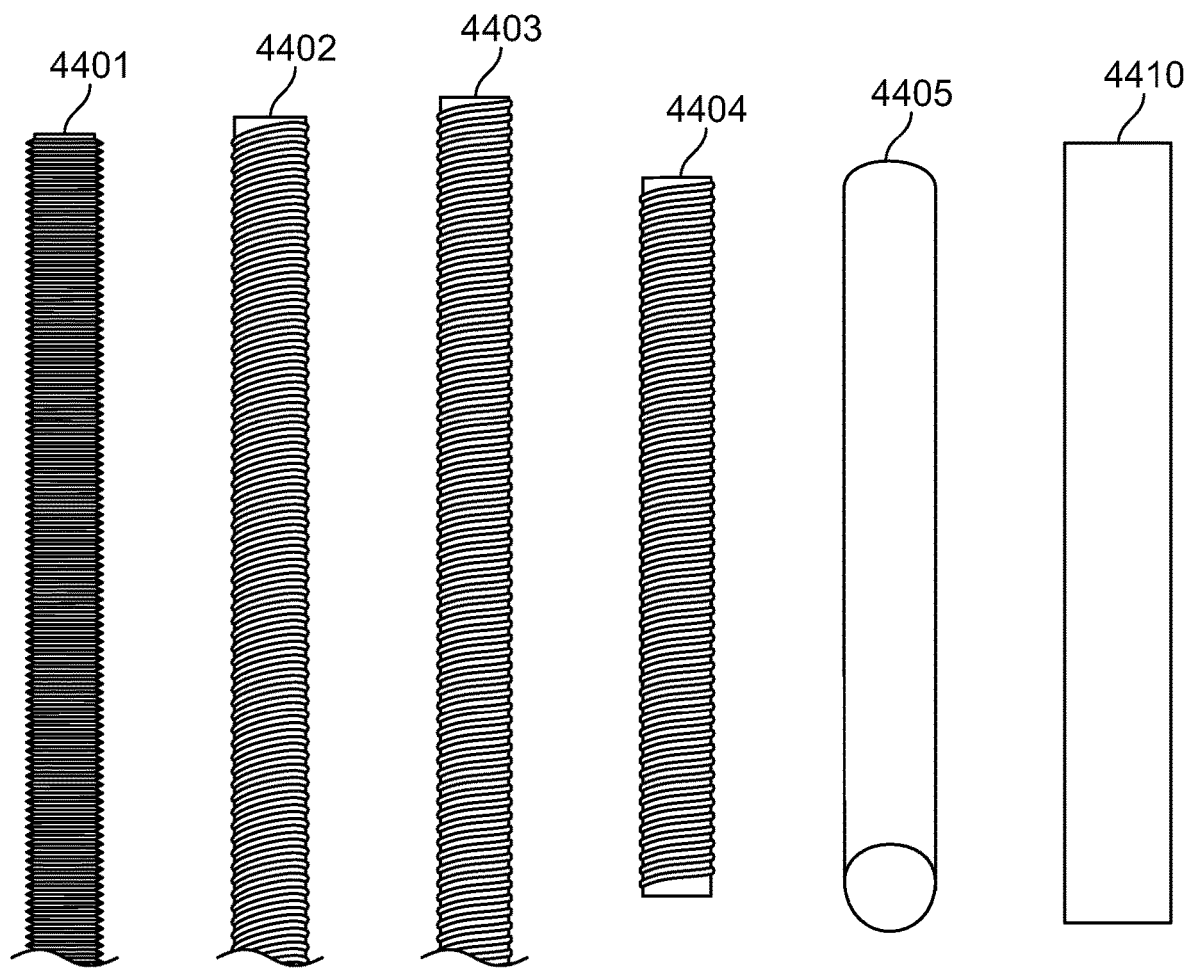
Figure 46C:
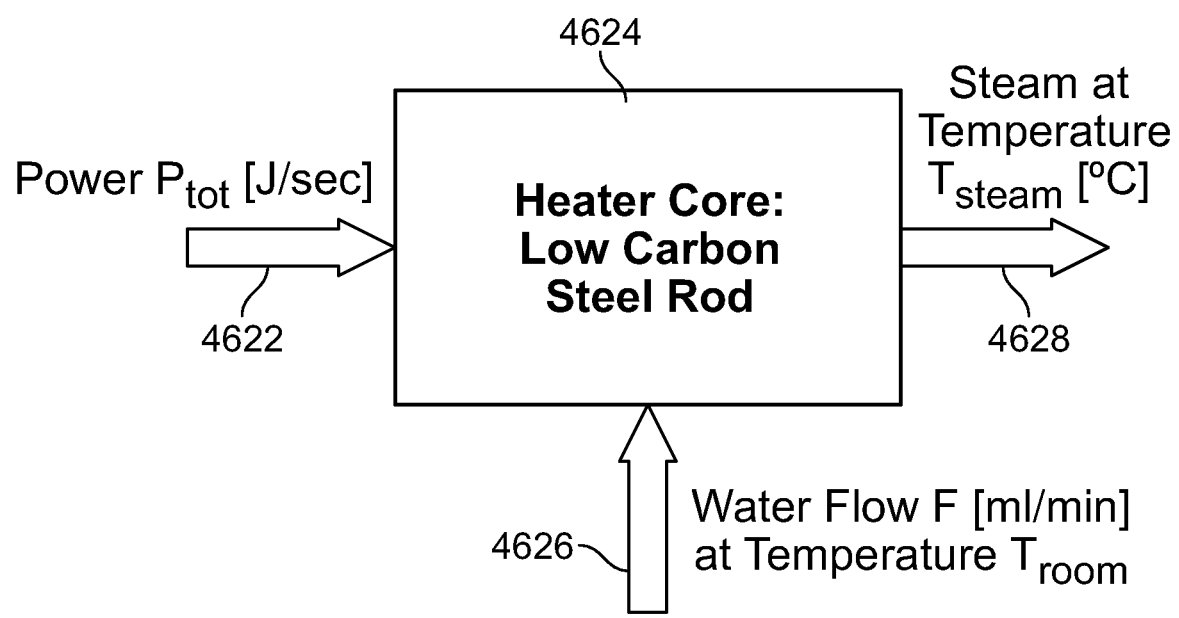
Figure 47:
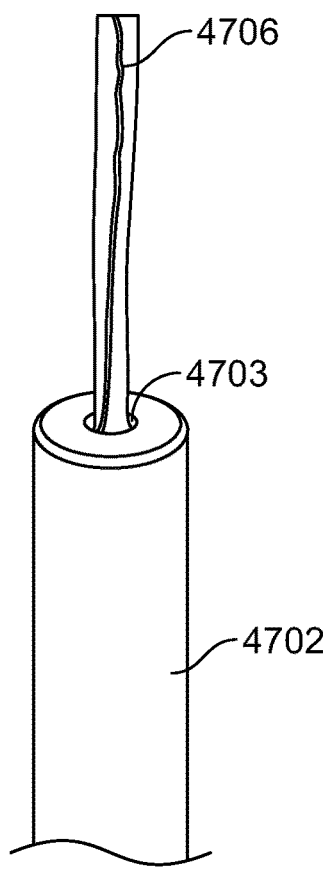
Figure 48A:
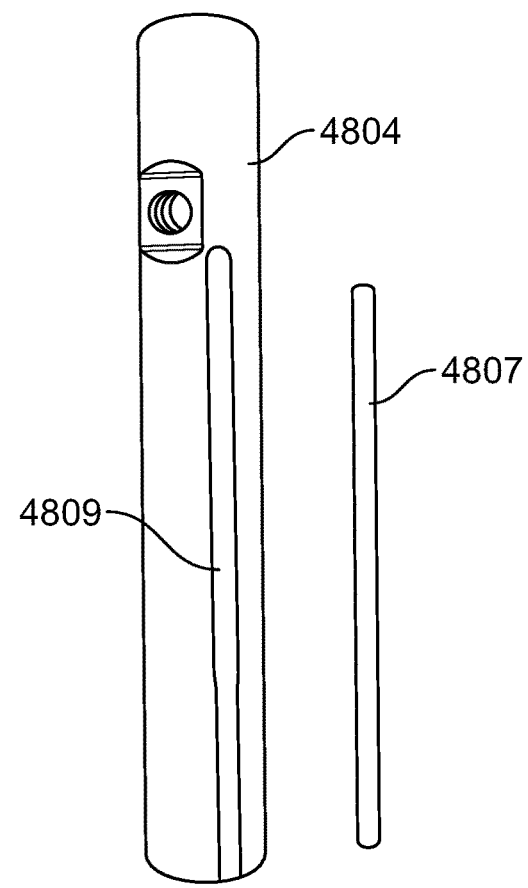
Figure 48B:
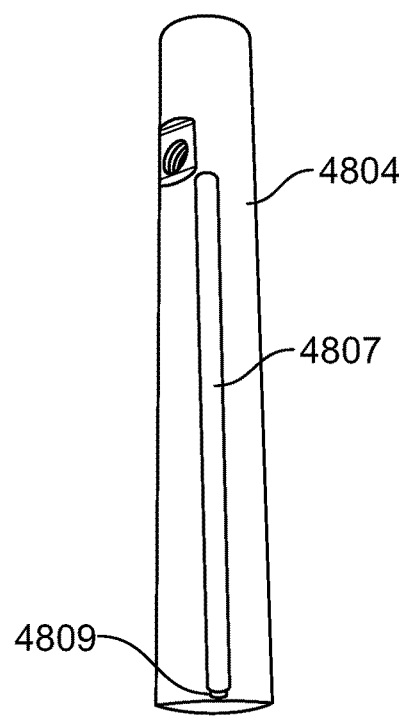
Figure 48D:
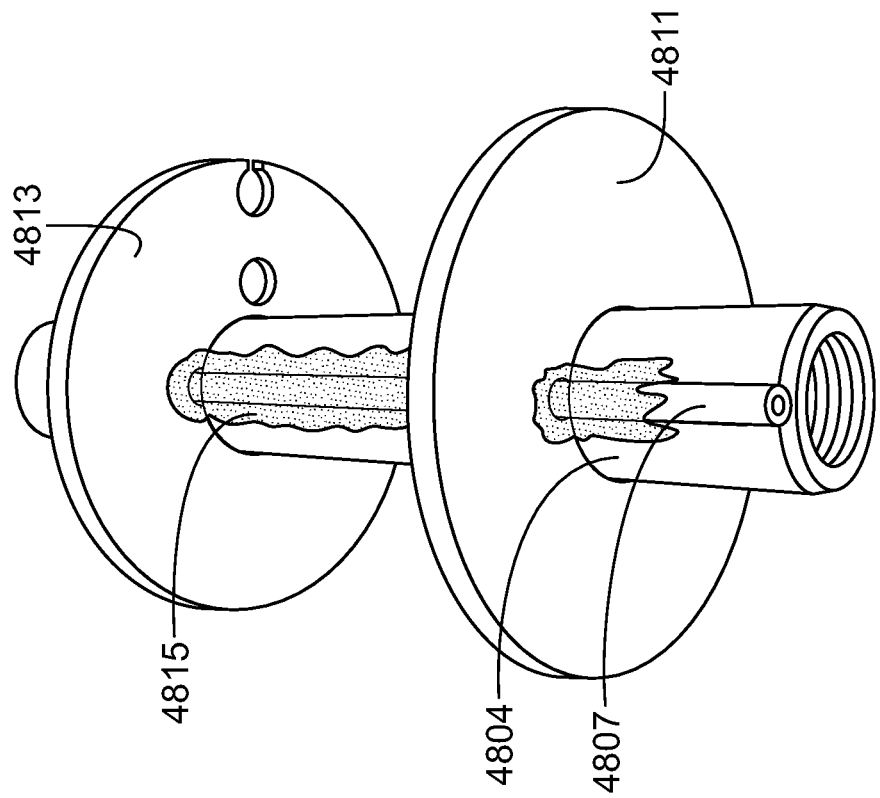
Figure 48C:
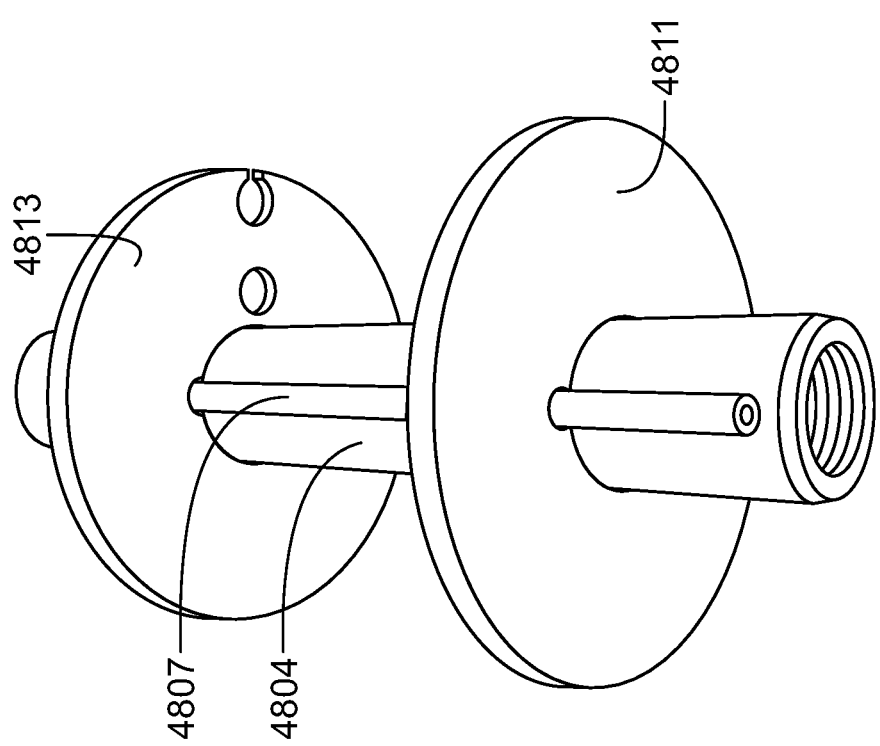
Figure 48E:
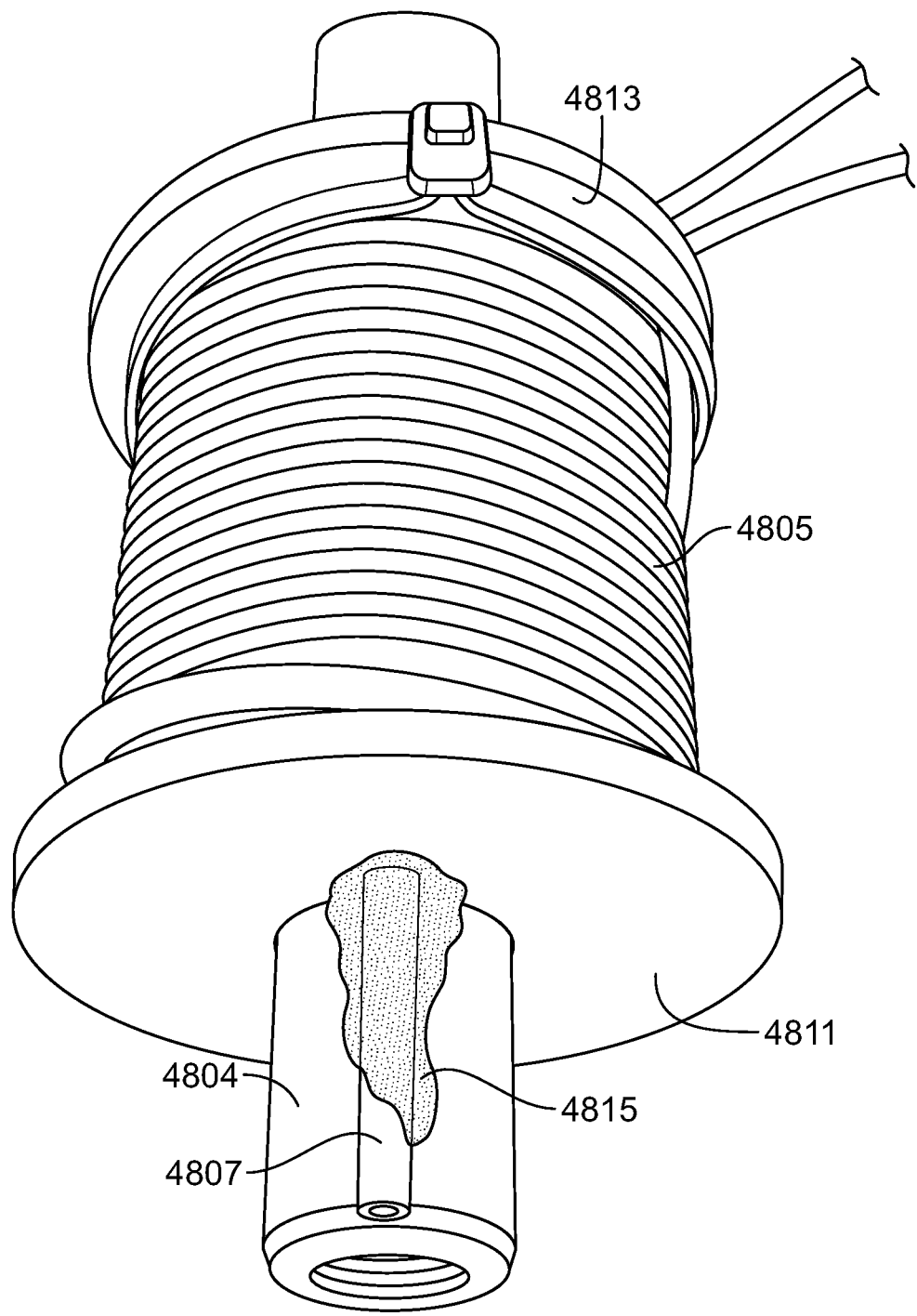
Figure 49A:
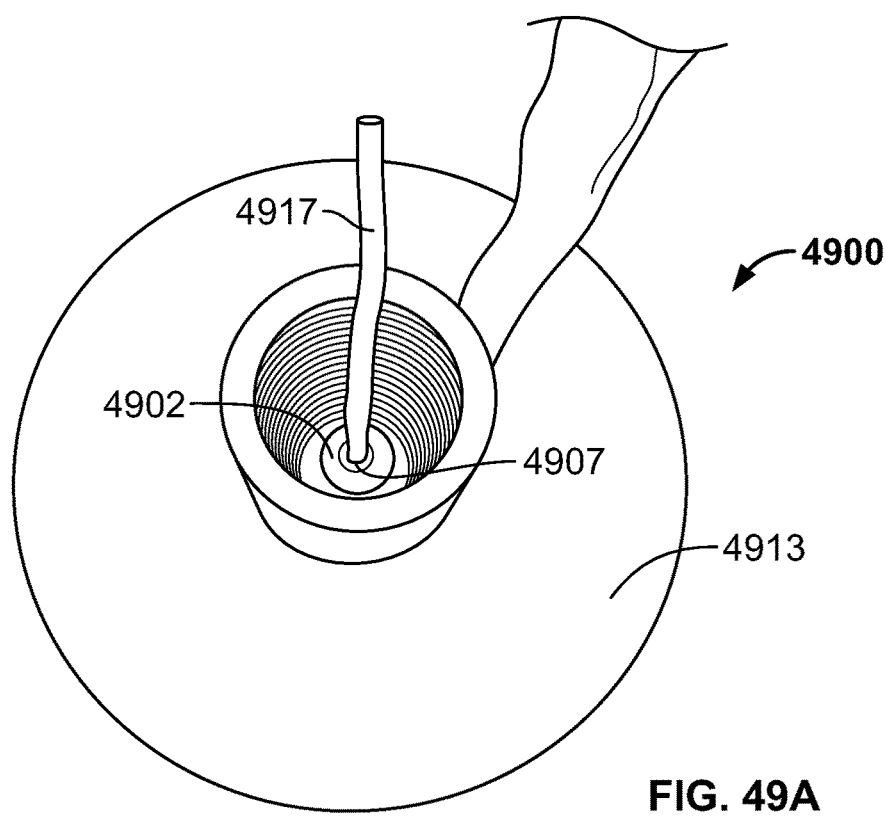
Figure 49B:
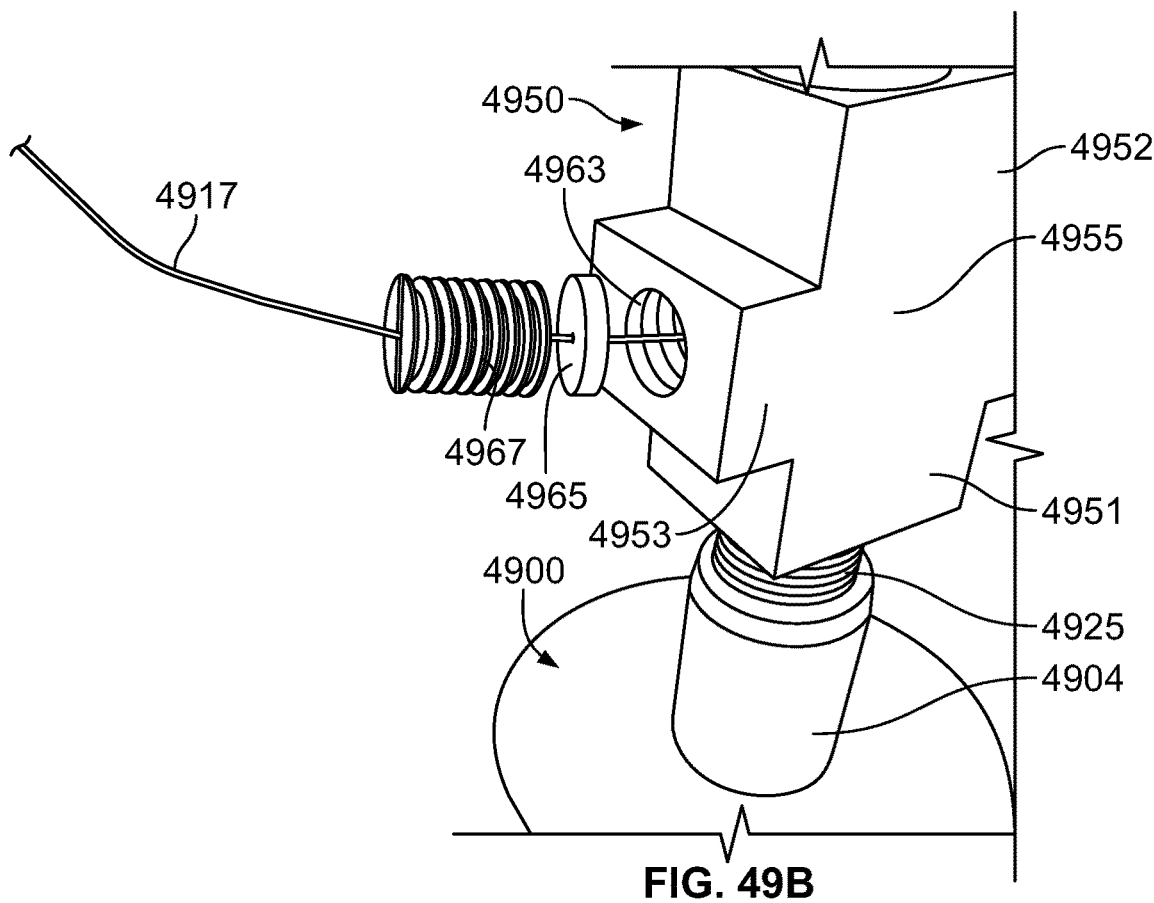
Figure 49C:
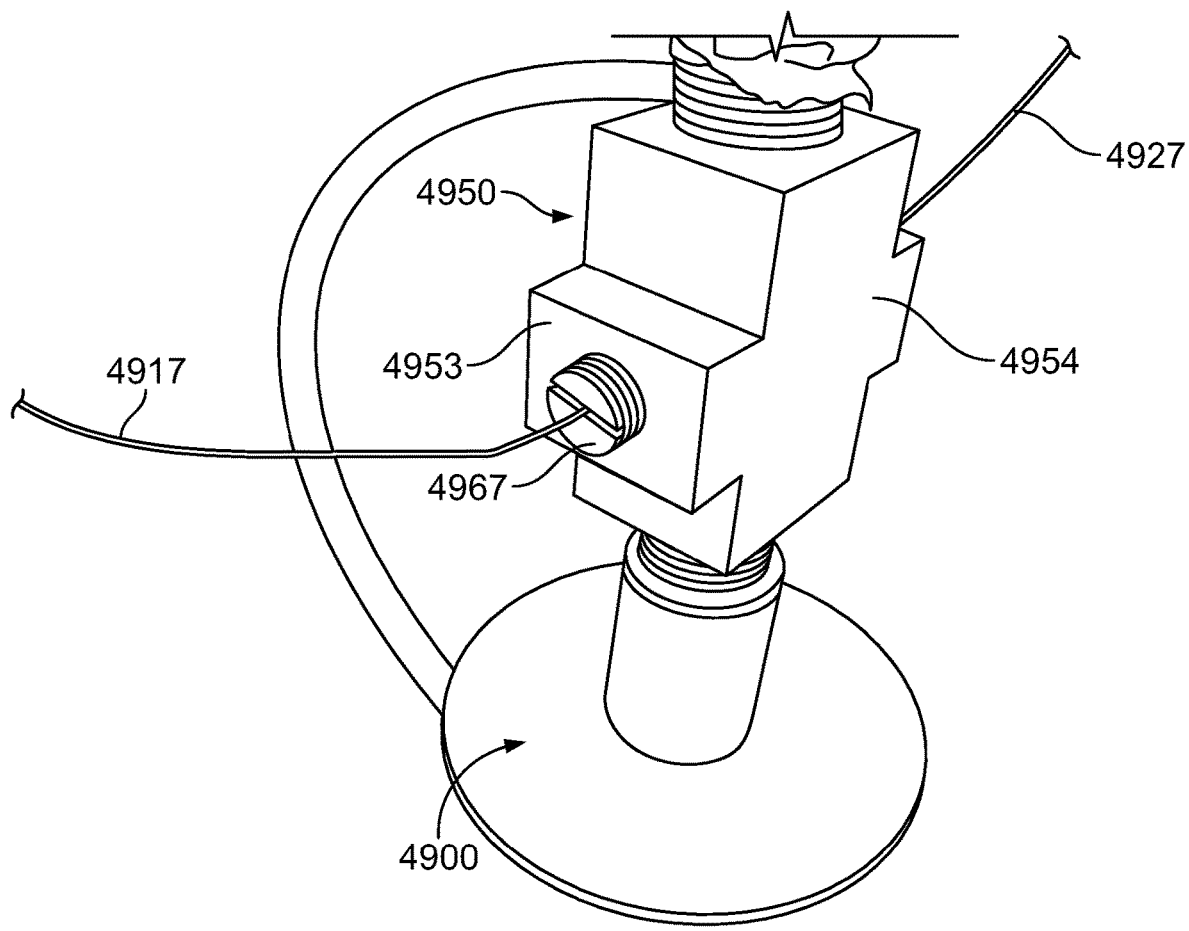
Figure 49D:
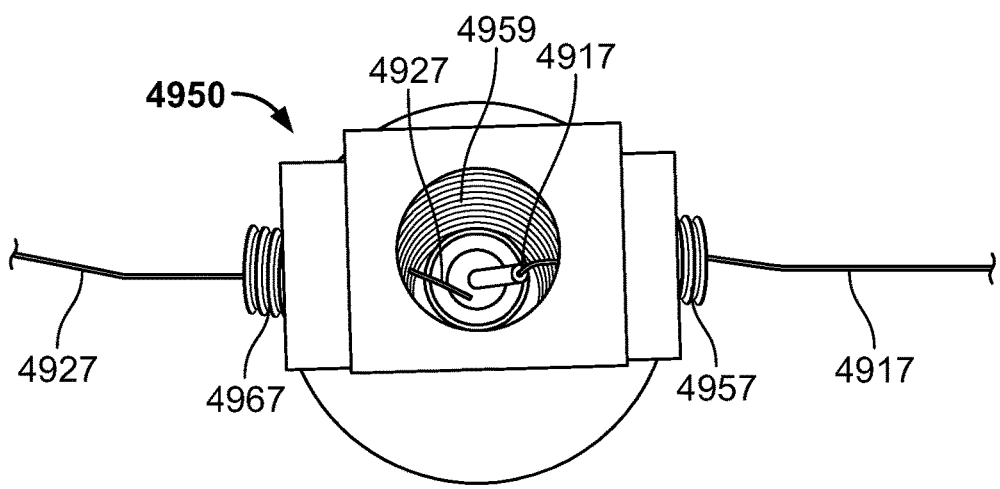
Figure 49E:
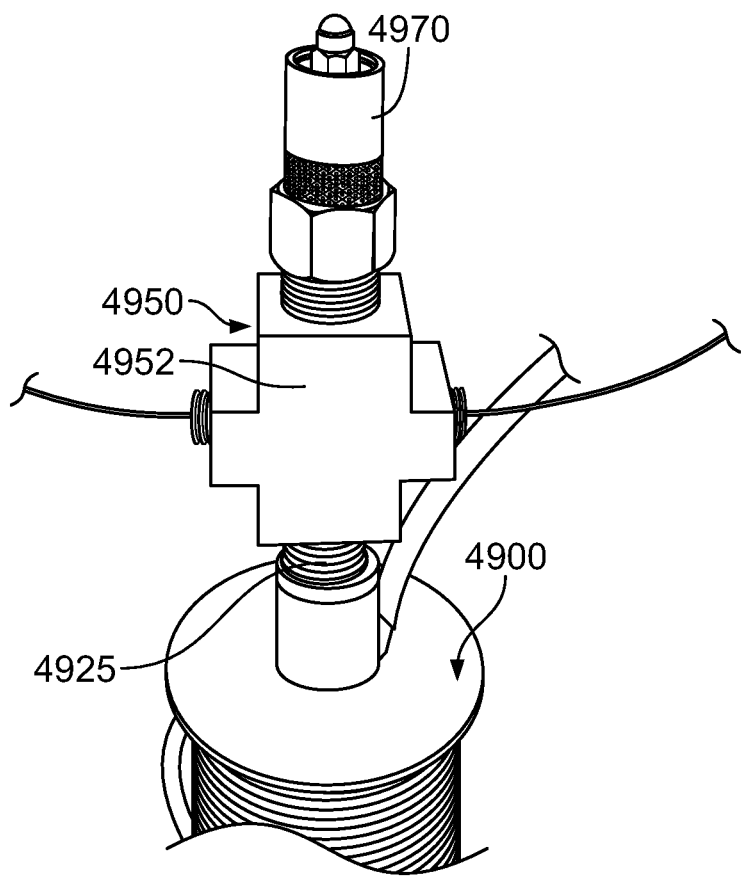
Figure 49F:
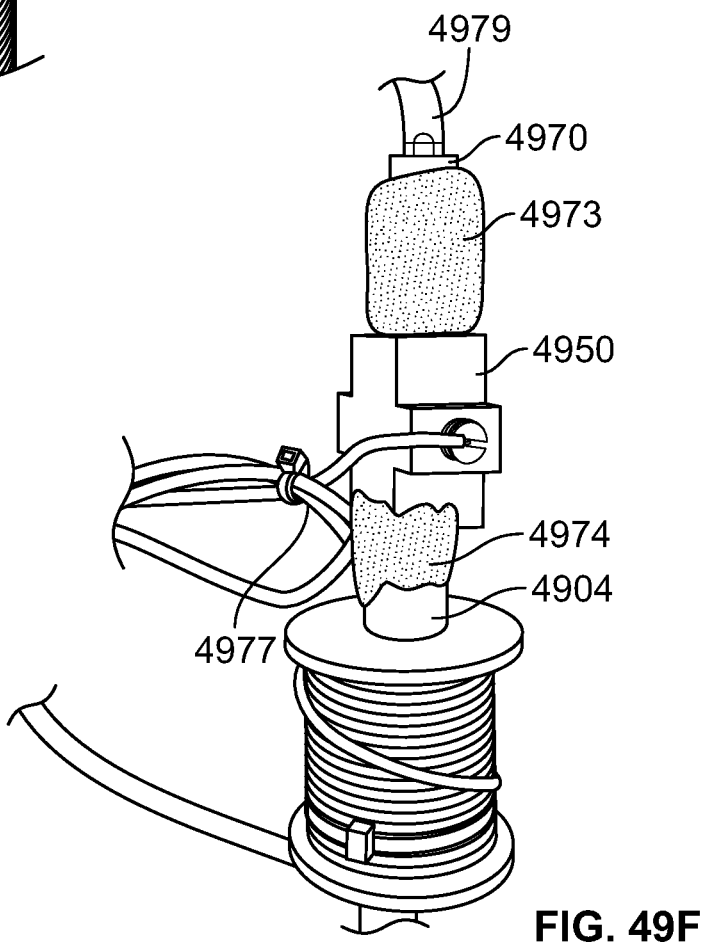
Figure 49G:
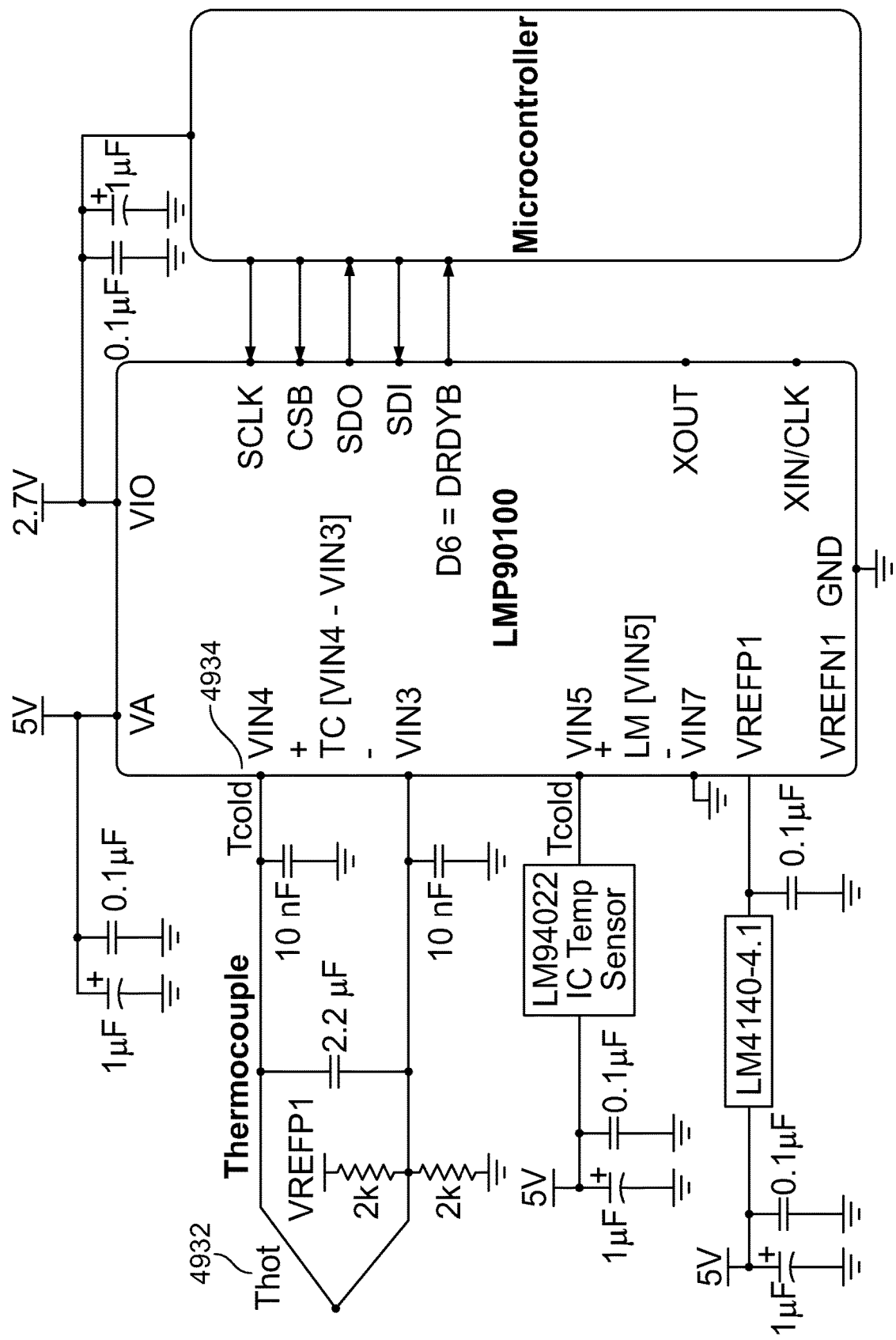
Figure 49I:
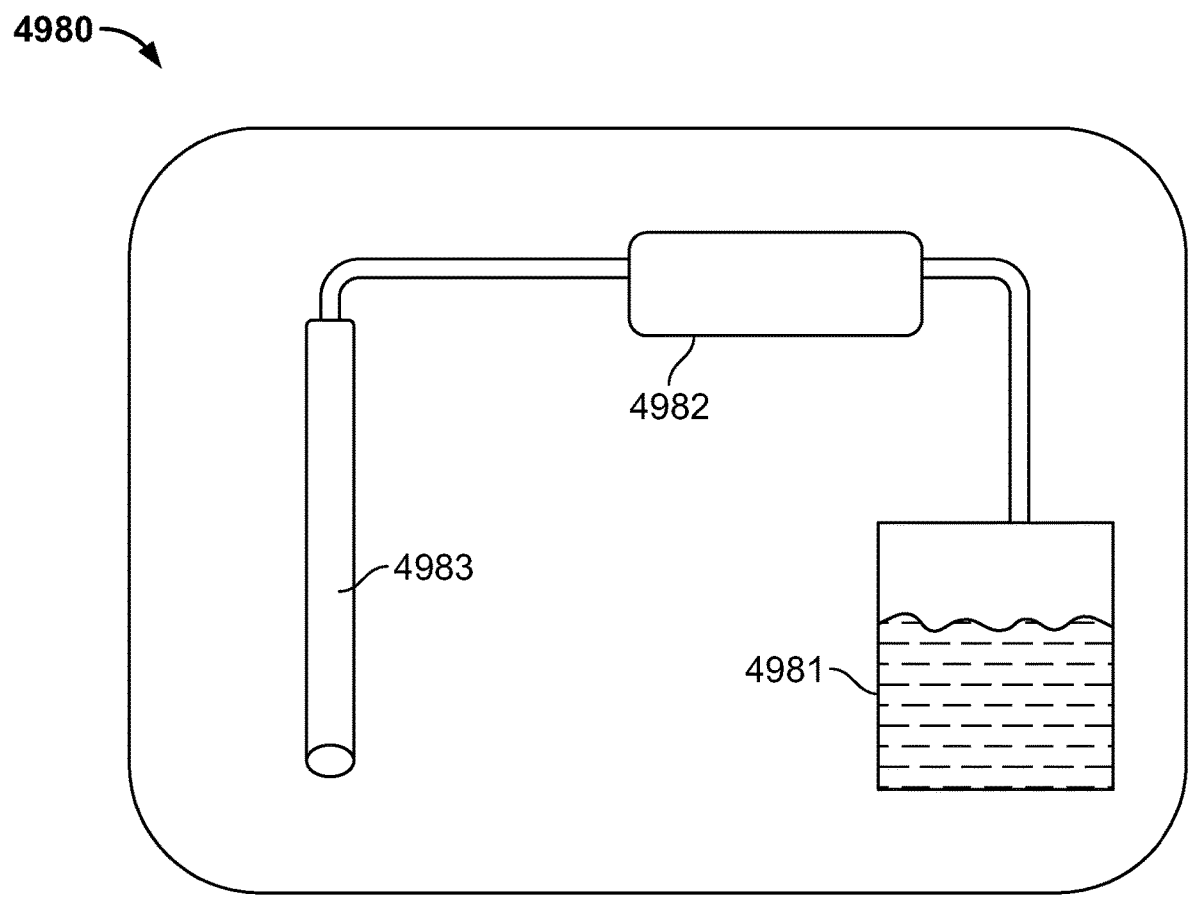
Figure 49J:
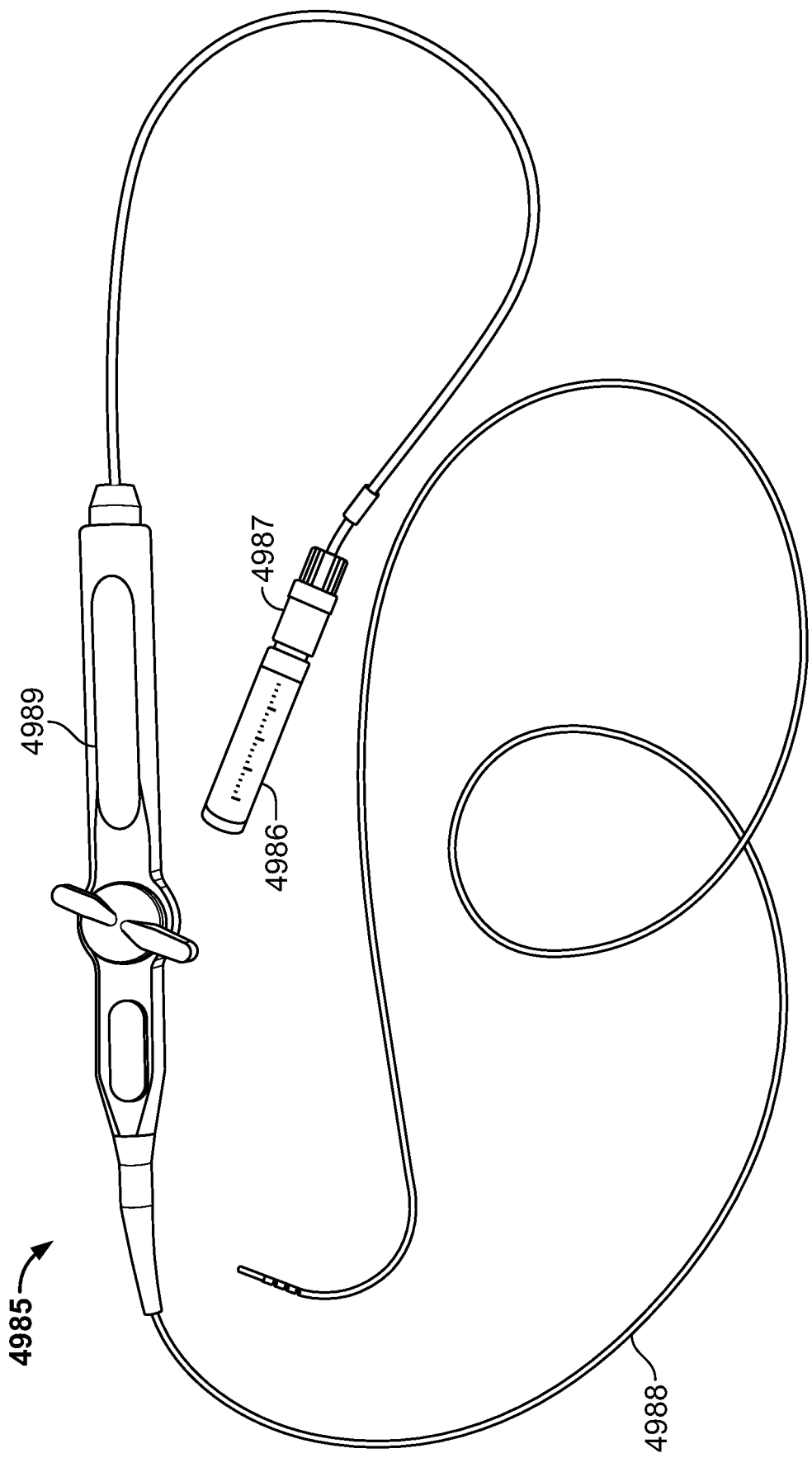
Figure 50:
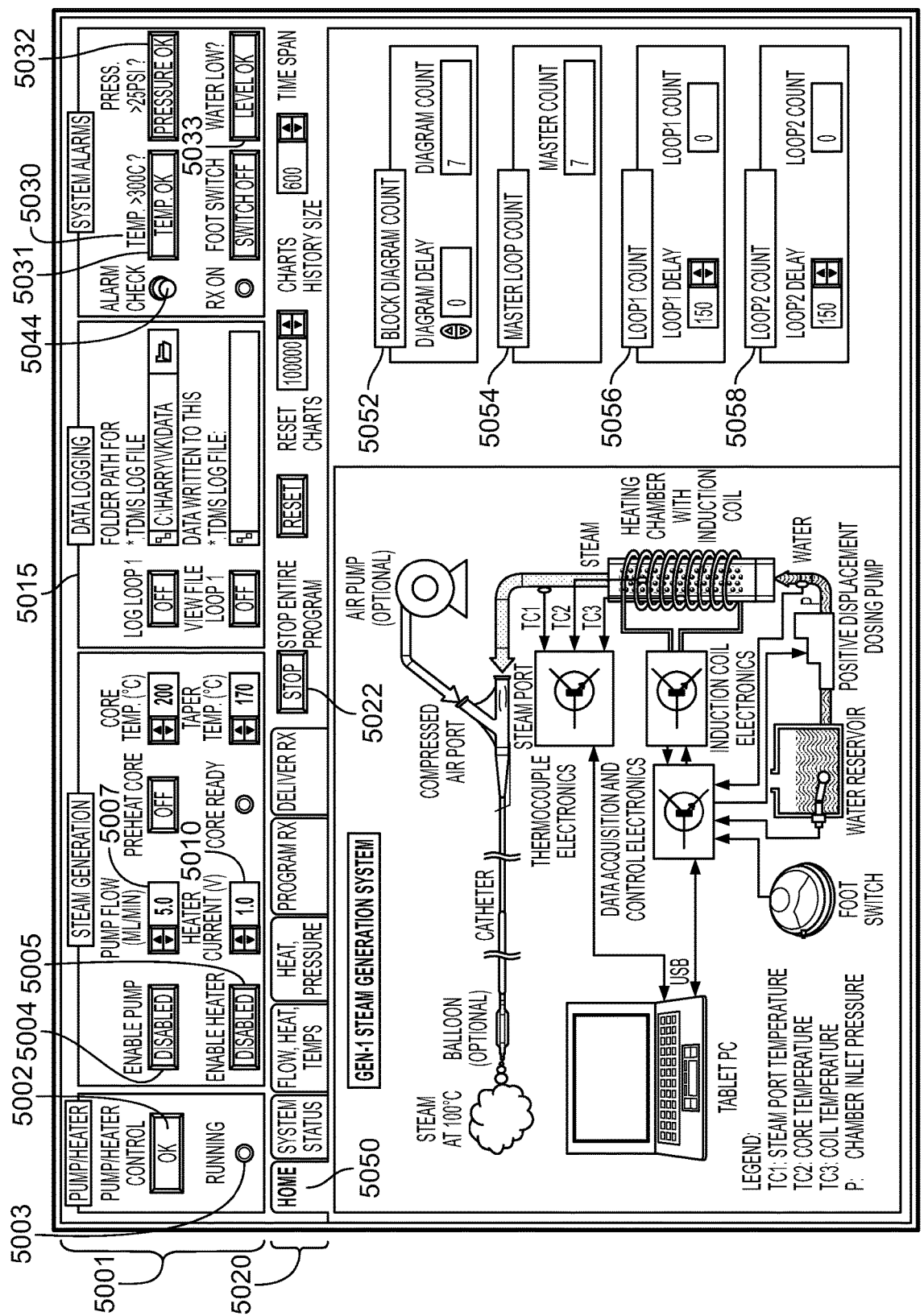
Figure 51:
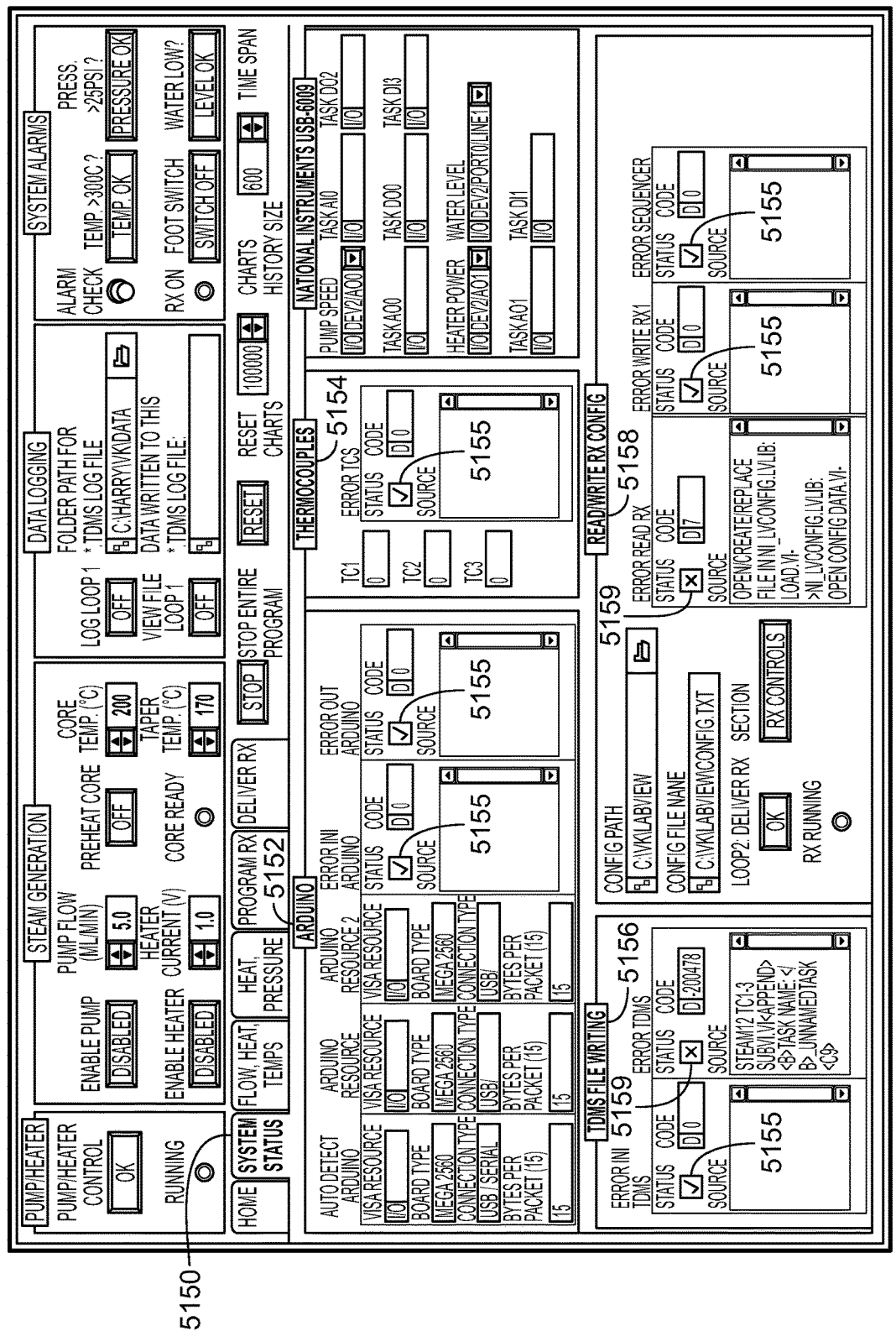
Figure 52:
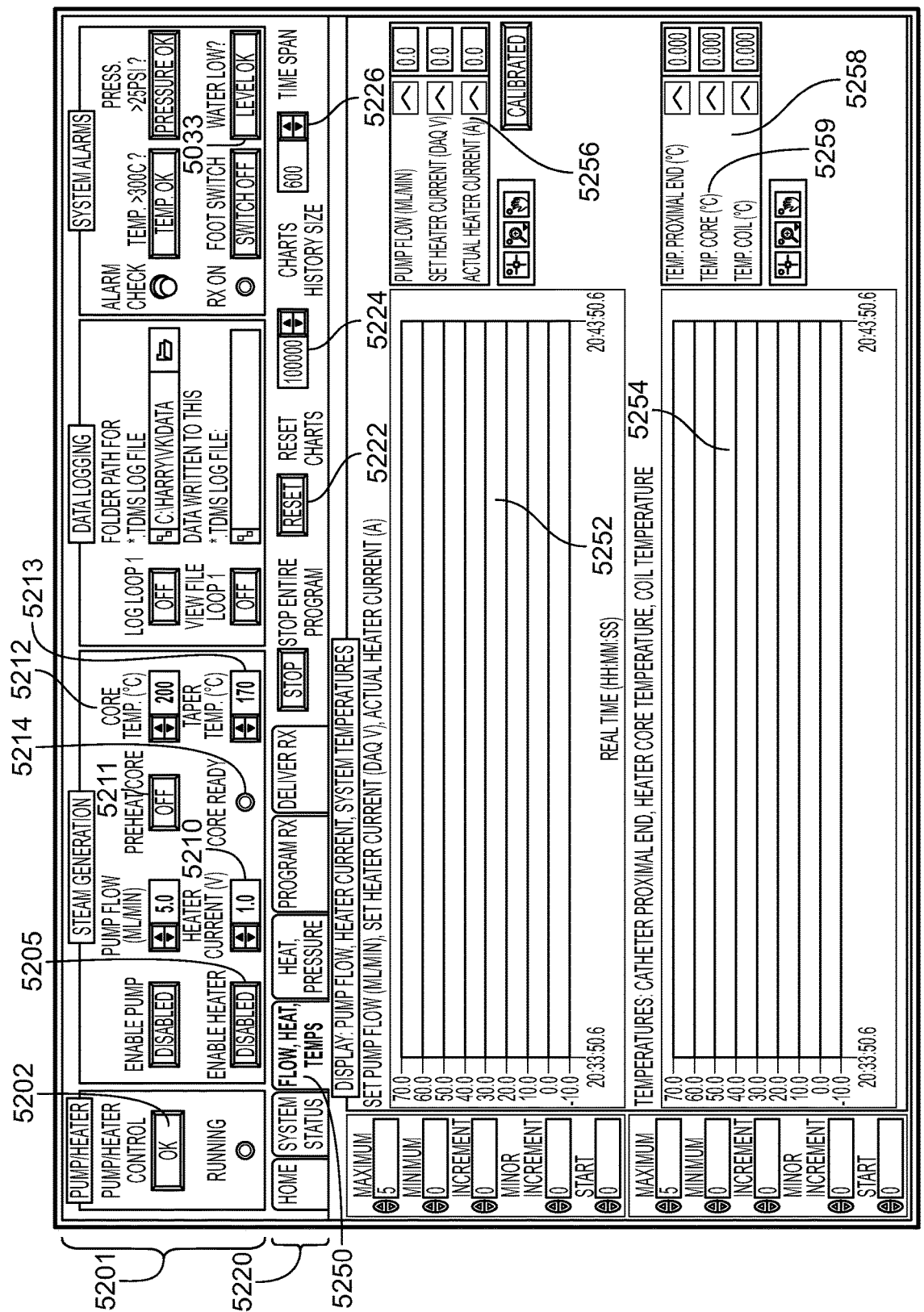
Figure 53:
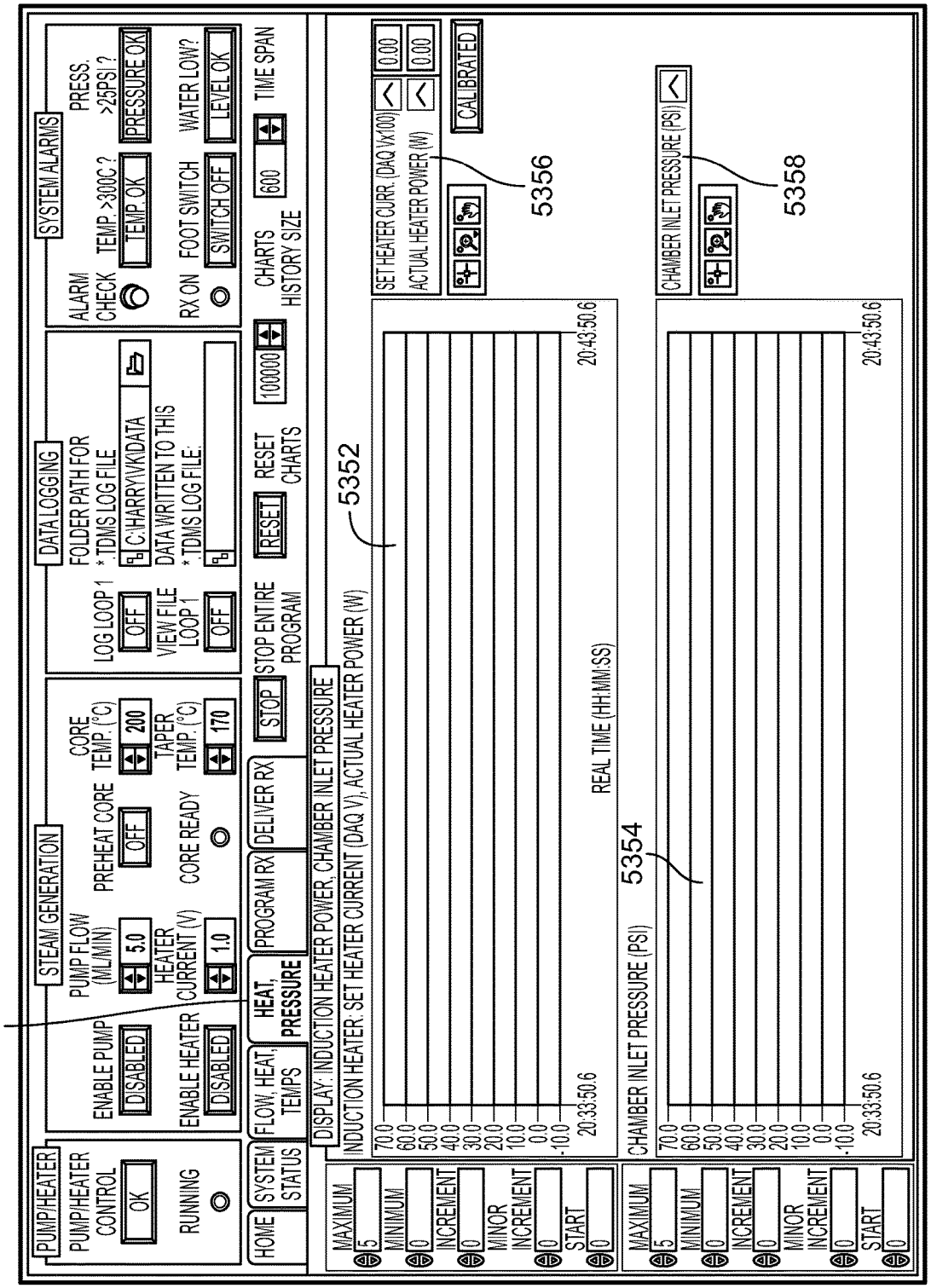
Figure 54:
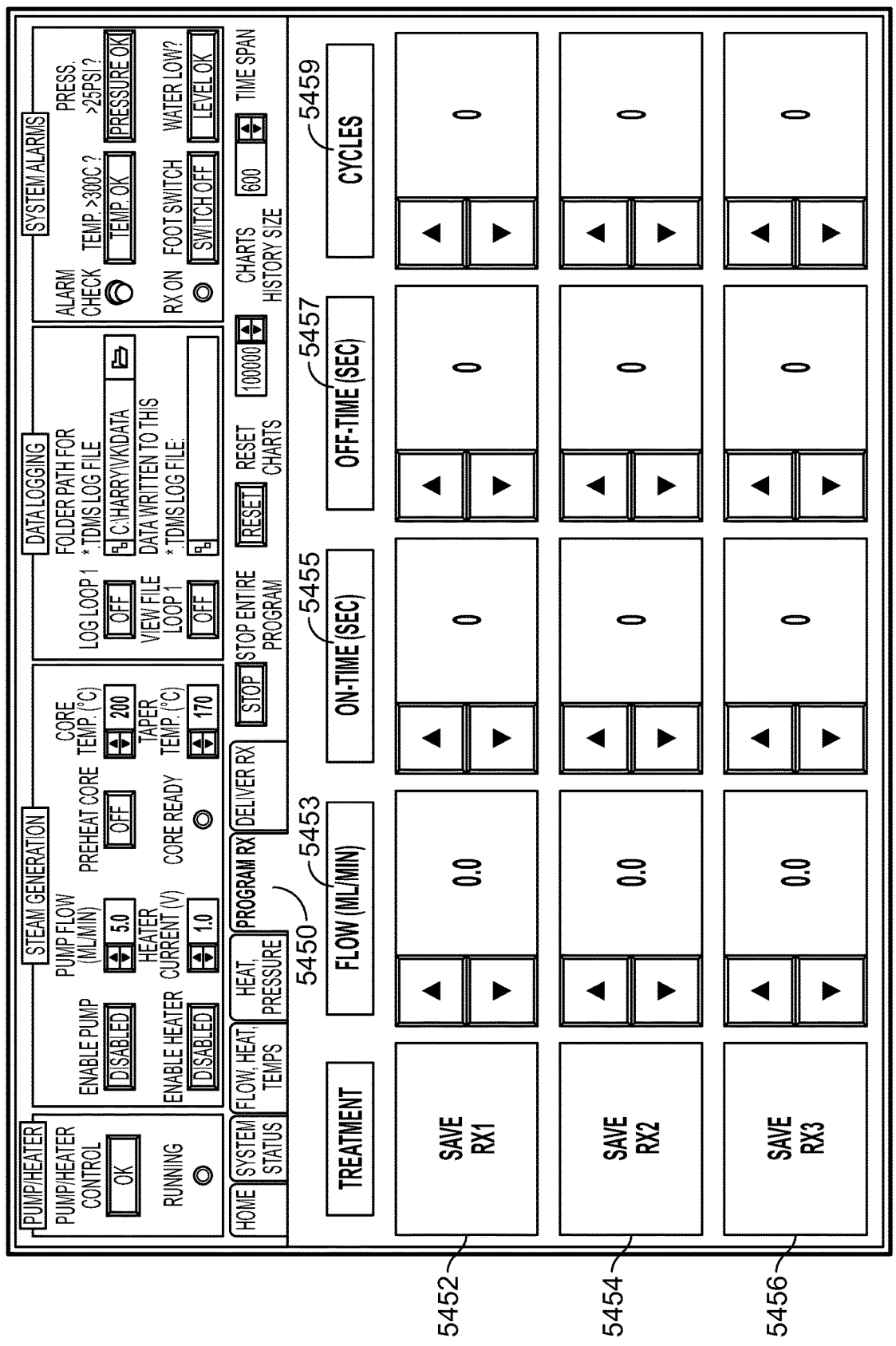
Figure 55:
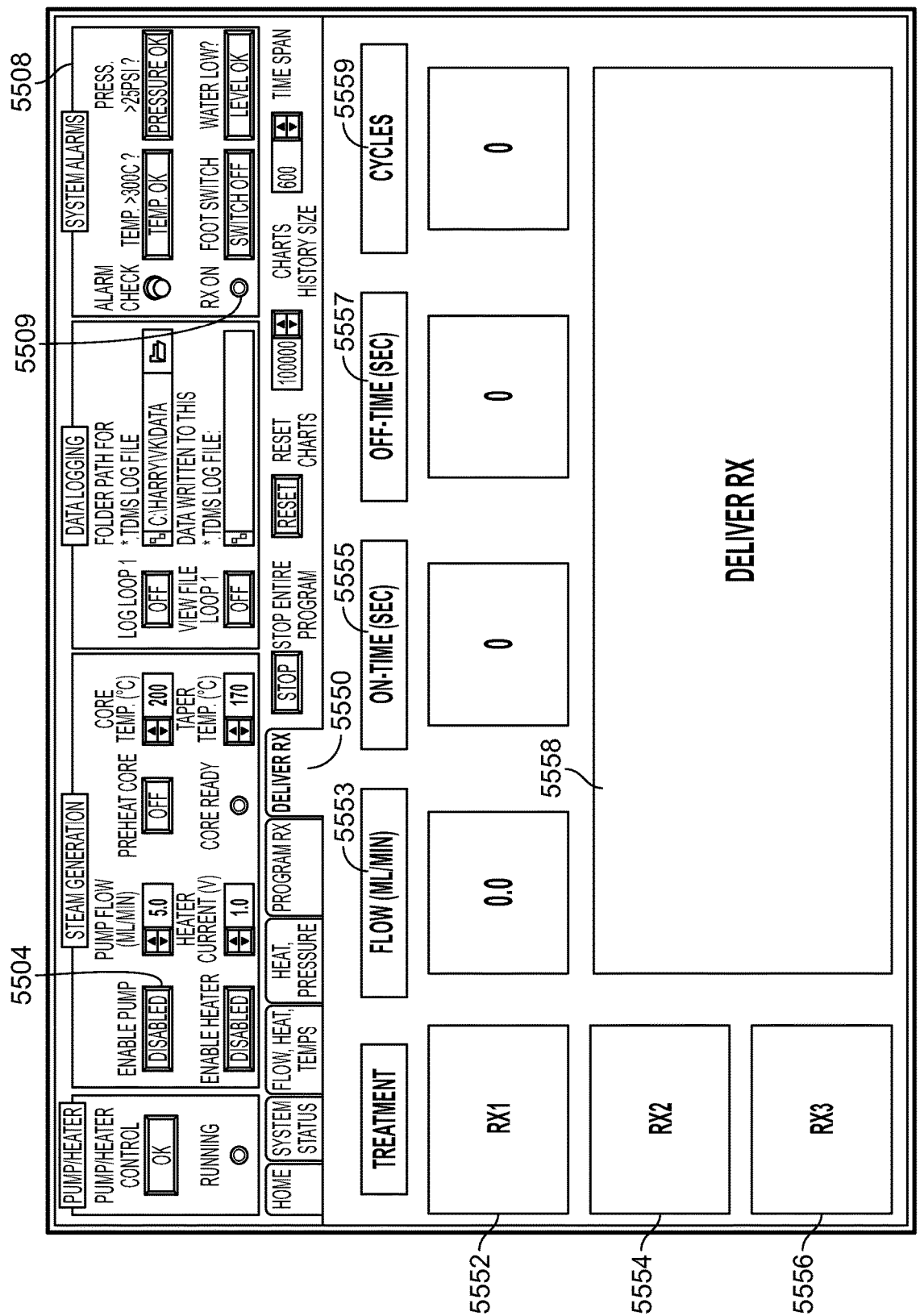

FIG. 41A is an illustration of the components of a vapor ablation system in accordance with one embodiment of the present specification;

FIG. 41B is an illustration of the vapor ablation system of FIG. 41A with the heating chamber cover removed;

FIG. 41C is a close-up illustration of the uncovered heating chamber of the vapor ablation system of FIG. 41B;

FIG. 41D is an illustration of the vapor ablation system of FIG. 41A with the covers removed from the system components;

FIG. 41E is a close-up illustration of the dosing pump and heavy-gauge steel enclosure of the vapor ablation system of FIG. 41A;

FIG. 41F is a close-up illustration of the dosing pump, with intake port and discharge ports, of the vapor ablation system of FIG. 41A;

FIG. 41G is a close-up illustration of the main electronics board with ancillary electronics within the heavy-gauge steel enclosure of the vapor ablation system of FIG. 41A;

FIG. 41H is a block diagram of the induction heater drive electronics in accordance with one embodiment of the present specification;

FIG. 41I is a graph illustrating waveforms generated by the induction heater drive electronics depicted in FIG. 41H;

FIG. 41J is an illustration of a triac phase control circuit of the induction heater drive electronics depicted in FIG. 41H;

FIG. 42 is an illustration of eddy currents induced by an alternating electromagnetic field;

FIG. 43 is a graph illustrating the variation in magnetic hysteresis between different ferromagnetic materials;

FIG. 44 is an illustration depicting a variety metal rods and a covering tube for an induction heating chamber in accordance with some embodiments of the present specification;

FIG. 45 is an illustration of a metal rod having a threaded outer surface and a tube having a threaded inner surface for a heating chamber in accordance with one embodiment of the present specification;

FIG. 46A is an illustration of a smooth metal rod and a tube of a heating chamber in accordance with one embodiment of the present specification;

FIG. 46B is a top-down illustration of the metal rod positioned within the tube of the heating chamber of FIG. 46A;

FIG. 46C is a flow chart illustrating the steps involved in generating steam using an induction heated metal core, in accordance with one embodiment of the present specification;

FIG. 47 is an illustration of a distal end of a metal rod of a heating chamber with a thermocouple positioned therein;

FIG. 48A is an illustration of a tube of a heating chamber and a thermocouple sheath in accordance with one embodiment of the present specification;

FIG. 48B is an illustration of the tube of FIG. 48A with the thermocouple sheath positioned within the cutout;

FIG. 48C is an illustration of the tube and thermocouple sheath of FIG. 48B with first and second flanges positioned over said tube and sheath in accordance with one embodiment of the present specification;

FIG. 48D is an illustration of the tube, sheath, and flanges of FIG. 48C with a thermal compound applied to the components in accordance with one embodiment of the present specification;

FIG. 48E is an illustration of the tube, sheath, flanges, and thermal compound of FIG. 48D with an induction coil wrapped about said tube and sheath;

FIG. 49A is an illustration of the distal end of a heating chamber depicting a lead of a thermocouple positioned within the metal core of the chamber in accordance with one embodiment of the present specification;

FIG. 49B is an illustration of a manifold configured to route the leads of a heating core thermocouple in accordance with one embodiment of the present specification;

FIG. 49C is an illustration of the manifold of FIG. 49B with a compression screw positioned in the left section;

FIG. 49D is a top-down illustration of the manifold of FIG. 49C depicting the routes taken by the thermocouple leads within the manifold as they exit the fluid pathway;

FIG. 49E is an illustration of the manifold of FIG. 49D with a luer lock connector attached to the distal end of the manifold;

FIG. 49F is an illustration of the manifold of FIG. 49E depicting the luer lock connector and adapter wrapped in a thermally insulating material;

FIG. 49G is a schematic diagram of a thermocouple analog front end in accordance with one embodiment of the present specification;

FIG. 49H is a flowchart listing the steps involved in regulating steam temperature and vapor ablation system stability, in accordance with one embodiment of the present specification;

FIG. 49I is a block diagram illustrating a vapor ablation kit comprising a handheld induction heating mechanism in accordance with one embodiment of the present specification;

FIG. 49J is an illustration of a vapor ablation kit comprising a water reservoir, heating chamber, and catheter, in accordance with another embodiment of the present specification;

FIG. 50 is a screenshot of a graphical user interface (GUI) home screen in accordance with one embodiment of the present specification;

FIG. 51 is a screenshot of a graphical user interface (GUI) system status screen in accordance with one embodiment of the present specification;

FIG. 52 is a screenshot of a graphical user interface (GUI) flow, heat, temps screen in accordance with one embodiment of the present specification;

FIG. 53 is a screenshot of a graphical user interface (GUI) heat, pressure screen in accordance with one embodiment of the present specification;

FIG. 54 is a screenshot of a graphical user interface (GUI) program Rx screen in accordance with one embodiment of the present specification; and FIG. 55 is a screenshot of a graphical user interface (GUI) deliver Rx screen in accordance with one embodiment of the present specification.

DETAILED DESCRIPTION

The present specification is directed toward an ablation device comprising a catheter with one or more centering or positioning attachments at one or more ends of the catheter to affix the catheter and its infusion port at a fixed distance from the ablative tissue which is not affected by the movements of the organ. The arrangement of one or more spray ports allows for uniform spray of the ablative agent producing a uniform ablation of a large area, such as encountered in Barrett's esophagus or for endometrial ablation. The flow of ablative agent is controlled by the microprocessor and depends upon one or more of the length or area of tissue to be ablated, type and depth of tissue to be ablated, and distance of the infusion port from or in the tissue to be ablated.

The present specification is also directed toward a disposable steam generation system which enables the real-time, on demand generation of micro-dose amounts of steam. The disposable portion comprises a water source, such as a syringe or bag, in fluid communication with a heating chamber which is in fluid communication with a catheter. The disposable, single-use water source-heating chamber-catheter series of connected components is designed to reliably deliver steam without worrying about the sterility of the water, contamination arising from multiple uses, the cost and/or logistics of cleaning, or the risk of leakage of vapor causing injury to the operator.

The present specification is also directed toward a device to be used in conjunction with a tissue ablation system, comprising: a handle with a pressure-resistant port on its distal end, a flow channel through which an ablative agent can travel, and one or more connection ports on its proximal end for the inlet of said ablative agent and for an RF feed or an electrical feed; an insulated catheter that attaches to said pressure-resistant port of said handle, containing a shaft through which an ablative agent can travel and one or more ports along its length for the release of said ablative agent; and, one or more positioning elements attached to said catheter shaft at one or more separate positions, wherein said positioning element(s) is configured to position said catheter at a predefined distance from or in the tissue to be ablated.

In one embodiment, the handle has one pressure-resistant port for the attachment of both an ablative agent inlet and an RF feed. In another embodiment, the handle has one separate pressure-resistant port for the attachment of an ablative agent inlet and one separate port for the attachment of an RF feed or an electrical feed.

The present specification is also directed toward a device to be used in conjunction with a tissue ablation system, comprising: a handle with a pressure-resistant port on its distal end, a flow channel passing through said handle which is continuous with a pre-attached cord through which an ablative agent can travel, and a connection port on its proximal end for an RF feed or an electrical feed; an insulated catheter that attaches to said pressure-resistant port of said handle, containing a shaft through which an ablative agent can travel and one or more ports along its length for the release of said ablative agent; and, one or more positioning elements attached to said catheter shaft at one or more separate positions, wherein said positioning element(s) is configured to position said catheter at a predefined distance from or in the tissue to be ablated. In one embodiment, the distal end of said catheter is designed to puncture the target tissue to deliver ablative agent to the correct depth and location.

The present specification is also directed toward a device to be used in conjunction with a tissue ablation system, comprising: an esophageal probe with a pressure-resistant port on its distal end, a flow channel through which an ablative agent can travel, and one or more connection ports on its proximal end for the inlet of said ablative agent and for an RF feed; an insulated catheter that attaches to said pressure-resistant port of said esophageal probe, containing a shaft through which an ablative agent can travel and one or more ports along its length for the release of said ablative agent; and, one or more inflatable positioning balloons at either end of said catheter positioned beyond said one or more ports, wherein said positioning balloons are configured to position said catheter at a predefined distance from the tissue to be ablated.

In one embodiment, the catheter is dual lumen, wherein a first lumen facilitates the transfer of ablative agent and a second lumen contains an electrode for RF ablation.

In one embodiment, the catheter has differential insulation along its length.

In one embodiment, the one or more balloons are filled with air which is in thermal contact with the ablative agent being delivered such that the air expands during the delivery of ablative agent and contracts after the cessation of delivery of the ablative agent. This results in a first volume of the balloon prior to the initiation of therapy which is used for measurement of the dimensions of the hollow organ. The volume of the balloon increases to a second volume during the initiation of therapy which serves an occlusive function to better control the distribution of ablative energy. In various embodiments, the second volume is greater than the first volume.

In one embodiment, the volume of the inner balloon is used to control the pressure exerted by the outer balloon on the wall of the hollow organ. The pressure in the inner balloon is monitored and air is added to or removed from the inner balloon to maintain a desirable therapeutic pressure in the outer balloon.

The present specification is also directed toward a vapor delivery system used for supplying vapor to an ablation device, comprising: a liquid reservoir, wherein said reservoir includes a pressure-resistant outlet connector for the attachment of a reusable cord; a reusable cord connecting the outlet of said reservoir to the inlet of a heating component; a powered heating component containing a length of coiled tubing within for the conversion of liquid to vapor and pressure-resistant connections on both the inlet and outlet ends of said heating component; and, a single use cord connecting a pressure-resistant inlet port of a vapor based ablation device to the outlet of said heating component.

In one embodiment, the liquid reservoir is integrated within an operating room equipment generator.

In one embodiment, the liquid is water and resultant said vapor is steam.

In one embodiment, the pressure-resistant connections are of a luer lock type.

In one embodiment, the coiled tubing is copper.

In one embodiment, the vapor delivery system used for supplying vapor to an ablation device further comprises a foot pedal used by the operator to deliver more vapor to the ablation device.

The present specification is also directed toward a device and a method for ablating a hollow tissue or organ by replacing the natural contents of the tissue or organ with a conductive medium and then delivering an ablative agent to the conductive medium to ablate the tissue or organ.

The present specification is also directed toward a device and method for ablating a blood vessel consisting of replacing the blood in the targeted vessel with a conductive medium and then delivering an ablative agent to the conductive medium to ablate the vessel. In one embodiment, the device and method further comprise a means or step for stopping the flood of blood into the target vessel. In one embodiment, blood flow is occluded by the application of a tourniquet proximal to the target vessel. In another embodiment, blood flow is occluded by the application of at least one intraluminal occlusive element. In one embodiment, the at least one intraluminal occlusive element includes at least one unidirectional valve. In one embodiment, the intraluminal occlusive element is used to position the source or port delivering the ablative agent in the vessel.

The present specification is also directed toward a device and a method for ablating a cyst by inserting a catheter into the cyst, replacing a portion of the contents of the cyst with a conductive medium, adding an ablative agent to the conductive medium, and conducting ablative energy to the cyst wall through the medium to ablate the cyst.

The present specification is also directed toward a device and a method for ablating a tumor by inserting a catheter into the tumor, replacing a portion of the contents of the tumor with a conductive medium, adding an ablative agent to the conductive medium, and conducting ablative energy to the tumor wall through the medium to ablate the tumor.

The present specification is also directed toward a device and method for ablating a structure in or proximate the wall of a hollow organ by inserting a catheter with a thermally insulating balloon at a distal end into the hollow organ and proximate the structure to be ablated, inflating the balloon to a pre-determined volume with air such that a surface of the balloon becomes positioned proximate said wall, and delivering thermal energy through a thermally conducting member in the balloon and into said structure. The balloon includes a thermally conductive member for the conduction of thermal energy from inside of the balloon to the wall of the hollow organ. The passage of thermal energy into the balloon heats the air in the balloon, further expanding the balloon and forcing the thermally conducting member into the wall of the hollow organ and simultaneously delivering thermal energy to said wall. In various embodiments, the thermally conductive member comprises a solid or hollow needle. In various embodiments, the thermally conductive member further comprises a valve which is regulated by temperature, pressure or both.

In various embodiments, any one of the devices described above comprises a catheter and includes at least one port for delivering the conductive medium and at least one separate port for delivering the ablative agent. In another embodiment, the device comprises a catheter and includes at least one port for delivering both the conductive medium and the ablative agent. Optionally, in one embodiment, the device further includes at least one port for removing the contents of the hollow organ or tissue or for removing the conductive medium. In various embodiments, the at least one port for removing contents or conductive medium is the same port for delivering the conductive medium and/or ablative agent or is a separate port. In one embodiment, the ablative agent is a thermal agent, such as steam. In another embodiment, the ablative agent is a cryogen, such as liquid nitrogen.

Optionally, in one embodiment, sensors are included in the device to measure and control the flow of the ablative agent. In one embodiment, conductive medium is water. In another embodiment, the conductive medium is saline.

In various embodiments, any one of the devices described above comprises a coaxial catheter having an outer, insulating sheath and an inner tubular member for delivery of the conductive medium and the ablative agent. In various embodiments, the inner tubular member is thermally insulating.

Optionally, in various embodiments, any one of the devices described above includes echogenic elements to assist with the placement of the device into the target tissue under ultrasonic guidance. Optionally, in various embodiments, any one of the devices described above includes radio-opaque elements to assist with the placement of the device into the target tissue under radiologic guidance.

The present specification is also directed toward a system and method of internal hemorrhoid ablation by inserting a hollow, tubular device into a patient's rectum, applying suction to the device to draw the target hemorrhoid tissue into a slot in the device, and delivering an ablative agent, such as steam, through a port in the device to ablate the hemorrhoid. In one embodiment, the system includes a device composed of a thermally insulated material to avoid transfer of vapor heat to surrounding rectal mucosa. In another embodiment, the system has a mechanism for puncturing the mucosa to deliver the ablative agent directly into the submucosa closer to the hemorrhoid. In another embodiment, the system has a mechanism for cooling the mucosa so as to reduce the ablative damage to the mucosa.

The present specification is also directed toward a system and method of internal hemorrhoid ablation by inserting a hollow, tubular device into a patient's rectum, applying suction to the device to draw the target hemorrhoid tissue into a slot in the device, inserting a needle through the slot and into the rectal submucosa or the wall of the hemorrhoid vessel, and delivering an ablative agent through the needle to ablate the hemorrhoid.

The present specification is also directed toward a system and method of internal hemorrhoid ablation by inserting a device into a patient's anal canal, thus opening said anal canal, identifying the abnormal hemorrhoid tissue, engaging said hemorrhoid tissue with the device, compressing said hemorrhoid tissue to reduce its cross-sectional area, and delivering ablative energy to the hemorrhoid tissue to ablate the hemorrhoid.

The present specification is also directed toward a device and method for endometrial treatment by inserting a coaxial catheter comprising an internal catheter and an external catheter into the cervix, wherein the external catheter engages the cervix and the internal catheter extends into the uterus. The internal catheter continues until it reaches the fundus of the uterus, at which point the depth of insertion of the internal catheter is used to measure the depth of the uterine cavity. An ablative agent, such as steam, is then delivered via the at least one port on the internal catheter to provide treatment to the endometrium. Optionally, in various embodiments, the catheter includes pressure sensors and/or temperature sensors to measure the intrauterine pressure or temperature. Optionally, in one embodiment, the external catheter further comprises a plurality of fins which engage the cervix and prevent the escape of ablative agent. In one embodiment, the fins are composed of silicon. Optionally in one embodiment, the coaxial catheter further includes a locking mechanism between the external catheter and internal catheter that, when engaged, prevents the escape of ablative agent. In one embodiment, the locking mechanism is of a luer lock type. Optionally, the flow of ablative agent is controlled by the number of open ports which in turn is controlled by the length of the exposed internal catheter.

The present specification is also directed toward a device and method for endometrial ablation using a balloon catheter with a plurality of coaxial balloon structures wherein an inner balloon is a compliant balloon structure and an outer balloon is a non-compliant balloon structure shaped to approximate the uterine cavity shape, size or volume. The inflation of the inner balloon with air results in expansion of the outer balloon to approximate the endometrial cavity. An ablative agent is passed through a space between the two balloons. Thermal energy from the ablative agent is delivered through the outer balloon into the endometrial cavity. In various embodiments, the outer balloon is porous, allowing the passage of vapor and thermal energy, or non-porous, allowing the passage of thermal energy only. The passage of thermal energy between the two balloons leads to expansion of the air in the inner balloon, further approximating the outer balloon shape closer to the endometrium for more efficient thermal energy delivery during therapy. The air cools when ablative energy is not being delivered, relieving the pressure on the outer balloon and the endometrial cavity and preventing endometrial perforation from prolonged overexpansion. In another embodiment, the outer balloon is partially compliant. In another embodiment, the compliance of the two balloons is substantially equivalent.

The present specification is also directed toward device and method for tissue ablation comprising a stent covered by a membrane that conducts an ablative agent, such as steam, or ablative energy from inside the stent lumen to the external surface of the stent for ablation of surrounding tissue. In one embodiment, the stent has a pre-deployment shape and a post-deployment shape. The pre-deployment shape is configured to assist with placement of the stent. In one embodiment, the membrane is composed of a thermally conductive material. In one embodiment, the membrane includes a plurality of openings that allow for the passage of ablative agent or energy from the stent lumen to the tissue surrounding the stent. In one embodiment, the stent is used to treat obstruction in a hollow organ. In one embodiment, the membrane is made of a thermally conductive material that allows for transfer of energy from the inside of the stent to the outside of the stent into the surrounding tissue.

In one embodiment, a catheter is used to deliver the ablative agent to the stent. The catheter includes at least one port at its distal end for the delivery of ablative agent into the lumen of the stent. In one embodiment, the catheter includes one or more positioning elements configured to fix the catheter at a predefined distance from the stent. The positioning element(s) also acts as an occlusive member to prevent the flow of ablative agent out of the ends of the stent. In one embodiment, the catheter is composed of a thermally insulating material. Optionally, in various embodiments, the catheter includes additional lumens for the passage of a guidewire or radiologic contrast material.

The present specification is also directed toward a device and method for transrectal prostate ablation. An endoscope is inserted into the rectum for visualization of the prostate. In one embodiment, the endoscope is an echoendoscope. In another embodiment, the visualization is achieved via transrectal ultrasound. A catheter with a needle tip is passed transrectally into the prostate and an ablative agent, such as vapor, is delivered through the needle tip and into the prostatic tissue. The prostatic tissue chosen is ideally away from the prostatic urethra to avoid damage to the prostatic urethra. In one embodiment, the needle tip is an echotip or sonolucent tip that can be detected by the echoendoscope to aid in placement within the prostatic tissue. In one embodiment, the catheter and needle tip are composed of a thermally insulating material. Optionally, in one embodiment, an additional catheter is placed in the patient's urethra to insert fluid to cool the prostatic urethra. In one embodiment, the cooling fluid has a temperature of less than 37° C. Optionally, in one embodiment, the catheter further comprises a positioning element which positions the needle tip at a predetermined depth in the prostatic tissue. In one embodiment, the positioning element is a compressible disc.

The present specification is also directed toward an ablation catheter assembly comprising a catheter body, a first inline chamber for heating an ablative agent, and a second inline chamber for storing said ablative agent. A pump drives a piston located within the second inline chamber to push a fluid through a one-way valve and into the first inline chamber. A heating element heats the first inline chamber, converting the fluid from a liquid into a vapor. The vapor then travels through the catheter and is delivered to the target tissue site for ablation. In various embodiments, the first chamber is composed of a ferromagnetic or thermally conducting material. In one embodiment, the pump is controlled by a microprocessor to deliver ablative agent at a predetermined rate. In one embodiment, sensors in the catheter provide information microprocessor to control the delivery rate. In one embodiment, the catheter includes an insulated handle to allow for safe manipulation of the catheter assembly by an operator. In various embodiments, the heating element is a resistive heater, RF heater, microwave heater, or electromagnetic heater.

In various embodiments, the first inline chamber comprises a plurality of channels within to increase the contact surface area of the ablative agent with the walls of the chamber to provide for more efficient heating of said agent. In various embodiments, the channels comprise metal tubes, metal beads, or metal filings. In various embodiments, the chamber has adequate thermal mass to maintain the chamber at a constant temperature (+/−25% of ideal temperature) during heating of the ablative agent. In one embodiment, the inner surface of the catheter includes a groove pattern to reduce the resistance to flow of the ablative agent within the catheter. In one embodiment, the catheter comprises two walls, an inner wall and an outer wall, with a thin insulating layer in between, to insulate the catheter and prevent thermal trauma to an operator from the heated ablative agent within said catheter.

In various embodiments, the ablation devices and catheters described in the present specification are used in conjunction with any one or more of the heating systems described in U.S. patent application Ser. No. 13/486,980, entitled "Method and Apparatus for Tissue Ablation", filed on Jun. 1, 2012 and assigned to the applicant of the present invention, which is herein incorporated by reference in its entirety.

"Treat," "treatment," and variations thereof refer to any reduction in the extent, frequency, or severity of one or more symptoms or signs associated with a condition.

"Duration" and variations thereof refer to the time course of a prescribed treatment, from initiation to conclusion, whether the treatment is concluded because the condition is resolved or the treatment is suspended for any reason. Over the duration of treatment, a plurality of treatment periods may be prescribed during which one or more prescribed stimuli are administered to the subject.

"Period" refers to the time over which a "dose" of stimulation is administered to a subject as part of the prescribed treatment plan.

The term "and/or" means one or all of the listed elements or a combination of any two or more of the listed elements.

The terms "comprises" and variations thereof do not have a limiting meaning where these terms appear in the description and claims.

Unless otherwise specified, "a," "an," "the," "one or more," and "at least one" are used interchangeably and mean one or more than one.

For any method disclosed herein that includes discrete steps, the steps may be conducted in any feasible order. And, as appropriate, any combination of two or more steps may be conducted simultaneously.

Also herein, the recitations of numerical ranges by endpoints include all numbers subsumed within that range (e.g., 1 to 5 includes 1, 1.5, 2, 2.75, 3, 3.80, 4, 5, etc.). Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present specification. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the specification are approximations, the numerical values set forth in the specific examples are reported as precisely as possible. All numerical values, however, inherently contain a range necessarily resulting from the standard deviation found in their respective testing measurements.

Ablative agents such as steam, heated gas or cryogens, such as, but not limited to, liquid nitrogen are inexpensive and readily available and are directed via the infusion port onto the tissue, held at a fixed and consistent distance, targeted for ablation. This allows for uniform distribution of the ablative agent on the targeted tissue. The flow of the ablative agent is controlled by a microprocessor according to a predetermined method based on the characteristic of the tissue to be ablated, required depth of ablation, and distance of the port from the tissue. The microprocessor may use temperature, pressure or other sensing data to control the flow of the ablative agent. In addition, one or more suction ports are provided to suction the ablation agent from the vicinity of the targeted tissue. The targeted segment can be treated by a continuous infusion of the ablative agent or via cycles of infusion and removal of the ablative agent as determined and controlled by the microprocessor.

It should be appreciated that the devices and embodiments described herein are implemented in concert with a controller that comprises a microprocessor executing control instructions. The controller can be in the form of any computing device, including desktop, laptop, and mobile device, and can communicate control signals to the ablation devices in wired or wireless form.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

FIG. 1A illustrates an ablation device, in accordance with an embodiment of the present specification. The ablation device comprises a catheter 10 having a distal centering or positioning attachment which is an inflatable balloon 11. The catheter 10 is made of or covered with an insulated material to prevent the escape of ablative energy from the catheter body. The ablation device comprises one or more infusion ports 12 for the infusion of ablative agent and one or more suction ports 13 for the removal of ablative agent. In one embodiment, the infusion port 12 and suction port 13 are the same. In one embodiment, the infusion ports 12 can direct the ablative agent at different angles. Ablative agent is stored in a reservoir 14 connected to the catheter 10. Delivery of the ablative agent is controlled by a microprocessor 15 and initiation of the treatment is controlled by a treating physician using an input device, such as a foot-paddle 16. In other embodiments, the input device could be a voice recognition system (that is responsive to commands such as "start", "more", "less", etc.), a mouse, a switch, footpad, or any other input device known to persons of ordinary skill in the art. In one embodiment, microprocessor 15 translates signals from the input device, such as pressure being placed on the foot-paddle or vocal commands to provide "more" or "less" ablative agent, into control signals that determine whether more or less ablative agent is dispensed. Optional sensor 17 monitors changes in an ablative tissue or its vicinity to guide flow of ablative agent. In one embodiment, optional sensor 17 also includes a temperature sensor. Optional infrared, electromagnetic, acoustic or radiofrequency energy emitters and sensors 18 measure the dimensions of the hollow organ.

In one embodiment, a user interface included with the microprocessor 15 allows a physician to define device, organ, and condition which in turn creates default settings for temperature, cycling, volume (sounds), and standard RF settings. In one embodiment, these defaults can be further modified by the physician. The user interface also includes standard displays of all key variables, along with warnings if values exceed or go below certain levels.

The ablation device also includes safety mechanisms to prevent users from being burned while manipulating the catheter, including insulation, and optionally, cool air flush, cool water flush, and alarms/tones to indicate start and stop of treatment.

In one embodiment, the inflatable balloon has a diameter of between 1 mm and 10 cm. In one embodiment, the inflatable balloon is separated from the ports by a distance of 1 mm to 10 cm. In one embodiment, the size of the port openings is between 1 μm and 1 cm. It should be appreciated that the inflatable balloon is used to fix the device and therefore is configured to not contact the ablated area. The inflatable balloon can be any shape that contacts the hollow organ at 3 or more points. One of ordinary skill in the art will recognize that, using triangulation, one can calculate the distance of the catheter from the lesion. Alternatively, the infrared, electromagnetic, acoustic or radiofrequency energy emitters and sensors 18 can measure the dimensions of the hollow organ. The infrared, electromagnetic, acoustic or radiofrequency energy is emitted from the emitter 18 and is reflected back from the tissue to the detector in the emitter 18. The reflected data can be used to determine the dimension of the hollow cavity. It should be appreciated that the emitter and sensor 18 can be incorporated into a single transceiver that is capable of both emitting energy and detecting the reflected energy.

FIG. 1B illustrates another embodiment of a catheter 110 for use with the ablation device of FIG. 1A. The catheter 110 includes an inlet port 119 and an insufflation port 120 at its proximal end. An ablative agent is introduced into the catheter 110 via the inlet port 119 and is delivered to a target region by at least one delivery port 112 at the distal end of the catheter 110. Air is introduced at the insufflation port 120 to inflate at least one positioning element 111 at the distal end of the catheter. In one embodiment, the at least one positioning element 111 is a balloon.

FIG. 2A illustrates a longitudinal section of the ablation device, depicting a distribution of infusion ports. FIG. 2B illustrates a cross section of a distribution of infusion ports on the ablation device, in accordance with an embodiment of the present specification. The longitudinal and cross sectional view of the catheter 10 as illustrated in FIGS. 2A and 2B respectively, show one arrangement of the infusion ports 12 to produce a uniform distribution of ablative agent 21 in order to provide a circumferential area of ablation in a hollow organ 20. FIG. 2C illustrates a cross section of a distribution of infusion ports on the ablation device, in accordance with another embodiment of the present specification. The arrangement of the infusion ports 12 as illustrated in FIG. 2C produce a focal distribution of ablative agent 21 and a focal area of ablation in a hollow organ 20.

For all embodiments described herein, it should be appreciated that the size of the port, number of ports, and distance between the ports will be determined by the volume of ablative agent needed, pressure that the hollow organ can withstand, size of the hollow organ as measured by the distance of the surface from the port, length of the tissue to be ablated (which is roughly the surface area to be ablated), characteristics of the tissue to be ablated and depth of ablation needed. In one embodiment, there is at least one port opening that has a diameter between 1 μm and 1 cm. In another embodiment, there are two or more port openings that have a diameter between 1 μm and 1 cm and that are equally spaced around the perimeter of the device. In some embodiments, the ports optionally have valves for the control of release of the ablative agent. In various embodiments, the valves are regulated either by pressure, temperature, or both.

Figure 2D:
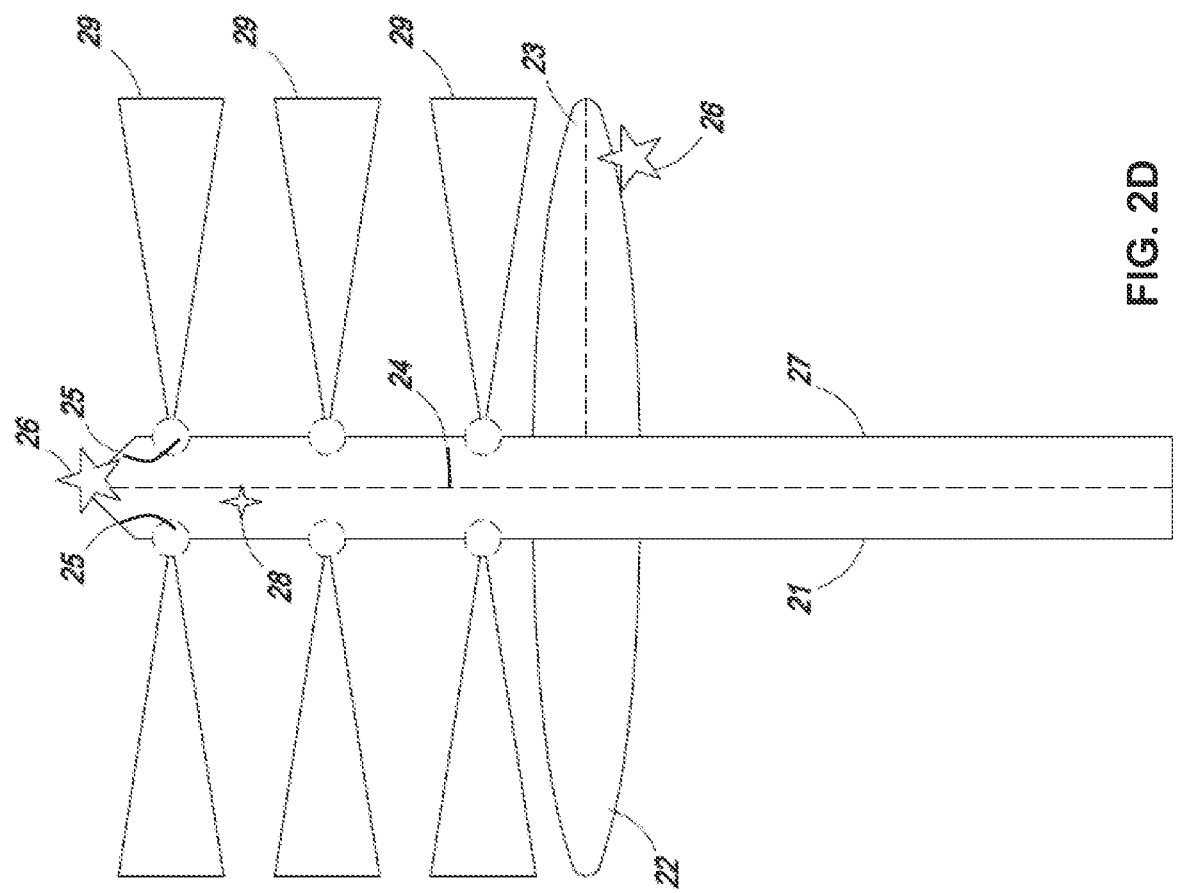
FIG. 2D illustrates a catheter of the ablation device, in accordance with an embodiment of the present specification.

FIG. 2D illustrates another embodiment of the ablation device. The vapor ablation catheter comprises an insulated catheter 21 with one or more positioning attachments 22 of known length 23. The vapor ablation catheter has one or more vapor infusion ports 25. The length 24 of the vapor ablation catheter 21 with infusion ports 25 is determined by the length or area of the tissue to be ablated. Vapor 29 is delivered through the vapor infusion ports 25. The catheter 21 is preferably positioned in the center of the positioning attachment 22, and the infusion ports 25 are arranged circumferentially for circumferential ablation and delivery of vapor. In another embodiment, the catheter 21 can be positioned toward the periphery of the positioning attachment 22 and the infusion ports 25 can be arranged non-circumferentially, preferably linearly on one side for focal ablation and delivery of vapor. The positioning attachment 22 is one of an inflatable balloon, a wire mesh disc with or without an insulated membrane covering the disc, a cone shaped attachment, a ring shaped attachment or a freeform attachment designed to fit the desired hollow body organ or hollow body passage, as further described below. Optional infrared, electromagnetic, acoustic or radiofrequency energy emitters and sensors 28 are incorporated to measure the dimensions of the hollow organ.

The vapor ablation catheter may also comprise an optional coaxial sheet 27 to restrain the positioning attachment 22 in a manner comparable to a coronary metal stent. In one embodiment, the sheet is made of memory metal or memory material with a compressed linear form and a non-compressed form in the shape of the positioning attachment. Alternatively, the channel of an endoscope may perform the function of restraining the positioning attachment 22 by, for example, acting as a constraining sheath. Optional sensor 26 is deployed on the catheter to measure changes associated with vapor delivery or ablation. The sensor is one of temperature, pressure, photo or chemical sensor.

Optionally, one or more, infrared, electromagnetic, acoustic or radiofrequency energy emitters and sensors 28 can measure the dimensions of the hollow organ. The infrared, electromagnetic, acoustic or radiofrequency energy is emitted from the emitter 28 and is reflected back from the tissue to the detector in the emitter 28. The reflected data can be used to determine the dimension of the hollow cavity. The measurement is performed at one or multiple points to get an accurate estimate of the dimension of the hollow organ. The data can also be used to create a topographic representation of the hollow organ. Additional data from diagnostic tests can be used to validate or add to the data from the above measurements.

FIG. 2E illustrates a catheter 21 of the ablation device, in accordance with another embodiment of the present specification. The catheter 21 is similar to that described with reference to FIG. 2D, however, the catheter 21 of FIG. 2E additionally includes at least one port 19 for the delivery of a conductive medium 31. In one embodiment, the conductive medium 31 is injected into the hollow tissue or organ prior to the introduction of the ablative agent 29. Once the tissue has been filled to an appropriate level with the conductive medium 31, ablative agent 29 is then delivered into the conductive medium 31 filled tissue. The conductive medium 31 acts to evenly distribute the ablative agent 29, resulting in more consistent and effective ablation of the target tissue.

Figure 2F:
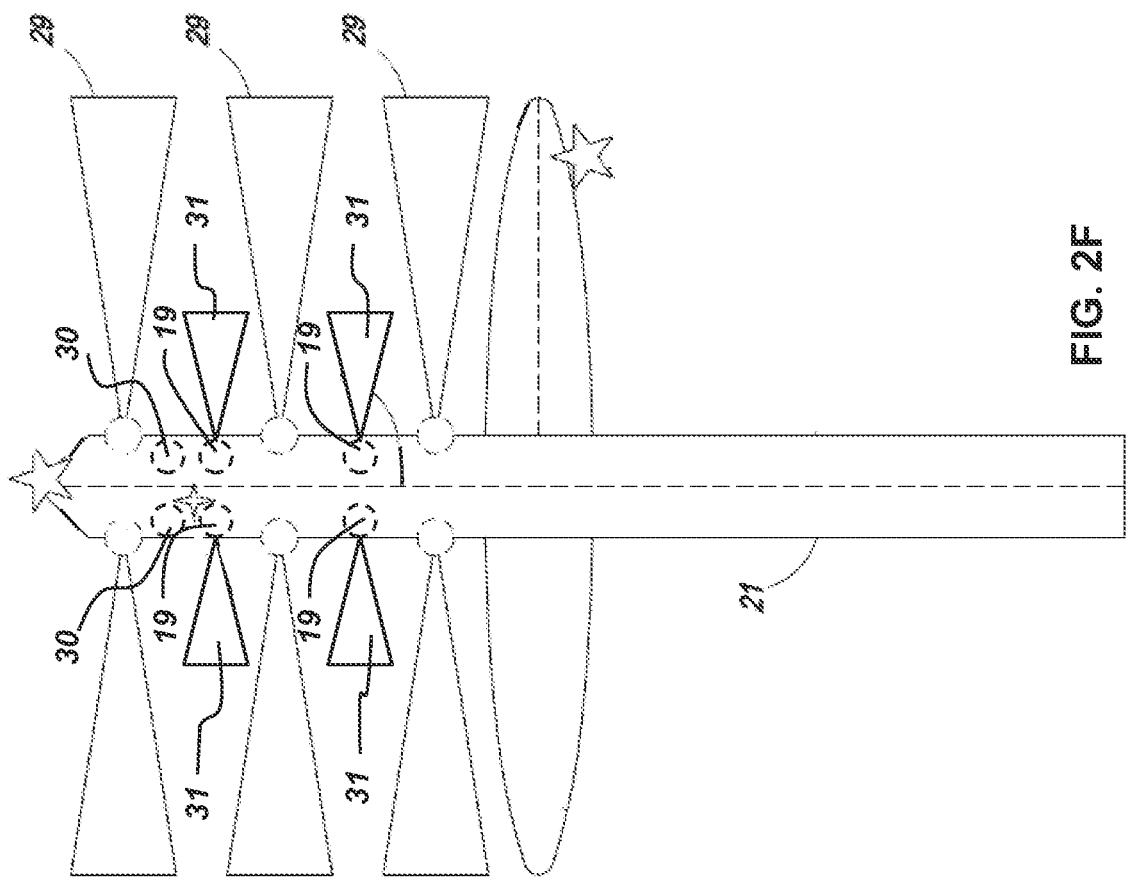
FIG. 2F illustrates a catheter of the ablation device, in accordance with yet another embodiment of the present specification.

FIG. 2F illustrates a catheter 21 of the ablation device, in accordance with yet another embodiment of the present specification. The catheter 21 is similar to that described with reference to FIG. 2E, however, the catheter 21 of FIG. 2F additionally includes at least one port 30 for the removal via suction of the natural contents of the hollow tissue or organ. In one embodiment, the natural contents of the hollow tissue or organ are removed prior to the introduction of the conductive medium 31 or the ablative agent 29.

In another embodiment, as depicted in FIG. 2E, wherein the catheter includes at least one port 25 for the delivery of ablative agent and at least one other port 19 for the delivery of a conductive medium, the natural contents of the hollow tissue or organ can be removed via suction using the ablative agent delivery port 25. In another embodiment, as depicted in FIG. 2E, wherein the catheter includes at least one port 25 for the delivery of ablative agent and at least one other port 19 for the delivery of a conductive medium, the natural contents of the hollow tissue or organ can be removed via suction using the conductive medium delivery port 19. In yet another embodiment, as depicted in FIG. 2D, the conductive medium can be delivered, and, the natural contents of the hollow tissue or organ can be removed via suction, using the ablative agent delivery port 25. In various embodiments, after ablation of the target tissue(s), the remaining contents of the hollow tissue or organ are removed via suction using one or more of the ports described above.

In various embodiments, with respect to the catheters depicted in FIGS. 2A-2F, the ablative agent can be any one of steam, liquid nitrogen, or any other suitable ablative agent.

Figure 2G:
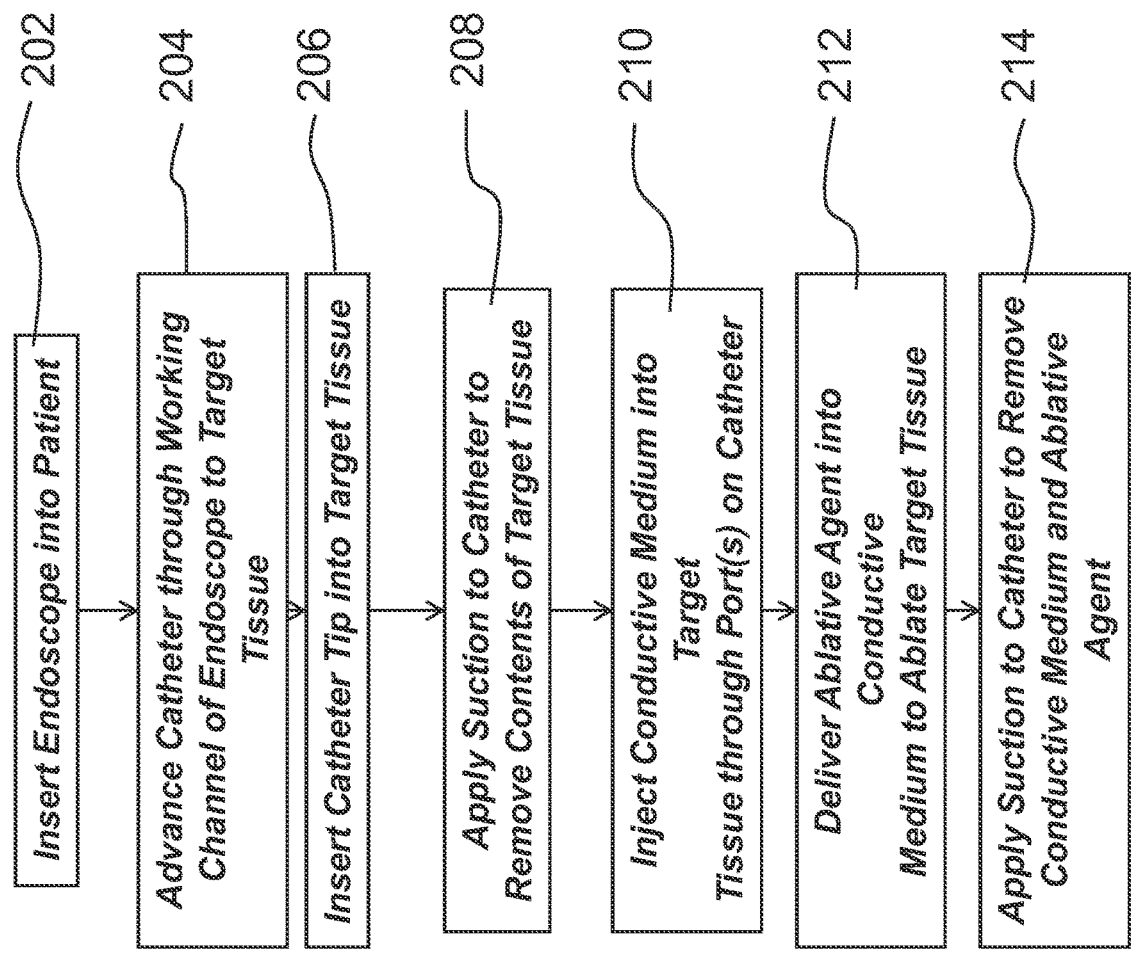
FIG. 2G is a flow chart listing the steps involved in a hollow tissue or organ ablation process using an ablation device, in accordance with one embodiment of the present specification.

FIG. 2G is a flow chart listing the steps involved in a hollow tissue or organ ablation process using the ablation device, in accordance with one embodiment of the present specification. At step 202, an endoscope is inserted into a patient. An ablation device comprising a catheter in accordance with one embodiment of the present specification, is advanced through a working channel of the endoscope and to a target tissue at step 204. At step 206, the distal end or tip of the catheter is inserted into the target hollow tissue or organ. Then, at step 208, suction is applied at the proximal end of the catheter to remove the natural contents of the hollow tissue or organ. A conductive medium is then injected, at step 210, into the hollow tissue or organ via at least one port on the distal end of the catheter. At step 212, an ablative agent is delivered into the conductive medium for ablation of the target tissue. At step 214, the remaining contents of the tissue, including conductive medium and ablative agent, are removed via suction using the catheter. In another embodiment, step 214 is optional, and the remaining contents of the hollow tissue or organ are reabsorbed by the body. In another embodiment, the removal of the natural contents of the hollow tissue or organ at step 208 is optional, and the procedure moves directly to the injection of conductive medium at step 210 from entering the target tissue with the catheter at step 206. Optionally, in some embodiments, the natural contents of the hollow organ can be used as the conductive media.

Figure 2H:
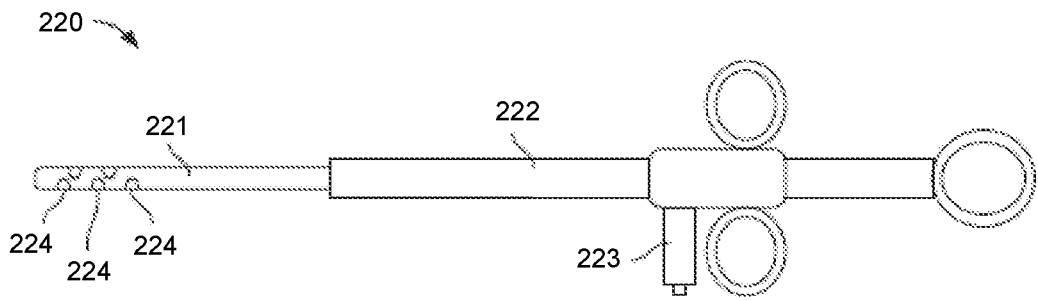
FIG. 2H illustrates an ablation device in the form of a catheter extending from a conventional snare handle, in accordance with an embodiment of the present specification.

FIG. 2H illustrates an ablation device 220 in the form of a catheter 221 extending from a conventional handle 222, in accordance with an embodiment of the present specification. The catheter 221 is of a type as described above and extends from and attaches to the handle 222. In one embodiment, the catheter 221 is insulated to protect the user from burns that could result from hot vapor heating the catheter. In one embodiment, the catheter is composed of a material that will ensure that the outer temperature of the catheter will remain below 60° C. during use. The handle 222 includes a pressure resistant port at the point of attachment with the catheter 221. The handle 222 also includes a flow channel within that directs vapor through to the catheter 221.

In one embodiment, the snare handle 222 includes a single attachment port 223 for the connection of a vapor stream and an RF feed. In another embodiment (not shown), the snare handle includes two separate attachment ports for the connection of a vapor stream and an RF feed. The attachment port 223 interfaces with the vapor supply cord via pressure-resistant connectors. In one embodiment, the connectors are of a luer lock type. In one embodiment, the catheter 221 is a dual lumen catheter. The first lumen serves to deliver vapor to the site of ablation. In one embodiment, the vapor is released through small ports 224 positioned proximate the distal end of the catheter 221. The distal end of the catheter 221 is designed so that it can puncture the tissue to deliver vapor to the desired depth and location within the target tissue. In one embodiment, the distal end of the catheter 221 tapers to a point. The second lumen houses the electrode used for RF ablation. In one embodiment, the delivery of vapor or RF waves is achieved through the use of a microprocessor. In another embodiment, the user can release vapor or subject the target tissue to RF waves by the use of actuators (not shown) on the handle 222. In one embodiment, the catheter has varying or differential insulation along its length. In one embodiment, the ablation device 220 includes a mechanism in which a snare to grasp the tissue to be ablated and sizing the tissue in the snare is used to determine the amount of vapor to be delivered.

Figure 2I:
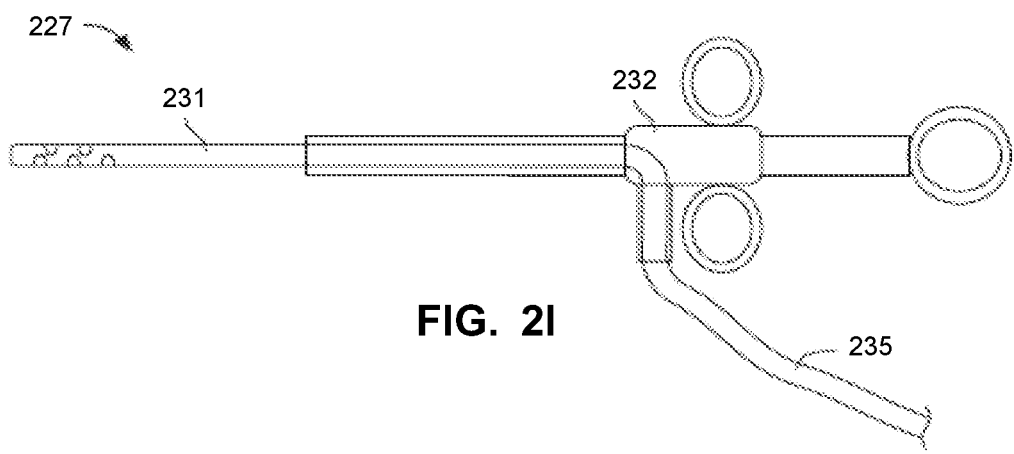
FIG. 2I illustrates a cross section of an ablation device in the form of a catheter extending from a conventional snare handle with a pre-attached cord, in accordance with another embodiment of the present specification.

FIG. 2I illustrates a cross section of an ablation device 227 in the form of a catheter 231 extending from a conventional handle 232 with a pre-attached cord 235, in accordance with another embodiment of the present specification. The cord 235 attaches directly to the vapor delivery system, eliminating one interface between the system and the ablation device and thereby decreasing the chance of system failure as a result of disconnection. In this embodiment, the handle 232 includes a separate attachment port (not shown) for the RF or an electric feed.

Figure 2J:
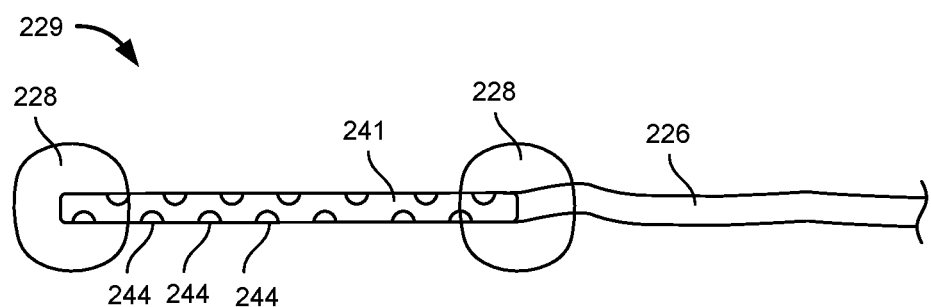
FIG. 2J illustrates an ablation device in the form of a catheter extending from a conventional esophageal probe, in accordance with an embodiment of the present specification.

FIG. 2J illustrates an ablation device 229 in the form of a catheter 241 extending from a conventional esophageal probe 226, in accordance with an embodiment of the present specification. In one embodiment, the catheter 241 is insulated and receives vapor from a flow channel contained within the probe 226. The catheter 241 includes a multitude of small ports 244 for the delivery of vapor to the target tissue. The delivery of vapor is controlled by a microprocessor. In one embodiment, the catheter 241 also includes two inflatable balloons 228, one at its distal end beyond the last vapor port 244, and one at its proximal end, proximate the catheter's 241 attachment to the probe 226. All vapor ports are positioned between these two balloons. Once the device 229 is inserted within the esophagus, the balloons 228 are inflated to keep the catheter 241 positioned and to contain the vapor within the desired treatment area. In one embodiment, the balloons must be separated from the ablation region by a distance of greater than 0 mm, preferably 1 mm and ideally 1 cm. In one embodiment, the diameter of each balloon when inflated is in the range of 10 to 100 mm, preferably 15-40 mm, although one of ordinary skill in the art would appreciate that the precise dimensions are dependent on the size of the patient's esophagus.

In one embodiment, the catheter 241 attached to the esophageal probe 226 is a dual lumen catheter. The first lumen serves to deliver vapor to the site of ablation as described above. The second lumen houses the electrode used for RF ablation.

Figure 3A:
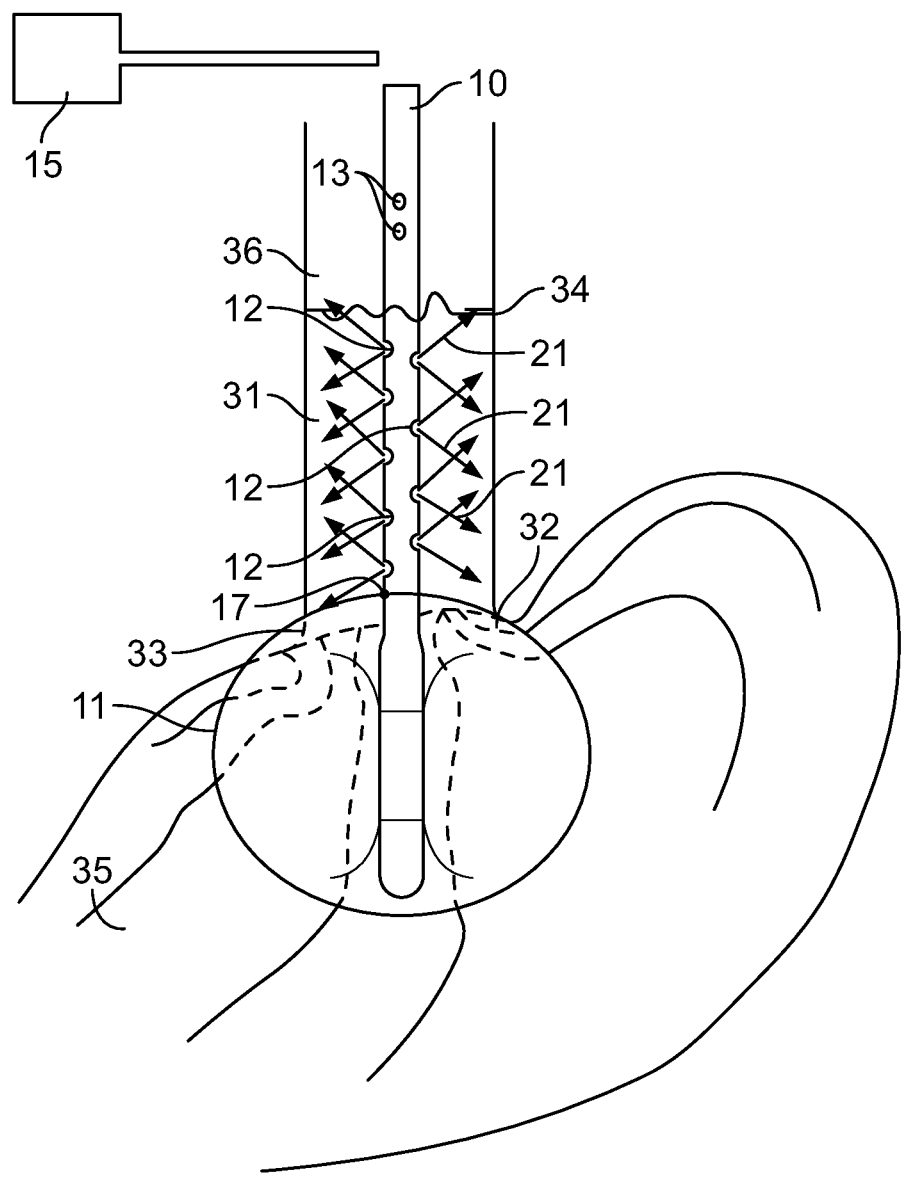
FIG. 3A illustrates the ablation device placed in an upper gastrointestinal tract with Barrett's esophagus to selectively ablate the Barrett's tissue, in accordance with an embodiment of the present specification.

FIG. 3A illustrates the ablation device placed in an upper gastrointestinal tract with Barrett's esophagus to selectively ablate the Barrett's tissue, in accordance with an embodiment of the present specification. The upper gastrointestinal tract comprises Barrett's esophagus 31, gastric cardia 32, gastroesophageal junction 33 and displaced squamo-columnar junction 34. The area between the gastroesophageal junction 33 and the displaced squamo-columnar junction 34 is Barrett's esophagus 31, which is targeted for ablation. Distal to the cardia 32 is the stomach 35 and proximal to the cardia 32 is the esophagus 36. The ablation device is passed into the esophagus 36 and the positioning device 11 is placed in the gastric cardia 32 abutting the gastroesophageal junction 33. This affixes the ablation catheter 10 and its ports 12 in the center of the esophagus 36 and allows for uniform delivery of the ablative agent 21 to the Barrett's esophagus 31.

In one embodiment, the positioning device is first affixed to an anatomical structure, not being subjected to ablation, before ablation occurs. Where the patient is undergoing circumferential ablation or first time ablation, the positioning attachment is preferably placed in the gastric cardia, abutting the gastroesophageal junction. Where the patient is undergoing a focal ablation of any residual disease, it is preferable to use the catheter system shown in FIG. 4B, as discussed below. In one embodiment, the positioning attachment must be separated from the ablation region by a distance of greater than 0 mm, preferably 1 mm and ideally 1 cm. In one embodiment, the size of the positioning device is in the range of 10 to 100 mm, preferably 20-40 mm, although one of ordinary skill in the art would appreciate that the precise dimensions are dependent on the size of the patient's esophagus.

The delivery of ablative agent 21 through the infusion port 12 is controlled by the microprocessor 15 coupled with the ablation device. The delivery of ablative agent is guided by predetermined programmatic instructions, depending on the tissue to be ablated and the depth of ablation required. In one embodiment, the target procedural temperature will need to be between −100 degrees Celsius and 200 degrees Celsius, preferably between 50 degrees Celsius and 75 degrees Celsius, as further shown in the dosimetery table below. In one embodiment, esophageal pressure should not exceed 5 atm, and is preferably below 0.5 atm. In one embodiment, the target procedural temperature is achieved in less than 1 minute, preferably in less than 5 seconds, and is capable of being maintained for up to 10 minutes, preferably 1 to 10 seconds, and then cooled close to the body temperature. One of ordinary skill in the art would appreciate that the treatment can be repeated until the desired ablation effect is achieved.

Figure 3B:
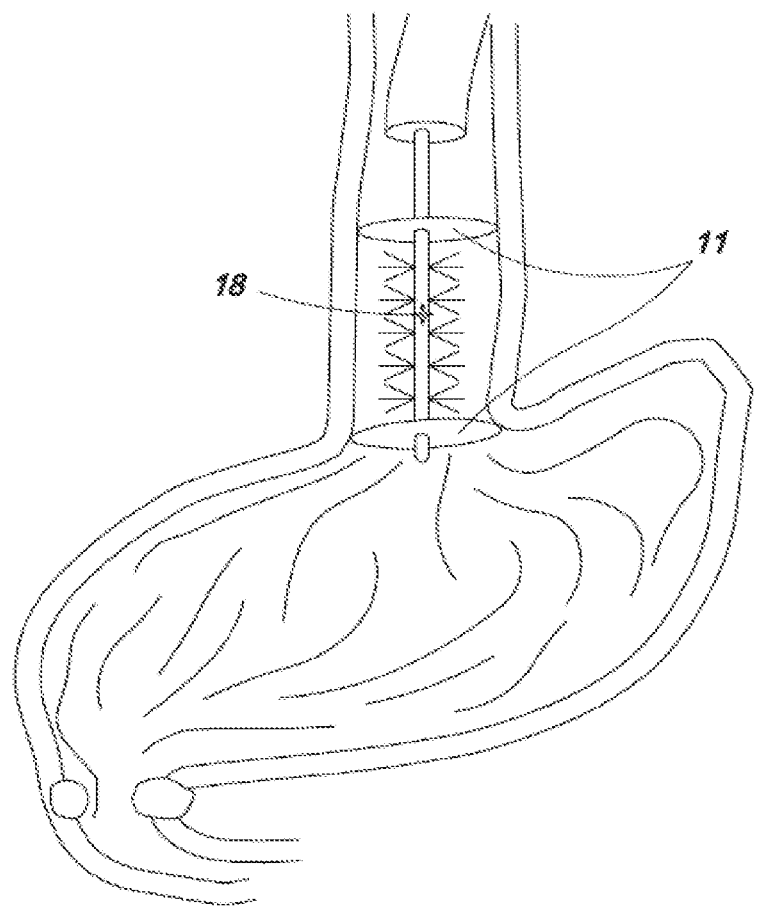
FIG. 3B illustrates the ablation device placed in an upper gastrointestinal tract with Barrett's esophagus to selectively ablate the Barrett's tissue, in accordance with another embodiment of the present specification.

Optional sensor 17 monitors intraluminal parameters such as temperature and pressure and can increase or decrease the flow of ablative agent 21 through the infusion port 12 to obtain adequate heating or cooling, resulting in adequate ablation. The sensor 17 monitors intraluminal parameters such as temperature and pressure and can increase or decrease the removal of ablative agent 21 through the optional suction port 13 to obtain adequate heating or cooling resulting in adequate ablation of Barrett's esophagus 31. FIG. 3B illustrates the ablation device placed in an upper gastrointestinal tract with Barrett's esophagus to selectively ablate the Barrett's tissue, in accordance with another embodiment of the present specification. As illustrated in FIG. 3B, the positioning device 11 is a wire mesh disc. In one embodiment, the positioning attachment must be separated from the ablation region by a distance of greater than 0 mm, preferably 1 mm and ideally 1 cm. In one embodiment, the positioning attachment is removably affixed to the cardia or gastroesophageal (EG) junction (for the distal attachment) or in the esophagus by a distance of greater than 0.1 mm, preferably around 1 cm, above the proximal most extent of the Barrett's tissue (for the proximal attachment).

FIG. 3B is another embodiment of the Barrett's ablation device where the positioning element 11 is a wire mesh disc. The wire mesh may have an optional insulated membrane to prevent the escape of the ablative agent. In the current embodiment, two wire mesh discs are used to center the ablation catheter in the esophagus. The distance between the two discs is determined by the length of the tissue to be ablated which, in this case, would be the length of the Barrett's esophagus. Optional infrared, electromagnetic, acoustic or radiofrequency energy emitters and sensors 18 are incorporated to measure the diameter of the esophagus.

Figure 3C:
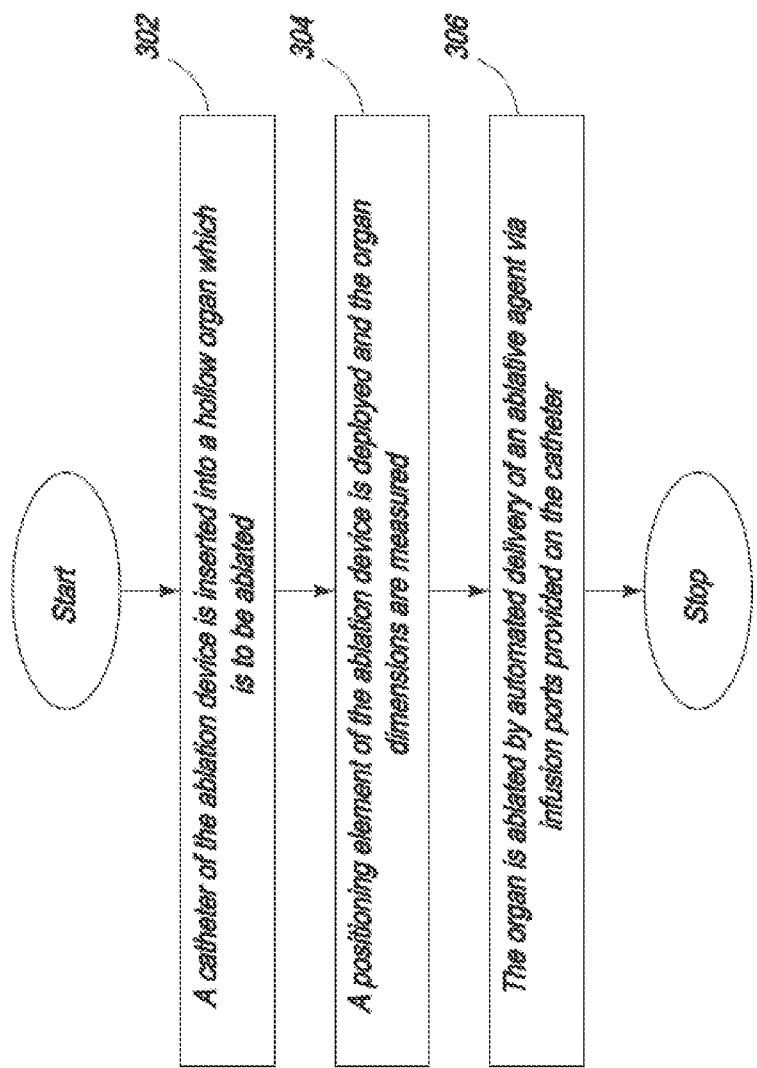
FIG. 3C is a flowchart illustrating the basic procedural steps for using the ablation device, in accordance with an embodiment of the present specification.

FIG. 3C is a flowchart illustrating the basic procedural steps for using the ablation device, in accordance with an embodiment of the present specification. At step 302, a catheter of the ablation device is inserted into an organ which is to be ablated. For example, in order to perform ablation in a Barrett's esophagus of a patient, the catheter is inserted into the Barrett's esophagus via the esophagus of the patient.

At step 304, a positioning element of the ablation device is deployed and organ dimensions are measured. In an embodiment, where the positioning element is a balloon, the balloon is inflated in order to position the ablation device at a known fixed distance from the tissue to be ablated. In various embodiments, the diameter of the hollow organ may be predetermined by using radiological tests such as barium X-rays or computer tomography (CT) scan, or by using pressure volume cycle, i.e. by determining volume needed to raise pressure to a fixed level (for example, 1 atm) in a fixed volume balloon. In another embodiment, where the positioning device is disc shaped, circumferential rings are provided in order to visually communicate to an operating physician the diameter of the hollow organ. In various embodiments of the present specification, the positioning device enables centering of the catheter of the ablation device in a non-cylindrical body cavity, and the volume of the cavity is measured by the length of catheter or a uterine sound.

Optionally, one or more infrared, electromagnetic, acoustic or radiofrequency energy emitters and sensors can be used to measure the dimensions of the hollow organ. The infrared, electromagnetic, acoustic or radiofrequency energy is emitted from the emitter and is reflected back from the tissue to a detector in the emitter. The reflected data can be used to determine the dimensions of the hollow cavity. The measurement can be performed at one or multiple points to get an accurate estimate of the dimensions of the hollow organ. The data from multiple points can also be used to create a topographic representation of the hollow organ or to calculate the volume of the hollow organ.

In one embodiment, the positioning attachment must be separated from the ports by a distance of 0 mm or greater, preferably greater than 0.1 mm, and more preferably 1 cm. The size of the positioning device depends on the hollow organ being ablated and ranges from 1 mm to 10 cm. In one embodiment, the diameter of the positioning element is between 0.01 mm and 100 mm. In one embodiment, the first positioning element comprises a circular body with a diameter between 0.01 mm and 10 cm.

At step 306, the organ is ablated by automated delivery of an ablative agent, such as steam, via infusion ports provided on the catheter. The delivery of the ablative agent through the infusion ports is controlled by a microprocessor coupled with the ablation device. The delivery of ablative agent is guided by predetermined programmatic instructions depending on the tissue to be ablated and the depth of ablation required. In an embodiment of the present specification where the ablative agent is steam, the dose of the ablative agent is determined by conducting dosimetery study to determine the dose to ablate endometrial tissue. The variable that enables determination of total dose of ablative agent is the volume (or mass) of the tissue to be treated which is calculated by using the length of the catheter and diameter of the organ (for cylindrical organs). The determined dose of ablative agent is then delivered using a micro-processor controlled steam generator. Optionally, the delivery of the ablative agent can be controlled by the operator using predetermined dosimetry parameters.

In one embodiment, the dose is provided by first determining what the disorder being treated is and what the desired tissue effect is, and then finding the corresponding temperature, as shown in Tables 1 and 2, below.

TABLE 1

| Temp in ° C. | Tissue Effect |
| --- | --- |
| 37-40 | No significant tissue effect |
| 41-44 | Reversible cell damage in few hours |
| 45-49 | Irreversible cell damage at shorter intervals |
| 50-69 | Irreversible cell damage - ablation necrosis at shorter intervals |
| 70 | Threshold temp for tissue shrinkage, H-bond breakage |
| 70-99 | Coagulation and Hemostasis |
| 100-200 | Desiccation and Carbonization of tissue |
| >200 | Charring of tissue glucose |

TABLE 2

| Disorder | Max. Temp in ° C. |
| --- | --- |
| ENT/Pulmonary | |
| Nasal Polyp | 60-80 |
| Turbinectomy | 70-85 |
| Bullous Disease | 70-85 |
| Lung Reduction | 70-85 |
| Genitourinary | |
| Uterine Menorrhagia | 80-90 |
| Endometriosis | 80-90 |
| Uterine Fibroids | 90-100 |
| Benign Prostatic Hypertrophy | 90-100 |
| Gastroenterology | |
| Barrett's Esophagus | 60-75 |
| Esophageal Dysplasia | 60-80 |
| Vascular GI Disorders | 55-75 |
| Flat Polyps | 60-80 |

In addition, the depth of ablation desired determines the holding time at the maximum temperature. For superficial ablation (Barrett), the holding time at the maximum temperature is very short (flash burn) and does not allow for heat to transfer to the deeper layers. This will prevent damage to deeper normal tissue and hence prevent patient discomfort and complications. For deeper tissue ablation, the holding time at the maximum temperature will be longer, thereby allowing the heat to percolate deeper.

Figure 3D:
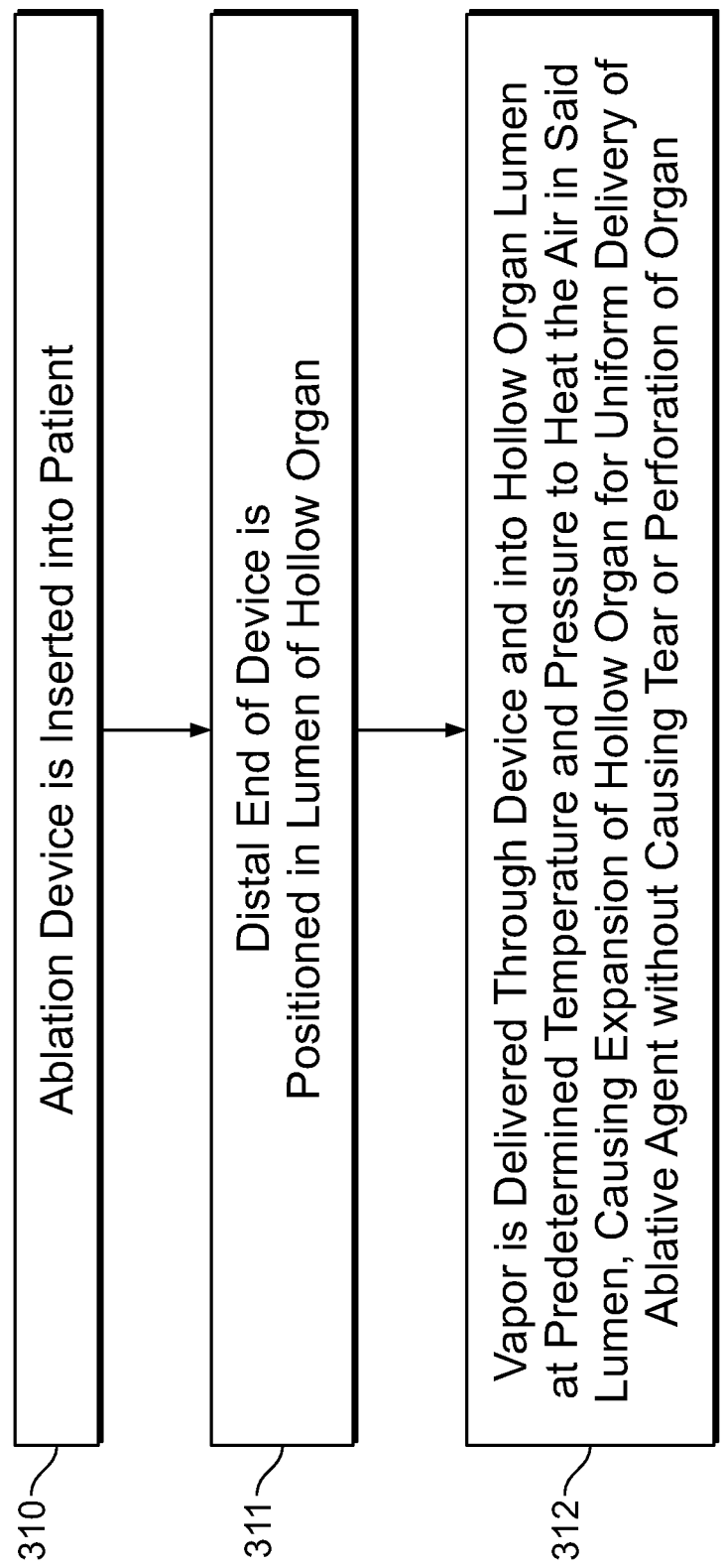
FIG. 3D is a flowchart listing the steps of one embodiment of a method of providing vapor to a hollow organ where the vapor heats the air in the hollow organ, thus expanding the organ for uniform delivery of ablative energy.

The prior art describes the need to provide an expansion mechanism to open a collapsed hollow organ to provide uniform ablation. This is routinely performed using balloons, shaped meshes or other structures. It is desirable to provide a method for ablation not requiring an expansion mechanism. FIG. 3D is a flowchart listing the steps of one embodiment of a method of providing vapor to a hollow organ where the vapor heats the air in the hollow organ, thus expanding the organ and eliminating the mucosal folds for uniform delivery of ablative energy. At step 310, an ablation device is inserted into a patient. The distal end of the device is positioned in a lumen of a hollow organ targeted for ablation therapy at step 311. Then, at step 312, vapor is delivered to the lumen at a predetermined temperature and pressure to cause adequate expansion of the hollow organ and target tissue for uniform delivery of the ablative agent without over expanding the hollow organ and causing a tear or perforation.

Figure 3E:
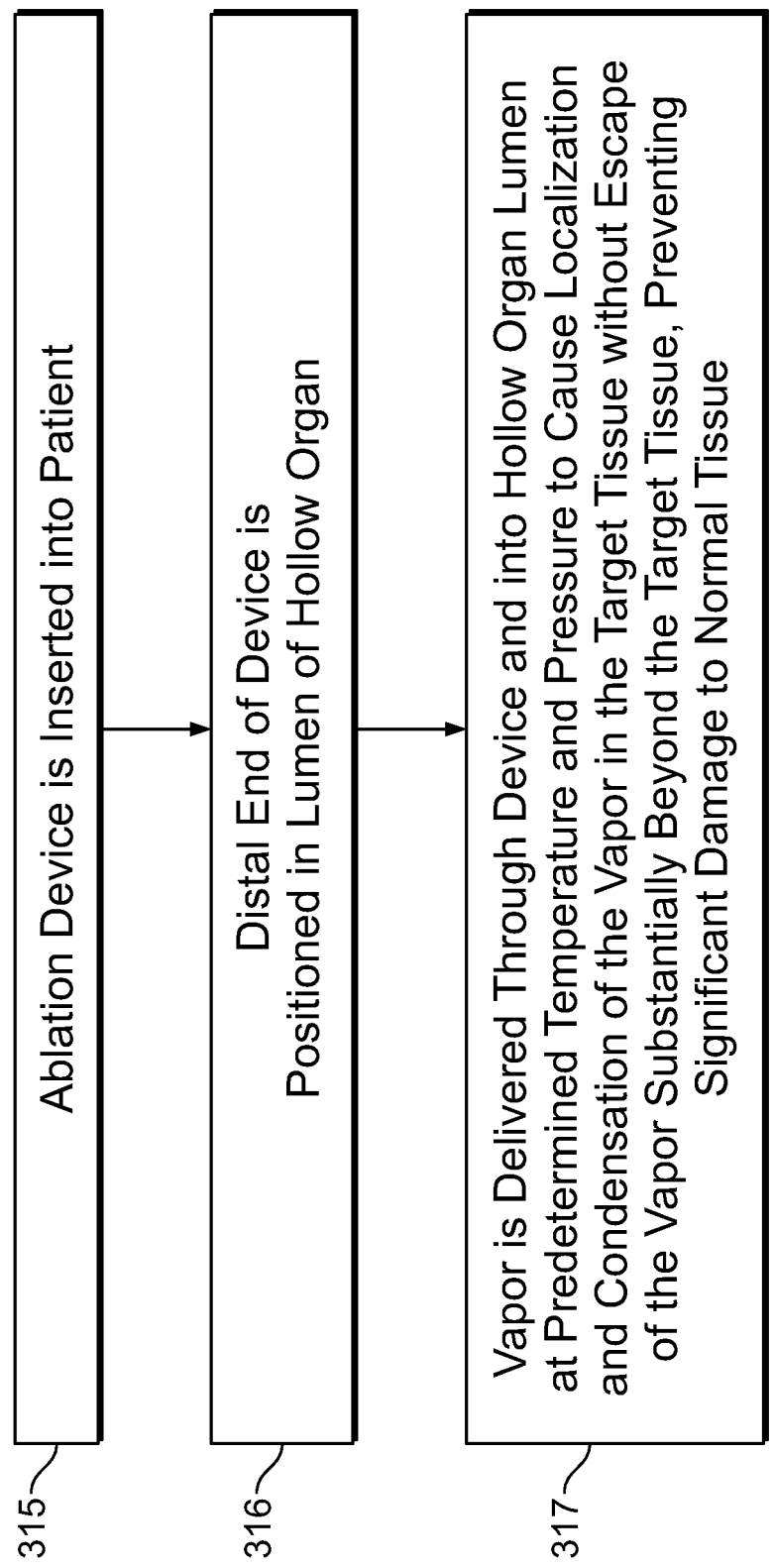
FIG. 3E is a flowchart listing the steps of one embodiment of a method of providing vapor to a hollow organ wherein the vapor does not escape substantially beyond the target tissue to be ablated.

The prior art also describes the need for an occlusive mechanism to prevent the flow of ablative energy out of the target tissue region. It is desirable to provide a method for ablation which does not require the use of an occlusive agent to prevent the flow of energy beyond the targeted tissue to prevent damage to healthy tissue. FIG. 3E is a flowchart listing the steps of one embodiment of a method of providing vapor to a hollow organ wherein the vapor does not escape substantially beyond the target tissue to be ablated. At step 315, an ablation device is inserted into a patient. The distal end of the device is positioned in a lumen of a hollow organ targeted for ablation therapy at step 316. Then, at step 317, the vapor is delivered to the lumen at a predetermined temperature and pressure to cause localization and condensation of the vapor in the target tissue without escape of the vapor substantially beyond the target tissue, thus preventing significant damage to nearby normal tissue.

Figure 4A:
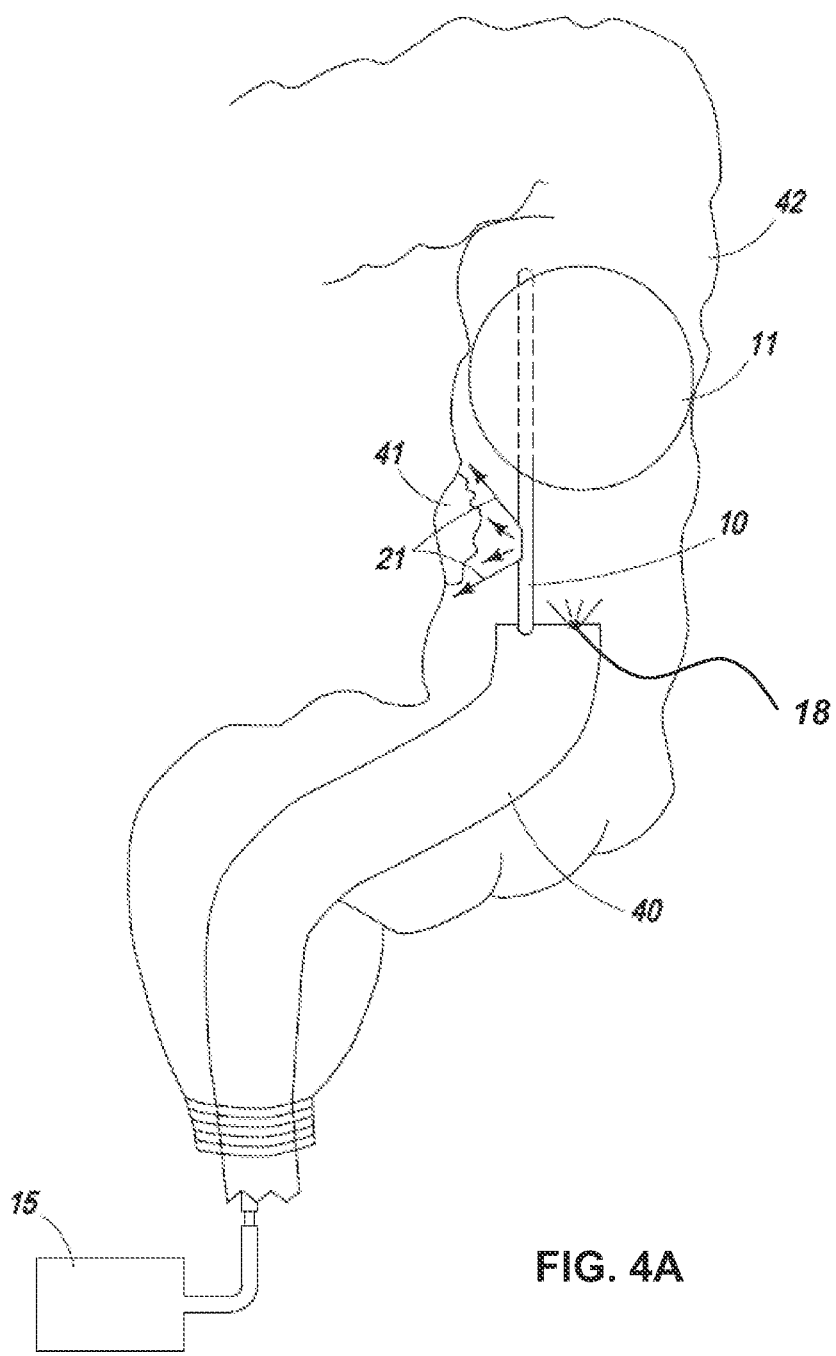
FIG. 4A illustrates the ablation device placed in a colon to ablate a flat colon polyp, in accordance with an embodiment of the present specification.

FIG. 4A illustrates the ablation device placed in a colon to ablate a flat colon polyp, in accordance with an embodiment of the present specification. The ablation catheter 10 is passed through a colonoscope 40. The positioning device 11 is placed proximal, with respect to the patient's GI tract, to a flat colonic polyp 41 which is to be ablated, in the normal colon 42. The positioning device 11 is one of an inflatable balloon, a wire mesh disc with or without an insulated membrane covering the disc, a cone shaped attachment, a ring shaped attachment or a freeform attachment designed to fit the colonic lumen. The positioning device 11 has the catheter 10 located toward the periphery of the positioning device 11 placing it closer to the polyp 41 targeted for non-circumferential ablation. Hence, the positioning device 11 fixes the catheter to the colon 42 at a predetermined distance from the polyp 41 for uniform and focused delivery of the ablative agent 21. The delivery of ablative agent 21 through the infusion port 12 is controlled by the microprocessor 15 attached to the ablation device and depends on tissue and the depth of ablation required. The delivery of ablative agent 21 is guided by predetermined programmatic instructions depending on the tissue to be ablated and the area and depth of ablation required. Optional infrared, electromagnetic, acoustic or radiofrequency energy emitters and sensors 18 are incorporated to measure the diameter of the colon. The ablation device allows for focal ablation of diseased polyp mucosa without damaging the normal colonic mucosa located away from the catheter ports.

In one embodiment, the positioning attachment must be separated from the ablation region by a distance of greater than 0.1 mm, ideally more than 5 mm. In one embodiment, the positioning element is proximal, with respect to the patient's GI tract, to the colon polyp. For this application, the embodiment shown in FIG. 4B would be preferred.

Figure 4B:
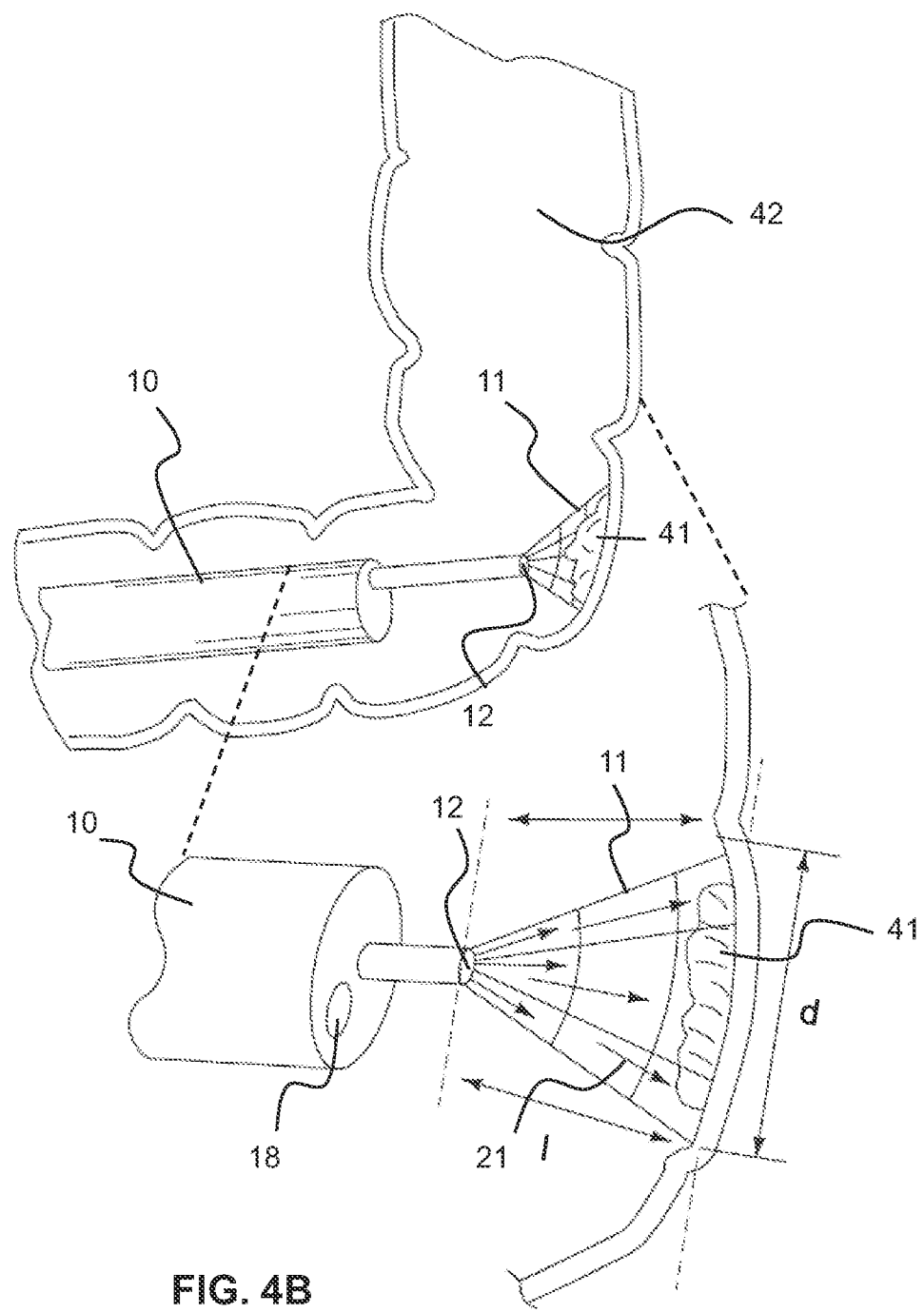
FIG. 4B illustrates the ablation device placed in a colon to ablate a flat colon polyp, in accordance with another embodiment of the present specification.

FIG. 4B illustrates the ablation device placed in a colon 42 to ablate a flat colon polyp 41, in accordance with another embodiment of the present specification. As illustrated in FIG. 4B, the positioning device 11 is a conical attachment at the tip of the catheter 10. The conical attachment has a known length 'l' and diameter 'd' that is used to calculate the amount of thermal energy needed to ablate the flat colon polyp 41. Ablative agent 21 is directed from the infusion port 12 to polyp 41 by the positioning device 11. In one embodiment, the positioning attachment 11 must be separated from the ablation region by a distance of greater than 0.1 mm, preferably 1 mm and more preferably 1 cm. In one embodiment, the length 'l' is greater than 0.1 mm, preferably between 5 and 10 mm. In one embodiment, diameter 'd' depends on the size of the polyp and can be between 1 mm and 10 cm, preferably 1 to 5 cm. Optional infrared, electromagnetic, acoustic or radiofrequency energy emitters and sensors 18 are incorporated to measure the diameter of the colon. This embodiment can also be used to ablate residual neoplastic tissue at the edges after endoscopic snare resection of a large sessile colon polyp.

Figure 4C:
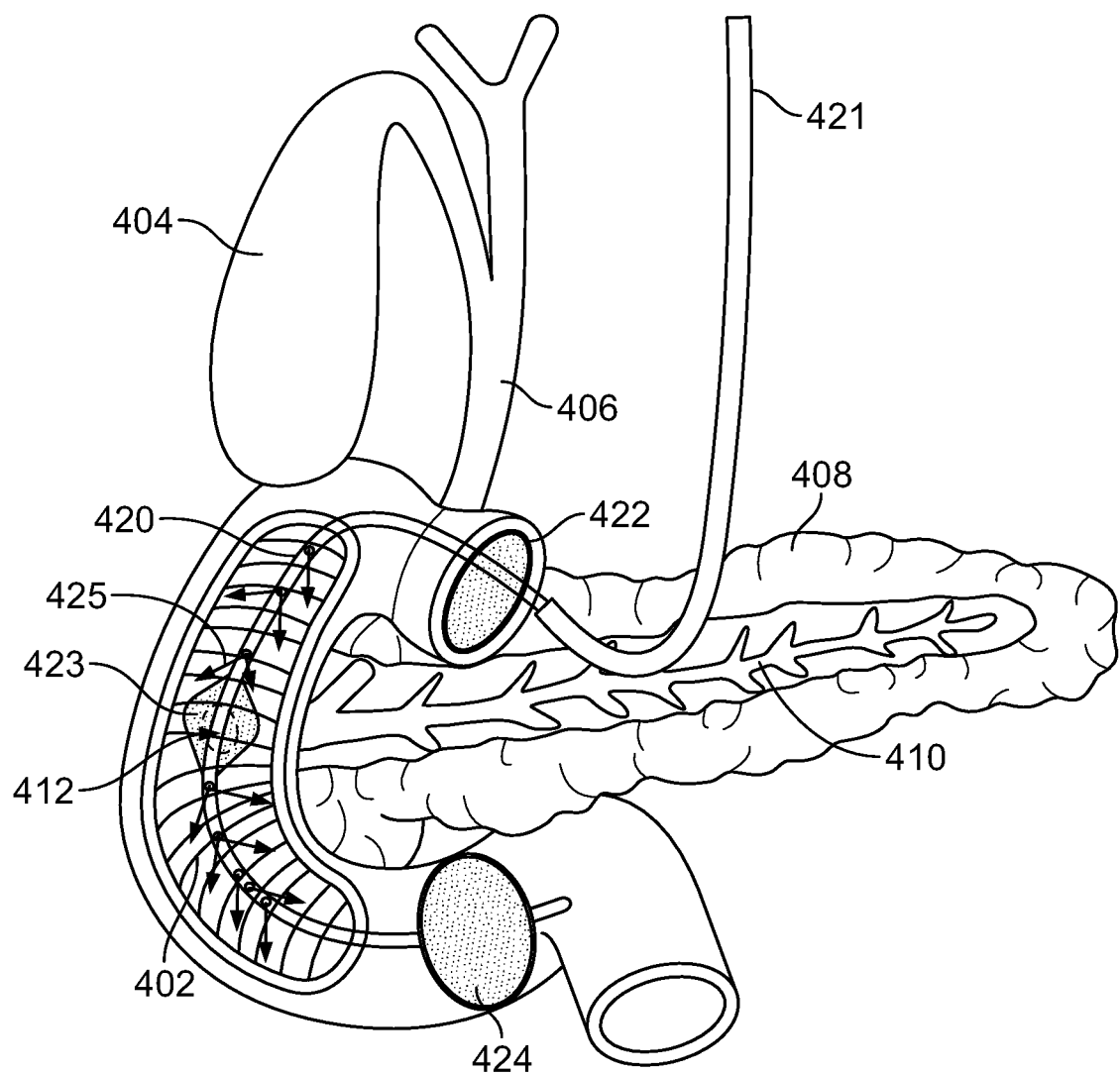
FIG. 4C illustrates an ablation catheter having an ampullary shield inserted in the duodenum of a patient, in accordance with one embodiment of the present specification.

In some instances, it is desirable to ablate a portion of a patient's duodenal mucosa for the treatment of various gastrointestinal (GI) disorders. However, it is not advisable to ablate or inflict trauma upon the patient's nearby ampulla of Vater during such a procedure. Trauma to the ampulla increases the risk of causing pancreatitis, pancreatic or biliary stricture, or cholangitis. FIG. 4C illustrates an ablation catheter 420 having an ampullary shield 423 inserted in the duodenum 402 of a patient, in accordance with one embodiment of the present specification. Also depicted are the patient's gall bladder 404, common bile duct 406, pancreas 408, and pancreatic duct 410. The catheter 420 is passed through an endoscope 421 to position the distal end of the catheter 420 within the duodenum 402. In one embodiment, first and second positioning elements, or balloons 422, 424 on the catheter 420 assist in positioning the catheter 420 within the patient's antroduodenal area. The ampullary shield 423, attached to the catheter 420, covers the patient's ampulla of Vater 412 and prevents ablative agent 425 from coming into contact with said ampulla 412. In various embodiments, the ampullary shield 423 is composed of silicone and approximates a rectangular, square, circular, or oval shape.

Figure 4D:
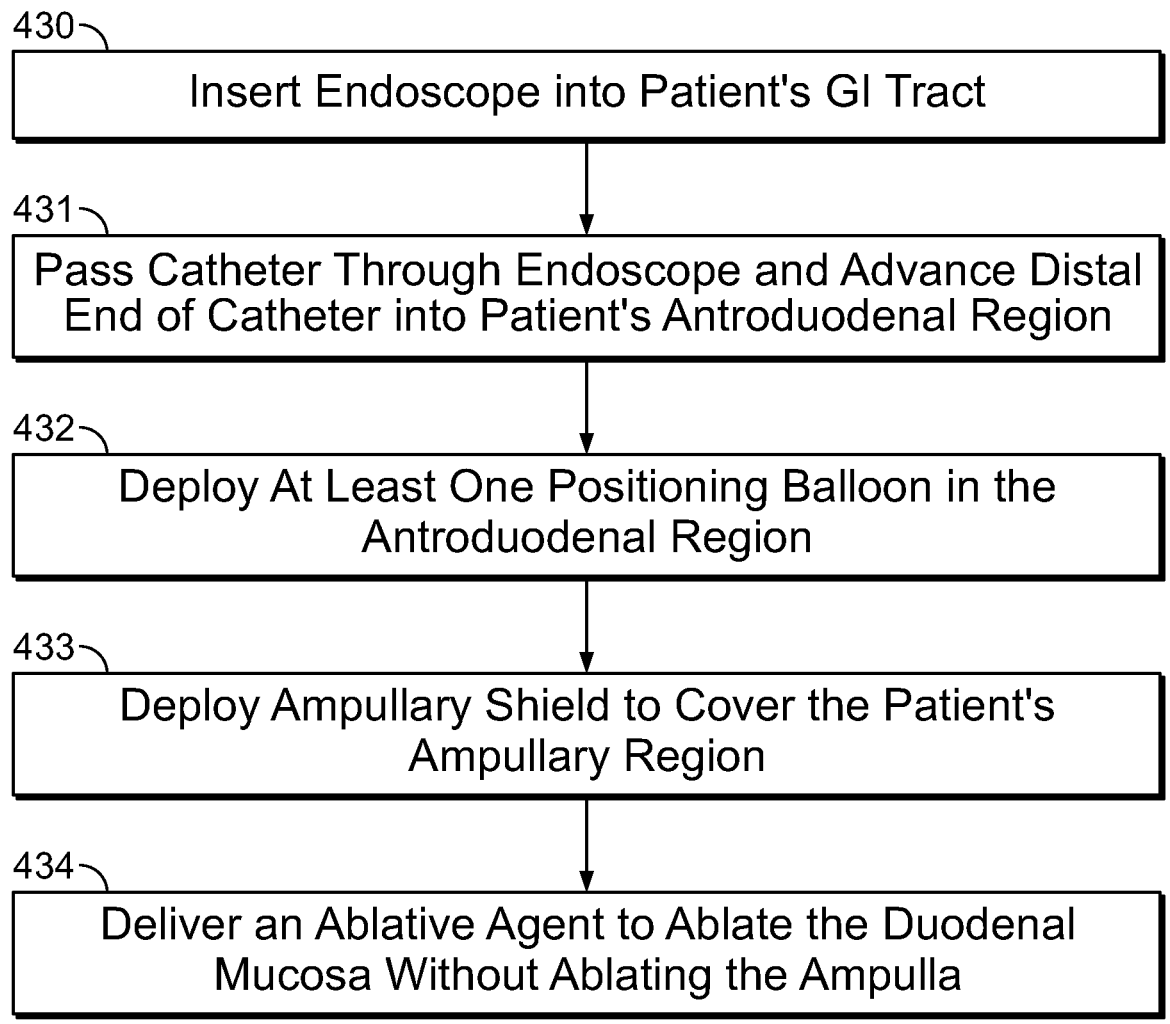
FIG. 4D is a flowchart listing the steps in one embodiment of a method of using the ablation catheter having an ampullary shield of FIG. 4C.

FIG. 4D is a flowchart listing the steps in one embodiment of a method of using the ablation catheter having an ampullary shield of FIG. 4C. At step 430, an endoscope is inserted into a patient's gastrointestinal (GI) tract. The catheter is passed through the endoscope and its distal end advanced into the patient's antroduodenal region at step 431. Then, at step 432, at least one positioning balloon is deployed in said antroduodenal region. The ampullary shield is deployed at step 433 to cover the patient's ampullary region. Ablative agent is then delivered at step 434 to ablate a portion of the duodenal mucosa without ablating or damaging the patient's ampulla of Vater.

FIG. 5A illustrates the ablation device with a coaxial catheter design, in accordance with an embodiment of the present specification. The coaxial design has a handle 52a, an infusion port 53a, an inner sheath 54a and an outer sheath 55a. The outer sheath 55a is used to constrain the positioning device 56a in the closed position and encompasses ports 57a. FIG. 5B shows a partially deployed positioning device 56b, with the ports 57b still within the outer sheath 55b. The positioning device 56b is partially deployed by pushing the catheter 54b out of sheath 55b.

FIG. 5C shows a completely deployed positioning device 56c. The infusion ports 57c are out of the sheath 55c. The length 'l' of the catheter 54c that contains the infusion ports 57c and the diameter 'd' of the positioning element 56c are predetermined/known and are used to calculate the amount of thermal energy needed. FIG. 5D illustrates a conical design of the positioning element. The positioning element 56d is conical with a known length 'l' and diameter 'd' that is used to calculate the amount of thermal energy needed for ablation. FIG. 5E illustrates a disc shaped design of the positioning element 56e comprising circumferential rings 59e. The circumferential rings 59e are provided at a fixed predetermined distance from the catheter 54e and are used to estimate the diameter of a hollow organ or hollow passage in a patient's body.

Figure 6:
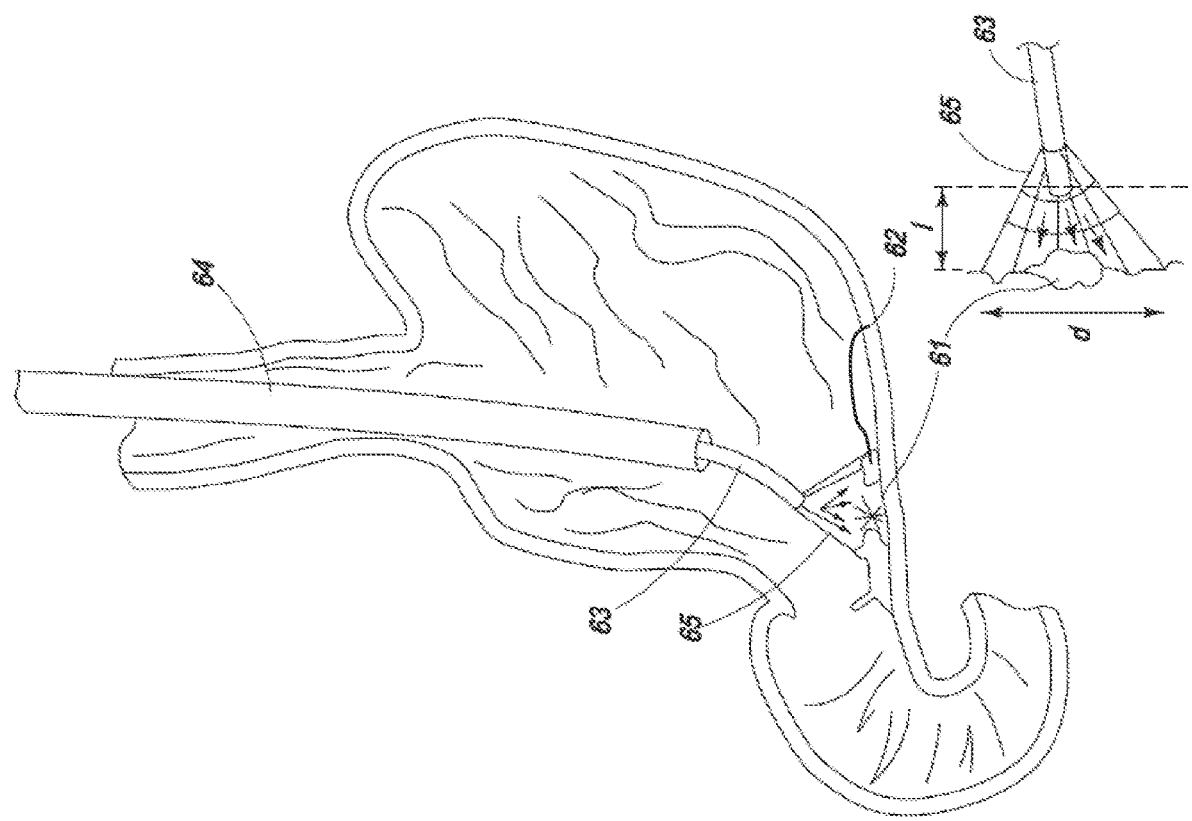
FIG. 6 illustrates an upper gastrointestinal tract with a bleeding vascular lesion being treated by the ablation device, in accordance with an embodiment of the present specification.

FIG. 6 illustrates an upper gastrointestinal tract with a bleeding vascular lesion being treated by the ablation device, in accordance with an embodiment of the present specification. The vascular lesion is a visible vessel 61 in the base of an ulcer 62. The ablation catheter 63 is passed through the channel of an endoscope 64. The conical positioning element 65 is placed over the visible vessel 61. The conical positioning element 65 has a known length 'l' and diameter 'd', which are used to calculate the amount of thermal energy needed for coagulation of the visible vessel to achieve hemostasis. The conical positioning element has an optional insulated membrane that prevents escape of thermal energy or vapor away from the disease site.

In one embodiment, the positioning attachment must be separated from the ablation region by a distance of greater than 0.1 mm, preferably 1 mm and more preferably 1 cm. In one embodiment, the length 'l' is greater than 0.1 mm, preferably between 5 and 10 mm. In one embodiment, diameter 'd' depends on the size of the lesion and can be between 1 mm and 10 cm, preferably 1 to 5 cm.

Figure 7A:
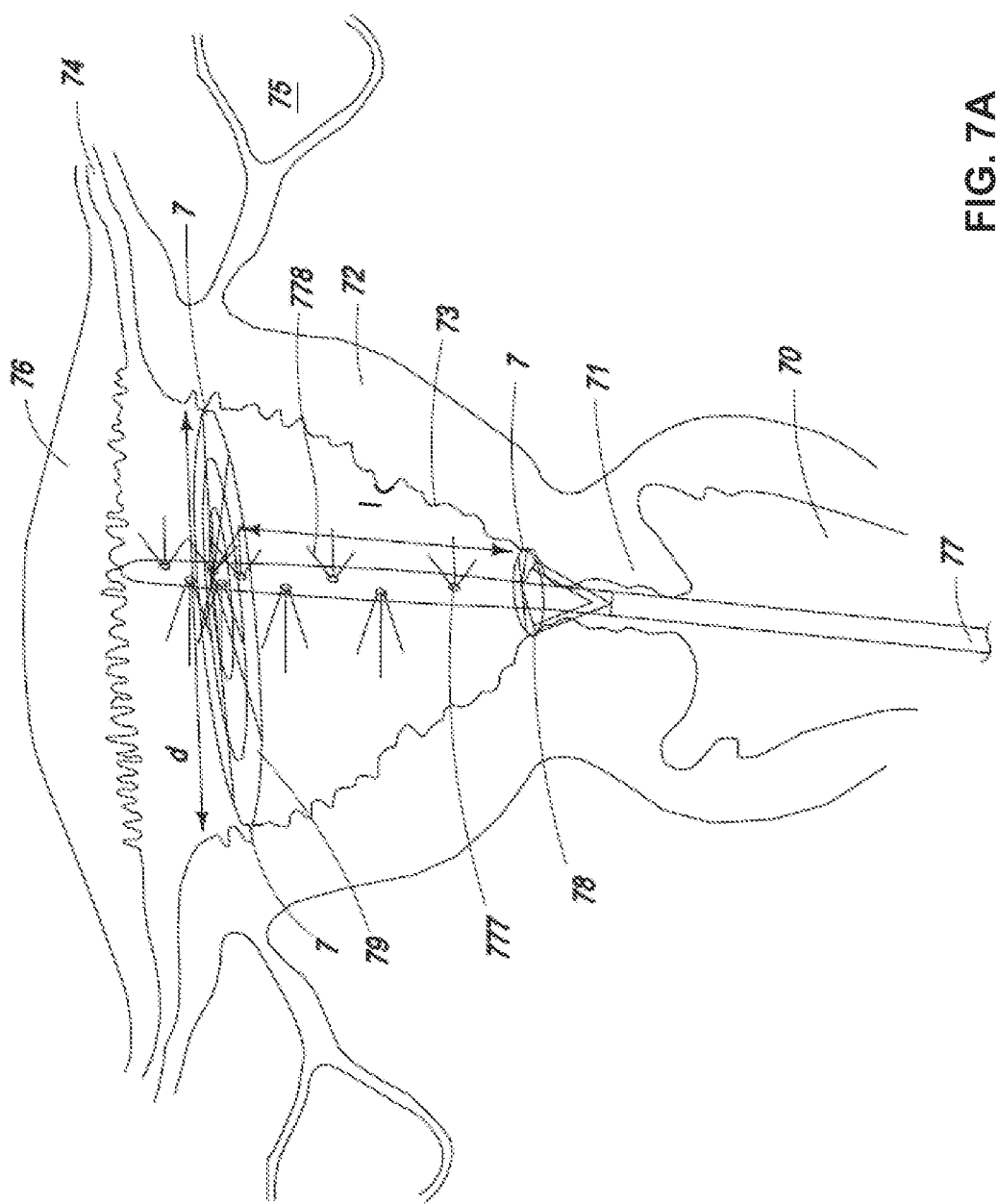
FIG. 7A illustrates endometrial ablation being performed in a female uterus by using the ablation device, in accordance with an embodiment of the present specification.

FIG. 7A illustrates endometrial ablation being performed in a female uterus by using the ablation device, in accordance with an embodiment of the present specification. A cross-section of the female genital tract comprising a vagina 70, a cervix 71, a uterus 72, an endometrium 73, fallopian tubes 74, ovaries 75 and the fundus of the uterus 76 is illustrated. A catheter 77 of the ablation device is inserted into the uterus 72 through the cervix 71 at the cervical os. In an embodiment, the catheter 77 has two positioning elements, a conical positioning element 78 and a disc shaped positioning element 79. The positioning element 78 is conical with an insulated membrane covering the conical positioning element 78. The conical element 78 positions the catheter 77 in the center of the cervix 71 and the insulated membrane prevents the escape of thermal energy or ablative agent out the cervix 71 through the os. The second disc shaped positioning element 79 is deployed close to the fundus of the uterus 76 positioning the catheter 77 in the middle of the cavity. An ablative agent 778 is passed through infusion ports 777 for uniform delivery of the ablative agent 778 into the uterine cavity. Predetermined length 'l' of the ablative segment of the catheter and diameter 'd' of the positioning element 79 allows for estimation of the cavity size and is used to calculate the amount of thermal energy needed to ablate the endometrial lining. In one embodiment, the positioning elements 78, 79 also act to move the endometrial tissue away from the infusion ports 777 on the catheter 77 to allow for the delivery of ablative agent. Optional temperature sensors 7 deployed close to the endometrial surface are used to control the delivery of the ablative agent 778. Optional topographic mapping using multiple infrared, electromagnetic, acoustic or radiofrequency energy emitters and sensors can be used to define cavity size and shape in patients with an irregular or deformed uterine cavity due to conditions such as fibroids. Additionally, data from diagnostic testing can be used to ascertain the uterine cavity size, shape, or other characteristics.

In an embodiment, the ablative agent is vapor or steam which contracts on cooling. Steam turns to water which has a lower volume as compared to a cryogen that will expand or a hot fluid used in hydrothermal ablation whose volume stays constant. With both cryogens and hot fluids, increasing energy delivery is associated with increasing volume of the ablative agent which, in turn, requires mechanisms for removing the agent, otherwise the medical provider will run into complications, such as perforation. However, steam, on cooling, turns into water which occupies significantly less volume; therefore, increasing energy delivery is not associated with an increase in volume of the residual ablative agent, thereby eliminating the need for continued removal. This further decreases the risk of leakage of the thermal energy via the fallopian tubes 74 or the cervix 71, thus reducing any risk of thermal injury to adjacent healthy tissue.

In one embodiment, the positioning attachment must be separated from the ablation region by a distance of greater than 0.1 mm, preferably 1 mm and more preferably 1 cm. In another embodiment, the positioning attachment can be in the ablated region as long as it does not cover a significant surface area. For endometrial ablation, 100% of the tissue does not need to be ablated to achieve the desired therapeutic effect.

In one embodiment, the preferred distal positioning attachment is an uncovered wire mesh that is positioned proximate to the mid body region. In one embodiment, the preferred proximal positioning device is a covered wire mesh that is pulled into the cervix, centers the device, and occludes the cervix. One or more such positioning devices may be helpful to compensate for the anatomical variations in the uterus. The proximal positioning device is preferably oval, with a long axis between 0.1 mm and 10 cm (preferably 1 cm to 5 cm) and a short axis between 0.1 mm and 5 cm (preferably 0.5 cm to 1 cm). The distal positioning device is preferably circular with a diameter between 0.1 mm and 10 cm, preferably 1 cm to 5 cm.

In another embodiment, the catheter is a coaxial catheter comprising an external catheter and an internal catheter wherein, upon insertion, the distal end of the external catheter engages and stops at the cervix while the internal extends into the uterus until its distal end contacts the fundus of the uterus. The length of the internal catheter that has passed into the uterus is then used to measure the depth of the uterine cavity and determines the amount of ablative agent to use. Ablative agent is then delivered to the uterine cavity via at least one port on the internal catheter. In one embodiment, during treatment, intracavitary pressure within the uterus is kept below 100 mm Hg. In one embodiment, the coaxial catheter further includes a pressure sensor to measure intracavitary pressure. In one embodiment, the coaxial catheter further includes a temperature sensor to measure intracavitary temperature. In one embodiment, the ablative agent is steam and the steam is released from the catheter at a pressure of less than 100 mm Hg. In one embodiment, the steam is delivered with a temperature between 90 and 100° C.

Figure 7B:
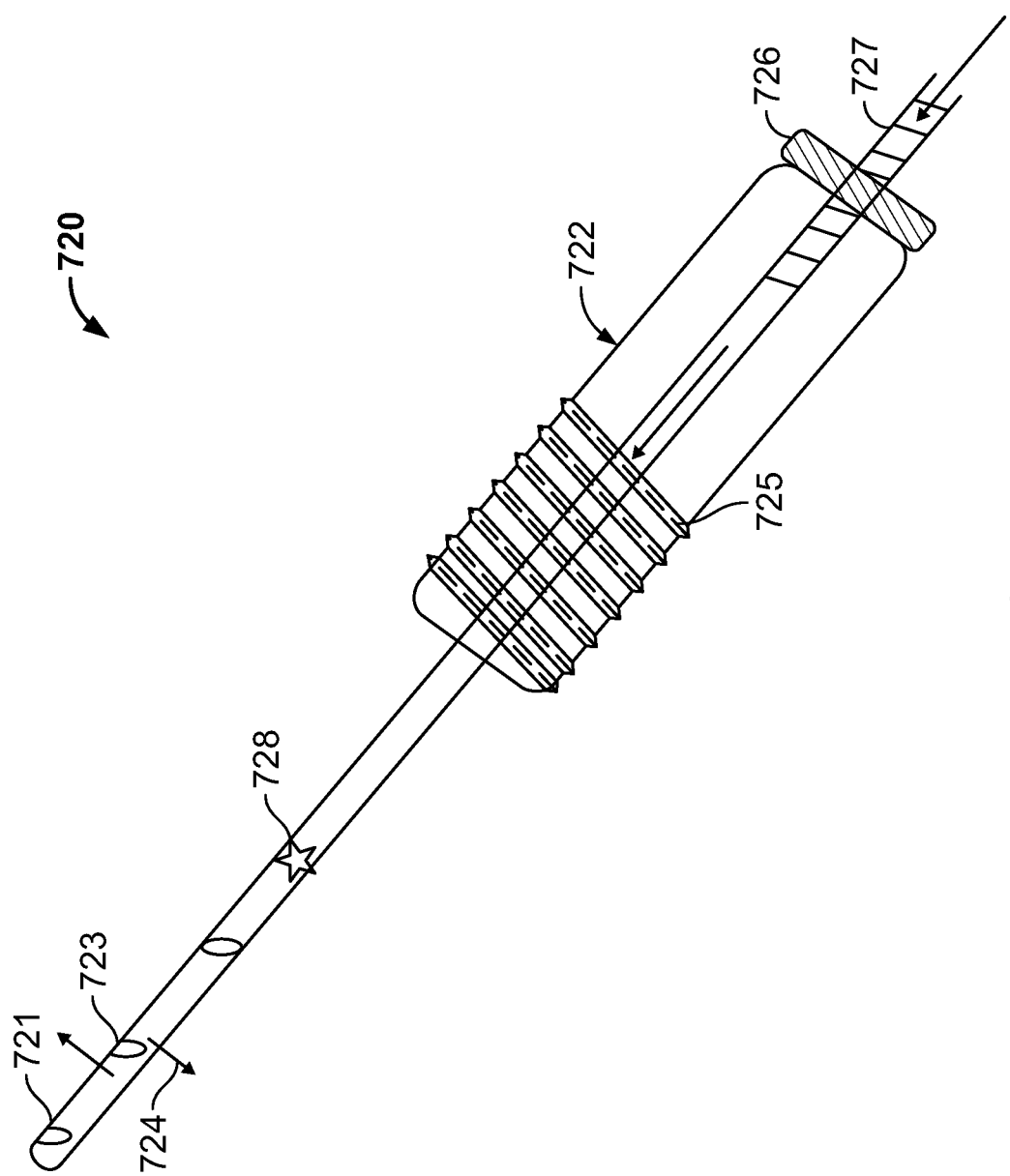
FIG. 7B is an illustration of a coaxial catheter used in endometrial tissue ablation, in accordance with one embodiment of the present specification.

FIG. 7B is an illustration of a coaxial catheter 720 used in endometrial tissue ablation, in accordance with one embodiment of the present specification. The coaxial catheter 720 comprises an inner catheter 721 and outer catheter 722. In one embodiment, the inner catheter 721 has one or more ports 723 for the delivery of an ablative agent 724. In one embodiment, the ablative agent is steam. In one embodiment, the outer catheter 722 has multiple fins 725 to engage the cervix to prevent the escape of vapor out of the uterus and into the vagina. In one embodiment, the fins are composed of silicone. In one embodiment, the outer catheter 722 includes a luer lock 726 to prevent the escape of vapor between the inner catheter 721 and outer catheter 722. In one embodiment, the inner catheter 721 includes measurement markings 727 to measure the depth of insertion of the inner catheter 721 beyond the tip of the outer catheter 722. Optionally, in various embodiments, one or more sensors 728 are incorporated into the inner catheter 721 to measure intracavitary pressure or temperature.

Figure 7C:
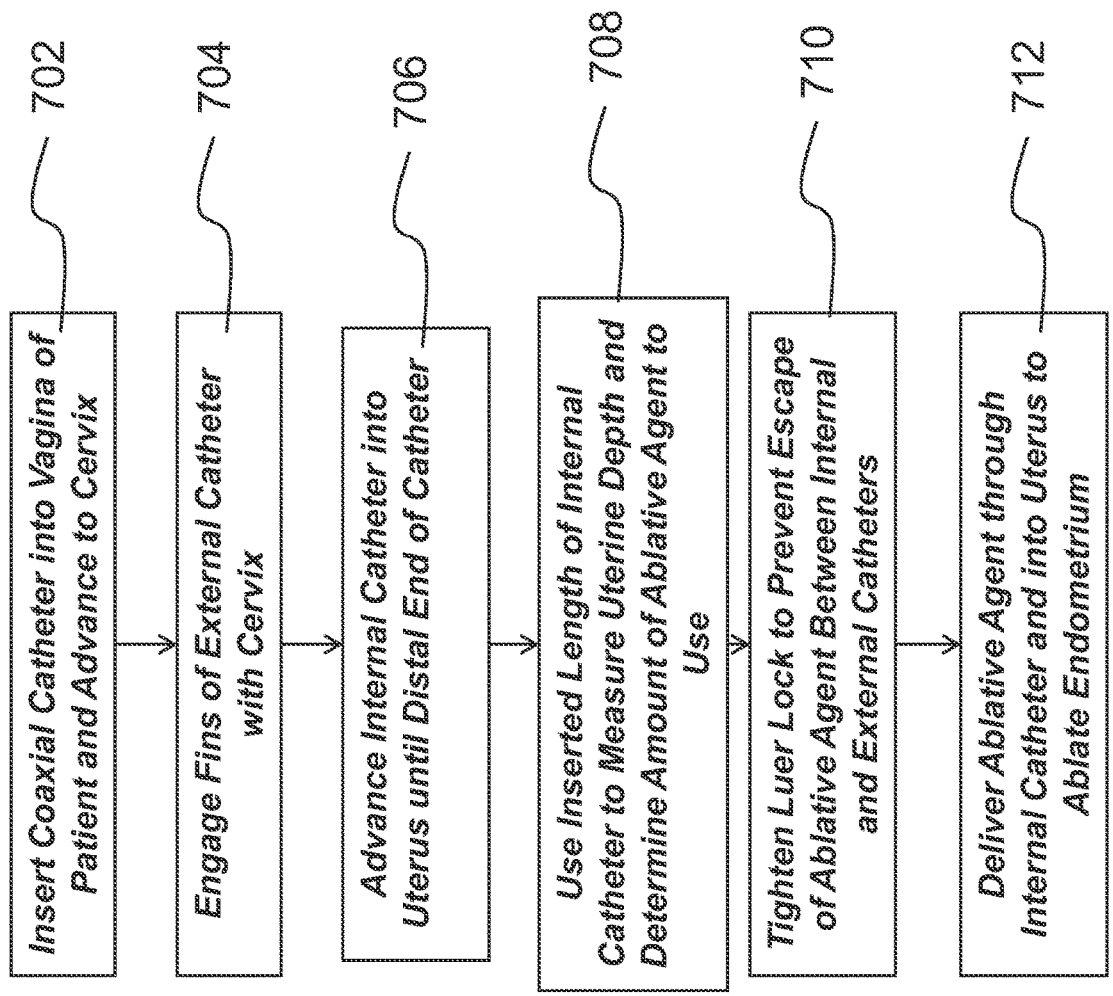
FIG. 7C is a flow chart listing the steps involved in an endometrial tissue ablation process using a coaxial ablation catheter, in accordance with one embodiment of the present specification.

FIG. 7C is a flow chart listing the steps involved in an endometrial tissue ablation process using a coaxial ablation catheter, in accordance with one embodiment of the present specification. At step 702, the coaxial catheter is inserted into the patient's vagina and advanced to the cervix. Then, at step 704, the coaxial catheter is advanced such that the fins of the outer catheter engage the cervix, effectively stopping advancement of the outer catheter at that point. The inner catheter is then advanced, at step 706, until the distal end of the internal catheter contacts the fundus of the uterus. The depth of insertion is then measured using the measurement markers on the internal catheter at step 708, thereby determining the amount of ablative agent to use in the procedure. At step 710, the luer lock is tightened to prevent any escape of vapor between the two catheters. The vapor is then delivered, at step 712, through the lumen of the inner catheter and into the uterus via the delivery ports on the internal catheter to ablate the endometrial tissue.

Figure 7D:
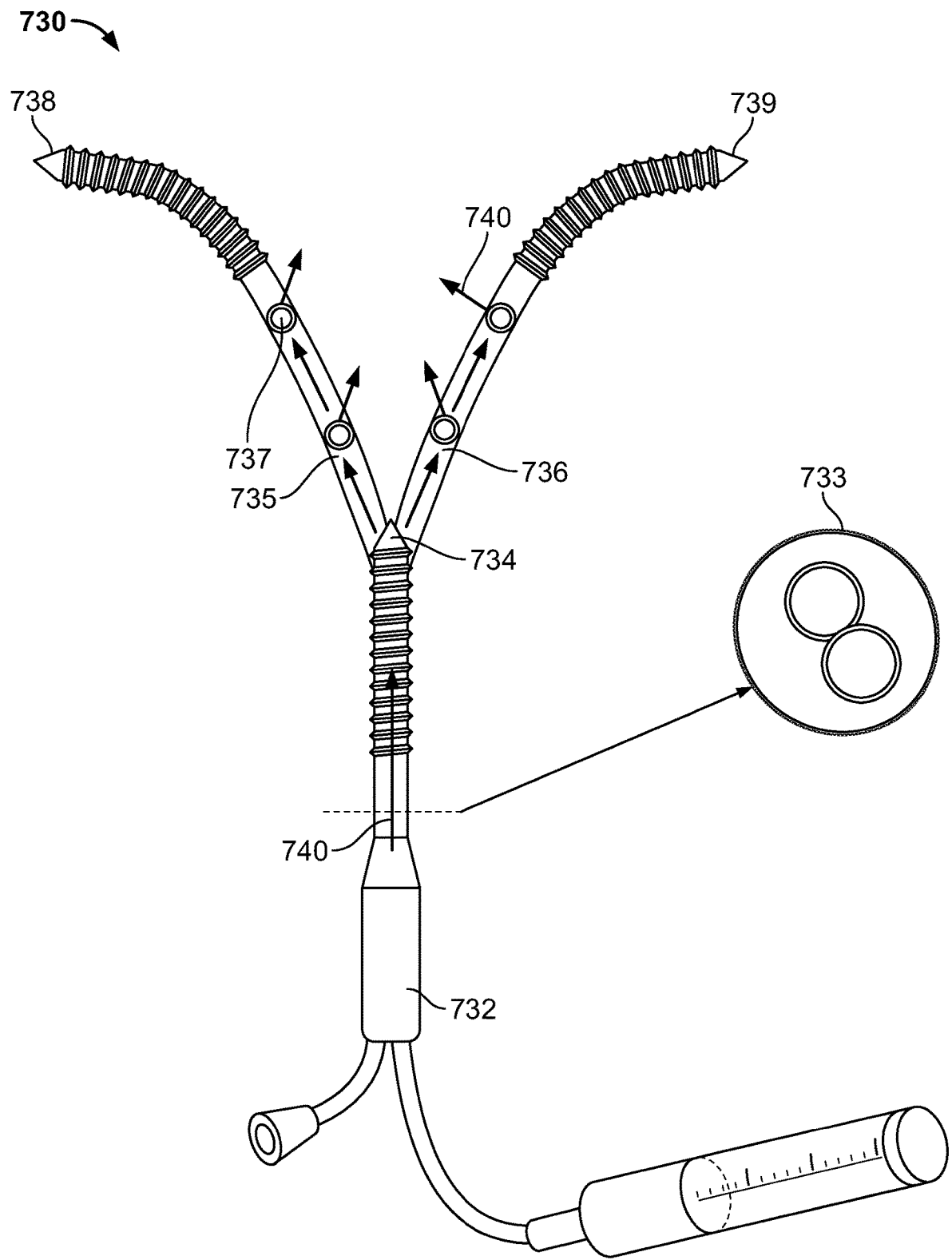
FIG. 7D is an illustration of a bifurcating coaxial catheter used in endometrial tissue ablation, in accordance with one embodiment of the present specification.

FIG. 7D is an illustration of a bifurcating coaxial catheter 730 used in endometrial tissue ablation, in accordance with one embodiment of the present specification. The catheter 730 includes a first elongate shaft 732 having a proximal end, a distal end and a first lumen within. The first lumen splits in the distal end to create a coaxial shaft 733. The distal end of the first shaft 732 also includes a first positioning element, or cervical plug 734, that occludes a patient's cervix. The catheter 730 bifurcates as it extends distally from the cervical plug 734 to form a second catheter shaft 735 and a third catheter shaft 736. The second and third catheter shafts 735, 736 each include a proximal end, a distal end, and a shaft body having one or more vapor delivery ports 737. The second and third catheter shafts 735, 736 include second and third lumens respectively, for the delivery of ablative agent. The distal ends of the second and third catheter shafts 735, 736 include second and third positioning elements, or fallopian tube plugs 738, 739 respectively, designed to engage a patient's fallopian tubes during an ablation therapy procedure and prevent the escape of ablative energy. The fallopian tube plugs 738, 739 also serve to position the second and third shafts 735, 736 respectively, in an intramural portion or isthmus of a patient's fallopian tube. The second and third catheter shafts 735, 736 are independently coaxially extendable and the length of each shaft 735, 736 is used to determine the dimension of a patient's endometrial cavity. An ablative agent 740 travels through the first catheter shaft 732, through both second and third catheter shaft 735, 736, and out the vapor delivery ports 737 and into the endometrial cavity to ablate endometrial tissue.

Figure 7E:
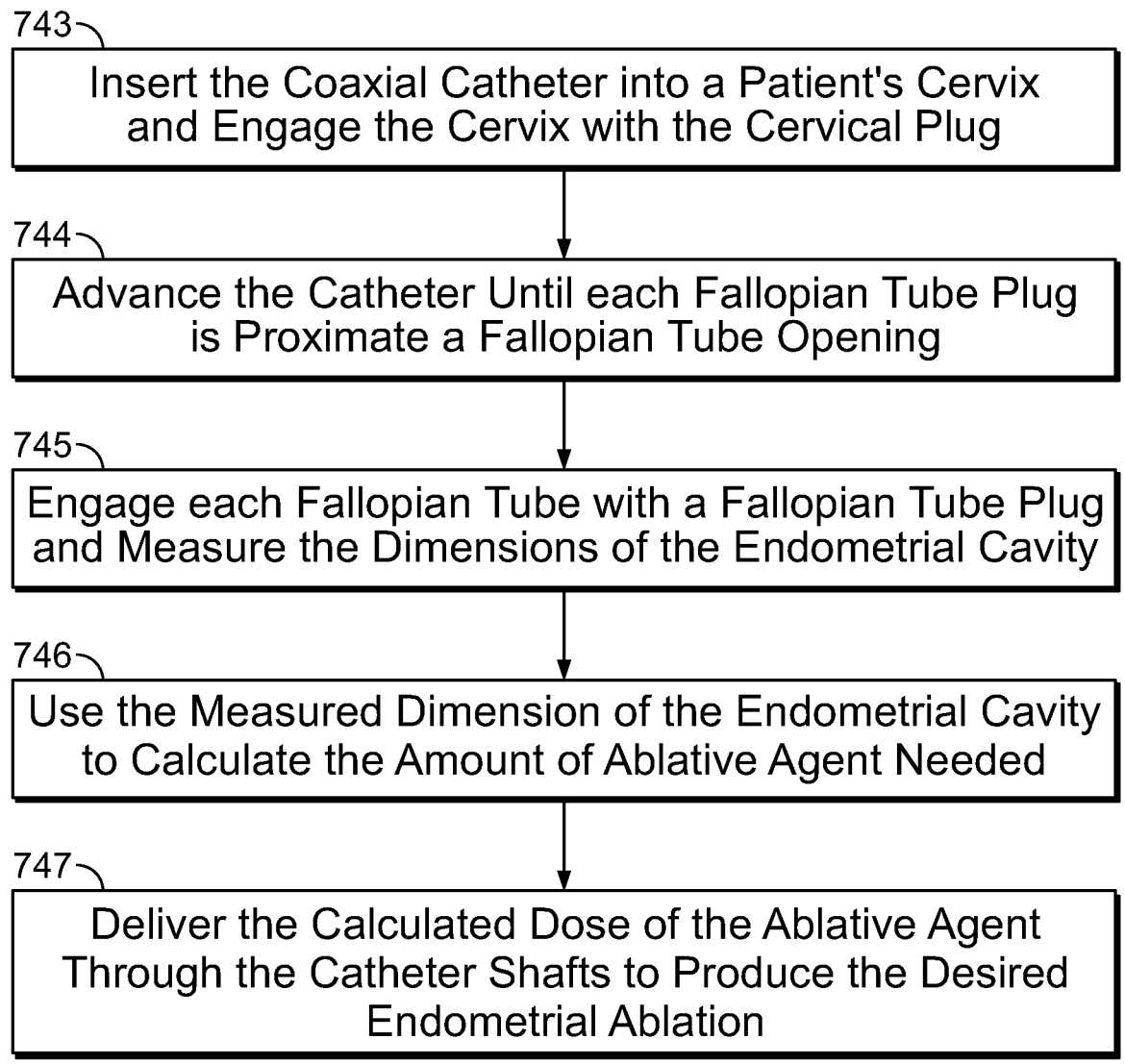
FIG. 7E is a flowchart listing the steps of a method of using the ablation catheter of FIG. 7D to ablate endometrial tissue, in accordance with one embodiment of the present specification.

FIG. 7E is a flowchart listing the steps of a method of using the ablation catheter of FIG. 7D to ablate endometrial tissue, in accordance with one embodiment of the present specification. At step 743, the coaxial catheter is inserted into a patient's cervix and the cervix is engaged with the cervical plug. The catheter is then advanced until each fallopian tube plug is proximate a fallopian tube opening at step 744. Each fallopian tube is then engaged with a fallopian tube plug at step 745 and the dimensions of the endometrial cavity are measured. The measurements are based on the length of each catheter shaft that has been advanced. At step 746, the measured dimensions are used to calculate the amount of ablative agent needed to carry out the ablation. The calculated dose of ablative agent is then delivered through the catheter shafts and into the endometrial cavity to produce the desired endometrial ablation at step 747.

Figure 7F:
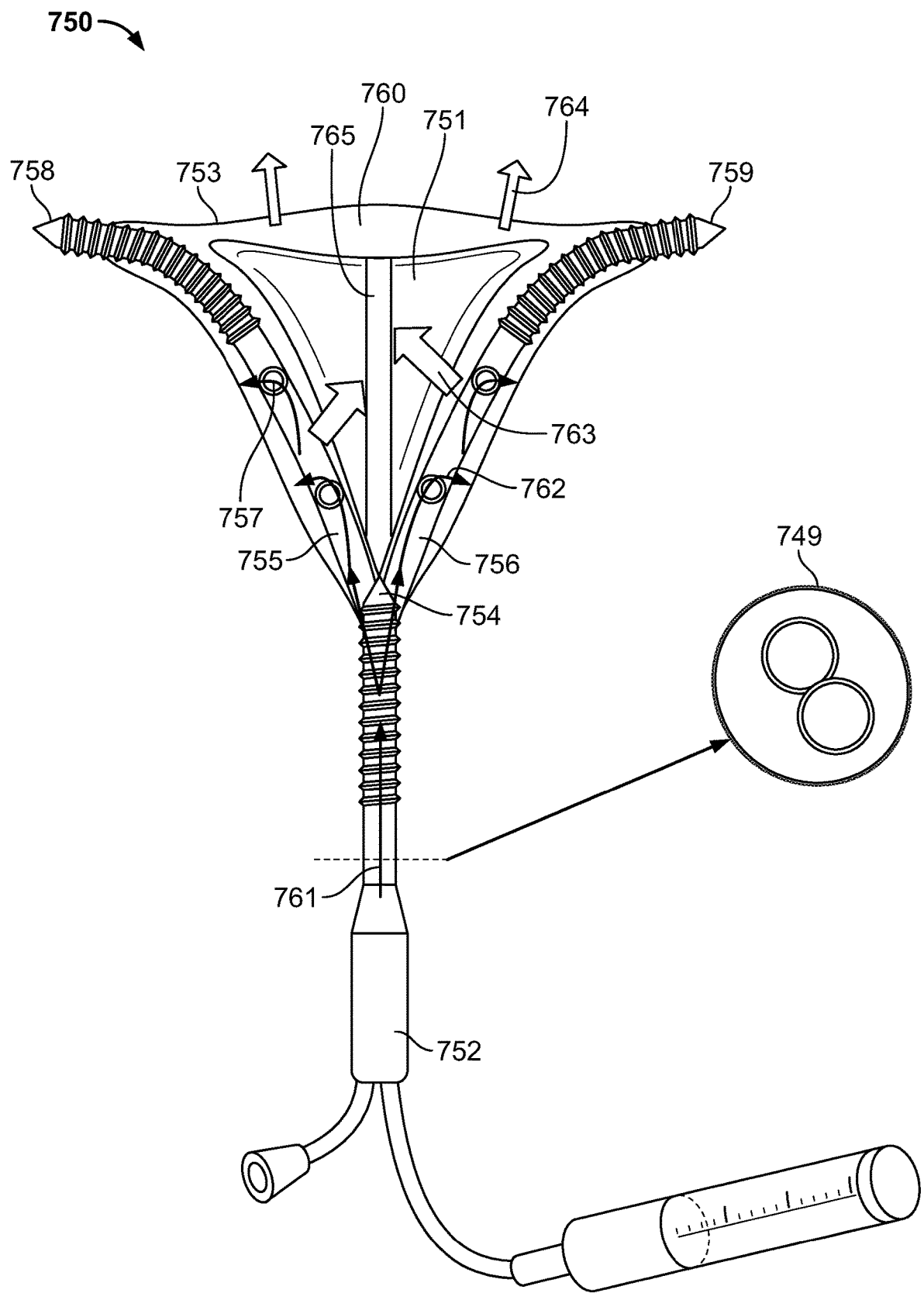
FIG. 7F is an illustration of a bifurcating coaxial catheter with expandable elements used in endometrial tissue ablation, in accordance with one embodiment of the present specification.

FIG. 7F is an illustration of a bifurcating coaxial catheter 750 with expandable elements 751, 753 used in endometrial tissue ablation, in accordance with one embodiment of the present specification. Similar to the catheter 730 of FIG. 7D, the catheter 750 depicted in FIG. 7F includes a first elongate coaxial shaft 752 having a proximal end, a distal end and a first lumen within. The first lumen splits in the distal end to create a coaxial shaft 749. The distal end of the first shaft 752 also includes a first positioning element, or cervical plug 754, that occludes a patient's cervix. The catheter 750 bifurcates as it extends distally from the cervical plug 754 to form a second catheter shaft 755 and a third catheter shaft 756. The second and third catheter shafts 755, 756 each include a proximal end, a distal end, and a catheter shaft body having one or more vapor delivery ports 757. The second and third catheter shafts 755, 756 include second and third lumens respectively, for the delivery of ablative agent. The distal ends of the second and third catheter shafts 755, 756 include second and third positioning elements, or fallopian tube plugs 758, 759 respectively, designed to engage a patient's fallopian tubes during an ablation therapy procedure and prevent the escape of ablative energy. The fallopian tube plugs 758, 759 also serve to position the second and third shafts 755, 756 respectively, in an intramural portion or isthmus of a patient's fallopian tube. The second and third catheter shafts 755, 756 are independently coaxially extendable and the length of each catheter shaft 755, 756 is used to determine the dimension of a patient's endometrial cavity.

The catheter 750 further includes a first expandable member or balloon 751 and a second expandable member or balloon 753 comprising a coaxial balloon structure. In one embodiment, the first balloon 751 is a compliant balloon structure and the second balloon 753 is a non-compliant balloon structure shaped to approximate the uterine cavity shape, size or volume. In another embodiment, the second balloon 753 is partially compliant. In another embodiment, the compliance of the two balloons 751, 753 is substantially equivalent. The balloons 751, 753 are attached to the second and third catheter shafts 755, 756 along an inner surface of each shaft 755, 756. The first, inner balloon 751 is positioned within the second, outer balloon 753. The inner balloon 751 is designed to be inflated with air and a first volume of the inner balloon 751 is used to measure a dimension of a patient's endometrial cavity. An ablative agent 761 is introduced into the catheter 750 at its proximal end and travels through the first catheter shaft 752 and into the second and third catheter shafts 755, 756. The second and third catheter shafts 755, 756 are designed to release ablative energy 762 through delivery ports 757 and into a space 760 between the two balloons 751, 753. Some of the ablative energy 763 is transferred to the air in the inner balloon 751, expanding its volume from said first volume to a second volume, resulting in further expansion of said inner balloon 751 to further occlude the patient's endometrial cavity for ideal vapor delivery. In one embodiment, the second volume is less than 25% greater than the first volume. The expansion also forces the fallopian tube plugs 758, 759 to further engage the openings of the fallopian tubes. A portion of the ablative agent or ablative energy 764 diffuses out of the thermally permeable outer balloon 753 and into the endometrial cavity, ablating the endometrial tissue. In various embodiments, the thermal heating of the air in the balloon occurs either through the walls of the inner balloon, through the length of the catheter, or through both. In one embodiment, the catheter 750 includes an optional fourth catheter shaft 765 extending from the first catheter shaft 752 and between the second and third catheter shaft 755, 756 within the inner balloon 751. Thermal energy from within the fourth catheter shaft 765 is used to further expand the inner balloon 751 and assist with ablation.

In one embodiment, the volume of the inner balloon 751 is used to control the pressure exerted by the outer balloon 753 on the wall of the uterus. The pressure in the inner balloon 751 is monitored and air is added to or removed from the inner balloon 751 to maintain a desirable therapeutic pressure in the outer balloon 753.

Figure 7G:
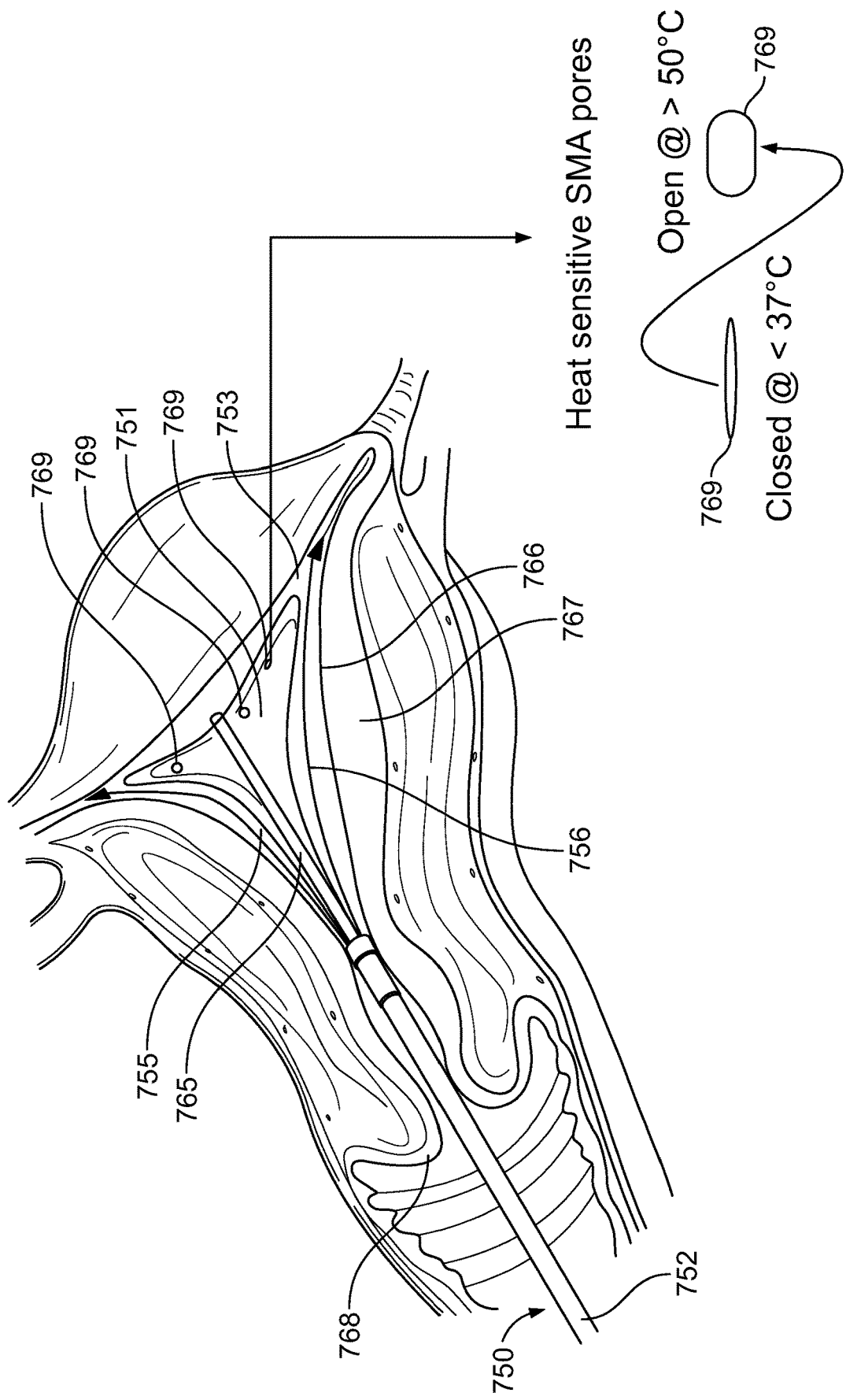
FIG. 7G is an illustration of the catheter of FIG. 7F inserted into a patient's uterine cavity for endometrial tissue ablation, in accordance with one embodiment of the present specification.

FIG. 7G is an illustration of the catheter 750 of FIG. 7F inserted into a patient's uterine cavity 766 for endometrial tissue 767 ablation, in accordance with one embodiment of the present specification. The catheter 750 has been inserted with the first shaft 752 extending through the patient's cervix 768 such that the second shaft 755 is positioned along a first side of the patient's uterine cavity 766 and the third shaft 756 is positioned along a second side opposite said first side. This positioning deploys the inner balloon 751 and outer balloon 753 between the second and third shafts 755, 756. In the pictured embodiment, the catheter 750 includes an optional fourth shaft 765 to further expand the inner balloon 751 with thermal energy and assist with ablation of endometrial tissue 767. In one embodiment, the inner balloon 751 is optional and the outer balloon 753 performs the function of both sizing and delivery of the ablative agent. In one embodiment, the outer balloon includes heat sensitive pores 769 which are closed at room temperature and open at a temperature higher than the body temperature. In one embodiment, the pores are composed of a shape memory alloy (SMA). In one embodiment, the SMA is Nitinol. In one embodiment, the austenite finish (Af) temperature, or temperature at which the transformation from martensite to austenite finishes on heating (alloy undergoes a shape change to become an open pore 769), of the SMA is greater than 37° C. In other embodiments, the Af temperature of the SMA is greater than 50° C. but less than 100° C.

Figure 7H:
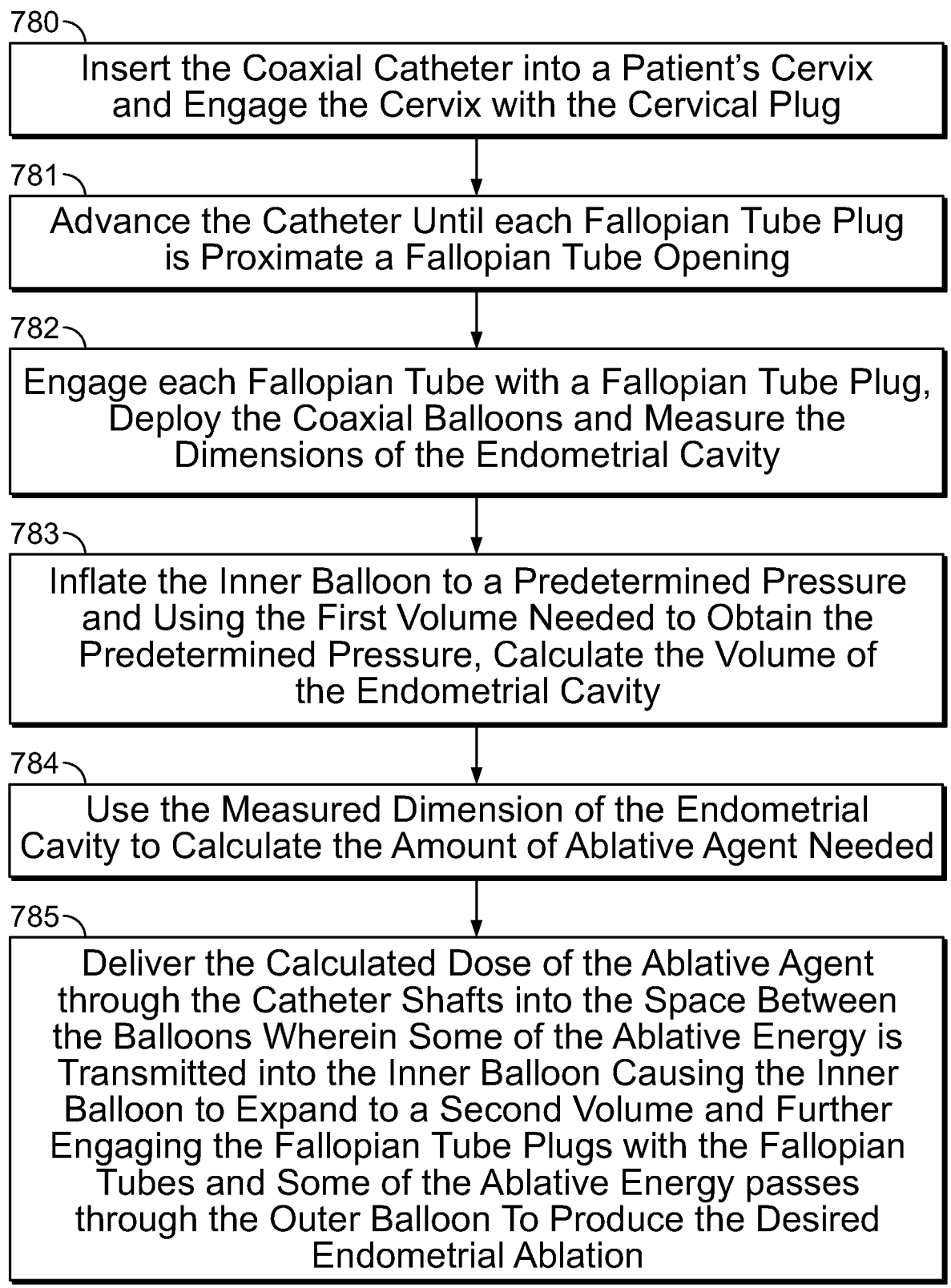
FIG. 7H is a flowchart listing the steps of a method of using the ablation catheter of FIG. 7F to ablate endometrial tissue, in accordance with one embodiment of the present specification.

FIG. 7H is a flowchart listing the steps of a method of using the ablation catheter of FIG. 7F to ablate endometrial tissue, in accordance with one embodiment of the present specification. At step 780, the coaxial catheter is inserted into a patient's cervix and the cervix is engaged with the cervical plug. The catheter is then advanced until each fallopian tube plug is proximate a fallopian tube opening at step 781. Each fallopian tube is then engaged with a fallopian tube plug at step 782, which also deploys the coaxial balloons in the endometrial cavity, and the dimensions of the endometrial cavity are measured. The measurements are based on the length of each catheter shaft that has been advanced and a first volume needed to expand the inner balloon to a predetermined pressure. At step 783, the inner balloon is inflated to said predetermined pressure and a first volume of the inner balloon at said pressure is used to calculate the volume of the endometrial cavity. The measured dimensions are then used at step 784 to calculate the amount of ablative agent needed to carry out the ablation. The calculated dose of ablative agent is then delivered through the catheter shafts and into the space between the coaxial balloons at step 785. Some of the ablative energy is transmitted into the inner balloon to expand the inner balloon to a second volume which further expands the endometrial cavity and, optionally, further pushes the fallopian tube plugs into the fallopian tube openings to prevent the escape of thermal energy. Another portion of the ablative energy passes through the thermally permeable outer balloon to produce the desired endometrial ablation.

In another embodiment, a vapor ablation device for ablation of endometrial tissue comprises a catheter designed to be inserted through a cervical os and into an endometrial cavity, wherein the catheter is connected to a vapor generator for generation of vapor and includes at least one port positioned in the endometrial cavity to deliver the vapor into the endometrial cavity. The vapor is delivered through the port and heats and expands the air in the endometrial cavity to maintain the endometrial cavity pressure below 200 mm Hg and ideally below 50 mm of Hg. In one embodiment, an optional pressure sensor measures the pressure and maintains the intracavitary pressure at the desired therapeutic level, wherein the endometrial cavity is optimally expanded to allow for uniform distribution of ablative energy without the risk of significant leakage of the ablative energy beyond the endometrial cavity and damage to the adjacent normal tissue.

Figure 8:
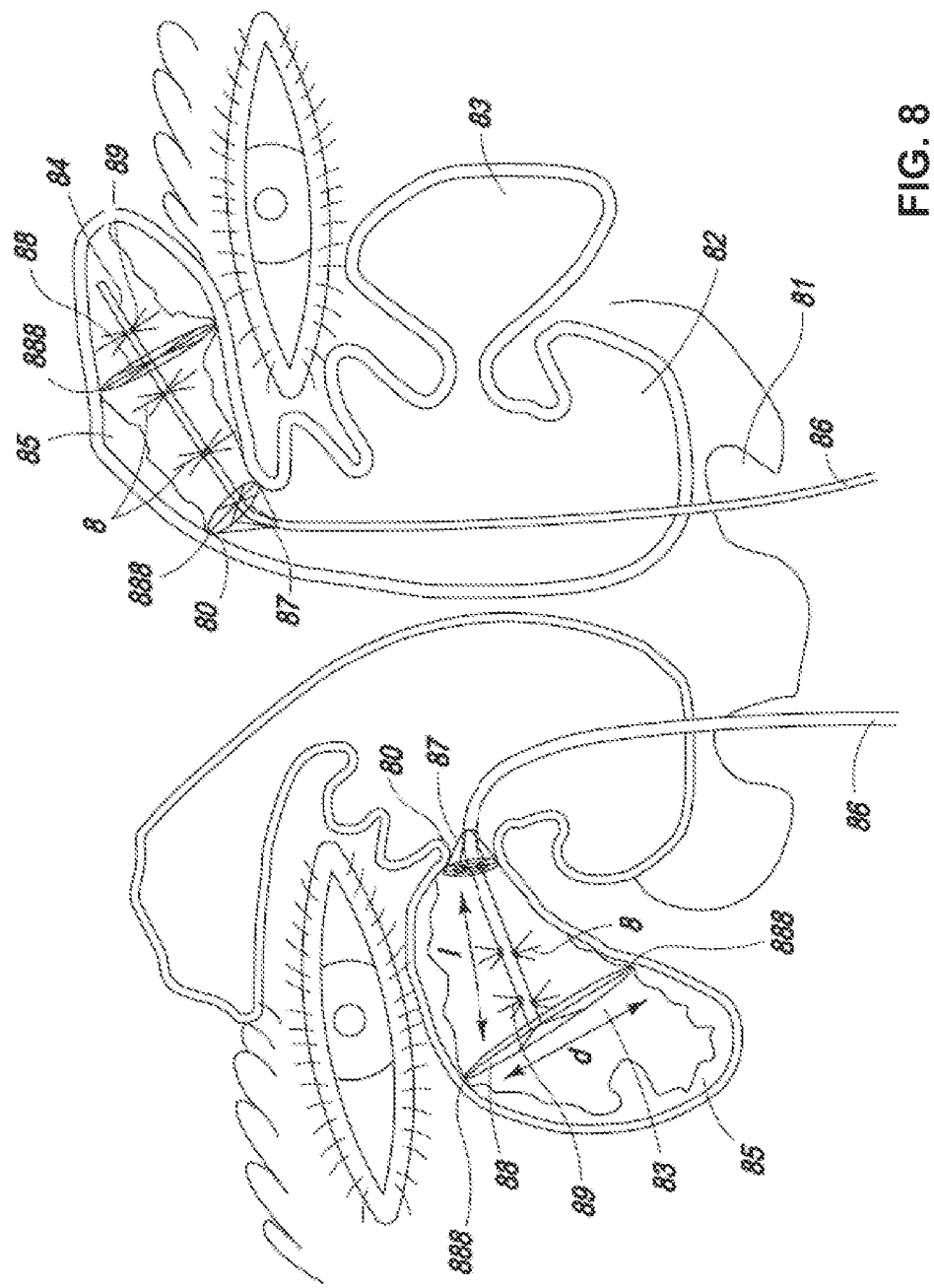
FIG. 8 illustrates sinus ablation being performed in a nasal passage by using the ablation device, in accordance with an embodiment of the present specification.

FIG. 8 illustrates sinus ablation being performed in a nasal passage by using the ablation device, in accordance with an embodiment of the present specification. A cross-section of the nasal passage and sinuses comprising nares 81, nasal passages 82, frontal sinus 83, ethmoid sinus 84, and diseased sinus epithelium 85 is illustrated. The catheter 86 is inserted into the frontal sinus 83 or the ethmoid sinus 84 through the nares 81 and nasal passages 82.

In an embodiment, the catheter 86 has two positioning elements, a conical positioning element 87 and a disc shaped positioning element 88. The positioning element 87 is conical and has an insulated membrane covering. The conical element 87 positions the catheter 86 in the center of the sinus opening 80 and the insulated membrane prevents the escape of thermal energy or ablative agent through the opening. The second disc shaped positioning element 88 is deployed in the frontal sinus cavity 83 or ethmoid sinus cavity 84, positioning the catheter 86 in the middle of either sinus cavity. The ablative agent 8 is passed through the infusion port 89 for uniform delivery of the ablative agent 8 into the sinus cavity. The predetermined length 'l' of the ablative segment of the catheter and diameter 'd' of the positioning element 88 allows for estimation of the sinus cavity size and is used to calculate the amount of thermal energy needed to ablate the diseased sinus epithelium 85. Optional temperature sensors 888 are deployed close to the diseased sinus epithelium 85 to control the delivery of the ablative agent 8. In an embodiment, the ablative agent 8 is steam which contracts on cooling. This further decreases the risk of leakage of the thermal energy thus reducing any risk of thermal injury to adjacent healthy tissue. In one embodiment, the dimensional ranges of the positioning elements are similar to those in the endometrial application, with preferred maximum ranges being half thereof. Optional topographic mapping using multiple infrared, electromagnetic, acoustic or radiofrequency energy emitters and sensors can be used to define cavity size and shape in patients with an irregular or deformed nasal cavity due to conditions such as nasal polyps. In various embodiments, the ablative agent is combined with an antibiotic or anti-inflammatory agent, including a long-acting steroid.

FIG. 9A illustrates bronchial and bullous ablation being performed in a pulmonary system by using the ablation device, in accordance with an embodiment of the present specification. A cross-section of the pulmonary system comprising bronchus 91, normal alveolus 92, bullous lesion 93, and a bronchial neoplasm 94 is illustrated.

In one embodiment, the catheter 96 is inserted through the channel of a bronchoscope 95 into the bronchus 91 and advanced into a bullous lesion 93. The catheter 96 has two positioning elements, a conical positioning element 97 and a disc shaped positioning element 98. The positioning element 97 is conical having an insulated membrane covering. The conical element 97 positions the catheter 96 in the center of the bronchus 91 and the insulated membrane prevents the escape of thermal energy or ablative agent through the opening into the normal bronchus. The second disc shaped positioning element 98 is deployed in the bullous cavity 93 positioning the catheter 96 in the middle of the bullous cavity 93. An ablative agent 9 is passed through the infusion port 99 for uniform delivery into the sinus cavity. Predetermined length 'l' of the ablative segment of the catheter 96 and diameter 'd' of the positioning element 98 allow for estimation of the bullous cavity size and is used to calculate the amount of thermal energy needed to ablate the diseased bullous cavity 93. Optionally, the size of the cavity can be calculated from radiological evaluation using a chest CAT scan or MRI. Optional temperature sensors are deployed close to the surface of the bullous cavity 93 to control the delivery of the ablative agent 9. In an embodiment, the ablative agent is steam which contracts on cooling. This further decreases the risk of leakage of the thermal energy into the normal bronchus thus reducing any risk of thermal injury to adjacent normal tissue.

In one embodiment, the positioning attachment must be separated from the ablation region by a distance of greater than 0.1 mm, preferably 1 mm and more preferably 1 cm. In another embodiment, the positioning attachment can be in the ablated region as long as it does not cover a significant surface area.

In one embodiment, there are preferably two positioning attachments. In another embodiment, the endoscope is used as one fixation point with one positioning element. The positioning device is between 0.1 mm and 5 cm (preferably 1 mm to 2 cm). The distal positioning device is preferably circular with a diameter between 0.1 mm and 10 cm, preferably 1 cm to 5 cm.

In another embodiment for the ablation of a bronchial neoplasm 94, the catheter 96 is inserted through the channel of a bronchoscope 95 into the bronchus 91 and advanced across the bronchial neoplasm 94. The positioning element 98 is disc shaped having an insulated membrane covering. The positioning element 98 positions the catheter in the center of the bronchus 91 and the insulated membrane prevents the escape of thermal energy or ablative agent through the opening into the normal bronchus. The ablative agent 9 is passed through the infusion port 99 in a non-circumferential pattern for uniform delivery of the ablative agent to the bronchial neoplasm 94. The predetermined length 'l' of the ablative segment of the catheter and diameter 'd' of the positioning element 98 are used to calculate the amount of thermal energy needed to ablate the bronchial neoplasm 94.

The catheter could be advanced to the desired location of ablation using endoscopic, laparoscopic, stereotactic or radiological guidance. Optionally the catheter could be advanced to the desired location using magnetic navigation.

In another embodiment, a positioning element is an inflatable balloon in thermal communication with the vapor delivery catheter. The balloon is inflated to a first volume which is used to measure the inner diameter of the bronchus. On delivery of ablative energy through the catheter, a portion of thermal energy is transferred to the air in the balloon which further expands the balloon to a second volume which is up to 25% greater than the first volume and is ideally optimized to occlude the bronchus, preventing the leakage of ablative agent.

Figure 9B:
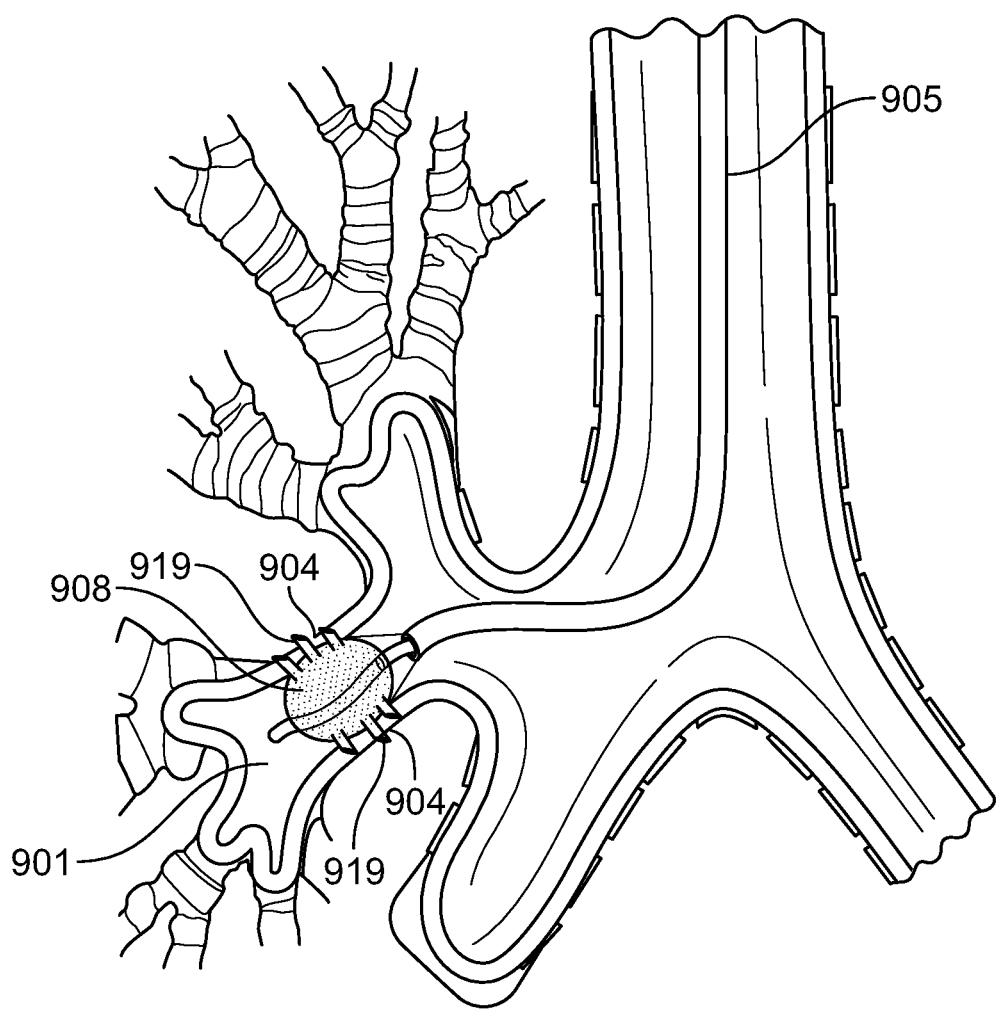
FIG. 9B illustrates bronchial ablation being performed by an ablation device having an inflatable balloon with at least one thermally conducting element attached thereto, in accordance with one embodiment of the present specification.

FIG. 9B illustrates bronchial ablation being performed by an ablation device 905 having an inflatable balloon 908 with at least one thermally conducting element 919 attached thereto, in accordance with one embodiment of the present specification. The ablation device 905 is inserted with its distal end positioned in a patient's bronchus 901 proximate a bronchial wall 904 with a target tissue. The balloon 908 is inflated to a first volume to bring the thermally conducting element 919 into contact with a bronchial wall 904. The ablative agent is then released into the balloon 908, further expanding the volume of the balloon 908 and pushing the thermally conducting element 919 into the bronchial wall 904 and releasing the ablative energy into said wall 904, thus ablating structures in or around the wall 904. In various embodiments, the thermally conducting element 919 comprises a solid or hollow needle. In various embodiments, a hollow needle includes a valve which is controlled by pressure, temperature, or both, and opens when the pressure or temperature in the vicinity of the valve exceeds a predefined threshold value.

Figure 10A:
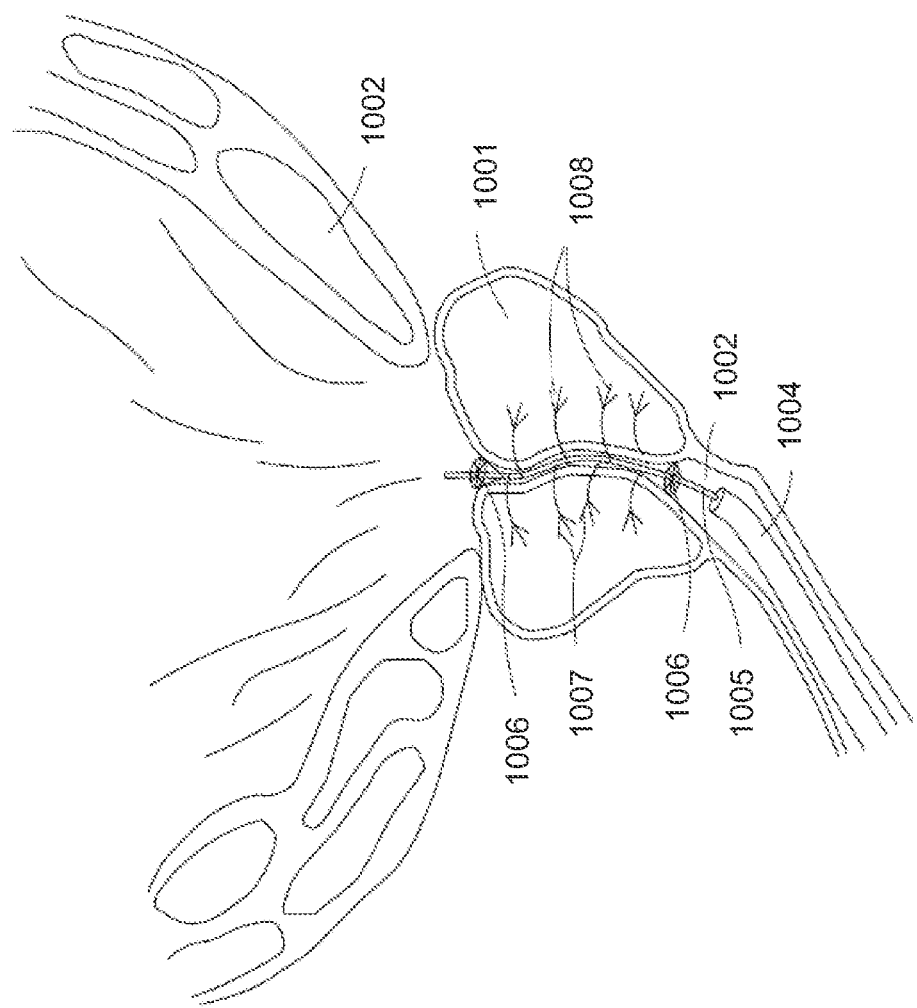
FIG. 10A illustrates prostate ablation being performed on an enlarged prostrate in a male urinary system by using the device, in accordance with an embodiment of the present specification.

FIG. 10A illustrates prostate ablation being performed on an enlarged prostate in a male urinary system by using the device, in accordance with an embodiment of the present specification. A cross-section of a male genitourinary tract having an enlarged prostate 1001, bladder 1002, and urethra 1003 is illustrated. The urethra 1003 is compressed by the enlarged prostate 1001. The ablation catheter 1005 is passed through the cystoscope 1004 positioned in the urethra 1003 distal to the obstruction. The positioning elements 1006 are deployed to center the catheter in the urethra 1003 and one or more insulated needles 1007 are passed to pierce the prostate 1001. The vapor ablative agent 1008 is passed through the insulated needles 1007 thus causing ablation of the diseased prostatic tissue resulting in shrinkage of the prostate.

The size of the enlarged prostate could be calculated by using the differential between the extra-prostatic and intra-prostatic urethra. Normative values could be used as baseline. Additional ports for infusion of a cooling fluid into the urethra can be provided to prevent damage to the urethra while the ablative energy is being delivered to the prostate for ablation, thus preventing complications such as stricture formation.

In one embodiment, the positioning attachment must be separated from the ablation region by a distance of greater than 0.1 mm, preferably 1 mm to 5 mm and no more than 2 cm. In another embodiment, the positioning attachment can be deployed in the bladder and pulled back into the urethral opening/neck of the bladder thus fixing the catheter. In one embodiment, the positioning device is between 0.1 mm and 10 cm in diameter.

Figure 10C:
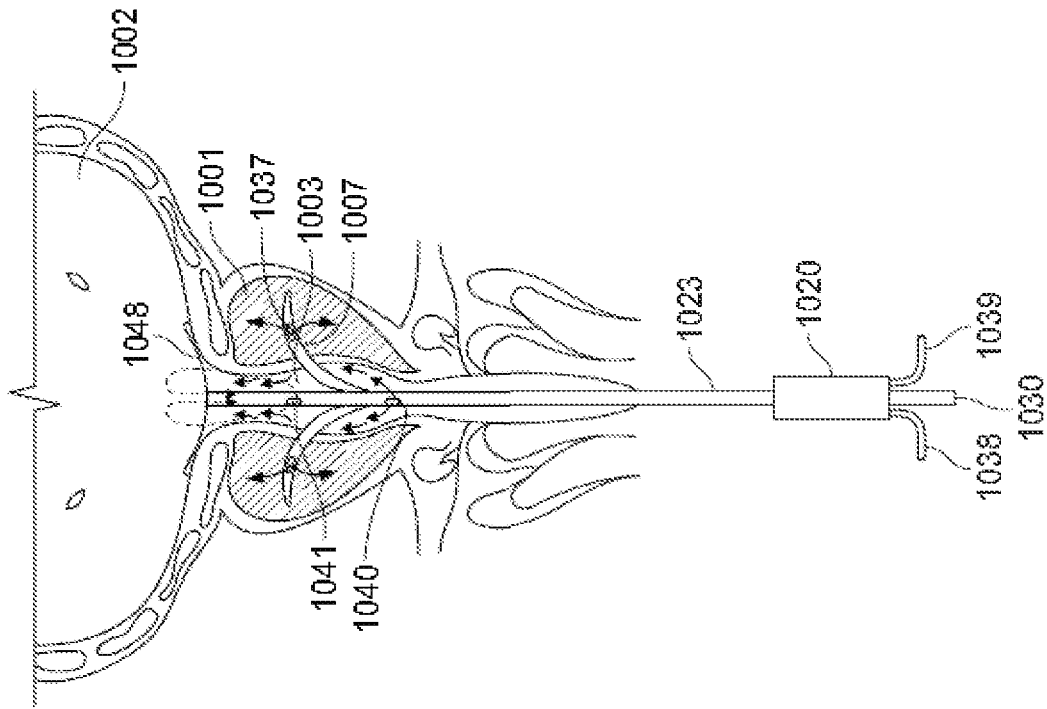
FIG. 10C is an illustration of transurethral prostate ablation being performed on an enlarged prostrate in a male urinary system using an ablation device, in accordance with another embodiment of the present specification.
Figure 10B:
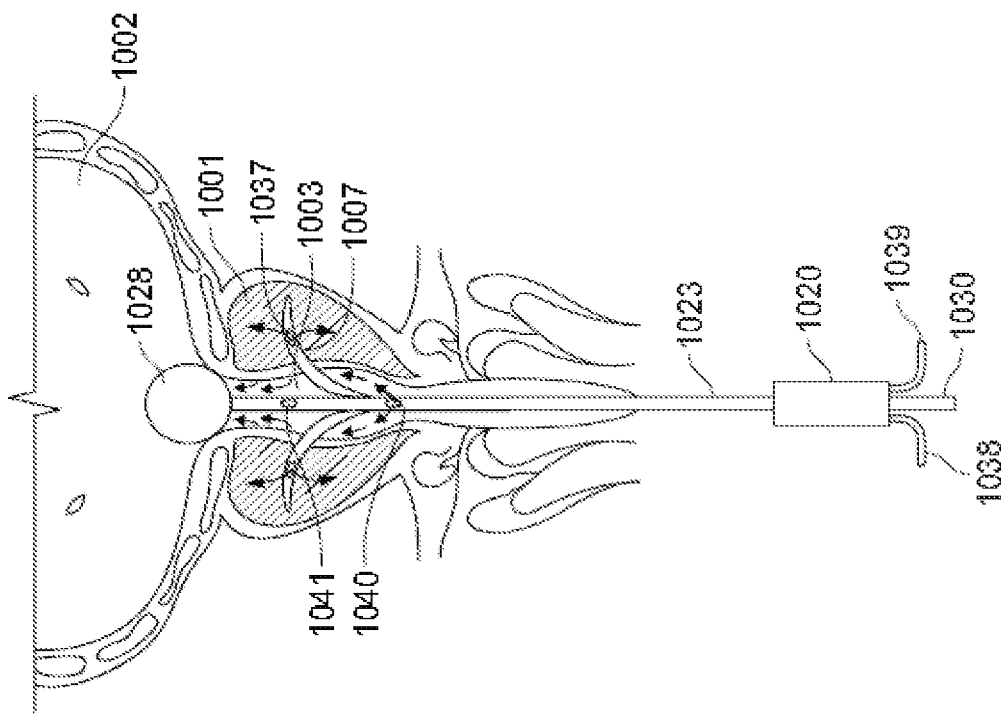
FIG. 10B is an illustration of transurethral prostate ablation being performed on an enlarged prostrate in a male urinary system using an ablation device, in accordance with one embodiment of the present specification.

FIG. 10B is an illustration of transurethral prostate ablation being performed on an enlarged prostate 1001 in a male urinary system using an ablation device, in accordance with one embodiment of the present specification. Also depicted in FIG. 10B are the urinary bladder 1002 and prostatic urethra 1003. An ablation catheter 1023 with a handle 1020 and a positioning element 1028 is inserted into the urethra 1003 and advanced into the bladder 1002. The position element 1028 is inflated and pulled to the junction of the bladder with the urethra, thus positioning needles 1007 at a predetermined distance from the junction. Using a pusher 1030, the needles 1007 are then pushed out at an angle between 30 and 90 degree from the catheter 1023 through the urethra 1003 into the prostate 1001. Vapor is administered through a port 1038 that travels through the shaft of the catheter 1023 and exits from openings 1037 in the needles 1007 into the prostatic tissue, thus ablating the prostatic tissue. In one embodiment, the needles 1007 are insulated. Optional port 1039 allows for insertion of cool fluid at a temperature <37 degree C. through opening 1040 to cool the prostatic urethra. Optional temperature sensors 1041 can be installed to detect the temperature of the prostatic urethra and modulate the delivery of vapor.

FIG. 10C is an illustration of transurethral prostate ablation being performed on an enlarged prostate 1001 in a male urinary system using an ablation device, in accordance with another embodiment of the present specification. Also depicted in FIG. 10B are the urinary bladder 1002 and prostatic urethra 1003. An ablation catheter 1023 with a handle 1020 and a positioning element 1048 is inserted into the urethra 1003 and advanced into the bladder 1002. The positioning element 1048 is a compressible disc that is expanded in the bladder 1002 and pulled to the junction of the bladder with the urethra, thus positioning needles 1007 at a predetermined distance from the junction. Using a pusher 1030, the needles 1007 are then pushed out at an angle between 30 and 90 degree from the catheter 1023 through the urethra 1003 into the prostate 1001. Vapor is administered through a port 1038 that travels through the shaft of the catheter 1023 and exits through openings 1037 in the needles 17 into the prostatic tissue, thus ablating the prostatic tissue. In one embodiment, the needles 1007 are insulated. Optional port 1039 allows for insertion of cool fluid at a temperature <37 degree C. through opening 1040 to cool the prostatic urethra. Optional temperature sensors 1041 can be installed to detect the temperature of the prostatic urethra and modulate the delivery of vapor.

Figure 10D:
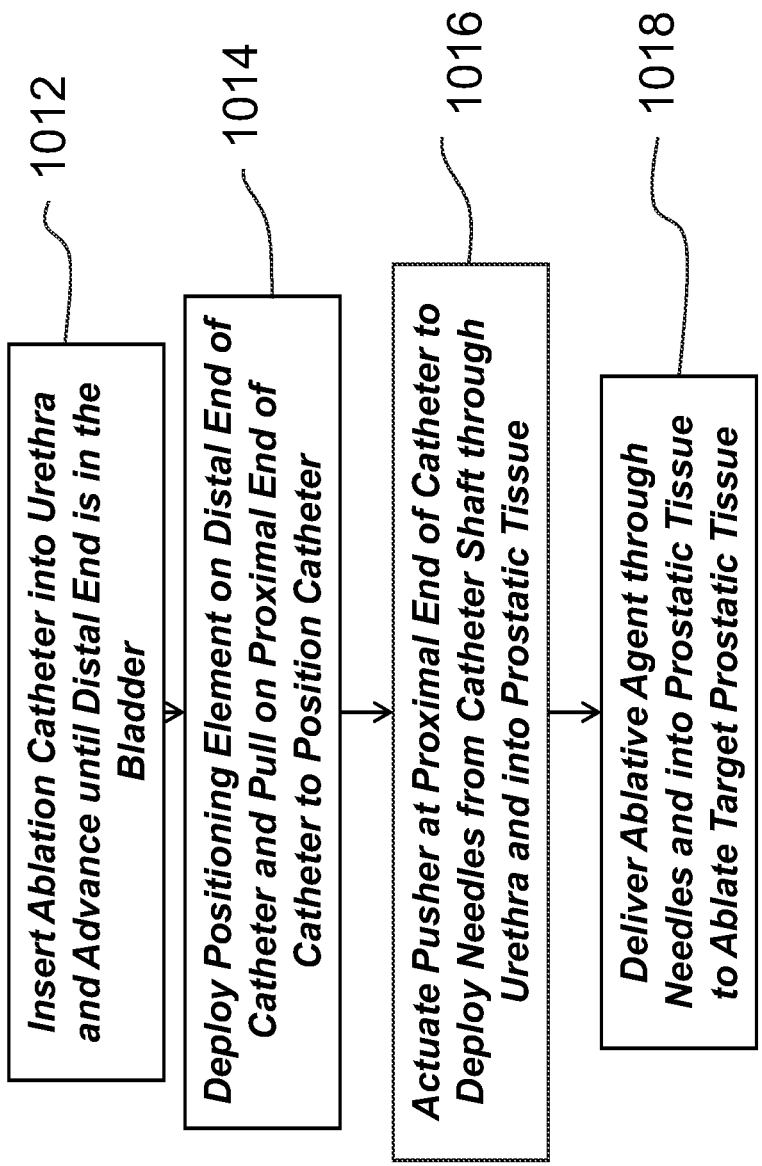
FIG. 10D is a flow chart listing the steps involved in a transurethral enlarged prostate ablation process using an ablation catheter, in accordance with one embodiment of the present specification.

FIG. 10D is a flow chart listing the steps involved in a transurethral enlarged prostate ablation process using an ablation catheter, in accordance with one embodiment of the present specification. At step 1012, an ablation catheter is inserted into the urethra and advanced until its distal end is in the bladder. A positioning element is then deployed on the distal end of the catheter, at step 1014, and the proximal end of the catheter is pulled so that the positioning element abuts the junction of the bladder with the urethra, thereby positioning the catheter shaft within the urethra. A pusher at the proximal end of the catheter is actuated to deploy needles from the catheter shaft through the urethra and into the prostatic tissue at step 1016. At step 1018, an ablative agent is delivered through the needles and into the prostate to ablate the target prostatic tissue.

Figure 10E:
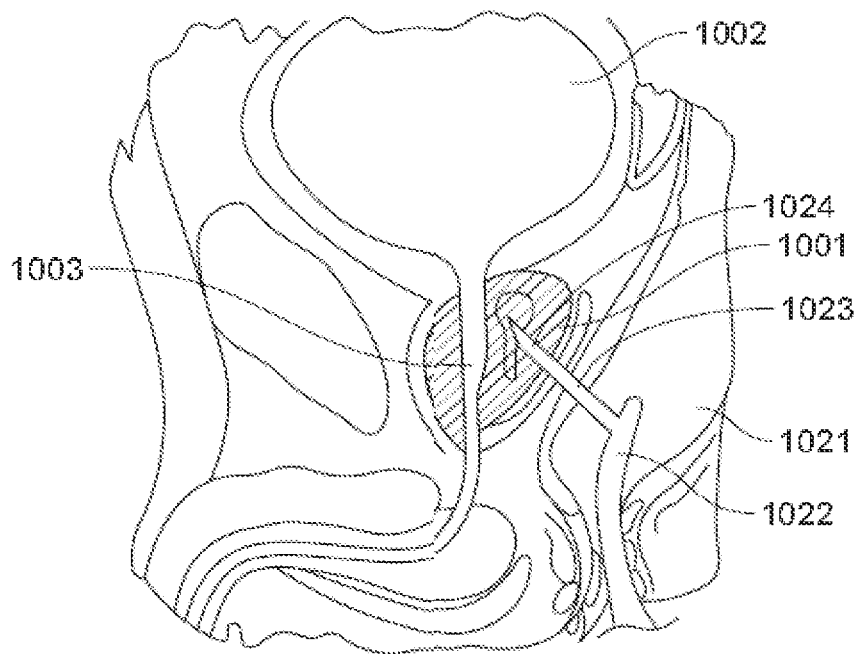
FIG. 10E is an illustration of transrectal prostate ablation being performed on an enlarged prostrate in a male urinary system using an ablation device, in accordance with one embodiment of the present specification.

FIG. 10E is an illustration of transrectal prostate ablation being performed on an enlarged prostrate in a male urinary system using an ablation device, in accordance with one embodiment of the present specification. Also depicted in FIG. 10E are the urinary bladder 1002 and prostatic urethra 1003. The ablation device comprises a catheter 1023 with a needle tip 1024. An endoscope 1022 is inserted into the rectum 1021 for the visualization of the enlarged prostate 1001. In various embodiments, the endoscope 1022 is an echoendoscope or a transrectal ultrasound such that the endoscope can be visualized using radiographic techniques. The catheter 1023 with needle tip 1024 is passed through a working channel of the endoscope and the needle tip 1024 is passed transrectally into the prostate 1001. A close-up illustration of the distal end of the catheter 1023 and needle tip 1204 is depicted in FIG. 10G. An ablative agent is then delivered through the needle tip 1024 into the prostatic tissue for ablation. In one embodiment, the catheter 1023 and needle tip 1024 are composed of a thermally insulated material. In various embodiments, the needle tip 1024 is an echotip or sonolucent tip that can be observed using radiologic techniques for accurate localization in the prostate tissue. In one embodiment, an optional catheter (not shown) can be placed in the urethra to insert fluid to cool the prostatic urethra 1003. In one embodiment, the inserted fluid has a temperature less than 37° C.

Figure 10F:
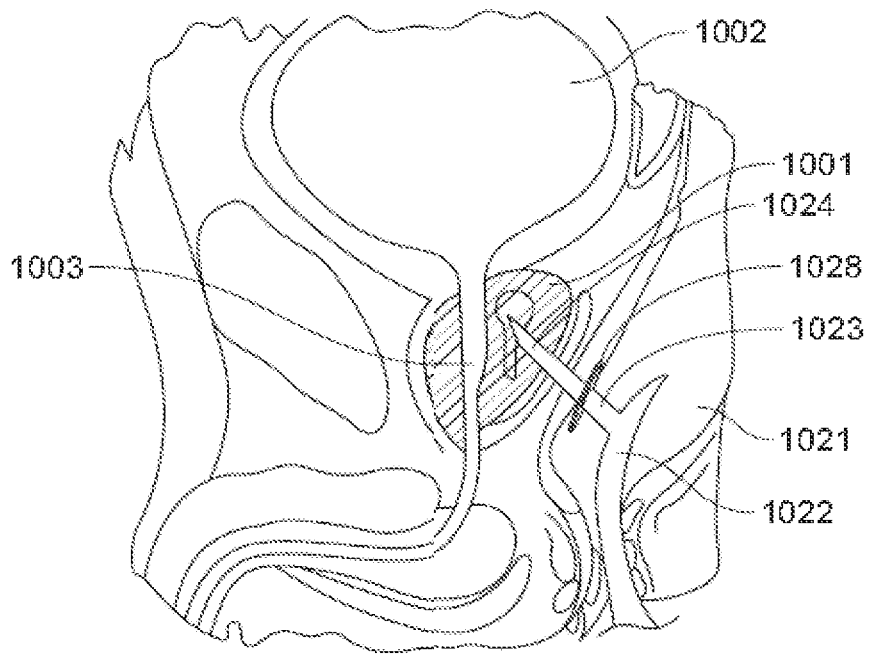
FIG. 10F is an illustration of transrectal prostate ablation being performed on an enlarged prostrate in a male urinary system using a coaxial ablation device having a positioning element, in accordance with another embodiment of the present specification.
Figure 10G:
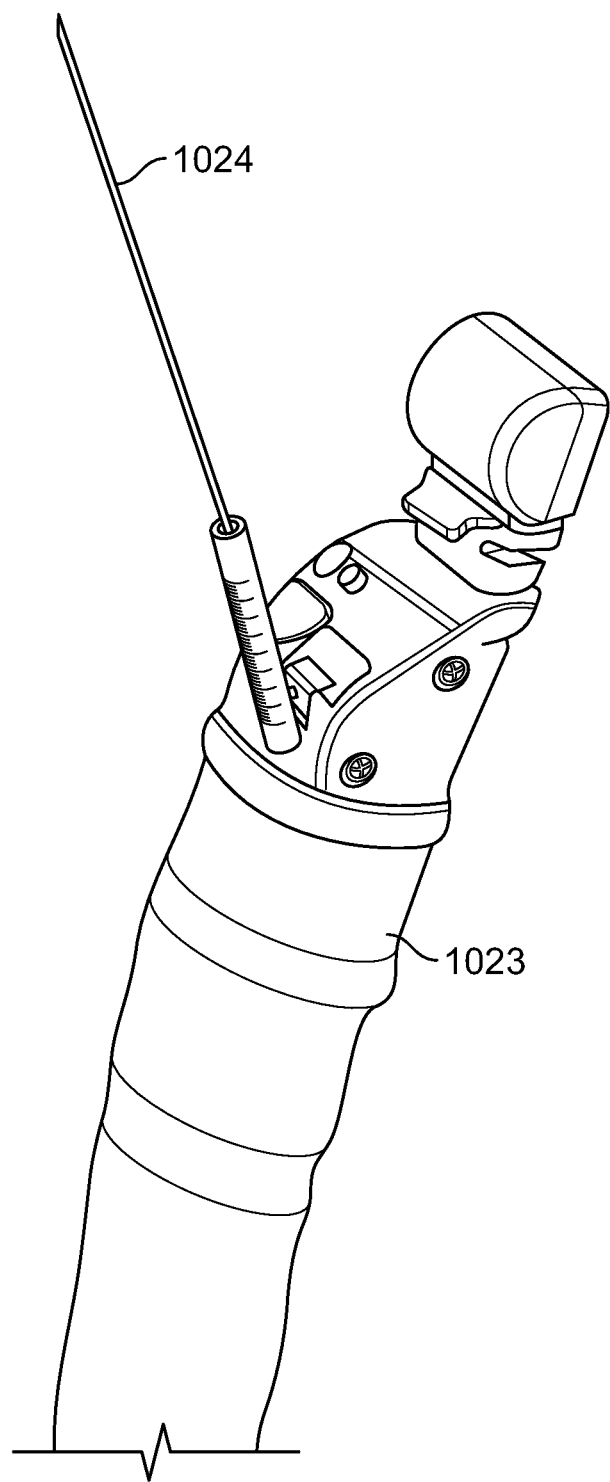
FIG. 10G is a close-up illustration of the distal end of the catheter and needle tip of the ablation device of FIGS. 10E and 10F.

FIG. 10F is an illustration of transrectal prostate ablation being performed on an enlarged prostrate in a male urinary system using a coaxial ablation device having a positioning element, in accordance with another embodiment of the present specification. Also depicted in FIG. 10F are the urinary bladder 1002 and prostatic urethra 1003. The ablation device comprises a coaxial catheter 1023 having an internal catheter with a needle tip 1024 and an external catheter with a positioning element 1028. An endoscope 1022 is inserted into the rectum 1021 for the visualization of the enlarged prostate 1001. In various embodiments, the endoscope 1022 is an echoendoscope or a transrectal ultrasound such that the endoscope can be visualized using radiographic techniques. The coaxial catheter 1023 with needle tip 1024 and positioning element 1028 is passed through a working channel of the endoscope such that the positioning element 1028 comes to rest up against the rectal wall and the internal catheter is advanced transrectally, thereby positioning the needle tip 1024 at a predetermined depth in the prostate 1001. A close-up illustration of the distal end of the catheter 1023 and needle tip 1204 is depicted in FIG. 10G. In one embodiment, the positioning element is a compressible disc that has a first, compressed pre-employment configuration and a second, expanded deployed configuration once it has passed beyond the distal end of the endoscope 1022. An ablative agent is then delivered through the needle tip 1024 into the prostatic tissue for ablation. In one embodiment, the coaxial catheter 1023, needle tip 1024, and positioning element 1028 are composed of a thermally insulated material. In various embodiments, the needle tip 1024 is an echotip or sonolucent tip that can be observed using radiologic techniques for accurate localization in the prostate tissue. In one embodiment, an optional catheter (not shown) can be placed in the urethra to insert fluid to cool the prostatic urethra 1003. In one embodiment, the inserted fluid has a temperature less than 37° C.

Figure 10H:
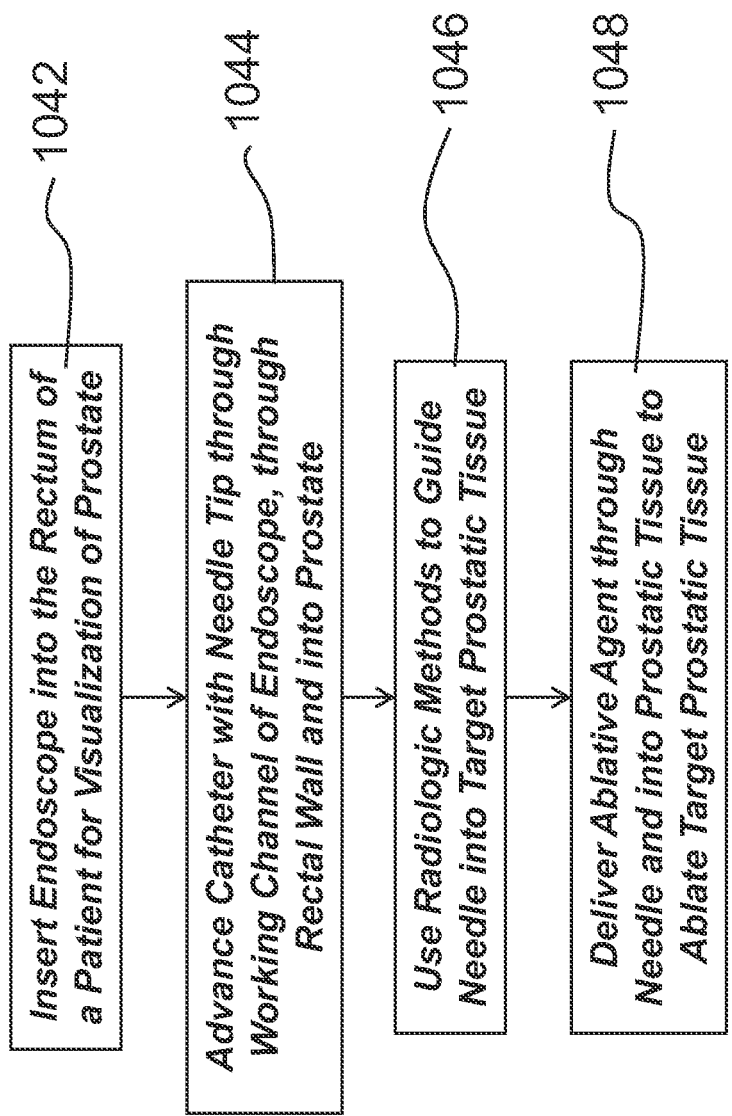
FIG. 10H is a flow chart listing the steps involved in a transrectal enlarged prostate ablation process using an ablation catheter, in accordance with one embodiment of the present specification.

FIG. 10H is a flow chart listing the steps involved in a transrectal enlarged prostate ablation process using an ablation catheter, in accordance with one embodiment of the present specification. At step 1042, an endoscope is inserted into the rectum of a patient for visualization of the prostate. A catheter with a needle tip is then advanced, at step 1044, through a working channel of the endoscope and through the rectal wall and into the prostate. Radiologic methods are used to guide the needle into the target prostatic tissue at step 1046. At step 1048, an ablative agent is delivered through the needle and into the prostate to ablate the target prostatic tissue.

Figure 10I:
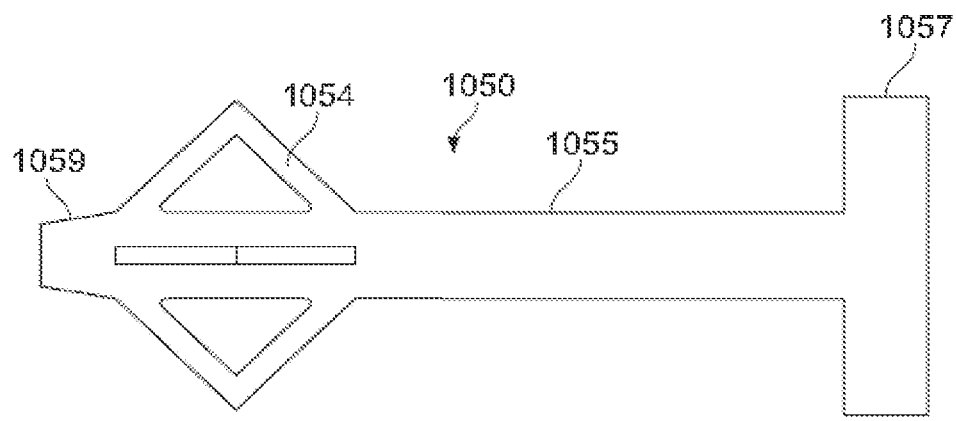
FIG. 10I is an illustration of an ablation catheter for permanent implantation in the body to deliver repeat ablation, in accordance with one embodiment of the present specification.
Figure 10J:
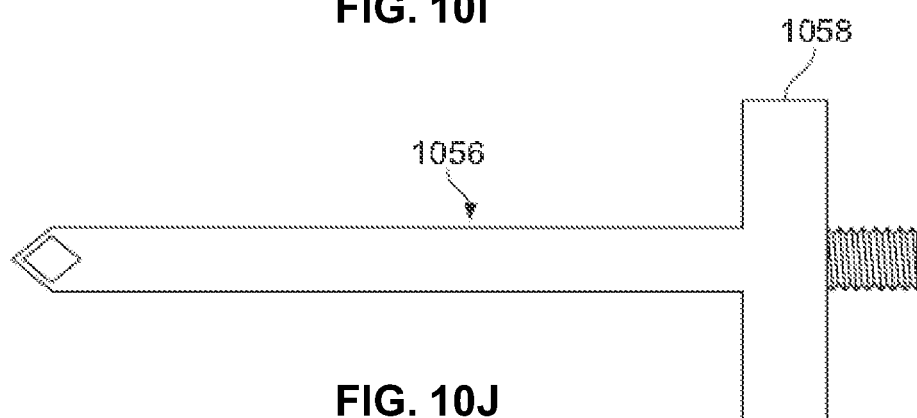
FIG. 10J is an illustration of a trocar used to place the ablation catheter of FIG. 10I in the body, in accordance with one embodiment of the present specification.
Figure 10K:
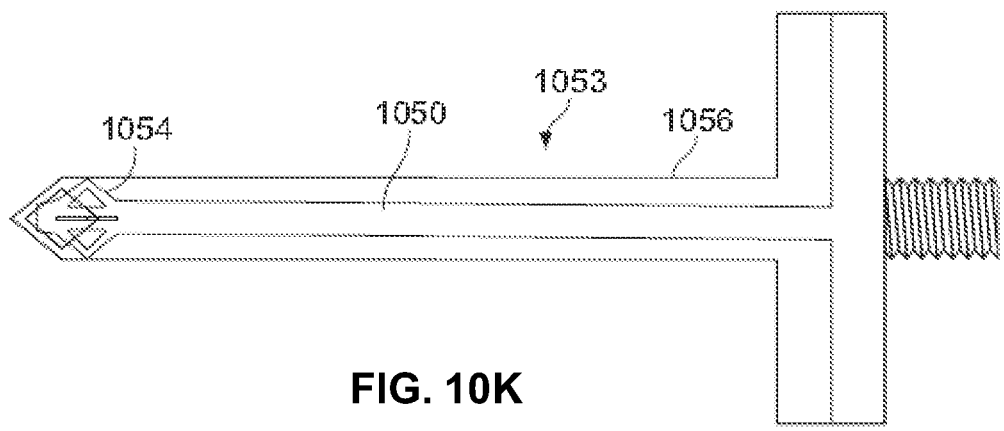
FIG. 10K is an illustration of the catheter of FIG. 10I and the trocar of FIG. 10J assembled for placement of the catheter into tissue targeted for ablation in the human body, in accordance with one embodiment of the present specification.

FIG. 10I is an illustration of an ablation catheter 1050 for permanent implantation in the body to deliver repeat ablation and FIG. 10J is a trocar 1056 used to place the ablation catheter 1050 in the body. FIG. 10K is an illustration of the catheter 1050 of FIG. 10I and trocar 1056 of FIG. 10J assembled for placement of the catheter 1050 into tissue targeted for ablation in the human body. The catheter 1050 of FIG. 10I has an anchoring unit 1054, a shaft 1055 and a port 1057. The anchoring unit 1054 anchors the catheter 1050 in the tissue targeted for ablation and houses one or more openings 1059 for the exit of the ablative agent. Port 1057 resides in the subcutaneous tissue or at a site that is easily accessible for repeat ablation. An ablative agent is introduced into the port 1057 and travels through the shaft 1055 to the site for ablation and exits through the one or more openings 1059 in the anchoring unit 1054. As illustrated in FIG. 10K, in the assembled configuration 1053, the trocar 1056 locks with the catheter 1050 and straightens the anchoring unit 1054 for easy placement of the catheter 1050. Alternatively, in one embodiment (not pictured), the anchoring unit is a balloon that is inflated to anchor the device in the desired tissue. The subcutaneous port 1057, in a manner similar to a subcutaneous port for chemotherapy, can be easily accessed using an insulated needle or catheter for delivery of ablative agent for multiple repeat ablations over time. The port 1057 obviates the need for repeat invasive procedures and the cost of catheter placement into the tissue for ablation.

Figure 11:
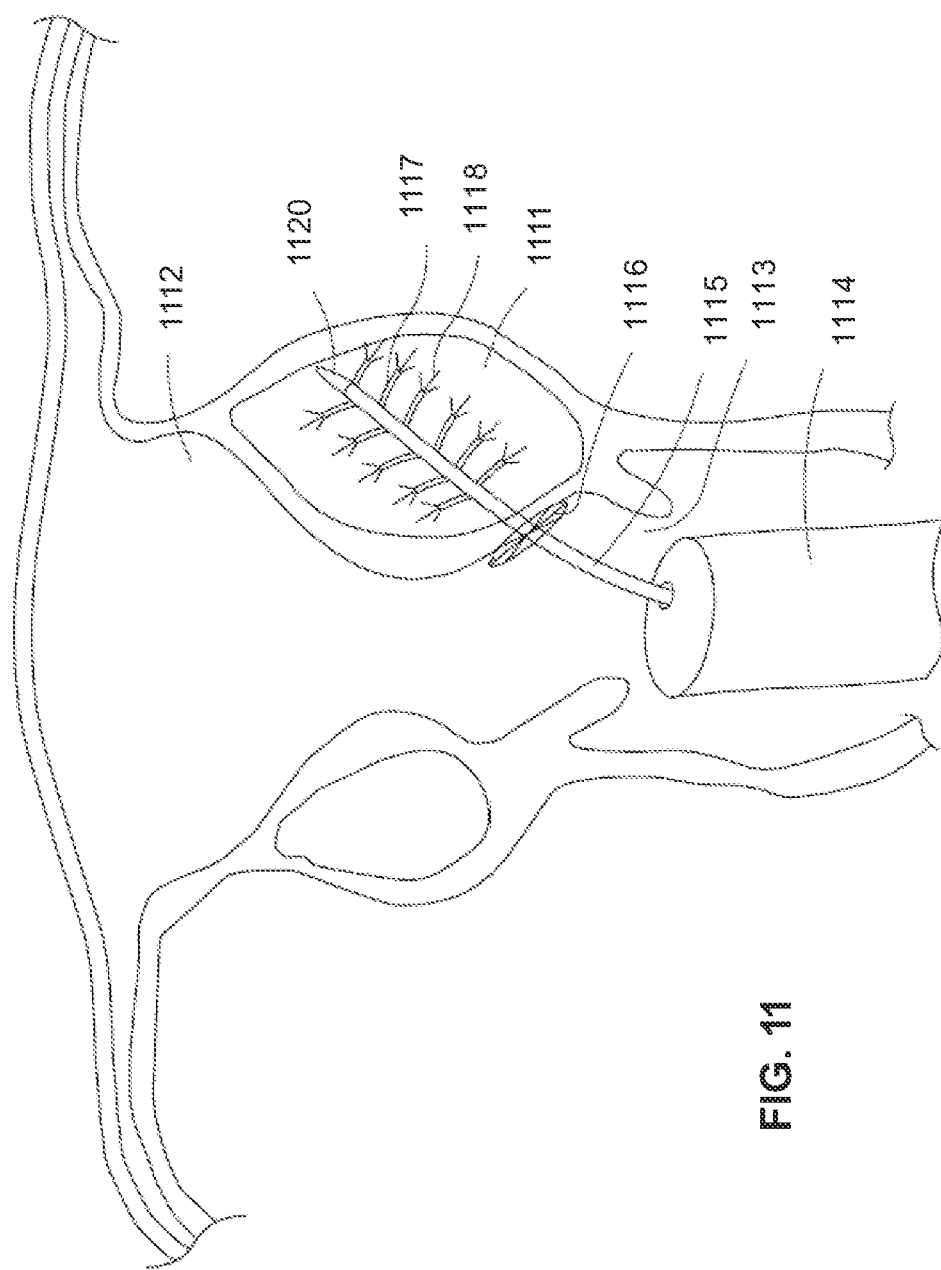
FIG. 11 illustrates fibroid ablation being performed in a female uterus by using the ablation device, in accordance with an embodiment of the present specification.

FIG. 11 illustrates fibroid ablation being performed in a female uterus by using the ablation device, in accordance with an embodiment of the present specification. A cross-section of a female genitourinary tract comprising a uterine fibroid 1111, uterus 1112, and cervix 1113 is illustrated. The ablation catheter 1115 is passed through the hysteroscope 1114 positioned in the uterus distal to the fibroid 1111. The ablation catheter 1115 has a puncturing tip 1120 that helps puncture into the fibroid 1111. The positioning elements 1116 are deployed to center the catheter in the fibroid and insulated needles 1117 are passed to pierce the fibroid tissue 1111. The vapor ablative agent 1118 is passed through the needles 1117 thus causing ablation of the uterine fibroid 1111 resulting in shrinkage of the fibroid.

Figure 12A:
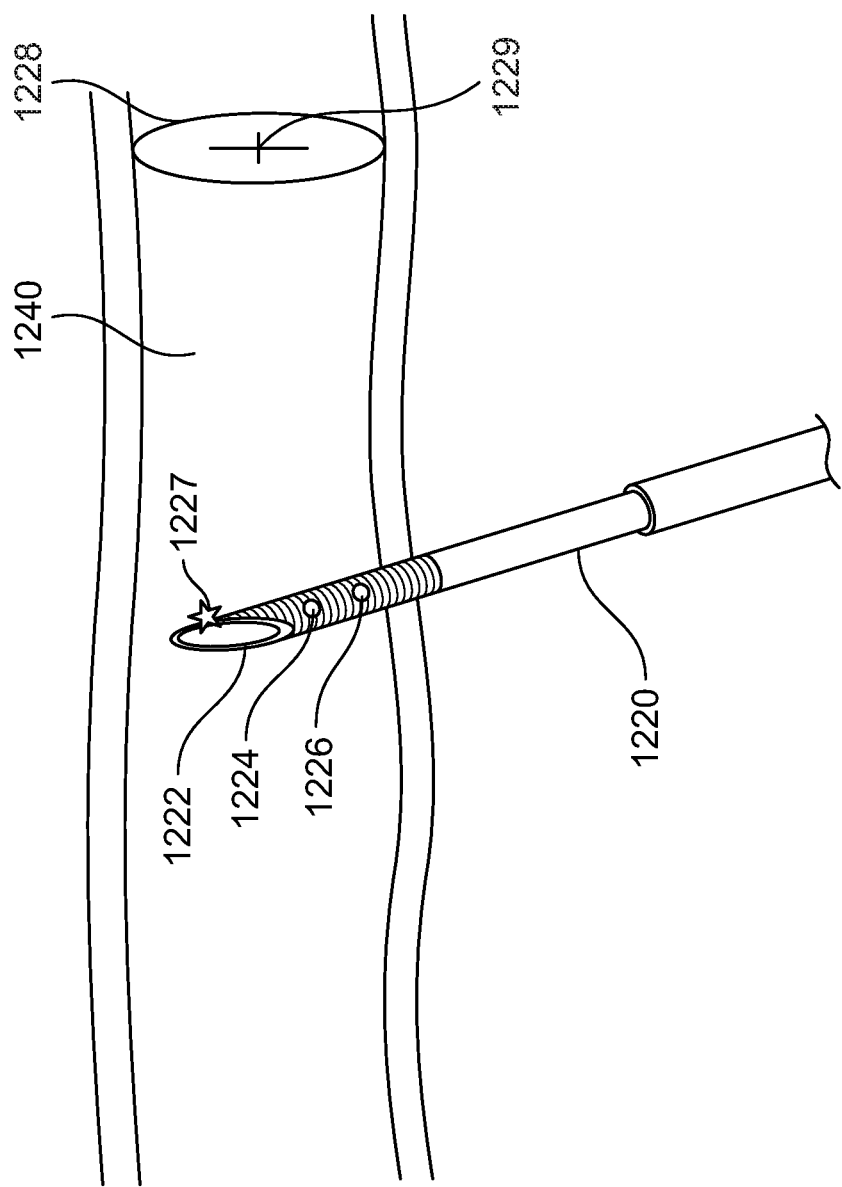
FIG. 12A illustrates a blood vessel ablation being performed by an ablation device, in accordance with one embodiment of the present specification.

FIG. 12A illustrates a blood vessel ablation 1240 being performed by an ablation device, in accordance with one embodiment of the present specification. The ablation involves replacing the blood within the vessel with a conductive medium used to distribute and conduct an ablative agent in the vessel. In one embodiment, the device used for the ablation comprises a catheter 1220 with a distal end and a proximal end. The distal end of the catheter 1220 is provided with at least one port 1222 used to remove blood from the vessel 1240, at least one other port 1224 for injecting a conductive medium into the vessel 1240, and at least one other port for delivering an ablative agent 1226 into the vessel 1240. In various embodiments, each port or any combination of ports is capable of removing blood, injecting a conductive medium, and/or delivering an ablative agent, as discussed with reference to the ablation catheter of FIG. 2F. In one embodiment, the conductive medium is water. In another embodiment, the conductive medium is saline. In one embodiment, the ablative agent is steam. The proximal end of the catheter 1220 is coupled to at least one source to provide suction, the conductive medium, and the ablative agent. In one embodiment, the catheter 1220 further includes a sensor 1227 wherein measurements provided by said sensor are used to control the flow of the ablative agent. In various embodiments, the sensor is configured to sense any one or combination of blood flow and ablation parameter, including flow of ablative agent, temperature, and pressure.

In one embodiment, a first means for occluding blood flow is applied proximally to the insertion point of the catheter into the blood vessel. In one embodiment, the first means comprises a tourniquet (not shown). In another embodiment, the first means comprises an intraluminal occlusive element 1228. In one embodiment, the intraluminal occlusive element 1228 includes a unidirectional valve 1229 to permit the flow of blood into the ablation area and to restrict the flow of conductive medium or ablative agent out of the ablation area. In one embodiment, a second means for occluding blood flow is applied distally from the insertion point of the catheter into the blood vessel. The second means for occluding blood flow acts to prevent blood flow back into the ablation area and also prevents the passage of conductive medium and ablative agent beyond the ablation area. In one embodiment, the second means comprises a tourniquet. In another embodiment, the second means comprises a second intraluminal occlusive element. In one embodiment, the second intraluminal occlusive element includes a unidirectional valve to permit the flow of blood into the ablation area and to restrict the flow of conductive medium or ablative agent out of the ablation area.

Figure 12B:
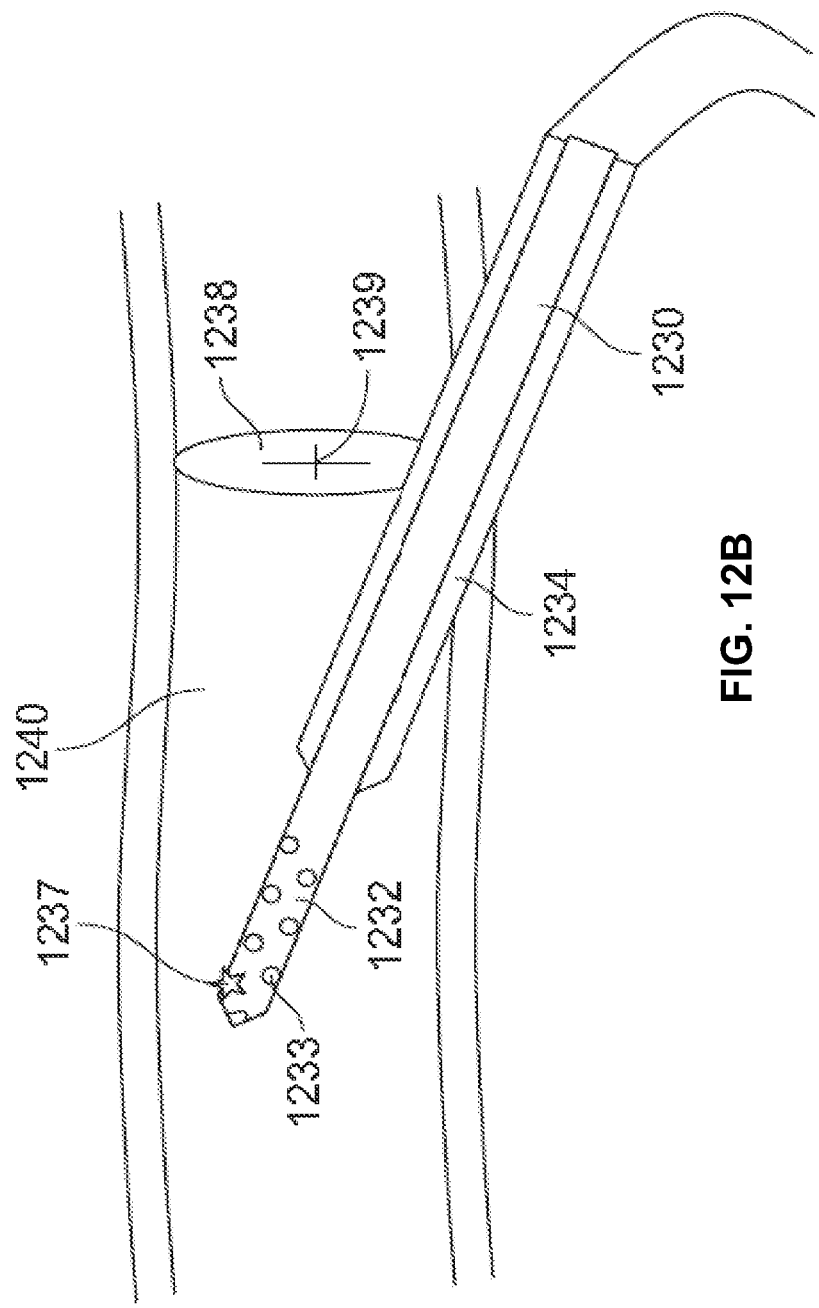
FIG. 12B illustrates a blood vessel ablation being performed by an ablation device, in accordance with another embodiment of the present specification.

FIG. 12B illustrates a blood vessel 1240 ablation being performed by an ablation device, in accordance with another embodiment of the present specification. The ablation device is a coaxial catheter 1230 comprising an internal catheter 1232 and an external catheter 1234. In one embodiment, the internal catheter has a distal end with ports 1233 that function in the same manner as those on the catheter of FIG. 12A and a proximal end coupled to a source in the same manner as the catheter of FIG. 12A. The external catheter 1234 is composed of an insulated material and functions as an insulating sheath over the internal catheter 1232. In the embodiment pictured in FIG. 12B, the device includes at least one intraluminal occlusive device 1238 with a unidirectional valve 1239, coupled to the external catheter 1234 and positioned proximally, with respect to blood flow, to the ablation device. The intraluminal occlusive device 1238 functions in the same manner as that referenced with respect to FIG. 12A. In another embodiment, the intraluminal occlusive device is not coupled to the external catheter. In another embodiment, an additional intraluminal device is positioned distally from the ablation catheter. In various other embodiments, the flow of blood is stopped by the application of at least one tourniquet positioned proximally or distally from the ablation device, or a plurality of tourniquets positioned both proximally and distally from the ablation device. In one embodiment, the internal catheter 1232 further includes a sensor 1237 wherein measurements provided by said sensor are used to control the flow of the ablative agent. In various embodiments, the sensor is configured to sense any one or combination of blood flow and ablation parameter, including flow of ablative agent, temperature, and pressure.

FIG. 12C is a flow chart listing the steps involved in a blood vessel ablation process using an ablation catheter, in accordance with one embodiment of the present specification. At step 1202, a catheter is inserted into a patient and advanced to the target blood vessel. The flow of blood into the target vessel is stopped at step 1204. The catheter tip is then inserted into the target vessel at step 1206. At step 1208, suction is applied to the catheter to remove blood from the target vessel. A conductive medium is then injected into the target vessel through ports on the catheter at step 1210. Then, at step 1212, an ablative agent is delivered into the conductive medium to ablate the target vessel. Suction is applied to the catheter at step 1214 to remove the conductive medium and ablative agent.

In another embodiment, a coaxial balloon is used to ablate a blood vessel. The coaxial balloon is made of an inner thermally permeable balloon which is air-tight and an outer thermally permeable balloon that optionally allows for passage of an ablative agent. The inner balloon is inflated with air until it comes into contact with the vessel wall. The inflated inner balloon serves to displace the blood from the vessel wall. Using a pressure volume calculation, the inner dimensions of the vessel wall are calculated and these dimensions are used to calculate the ablative energy needed. The ablative energy is then delivered into a space between the inner and outer balloons. The passage of thermal energy results in expansion of the inner balloon as previously described, further occluding the vessel wall while the ablative energy permeates through the wall of the outer balloon to ablate the vessel wall. On stoppage of the delivery of the ablative agent, the air in the inner balloon cools and the volume of the inner balloon is reduced to the pre-treatment volume.

Figure 13A:
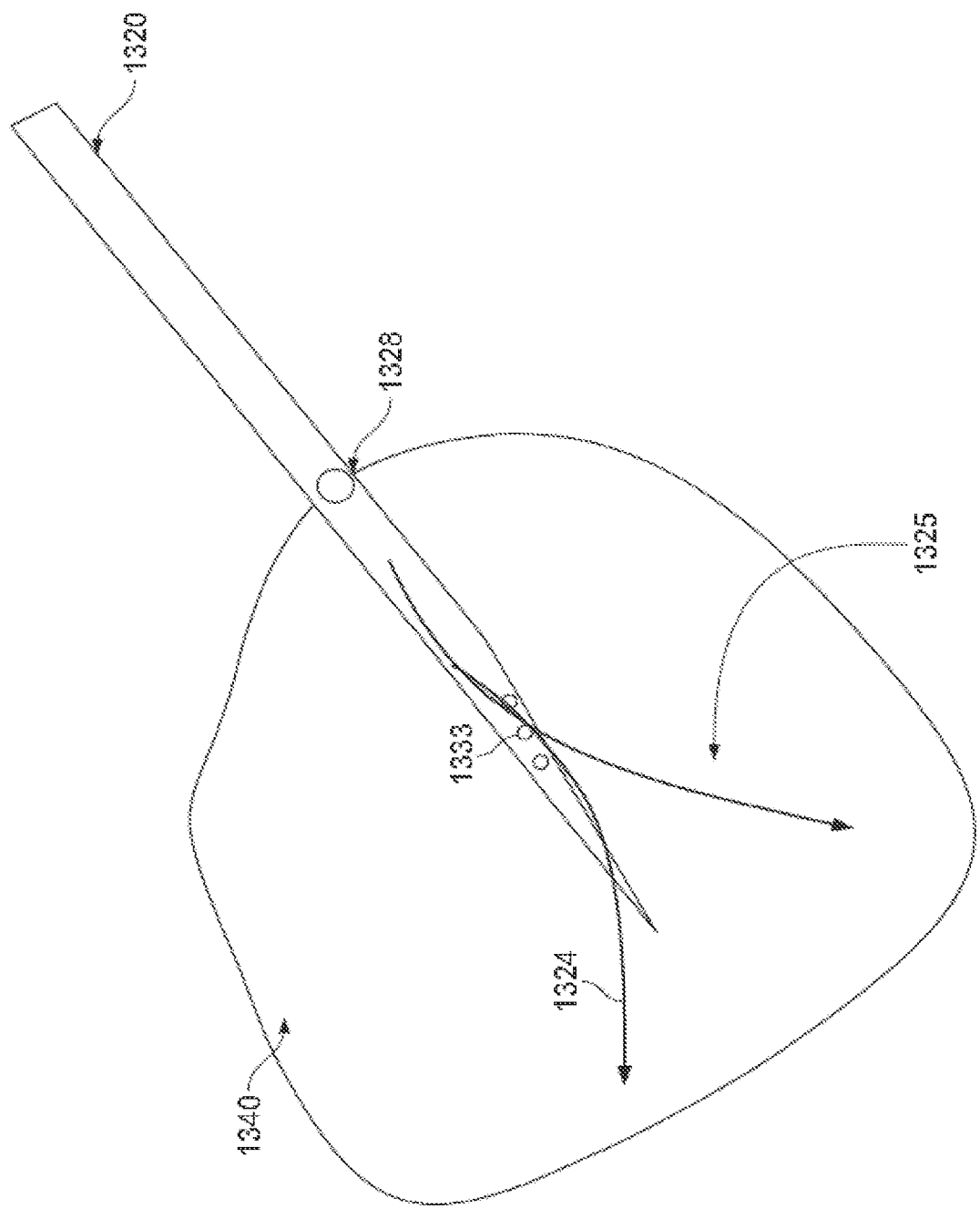
FIG. 13A illustrates a cyst ablation being performed by an ablation device, in accordance with one embodiment of the present specification.

FIG. 13A illustrates a cyst ablation being performed by an ablation device, in accordance with one embodiment of the present specification. The device comprises an ablation catheter 1320 similar to those described with reference to FIGS. 2D-2F. The catheter 1320 is inserted into the cyst 1340 and the contents of the cyst are removed via suction through the ports 1333 at the distal end of the catheter 1320. A conductive medium 1324 is then injected into the cyst 1340, followed by the delivery of an ablative agent 1325 to ablate the cyst. In one embodiment, the catheter 1320 includes a sensor 1328 wherein measurements provided by said sensor are used to control the flow of the ablative agent. In one embodiment, the catheter includes echogenic elements to assist with the placement of the catheter into the cyst under ultrasonic guidance. In another embodiment, the catheter includes radio-opaque elements to assist with the placement of the catheter into the cyst under radiologic guidance.

Figure 13B:
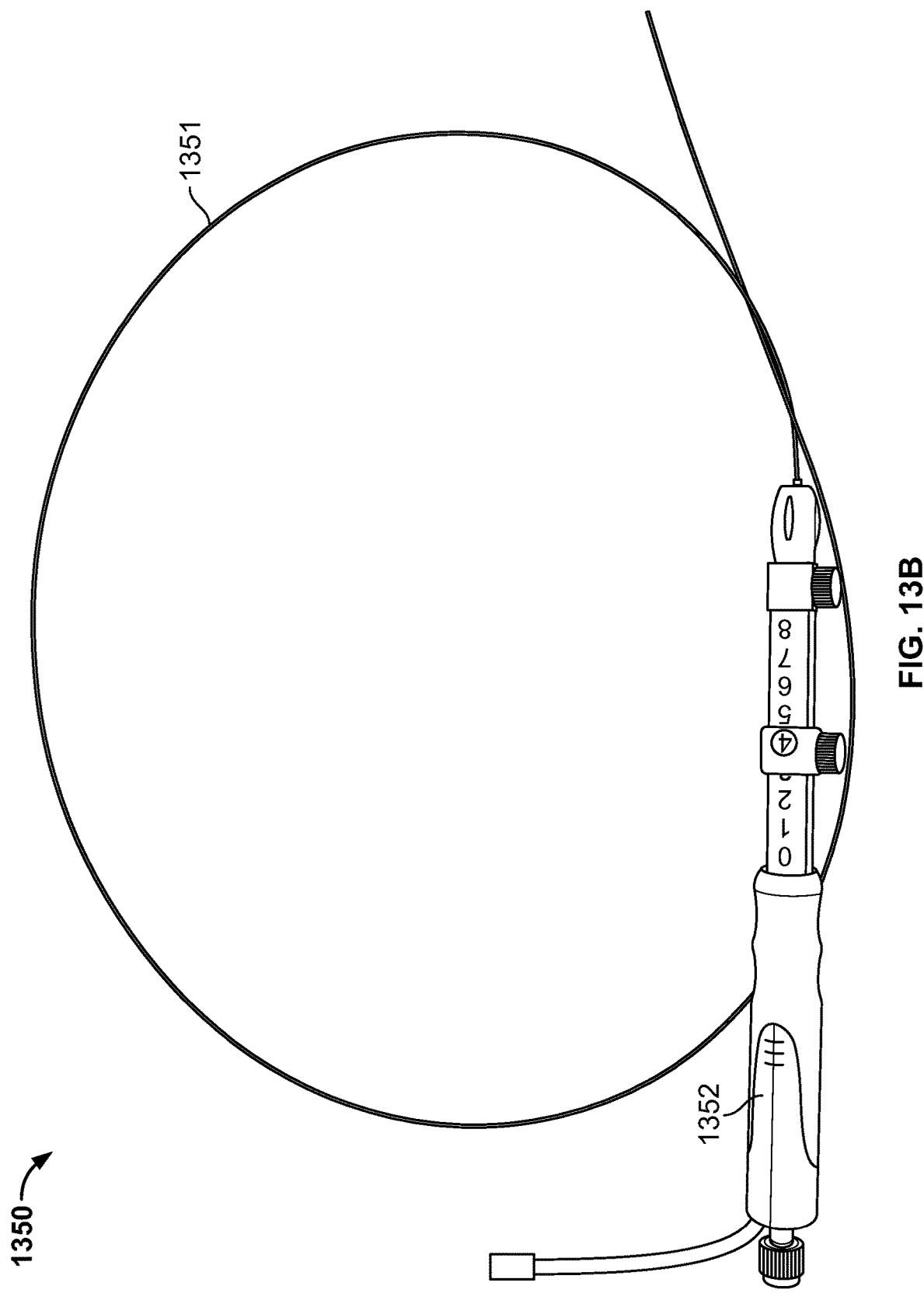
FIG. 13B illustrates an ablation device for cyst ablation or solid tumor ablation, in accordance with one embodiment of the present specification.
Figure 13C:
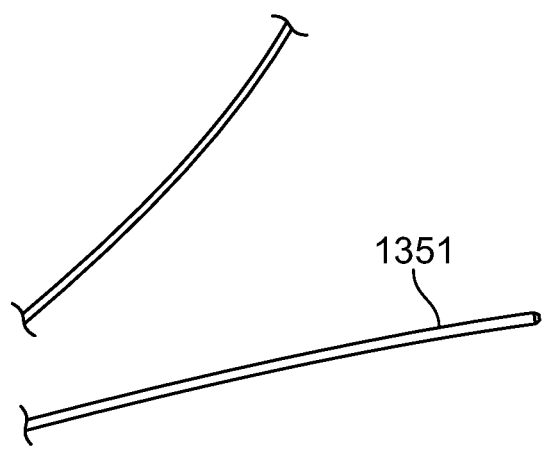
FIG. 13C illustrates the distal end of the catheter of the ablation device of FIG. 13B.
Figure 13D:
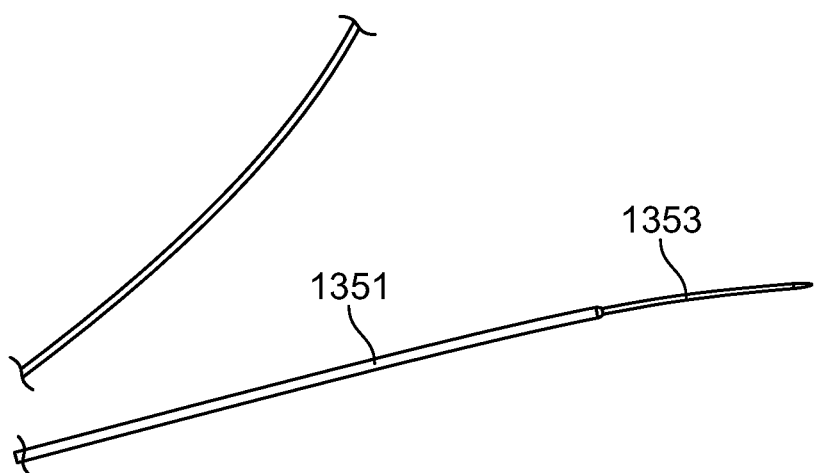
FIG. 13D illustrates a needle extending from the distal end of the catheter of the ablation device of FIG. 13B.
Figure 13E:
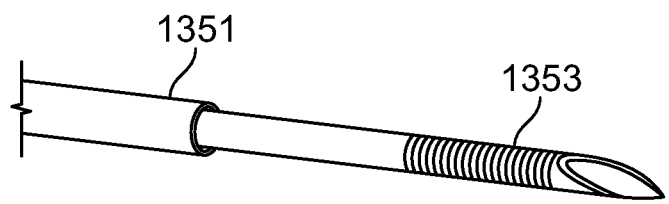
FIG. 13E is a close-up illustration of the needle of the ablation device of FIG. 13B.

FIG. 13B illustrates an ablation device 1350 for cyst ablation or solid tumor ablation, in accordance with one embodiment of the present specification. The device 1350 includes a catheter 1351 attached to a handle 1352. FIG. 13C illustrates the distal end of the catheter 1351 of the ablation device of FIG. 13B. FIG. 13D illustrates a needle 1353 extending from the distal end of the catheter 1351 of the ablation device of FIG. 13B. FIG. 13E is a close-up illustration of the needle 1353 extending from the distal end of the catheter 1351 of the ablation device of FIG. 13B.

Figure 13F:
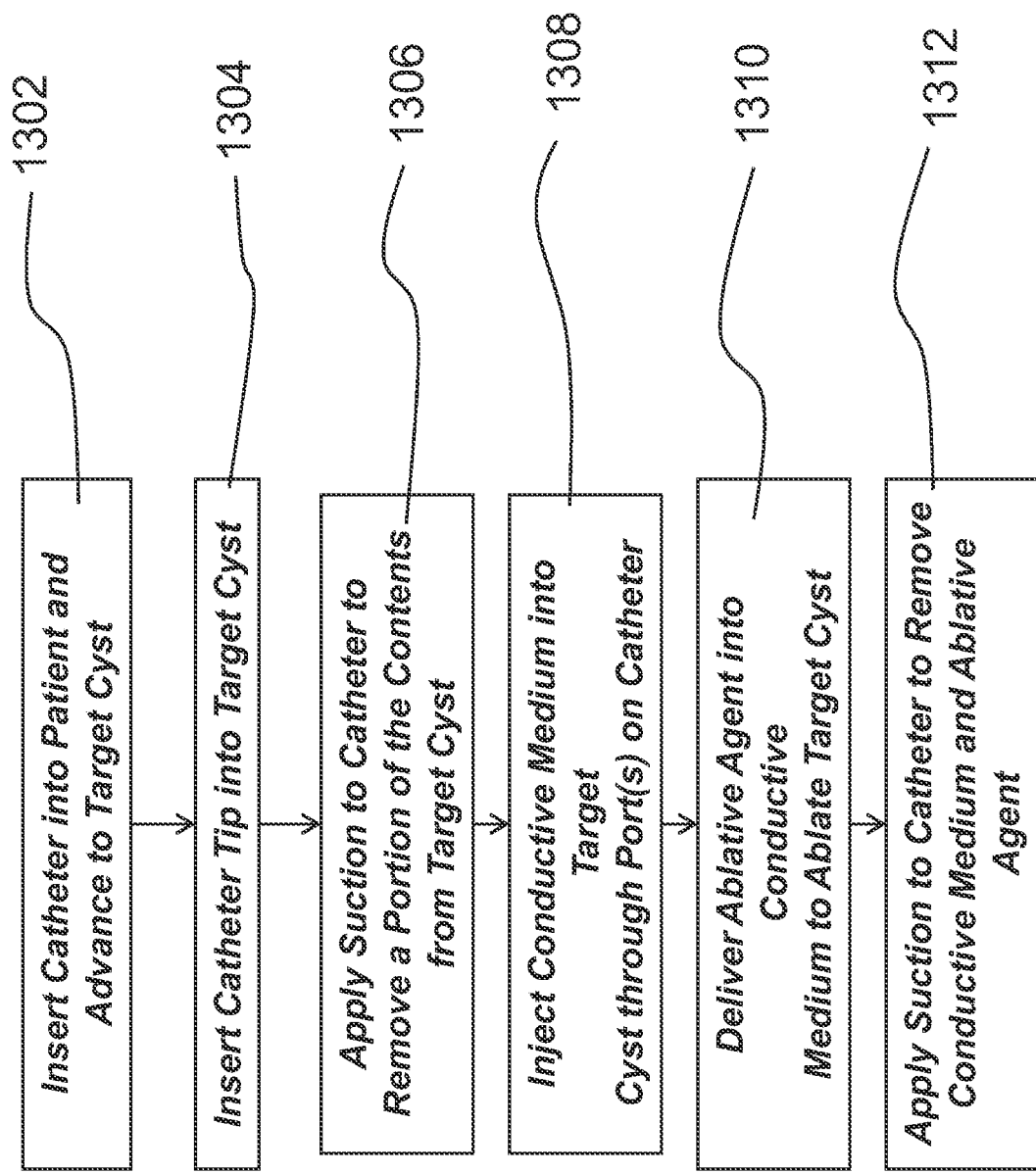
FIG. 13F is a flow chart listing the steps involved in a cyst ablation process using an ablation catheter, in accordance with one embodiment of the present specification.

FIG. 13F is a flow chart listing the steps involved in a cyst ablation process using an ablation catheter, in accordance with one embodiment of the present specification. At step 1302, a catheter is inserted into a patient and advanced to the target cyst. The catheter tip is then inserted into the target cyst at step 1304. At step 1306, suction is applied to the catheter to remove at least a portion of the contents of the target cyst. A conductive medium is then injected into the target cyst through ports on the catheter at step 1308. Then, at step 1310, an ablative agent is delivered into the conductive medium to ablate the target cyst. Suction is applied to the catheter at step 1312 to remove the conductive medium and ablative agent.

Figure 14:
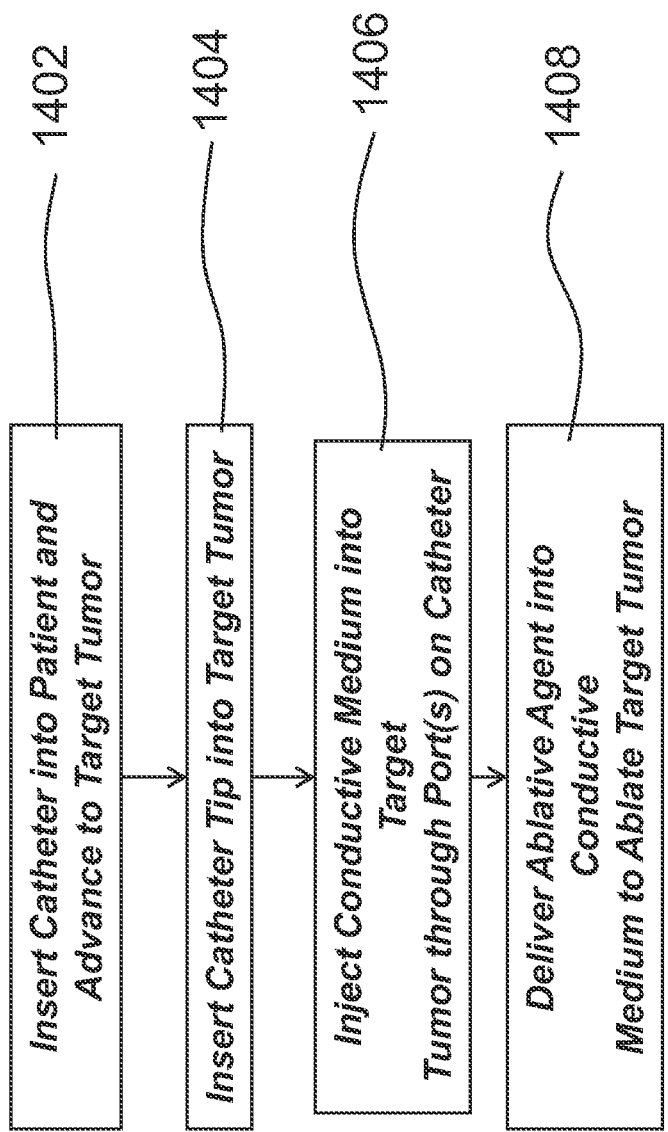
FIG. 14 is a flow chart listing the steps involved in a tumor ablation process using an ablation catheter, in accordance with one embodiment of the present specification.

FIG. 14 is a flow chart listing the steps involved in a solid tumor ablation process using an ablation catheter, in accordance with one embodiment of the present specification. At step 1402, a catheter is inserted into a patient and advanced to the target tumor. The catheter tip is then inserted into the target tumor at step 1404. A conductive medium is injected into the target tumor through ports on the catheter at step 1406. Then, at step 1408, an ablative agent is delivered into the conductive medium to ablate the target tumor. In one embodiment, the catheter includes a sensor wherein measurements provided by said sensor are used to control the flow of the ablative agent. In one embodiment, the catheter includes echogenic elements to assist with the placement of the catheter into the tumor under ultrasonic guidance. In another embodiment, the catheter includes radio-opaque elements to assist with the placement of the catheter into the tumor under radiologic guidance.

Figure 15A:
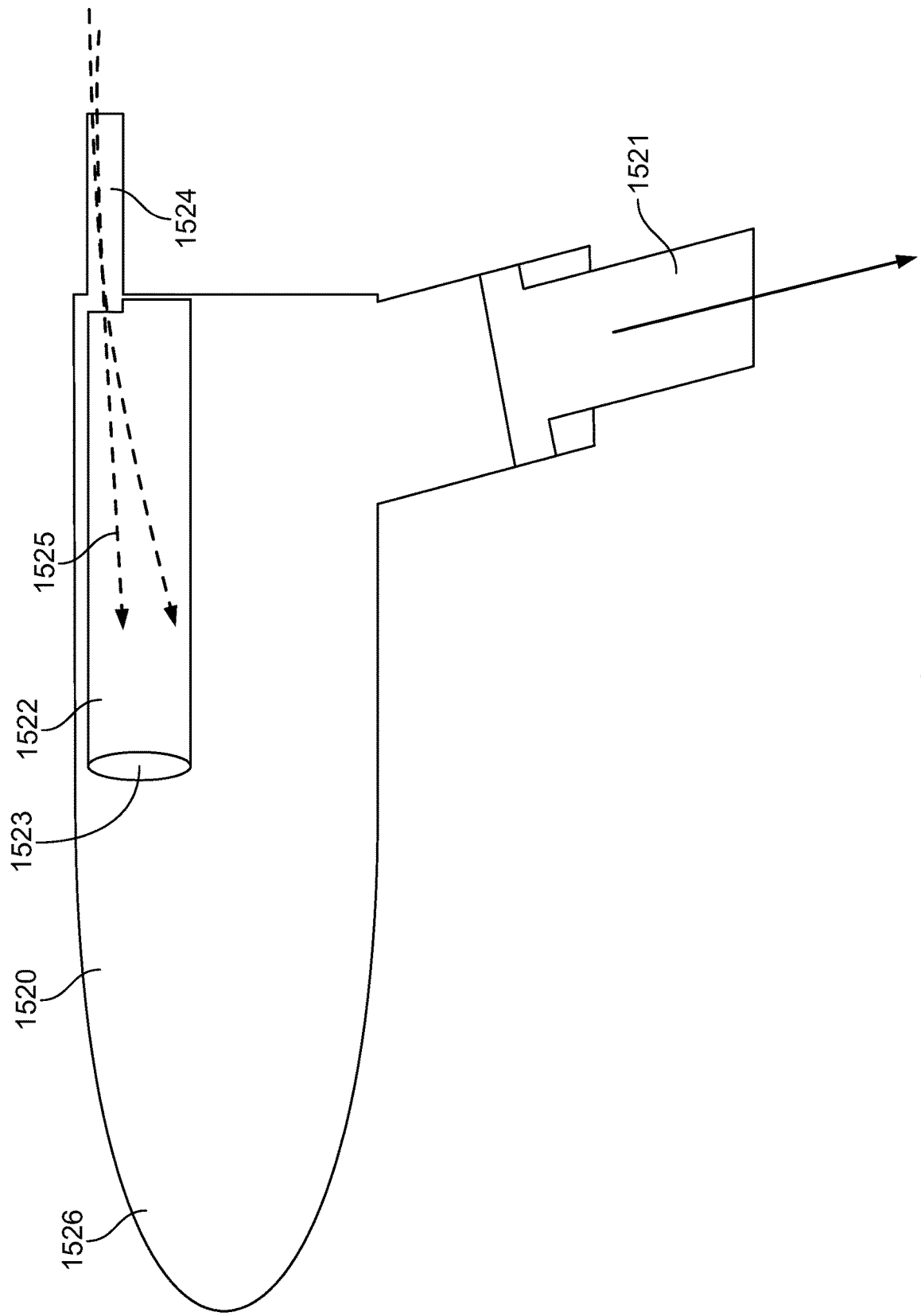
FIG. 15A illustrates a first view of a non-endoscopic device used for internal hemorrhoid ablation, in accordance with one embodiment of the present specification.
Figure 15B:
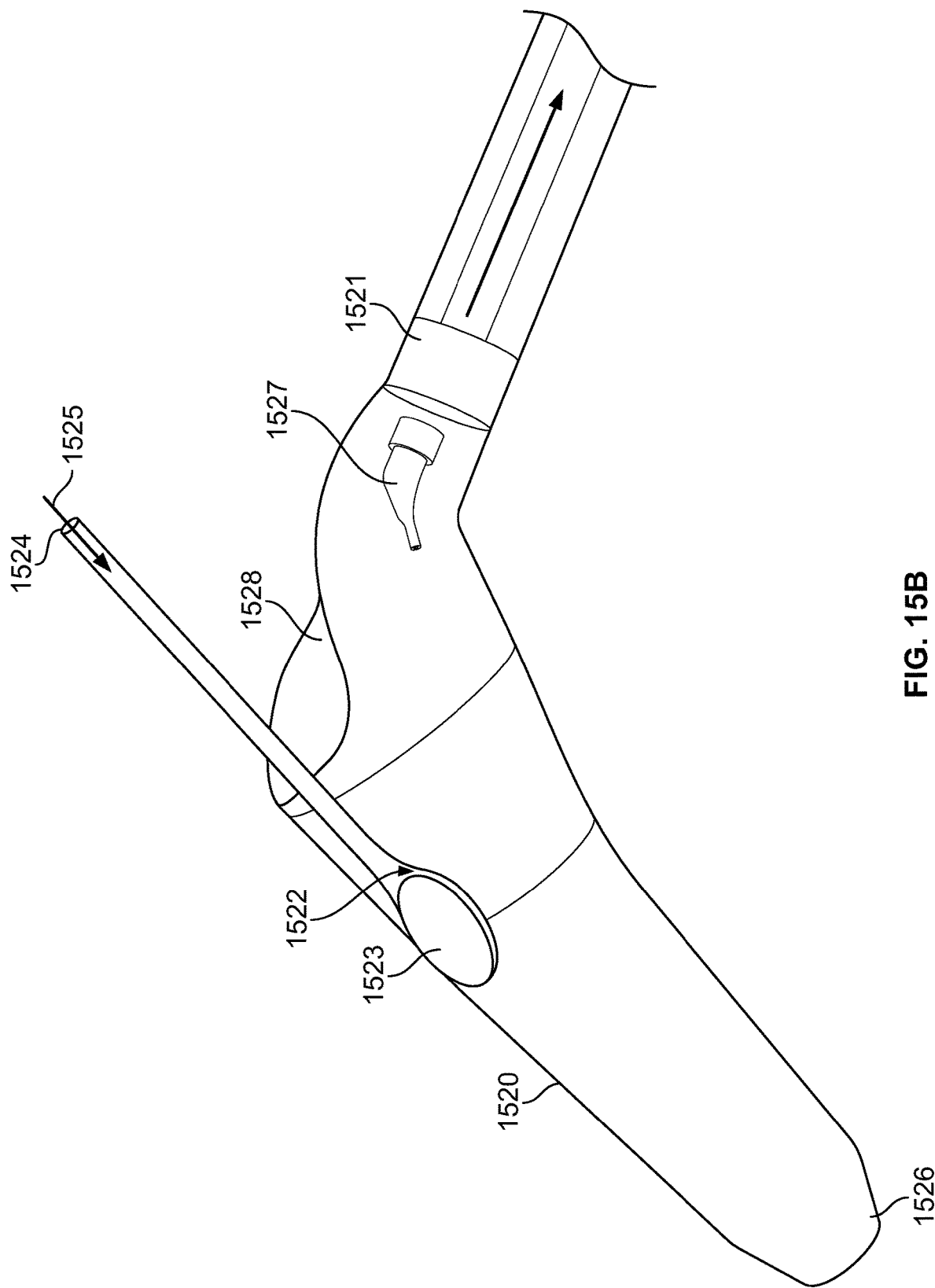
FIG. 15B illustrates a second view of the non-endoscopic device used for internal hemorrhoid ablation of FIG. 15A, in accordance with one embodiment of the present specification.
Figure 15C:
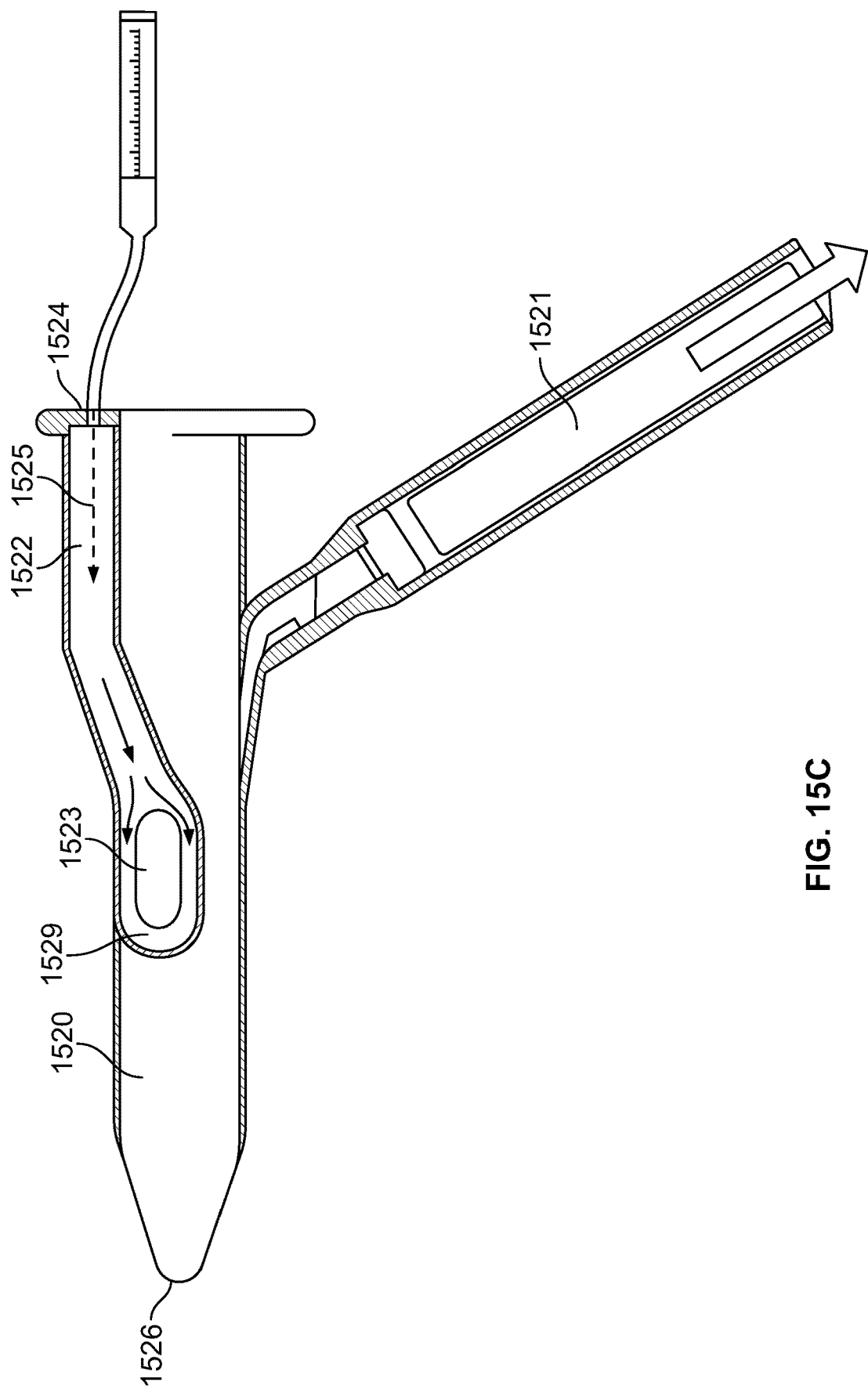
FIG. 15C illustrates a third view of the non-endoscopic device used for internal hemorrhoid ablation of FIG. 15A, in accordance with one embodiment of the present specification.

FIGS. 15A, 15B, and 15C illustrate a non-endoscopic device 1520 used for internal hemorrhoid ablation, in accordance with one embodiment of the present specification. The device 1520 is inserted into the rectum of a patient to selectively ablate internal hemorrhoids. The device includes a blind, atraumatic and clear distal end 1526 for insertion into a patient's rectum. The device 1520 includes a piston 1521 that, when pulled down, creates suction in a chamber or slot 1522 within the device 1520. The suction draws a portion of rectal tissue with a hemorrhoid through an opening 1523 positioned along an outer surface of the device 1520 and into the chamber 1522. A port 1524 on the proximal end of the device 1520 is used to provide an ablative agent 1525 to the chamber 1522 to ablate the hemorrhoid. In one embodiment, the device is composed of a thermally insulated material to avoid the transfer of ablative energy to the surrounding rectal mucosa. In one embodiment, the ablative agent is steam. Referring to FIG. 15B, in one embodiment, the device 1520 includes a viewing port 1528 through which an operator can observe capturing of the target tissue to ensure proper hemorrhoid ablation. In one embodiment, the device 1520 further includes at least one illumination source 1527 for illuminating the rectal tissue and hemorrhoid to assist the operator with locating the target tissue. Referring to FIG. 15C, in one embodiment, the device 1520 further includes a track 1529 configured to circulate ablative agent 1525 about the target tissue that has been captured through opening 1523.

Figure 15D:
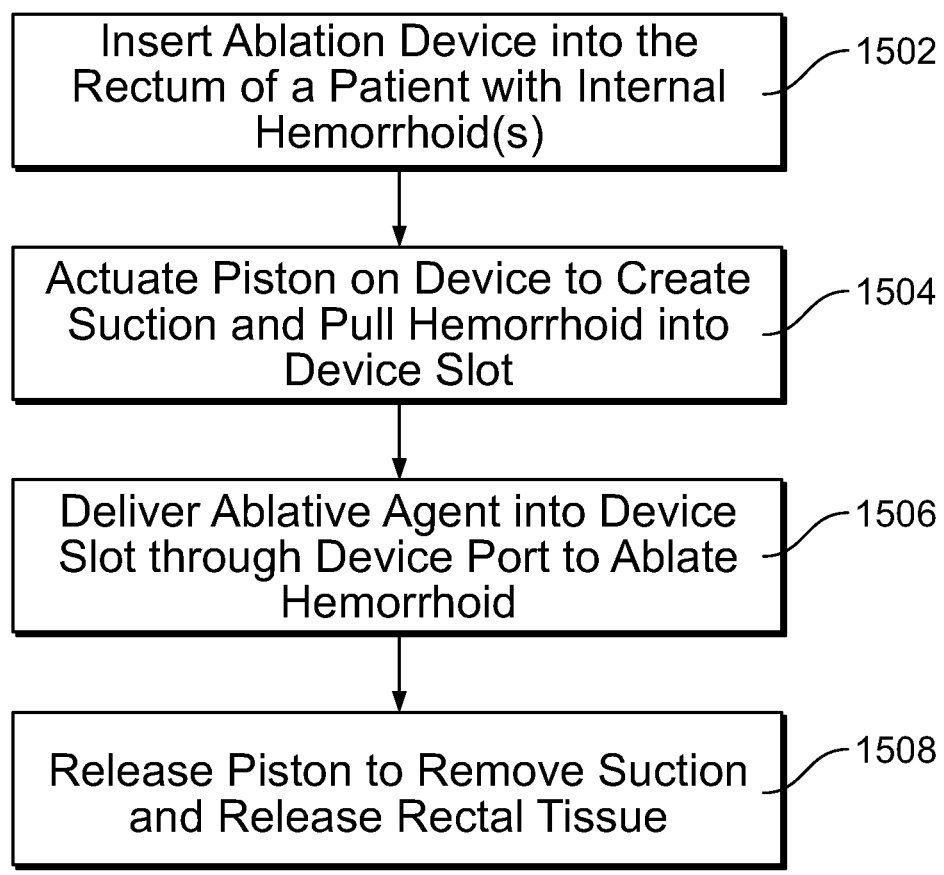
FIG. 15D is a flow chart listing the steps involved in an internal hemorrhoid ablation process using an ablation device, in accordance with one embodiment of the present specification.

FIG. 15D is a flow chart listing the steps involved in an internal hemorrhoid ablation process using a non-endoscopic ablation device, in accordance with one embodiment of the present specification. At step 1502, the device described with reference to FIGS. 15A, 15B, and 15C is inserted into the rectum of a patient with internal hemorrhoids. A piston on the device is actuated to create suction and draw a portion of hemorrhoid tissue into a slot in the device at step 1504. Then, at step 1506, an ablative agent is delivered into the slot via a port on the device to ablate the hemorrhoid. The piston is released at step 1508 to remove suction, thereby releasing the portion of rectal tissue.

Figure 15E:
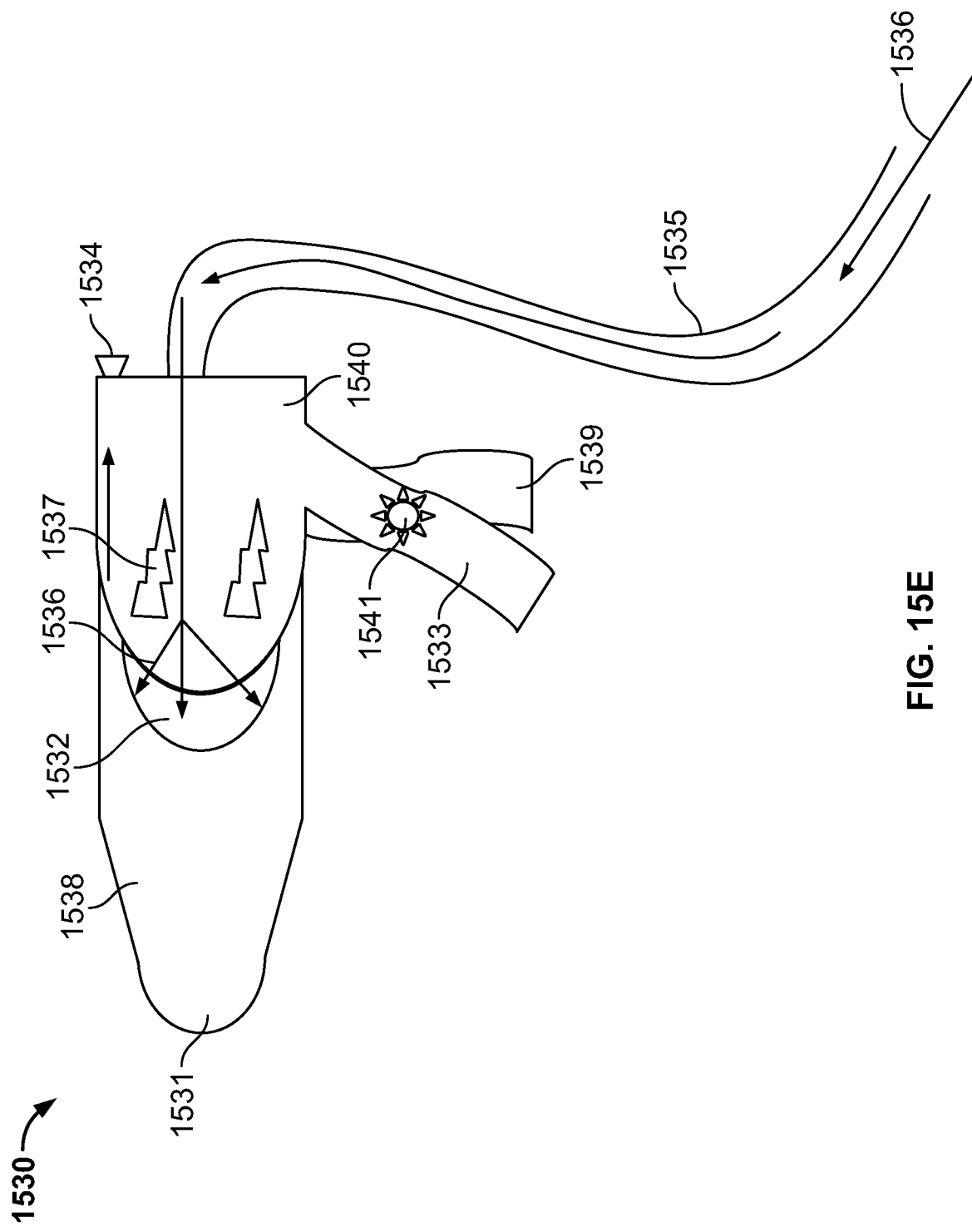
FIG. 15E illustrates a non-endoscopic device used for internal hemorrhoid ablation, in accordance with another embodiment of the present specification.

FIG. 15E illustrates a non-endoscopic device 1530 used for internal hemorrhoid ablation, in accordance with another embodiment of the present specification. The device 1530 includes a device body 1538 having a proximal end, a distal end, and a lumen within. The device includes a blind, atraumatic and clear distal end 1531 for insertion into a patient's rectum. An articulating arm 1533 is coupled to a handle 1539 on the device body 1538 about a pivot point 1541. A compression component 1540 is attached to the articulating arm 1533 and is positioned and movable within the proximal end of the device body 1538. The device 1530 is inserted into a rectum of a patient and includes an opening, chamber, or slot 1532 positioned along an outer surface of the device body 1538 for receiving a portion of rectal tissue with a hemorrhoid. Rotating the articulating arm 1533 relative to the handle 1539 in a first direction causes the compression component 1540 to move in a proximal direction within the proximal end of the device body 1538, creating suction and drawing the received rectal tissue and hemorrhoid into the opening 1532. The articulating arm 1533 is rotated in a second direction opposite said first direction to move the compression component 1540 in a distal direction within the proximal end of the device body 1538, compressing the captured hemorrhoid within the opening 1532 to reduce a cross-sectional area of the hemorrhoid. The compression component 1540 includes a one-way valve 1534 to allow for air within the opening 1532 to escape during compression. An ablative agent 1536 is introduced via an inlet tube 1535 attached to the compression component 1540 to ablate the hemorrhoid captured in the opening 1532. In one embodiment, the ablative agent is steam. In one embodiment, the device 1530 further includes at least one illumination source 1537 for illuminating the rectal tissue and hemorrhoid to assist the operator with locating the target tissue.

Figure 15F:
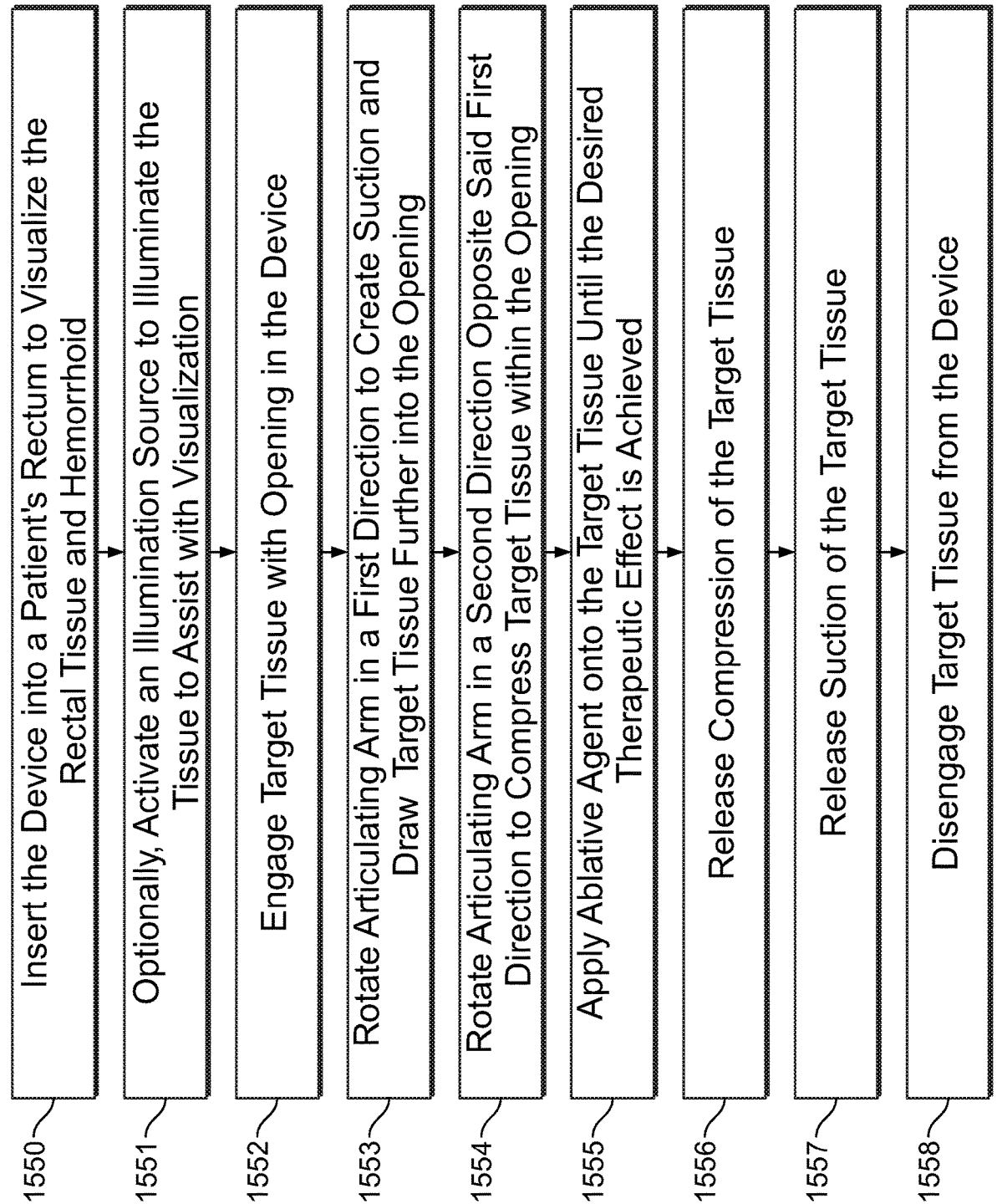
FIG. 15F is a flowchart listing the steps of a method for ablating an internal hemorrhoid using the device of FIG. 15E, in accordance with one embodiment of the present specification.

FIG. 15F is a flowchart listing the steps of a method for ablating an internal hemorrhoid using the device of FIG. 15E, in accordance with one embodiment of the present specification. At step 1550, the device is inserted into a patient's rectum to visualize the rectal tissue and hemorrhoid. In one embodiment, an optional illumination source is illuminated to assist with visualization of the target tissue at step 1551. The target tissue is engaged with the opening in the device at step 1552. At step 1553, the articulating arm is rotated in a first direction to create suction and draw the engaged target tissue further into the opening. Then, at step 1554, the articulating arm is rotated in a second direction opposite said first direction to compress the target tissue within the opening, thereby reducing the cross-sectional area of the target tissue. Ablative agent is applied to the compressed target tissue at step 1555 until the desired therapeutic effect is achieved. Compression of the target tissue is released at step 1556 and suction of the target tissue is then released at step 1557. The target tissue is then disengaged from the device at step 1558.

Figure 15G:
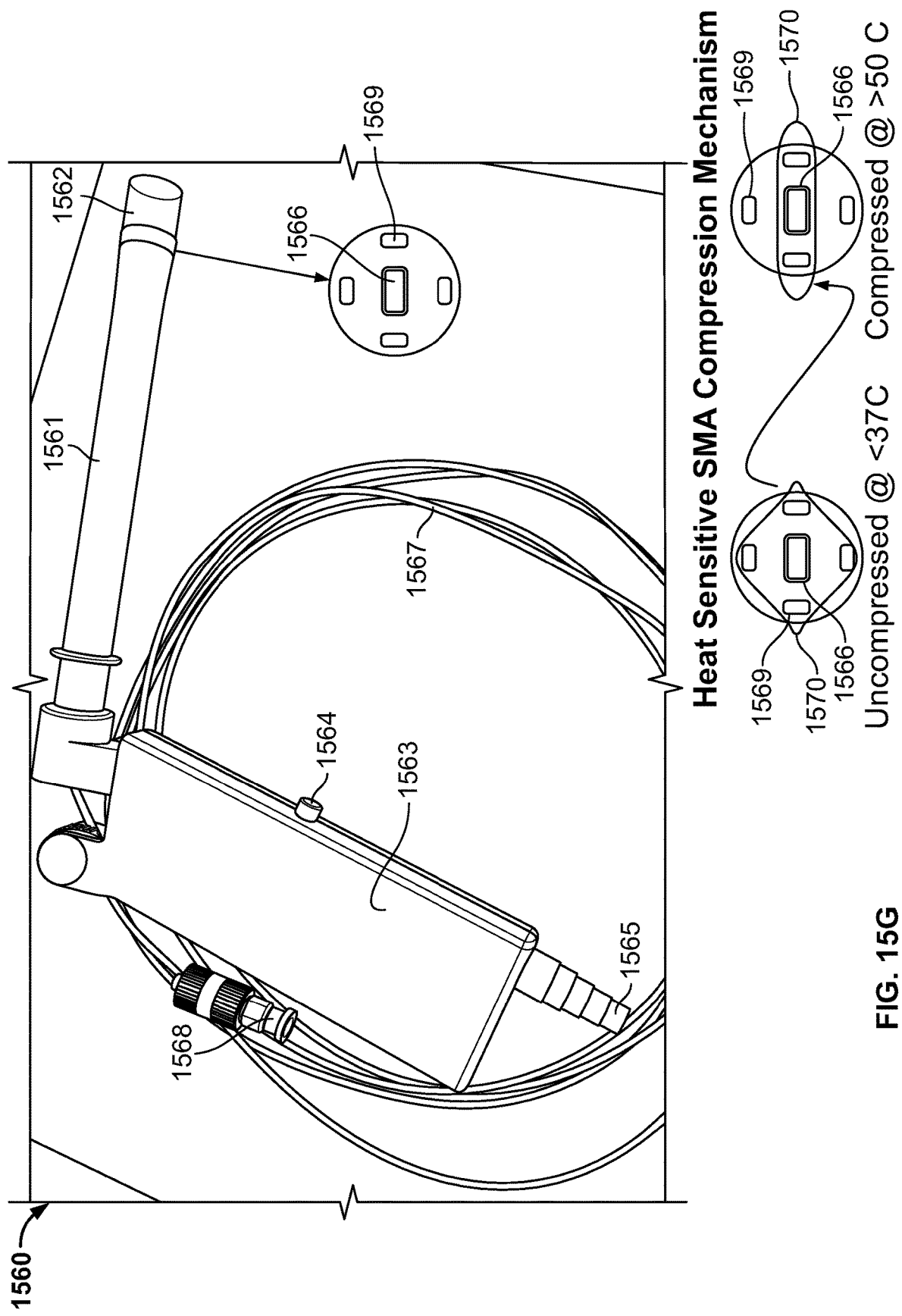
FIG. 15G illustrates a non-endoscopic device used for internal hemorrhoid ablation, in accordance with yet another embodiment of the present specification.

FIG. 15G illustrates a non-endoscopic device 1560 used for internal hemorrhoid ablation, in accordance with yet another embodiment of the present specification. The device 1560 includes an insertion member 1561 having an elongate cylindrical body, a proximal end, and a distal end. A clear tubular member 1562 is attached to the distal end of the insertion member 1561. The clear tubular member 1562 functions to capture the hemorrhoid (target tissue) and allows the operator to visualize the hemorrhoid within. The proximal end of the insertion member 1561 is attached to a handle 1563. The handle 1563 includes a switch control 1564 for controlling suction on the device 1560 and a suction inlet 1565 for connection to a suction source. The insertion member 1561 includes a suction lumen extending along its length and in fluid communication with a similar suction lumen within the handle 1563. The suction lumen in the handle 1563 is in fluid communication with the suction inlet 1565. The suction lumen in the insertion member 1561 is positioned in the center of the insertion member 1561 and ends in a suction port 1566, as depicted in the cross section view of the distal end of the insertion member 1561 shown in FIG. 15G. Suction provided at the suction inlet 1565 is transferred to the suction port 1566, where said suction draws the target tissue into the tubular member 1562.

A catheter 1567 having a proximal end and a distal end is attached via its distal end to the proximal end of the insertion member 1561 and includes a vapor inlet 1568 at its proximal end. The insertion member 1561 includes at least one vapor lumen extending along its length and in fluid communication with the catheter 1567. In one embodiment, the vapor lumen splits into four separate vapor lumens positioned about the periphery of the insertion member 1561 which all end in vapor ports 1569, as depicted in the cross section view of the distal end of the insertion member 1561 shown in FIG. 15G. Vapor provided at the vapor inlet 1568 is transferred to the vapor ports 1569, where said vapor ablates the target tissue captured in the tubular member 1562. In one embodiment, as depicted in the cross section view of the distal end of the insertion member 1561, the clear tubular member 1562 includes a heat sensitive compression mechanism 1570 which is open at room temperature and compresses the engaged hemorrhoid at a temperature higher than the body temperature. In one embodiment, the compression mechanism 1570 is composed of a shape memory alloy (SMA). In one embodiment, the SMA is Nitinol. In one embodiment, the austenite finish (Af) temperature, or temperature at which the transformation from martensite to austenite finishes on heating (alloy undergoes a shape change to become a compressed mechanism 1570), of the SMA is greater than 37° C. In other embodiments, the Af temperature of the SMA is greater than 50° C. but less than 100° C.

Figure 15H:
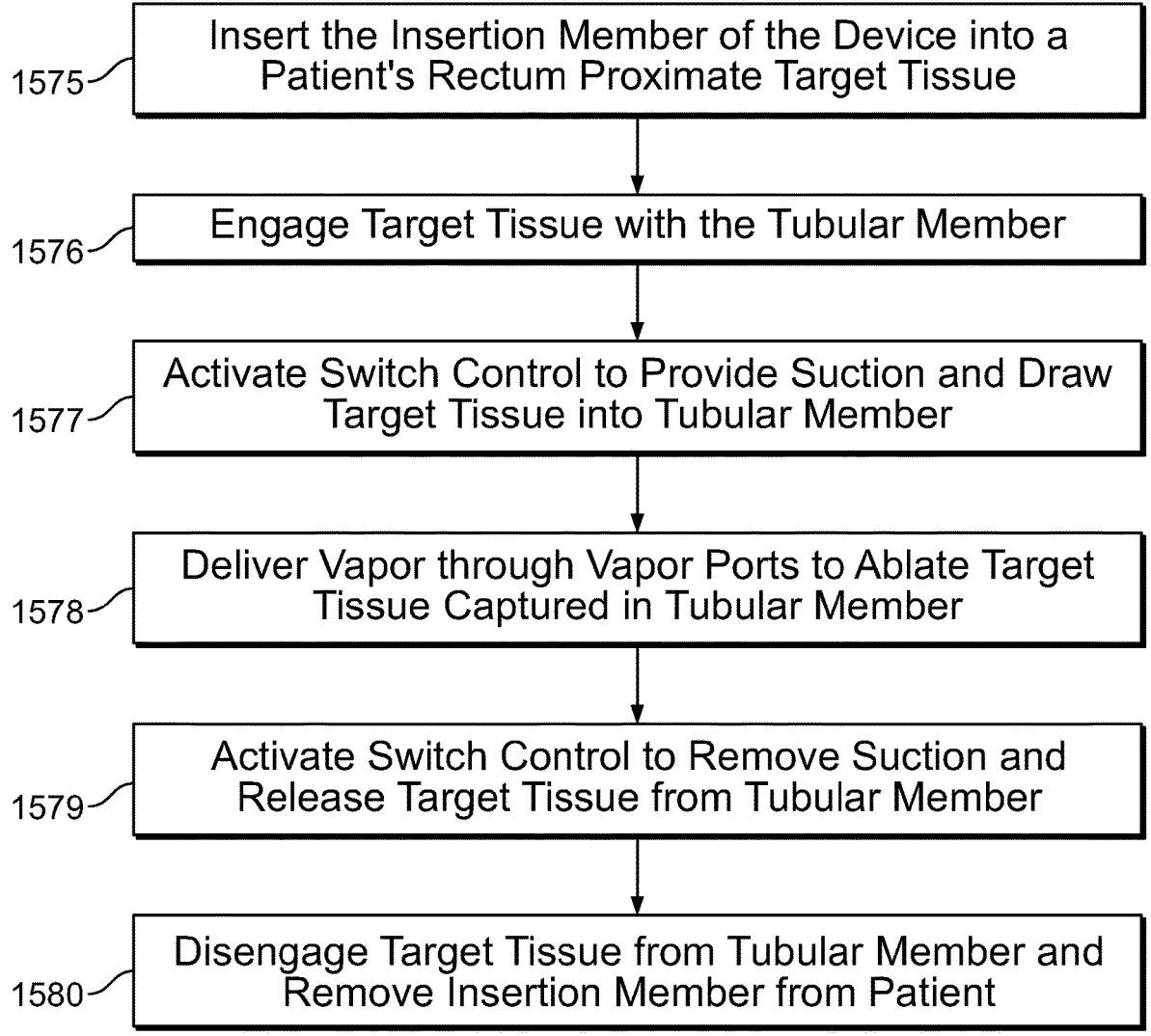
FIG. 15H is a flowchart listing the steps of a method for ablating an internal hemorrhoid using the device of FIG. 15G, in accordance with one embodiment of the present specification.

FIG. 15H is a flowchart listing the steps of a method for ablating an internal hemorrhoid using the device of FIG. 15G, in accordance with one embodiment of the present specification. At step 1575, the insertion member of the device is inserted into a patient's rectum proximate a target tissue. The device is manipulated to engage the target tissue with the tubular member at step 1576. At step 1577, the switch control is activated to provide suction and draw the target tissue into the tubular member. Then, at step 1578, vapor is delivered through the vapor ports to ablate the target tissue captured in the tubular member. Once the desired level of treatment has been achieved, the switch control is activated to remove the suction and release the target tissue from the tubular member at step 1579. The target tissue is disengaged from the tubular member and the insertion member is removed from the patient at step 1580.

Figure 16A:
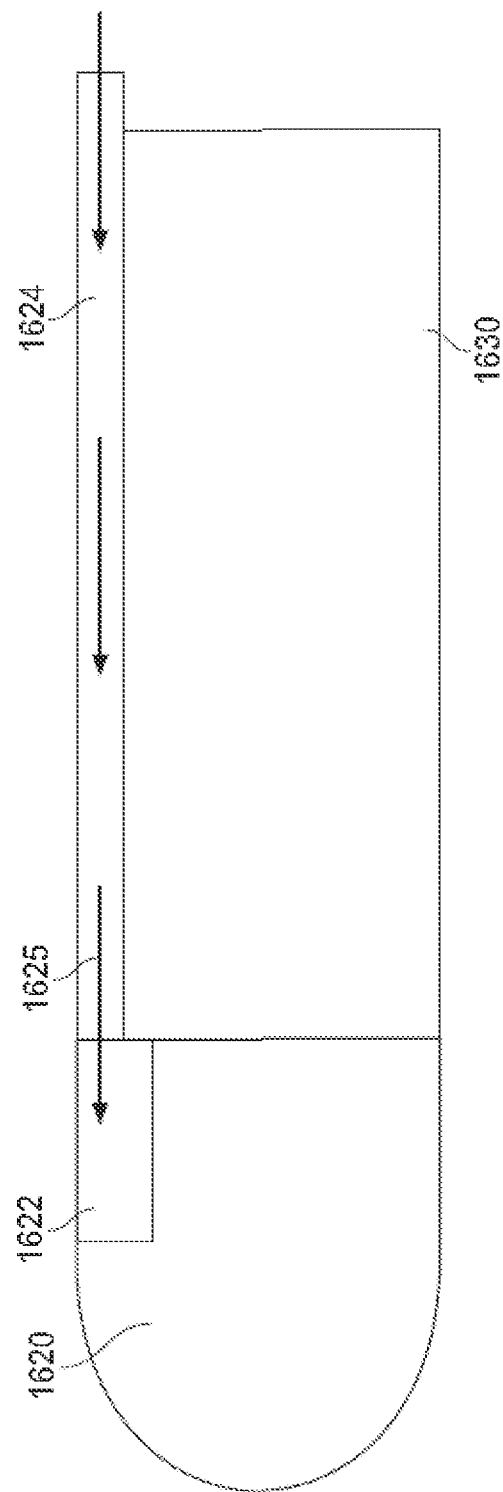
FIG. 16A illustrates an endoscopic device used for internal hemorrhoid ablation, in accordance with one embodiment of the present specification.

FIG. 16A illustrates an endoscopic device 1620 used for internal hemorrhoid ablation, in accordance with one embodiment of the present specification. In one embodiment, the device 1620 is composed of a thermally insulated, transparent material. The device 1620 is mounted to the distal end of an endoscope 1630 and both are inserted into the patient's rectum. Suction is applied to the endoscope 1630, drawing a portion of rectal tissue with a hemorrhoid into a chamber or slot 1622 in the device 1620.

In one embodiment, an ablative agent 1625 is delivered to the chamber or slot 1622 through a port 1624 in the device 1620. In another embodiment, a needle (not shown) is advanced through the port 1624 and inserted into the rectal submucosa at the position of the hemorrhoid. An ablative agent is then injected directly into the hemorrhoid through the needle for selective hemorrhoid ablation.

Figure 16B:
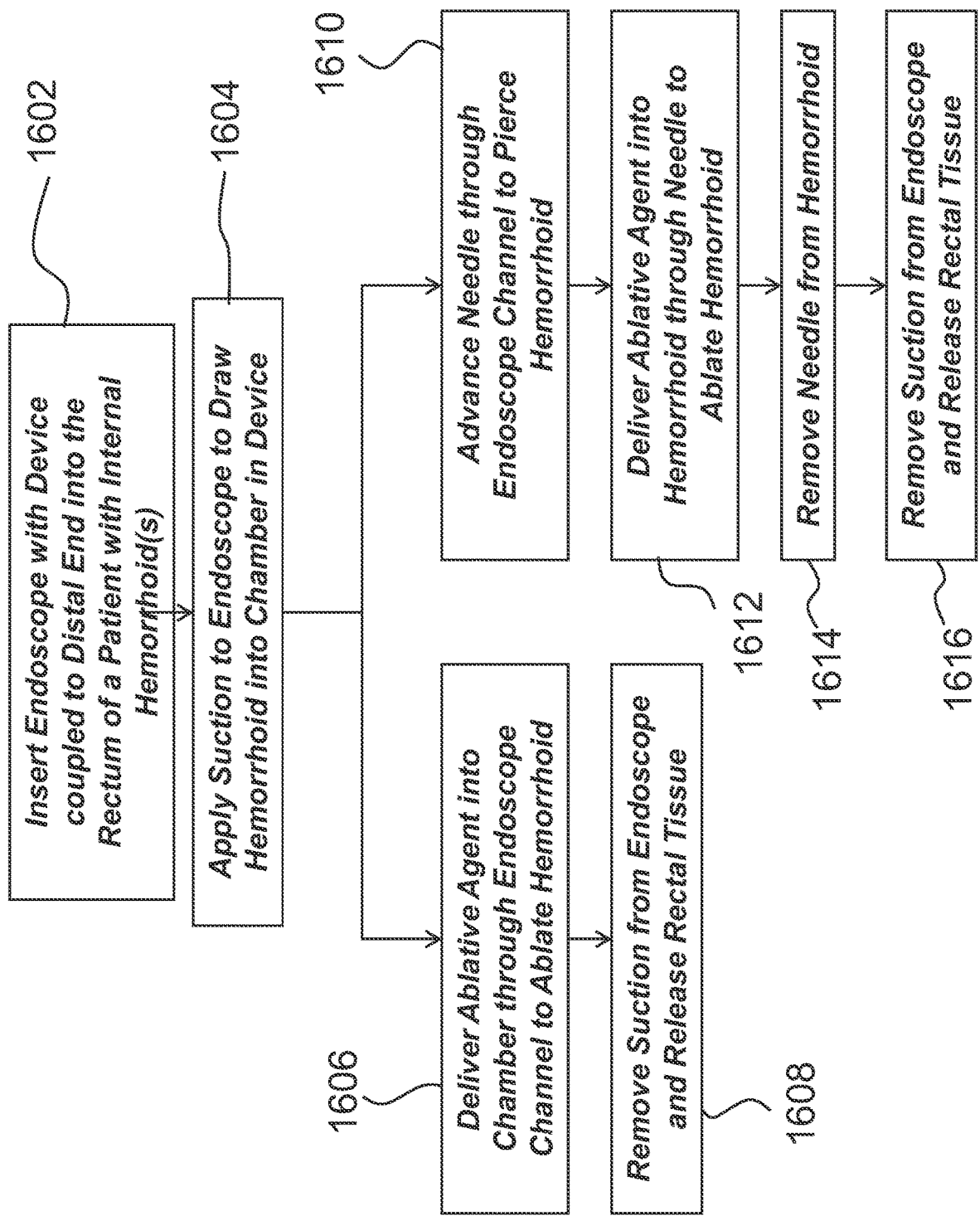
FIG. 16B is a flow chart listing the steps involved in an internal hemorrhoid ablation process using an endoscopic ablation device, in accordance with one embodiment of the present specification.

FIG. 16B is a flow chart listing the steps involved in an internal hemorrhoid ablation process using an endoscopic ablation device, in accordance with one embodiment of the present specification. At step 1602, an endoscope with an ablation device coupled to its distal end is inserted into the rectum of a patient with internal hemorrhoids. At step 1604, suction is applied to the endoscope to draw a portion of rectal tissue with a hemorrhoid into a chamber in the device.

In one embodiment, at step 1606, an ablative agent is delivered through a port on the device into the chamber to ablate the hemorrhoid. Suction is then removed from the endoscope at step 1608 to release the portion of rectal tissue.

In another embodiment, at step 1610, a needle is advanced through the port on the device, through the chamber, and into the hemorrhoid. An ablative agent is then injected at step 1612 through the needle into the hemorrhoid to ablate said hemorrhoid. At step 1614, the needle is removed from the hemorrhoid. Suction is then removed from the endoscope at step 1616 to release the portion of rectal tissue.

In another embodiment, compressive force is applied to the engaged hemorrhoid to reduce the cross-sectional area of the hemorrhoid prior to applying the thermal ablation, improving the efficacy of thermal ablation. In one embodiment, compressive force is applied by a heat sensitive compression mechanism which is uncompressed at room temperature and compresses the engaged hemorrhoid at a temperature higher than the body temperature. In one embodiment, the compression mechanism is composed of a shape memory alloy (SMA). In one embodiment, the SMA is Nitinol. In one embodiment, the Af temperature of the SMA is greater than 37° C. In other embodiments, the Af temperature of the SMA is greater than 50° C. but less than 100° C.

Figure 17A:
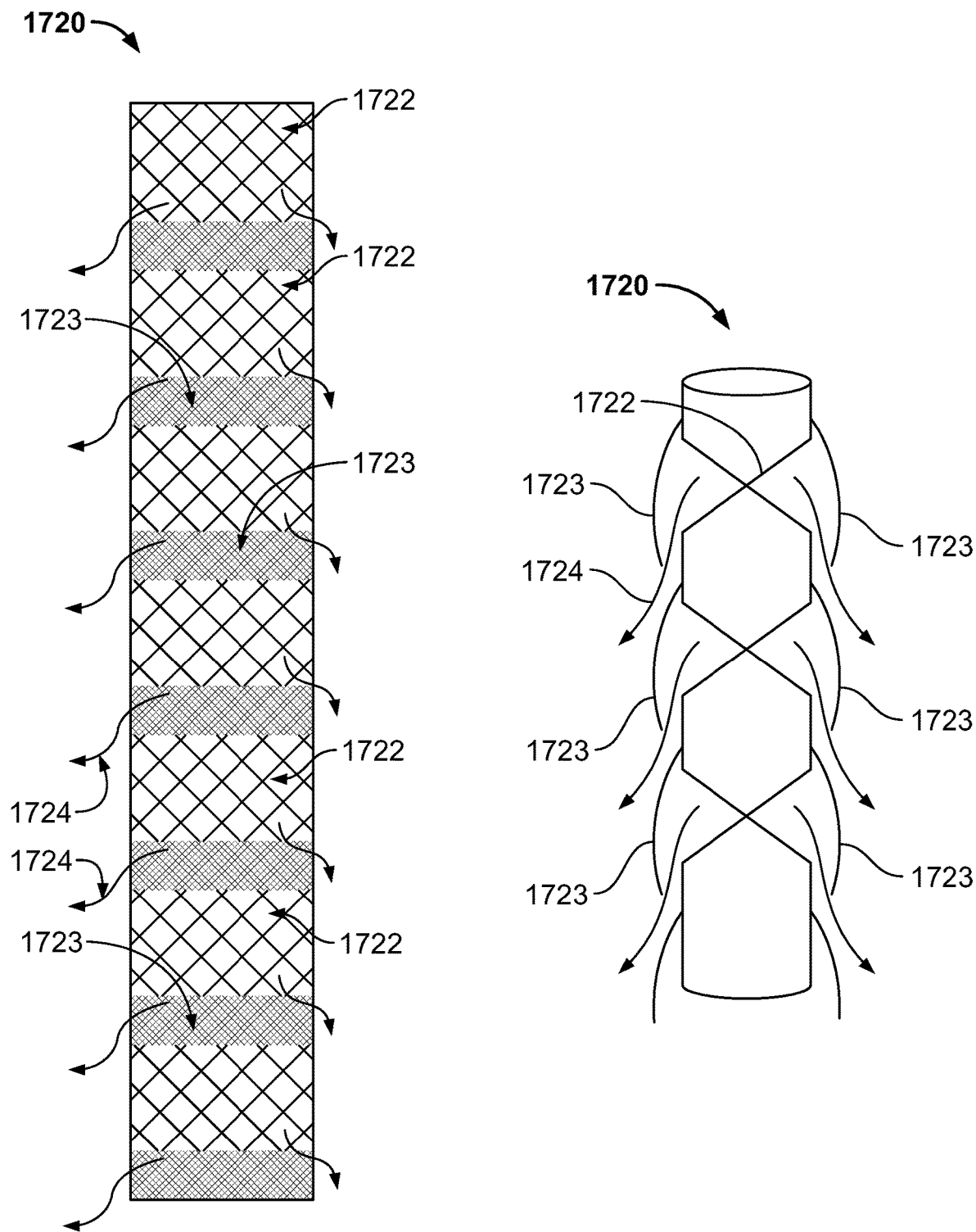
FIG. 17A illustrates a stent used to provide localized ablation to a target tissue, in accordance with one embodiment of the present specification.

FIG. 17A illustrates a stent 1720 used to provide localized ablation to a target tissue, in accordance with one embodiment of the present specification. Similar to conventional stents, the ablation stent 1720 of the present specification has a compressed, pre-deployment configuration and an expanded, post-deployment configuration. The pre-deployment configuration assists with delivery of the stent and the post-deployment configuration helps to keep the stent positioned correctly. The stent 1720 is covered with a semipermeable or conductive membrane 1722 that conducts an ablative agent or ablative energy from within the stent lumen to the external surface of the stent in a sufficient amount, resulting in ablation of the tissue in contact with the stent 1720. The membrane allows for the transfer of ablative energy from inside the stent to the surrounding tissue while preventing leakage of a significant amount of fluid from inside the stent to the surrounding tissue. In various embodiments, the membrane 1722 includes at least one opening or movable flap of membrane material 1723 for the transfer of an ablative agent 1724 from the stent lumen to the surrounding tissue. In some embodiments, the flaps 1723 comprise a plurality of individual overlapping membranes attached to the stent 1720 with intervening unattached areas. The flaps 1723 can be moved in a direction away from the stent 1720 by force of the ablative agent 1724 pushing against the membrane 1722, allowing the ablative agent 1724 to escape from the stent lumen into the surrounding tissues. The unattached portions of the flaps 1723 act as unidirectional flap valves (similar to a drape), allowing for ablative agent 1724 to exit the stent lumen but preventing the ingrowth of tumor or tissue into the stent 1720. After the ablative agent 1724 has exited the stent 1720, the flaps 1723 lay back against the stent 1720 and block the ablative agent 1724 from re-entering the stent 1724 or tissue in-growth into the stent. In one embodiment, the stent 1720 is composed of a wire mesh. In one embodiment, the membrane 1722 is composed of a thermally conductive material. In one embodiment, the membrane is composed of silicone. Optionally, in some embodiments, the silicone membrane includes pores which allow for the transmission of the ablative agent without allowing for substantial ingrowth of tumor tissue. The pores could optionally be expandable and have a greater dimension when the ablative agent is applied to allow for passage of ablative agent or energy while the dimension shrinks to a smaller dimension during non-therapy times to prevent tumor ingrowth. In other embodiments, the membrane is composed of polytetrafluoroethylene (PTFE), perfluoroelastomer (PFE), fluorinated ethylene propylene (FEP) or any other suitable material known in the field.

FIG. 17B illustrates a catheter 1730 used to deploy, and provide an ablative agent to, the stent of FIG. 17A. The catheter 1730 has a proximal end and a distal end with a shaft 1731 having a lumen therebetween. In one embodiment, the catheter 1730 is composed of a thermally insulated material. The ablative agent 1733 enters the lumen of the catheter from the proximal end 1732. The catheter 1730 has one or more openings 1735 at the distal end that allow for the ablative agent 1733 to exit the catheter shaft 1731 and enter the stent lumen. In various embodiments, the catheter shaft 1731 has one or more positioning elements 1734 to position the at least one opening 1735 at a desired location inside the stent lumen. These positioning elements 1734 also act as occlusive elements to prevent the passage of ablative agent into the adjacent normal tissue. In one embodiment, the positioning elements have a smaller first volume for positioning and a higher second volume for occlusion. The increase in volume from said first volume to said second volume is triggered by passage of the ablative agent wherein thermal energy of the ablative agent heats the air in the positioning element to the second volume, resulting in a better seal while the ablative agent is being delivered. The transfer of thermal energy to the air in the balloon occurs along the length of the catheter. On discontinuation of the thermal energy delivery, the air inside the balloon cools and the balloon volume gradually decreases from the occlusive second volume to the positioning first volume. In some embodiments, this increase in volume is undesirable and a balloon made of a non-compliant material that does not expand is used. In various embodiments, optional lumens are available for the passage of a guidewire or injection of radiologic contrast material.

FIG. 17C illustrates the stent 1720 of FIG. 17A working in conjunction with the catheter 1730 of FIG. 17B. Ablative agent 1733 is provided to the proximal end 1732 of the catheter 1730 and travels through the catheter shaft 1731 to the distal end of the catheter 1730. The ablative agent 1733 exits the catheter 1730 through the openings 1735 at the distal end of the catheter 1730. The ablative agent 1733 is transferred to the surrounding tissues via the conductive membrane on the stent 1720. The positioning elements 1734 prevent the escape of ablative agent 1733 from the proximal and distal ends of the stent 1720.

Figure 17D:
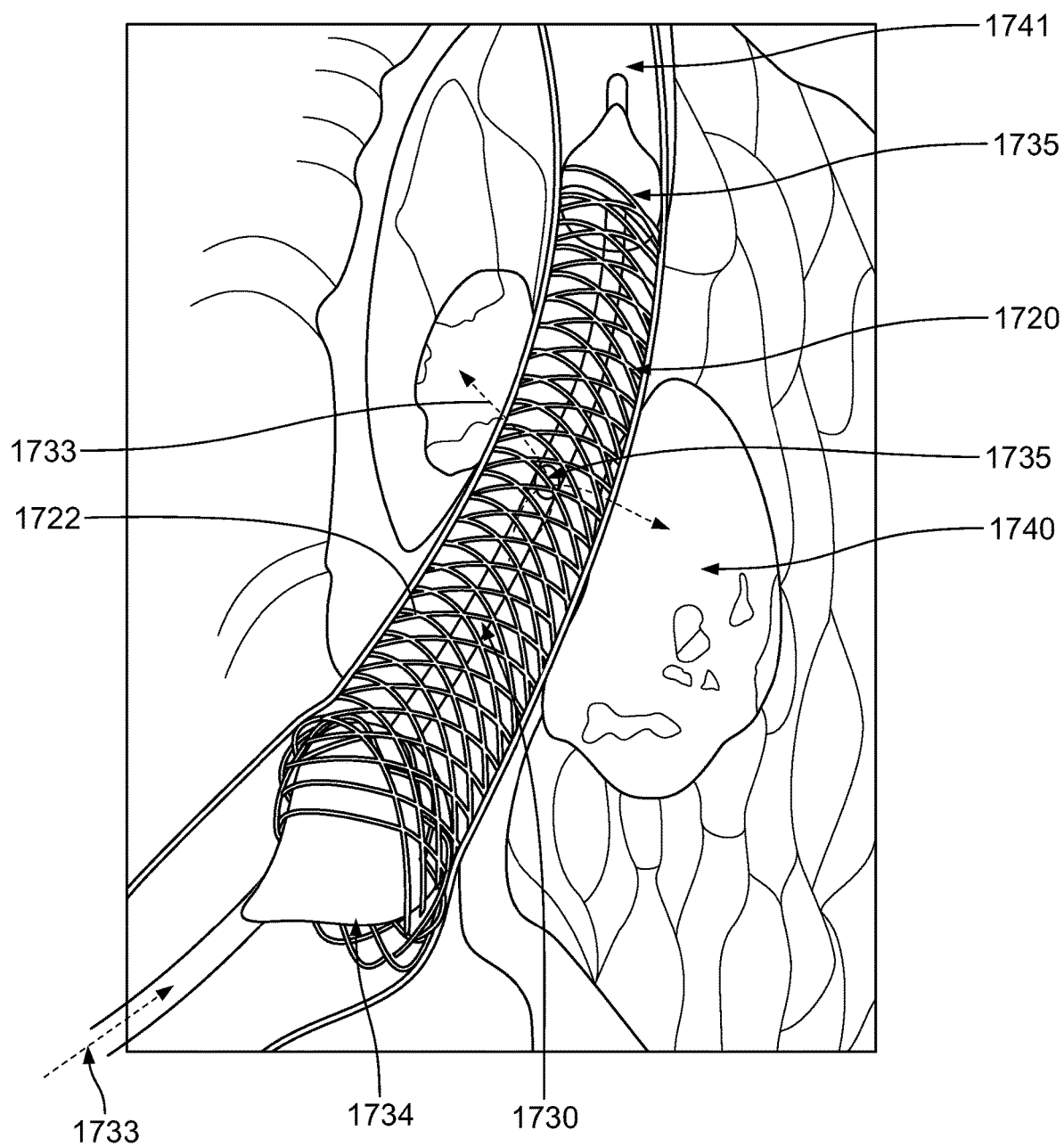
FIG. 17D illustrates the stent of FIG. 17A and the catheter of FIG. 17B positioned in a bile duct obstructed by a pancreatic tumor.

FIG. 17D illustrates the stent of FIG. 17A and the catheter of FIG. 17B positioned in a bile duct 1741 obstructed by a pancreatic tumor 1740. A stent 1720 is placed in the bile duct to open the obstruction. The stent 1720 has a thermally conducting membrane 1722 that allows for transfer of ablative energy from inside the stent lumen to the surrounding tissue. In one embodiment, the membrane 1722 has openings to allow for the passage of the ablative agents from inside the stent lumen to the surrounding tissue. The catheter 1730 is used to deliver the catheter at initial deployment and to deliver ablative agent. The catheter 1730 is also used for subsequent ablation in an already deployed stent 1720. The ablative agent 1733 is delivered to the lumen of the stent through at least one opening 1735 in the catheter shaft. The ablative agent then delivers the ablative energy from the ablative agent 1733 through the thermally conducting membrane 1724 or allows for passage of the ablative agent 1733 through the openings into the surrounding tissue to ablate the tumor 1740. The catheter has a first positioning element 1734 at the distal end to position the catheter at a fixed distance from the distal end of the stent 1720. This positioning element is also used an occlusive member to prevent the flow of the ablative agent 1733 outside the lumen of the stent into the normal healthy tissue of the bile duct 1741. In one embodiment, the catheter has a second positioning element 1735 at the proximal end of the stent serving similar function as the first positioning element 1734. In another embodiment, a bare metal stent is used and the ablative energy is passed through the interstices of the stent.

Figure 17E:
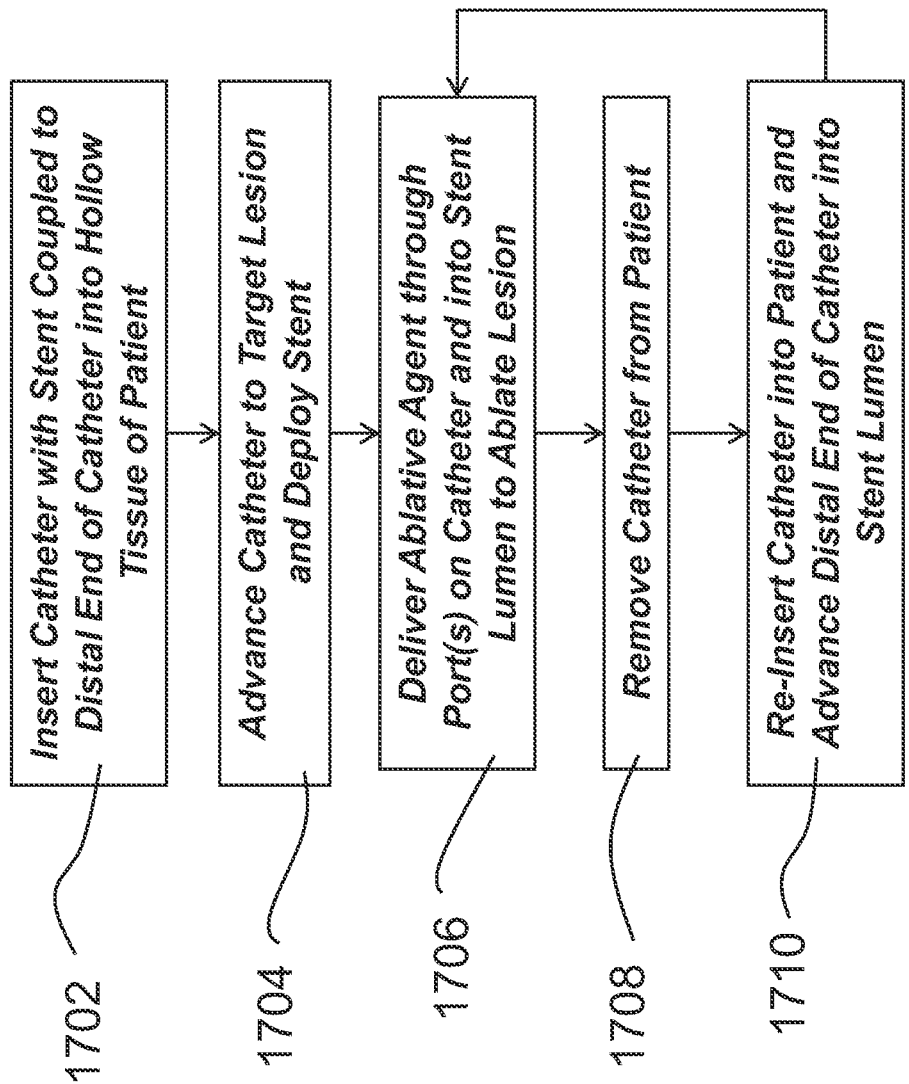
FIG. 17E is a flow chart listing the steps involved in a hollow tissue or organ ablation process using an ablation stent and catheter, in accordance with one embodiment of the present specification.

FIG. 17E is a flow chart listing the steps involved in a hollow tissue or organ ablation process using an ablation stent and catheter, in accordance with one embodiment of the present specification. At step 1702, the catheter with the ablation stent coupled to its distal end is inserted into a hollow tissue of a patient. The catheter is then advanced at step 1704 to the target lesion and the stent is deployed. At step 1706, ablative agent is delivered to the stent lumen via ports on the catheter. The ablative agent or energy is then conducted to the surrounding tissue via the conductive membrane on the stent. Once ablation is completed, the catheter is removed from the patient at step 1708. If further ablation is needed, the catheter is re-inserted at step 1710 and advanced to the location of the stent. Ablation is then re-performed at step 1706. The deployment of the stent and delivery of ablative energy can be performed in separate steps and at separate times. For example, the ablation can be performed at a future time after the placement of the stent to shrink the growth of an expanding tumor. Multiple serial ablations can be performed through the same stent over time.

Figure 18:
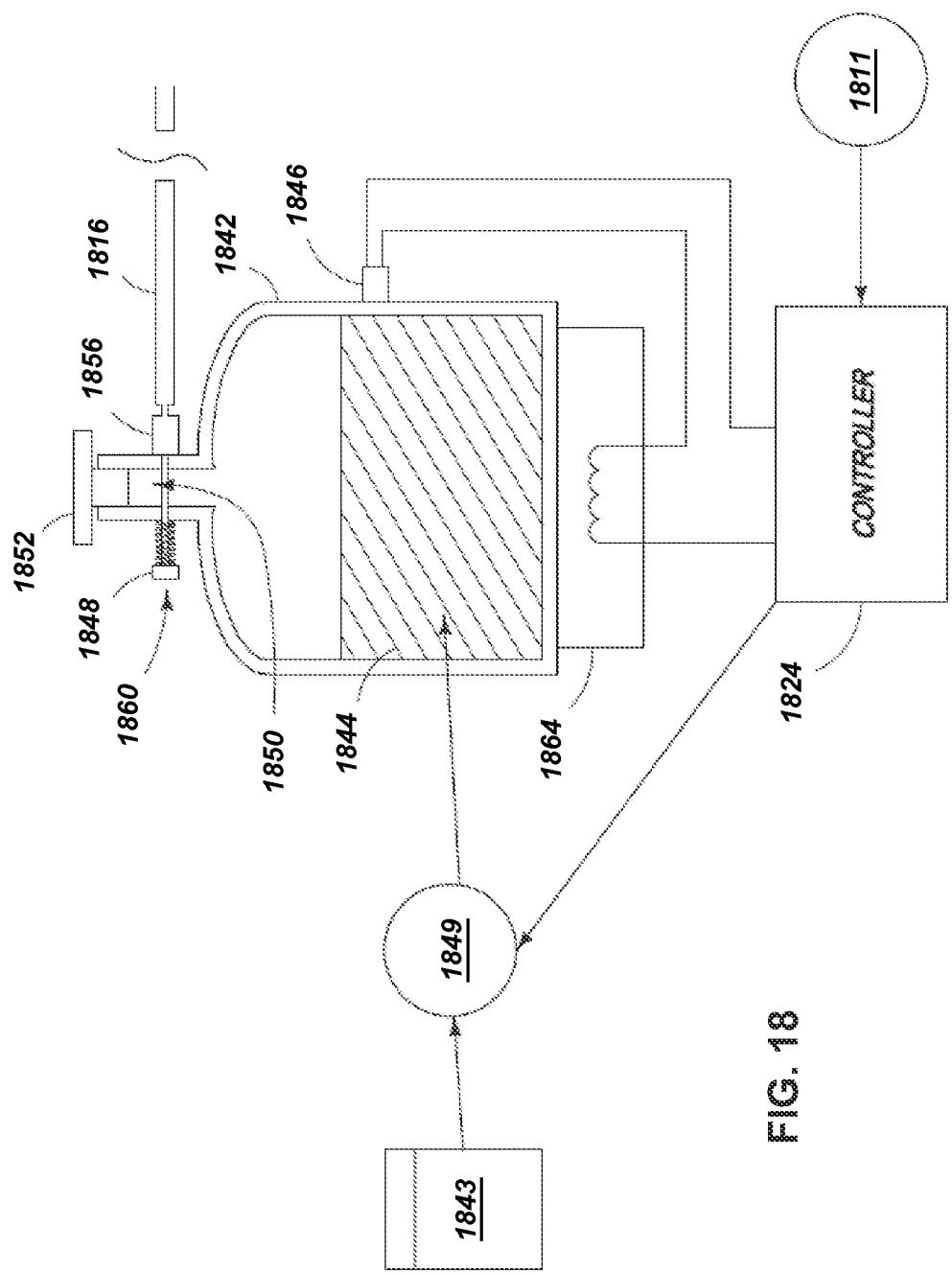
FIG. 18 illustrates a vapor delivery system using an RF heater for supplying vapor to the ablation device, in accordance with an embodiment of the present specification.

FIG. 18 illustrates a vapor delivery system using an RF heater for supplying vapor to the ablation device, in accordance with an embodiment of the present specification. In an embodiment, the vapor is used as an ablative agent in conjunction with the ablation device described in the present specification. RF heater 1864 is located proximate a pressure vessel 1842 containing a liquid 1844. RF heater 1864 heats vessel 1842, in turn heating the liquid 1844. The liquid 1844 heats up and begins to evaporate causing an increase in pressure inside the vessel 1842. The pressure inside vessel 1842 can be kept fairly constant by providing a thermal switch 1846 that controls resistive heater 1864. Once the temperature of the liquid 1844 reaches a predetermined temperature, the thermal switch 1846 shuts off RF heater 1864. The vapor created in pressure vessel 1842 may be released via a control valve 1850. As the vapor exits vessel 1842, a pressure drop is created in the vessel resulting in a reduction in temperature. The reduction of temperature is measured by thermal switch 1846, and RF heater 1864 is turned back on to heat liquid 1844. In one embodiment, the target temperature of vessel 1842 may be set to approximately 108° C., providing a continuous supply of vapor. As the vapor is released, it undergoes a pressure drop, which reduces the temperature of the vapor to a range of approximately 90-100° C. As liquid 1844 in vessel 1842 evaporates and the vapor exits vessel 1842, the amount of liquid 1844 slowly diminishes. The vessel 1842 is optionally connected to reservoir 1843 containing liquid 1844 via a pump 1849 which can be turned on by the controller 1824 upon sensing a fall in pressure or temperature in vessel 1842, delivering additional liquid 1844 to the vessel 1842.

Vapor delivery catheter 1816 is connected to vessel 1842 via a fluid connector 1856. When control valve 1850 is open, vessel 1842 is in fluid communication with delivery catheter 1816 via connector 1856. Control switch 1860 may serve to turn vapor delivery on and off via actuator 1848. For example, control switch 1860 may physically open and close the valve 1850, via actuator 1848, to control delivery of vapor stream from the vessel 1842. Switch 1860 may be configured to control other attributes of the vapor such as direction, flow, pressure, volume, spray diameter, or other parameters.

Instead of, or in addition to, physically controlling attributes of the vapor, switch 1860 may electrically communicate with a controller 1824. Controller 1824 controls the RF heater 1864, which in turn controls attributes of the vapor, in response to actuation of switch 1860 by the operator. In addition, controller 1824 may control valves temperature or pressure regulators associated with catheter 1816 or vessel 1842. A flow meter 1852 may be used to measure the flow, pressure, or volume of vapor delivery via the catheter 1816. The controller 1824 controls the temperature and pressure in the vessel 1842 and the time, rate, flow, and volume of vapor flow through the control valve 1850. These parameters are set by the operator 1811. The pressure created in vessel 1842, using the target temperature of 108° C., may be in the order of 25 pounds per square inch (psi) (1.72 bars).

Figure 19:
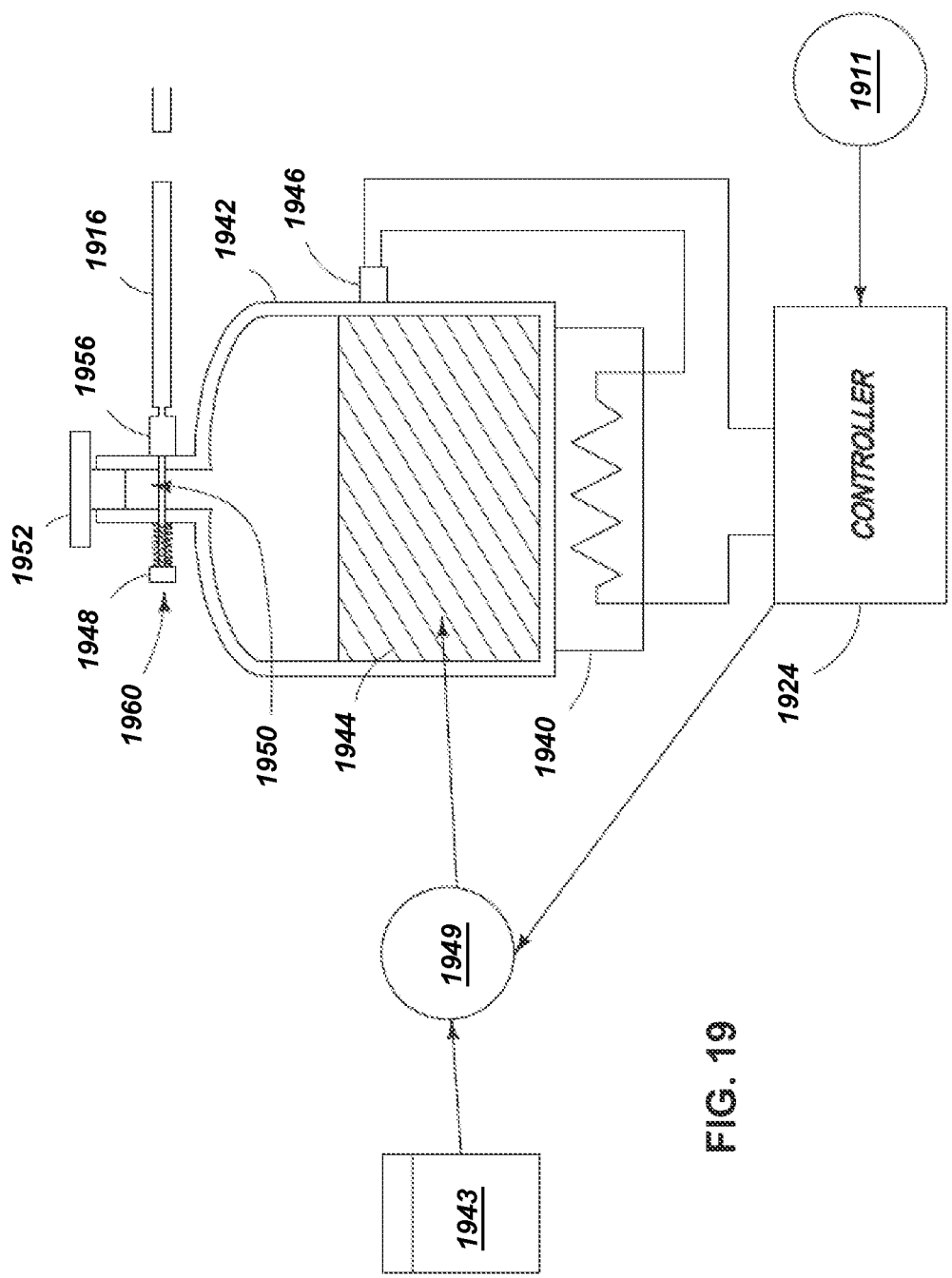
FIG. 19 illustrates a vapor delivery system using a resistive heater for supplying vapor to the ablation device, in accordance with an embodiment of the present specification.

FIG. 19 illustrates a vapor delivery system using a resistive heater for supplying vapor to the ablation device, in accordance with an embodiment of the present specification. In an embodiment, the generated vapor is used as an ablative agent in conjunction with the ablation device described in the present specification. Resistive heater 1940 is located proximate a pressure vessel 1942. Vessel 1942 contains a liquid 1944. Resistive heater 1940 heats vessel 1942, in turn heating liquid 1944. Accordingly, liquid 1944 heats and begins to evaporate. As liquid 1944 begins to evaporate, the vapor inside vessel 1942 causes an increase in pressure in the vessel. The pressure in vessel 1942 can be kept fairly constant by providing a thermal switch 1946 that controls resistive heater 1940. When the temperature of liquid 1944 reaches a predetermined temperature, thermal switch 1946 shuts off resistive heater 1940. The vapor created in pressure vessel 1942 may be released via a control valve 1950. As the vapor exits vessel 1942, vessel 1942 experiences a pressure drop. The pressure drop of vessel 1942 results in a reduction of temperature. The reduction of temperature is measured by thermal switch 1946, and resistive heater 1940 is turned back on to heat liquid 1944. In one embodiment, the target temperature of vessel 1942 may be set to approximately 108° C., providing a continuous supply of vapor. As the vapor is released, it undergoes a pressure drop, which reduces the temperature of the vapor to a range of approximately 90-100° C. As liquid 1944 in vessel 1942 evaporates and the vapor exits vessel 1942, the amount of liquid 1944 slowly diminishes. The vessel 1942 is connected to another vessel 1943 containing liquid 1944 via a pump 1949 which can be turned on by the controller 1924 upon sensing a fall in pressure or temperature in vessel 1942 delivering additional liquid 1944 to the vessel 1942.

Vapor delivery catheter 1916 is connected to vessel 1942 via a fluid connector 1956. When control valve 1950 is open, vessel 1942 is in fluid communication with delivery catheter 1916 via connector 1956. Control switch 1960 may serve to turn vapor delivery on and off via actuator 1948. For example, control switch 1960 may physically open and close the valve 1950, via actuator 1948, to control delivery of vapor stream from the vessel 1942. Switch 1960 may be configured to control other attributes of the vapor such as direction, flow, pressure, volume, spray diameter, or other parameters. Instead of, or in addition to, physically controlling attributes of the vapor, switch 1960 may electrically communicate with a controller 1924. Controller 1924 controls the resistive heater 1940, which in turn controls attributes of the vapor, in response to actuation of switch 1960 by the operator. In addition, controller 1924 may control valves temperature or pressure regulators associated with catheter 1916 or vessel 1942. A flow meter 1952 may be used to measure the flow, pressure, or volume of vapor delivery via the catheter 1916. The controller 1924 controls the temperature and pressure in the vessel 1942 as well as time, rate, flow, and volume of vapor flow through the control valve 1950. These parameters are set by the operator 1911. The pressure created in vessel 1942, using the target temperature of 108° C., may be on the order of 25 pounds per square inch (psi) (1.72 bars).

Figure 20:
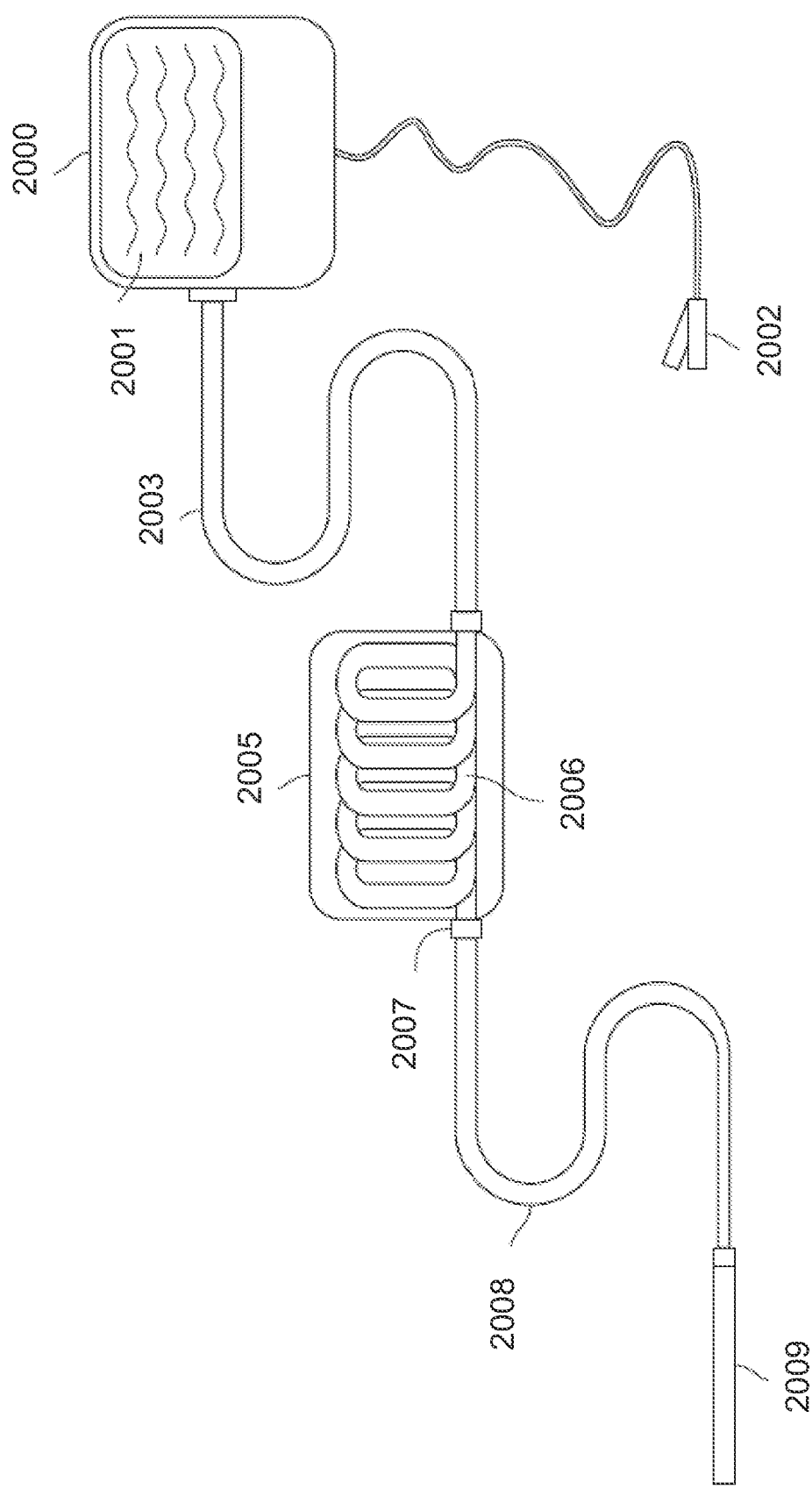
FIG. 20 illustrates a vapor delivery system using a heating coil for supplying vapor to the ablation device, in accordance with an embodiment of the present specification.

FIG. 20 illustrates a vapor delivery system using a heating coil for supplying vapor to the ablation device, in accordance with an embodiment of the present specification. In an embodiment, the generated vapor is used as an ablative agent in conjunction with the ablation device described in the present specification. The vapor delivery system includes a conventional generator 2000 that is commonly used in operating rooms to provide power to specialized tools, i.e., cutters. The generator 2000 is modified to include an integrated liquid reservoir 2001. In one embodiment, the reservoir 2001 is filled with room temperature pure water. The reservoir 2001 portion of the generator 2000 is connected to the heating component 2005 via a reusable active cord 2003. In one embodiment, the reusable active cord 2003 may be used up to 200 times. The cord 2003 is fixedly attached via connections at both ends to withstand operational pressures, and preferably a maximum pressure, such that the cord does not become disconnected. In one embodiment, the connections can resist at least 1 atm of pressure. In one embodiment, the connections are of a luer lock type. The cord 2003 has a lumen through which liquid flows to the heating component 2005. In one embodiment, the heating component 2005 contains a coiled length of tubing 2006. As liquid flows through the coiled tubing 2006, it is heated by the surrounding heating component 2005 in a fashion similar to a conventional heat exchanger. As the liquid is heated, it becomes vaporized. The heating component contains a connector 2007 that accommodates the outlet of vapor from the coiled tubing 2006. One end of a single use cord 2008 attaches to the heating component 2005 at the connector 2007. The connector 2007 is designed to withstand pressures generated by the vapor inside the coiled tubing 2006 during operation. In one embodiment, the connector 2007 is of a luer lock type. An ablation device 2009 is attached to the other end of the single use cord 2008 via a connection able to withstand the pressures generated by the system. In one embodiment, the ablation device is integrated with a catheter. In another embodiment, the ablation device is integrated with a probe. The single use cord 2008 has a specific luminal diameter and is of a specific length to ensure that the contained vapor does not condense into liquid while simultaneously providing the user enough slack to operate. In addition, the single use cord 2008 provides sufficient insulation so that personnel will not suffer burns when coming into contact with the cord. In one embodiment, the single use cord has a luminal diameter of less than 3 mm, preferably less than 2.6 mm, and is longer than 1 meter in length.

In one embodiment, the system includes a foot pedal 2002 by which the user can supply more vapor to the ablation device. Depressing the foot pedal 2002 allows liquid to flow from the reservoir 2001 into the heating component 2005 where it changes into vapor within the coiled tubing 2006. The vapor then flows to the ablation device via the single use tube 2008. The ablation device includes an actuator by which the user can open small ports on the device, releasing the vapor and ablating the target tissue.

Figure 21:
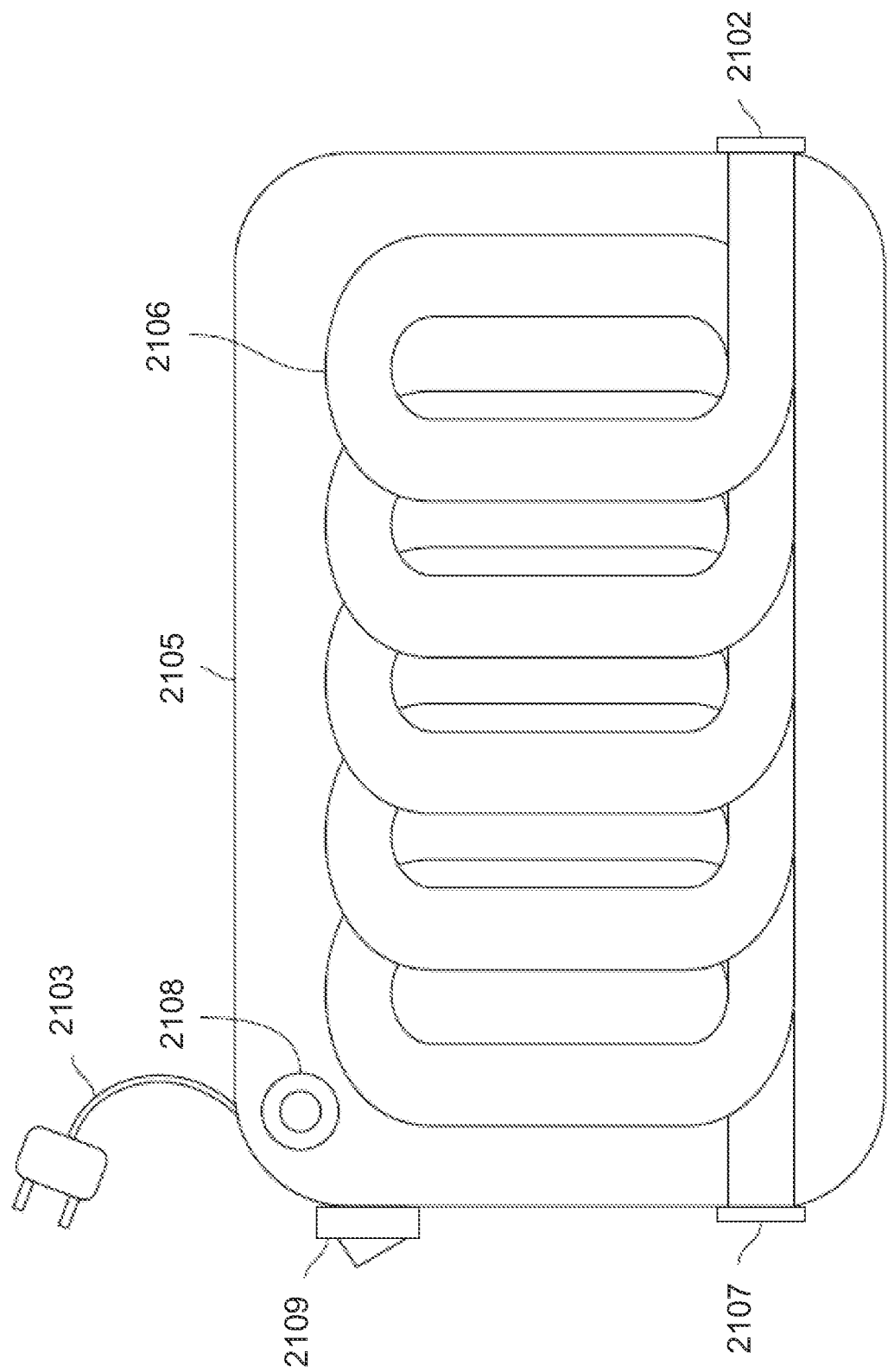
FIG. 21 illustrates the heating component and coiled tubing of the heating coil vapor delivery system of FIG. 20, in accordance with an embodiment of the present specification.

FIG. 21 illustrates the heating component 2105 and coiled tubing 2106 of the heating coil vapor delivery system of FIG. 20, in accordance with an embodiment of the present specification. Liquid arrives through a reusable active cord (not shown) at a connection 2102 on one side of the heating component 2105. The liquid then travels through the coiled tubing 2106 within the heating component 2105. The coiled tubing is composed of a material and configured specifically to provide optimal heat transfer to the liquid. In one embodiment, the coiled tubing 2106 is copper. The temperature of the heating component 2105 is set to a range so that the liquid is converted to vapor as it passes through the coiled tubing 2106. In one embodiment, the temperature of the heating component 2105 can be set by the user through the use of a temperature setting dial 2108. In one embodiment, the heating component contains an on/off switch 2109 and is powered through the use of an attached AC power cord 2103. In another embodiment, the heating component receives power through an electrical connection integrated into and/or facilitated by the active cord connection to the reservoir. The vapor passes through the end of the coiled tubing 2106 and out of the heating component 2105 through a connector 2107. In one embodiment, the connector 2107 is located on the opposite side of the heating component 2105 from the inlet connection 2102. A single use cord (not shown) attaches to the connector 2107 and supplies vapor to the ablation device.

FIG. 22A illustrates the unassembled interface connection between the ablation device 2208 and the single use cord 2201 of the heating coil vapor delivery system of FIG. 20, in accordance with an embodiment of the present specification. In this embodiment, the ablation device 2208 and single use cord 2201 are connected via a male-to-male double luer lock adapter 2205. The end of the single use cord 2201 is threaded to form a female end 2202 of a luer lock interface and connects to one end of the adapter 2205. The ablation device 2208 includes a small protrusion at its non-operational end which is also threaded to form a female end 2207 of a luer lock interface and connects to the other end of the adapter 2205. The threading luer lock interface provides a secure connection and is able to withstand the pressures generated by the heating coil vapor delivery system without becoming disconnected.

FIG. 22B illustrates the assembled interface connection between the ablation device 2208 and the single use cord 2201 of the heating coil vapor delivery system of FIG. 20, in accordance with an embodiment of the present specification. The male-to-male double luer lock adapter 2205 is pictured securing the two components together. The double luer lock interface provides a stable seal, allows interchangeability between ablation devices, and enables users to quickly replace single use cords.

FIG. 23 illustrates a vapor ablation system using a heater or heat exchange unit for supplying vapor to the ablation device, in accordance with another embodiment of the present specification. In the pictured embodiment, water for conversion to vapor is supplied in a disposable, single use sterile fluid container 2305. The container 2305 is sealed with a sterile screw top 2310 that is punctured by a needle connector 2315 provided on a first end of a first filter member 2320. The second end of the first filter member 2320, opposite the first end, is connected to a pump 2325 for drawing the water from the fluid container 2305, through the first filter member 2320, and into the heater or heat exchange unit 2330. The system includes a microcontroller or microprocessor 2335 for controlling the actions of the pump 2325 and heater or heat exchange unit 2330. The heater or heat exchange unit 2330 converts the water into vapor (steam). The increase in pressure generated during the heating step drives the vapor through an optional second filter member 2340 and into the ablation catheter 2350. In one embodiment, the heater or heat exchange unit 2330 includes a one-way valve at its proximal end to prevent the passage of vapor back toward the pump 2325. In various embodiments, optional sensors 2345 positioned proximate the distal end of the catheter 2350 measure one or more of temperature, pressure, or flow of vapor and transmit the information to the microcontroller 2335, which in turn controls the rate of the pump 2325 and the level of vaporizing energy provided by the heater or heat exchange unit 2330.

Figure 24:
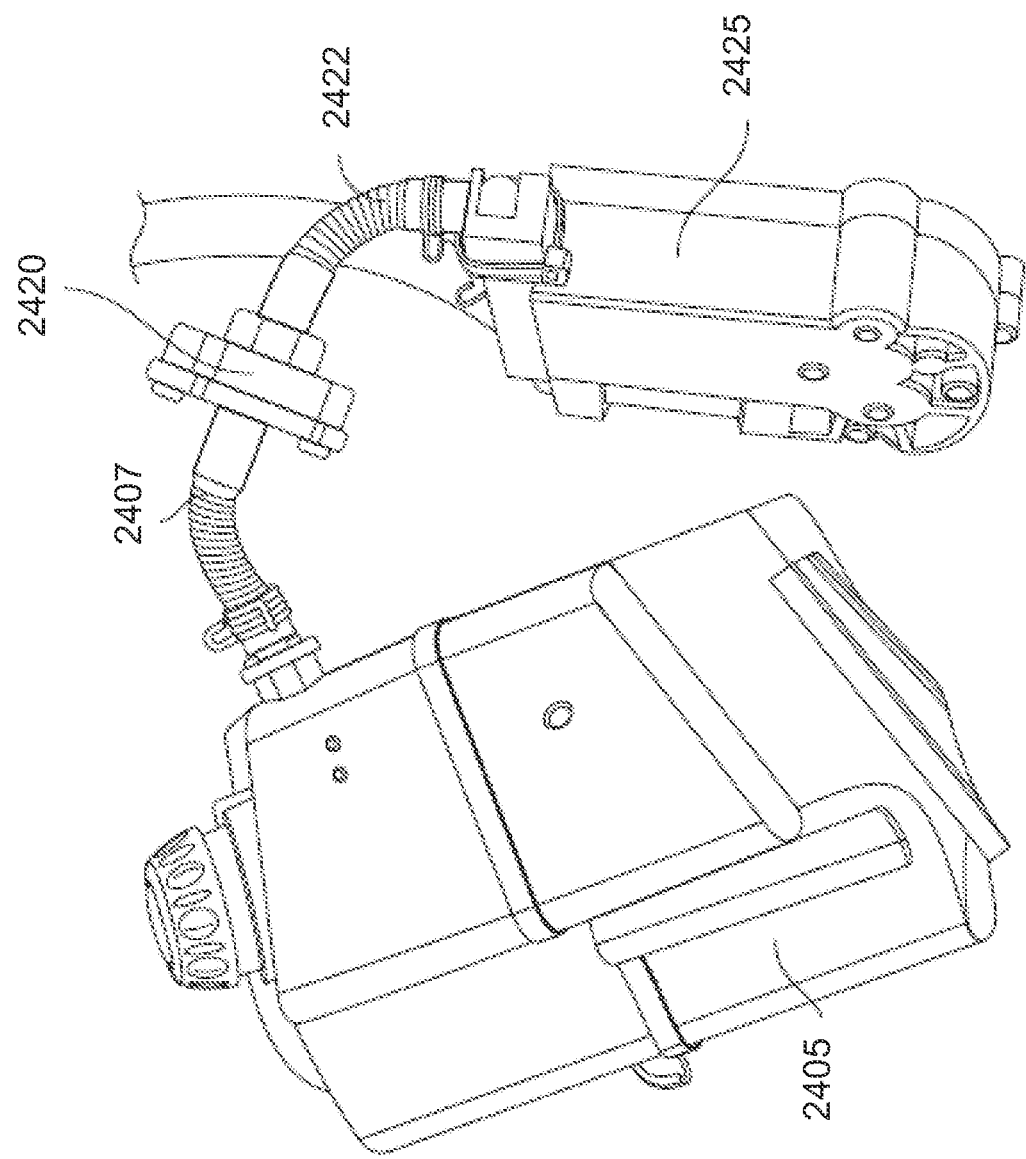
FIG. 24 illustrates the fluid container, filter member, and pump of the vapor ablation system of FIG. 23.

FIG. 24 illustrates the fluid container 2405, first filter member 2420, and pump 2425 of the vapor ablation system of FIG. 23. As can be seen in the pictured embodiment, the system includes a water-filled, disposable, single use sterile fluid container 2405 and a pump 2425 with a first filter member 2420 disposed therebetween. The first filter member 2420 is connected to the container 2405 and pump 2425 by two first and second lengths of sterile tubing 2407, 2422 respectively, and includes a filter for purifying the water used in the ablation system.

Figure 25:
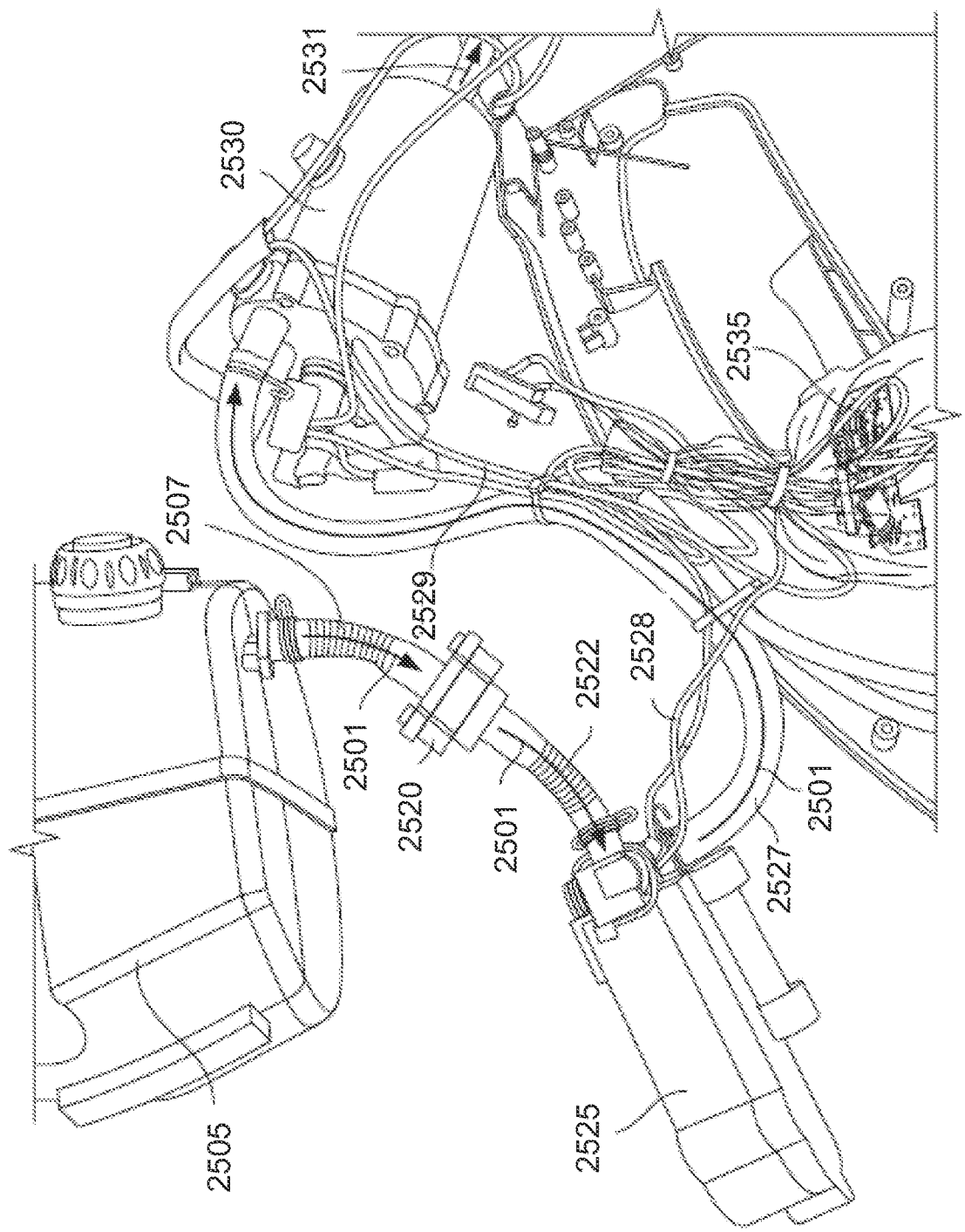
FIG. 25 illustrates a first view of the fluid container, filter member, pump, heater or heat exchange unit, and microcontroller of the vapor ablation system of FIG. 23.
Figure 26:
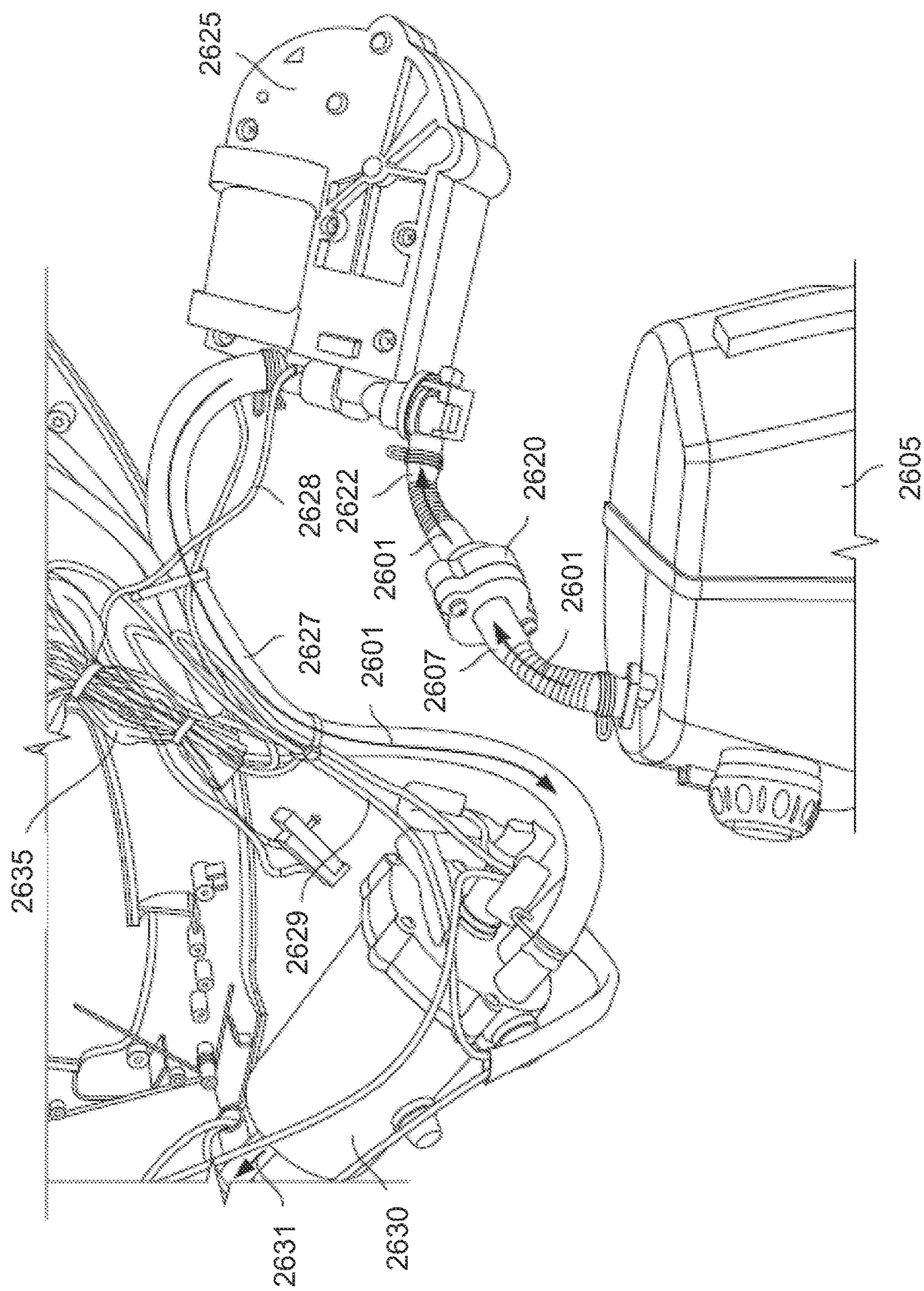
FIG. 26 illustrates a second view of the fluid container, filter member, pump, heater or heat exchange unit, and microcontroller of the vapor ablation system of FIG. 23.

FIGS. 25 and 26 illustrate first and second views respectively, of the fluid container 2505, 2605, first filter member 2520, 2620, pump 2525, 2625, heater or heat exchange unit 2530, 2630, and microcontroller 2535, 2635 of the vapor ablation system of FIG. 23. The container 2505, 2605 is connected to the first filter member 2520, 2620 by a first length of sterile tubing 2507, 2607 and the first filter member 2520, 2620 is connected to the pump 2525, 2625 by a second length of sterile tubing 2522, 2622. A third length of sterile tubing 2527, 2627 connects the pump 2525, 2625 to the heater or heat exchange unit 2530, 2630. The microcontroller 2535, 2635, is operably connected to the pump 2525, 2625 by a first set of control wires 2528, 2628 and to the heater or heat exchange unit 2530, 2630 by a second set of control wires 2529, 2629. The arrows 2501, 2601 depict the direction of the flow of water from the container 2505, 2605, through the first filter member 2520, 2620 and pump 2525, 2625 and into the heater or heat exchange member 2530, 2630 where it is converted to vapor. Arrow 2531, 2631 depicts the direction of flow of vapor from the heater or heat exchange unit 2530, 2630 into the ablation catheter (not shown) for use in the ablation procedure.

Figure 27:
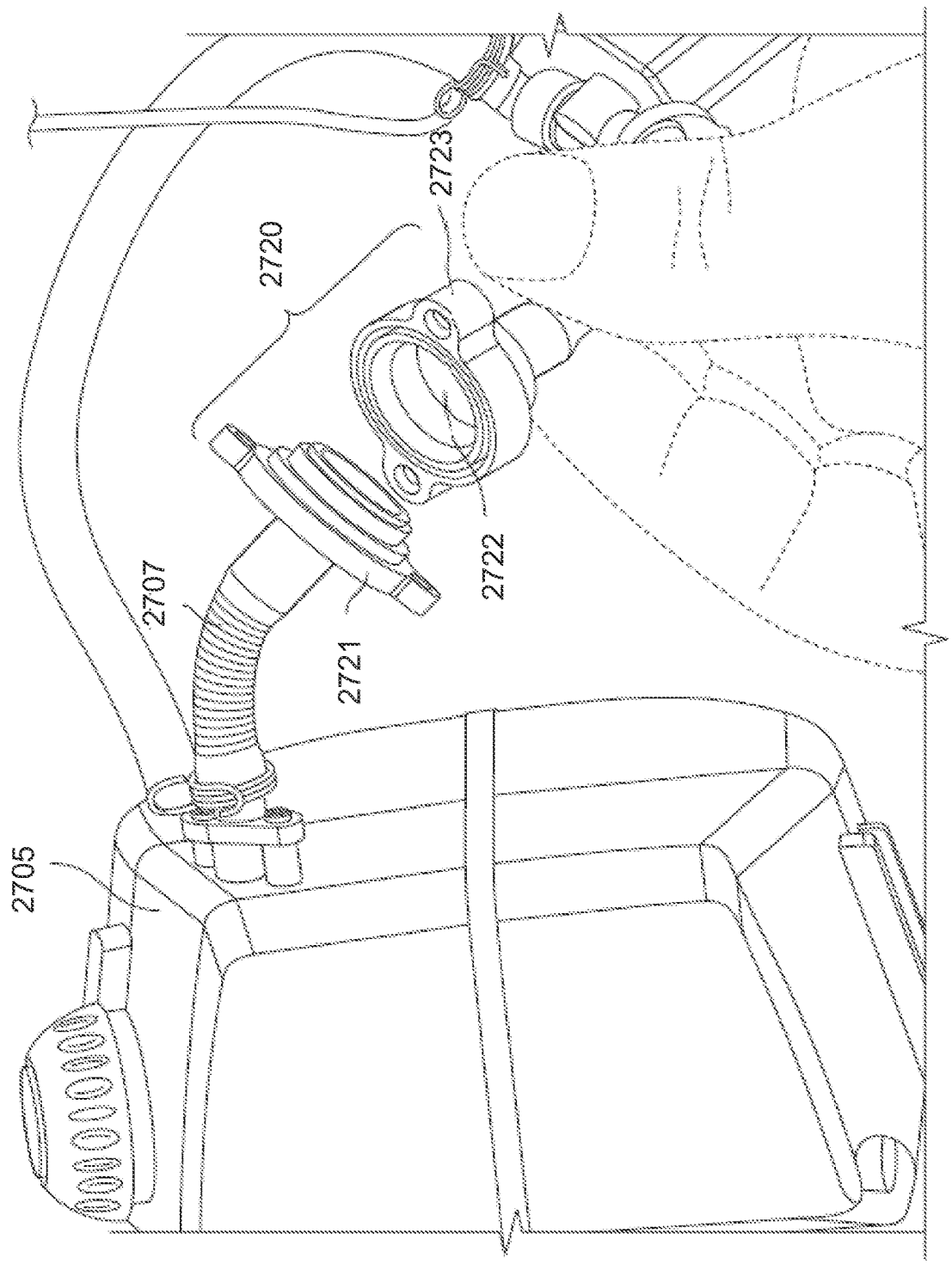
FIG. 27 illustrates the unassembled filter member of the vapor ablation system of FIG. 23, depicting the filter positioned within.

FIG. 27 illustrates the unassembled first filter member 2720 of the vapor ablation system of FIG. 23, depicting the filter 2722 positioned within. In one embodiment, the first filter member 2720 includes a proximal portion 2721, a distal portion 2723, and a filter 2722. The proximal portion 2721 and distal portion 2723 secure together and hold the filter 2722 within. Also depicted in FIG. 27 are the disposable, single use sterile fluid container 2705 and the first length of sterile tubing 2707 connecting the container 2705 to the proximal portion 2721 of the first filter member 2720.

Figure 28:
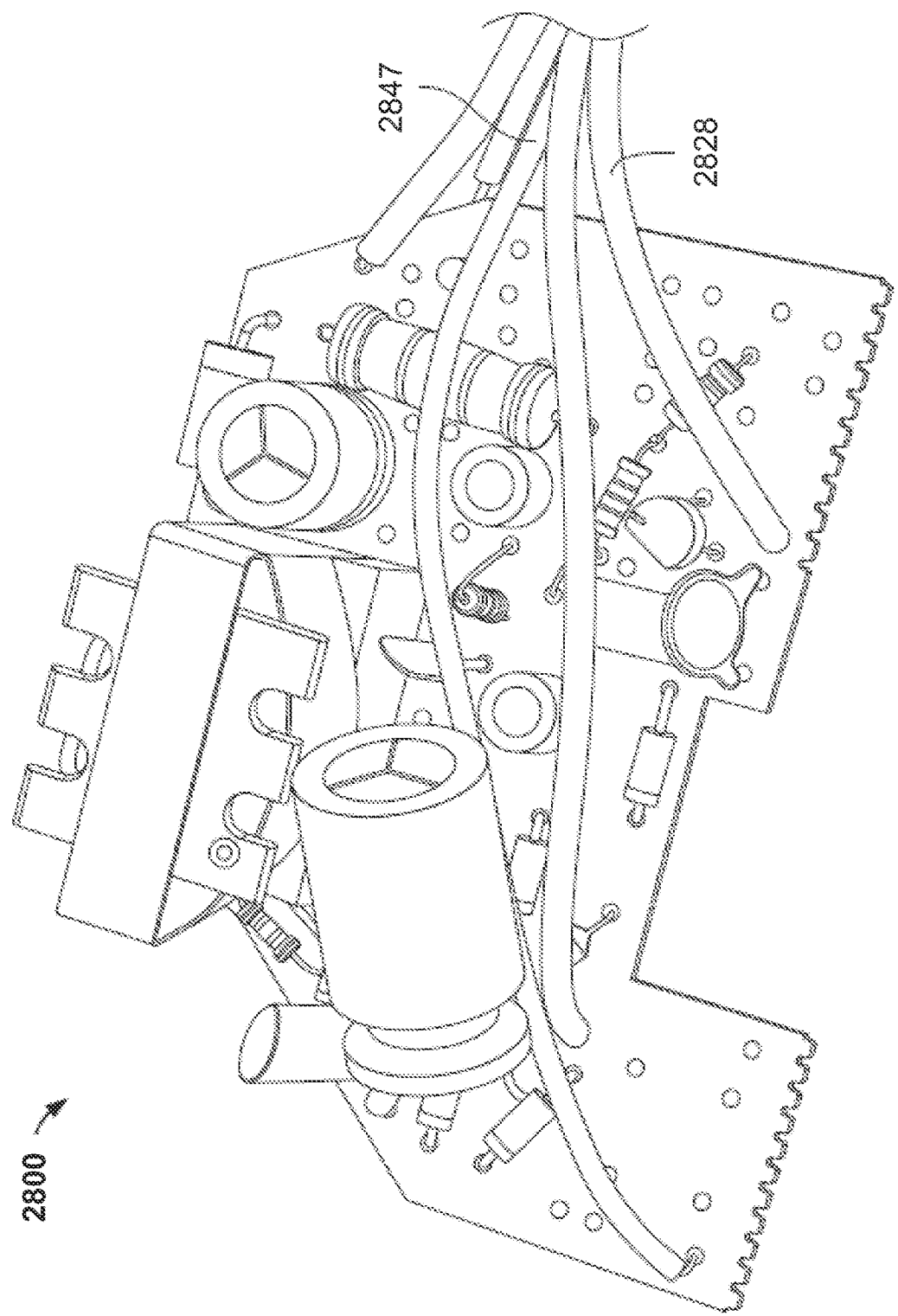
FIG. 28 illustrates one embodiment of the microcontroller of the vapor ablation system of FIG. 23.

FIG. 28 illustrates one embodiment of the microcontroller 2800 of the vapor ablation system of FIG. 23. In various embodiments, the microcontroller 2800 includes a plurality of control wires 2828 connected to the pump and heater or heat exchange unit for controlling said components and a plurality of transmission wires 2847 for receiving flow, pressure, and temperature information from optional sensors positioned proximate the distal end of the ablation catheter.

Figure 29:
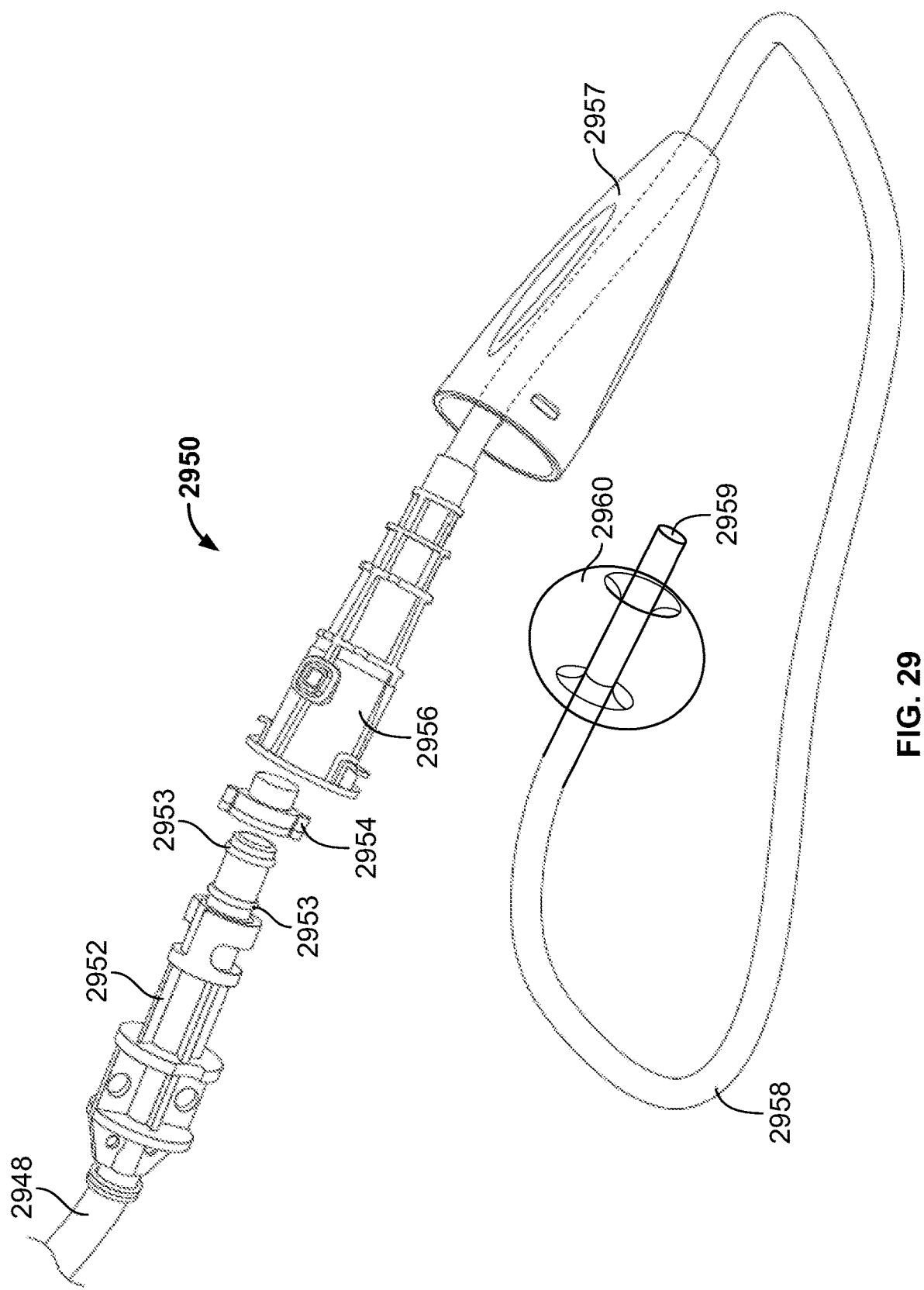
FIG. 29 illustrates one embodiment of a catheter assembly for use with the vapor ablation system of FIG. 23.

FIG. 29 illustrates one embodiment of a catheter assembly 2950 for use with the vapor ablation system of FIG. 23. Vapor is delivered from the heater or heat exchange unit to the catheter assembly 2950 via a tube 2948 attached to the proximal end of a connector component 2952 of the assembly 2950. A disposable catheter 2956 with a fixedly attached disposable length of flexible tubing 2958 at its distal end is fitted over the connector component 2952. A second filter member 2954 is positioned between the connector component 2952 and the disposable catheter 2956 for purifying the vapor supplied by the heater or heat exchange unit. The connector component 2952 includes two washers 2953 positioned apart a short distance at its distal end to engage the overlaying disposable catheter 2956 and form a double-stage seal, thereby preventing vapor leakage between the components. Once the disposable catheter 2956 has been fitted to the distal end of the connector component 2952, a catheter connector 2957 is slid over the disposable flexible tubing 2958 and disposable catheter 2956 and is then snapped into place onto the connector component 2952. The catheter connector 2957 acts to keep the disposable catheter 2956 in place and also assists in preventing vapor leakage. In various embodiments, the disposable flexible tubing 2958 includes one or more holes or ports 2959 at or proximate its distal end for the delivery of ablative vapor to target tissues. Optionally, in one embodiment, the disposable catheter 2957 includes at least one inflatable positioning member 2960 proximate its distal end.

Figure 30:
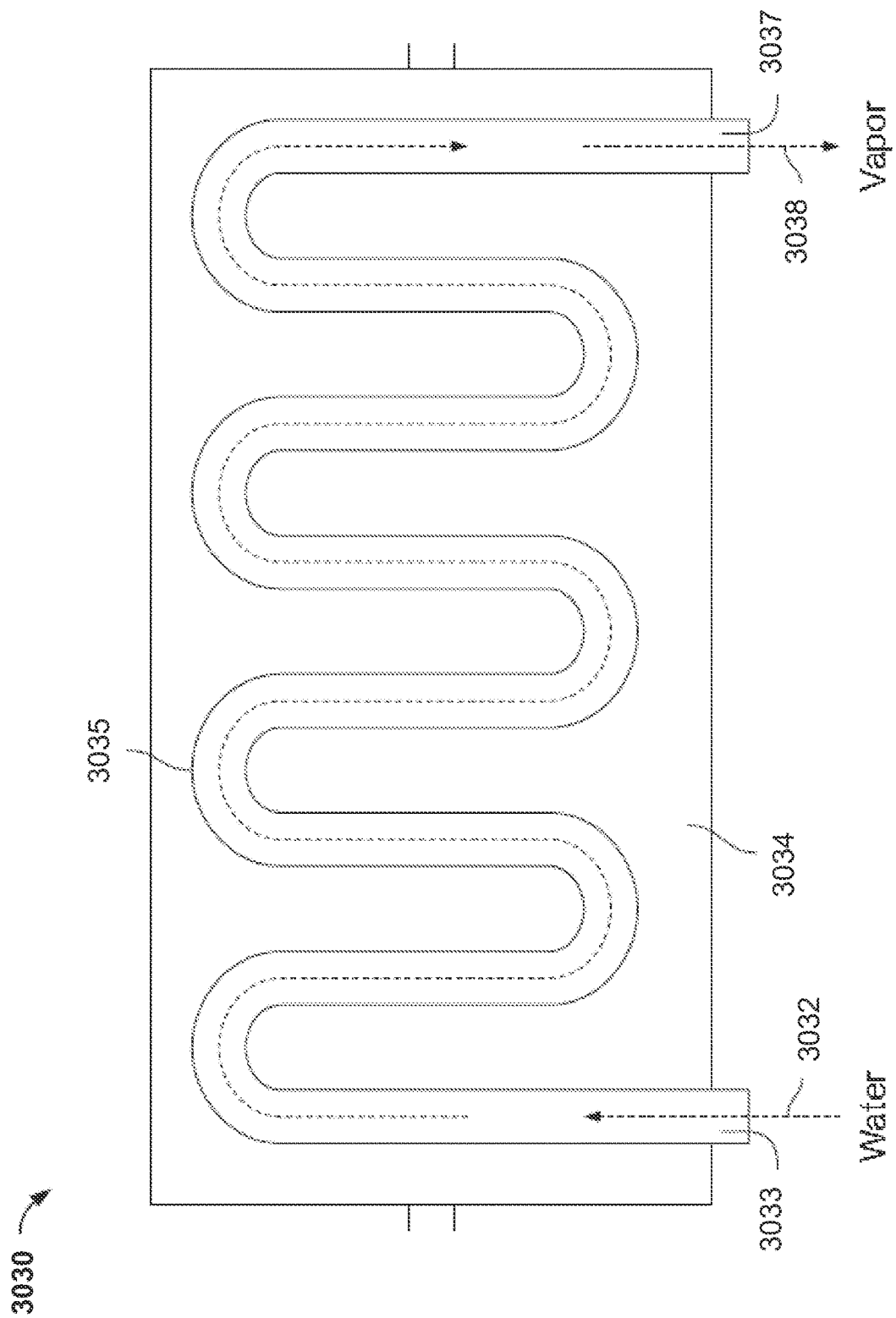
FIG. 30 illustrates one embodiment of a heat exchange unit for use with the vapor ablation system of FIG. 23.

FIG. 30 illustrates one embodiment of a heat exchange unit 3030 for use with the vapor ablation system of FIG. 23. The heat exchange unit 3030 comprises a length of coiled tubing 3035 surrounded by a heating element 3034. Water 3032 enters the coiled tubing 3035 of the heat exchange unit 3030 at an entrance port 3033 proximate a first end of said heat exchange unit 3030. As the water 3032 flows within the coiled tubing 3035, it is converted into vapor (steam) 3038 by the heat emanating from said coiled tubing 3035 which has been heated by the heating element 3034. The vapor 3038 exits the coiled tubing 3035 of the heat exchange unit 3030 at an exit port 3037 proximate a second end of said heat exchange unit 3030 and is then delivered to the ablation catheter (not shown) for use in the ablation procedure.

Figure 31A:
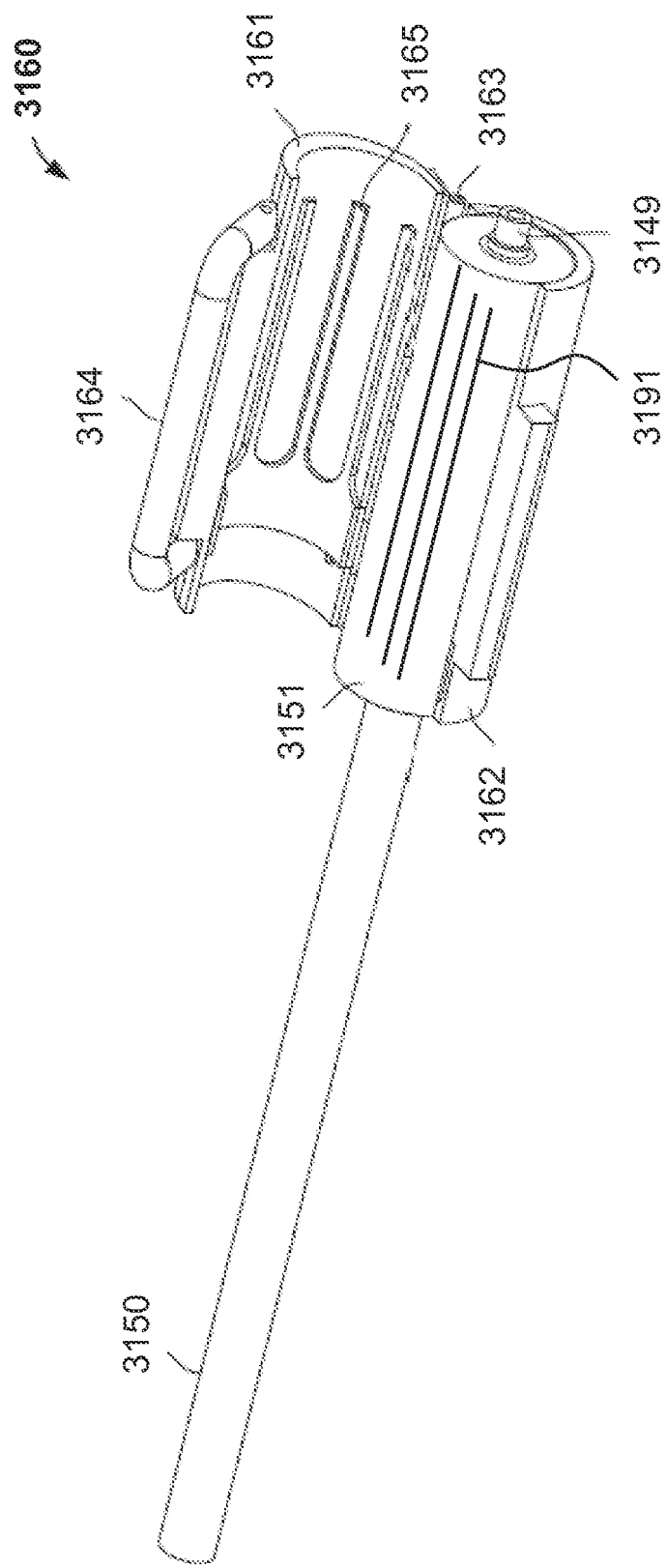
FIG. 31A illustrates another embodiment of a heat exchange unit for use with the vapor ablation system of the present specification.

FIG. 31A illustrates another embodiment of a heat exchange unit 3160 for use with the vapor ablation system of the present specification. In the pictured embodiment, the heat exchange unit 3160 comprises a cylindrically shaped, pen sized 'clamshell' style heating block. The heating block of the heat exchange unit 3160 includes a first half 3161 and a second half 3162 fixedly attached by a hinge 3163 along one side, wherein the halves 3161, 3162 fold together and connect on the opposite side. In one embodiment, the sides of the halves opposite the sides with the hinge include a clasp for holding the two halves together. In one embodiment, one of the halves includes a handle 3164 for manipulating the heat exchange unit 3160. When the halves are folded together, the heat exchange unit 3160 snugly envelopes a cylindrically shaped catheter fluid heating chamber 3151 attached to, in-line and in fluid communication with, the proximal end of the ablation catheter 3150. Each half 3161, 3162 of the heat exchange unit 3160 includes a plurality of heating elements 3165 for heating the block. In various embodiments, heat is transferred from the heating elements 3165 to the catheter fluid heating chamber 3151 using resistive or RF heating. The positioning and fit of the heating block place it in close thermal contact with the catheter fluid heating chamber 3151. When in operation, the heating elements 3165 heat the heating block which transfers heat to the catheter fluid heating chamber 3151, which in turn heats the water inside the chamber 3151, converting said water to vapor. The heating block does not directly contact the water. In one embodiment, the catheter fluid heating chamber 3151 comprises a plurality of linear indentations 3191 stretching along the length of the component and in parallel with the heating elements 3165. Upon closing the halves 3161, 3162, the heating elements 3165, which optionally protrude from the internal surfaces of the halves 3161, 3162 contact, and fit within, the linear indentations 3191. This also increases the surface area of contact between the heating block and the heating chamber, improving the efficiency of heat exchange. In another embodiment, the heat exchange unit 3160 uses induction heating to convert water in the heating chamber 3151 into vapor. The heating block includes an induction coil, which, when energized with electrical energy, causes heat to be generated in a metal core contained in the heating chamber 3151, as described in detail below. The catheter 3150 and heating chamber 3150 are single use and disposable, allowing for ease and lowered cost of manufacture. The outer surface of the heating block itself, comprising the two halves 3161, 3162, does not become heated and its temperature remains below 100° C. so it does not injure the operator.

A luer fitting coupler 3149 is provided at the proximal end of the catheter fluid heating chamber 3151 for connecting a tube supplying sterile water. In one embodiment, a one-way valve is included at the proximal end of the catheter fluid heating chamber 3151, distal to the luer fitting 3149, to prevent the passage of vapor under pressure toward the water supply.

Figure 31B:
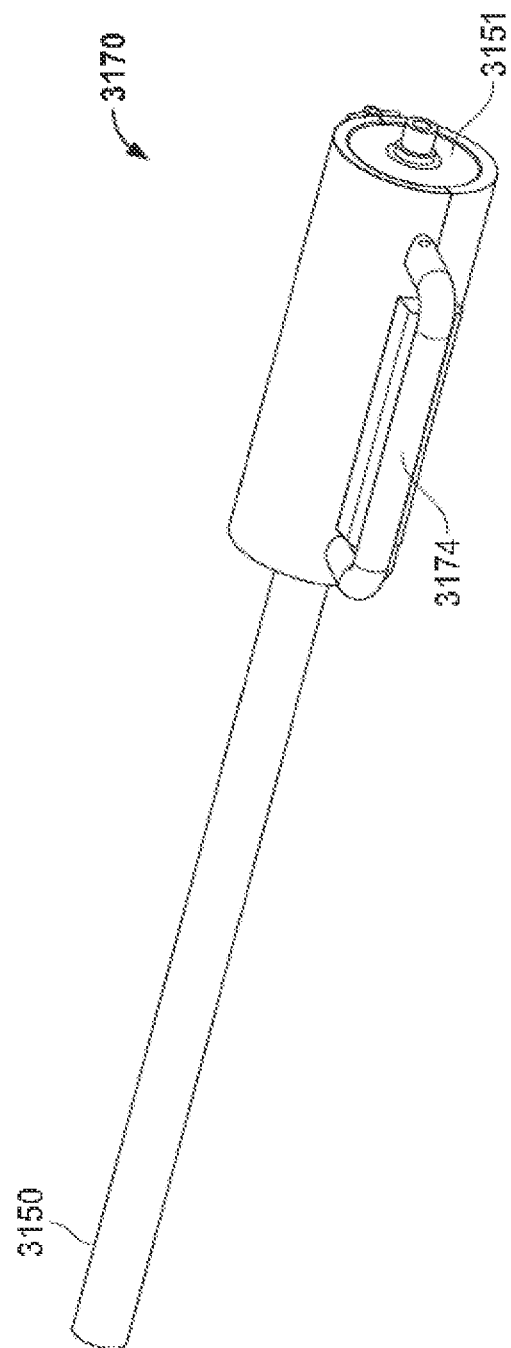
FIG. 31B illustrates another embodiment of a heat exchange unit for use with the vapor ablation system of the present specification.

FIG. 31B illustrates another embodiment of a heat exchange unit 3170 for use with the vapor ablation system of the present specification. The heat exchange unit 3170 of FIG. 31B functions similarly to the heat exchange unit 3160 pictured in FIG. 31A. However, rather than having an open design capable of opening and closing, heat exchange unit 3170 has a closed design and is configured to slide over the catheter fluid heating chamber 3151. In one embodiment, the heat exchange unit 3170 includes a handle 3174 for manipulation of said unit about the catheter 3150.

As described above, the catheter fluid heating chamber is designed as part of the ablation catheter and, along with the remainder of the catheter, is single use and disposable. In another embodiment, the chamber is reusable, in which case the luer fitting is positioned in between the catheter shaft and the chamber. The heating block is designed to be axially aligned with the heating chamber when in use, is reusable, and will not be damaged in the event that it falls to the floor. In one embodiment, the weight and dimensions of the heating block are designed such that it can be integrated into a pen-sized and shaped handle of the ablation catheter. The handle is thermally insulated to prevent injury to the operator.

In one embodiment, the heating block receives its power from a console which is itself line powered and designed to provide 700-1000 W of power, as determined by the fluid vaporization rate. The heating block and all output connections are electrically isolated from line voltage. In one embodiment, the console includes a user interface allowing adjustment of power with a commensurate fluid flow rate. In addition, in one embodiment, a pump, such as a syringe pump, is used to control the flow of fluid to the heating chamber and heating element. In one embodiment, the volume of the syringe is at least 10 ml and is ideally 60 ml.

Figure 31C:
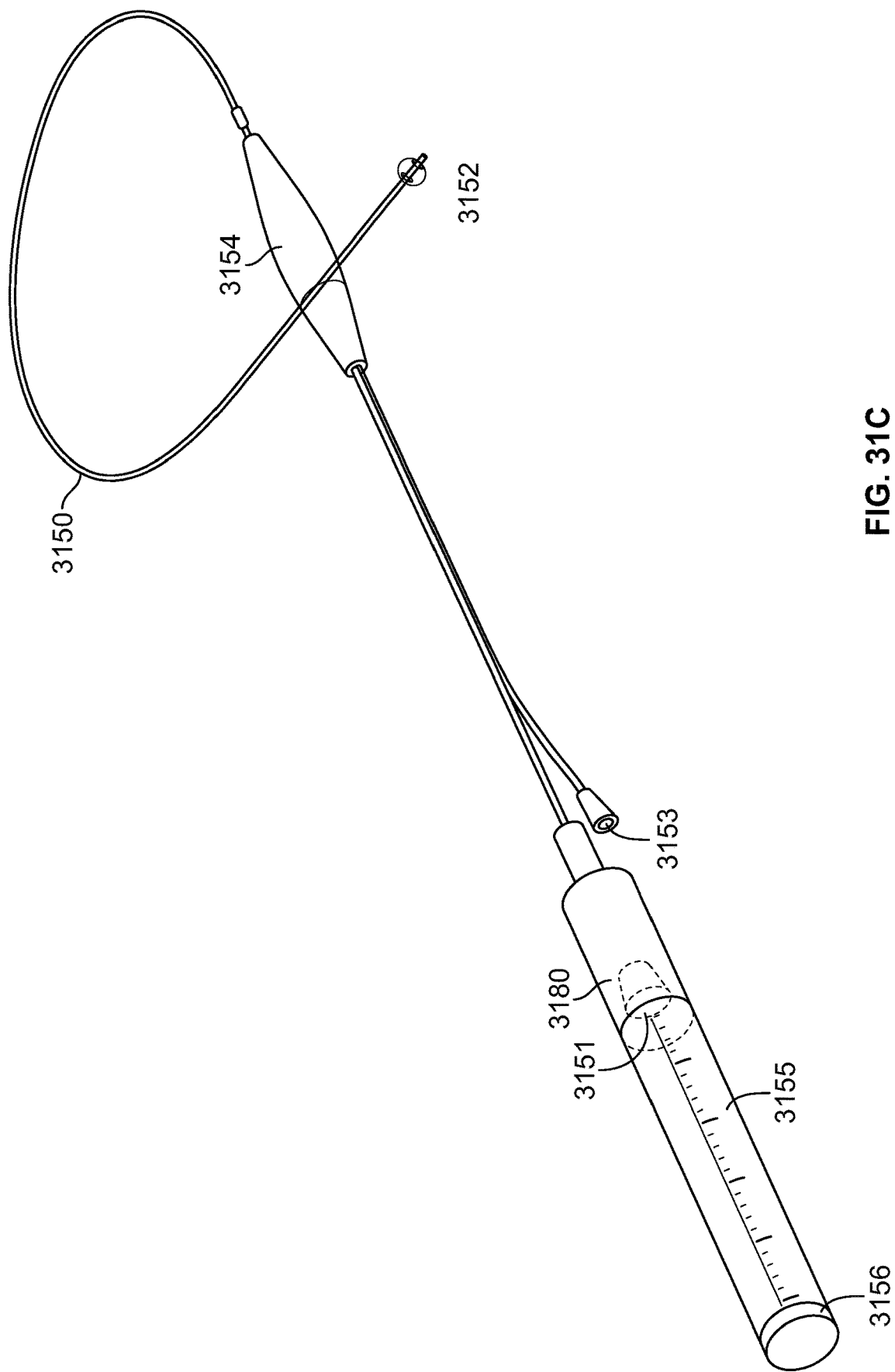
FIG. 31C illustrates a heat exchange unit and catheter with a syringe pump operationally coupled to a fluid filled syringe, in accordance with one embodiment of the present specification.

FIG. 31C illustrates a heat exchange unit 3180 and catheter 3150 with a syringe pump operationally coupled to a fluid filled syringe 3155, in accordance with one embodiment of the present specification. A fluid heating chamber 3151 is depicted within the heat exchange unit 3180 at the proximal end of the catheter 3150. In various embodiments, the heat exchange unit 3180 is similar to the heat exchange units depicted in FIGS. 31A and 31B. Referring to FIG. 31C, the catheter 3150 also includes a positioning balloon 3152 at its distal end and an insufflation port 3153 at its proximal end for inflating the balloon 3152. An insulating handle 3154 covers a proximal portion of the catheter 3150 where the insufflation port 3153 joins with the catheter 3150 allowing for the operator to manipulate the catheter without getting injured by the thermal energy. A syringe 3155 attaches to the proximal end of the heating chamber 3151 to provide fluid, such as water, to the heating chamber 3151. In another embodiment, the syringe 3155 is pre-attached to the proximal end of the heating chamber 3151 to provide fluid, such as water, to the heating chamber 3151 in order to prevent leakage of the fluid. The syringe 3155 includes a plunger 3156 at its distal end. In various embodiments, the plunger 3156 is a handle-less disc-shaped plunger and has a diameter matching a diameter of the syringe 3155. The fluid is converted into vapor in the heating chamber 3151 as a result of the transfer of thermal energy into the heating chamber 3151 from the surrounding heat exchange unit 3180. The vapor is delivered from the distal end of the catheter 3150 to ablate a target tissue.

In the above embodiment, the catheter to be used with the vapor ablation system is designed using materials intended to minimize cost. In one embodiment, the tubing used with the catheter is able to withstand a temperature of at least 125° C. and can flex through an endoscope's bend radius (approximately 1 inch) without collapse. In one embodiment, the section of the catheter that passes through an endoscope is 7 French (2.3 mm) diameter and has a minimum length of 215 cm. In one embodiment, thermal resistance is provided by the catheter shaft material which shields the endoscope from the super-heated vapor temperature. In one embodiment, the heat exchange unit is designed to interface directly with, or in very close proximity to, an endoscope's biopsy channel to minimize the likelihood of a physician handling heated components. Having the heat exchange unit in close proximity to the endoscope handle also minimizes the length of the catheter through which the vapor needs to travel, thus minimizing heat loss and premature condensation.

Figure 32A:
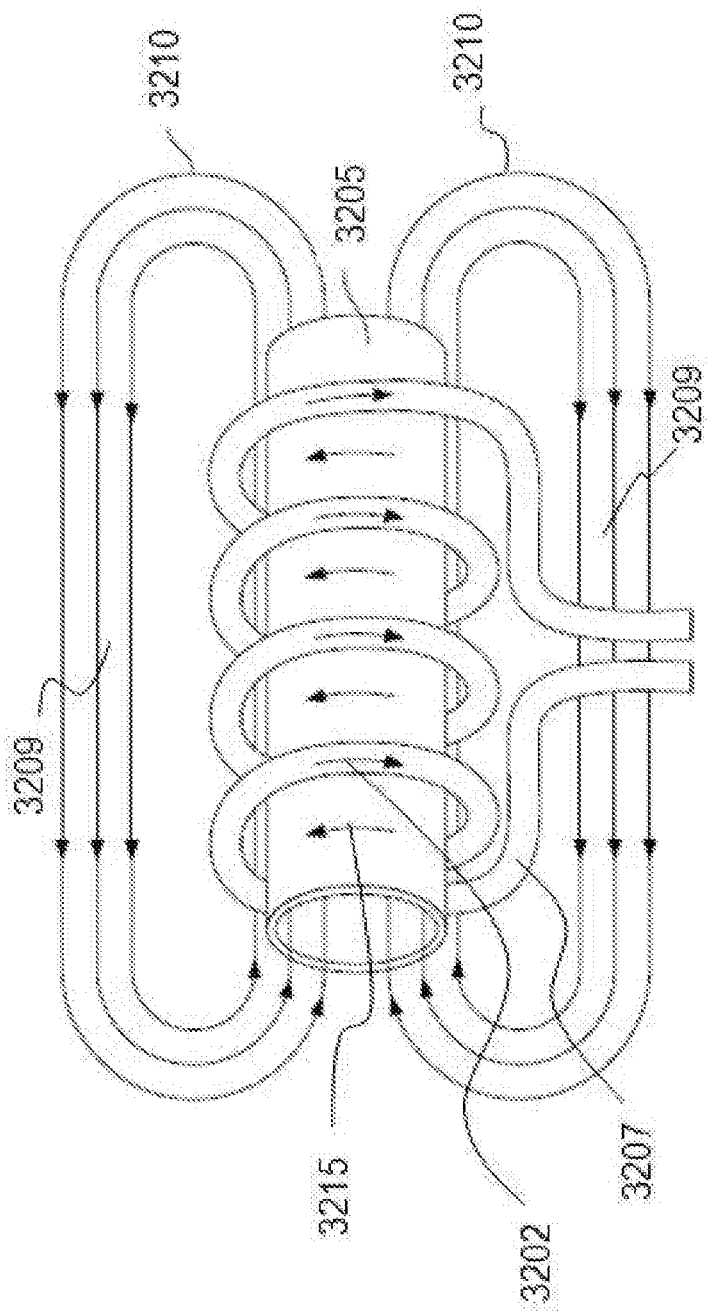
FIG. 32A illustrates the use of induction heating to heat a chamber.

In various embodiments, other means are used to heat the fluid within the catheter fluid heating chamber. FIG. 32A illustrates the use of induction heating to heat a chamber 3205. When an alternating electric current 3202 is passed through a coil 3207 of wire within the chamber 3205, the coil 3207 creates a magnetic field 3209. Magnetic lines of flux 3210 of the magnetic field 3209 cut through the air around the coil 3207. When the chamber 3205 is composed of a ferrous material, such as, iron, stainless steel, or copper, electrical currents known as eddy currents 3215 are induced to flow in the chamber 3205 as a result of the presence of the alternating current 3202 and magnetic field 3209 with lines of flux 3210. The eddy currents 3215 cause localized heating of the chamber 3205. When the chamber 3205 is filled with a fluid, such as water, the heat is transferred from the chamber to the fluid inside, resulting in vaporization of said fluid. In the embodiment depicted in FIG. 32A, the coil 3207 is looped about the chamber 3205 with four loops and spaced a distance away from said chamber 3205 to assist with visualization. The design of the chamber and coil in FIG. 32A depicts only one possible embodiment and is not intended to be limiting. Those skilled in the art will understand many different design configurations are possible with respect to the chamber and coil. In various embodiments, the coil includes at least one loop about the chamber and is looped about said chamber such that the coil is in physical contact with said chamber. In other embodiments, the coil includes at least one loop about the chamber and is looped about said chamber such that the coil is spaced away a specific distance from said chamber with a layer of air or other insulating material between said coil and said chamber. In various embodiments, the loops of the coil are arranged closely together such that they are in contact with one another. In other embodiments, the loops of the coil are arranged with a specific distance between one another. In one embodiment, the loops of the coil extend along the entire length of the chamber. In various embodiments, the loops of the coil extend beyond the length of the chamber. In other embodiments, the loops of the coil extend along a portion of the length of the chamber that is less than the chamber's total length.

Figure 32B:
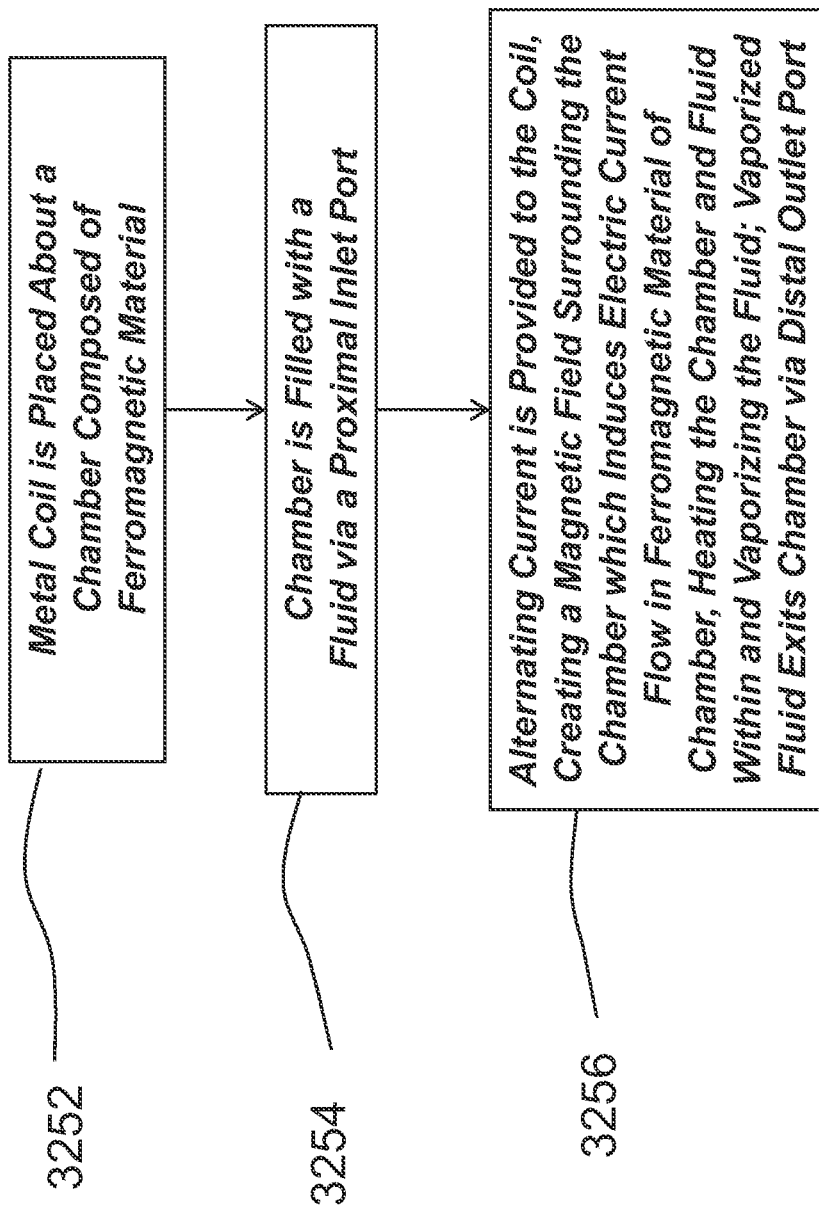
FIG. 32B is a flow chart listing the steps involved in using induction heating to heat a chamber.

FIG. 32B is a flow chart listing the steps involved in using induction heating to heat a chamber. At step 3252, a metal coil is placed about a chamber composed of a ferromagnetic material such that the coil surrounds the chamber. Then, at step 3254, the chamber is filled with a fluid via a proximal inlet port on said chamber. At step 3256, an alternating current is provided to the coil, creating a magnetic field in the area surrounding the chamber. The magnetic field induces electric (eddy) current flow in the ferromagnetic material which heats the chamber. The heat is transferred to the fluid inside the chamber and vaporizes the fluid. The vaporized fluid exits the chamber via the distal outlet port.

Figure 33A:
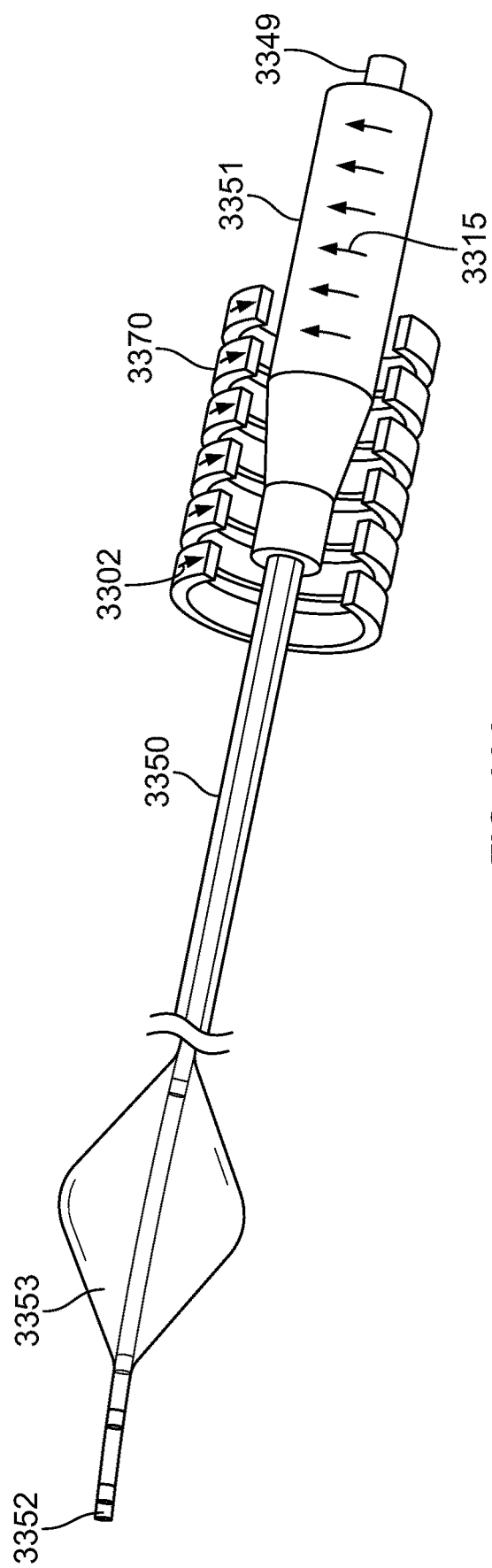
FIG. 33A illustrates one embodiment of a coil used with induction heating in the vapor ablation system of the present specification.

FIG. 33A illustrates one embodiment of a coil 3370 used with induction heating in the vapor ablation system of the present specification. A section of the coil 3370 has been cut away to assist with visualization. The coil 3370 is positioned surrounding the catheter fluid heating chamber 3351. An alternating current 3302 passing through the coil 3370 creates a magnetic field which induces eddy currents 3315 to flow in the chamber 3370 as described above. The flow of eddy currents 3315 results in heating of the catheter fluid heating chamber 3351. The heated chamber heats the fluid within, converting it into a vapor, which passes into the catheter 3350 for use in the ablation procedure. The catheter 3350 includes at least one delivery port 3352 at its distal end for the delivery of vapor. Optionally, the catheter 3350 includes at least one positioning element 3353 proximate its distal end. In one embodiment, the at least one positioning element 3353 is an inflatable balloon. The coil 3370 itself does not heat, making it safe to touch. A luer fitting coupler 3349 is provided at the proximal end of the catheter fluid heating chamber 3351 for connecting a tube supplying sterile water. In one embodiment, a one-way valve (not shown) is included at the proximal end of the catheter fluid heating chamber 3351, distal to the luer fitting 3349, to prevent the passage of vapor toward the water supply. In one embodiment, thermal insulating material (not shown) is positioned between the coil 3370 and the heating chamber 3351. In another embodiment, the chamber 3351 is suspended in the center of the coil 3370 with no physical contact between the two. In this embodiment, the intervening air acts as a thermally insulating material. The design of the chamber is optimized to increase its surface area to maximize contact and heat transfer, in turn resulting in more efficient vapor generation. In one embodiment, the coil 3370 is constructed in a 'clamshell' style design, similar to the heat exchange unit 3160 depicted in FIG. 31A, and opens and closes about the heating chamber 3351. In another embodiment, the coil 3370 is constructed in a closed style design, similar to the heat exchange unit 3170 depicted in FIG. 31B, and slides over the heating chamber 3351.

In various embodiments, the induction heating systems and structures described in FIGS. 32A and 33A can be applied to any of the fluid chambers shown in any of the disclosed embodiments of the present specification.

Figure 33B:
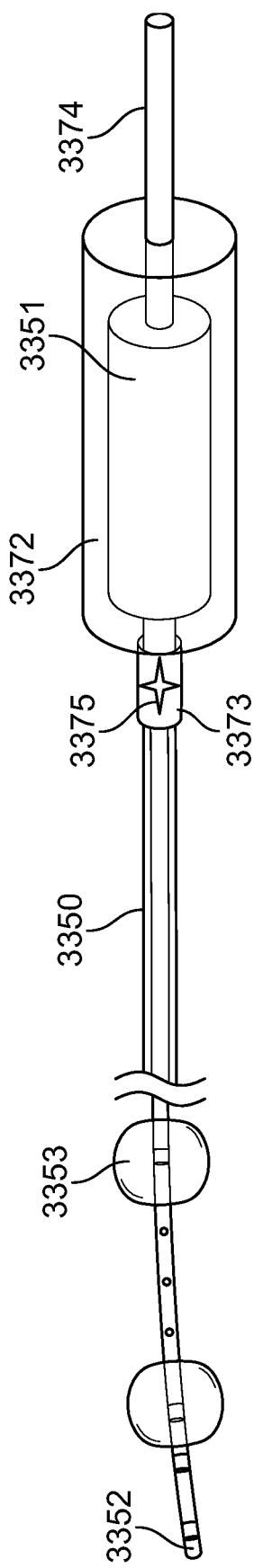
FIG. 33B illustrates one embodiment of a catheter handle used with induction heating in the vapor ablation system of the present specification.

FIG. 33B illustrates one embodiment of a catheter handle 3372 used with induction heating in the vapor ablation system of the present specification. The handle 3372 is thermally insulated and incorporates an induction coil. In one embodiment, the handle 3372 includes an insulated tip 3373 at its distal end that engages with an endoscope channel after the catheter is inserted into the endoscope. The catheter 3350 is connected to the heating chamber 3351 which in turn is connected with the pump via an insulated connector 3374. In one embodiment, the heating chamber 3351 length and diameter are less than those of the handle 3372 and the induction coil, thus the heating chamber 3351 can slide inside the handle 3372 in a coaxial fashion while maintaining a constant position within the magnetic field generated by the induction coil. The operator can manipulate the catheter 3350 by grasping on the insulated connector 3374 and moving it in and out of the handle 3372 which in turn moves the catheter tip in and out of the distal end of the endoscope. In this design, the heated portions of the catheter 3350 are within the channel of the endoscope and in the insulated handle 3372, thus not coming into contact with the operator at anytime during the operation. An optional sensor 3375 on the insulated tip 3373 can sense when the catheter is not engaged with the endoscope and temporarily disable the heating function of the catheter to prevent accidental activation and thermal injury to the operator. With respect to FIG. 33B, the catheter 3350 and heating chamber 3351 are the heated components of the system while the handle 3372, insulated tip 3373, and insulated connector 3374 are the cool components and therefore safe to touch by the user. The catheter 3350 includes at least one delivery port 3352 at its distal end for the delivery of vapor. Optionally, the catheter 3350 includes at least one positioning element 3353 proximate its distal end. In one embodiment, the at least one positioning element 3353 is an inflatable balloon.

Figure 34A:
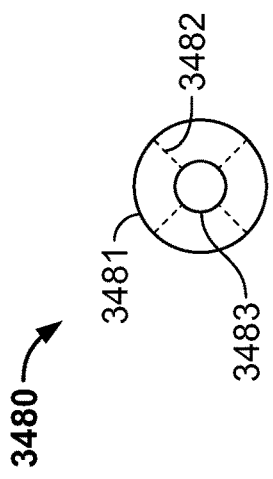
FIG. 34A is a front view cross sectional diagram illustrating one embodiment of a catheter used with induction heating in the vapor ablation system of the present specification.
Figure 34B:
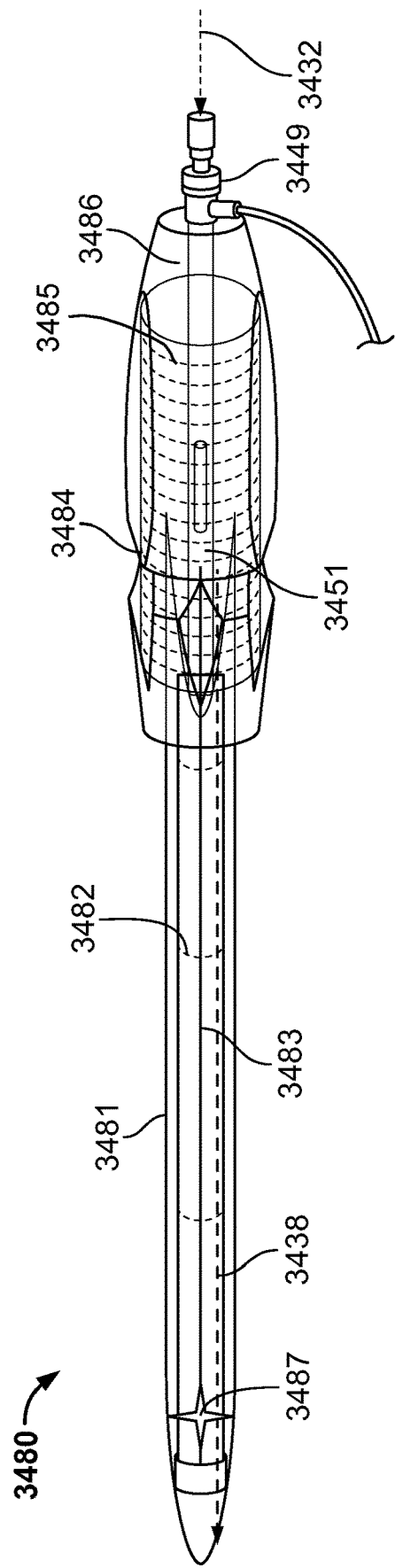
FIG. 34B is a longitudinal view cross sectional diagram illustrating one embodiment of a catheter used with induction heating in the vapor ablation system of the present specification.

FIGS. 34A and 34B are front and longitudinal view cross sectional diagrams respectively, illustrating one embodiment of a catheter 3480 used with induction heating in the vapor ablation system of the present specification. The catheter 3480 includes an insulated handle 3486 that contains a heating chamber 3451 and an induction coil 3484. The heating chamber 3451 includes a luer lock 3449 at its proximal end. The luer lock 3449 has a one-way valve that prevents the backward flow of vapor from the chamber 3451. Vaporization of fluid in the chamber results in volume expansion and an increase in pressure which pushes the vapor out of the chamber 3451 and into the catheter body. The induction coil 3484 includes a wire 3485 that extends from the proximal end of the catheter 3480 for the delivery of an alternating current. The handle 3486 is connected to the catheter 3480 with an outer insulating sheath 3481 made of a thermally insulating material.

In various embodiments, the insulating material is polyether ether ketone (PEEK), polytetrafluoroethylene (PTFE), fluorinated ethylene propylene (FEP), polyether block amide (PEBA), polyimide, ceramic, or a similar material. In various embodiments, optional sensors 3487 positioned proximate the distal end of the catheter 3480 measure one or more of temperature, pressure, or flow of vapor and transmit the information to a microprocessor, which in turn controls the flow rate of the fluid and the level of vaporizing energy provided to the chamber 3451. The microcontroller adjusts fluid flow rate and chamber temperature based on the sensed information, thereby controlling the flow of vapor and in turn, the flow of ablative energy to the target tissue.

In one embodiment, the catheter 3480 includes an inner flexible metal skeleton 3483. In various embodiments, the skeleton 3483 is composed of copper, stainless steel, or another ferric material. The skeleton 3483 is in thermal contact with the heating chamber 3451 so that the heat from the chamber 3451 is passively conducted through the metal skeleton 3483 to heat the inside of the catheter 3480, thus maintaining the steam in a vaporized state and at a relatively constant temperature. In various embodiments, the skeleton 3483 extends through a particular portion or the entire length of the catheter 3480. In one embodiment, the skeleton 3483 includes fins 3482 at regular intervals that keep the skeleton 3483 in the center of the catheter 3480 for uniform heating of the catheter lumen.

In another embodiment, as seen in FIG. 34C, the catheter includes an inner metal spiral 3488 in place of the skeleton. In yet another embodiment, as seen in FIG. 34D, the catheter includes an inner metal mesh 3489 in place of the skeleton. Referring to FIGS. 34B, 34C, and 34D simultaneously, water 3432 enters the luer lock 3449 at a predetermined rate. It is converted to vapor 3438 in the heating chamber 3451. The metal skeleton 3483, spiral 3488, and mesh 3489 all conduct heat from the heating chamber 3451 into the catheter lumen to prevent condensation of the vapor in the catheter and insure that ablating vapor will exit the catheter from one or more holes or ports at its distal end.

Figure 35:
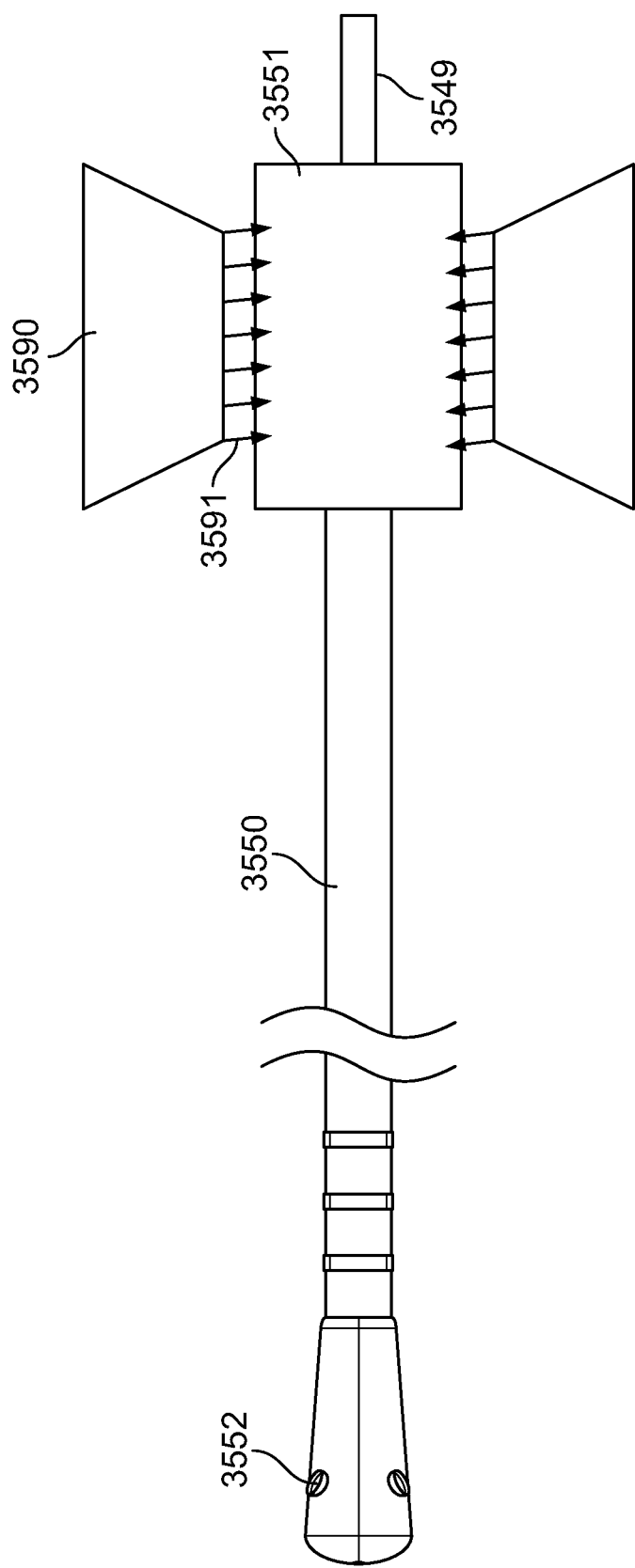
FIG. 35 illustrates one embodiment of a heating unit using microwaves to convert fluid to vapor in the vapor ablation system of the present specification.

FIG. 35 illustrates one embodiment of a heating unit 3590 using microwaves 3591 to convert fluid to vapor in the vapor ablation system of the present specification. The microwaves 3591 are directed toward the catheter fluid heating chamber 3551, heating the chamber 3551 and converting the fluid within into vapor. The vapor passes into the catheter 3550 for use in the ablation procedure. The catheter 3550 includes at least one delivery port 3552 at its distal end for the delivery of vapor. A luer fitting coupler 3549 is provided at the proximal end of the catheter fluid heating chamber 3551 for connecting a tube supplying sterile water. In one embodiment, a one-way valve (not shown) is included at the proximal end of the catheter fluid heating chamber 3551, distal to the luer fitting 3549, to prevent the passage of vapor toward the water supply.

In various embodiments, other energy sources, such as, High Intensity Focused Ultrasound (HIFU) and infrared energy, are used to heat the fluid in the catheter fluid heating chamber.

FIG. 36A illustrates a catheter assembly having an inline chamber 3610 for heat transfer in accordance with one embodiment of the present specification and FIG. 36B illustrates the catheter assembly of FIG. 36A including an optional handle 3630. Referring to FIGS. 36A and 36B simultaneously, the assembly includes a catheter 3605 having an elongate body with a lumen within, a proximal end, and a distal end. The catheter 3605 includes at least one delivery port 3606 at its distal end for the delivery of vapor. A first inline chamber 3610, having an elongate body with a lumen within, a proximal end and a distal end, is attached at its distal end to the proximal end of the catheter 3605. In various embodiments, the first inline chamber 3610 is composed of a ferromagnetic substance or a thermally conducting substance. The lumen of the catheter 3605 is in fluid communication with the lumen of the first inline chamber 3610. A second inline chamber 3620, having an elongate body with a lumen within, a proximal end and a distal end, is attached at its distal end to the proximal end of the first inline chamber 3610. The second inline chamber 3620 is filled with a fluid. The lumen of the first inline chamber 3610 is in fluid communication with the lumen of the second inline chamber 3620. In one embodiment, the connection between the first inline chamber 3610 and the second inline chamber 3620 includes an optional occlusion member 3615 to control the flow of fluid from said second inline chamber 3620 to said first inline chamber 3610. In one embodiment, the occlusion member 3615 comprises a membrane positioned between the first inline chamber 3610 and the second inline chamber 3620 which functions to prevent flow of the fluid from the second inline chamber 3620 into the first inline chamber 3610 until therapy is ready to be delivered. As pressure is applied to the fluid in the second inline chamber 3620 by action of a piston 3625, said pressure is transmitted to the membrane, resulting in rupture of the membrane. The fluid is then allowed to flow from the second inline chamber 3620 into the first inline chamber 3610.

In another embodiment, the occlusion member 3615 comprises a valve. As pressure is applied to the fluid in the second inline chamber 3620 by action of the piston 3625, said pressure is transmitted to the valve, resulting in opening of the valve. The fluid is then allowed to flow from the second inline chamber 3620 into the first inline chamber 3610. In yet another embodiment, the occlusion member 3615 comprises a heat sensitive plug. As the temperature in the first inline chamber 3610 rises above a predetermined level, the plug melts and the fluid is allowed to flow from the second inline chamber 3620 into the first inline chamber 3610. In another embodiment, the heat sensitive occlusion member 3615 is composed of a shape-memory metal which undergoes a shape change at a specific temperature to create a fluid pathway.

The catheter assembly is connected to a pump which controls the flow of fluid from said second inline chamber 3620 to said first inline chamber 3610. In one embodiment, the pump is a syringe pump that engages a piston 3625 within and proximate the proximal end of the second inline chamber 3620 which pushes the fluid from said second inline chamber 3620 into said first inline chamber 3610 at a predefined rate. In one embodiment, the pump is controlled by a microprocessor. In one embodiment, the microprocessor receives optional information from sensors in the catheter or in the tissue to control the flow of the fluid from chamber 3620 into chamber 3610. In various embodiments, the fluid is heated in chamber 3610 using any conventional methods of heating, including those discussed above. In various embodiments, the first inline chamber 3610 has more than one channel for the flow of the fluid to increase the surface area of contact of the fluid with the chamber 3610 surfaces, improving the efficiency of heating the fluid. In one embodiment, the first inline chamber 3610 is optionally covered by a material that is a poor thermal conductor, preventing the escape of heat from the chamber 3610. This embodiment is preferred if the method of heating is electromagnetic induction. In one embodiment, referring to FIG. 36B, the catheter 3605 includes an optional handle 3630 allowing for safe maneuvering of the catheter assembly. In one embodiment, the handle 3630 is composed of a material that is a poor thermal conductor to prevent thermal injury to the operator from over-heating of the catheter 3605.

It is desirable to have an integrated system as it eliminates any connections that may malfunction or leak causing system malfunction and/or injury to a patient or an operator. Additionally, it is desirable to have the fluid and heating chambers included as parts of the catheter assembly which eliminates problems encountered with corrosion of the metal in the heating chamber with multiple uses and also ensures sterility of the ablation fluid with multiple uses.

Figure 36C:
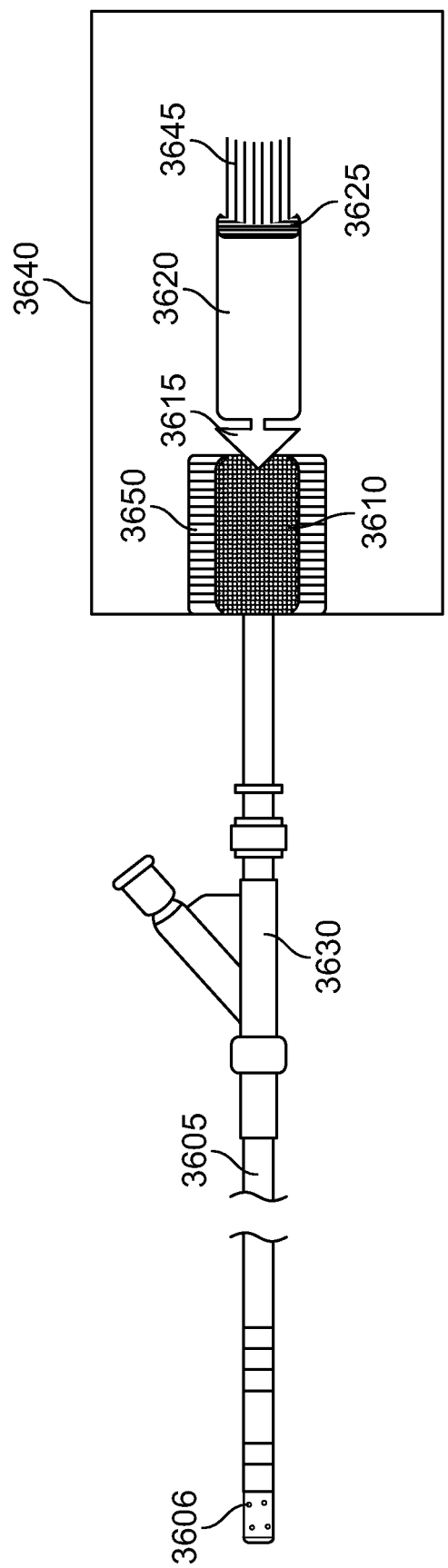
FIG. 36C illustrates the catheter assembly of FIG. 36B connected to a generator having a heating element and a pump, in accordance with one embodiment of the present specification.

FIG. 36C illustrates the catheter assembly of FIG. 36B connected to a generator 3640 having a heating element 3650 and a pump 3645, in accordance with one embodiment of the present specification. The catheter connects to the generator 3640 with the heating element 3650 and pump 3645. In various embodiments, the heating element 3650 is a resistive heater, an RF heater, a microwave heater, or an electromagnetic heater. The piston 3625 engages with the pump 3645. On initiating therapy, the pump 3645 pushes on the piston 3625 to deliver fluid from the second inline chamber 3620 into the first inline chamber 3610, opening occlusion member 3615 and delivering fluid at a predetermined rate. In one embodiment, the fluid is water. The water is heated in the first inline chamber 3610 to be converted into vapor. As the vapor expands it is pushed out through the distal end of the catheter 3605 to be delivered to the desired tissue for ablation. The catheter 3605 includes at least one delivery port 3606 at its distal end for the delivery of vapor. In the pictured embodiment, the catheter assembly includes a handle 3630 for manipulating the catheter 3605 which has been filled with heated water vapor.

Figure 36D:
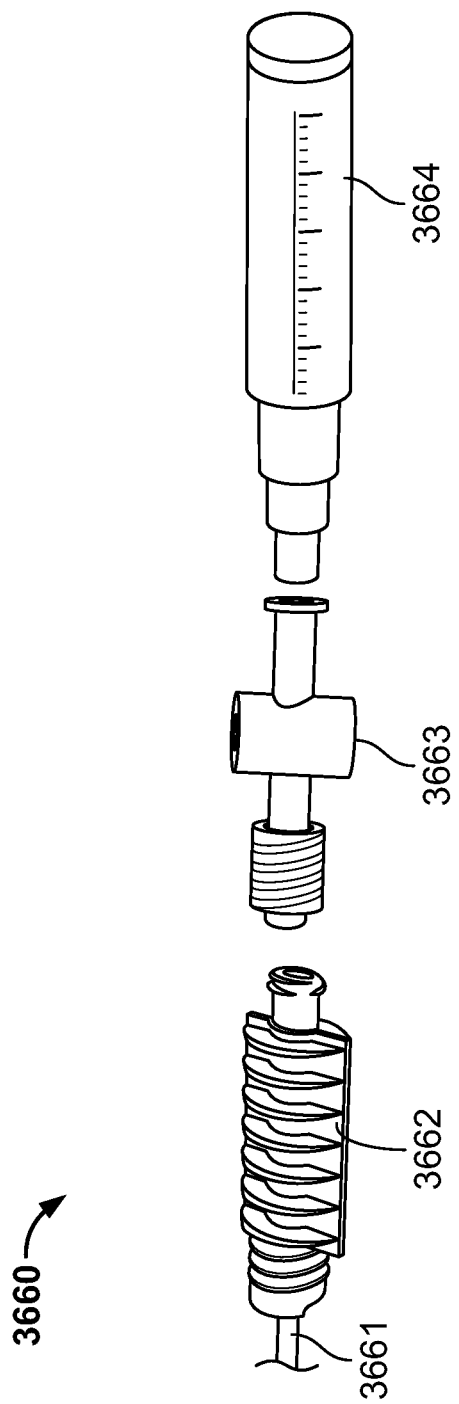
FIG. 36D illustrates a catheter assembly having an inline chamber for heat transfer in accordance with another embodiment of the present specification.

FIG. 36D illustrates a catheter assembly 3660 having an inline chamber 3662 for heat transfer in accordance with another embodiment of the present specification. The catheter assembly 3660 includes a catheter 3661 having an elongate body with a distal end, a proximal end, and a lumen within. An inline heating chamber 3662, having an elongate body, a distal end, a proximal end, and a lumen within, is attached via its distal end to the proximal end of the catheter 3661. In various embodiments, the heating chamber comprises a Curie point material, as further described below. In one embodiment, the Curie point material is in the form of a metal slug. A filter and one-way valve 3663, having a distal end and a proximal end, is attached via its distal end to the proximal end of the inline heating chamber 3662. In the pictured embodiment, the filter and one-way valve 3663 are separate from the heating chamber 3662. In another embodiment (not shown), the heating chamber is shaped into a filter media, serving a dual purpose as heating chamber and filter/valve, and a filter and one-way valve is not included. A pump 3664 is attached to the proximal end of the filter and one-way valve 3663. In one embodiment, the pump 3664 is a syringe pump. During operation, electrical energy is supplied to an induction coil wrapped about the heating chamber 3662. Magnetic fields created by the coil induce heat production within the heating chamber, as described in greater detail below, to cause water pumped into the heating chamber by the attached pump to convert into steam for ablation.

Figure 36E:
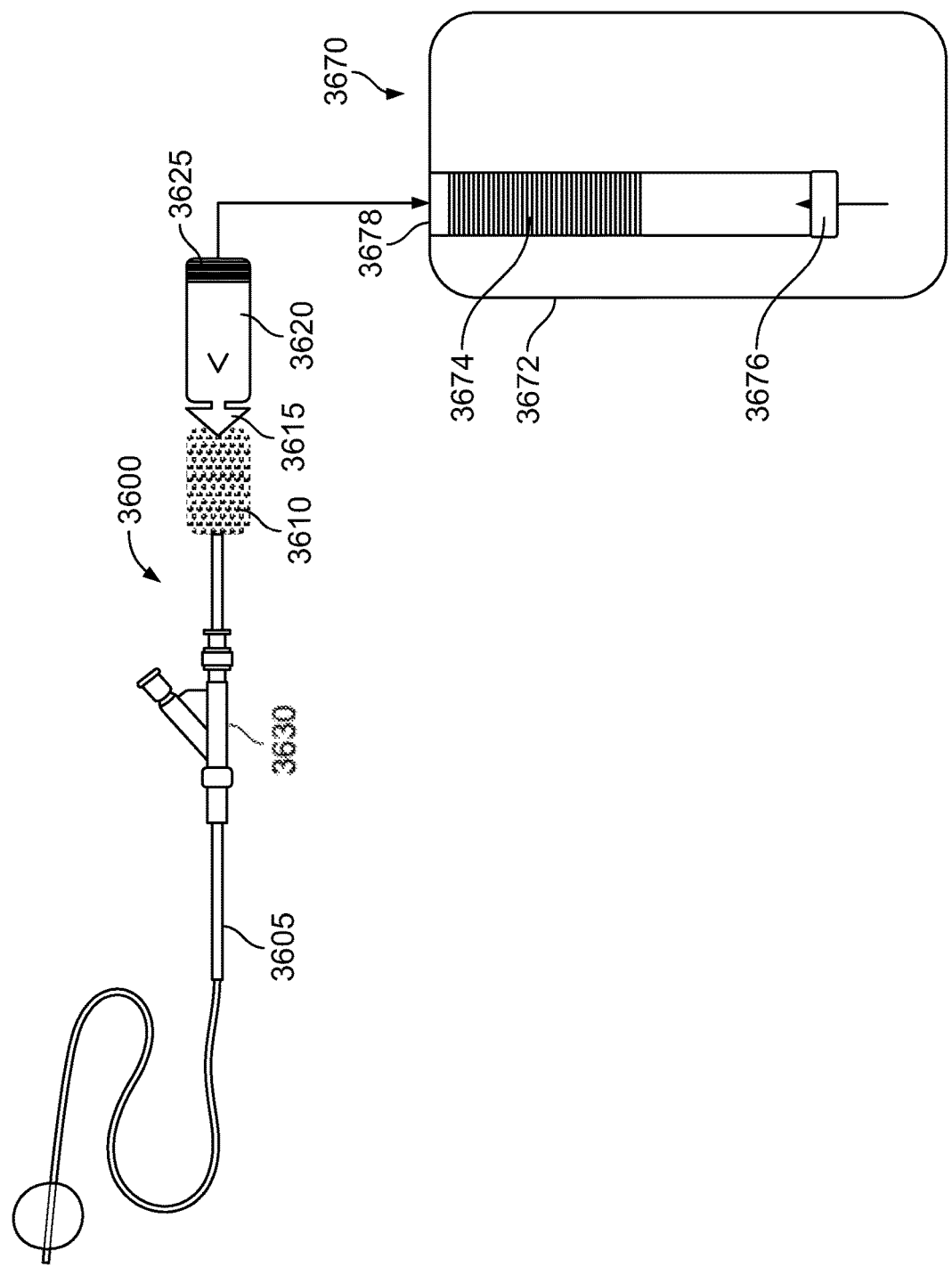
FIG. 36E illustrates a catheter assembly connected to a heating chamber in accordance with one embodiment of the present specification.

FIG. 36E illustrates a catheter assembly 3600 connected to a heating component 3670 in accordance with one embodiment of the present specification. The catheter assembly 3600 is similar to that described with reference to FIGS. 36A and 36B and includes a catheter 3605, a first inline chamber 3610 for heating water, an occlusion member 3615, a second inline chamber for storing water, a piston 3625, and a handle 3630. The heating component 3670 comprises a generator box 3672, an RF coil 3674, a pump 3676, and an opening/attachment point 3678 for the catheter assembly 3600. In one embodiment, the pump 3676 is a syringe pump.

The proximal end of the catheter assembly 3600 slides into the catheter attachment opening 3678 and the piston 3625 engages with the pump 3676 and the first inline chamber 3610 slides through the generator box 3672 and becomes centered in the coil 3674. In various embodiments, the first inline chamber 3610 comprises a ferromagnetic (FM) or curie-point metal. Upon initiation of therapy, the RF coil 3674 heats the first inline chamber 3610 while the pump 3676 pushes water or saline through the occlusion member 3615 from the second inline chamber 3620 into the first inline chamber 3610. The water is vaporized in the first inline chamber 3610 and the resultant vapor is pushed through the catheter 3605 lumen on to the tissue to be ablated. In one embodiment, the action of the pump controls the amount of vapor generated. In various embodiments, the heating component 3670 is positioned vertically, as pictured, so that any condensate flows back into the heated ferromagnetic chamber 3610.

In various embodiments, the temperature of the first inline (ferromagnetic) chamber is determined by the heat losses from the catheter body. The temperature of the ferromagnetic chamber and flow of the water are both controlled through feedback from an optional temperature sensor proximate the tip of catheter. Optional temperature sensors are deployed to measure the temperature of the ferromagnetic chamber and the temperature of the vapor exiting from the chamber. Additional optional sensors monitor the catheter body temperature and warn the operator of high catheter body temperatures. In one embodiment, the catheter includes a first sensor which communicates with a second sensor in the heating component to adjust vapor generation parameters based on the type of catheter being used. In one embodiment, the diameter of the lumen of the catheter gradually decreases toward the distal end of the catheter. In another embodiment, the inner diameter of the distal end of the catheter is different from the inner diameter of the proximal end of the catheter, resulting in a differential pressure along the length of the catheter. In another embodiment, the first inline chamber includes an outer coating which allows for the conduction of electromagnetic energy but is resistant to the transmission of heat from inside the chamber to outside the chamber or to the coil.

In various embodiments, the ablation system further includes a mechanism to prevent premature removal of the catheter to avoid operator injury from the heated ferromagnetic chamber. The safe temperature for removal of the catheter assembly from the generator box is less than 50° C. In one embodiment, the mechanism includes a shape memory metal which, when heated above 50° C., actuates a latch preventing release of the catheter assembly from the generator box. As the temperature drops below 50° C., the latch retracts and the catheter assembly can be released. In another embodiment, the mechanism is a locking mechanism controlled by the microprocessor which unlocks when a safe temperature is reached. In yet another embodiment, the mechanism is a warning light or sound controlled by the microprocessor which changes color or tone respectively, when a safe temperature is reached.

Figure 37A:
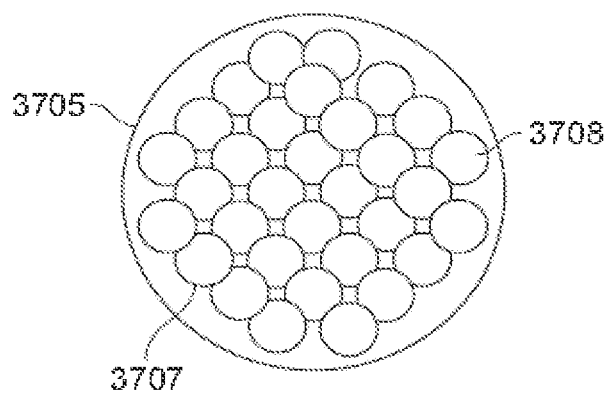
FIG. 37A illustrates a heating chamber packed with metal tubes in accordance with one embodiment of the present specification.
Figure 37B:
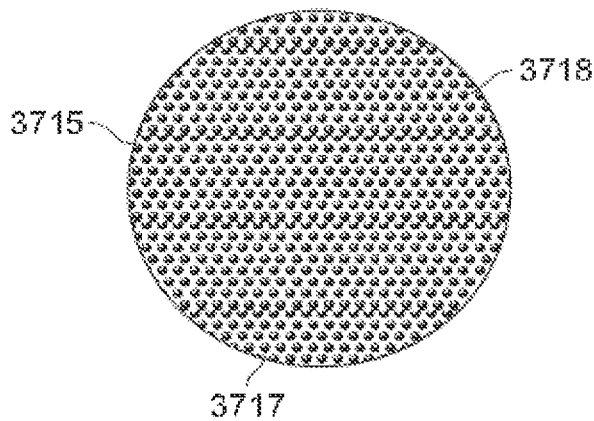
FIG. 37B illustrates a heating chamber packed with metal beads in accordance with one embodiment of the present specification.
Figure 37C:
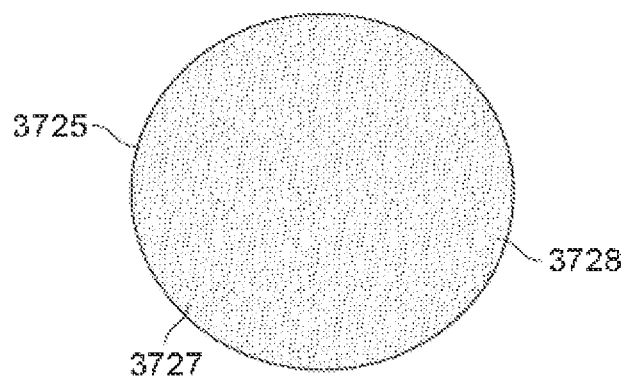
FIG. 37C illustrates a heating chamber packed with metal filings in accordance with one embodiment of the present specification.

In various embodiments, the catheter of the catheter assemblies of the vapor ablations systems of the present specification has two layers. The catheter includes an elongate body with a lumen within, a proximal end, and a distal end. The proximal end is in fluid communication with the vapor generating components of the system and the distal end includes one or more openings for the delivery of vapor. The catheter includes an inner layer and an outer layer. In one embodiment, the inner layer is a thermally conducting layer and the outer layer is a thermally insulating layer. The thermally conducting inner layer is in thermal contact with the heating mechanism of the vapor generation system to heat the lumen of the catheter to prevent premature condensation. In various embodiments, the inner layer is movable independently from and relative to the outer layer. In one embodiment, the inner layer is made of copper. In one embodiment, the outer layer is made of PEEK. Optionally, in various embodiments, a third layer is formed between the inner and outer layers. The third layer is an insulating layer and, in various embodiments, comprises a layer of air or a vacuum. In one embodiment, the catheter has a length of approximately 230 cm. In one embodiment, the inner layer has an inner diameter of approximately 1.0 mm and an outer diameter of approximately 1.4 mm and the outer layer has an inner diameter of approximately 1.5 mm and an outer diameter of approximately 2.5 mm. In one embodiment, both the inner and outer layers are comprised of PEEK. In one embodiment, the catheter further includes a covering sheath over its proximal end. In one embodiment, the sheath has a length of approximately 50 cm, an inner diameter of approximately 2.6 mm, and an outer diameter of approximately 3.5 mm. In various embodiments, the sheath is comprised of plastic, acetal polyoxymethylene (POM), or PEEK. As stated above, it is desirable to have a large surface area within the heating chamber for contact heating of the ablative agent. This is accomplished by having multiple small channels within the heating chamber. In various embodiments, the channels are created by packing the chamber with metal tubes, metal beads, or metal filings, all of which significantly increase the surface area for contact heating. FIG. 37A illustrates a heating chamber 3705 packed with metal tubes 3707 in accordance with one embodiment of the present specification. FIG. 37B illustrates a heating chamber 3715 packed with metal beads 3717 in accordance with one embodiment of the present specification. FIG. 37C illustrates a heating chamber 3725 packed with metal filings 3727 in accordance with one embodiment of the present specification. In various embodiments, the heating chamber 3705, 3715, 3725 and its channels 3707, 3717, 3727 are made of a ferromagnetic material or a thermally conducting material and the ablative agent 3708, 3718, 3728 flows through these channels 3707, 3717, 3727 where it is heated rapidly and in an efficient manner.

In one embodiment, the heat chamber and its channels are made of a material having a specific Curie point or Curie temperature ($T_c$). These materials cease to be ferromagnetic when heated above their $T_c$. If such a material is inside an electromagnet that is driven with alternating current, while the material is ferromagnetic below the Curie temperature $T_c$, the magnetization of the material due to an externally applied magnetic field causes the material to exhibit the typical ferromagnetic hysteresis known in the art as the current in a field coil alternates through its cycles. As the applied magnetic field changes, the magnetic domains inside the ferromagnetic material change direction to align themselves with the applied field. The changing (flips) of these domains requires energy that is extracted from the applied field and is converted to heat during the flipping of the domains. The heat generation inside the ferromagnetic material increases with the area swept by the magnetic hysteresis (materials with a larger area swept by the magnetic hysteresis are considered magnetically softer) and by the rate of flips, which increases with the frequency of the applied alternating current. For example, if the ferromagnetic material is subjected to a magnetic field of several kHz, the ferromagnetic material exhibits large magnetic hysteresis losses while it is ferromagnetic below $T_c$, which results in Joule heating. At $T_c$, the material abruptly loses its soft magnetic property, its magnetic hysteresis vanishes and the Joule heating is reduced by several orders of magnitude. As a result, the material absorbs less energy form the applied magnetic field and less Joule heating is generated in the material. If the heat dissipation is larger than the heat generation, then the material cools below $T_c$, the hysteresis re-appears and its losses increase again, heating resumes and the cycle is repeated.

This physical phenomenon is used to develop a heating device with an intrinsic and volumetrically distributed "thermostat". In essence, such an element absorbs the energy from the electromagnetic field precisely as needed and where needed to maintain its temperature at $T_c$ but will not heat substantially above it, making it inherently failsafe from overheating. Moreover, areas of the device that are cooled due to heat transfer to any surrounding media, such as water or steam, immediately reheat while areas where heat has not been transferred to the media cease heating.

$T_c$ can easily be adjusted by selecting the ratios of low-cost base metals in the material alloy. Industry standard soft magnetic nickel-iron alloys containing from about 28% to 70% nickel (Ni), with the balance substantially iron, have Curie temperatures ranging from room temperature to 600° C. For target temperatures of 100° C.-120° C., the class of low-nickel alloys containing 30% Ni are most suitable. For higher temperatures, higher Ni concentrations are desirable. Small additions of copper (Cu), silicon (Si), manganese (Mn), or chromium (Cr) allow for alloying of very precise Curie temperatures. For example, several low Curie temperature iron-chromium-nickel-manganese (Fe—Cr—Ni—Mn) alloys are listed in Table 3 below.

TABLE 3

| Chemical Composition [wt. %] | $T_c$ [° C.] |
|---|---|
| Cr4Ni32Fe62Mn1.5Si0.5 | 55 |
| Cr4Ni33Fe62.5Si0.5 | 120 |
| Cr10Ni33Fe53.5Mn3Si0.5 | 10 |
| Cr11Ni35Fe53.5Si0.5 | 66 |
| Ni37Fe62Traces1 | 250 |
| Ni77Fe14Cu5Mo4 | 400 |

Referring to Table 3, an alloy having a composition of Cr4Ni32Fe62Mn1.5Si0.5 has a Curie temperature of 55° C., an alloy with a composition of Cr4Ni33Fe62.5Si0.5 has a Curie temperature of 120° C., an alloy with a composition of Cr10Ni33Fe53.5Mn3Si0.5 has a Curie temperature of 10° C., and an alloy with a composition of Cr11Ni35Fe53.5Si0.5 has a Curie temperature of 66° C.

In various embodiments, other Curie materials with higher Curie temperatures may also be used. For example, referring to Table 3, Permenorm® 3601K5, having a composition of 37% Ni, 62% Fe, and 1% traces and a Curie temperature of 250° C., is used in one embodiment. In another embodiment, MuMetal®, having a composition of 77% Ni, 14% Fe, 5% Cu, and 4% Mo and a Curie temperature of 400° C., is used as a Curie material.

Figure 37D:
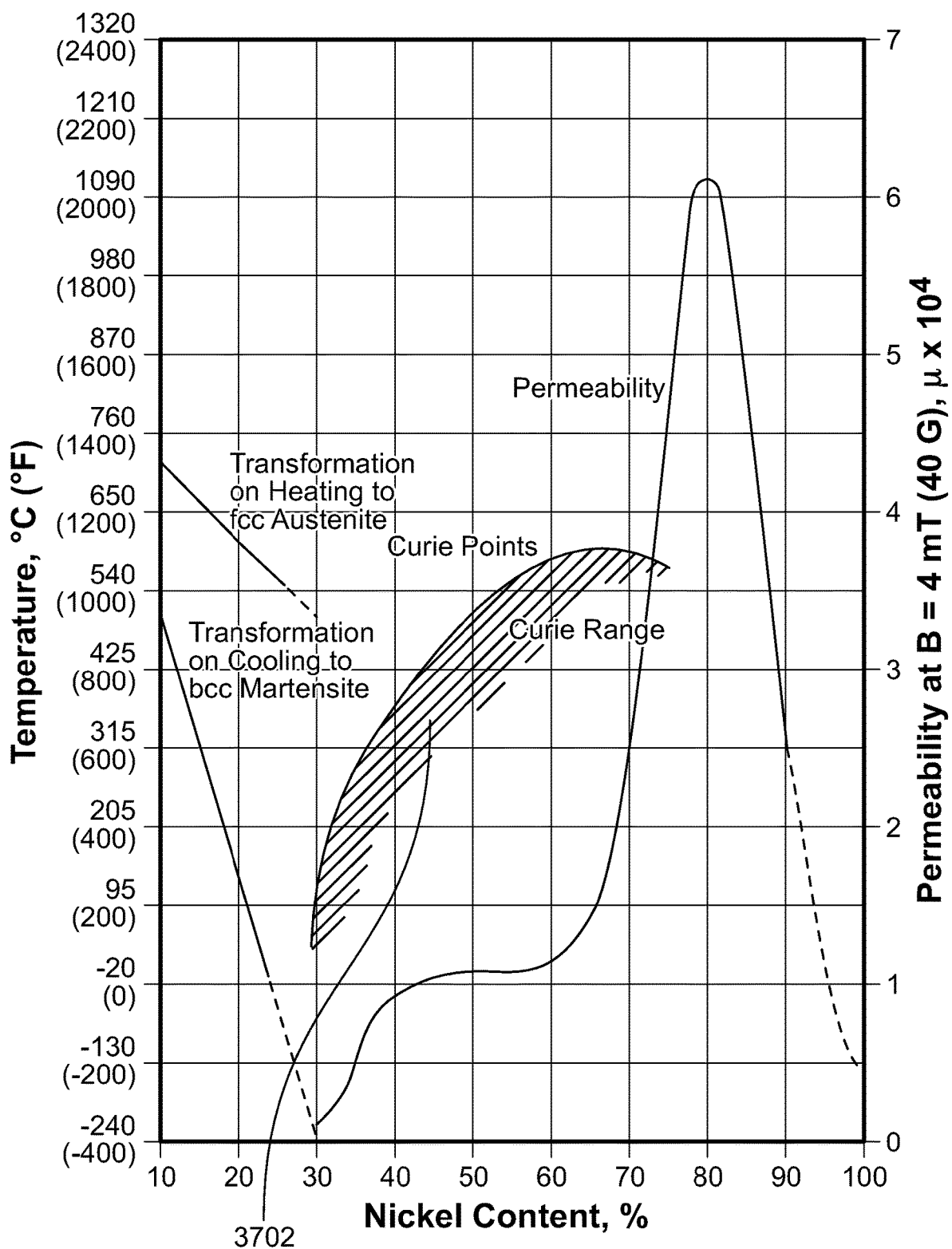
FIG. 37D is a graph illustrating Curie temperature ($T_c$) as a function of nickel content as described in *Special-Purpose Nickel Alloys, ASM Specialty Handbook: Nickel, Cobalt, and Their Alloys*, Dietrich, et al., ASM International, 2000, p 92-105, Fig 4.

FIG. 37D is a graph illustrating Curie temperature ($T_c$) as a function of nickel content as described in *Special-Purpose Nickel Alloys, ASM Specialty Handbook: Nickel, Cobalt, and Their Alloys*, Dietrich, et al., ASM International, 2000, p 92-105, Fig 4. As can be seen in the graph, the Curie temperature range 3702 of a material can be adjusted between room temperature and 600° C. by varying the nickel content of the material to between approximately 30 to 75% nickel.

Incorporating a heating chamber comprised of a Curie point material, as described above, provides a vapor ablation system that utilizes the full extent of steam as an ablative agent in a safe and responsive fashion. The system is safe because the steam cannot be heated to a temperature higher than the Curie temperature of the material being used, therefore minimizing the risk of burns to the user. For example, in one embodiment, an ablation system includes a heating chamber comprised of a Curie point material with a Curie temperature of 130 degrees Celsius. The Curie point material is a ferromagnetic material from room temperature up to the Curie temperature of 130 degrees Celsius. Once this material is heated to its Curie point (130° C.), it ceases to be ferromagnetic and heating due to magnetic hysteresis loss ceases. The heating chamber is placed in an induction coil and the induction coil is energized with high frequency electrical energy. In various embodiments, the energy is either AC power or RF energy. In one embodiment, the energy is equal to 20 kHz. The high frequency energy causes the Curie point material to flip its magnetic domains very quickly to align with the externally applied field. As the current applied to the induction coil is increased during one cycle of the alternating current, the magnetic field increases and the magnetization of the Curie material increases. As the magnetic field is increased, magnetization approaches and reaches saturation where the magnetization does not increase even though the applied magnetic field may increase. The current is then slowly reduced from the maximum applied current to zero. As the current is reduced, the magnetic field decreases and the Curie material undergoes the magnetic hysteresis known in the art, meaning as the current is reduced to zero, there remains magnetization in the material even though the magnetic field has vanished. The current then reverses polarity and the generated field reverses polarity as well. The applied field now reduces the remnant magnetization of the Curie material, reduces it to zero and then increases magnetization in the opposite direction. This current is continuously applied and increased to achieve negative magnetization saturation. The current is then reduced again to zero, during which the material undergoes the negative branch of the hysteresis loop. The above process is repeated very quickly, such as, in one embodiment, 20,000 times per second. During this process, the applied magnetic field causes the magnetic domains on the atomic scale to flip, generating heat in the material. This heat is considered electrical loss in the material and is used to heat the water coming in contact with the Curie point material in the ablation system and convert the water to steam. Any concurrent eddy current losses are small in comparison. The process continues to occur as long as the material is below the Curie point and thus ferromagnetic. Once the temperature of the material is increased above the Curie point, hysteresis collapses, the material ceases to be ferromagnetic and Joule heating due to ferromagnetism ceases. The material cools below the Curie point and then can be heated again by the above process but will never increase substantially above the Curie temperature.

Water is passed through the heating chamber having a Curie point material with a Curie temperature of 130° C. As the material temperature rises to 100° C., the water is converted to vapor by the heat generated by the process described above. Water enters one side of the flow-through heating chamber, turns to steam, and exits the other side of the heating chamber as vapor. In various embodiments, the temperature of the water as it enters the chamber is slightly lower than its boiling point, for example, 90-95° C. In one embodiment, the temperature of the water as it enters the chamber is room temperature. The benefit provided by the Curie point material is that the material will not heat substantially above its Curie point temperature, regardless of how much power is applied to the induction coil. Therefore, in the described embodiment, the steam is only heated to 130° C. and can never be substantially higher than this temperature. Using a Curie point material confers a built-in safety mechanism so the user and/or patient will not be burned by excessively heated vapor. The Curie point material acts as if it includes built-in and volumetrically distributed heat sensors, providing a closed feedback loop and preventing the material from rising above a specific temperature. A non-Curie point material will heat to a higher temperature and therefore the converted steam will also have a higher temperature, creating a significant burn risk for the user and patient. Another benefit provided by using a Curie point material is that it creates a steam ablation system that is consistently responsive. The intrinsic thermostatic properties of the Curie point materials produce a heating gradient. In the example above, the user can be confident that the system will always produce vapor that will be between 100 and 130° C. The use of a non-Curie material for the heating chamber results in a system in which the temperature of the generated steam is not easily controlled. A heating chamber comprised of a non-Curie point material would require temperature sensors so the user would know when to cease application of current. A non-Curie point material would eventually melt if the current were to be continuously applied and the material's Curie point is above its melting point. In some embodiments, the Curie point temperature could be as high as 300° C. based on the desired application or construction of the heating chamber or the amount of vapor needed for the desired therapeutic effect.

Use of a Curie point material in the heating chamber also provides a vapor ablation system that is inherently energy saving and cannot be exhausted. In other words, continued use of such a heating chamber will not cause the material to lose its Curie point properties. Once the Curie point material reaches its Curie temperature, it ceases to absorb the electrical energy supplied. The material absorbs only as much energy as it needs to reach the Curie temperature, therefore there is no excess draw of power. The system is scalable in terms of quantity of Curie point material. In various embodiments, the amount of Curie material used to generate steam varies from millimeters in size to tons of material.

Another benefit provided by the Curie point material heating chamber is that the impedance of the induction coil will change with the heat load. This is due to the fact that the Curie point material acts as the core material of an inductor coil whose magnetic properties determine the inductance and thus the impedance of the coil. This will be used as a sensing mechanism to precisely control the power delivered to the coil and thus to the heating chamber. The presence or absence of water at the heating chamber can instantaneously be determined and used for precise purging of entrapped air.

The use of steam as an ablative agent provides further benefits. Steam does not leave any harmful residues in the tissue, it simply returns to water. In addition, the steam does not create excessive gas volumes but is rather reduced in volume 600 times through condensation. Steam as an ablative agent also delivers its energy to a highly predictable depth without harming healthy tissue beneath.

Referring again to FIG. 37B, in one embodiment, a heating chamber 3715 is packed with metal beads, or ball bearing balls 3717, comprised of a Curie point material. The heating chamber 3715 is packed tightly with the ball bearing balls 3717. An ablative agent 3718, for example in the form of water, is passed through the heating chamber 3715 and over the ball bearings 3717. The tight packing of the ball bearings 3717 within the chamber 3715 provides a very large overall surface area for contact of the Curie point material with the ablative agent 3718. Through the induction process described above, the ball bearings 3717 generate heat and convert the water into steam. In one embodiment, the heating chamber is heated uniformly. In one embodiment, the heating chamber comprises a cylindrical tube with a proximal end and a distal end. The tube is filled with the Curie-point material ball bearing balls. The tube experiences less heat loss at its distal end as the ablative agent exits the heating chamber as vapor. In one embodiment, optional temperature sensors are added along the heating chamber to provide temperature feedback and fine-tuning of the application of current to the heating chamber based on said feedback.

In various embodiments, the system includes a microcontroller or computer and the electrical current supplied to the induction coil and thus to the Curie point material filled heating chamber is controlled by said computer or microcontroller. In various embodiments, the computer or microcontroller is pre-programmed to control the system to generate a specific amount of steam at a pre-determined temperature. In other embodiments, the current is not controlled by a computer or microcontroller and no programming is provided. In one embodiment, the system further includes at least one temperature sensor as described above. In one embodiment, the system further includes at least one pressure sensor. Feedback from said temperature and/or pressure sensors is used by the microcontroller or computer to regulate steam dosing and delivery. In one embodiment, the system further includes a user interface for input of vapor delivery parameters and monitoring of system status in real-time. In one embodiment, all components of the system are thermally insulated such that surface temperatures do not exceed more than 5° C. above ambient temperature. In another embodiment, the temperature of any external surface that has the potential for human contact is maintained below 60° C. Vapor is delivered rapidly and on-demand.

The vapor ablation systems of the present specification having Curie point materials to heat an ablative agent operate via a set of technical parameters in order to provide the physician with a specific set of end user parameters. In other words, for example, one embodiment of a vapor ablation system includes a catheter having a heating chamber wherein the heating chamber is filled with Curie point material ball bearing balls and the catheter and heating chambers each have specific lengths. The Curie temperature of the ball bearing balls is 130° C. and water is introduced into the system at a temperature of 95° C. An induction coil around the heating chamber is supplied with 20 kHz of electrical energy. The lengths of the catheter and heating chamber, the Curie temperature of the material, starting temperature of the water, and amount of energy supplied to the induction coil are all technical parameters of the system. When in operation, the system generates steam having a specific temperature, for example between 100 and 130° C., at a specific rate. The temperature of the steam and rate of its delivery are end user parameters dictated by the technical parameters. One of ordinary skill in the art would realize that many technical parameters and user parameters, and combinations thereof, are possible for such a system and the examples given above are not intended to be limiting.

In various embodiments, materials having different Curie temperatures can be created by modifying the elemental composition of said materials, as shown in Table 3 above. In some embodiments, vapor ablation systems of the present specification include Curie point materials having a Curie temperature ranging from 60 to 500° C., more preferably 100 to 400° C., even more preferably 150 to 300° C., and most preferably 250 to 280° C. The Curie temperature of the material should be low enough to minimize the risk of burns from exposure to the heated steam while also high enough to account for heat loss in the catheter of the ablation system to overcome condensation inside the catheter. Ideally, steam exiting the distal, or operational, end of the catheter should have a temperature between 98 and 120° C. at pressures between 1 and 2 atm. In various embodiments, the pressure of operation is less than 1 atm. In other embodiments, the pressure of operation is greater than 2 atm but less than 10 atm. As is known in the art, the boiling point of water varies depending on elevation and atmospheric pressure and such differences can be accounted for by changing the technical parameters of the system. Therefore, in various embodiments, the length of the catheter is considered when determining the Curie temperature of the material to be used. In various embodiments, catheters having a length of less than 6 feet are used with the ablation system. In other embodiments, catheters having a length of 6 feet and greater are used. A longer catheter will require a heating chamber having a higher Curie temperature to account for heat loss experienced by the steam as it travels distally through the catheter. Since the Curie temperature of a Curie point material is fixed and cannot be changed, each material will have a maximum possible temperature corresponding to its Curie temperature. As such, the steam generated can never have a higher temperature than the Curie temperature of the material used for heating. However, a Curie point material can have a temperature that is lower than its Curie temperature and this is controlled by the amount of electrical energy supplied to the induction coil. By adjusting the amount of energy supplied to the induction coil, a user can control the temperature of the ablative agent exiting the catheter, preferably within a range between 100° C. and the Curie temperature of the material to ensure steam generation. Therefore, in one embodiment, a vapor ablation system includes a Curie point material having a high enough Curie temperature to ensure delivery of steam from the distal end of any length of catheter common in the art. Since the temperature of the material can be reduced to anything lower than the Curie temperature of the material, the physician can use the same heating chamber to deliver steam through catheters of considerably shorter length or lower temperature.

In some embodiments, the heating chamber containing the Curie point material is a single use, disposable component of the system. The Curie point material comes into contact with water during a procedure, becoming non-sterile and precluding its use in subsequent procedures. Additionally, exposure of the metal to the fluid or its content could produce chemical byproducts with repeat use which could be harmful to a patient and may preclude repeat use of the heating element for medical applications. In another embodiment, the Curie point material is contained within a clam-shell shaped heating chamber similar to that described in FIGS. 31A and 31B. In this embodiment, the Curie point material does not come into physical contact with the water but instead transfers its generated heat to the water through the walls of the clam-shaped heating chamber. In one embodiment, the Curie point material filled, clam-shaped heating chamber is reusable. In one embodiment, the Curie point material filled, clam-shaped heating chamber is comprised of PEEK, a plastic of high impact strength, so that it will withstand a drop onto a concrete floor. In one embodiment, the outer surface of the clam-shell shaped heating chamber is insulated. In various embodiments, the Curie point materials used in the vapor ablation systems of the present specification include a nickel/iron alloy comprising at least 25% nickel.

The use of the vapor ablation systems of the current specification which include a Curie point material heating chamber provides sterile low-cost, disposable catheters to avoid the risk of infection in a medical operating environment. This necessitates that costly parts, such as the induction heater, must be reusable and ideally not be in contact with the sterile inside of the catheter. With conventional conduction heaters, this requirement would make it difficult to facilitate optimal heat transfer to the water for evaporation through the channel walls. However, placing a low-cost heating element inside the water channel in direct contact with the flowing water provides efficiency in vaporizing water through heat conduction.

Figure 37E:
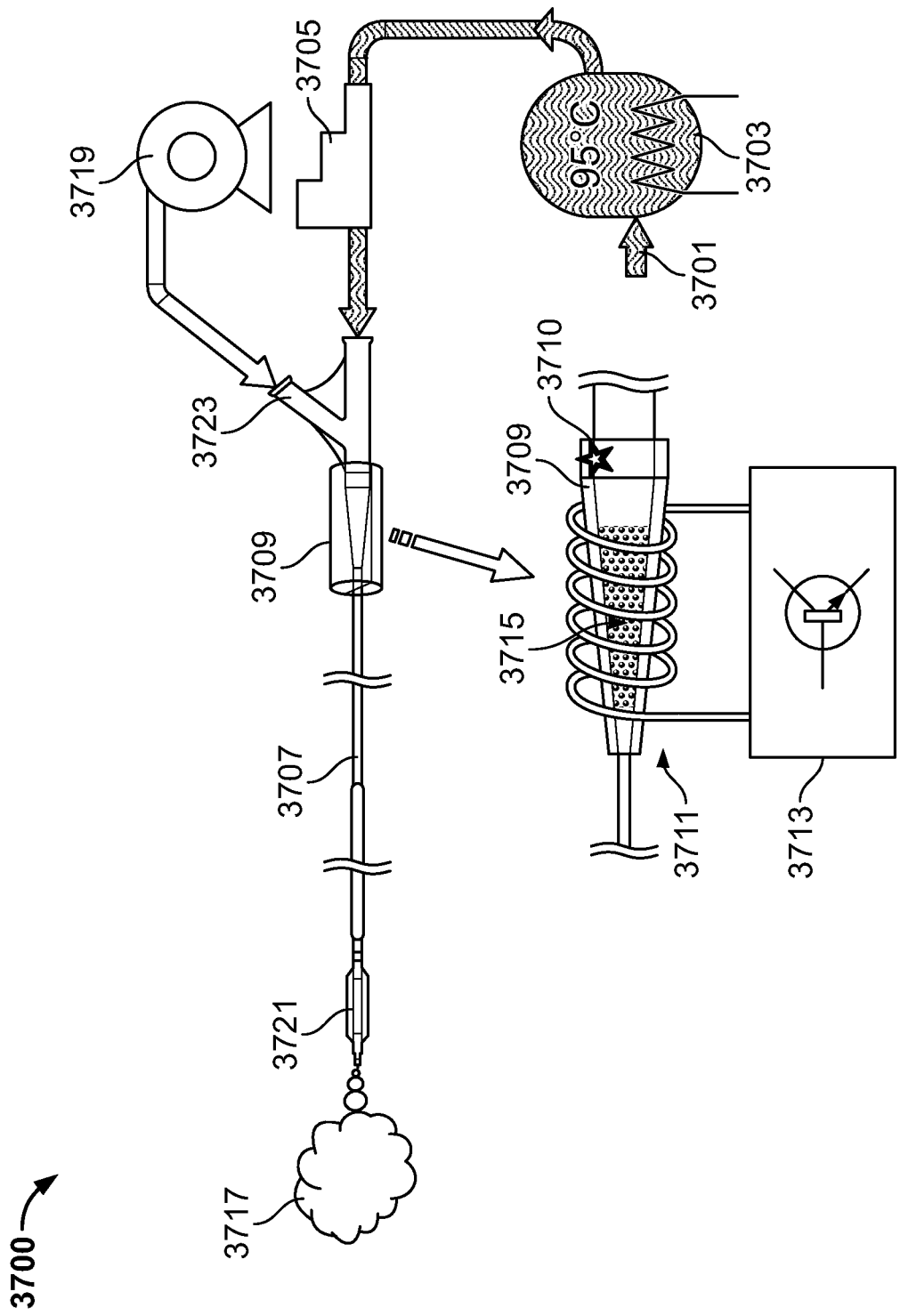
FIG. 37E is an illustration of one embodiment of a vapor ablation system with a Curie point induction heating chamber.

FIG. 37E is an illustration of one embodiment of a vapor ablation system 3700 with a Curie point material induction heating chamber 3709. Fluid 3701 from a sterile IV bag is pumped into an intermediary storage vessel 3703 where the solution is pre-heated to approximately 95° C. Pre-heating the water reduces the energy demand for steam generation to essentially the latent heat of water vaporization. A precisely controllable dosing pump 3705, of a positive displacement type in one embodiment, delivers exact amounts of water on demand into the catheter 3707 channel. With a low dead volume on the discharge side of the dosing pump 3705, the water immediately enters the heating chamber 3709, which has been energized shortly before. An induction coil 3711, connected to a flash heater with control electronics 3713, is wrapped about the heating chamber 3709 and provides energy to the heating chamber 3709. In one embodiment, the heating chamber 3709 is tightly packed with Curie point material ball bearing balls having a Curie temperature of 150° C. Fine pores 3715 are present about the ball bearings. The water is forced through the fine pores 3715 of the heating chamber 3709, assuring that all water contacts the metal surface and exits entirely as steam 3717. The described system is not susceptible to air bubbles or vapor lock. The heating chamber 3709 also acts as a filter and, in one embodiment, includes at least one pressure sensor 3710 to monitor the supply pressure to the catheter (back-pressure of the system during flow), providing crucial information regarding proper system operation. Too low pressure indicates a leak while excessive pressure signals an obstruction in the catheter.

In one embodiment, a sudden rise or decrease in pressure will cause an attached microcontroller to initiate a failsafe shutdown. Therefore, in various embodiments, the heating chamber 3709 serves a triple purpose as filter, heater, and high-surface area heat exchanger.

Optionally, in one embodiment, the system 3700 includes an air pump 3719 to inflate and deflate at least one optional positioning balloon 3721 at the distal tip of the catheter 3707. The pump 3719 will inflate the balloon to a preset pressure to create a vapor seal inside a body cavity and functions similarly to the positioning attachment 22 depicted in FIG. 2D. A microprocessor will then calculate the dimensions (diameter or volume) of the organ to be ablated. The air pump 3719 supplies pressure to the balloon 3721 through a separate air port 3723.

In various embodiments, the system includes resistors and/or valves along the path of the vapor to further increase the pressure, in turn increasing the temperature of the vapor according to Gay-Lussac's law. Raising the pressure of the vapor to 20 PSIG increases the boiling point of the water to approximately 125° C.

Figure 37F:
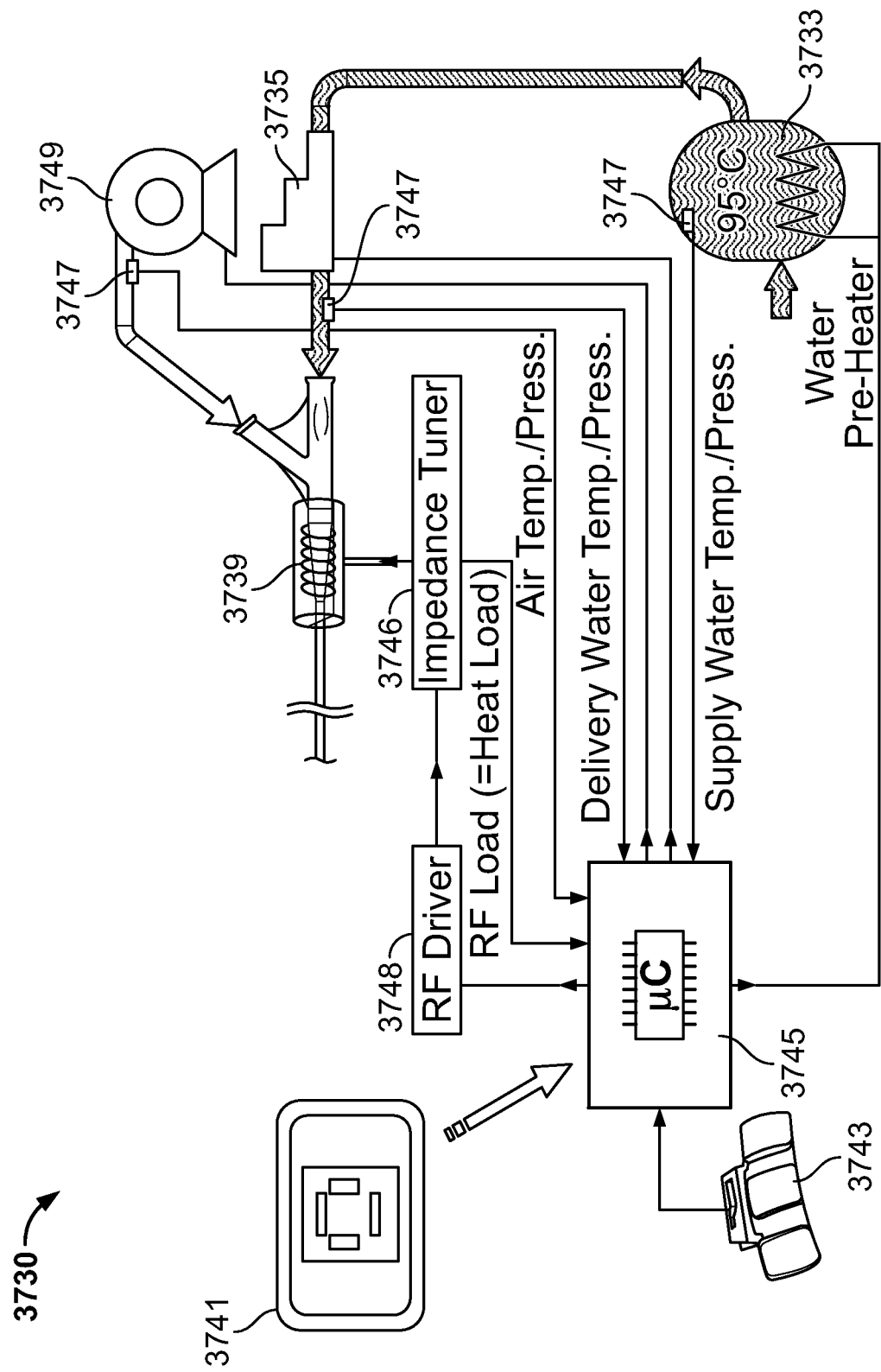
FIG. 37F is an illustration of another embodiment of a vapor ablation system with a Curie point material induction heating chamber including a user interface.

FIG. 37F is an illustration of another embodiment of a vapor ablation system 3730 with a Curie point material induction heating chamber 3739 including a user interface 3741. The physician interfaces with a console through a touch screen user interface 3741 to set treatment parameters. During operation, the physician may also use optional multi-function foot switches 3743 for hands-free control. A microcontroller 3745 processes sensor inputs in real-time and tightly controls the water pump 3735, optional air pump 3749, and heating chamber 3739 through closed feedback loops. At all times, a fault detection routine monitors proper system operation and immediately shuts the system down if triggered by parameters being detected to be outside the safe operating range. Warnings, such as low water supply, abnormal temperatures and pressures, and system default, will be issued audio-visually according to selectable criteria pre-set by the physician. The alarms are issued when information from any of the sensors falls outside of a predetermined value range. All sensor and control parameters will be logged with time stamps for later review of the procedure.

The amount of control of the Curie point material induction heating chamber 3739 will be increased by monitoring the coil impedance "seen" by an impedance tuner circuit 3746 which changes with changing heat load. While the impedance tuner 3746 will continuously attempt to match the output impedance of an RF driver 3748 stage to the input impedance of the induction coil, the degree of mismatch is a direct measure of the electrical load inside the coil. This electrical load in turn is a direct measure of the heat load. The impedance tuner 3746 communicates this mismatch to the microcontroller 3745 as input for process control. Together with the Curie point "thermostat" of the heating chamber 3739, this monitoring will provide increased control and responsiveness of the steam generation.

Optionally, in various embodiments, temperature and pressure sensors 3747 are installed in discharge lines of the air and water pumps. Together with pump drive parameters (particularly with positive displacement pumps), the mass flow of water and air can be determined. A positive displacement pump includes a reliable correlation between pump shaft revolutions and the pumped volume of fluid (gas or liquid). By measuring the pressure and temperature, the mass flow can be derived accurately. Controlling the mass flow of a fluid, either liquid or gas, yields a more meaningful parameter for process control because volume is temperature dependent and must be temperature-compensated. Deriving the mass flow mathematically from existing sensors 3747 eliminates the need for costly mass flow sensors.

In one embodiment, the water pre-heater 3733 includes a conventional resistance heater element and uses a proportional-integral-derivative controller (PID controller) for rapid heat-up without significant temperature overshoot. In one embodiment, the water pre-heater 3733 pre-heats the water to approximately 95° C., similarly to the system described above with reference to FIG. 37F. In another embodiment, the system does not include a water pre-heater and water is injected into the induction heating chamber 3739 at room temperature.

In one embodiment, the amount of steam generated by the vapor ablation systems having Curie point material heating chambers is selectable within a range of 15 to 150 ml/sec. In one embodiment, the touchscreen user interface allows intuitive, quick adjustment of parameters including power, steam flow, and pressure. In one embodiment, a syringe pump is used to control the fluid flow to the heating element. In one embodiment, the volume of the syringe pump is at least 60 ml. In one embodiment, the system includes a self-test feature to ensure proper function. In one embodiment, the system uses a maximum of 700 to 1000 Watts of power and requires only a standard 120 VAC/15 A outlet. In one embodiment, the system is double-insulated, includes a grounding pad and uses a separation transformer to electrically isolate the entire system from line voltage.

The above features of the vapor ablation systems allow a user to precisely maintain steam temperature and meter selected steam volume at a constant flow rate. The systems provide rapid start and stop of steam delivery and immediate shutdown after fault detection. In one embodiment, the system includes an inherent failsafe with interlock feature.

Figure 37G:
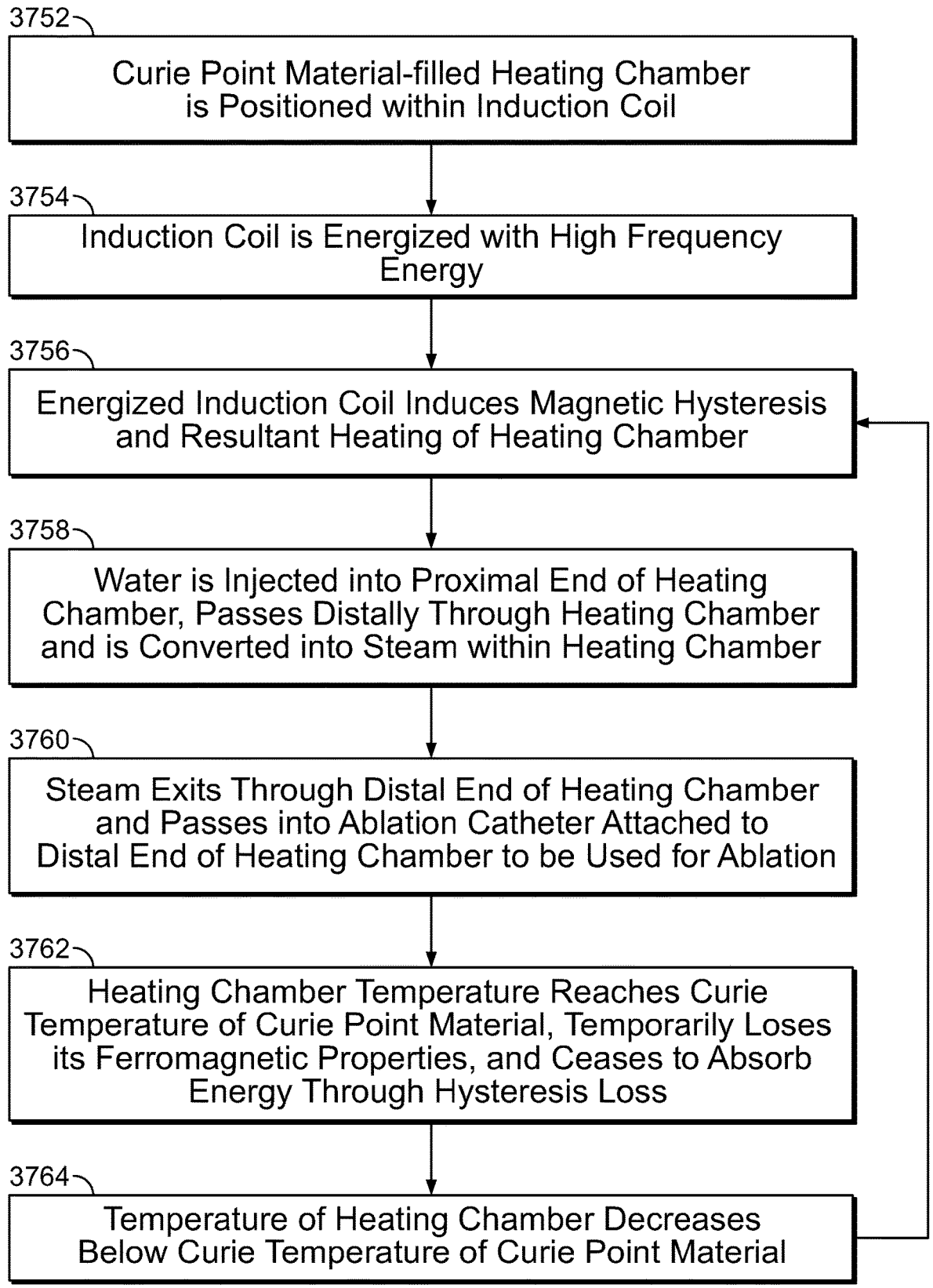
FIG. 37G is a flowchart illustrating the steps involved in one embodiment of a method of generating steam using a vapor ablation system having a Curie point material heating chamber.

FIG. 37G is a flowchart illustrating the steps involved in one embodiment of a method of generating steam using a vapor ablation system having a Curie point material heating chamber. At step 3752, a Curie point material-filled heating chamber is positioned within an induction coil. The induction coil is energized with high frequency energy at step 3754. The energized induction coil induces magnetic hysteresis and resultant heat generation within the heating chamber at step 3756. Then, at step 3758, water is injected into a proximal end of the heating chamber. The water passes distally through the heating chamber and is converted into steam via heat transfer within the heating chamber. The steam exits through a distal end of the heating chamber and passes into an ablation catheter attached to said distal end of the heating chamber to be used for ablation at step 3760. At step 3762, the temperature of the heating chamber reaches the Curie temperature of the Curie point material. The heating chamber temporarily loses its ferromagnetic properties and ceases to absorb energy through hysteresis loss. At step 3764, the temperature of the heating chamber decreases below the Curie temperature of the Curie point material as it is no longer absorbing energy and generating heat. Once below the Curie temperature, the heating chamber regains its ferromagnetic properties, can once again be heated, and the process continues back at step 3756.

Figure 37H:
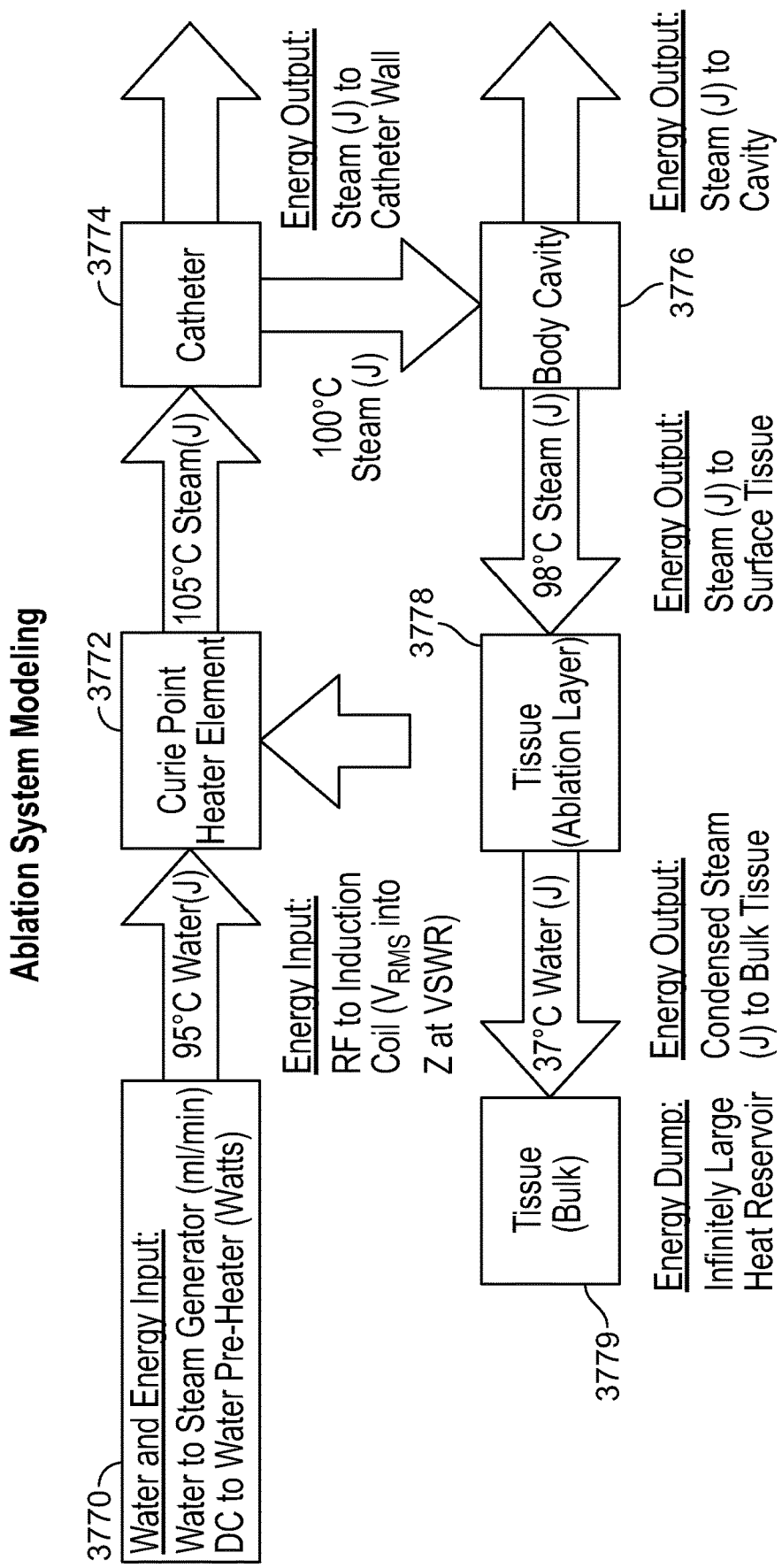
FIG. 37H is a flow chart illustrating the steps involved in tissue ablation using various ablation systems of the present specification.

FIG. 37H is a flow chart illustrating the steps involved in tissue ablation using various ablation systems of the present specification. At step 3770, water is pre-heated using DC power and the pre-heated water is delivered to a heating element at a pre-determined rate (ml/min). In one embodiment, the pre-heated water is at approximately 95° C. In another embodiment, the water is not pre-heated but rather room temperature water is provided to the heating element. At step 3772, the heating element heats and converts the water to steam. In one embodiment, the heating element is a Curie point material heater element. RF energy is provided to an induction coil positioned about the heating element to resulting in heating of the heating element and conversion of the water to steam. In various embodiments, steam generated by the heating element and delivered to a catheter of the ablation system is between 100 and 150° C. At step 3774, steam having a temperature of approximately 100° C. traveling through the catheter loses a small amount of its energy into the catheter wall while a majority of the steam is delivered into a body cavity. A small portion of the thermal energy of the steam heats the cavity itself while most of the thermal energy of the steam, now at approximately 98° C., is transferred to surface tissues surrounding the body cavity at step 3776. Then, at step 3778, the thermal energy causes tissue ablation in an ablation layer of the surface tissues. Finally, at step 3779, the steam, having released its thermal energy, converts back to water. The remaining energy during this conversion is dumped into bulk tissue which acts as an infinitely large heat reservoir.

Figure 38A:
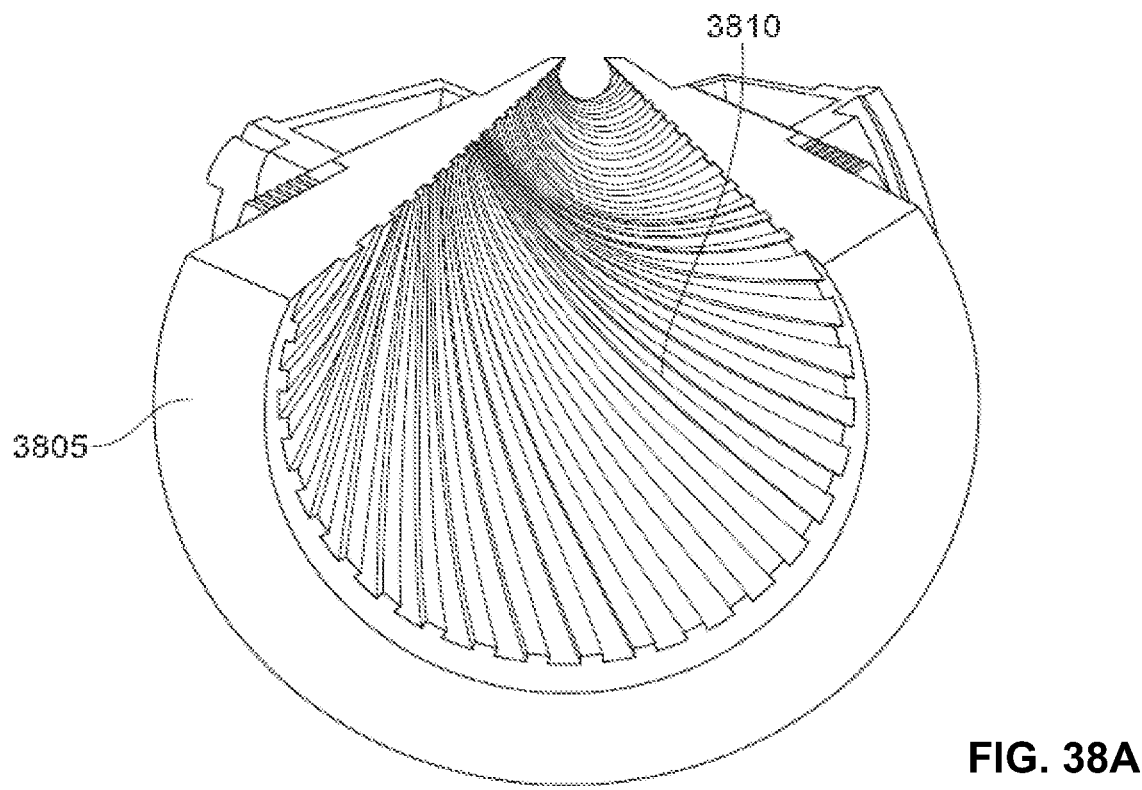
FIG. 38A illustrates a cross-sectional view of one embodiment of a catheter having an internal groove to decrease flow resistance.
Figure 38B:
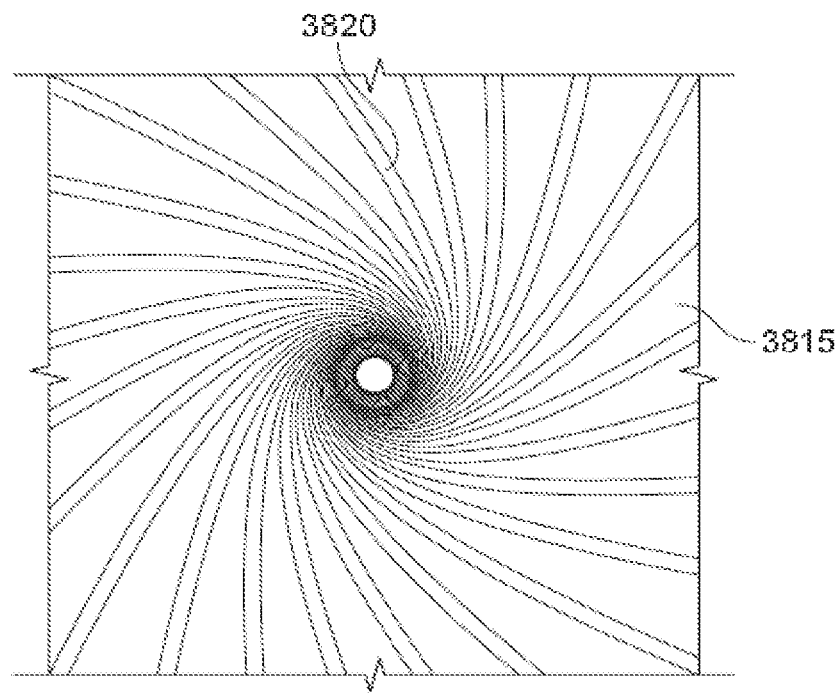
FIG. 38B illustrates an on-end view of one embodiment of a catheter having an internal groove to decrease flow resistance.

In order to have high insulation properties, the catheters described above require increased wall thickness. The increased wall thickness would decrease the size of the lumen and increase the resistance to flow of the ablative agent. Therefore, in various embodiments, the inner surface of the catheter includes a groove to decrease the resistance to flow of an ablative agent. FIG. 38A illustrates a cross-sectional view of one embodiment of a catheter 3805 having an internal groove 3810 to decrease flow resistance and FIG. 38B illustrates an on-end view of one embodiment of a catheter 3815 having an internal groove 3820 to decrease flow resistance.

In another embodiment, the resistance to flow is reduced by sending a sound wave down the catheter bore along with the ablative agent to create sympathetic resonances. The sympathetic resonances create a channeling effect where friction with the vessel wall is dramatically reduced.

Figure 39A:
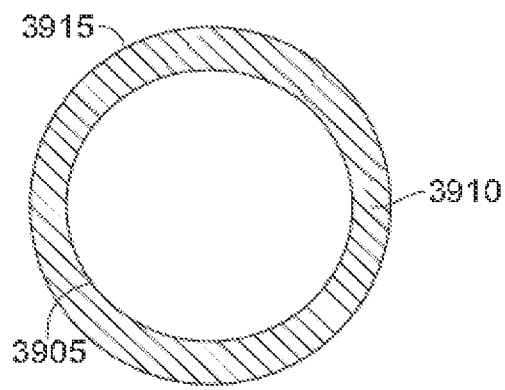
FIG. 39A illustrates a cross-sectional view of a double layered catheter in accordance with one embodiment of the present specification.
Figure 39B:
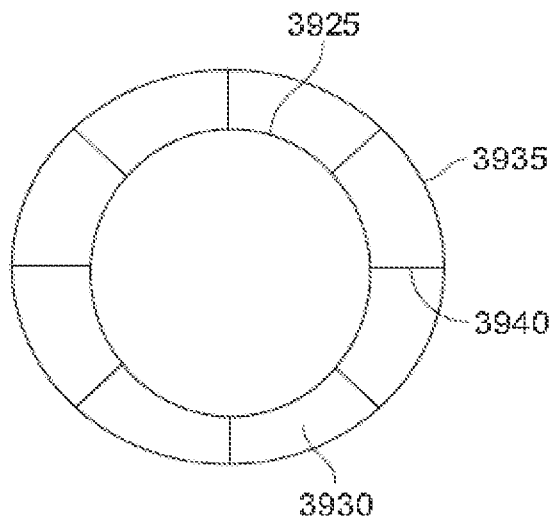
FIG. 39B illustrates a cross-sectional view of a double layered catheter in accordance with another embodiment of the present specification.

To improve the thermal insulation property of the catheter, a dual layered catheter can be formed with a thin layer of air or insulating fluid between the two catheter layers. In one embodiment, the insulating layer of air or fluid is circulated back into the power generator to facilitate heat transfer into the generator rather than through the catheter walls. FIG. 39A illustrates a cross-sectional view of a double layered catheter in accordance with one embodiment of the present specification. The catheter includes an inner wall 3905 and an outer wall 3915 separated by a thin layer 3910 of air or insulating fluid. The two walls 3905, 3910 are connected at their proximal and distal ends (not shown). FIGS. 39B and 39C illustrate cross-sectional views of a double layered catheter in accordance with another embodiment of the present specification. The catheter includes an inner wall 3925 and an outer wall 3935. The two walls 3925, 3935 are connected at their proximal and distal ends (not shown) and are connected at intervals by spokes 3940 which provide additional support. Multiple air or fluid filled channels 3930 are positioned between the two walls 3925, 3935. In one embodiment, the inner and outer walls (and spokes shown in FIG. 39B) are composed of polyether ether ketone (PEEK).

FIG. 39D illustrates a dual layered catheter 3950 having the internal structure depicted in FIG. 39B. The catheter 3950 includes an elongate body with a proximal and a distal end. The proximal end includes a first port 3951 for the input of an ablative agent, such as steam, and a second port 3952 for the insufflation of a pair of inflatable positioning attachments 3958 positioned proximate the distal end of the catheter 3950. In one embodiment, a length of catheter 3950 positioned between said positioning attachments 3958 includes at least one opening 3955 for the delivery of ablative agent. In one embodiment, the length of the catheter between said positioning attachments 3958 is approximately 5 cm. In one embodiment, the catheter includes a third layer 3954 about a portion of its proximal end. The third layer 3954 functions as a handle and thermally insulates the user from the remaining layers of the catheter. In one embodiment, the third layer 3954 has a length of approximately 50 cm. In one embodiment, the length of the catheter 3950 beyond the handle is equal to the length of an endoscope plus 2 cm. The catheter 3950 includes an outer layer 3956 and an inner layer 3957 separated by a plurality of spokes 3959. A plurality of air or fluid filled spaces 3960 separates each spoke 3959 from one another and the outer layer 3956 from the inner layer 3957. In one embodiment, the outer diameter $d_1$ of the outer layer 3956 is approximately 2.5 mm and the inner diameter $d_2$ of the inner layer 3957 is approximately 0.5 mm. The third layer 3954, or handle, includes an outer diameter $d_3$ of varying size as this portion of the catheter is not inserted into an endoscope during operation. In another embodiment, the catheter includes only one spoke 3961 separating the inner layer 3956 from the outer layer 3957 and a single air or fluid filled channel 3962 fills the remaining space between the two layers. The "honeycomb" arrangement of the catheter depicted in FIGS. 39B through 39D provides thermal insulation and a more flexible structure as some catheter material has been removed.

One advantage of a vapor delivery system utilizing a heating coil is that the vapor is generated closer to the point of use. Traditional vapor delivery systems often generate vapor close to or at the point in the system where the liquid is stored. The vapor must then travel through a longer length of tubing, sometimes over 2 meters, before reaching the point of use. As a result of the distance traveled, the system can sometimes deliver hot liquid as the vapor cools in the tubing from the ambient temperature.

The devices and methods of the present specification can be used to cause controlled focal or circumferential ablation of targeted tissue to varying depth in a manner in which complete healing with re-epithelialization can occur. Additionally, the vapor could be used to treat/ablate benign and malignant tissue growths resulting in destruction, liquefaction and absorption of the ablated tissue. The dose and manner of treatment can be adjusted based on the type of tissue and the depth of ablation needed. The ablation device can be used not only for the treatment of Barrett's esophagus and esophageal dysplasia, flat colon polyps, gastrointestinal bleeding lesions, endometrial ablation, pulmonary ablation, but also for the treatment of any mucosal, submucosal or circumferential lesion, such as inflammatory lesions, tumors, polyps and vascular lesions. The ablation device can also be used for the treatment of focal or circumferential mucosal or submucosal lesions of any hollow organ or hollow body passage in the body. The hollow organ can be one of gastrointestinal tract, pancreaticobiliary tract, genitourinary tract, respiratory tract or a vascular structure such as blood vessels. The ablation device can be placed endoscopically, radiologically, surgically or under direct visualization. In various embodiments, wireless endoscopes or single fiber endoscopes can be incorporated as a part of the device. In another embodiment, magnetic or stereotactic navigation can be used to navigate the catheter to the desired location. Radio-opaque or sonolucent material can be incorporated into the body of the catheter for radiological localization. Ferro- or ferrimagnetic materials can be incorporated into the catheter to help with magnetic navigation.

Figure 40A:
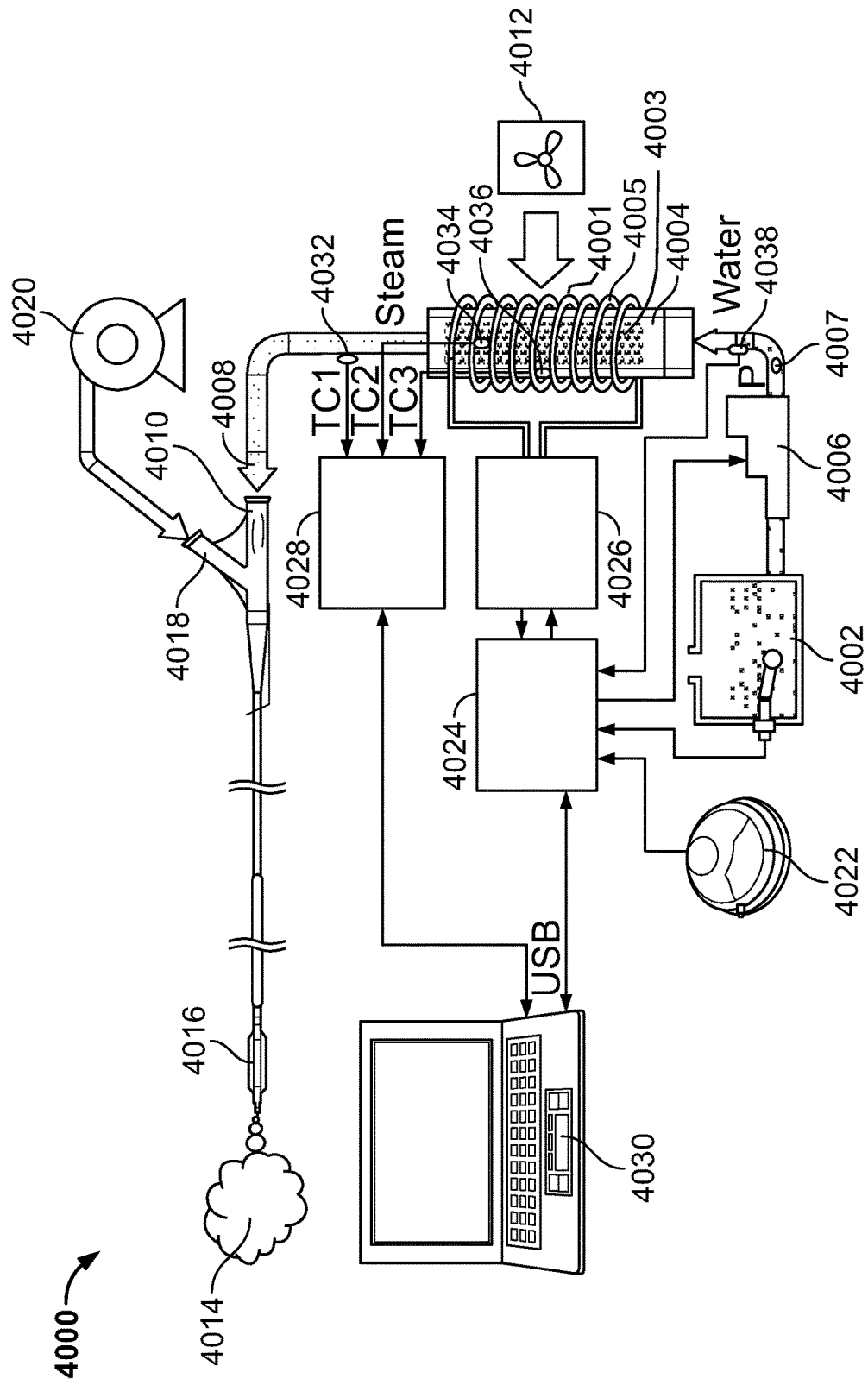

FIG. 40A is an illustration of a vapor ablation system 4000 using induction heating in accordance with one embodiment of the present specification. The vapor ablation system 4000 comprises a fluid circuit including a water reservoir 4002, a heating chamber 4004, and a catheter 4010 connected by a contiguous fluid channel. In various embodiments, the contiguous fluid channel connecting the components of the fluid circuit comprises flexible tubing having an internal lumen. In various embodiments, one or more of the components of the fluid circuit are disposable such that the separate components are discarded and replaced after a single use or the entire fluid circuit is discarded after a single use. In one embodiment, prior to use, a portion of the fluid channel positioned between the water reservoir 4002 and the heating chamber 4004 is blocked by a barrier, thereby blocking water from passively flowing from the water reservoir 4002 to the heating chamber 4004. In one embodiment, a check valve or a fracture diaphragm 4007 is positioned in the contiguous fluid channel between the water reservoir 4002 and the heating chamber 4004 to prevent water from entering the heating chamber 4004 until force is applied to the water to direct it into the heating chamber 4004. During operation, the barrier, check valve, or fracture diaphragm 4007 is breached by an increase in water pressure as water is acted upon by a pump or driving mechanism, permitting water to flow from the water reservoir 4002 to the heating chamber 4004.

Water travels from the reservoir 4002 into the heating chamber 4004 where it is converted to steam. The resulting steam travels into the catheter 4010 and out its distal end as ablative agent. The only pathway for water and steam to travel is from the reservoir 4002, through the heating chamber 4004, and out the distal end of the catheter 4010. In various embodiments, there are no other inputs, ports, or openings for receiving fluid from an external source into the fluid circuit. In various embodiments, there are no other outputs, ports, or openings, for receiving or expelling fluid external to the fluid circuit. In various embodiments, the water reservoir 4002 comprises a pliable bag, a syringe, or any three dimensional enclosure configured to contain a predetermined volume of water.

The heating chamber 4004 is configured to be positioned within an induction coil 4005. In various embodiments, the heating chamber can be cylindrical, cuboid, or any other shape. In some embodiments, the induction coil 4005 comprises an induction chamber 4001 having a cylindrical volume around which a plurality of coils are positioned and a lumen 4003 within configured to receive the heating chamber 4004. In other embodiments, the induction coil 4005 comprises only the coil itself which is wrapped about the heating chamber 4004. The induction coil 4005 comprises a plurality of coils for receiving an electrical current and generating a magnetic field which leads to induction heating of a ferromagnetic portion of the heating chamber 4004, as described in further detail with reference to FIGS. 42 and 43. In various embodiments, the frequency of the electrical current provided to the induction coil is in a range of 100 Hz-200 kHz, more preferably 1 kHz-100 kHz, more preferably yet 10 kHz-50 kHz, and most preferably 25 kHz-35 kHz. In various embodiments, the heating chamber 4004 is insulated to prevent heat losses from the chamber and/or thermal injury to an operator.

Water is directed from the reservoir 4002 into the heating chamber 4004 via force applied by a pump, motor, or other mechanism. In various embodiments, water is directed into the heating chamber 4004 by a pump driven by a motor as described further below. In other embodiments, the water reservoir 4002 is elevated relative to the heating chamber 4004 and water from the reservoir 4002 is gravity fed into the heating chamber 4004. In other embodiments, the mechanism for delivering water from the reservoir 4002 to the heating chamber 4004 comprises a bladder tank. In one embodiment, the bladder tank comprises a diaphragm separating two compartments within one tank. A first compartment contains compressed air while the second compartment contains water. The compressed air pushes on the diaphragm, which forces water out of the second compartment and into a heating chamber. In another embodiment, mechanism to deliver water from the reservoir 4002 to the heating chamber 4004 comprises an occluded water tank. The occluded water tank functions similarly to a toothpaste tube wherein a portion of the occluded water tank is compressible and is squeezed to force water out of the tank and into a heating chamber.

In various embodiments, fluid from the water reservoir 4002 is pumped with precise dosing into the heating chamber 4004. In one embodiment, the water reservoir 4002 is configured to contain 200 ml of water. A precisely controllable, positive displacement dosing pump 4006 delivers exact amounts of water on demand into the induction heater chamber 4004 for vaporization. Induction heating is preferred because it permits heating of an element inside a sterile catheter without comprising sterility and does not require complex electrical feed-throughs. In addition, the catheter itself can be disposable and therefore manufactured at a low cost. In one embodiment, the heating chamber includes 4004 a metal core and is mounted vertically. In one embodiment, the metal is steel. Water is introduced at the bottom of the heating chamber 4004 at an inlet port at its proximal end. As described further below, in one embodiment, the metal core is a smooth rod with a slightly smaller outer diameter than the inner diameter of a tube coaxially positioned over the core. An induction coil 4005 is wrapped about the tube of the heating chamber 4004. The core and the tube comprise the heating chamber 4004. Water introduced into the heating chamber 4004 passes through the space between the core and the tube. Therefore, all water is forced into close proximity of the core, contacting the metal surface, vaporizing and exiting the chamber entirely as steam as long as sufficient heating power is provided for a given flow rate. Steam created within the heating chamber 4004 exits via an outlet port at its distal end.

The generated steam is delivered to a luer lock connector 4008 connected to the input port of a catheter 4010. The catheter 4010 is designed such that all parts that come into direct contact with the steam are able to withstand temperatures in excess of 100° C., preventing melting and subsequent leaks or obstructions. The catheter 4010 includes one or more openings at its distal end for the delivery of steam 4014 to target tissues. In various embodiments, the catheter 4010 includes one or more positioning attachments 4016 proximate its distal end. In one embodiment, the positioning attachments 4016 comprise inflatable balloons and the catheter 4010 further comprises an insufflation port 4018 at its proximal end. An air pump 4020 connected to the insufflation port 4018 is used to inflate said balloons. In various embodiments, the positioning attachments, or balloons 4016, are inflated using air through the air pump 4020 and then the air expands once steam is generated by the system 4000. In some embodiments, the one or more balloons 4016 are first inflated to a positioning volume by the air pump 4020 and are then further expanded to an occlusive volume as the air is heated by the delivery of steam, establishing a non-puncturing seal. In one embodiment, the occlusive volume is less than 120% of the positioning volume. In various embodiments, the one or more balloons 4016 are comprised of silicone. The silicone is thermally insulating so heat generated from ablation in the area proximate the outside of the balloons 4016 will not transfer passively and expand the air inside the balloons 4016. Therefore, in some embodiments, the air used for insufflation must be actively heated from inside the catheter into the balloons 4016 to accomplish the desired heat expansion. In various embodiments, the catheter 4010 has a coaxial design such that heat energy from the steam is transferred to the air used for insufflation as they both travel along the catheter 4010. The coaxial design of the catheter 4010 allows for heat losses along the catheter to be captured and transferred to the air in the balloons 4016 to generate a treatment responsive seal. In other embodiments, the catheter 4010 includes a coaxial lumen for heating the air or the balloons 4016 include a conductive metal inside for conducting heat from vapors in the catheter to the air in the balloons 4016.

Figure 40B:
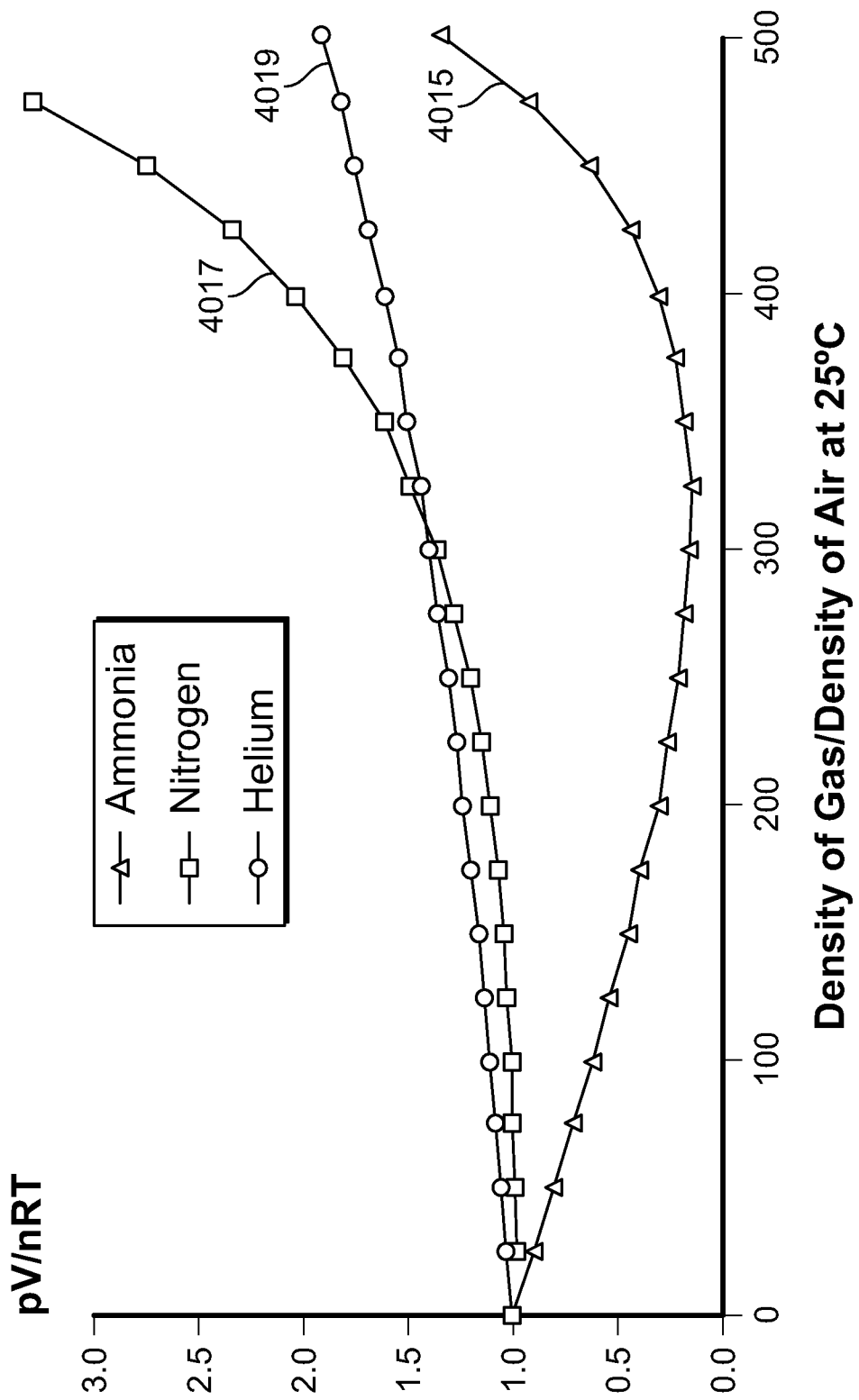

When heating air from 37° C. (body temperature) to 100° C., the air will expand by approximately 20%. Therefore, in one embodiment, the one or more balloons 4016 are inflated to approximately 75% using the air pump 4020, allowing for the remainder of the volume expansion to be effectuated by heat transfer from the steam. Since the steam is not being directed into the balloons 4016, pressure within the balloons 4016 will not change significantly. The air used to inflate the one or more balloons 4016 behaves like an ideal gas at temperatures below 400° C., as depicted in FIG. 40B, and follows approximately the ideal gas law below:

$$PV=nRT$$

where P is the absolute pressure of the gas, V is the volume of the gas, n is the amount of gas, R is the ideal gas constant, and T is the absolute temperature of the gas expressed in degrees Kelvin (degrees C.+273). Referring to FIG. 40B, the air behaves less like an ideal gas as it is heated beyond approximately 400° C., where the curves for the density of ammonia 4015, nitrogen 4017, and helium 4019 become less linear at temperatures over 400° C. In various embodiments, the air used to inflate the balloons is defined by at least three different temperatures: starting temperature ($T_{start}$); ideal temperature ($T_{ideal}$); and, maximum temperature ($T_{max}$). In various embodiments, $T_{start}$ is equal to 25° C. (room temperature), $T_{ideal}$ is less than or equal to 75° C., and $T_{max}$ is equal to 125° C. In various embodiments, the volume expansion of the balloons relative to the volume at $T_{start}$ ranges from 2% to 40% at $T_{max}$ and from 1% to 20% for $T_{ideal}$. In various embodiments, the system has a maximum continuous operating time of less than or equal to 5 minutes and an ideal continuous operating time of less than or equal to 2 minutes. In various embodiments, the balloons are configured to have a maximum diameter change, or expansion, of less than or equal to 5 mm and an ideal diameter change, or expansion, of less than or equal to 3 mm. Different temperatures at a substantially fixed pressure provide a volume ratio equal to the temperature ratio. Therefore, in one embodiment having the operating parameters listed above, heating the air from 25° C. ($T_{start}$) to 125° C. ($T_{max}$) provides a temperature increase of 100 K (398K/298K) which translates to a volume expansion of less than or equal to 33%. In one embodiment having the operating parameters listed above, heating the air from 25° C. ($T_{start}$) to 75° C. ($T_{ideal}$) provides a temperature increase of 50 K (348K/298K) which translates to a volume expansion of less than or equal to 17%. In various embodiments, the balloons have a first positioning diameter when inflated by action of an air pump and a second occlusion diameter when the pumped air is heated by the steam generated by the system, as listed in Table 4 below:

TABLE 4

| Positioning Diameter | Occlusion Diameter | Percent Change in Volume |
| --- | --- | --- |
| 18 mm | 21 mm | 36% |
| 20 mm | 23 mm | 32% |
| 22 mm | 25 mm | 29% |

Referring to Table 4, a balloon having a positioning diameter of 18 mm expands to have an occlusion diameter of 21 mm, a 36% increase, when the insufflation air is heated by the nearby steam. A balloon having a positioning diameter of 20 mm expands to have an occlusion diameter of 23 mm, a 32% increase, when the insufflation air is heated by the nearby steam. A balloon having a positioning diameter of 22 mm expands to have an occlusion diameter of 25 mm, a 29% increase, when the insufflation air is heated by the nearby steam.

In another embodiment, further volume expansion of the balloon is not desired and the volume of the balloons is kept constant by monitoring the pressure in the balloon and allowing a portion of expanded air to escape the balloon to keep the pressure, and therefore volume, constant.

Figure 40C:
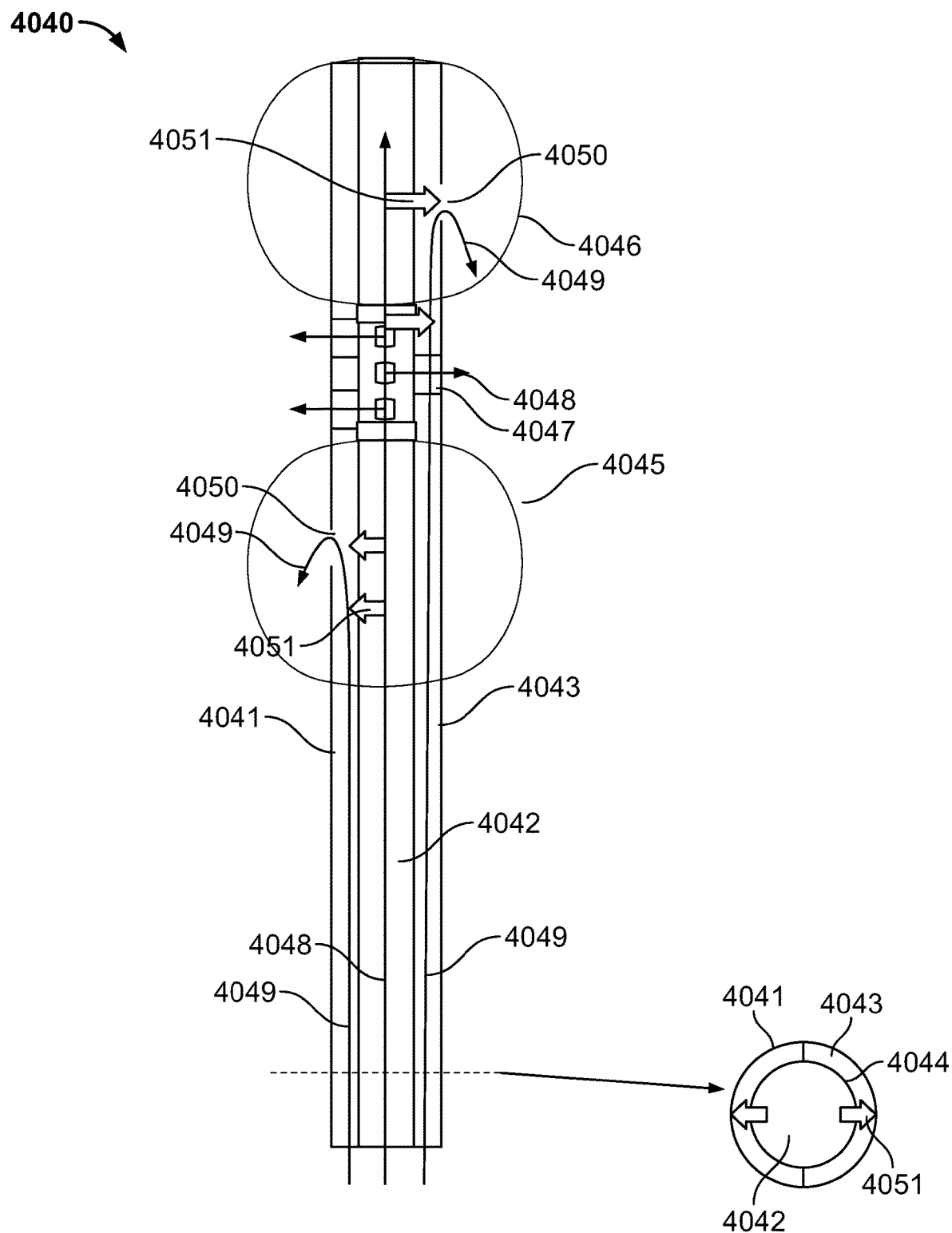

FIG. 40C is an illustration of one embodiment of a catheter 4040 for use with the vapor ablation systems of the present specification. The catheter 4040 includes an elongate body 4041 with a proximal end and a distal end. In one embodiment, the catheter body 4041 includes an inner lumen 4042 and an outer lumen 4043. The inner lumen 4042 is separated from the outer lumen 4043 by a thermally semi-permeable wall 4044 which allows a portion of the thermal energy to pass from the inner lumen 4042 to the outer lumen 4043. The catheter also includes at least one positioning balloon at its distal end. In the embodiment depicted in FIG. 40C, the catheter 4040 includes two positioning balloons 4045, 4046 at its distal end with a plurality of delivery ports 4047 located on the catheter body 4041 between the two balloons 4045, 4046. The delivery ports 4047 are in fluid communication with the inner lumen 4042. An ablative agent 4048 is introduced into the inner lumen 4042 at the proximal end of the catheter 4040 and exits through the delivery ports 4047 into a target tissue area for ablation. In one embodiment, the ablative agent 4048 is steam. Air 4049 is introduced into the outer lumen 4043 at the proximal end of the catheter 4040 and exits through inflation ports 4050 into the balloons 4045, 4046 to inflate said balloons 4045, 4046. Along the length of the catheter body 4041, the air 4049 in the outer lumen receives thermal energy 4051 through the thermally semi-permeable wall 4044 from the ablative agent 4048 being delivered. The thermal energy 4051 expands the air 4049, allowing for the air 4049 in the positioning balloons 4045, 4046 to thermally expand or contract to get a variable seal as ablative agent 4048 is delivered. This functionality provides a loose balloon seal (contacting without significantly expanding an elastic hollow organ) during dimension measurement (no ablative agent 4048 delivered) and a tighter balloon seal (contacting and sufficiently expanding an elastic hollow organ) during the delivery of ablative agent 4048. The seal loosens after cessation of delivery of ablative agent 4048. In various embodiments, the expansion of the balloons as a result of thermal energy 4051 expanding the air 4049 is less than 125% of the original inflated volume to prevent tearing or perforation of the hollow organ. In one embodiment, thermal energy 4051 is also conducted through the walls of the delivery ports 4047 and into the outer lumen 4043 as the delivery ports 4047 extend from the inner lumen 4042 to the exterior of the catheter 4040. In one embodiment, the delivery ports 4047 are comprised of metal for improved thermal conductivity.

Figure 40D:
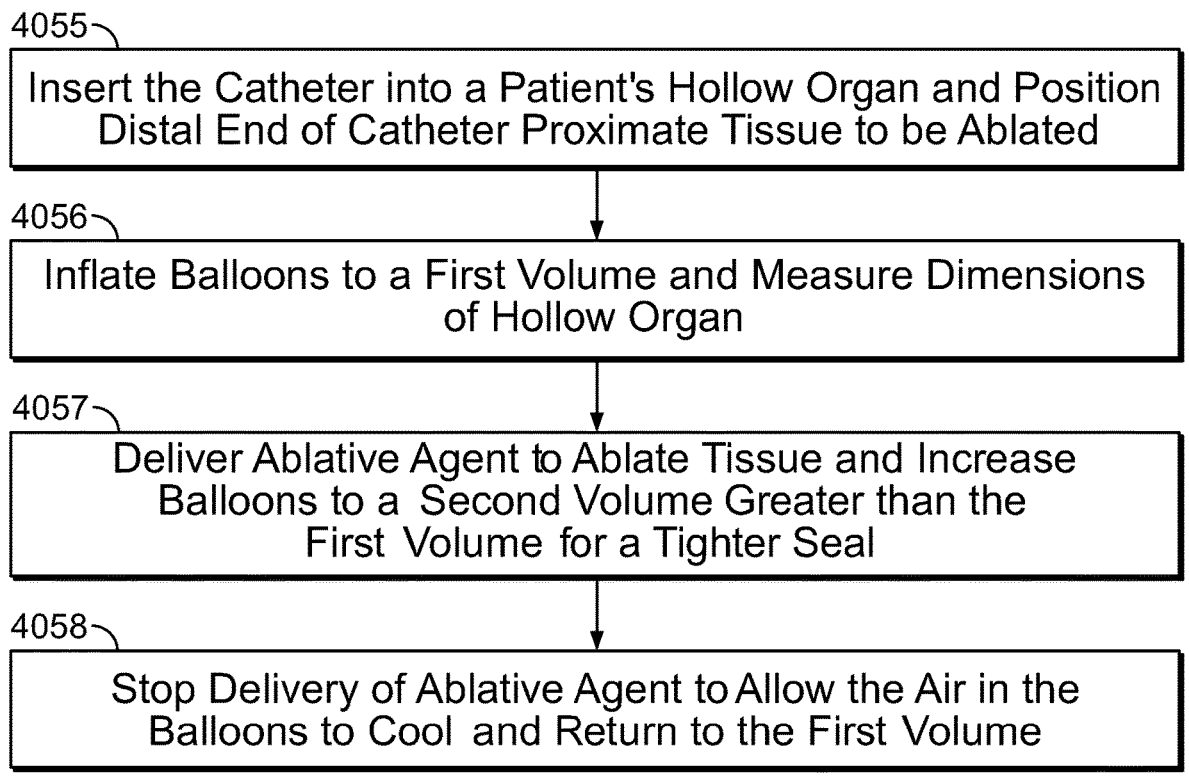

FIG. 40D is a flowchart listing the steps of a method of using the ablation catheter of FIG. 40C, in accordance with one embodiment of the present specification. At step 4055, the catheter is inserted into a patient's hollow organ and the distal end is positioned proximate the tissue to be ablated. The balloons are then inflated to a first volume at step 4056 and the dimensions of the hollow organ are measured. The ablative agent is then delivered to ablate the tissue at step 4057. The delivery of the ablative agent also acts to expand the air being used to inflate the balloons, which causes the balloons to expand to a second volume greater than the first volume for a tighter seal. In various embodiments, the second volume is less than 125% of the first volume. At step 4058, delivery of the ablative agent is stopped, allowing the air in the balloons to cool and the balloons to return to the first volume.

Figure 40E:
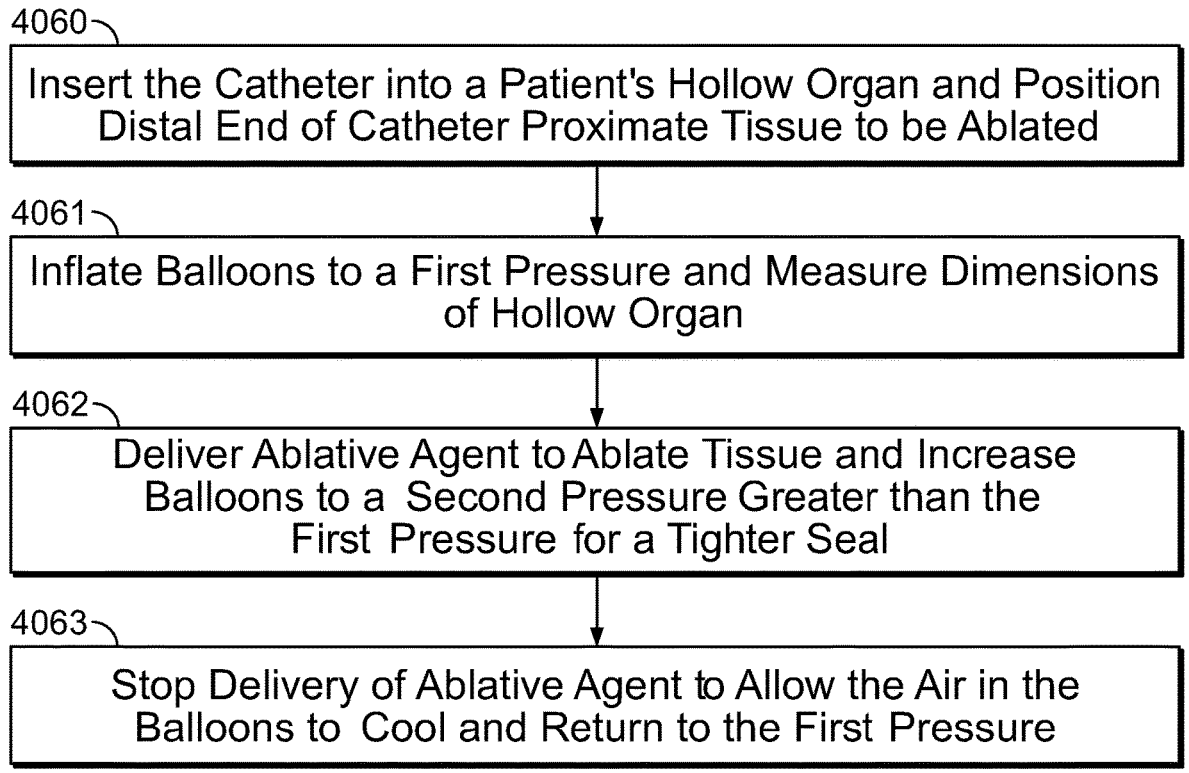

FIG. 40E is a flowchart listing the steps of a method of using the ablation catheter of FIG. 40C, in accordance with another embodiment of the present specification. At step 4060, the catheter is inserted into a patient's hollow organ and the distal end is positioned proximate the tissue to be ablated. The balloons are then inflated to a first pressure at step 4061 and the dimensions of the hollow organ are measured. The ablative agent is then delivered to ablate the tissue at step 4062. The delivery of the ablative agent also acts to expand the air being used to inflate the balloons, which causes the balloons to expand to a second pressure greater than the first pressure for a tighter seal. In various embodiments, the second pressure is less than 125% of the first pressure. At step 4063, delivery of the ablative agent is stopped, allowing the air in the balloons to cool and the balloons to return to the first pressure.

Figure 40F:
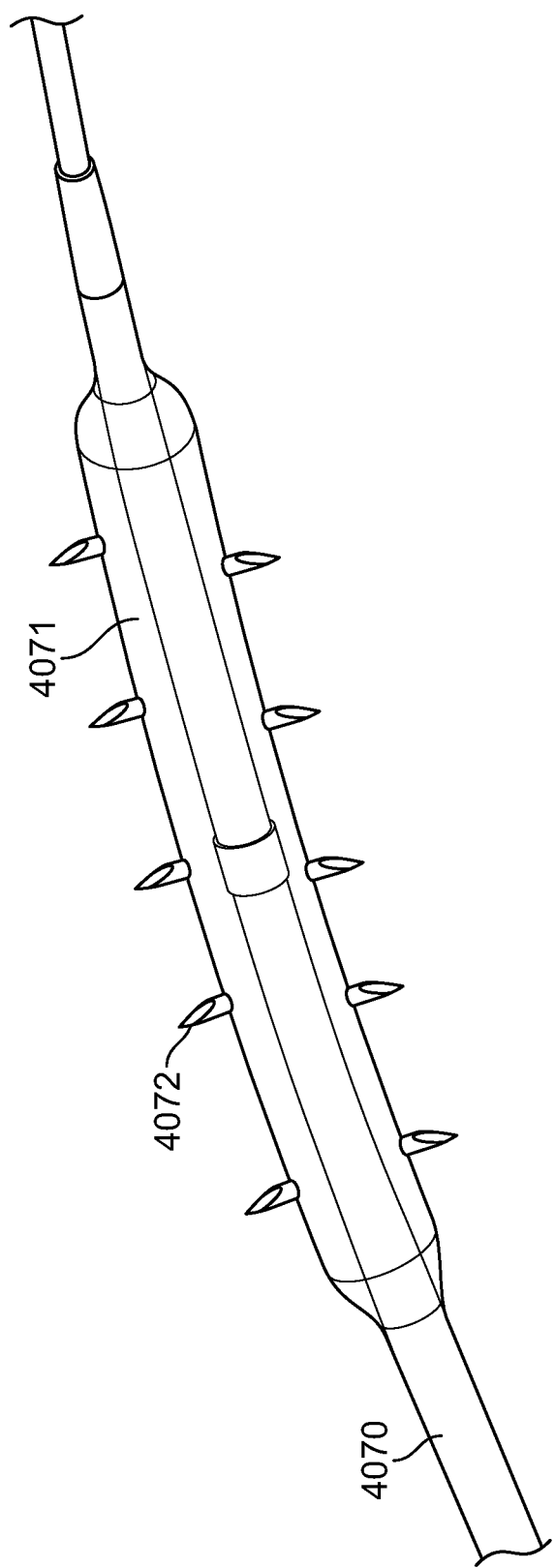

In various embodiments, the catheters of the present specification further include at least one thermally conducting element attached to the positioning element. The at least one thermally conducting element is configured to physically contact, and, in some embodiments, penetrate, a target tissue and enhance the delivery of thermal energy into the target tissue for ablation. FIG. 40F is an illustration of one embodiment of a positioning element 4071 of an ablation catheter 4070, depicting a plurality of thermally conducting elements 4072 attached thereto. In various embodiments, the positioning element 4071 is an inflatable balloon. The positioning element, or balloon 4071, is inflated to a first volume to bring the thermally conducting elements 4072 into contact with a target tissue. An ablative agent is then delivered to the target tissue through the catheter 4070 and out via at least one delivery port at the distal end of the catheter 4070. Thermal energy from the ablative agent is transferred from the lumen of the catheter 4070 into the air in the balloon 4071, further expanding the volume of the balloon 4071 and pushing the thermally conducting elements 4072 further into the target tissue. Thermal energy from the air in the balloon 4071 is transferred to the thermally conducting elements 4072 and is released into the target tissue for ablation. In various embodiments, the thermally conducting elements 4072 comprise solid or hollow metal spikes or needles. In various embodiments, the balloon 4071 is composed of a thermally insulating material so that ablative thermal energy is predominantly transferred from the thermally conducting elements 4072 into the target tissue.

Figure 40G:
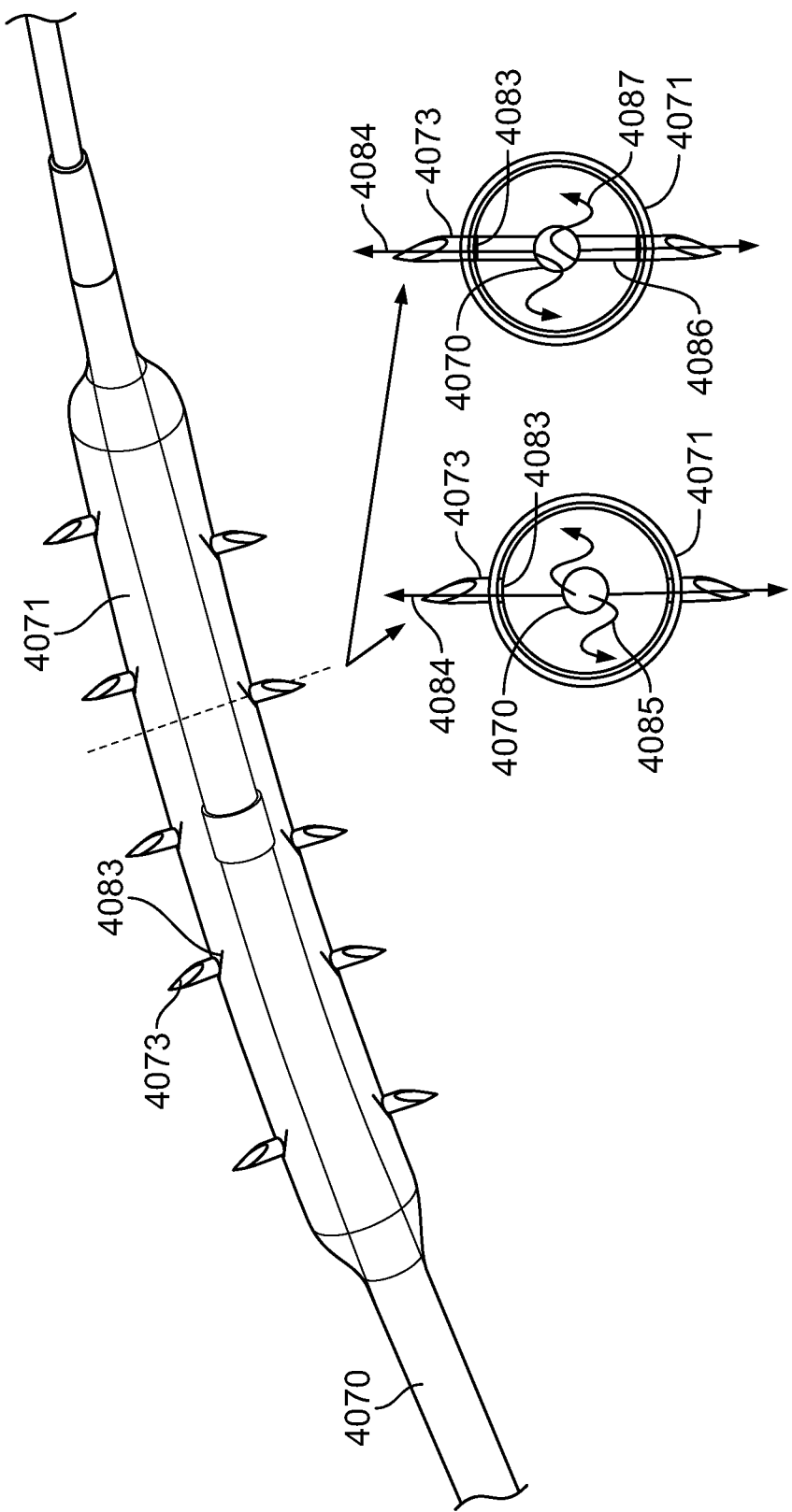

FIG. 40G is an illustration of one embodiment of a positioning element 4071 of an ablation catheter 4070, depicting a plurality of hollow thermally conducting elements 4073 attached thereto. In one embodiment, each hollow thermally conducting element 4073 includes a valve 4083 at the inlet from a lumen of the positioning element 4071 to a lumen of the hollow thermally conducting element 4073. In various embodiments, the positioning element 4071 is an inflatable balloon. The positioning element, or balloon 4071, is inflated to a first volume to bring the thermally conducting elements 4072 into contact with a target tissue. An ablative agent is then delivered to the target tissue through the catheter 4070 and out via at least one delivery port at the distal end of the catheter 4070. Thermal energy from the ablative agent is transferred from the lumen of the catheter 4070 into the air in the balloon 4071, further expanding the volume of the balloon 4071 and pushing the thermally conducting elements 4073 further into the target tissue. Thermal energy from the air in the balloon 4071 is transferred to the thermally conducting elements 4073 and is released into the target tissue for ablation. In various embodiments, the thermally conducting elements 4073 comprise hollow metal spikes or needles. The thermally conducting elements 4073 include at least one opening at their distal ends which are in fluid communication with a lumen of the thermally conducting elements 4073, which, in turn, is in fluid communication with the interior of the balloon 4071. As seen in the cross section of the catheter 4070, vapor follows a first pathway 4084 to pass from the interior of the balloon 4071, through the thermally conducting elements 4073, and out to the target tissue. In one embodiment, each thermally conducting element 4073 includes a valve 4083 positioned at its junction with the balloon 4071 to control the flow of vapor into each hollow thermally conducting element 4073. In one embodiment, the vapor also follows a second pathway 4085 into the interior of the balloon 4071 to transmit thermal energy and assist in balloon expansion 4071. In another embodiment, flexible tubes 4086 connect the lumen of each thermally conducting element 4073 with a lumen of the catheter 4070, bypassing the interior of the balloon 4071. In one embodiment, the tubes 4086 are composed of silicone. In this embodiment, the vapor can only travel via the first pathway 4084 and air 4087 is used to expand the balloon 4071. In various embodiments, the balloon 4071 is composed of a thermally insulating material so that ablative thermal energy is predominantly transferred from the thermally conducting elements 4073 into the target tissue. In various embodiments, the thermally conducting elements 4073 possess shape memory properties such that they change shape from being generally parallel to the catheter 4070 at a temperature below a patient's body temperature to being generally perpendicular to the catheter 4070 at temperatures above the patient's body temperature.

Figure 40H:
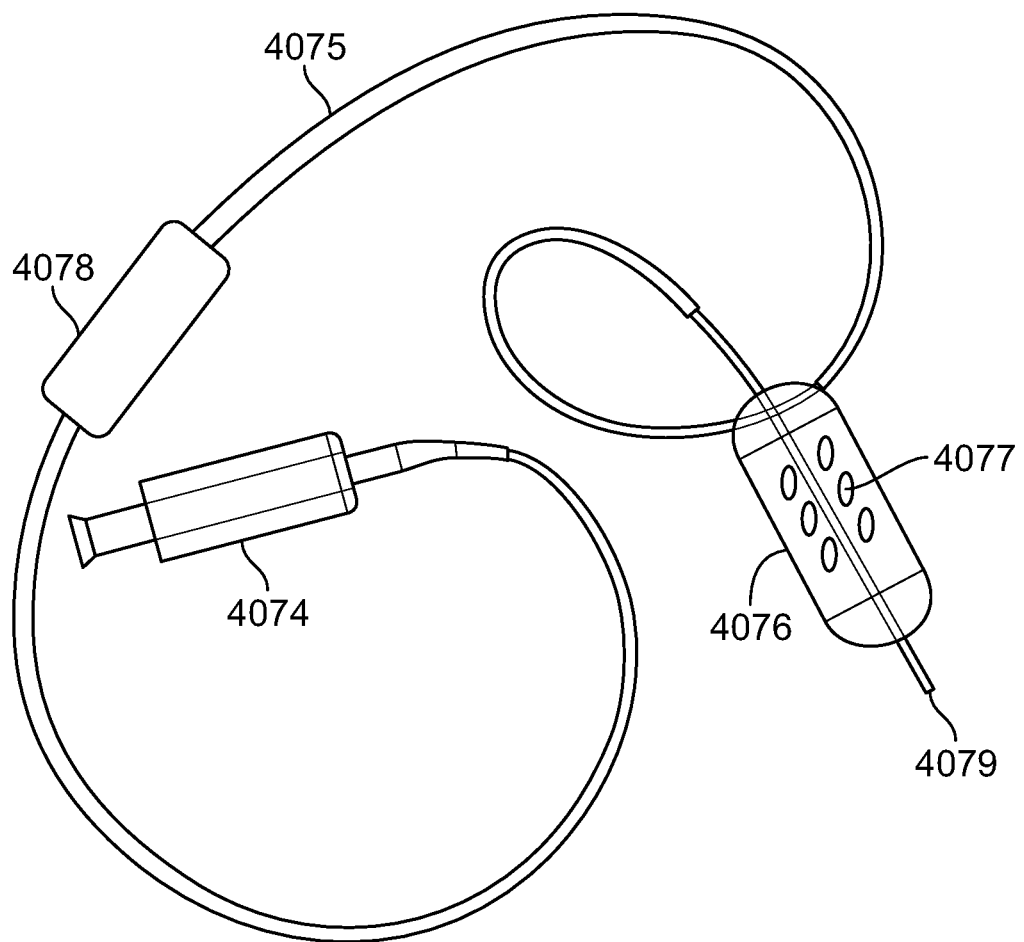

In other embodiments, the balloons, or positioning elements, are also thermally conducting and include at least one thermally conducting element within. FIG. 40H is an illustration of an ablation catheter 4075 having a plurality of thermally conducting elements 4077 within a positioning element 4076, in accordance with one embodiment of the present specification. The positioning element, or balloon 4076, is inflated to a first volume to bring the balloon 4076 into contact with a target tissue. An ablative agent is then delivered to the catheter 4075 via an inlet port 4074 at its proximal end. The ablative agent is converted to vapor by the transfer of thermal energy from a heat exchange unit 4078 into the lumen of the catheter 4075. The vapor travels through the catheter 4075 and out via at least one delivery port 4079 at its distal end. Thermal energy from the ablative agent is transferred from the lumen of the catheter 4075 into the air in the balloon 4076, further expanding the volume of the balloon 4076 and bringing the thermally conducting elements 4077 into close thermal contact with the target tissue. Thermal energy from the air in the balloon 4076 and from the lumen of the catheter is transferred to the thermally conducting elements 4077 and is released into the target tissue for ablation. In various embodiments, the thermally conducting elements 4077 comprise solid or hollow metal spikes, needles or strips. In various embodiments, the thermally conducting elements 4077 possess shape memory properties such that they change shape from being generally parallel to the catheter 4075 at a temperature below a patient's body temperature to being generally perpendicular to the catheter 4075 at temperatures above the patient's body temperature.

Figure 40I:
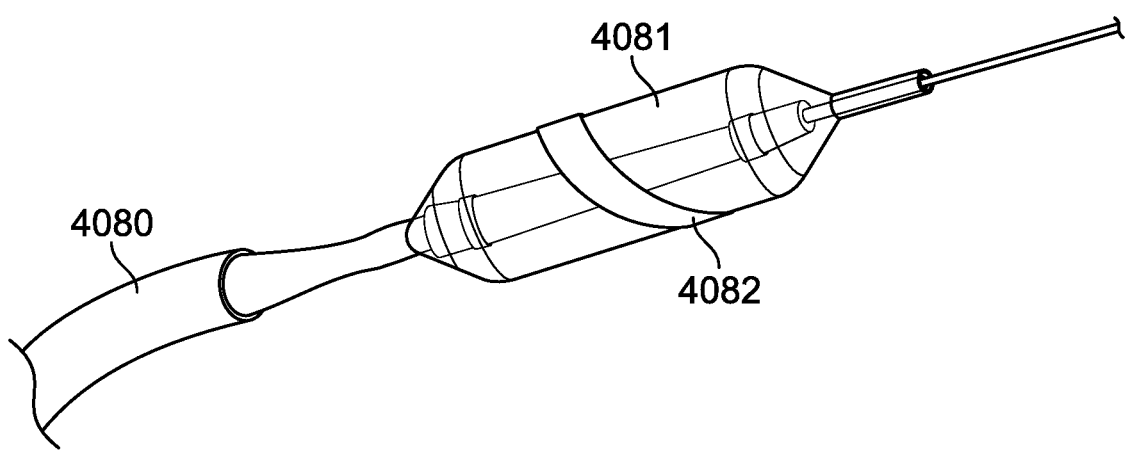

In other embodiments, a portion of the outer surface of the balloons, or positioning elements, includes at least one thermally conducting element. FIG. 40I is an illustration of an ablation catheter 4080 having a thermally conducting element 4082 attached to an outer surface of a positioning element 4081. The positioning element, or balloon 4081, is inflated to a first volume to bring the thermally conducting element 4082 into contact with a target tissue. An ablative agent is then delivered to the target tissue through the catheter 4080 and out via at least one delivery port at the distal end of the catheter 4080. Thermal energy from the ablative agent is transferred from the lumen of the catheter 4080 into the air in the balloon 4081, further expanding the volume of the balloon 4081 and pushing the thermally conducting element 4082 further against the target tissue. Thermal energy from the air in the balloon 4081 is transferred to the thermally conducting element 4082 and is released into the target tissue for ablation. In various embodiments, the thermally conducting element 4082 comprises a metal strip. In various embodiments, the balloon 4081 is composed of a thermally insulating material so that ablative thermal energy is only transferred from the thermally conducting element 4082 into the target tissue. In various embodiments, the pressure of the balloon is constantly monitored to prevent over inflation of the balloon. The pressure of the balloon controls the rate of flow of thermal energy.

In one embodiment, a small, high-speed fan 4012 provides air cooling to the induction coil 4005 to permit continuous operation without the risk of damage to the coil 4005 or heating chamber 4004. In one embodiment, the fan 4012 is manually controlled by a switch on the front panel of a main enclosure housing the induction coil drive electronics. In various embodiments, the system 4000 includes a foot switch 4022 for controlling delivery of steam and to free the hands of the operator during a procedure. In one embodiment, the foot switch 4022 connects with a ¼" standard audio plug into a corresponding jack (depicted as jack 4113 in FIG. 41B) on a front panel of one of the system electronics enclosures. When pressed, the foot switch 4022 sends a digital signal to a digital input terminal of a digital acquisition card. The signal is then acquired, processed and displayed by a graphical user interface (GUI) 4031 of a controller unit 4030. In one embodiment, the foot switch 4022 acts in parallel to a large "Deliver Rx" button under a tab with the same name on the GUI, as described with reference to the system software below. To start a selected therapy (Rx) program, the operator can either press the "Deliver Rx" button on the GUI or press the foot switch 4022.

The ablation system 4000 includes a plurality of electronics components for operating and monitoring the system. In various embodiments, the electronics include, but are not limited to, data acquisition and control electronics 4024, induction coil electronics 4026, and thermocouple electronics 4028. A controller unit 4030, comprising a graphical user interface (GUI) 4031, interfaces with the data acquisition and control electronics 4024 and with the thermocouple electronics 4028. In various embodiments, the controller unit 4030 comprises a laptop or tablet PC. In one embodiment, the controller unit 4030 interfaces with the data acquisition and control electronics 4024 and thermocouple electronics 4028 via USB connections. The data acquisition and control electronics 4024 interface with the induction coil electronics 4026, which control energy delivered to the induction coil 4005.

In various embodiments, the ablation system 4000 includes one or more sensors configured to sense operational parameters of the system 4000 and relay the sensed data to electronics components. In the pictured embodiment, the system 4000 includes a first temperature sensor, or thermocouple 4032, at the steam outlet port of the heating chamber 4004. The first thermocouple 4032 measures the temperature of the steam exiting the heating chamber 4004 and relays this information to the thermocouple electronics 4028. A second thermocouple 4034 is positioned at the core of the heating chamber 4004. The second thermocouple 4034 measures the temperature of the heating chamber core and relays this information to the thermocouple electronics 4028. A third thermocouple 4036 is positioned at the induction coil 4005. The third thermocouple 4036 measures the temperature of the induction coil 4005 and relays this information to the thermocouple electronics 4028. In the pictured embodiment, the system 4000 also includes a pressure sensor 4038 positioned at the inlet port of the heating chamber 4004. The pressure sensor 4038 measures pressure at the inlet port of the heating chamber 4004 and relays this information to the data acquisition and control electronics 4024. In one embodiment, the pressure sensor 4038 is in-line with the path of the fluid and the system 4000 shuts down heating when a predetermined pressure is sensed.

During operation, the system 4000 is controlled and monitored in real-time using the data acquisition and control electronics 4024 and controller unit 4030. In one embodiment, the data acquisition and control electronics 4024 comprises a National Instruments DAQ card (USB-6009) and an Arduino Mega 2560 microcontroller board. In various embodiments, the controller unit 4030 controls the following subsystems: temperature controlled core heating; the dosing pump 4006 via operator control on the GUI, a pre-determined program, or optional foot switch 4022; the induction heating chamber 4004 via setting the power level to the induction coil 4005, manually energizing the induction coil 4005 at a selected power level, or temperature controlling the heater core automatically; water pressure monitoring at the inlet port of the heating chamber 4004 to sense any blockage downstream, particularly when using a small bore catheter; steam temperature monitoring at the outlet port of the heating chamber 4004 (or at the luer lock or proximal end of the catheter 4010); heating chamber core temperature monitoring; induction coil 4005 temperature monitoring; monitoring of the current drawn by the induction coil 4005 to estimate input power and protect the system from over-current situations.

In various embodiments, the vapor ablation system 4000 includes the following specifications: steam generation of 15-150 ml/sec; a maximum steam temperature of 120° C.; pressure capability up to 25 PSIG; power consumption of less than 1000 W; power connection to a standard outlet 120V AC/15 A; temperature stabilized and controlled heater core up to 200° C.; and phase controlled, self-limiting heater power up to approximately 500 W at maximum setting. In various embodiments, for a particular procedure, a maximum volume of steam is delivered over a maximum time of continuous use, with the initial volume of steam being emitted within a specific time period of activating a button for releasing the steam. This requires a specific minimum volume of water.

The volume of steam delivered for each procedure is dependent on the steam temperature and the pressure in accordance with the ideal gas equation as discussed with reference to FIG. 40B. 1 mol of water is equal to 18 g of water. 1 g of water equates to 1 ml of water and therefore 1/18 mol of water. 1 mol of any gas at the National Institute of Standards and Technology (NIST) standard conditions (20° C. and 101.325 kPa) has a volume of 22.4 L. Therefore, 1/18 mol of vapor at standard conditions would have a volume of 1,244 ml (22.4 L/18). During operation, the vapor, or wet steam, has a temperature of 100° C. and therefore the volume is increased to 1,584 ml (1,244 ml*373K/293K).

Operational parameters are provided below for a variety of vapor ablation procedures. In each procedure, the solid metal core of the heating chamber (discussed in detail with reference to FIGS. 46A through 46C below) is preheated to a temperature in a range of 200-250° C. The metal core temperature is then increased to a range of 250-300° C. once therapy (vapor delivery) is started. The metal core temperature returns to the preheated range of 200-250° C. on cessation of each cycle of therapy.

Barrett's Esophagus Ablation

Example 1

Water is delivered at a rate of 5 ml/min into the heating chamber to contact an outer surface of the solid metal core. Each cycle is on for 5 seconds and off for 10 seconds for a total of 5 cycles, which will convert the water into approximately 132 ml steam/sec during the on phase of each cycle. At a water flow rate of 5 ml/min, steam at 100° C. will be generated at a rate of 7,920 ml/min (132 ml/sec).

Example 2

Water is delivered at a rate of 5 ml/min into the heating chamber to contact an outer surface of the solid metal core. Each cycle is on for 10 seconds and off for 10 seconds for a total of 5 cycles, which will convert the water into approximately 132 ml steam/sec during the on phase of each cycle.

Endometrial Ablation

Example 1

Water is delivered at a rate of 10 ml/min into the heating chamber to contact an outer surface of the solid metal core. Each cycle is on for 30 seconds and off for 30 seconds for a total of 5 cycles, which will convert the water into approximately 264 ml steam/sec during the on phase of each cycle.

Example 2

Water is delivered at a rate of 10 ml/min into the heating chamber to contact an outer surface of the solid metal core. Each cycle is on for 60 seconds and off for 60 seconds for a total of 3 cycles, which will convert the water into approximately 264 ml steam/sec during the on phase of each cycle.

Example 3

Water is delivered at a rate of 5 ml/min into the heating chamber to contact an outer surface of the solid metal core. Each cycle is on for 90 seconds and off for 90 seconds for a total of 2 cycles, which will convert the water into approximately 132 ml steam/sec during the on phase of each cycle.

Example 4

Water is delivered at a rate of 10 ml/min into the heating chamber to contact an outer surface of the solid metal core, generating vapor at a rate of ~264 ml/sec. The vapor is delivered until an intracavity pressure reaches 50 mm Hg. During each cycle, the pressure is maintained at 50 mm Hg (+/−20%) with continuous vapor delivery (on period) for 60 sec and then thermal delivery is turned off (off period) for 60 sec. A total of 2 cycles of vapor delivery are performed. The flow of vapor is varied from 0-264 ml/sec to maintain a desired intracavity pressure for the duration of the therapy. At 50 mm Hg pressure, the volume of the delivered steam decreases to 247.7 ml/sec (264 ml/sec*760 mm/810 mm) from its volume at standard conditions.

Example 5

Water is delivered at a rate of 5 ml/min into the heating chamber to contact an outer surface of the solid metal core, generating vapor at a rate of ~132 ml/sec. The vapor is delivered until an intracavity pressure reaches 50 mm Hg. During a first cycle, the pressure is maintained at 50 mm Hg (+/−20%) with continuous vapor delivery (on period) for 60 sec and then thermal delivery is turned off (off period) for 60 sec. A second cycle, having an on period of 90 sec and an off period of 90 sec, is performed and then the therapy is concluded. The flow of vapor is varied from 0-132 ml/sec to maintain a desired intracavity pressure for the duration of the therapy.

Example 6

Water is delivered at a rate of 5 ml/min into the heating chamber to contact an outer surface of the solid metal core, generating steam at a rate of ~132 ml/sec. The steam is delivered for 90 seconds. The intracavity pressures are maintained at ~50 mm Hg throughout the delivery of steam.

Prostate Ablation

Example 1

Water is delivered at a rate of 1 ml/min into the heating chamber to contact an outer surface of the solid metal core. Each cycle is on for 10 seconds and off for 60 seconds for a total of 10 cycles, which will convert the water into approximately 26.4 ml steam/sec during the on phase of each cycle.

Example 2

Water is delivered at a rate of 2 ml/min into the heating chamber to contact an outer surface of the solid metal core. Each cycle is on for 5 seconds and off for 60 seconds for a total of 5 cycles, which will convert the water into approximately 52.8 ml steam/sec during the on phase of each cycle.

Example 3

Water is delivered at a rate of 5 ml/min into the heating chamber to contact an outer surface of the solid metal core. Each cycle is on for 2 seconds and off for 30 seconds for a total of 10 cycles, which will convert the water into approximately 132 ml steam/sec during the on phase of each cycle.

Vessel Ablation

Example 1

Water is delivered at a rate of 5 ml/min into the heating chamber to contact an outer surface of the solid metal core. Each cycle is on for 10 seconds and off for 30 seconds for a total of 3 cycles, which will convert the water into approximately 132 ml steam/sec during the on phase of each cycle.

Example 2

Water is delivered at a rate of 5 ml/min into the heating chamber to contact an outer surface of the solid metal core. Each cycle is on for 20 seconds and off for 40 seconds for a total of 2 cycles, which will convert the water into approximately 132 ml steam/sec during the on phase of each cycle.

Bleeding Gastric Ulcer

Example 1

Bleeding Ulcer—Water is delivered at a rate of 10 ml/min into the heating chamber to contact an outer surface of the solid metal core. Each cycle is on for 10 seconds and off for 10 seconds for a total of 5 cycles, which will convert the water into approximately 264 ml steam/sec during the on phase of each cycle.

Example 2

Bleeding Angioectasia—Water is delivered at a rate of 5 ml/min into the heating chamber to contact an outer surface of the solid metal core. Each cycle is on for 5 seconds and off for 10 seconds for a total of 3 cycles, which will convert the water into approximately 132 ml steam/sec during the on phase of each cycle.

Bronchial Ablation

Example 1

Water is delivered at a rate of 2 ml/min into the heating chamber to contact an outer surface of the solid metal core. Each cycle is on for 5 seconds and off for 10 seconds for a total of 5 cycles, which will convert the water into approximately 52.8 ml steam/sec during the on phase of each cycle.

Example 2

Water is delivered at a rate of 1 ml/min into the heating chamber to contact an outer surface of the solid metal core. Each cycle is on for 10 seconds and off for 10 seconds for a total of 5 cycles, which will convert the water into approximately 26.4 ml steam/sec during the on phase of each cycle.

Sinus Ablation

Example 1

Water is delivered at a rate of 1 ml/min into the heating chamber to contact an outer surface of the solid metal core. Each cycle is on for 30 seconds and off for 30 seconds for a total of 5 cycles, which will convert the water into approximately 26.4 ml steam/sec during the on phase of each cycle.

Polyp Ablation

Example 1

Water is delivered at a rate of 5 ml/min into the heating chamber to contact an outer surface of the solid metal core, generating approximately 132 ml steam/sec. The polyp is grasped and the steam delivered until the visible tissue turns white. Pressure is applied to transect the tissue while simultaneously applying vapor until the tissue is completely transected. If bleeding is visualized, the pressure is released and the vapor is continuously applied until bleeding ceases. Once bleeding has been stopped, pressure transection and vapor ablation is continued.

Figure 40J:
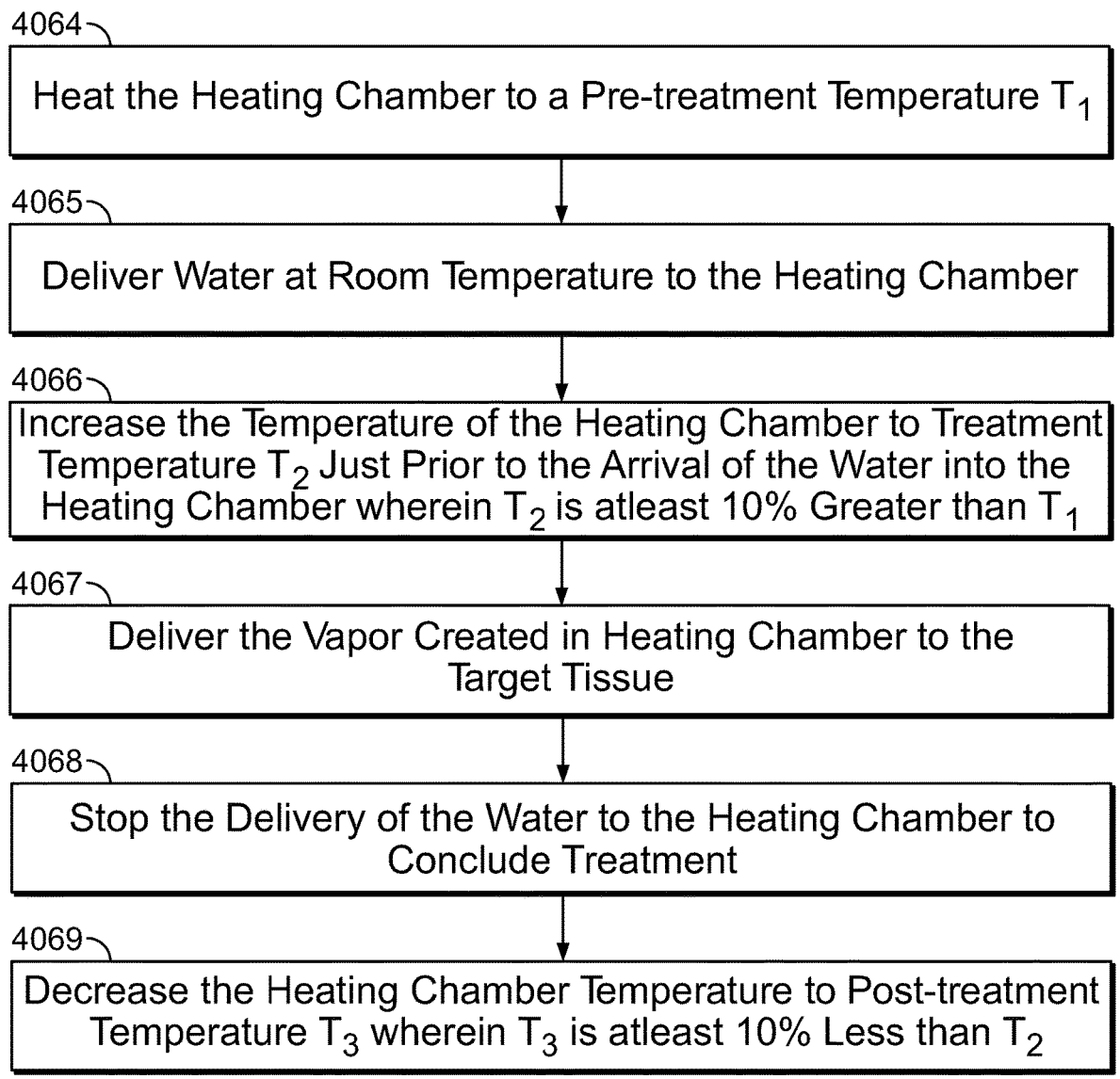

FIG. 40J is a flowchart listing the steps of a method of using a vapor ablation system in accordance with one embodiment of the present specification. At step 4064, the heating chamber is heated to a pre-treatment temperature $T_1$. Room temperature water is delivered to the heating chamber at step 4065. Then, at step 4066, the temperature of the heating chamber is increased to a treatment temperature $T_2$ just prior to the arrival of the water into the heating chamber. In various embodiments, $T_2$ is at least 10% greater than $T_1$. The temperature of the heating chamber at $T_2$ vaporizes the water in the heating chamber. The vapor created in the heating chamber is delivered to the target tissue at step 4067. At step 4068, delivery of water to the heating chamber is stopped to conclude treatment. The temperature of the heating chamber is then decreased to a post-treatment temperature $T_3$ at step 4069. In various embodiments, $T_3$ is at least 10% less than $T_2$. The steps may be repeated to deliver multiple treatment cycles.

Figure 40K:
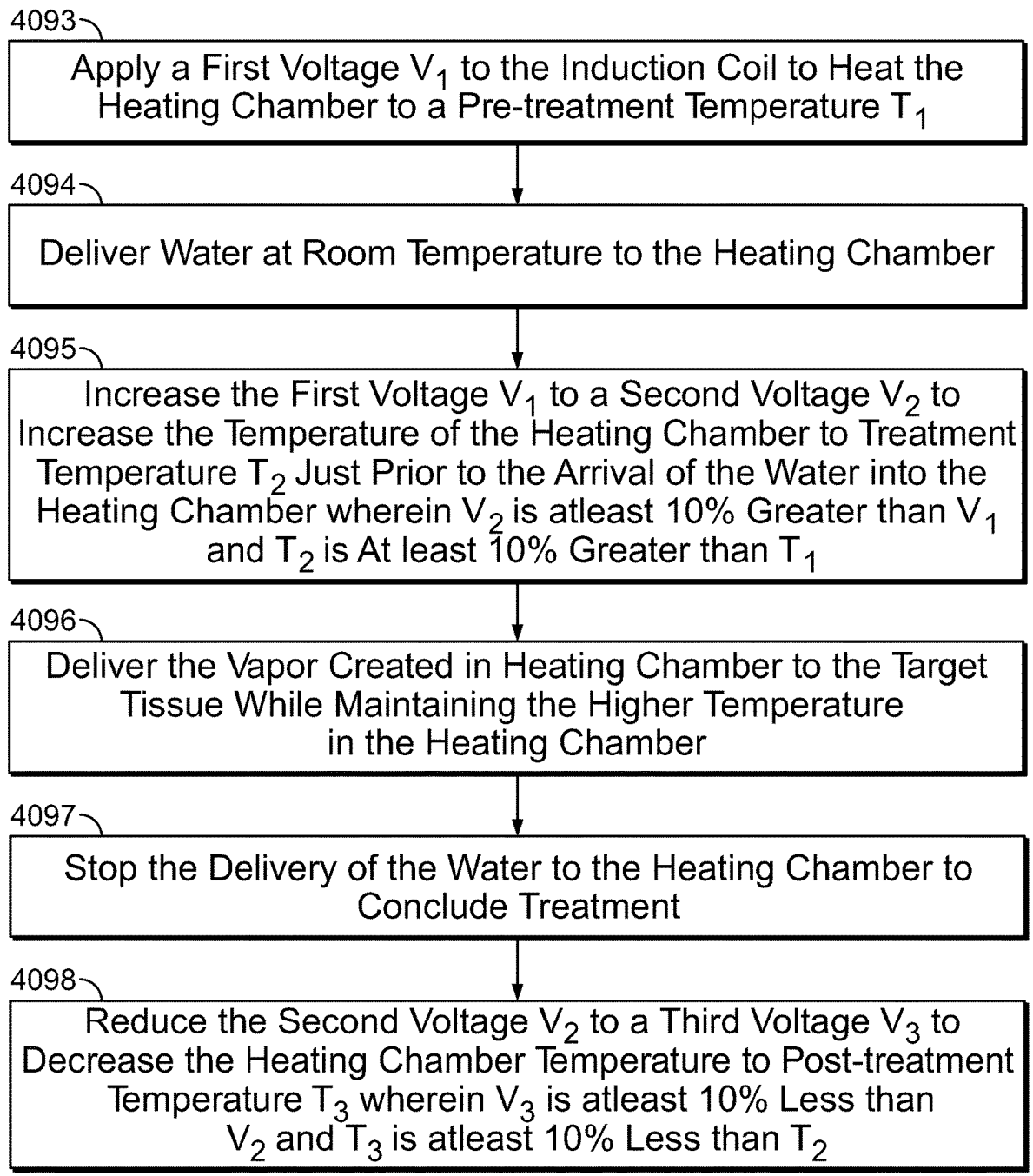

FIG. 40K is a flowchart listing the steps of a method of using a vapor ablation system in accordance with another embodiment of the present specification. At step 4093, a first voltage $V_1$ is applied to the induction coil to heat the heating chamber to a pre-treatment temperature $T_1$. Room temperature water is delivered to the heating chamber at step 4094. Then, at step 4095, the first voltage $V_1$ is increased to a second voltage $V_2$ to increase the temperature of the heating chamber to a treatment temperature $T_2$ just prior to the arrival of the water into the heating chamber. In various embodiments, $V_2$ is at least 10% greater than $V_1$ and $T_2$ is at least 10% greater than $T_1$. The temperature of the heating chamber at $T_2$ vaporizes the water in the heating chamber. The vapor created in the heating chamber is delivered to the target tissue at step 4096 while the higher temperature in the heating chamber is maintained. At step 4097, delivery of water to the heating chamber is stopped to conclude treatment. The second voltage $V_2$ is then reduced to a third voltage $V_3$ at step 4098 to decrease the temperature of the heating chamber to a post-treatment temperature $T_3$. In various embodiments, $V_3$ is at least 10% less than $V_2$ and $T_3$ is at least 10% less than $T_2$. The steps may be repeated to deliver multiple treatment cycles.

System Hardware

FIG. 41A is an illustration of the components of a vapor ablation system 4100 in accordance with one embodiment of the present specification. The vapor ablation system 4100 includes a controller unit 4130, or tablet PC, a USB hub 4140, and a power block 4142. In one embodiment, the USB hub 4140 is a 7-port USB hub and the power block 4142 is a 4-outlet AC connector block so that only a single AC power plug is needed to operate the system. The power block 4142 includes two AC adapters, a first adapter to charge the controller unit 4130 and a second adapter to supply external power to the USB hub 4140. The controller unit 4130, or tablet PC, does not need to supply any power to the USB devices as power is supplied directly to the USB hub 4140 by the power block 4142. This becomes particularly beneficial when the controller unit 4130 is operating in battery mode, conserving battery power of the controller unit 4130 and therefore prolonging battery life. The two remaining outlets on the power block 4142 provide convenience for connecting and powering any additional devices in the future. The USB hub 4140 expands the controller unit's 4130 limited USB connectivity and permits further flexibility and expansion in the future.

The system 4100 also includes a water reservoir 4102, a cover 4144 over the heating chamber and induction coil, and system electronics 4150, 4152, 4154. The outlet port 4146 of a manifold attached to the distal end of the heating chamber is visible protruding through cover 4144. The controller unit 4130 interfaces with the system electronics 4150, 4152, 4154 via USB connections through the USB hub 4140. An induction coil driver circuit is located within system electronics 4150, which comprises a heavy-gauge steel shielded enclosure. Data acquisition electronics and a circuit board with cable interconnects and signal processing electronics are located within system electronics 4152. The induction coil driver circuit and data acquisition electronics comprise the control electronics for the induction coil. The induction coil driver circuit is located within a shielded enclosure because it operates in switch-mode which is known for creating electronic noise that can interfere with sensitive sensor signals. The enclosure for system electronics 4150 is also shielded because it contains AC line voltage as well as high-voltage kickback voltage spikes, both of which are dangerous to operators. In one embodiment, a lid to system electronics 4150 includes a lock and key 4151 to prevent unauthorized or accidental access to the voltages. In one embodiment, the components of the vapor ablation system, with the exception of the controller unit 4130, are secured to a backboard 4101.

FIG. 41B is an illustration of the vapor ablation system 4100 of FIG. 41A with the heating chamber cover removed. The controller unit and USB hub are also removed in FIG. 41B. With the cover removed, the heating chamber 4104 and induction coil 4105 are visible. Also visible are the front end electronics of the thermocouple electronics 4128. The front panel of system electronics 4150 includes an on/off fan switch 4127 and a power indication light 4129. FIG. 41B also depicts the front end of a data acquisition card 4124 contained within system electronics 4152. The card 4124 includes an LES operation status light 4125 and a USB port 4126. The card 4124 receives a voltage of 0-5 V that is determined using a numeric control on the GUI. The analog output of the card 4124 is converted to a pulse train of variable frequency in a voltage-to-frequency converter. The pulse train is further conditioned to maintain a 50% duty cycle, independent of frequency, as required by a stepper motor controller of the pump. The 50% duty cycle, variable frequency pulse train is input to a stepper motor driver circuit. The stepper motor driver circuit translates the pulse train into the appropriate wave forms that energize two coils of the stepper motor, resulting in the controlled movement of the motor's armature in speed and direction. The known and controlled shaft speed of the motor directly drives the pump head of the positive displacement pump resulting in known and controlled water flow. After careful calibration, this signal chain thus allows the operator to set a flow rate in units of ml/min on the GUI and the resulting water flow to the heater chamber will be accurate to approximately ±5%.

FIG. 41C is a close-up illustration of the uncovered heating chamber 4104 and induction coil 4105 of the vapor ablation system of FIG. 41B. The heating chamber 4104 includes a manifold 4148 covered by a thermally insulating material attached to its distal end. A luer lock connector 4149 is positioned at an outlet port of the manifold 4148. Also depicted in FIG. 41C is a terminal block 4147 to which a plurality of thermocouple leads are connected. The thermocouples are used to sense temperatures within the system as described with reference to FIGS. 49A through 49G. In one embodiment, the water reservoir 4102 includes a water level sensor 4103. When the water level is low within the reservoir 4102, the sensor 4103 sends a digital signal to a digital input terminal of a data acquisition card. The signal is then acquired and displayed by the GUI. In one embodiment, the sensor activates when the water level drops approximately to ⅓ of the capacity of the reservoir. An alarm is displayed and a sound is generated by the GUI to warn the user to refill the water reservoir 4102.

FIG. 41D is an illustration of the vapor ablation system 4100 of FIG. 41A with the covers removed from the system components. The system 4100 includes a 4-outlet power block 4142 which provides additional AC outlets for auxiliary devices such as a computer charge adapter and a 5V DC adapter to externally power the USB hub 4140. The use of a USB hub 4140 provides the convenience of requiring only one USB cable to the controller unit, or tablet computer, to control the entire system. The system 4100 also includes a microcontroller board inside a shielding box 4162 and a water reservoir 4102. Also depicted in FIG. 41D are a dosing pump 4164 and the heating chamber 4104. A heavy-gauge steel enclosure 4165 with hinged lid the accommodates the power electronics to drive the induction coil as well as circuit boards for power phase control, status indication, current-sensing circuitry, 12V power supply for a cooling fan and pump and an AC current meter. An RMS clamp-on ammeter 4169 with readout and signal conditioning circuit is located within the heavy-gauge steel enclosure 4165. The clamp-on ammeter 4169 monitors the current drawn by the induction power circuit of the system which is a direct measure of the energy supplied to the heater core and thus to the water to generate steam.

FIG. 41E is a close-up illustration of the dosing pump 4164 and heavy-gauge steel enclosure 4165 of the vapor ablation system of FIG. 41A. Referring to FIG. 41E, the lid 4163 of the heavy-gauge steel enclosure 4165 is in place. The lid includes two status lights labeled "SYSTEM OK" 4166 and "ARMED STATUS" 4167. The "SYSTEM OK" 4166 status light illuminates green and indicates that the oscillator of the power switching circuit is free-running. This light must be lit green any time the mains power switch is turned on. If the light is not illuminated, then there is a system fault that must be investigated. The "ARMED STATUS" 4167 status light illuminates red and indicates that the induction power drive is enabled, feeding the coil with resonant current. This light will illuminate when the heater is activated manually or engaged programmatically.

FIG. 41F is a close-up illustration of the dosing pump 4164, with intake port 4155 and discharge ports 4156, of the vapor ablation system of FIG. 41A. The pump 4164 provides a highly controlled flow of water into the heating chamber nearly independent of back pressure. In one embodiment, the pump 4164 is a valve-less, reciprocating-and-rotating piston pump with a tilt-mounted pump head 4157 to adjust the stroke volume per revolution. In one embodiment, the piston and cylinder of the pump 4164 are precision-ground and do not require any lubrication. In one embodiment, the pump 4164 is self-priming, capable of generating very high pressures and its flow rate can be directly related to the revolutions of the drive shaft. The pump 4164 is driven by a stepper motor 4158 which precisely translates a signal pulse rate into shaft speed and thus flow rate. Drive electronics for the stepper motor 4158 are located inside a pump pedestal 4159. Water from a reservoir is delivered via the intake port 4155 into the pump head 4157. The pump 4164 then pumps the water via two discharge ports 4156 into an enclosure 4133. A pressure sensor 4135 is mounted to the enclosure 4133 for sensing the pressure of the water being delivered by the pump 4164. The pressure sensor 4135 is able to detect blockages downstream from the pump 4164. The sensor is excited with 5V DC and outputs 0.5-4.5V as the pressure varies from 0-25 PSIG. The voltage is read by an analog input terminal of the data acquisition card and acquired and displayed by the GUI. An output port 4136 delivers water from the enclosure 4133 to the heating chamber. By controlling the pulse rate to the stepper motor driver circuit, the shaft speed and therefore the flow rate of the pump 4164 can be precisely calibrated. This is the basis of the flow rate setting in the graphical user interface (GUI) and the determination of the actual flow rate of water into the heater chamber. Since the pump 4164 is a reciprocating positive displacement type pump, it delivers water in well-defined strokes which results in pulsating pressure and flow characteristics. To minimize pulsations, in one embodiment, the pump head 4157 tilt angle is adjusted to the minimum angle required to deliver at least 5.0 ml/min flow at the highest reliable stepper motor speed.

FIG. 41G is a close-up illustration of the main electronics board 4170 with ancillary electronics within the heavy-gauge steel enclosure of the vapor ablation system of FIG. 41A. The main electronics board 4170 includes the large power components of the induction coil drive stage, such as IGBT switching devices mounted below a large heat sink, filter and resonant capacitors, toroidal filter inductors and the smaller passive and active components of the IGBT gate driver electronics and control logic. A status indicator board 4171 controls the status indicator lights described with reference to FIG. 41E. A triac phase control circuit 4172 controls the power delivered by the induction drive circuit. Block capacitors 4178 are positioned above and below the triac phase control circuit 4172. The triac phase control circuit 4178 is positioned proximate the main power entry terminals to minimize the length of the cables that carry large currents and separate them from the more sensitive electronics to minimize noise pickup. The current-sensing circuitry employs a commercial clamp-on AC current meter and ties into its processing electronics. Circuit board 4173 comprises signal-processing circuitry to form a DC signal from the sensed AC current to be read by the data acquisition system. The main electronics board 4170 further includes a miniature, high-speed fan 4174 used to continuously air-cool the induction coil. In one embodiment, the fan 4174 may be switched off on a front panel of the heavy-gauge steel enclosure with a dedicated switch. The fan 4174 also provides cooling of the IGBT heat sink 4175 by moving air in the vicinity of the intake. A 12V/2 A switching power supply 4176 supplies power to the pump, fan 4174, and signal processing electronics located on the outside of enclosure lid. A resistor 4177 ensures proper operation of an induction circuit described with reference to FIGS. 41H and 41I below. In one embodiment, the resistor 4177 has a value of 1.5 kΩ.

FIG. 41H is a block diagram of the induction heater drive electronics 4180 in accordance with one embodiment of the present specification. The circuit used in the electronics is based on single-ended induction heating topology. It uses a high-current, high-voltage semiconductor switching device, in the form of an insulated-gate bipolar transistor (IGBT) 4181, to momentarily apply rectified line voltage across a parallel tank circuit ($L_r$ and Cr) 4182, of which the inductor coil $L_r$ is the inductivity. The controlled switch is timed to approximately match the resonance frequency of the tank circuit 4182. The power delivered to the induction coil is controlled by a triac phase-control circuit 4184, essentially connecting the AC line voltage to the rectifier 4185 at a precisely timed moment of each half-wave of the AC line voltage. The triac phase-control circuit 4184 commutates (switches itself off) at the zero-crossing points of the line voltage. Therefore, it must be re-triggered for every AC half-wave and means that the power control has a resolution of 83 ms (1 second/120 half-waves for a 60 Hz line frequency) and can therefore be very responsive. The triac phase-control circuit 4184 allows the switch to pass a fraction of the power contained in the AC line to the induction power circuit. The IGBT gate drive 4181 circuit operates continuously.

In one embodiment, the magnetic field generated about the metal core of the heating chamber has a vibration of 15-25 kHz. The conversion of electrical energy into het energy is very efficient. The induction coil is driven in the power stage with high amps and high current line voltage. An oscillating circuit turns the switches of the induction heater drive electronics 4180 on and off approximately 15,000 times per second. The voltage is rectified and filtered 4185 to produce a DV voltage of approximately 170 V. Once the magnetic field generated by the induction coil is fully saturated, the switches are turned off to prevent blowing the fuse to the system. Once the switches are turned off, all of the energy is contained in the magnetic field. The magnetic field collapses and the coil discharges the energy into an electric pulse. The electrical energy is input at 120 V AC, rectified and filtered to 170 V DC, and up to a 1000 V electrical kickback pulse is generated, in the opposite direction, when the switches are turned off and the magnetic field collapses. In one embodiment, as seen in FIG. 41G, the system includes two capacitors 4178 which absorb the energy from the kickback pulse. The capacitors then discharge the energy back into the coil. During this process, the metal core of the heating chamber absorbs a large amount of the energy (to convert to heat energy) so only some energy oscillates between the coil and the capacitors. The frequency of the line voltage is timed across the coil. In one embodiment, when approximately 10% of the electrical energy remains in the capacitors, the line voltage is switched back on and the process begins again. In one embodiment, the self-resonance frequency of the capacitors triggers the switches.

FIG. 41I is a graph illustrating waveforms generated by the induction heater drive electronics (induction circuit) depicted in FIG. 41H. In various embodiments, an inductor current 4186 is semi-sinusoidal, meaning it approaches the ideal waveform. In one embodiment, the inductor circuit generates a sinusoidal wave form. The voltage across the IGBT device 4187 is instructive to follow the waveform through one cycle. When the IGBT is conducting (switch is closed), energy is transferred into the inductor to build up its magnetic field and the capacitor is also partially charged. Upon opening of the switch, the parallel resonant tank circuit undergoes self-oscillation at its natural resonance frequency. At the time $t_1$ 4121, the IGBT's gate is driven and the device is turned on, resulting in a collapse of the voltage across the device as indicated by $V_{CE} \approx 0$. This is the equivalent of closing the switch. The inductor current 4186 rises relatively slowly as it builds up the magnetic field in the inductor, a process that does not occur instantaneously because of the self-induction of the inductivity which opposes any current change with a voltage change. At $t_2$ 4122, the IGBT is turned off and the tank circuit self-resonates. Starting with the collapsing magnetic field that induces a large induction voltage "kick", the current begins to flow from the coil into the parallel capacitor. When the capacitor is fully charged, the capacitor discharges into the coil with reverse polarity building up its magnetic field anew, but in the opposite direction. When the capacitor is fully discharged, the energy is transferred back into the coil. At $t_6$ 4123, the IGBT's gate is driven again and the cycle repeats. Optionally, in one embodiment, a resistor, depicted as resistor 4177 in FIG. 41G, assures that the oscillator of the gate driver circuitry is free-running for proper operation of the IGBTs. Since the heater core absorbs much of the coil energy, the wave form is distorted and dampened. In another embodiment, an H-bridge switching topology is used to increase system efficiency.

FIG. 41J is an illustration of a triac phase control circuit of the induction heater drive electronics depicted in FIG. 41H. The triac $V_{TRIAC}$ 4188 connects the induction heater power electronics to the line voltage when triggered and disconnects it during the next zero-crossing of the same AC half wave. The triac's gate is precisely triggered by an optically-isolated drive circuit controlled by a voltage from 0-5V supplied by the analog output of the data acquisition card 4124 of FIG. 41B, which in turn is controlled by the GUI.

Induction Heating

The induction heating chamber in the vapor ablation systems of FIGS. 40 through 41C includes a length and comprises a ferromagnetic material within a non-ferromagnetic material. In one embodiment, the non-ferromagnetic material comprises a cylinder or tube. The non-ferromagnetic tube has a lumen within for receiving the ferromagnetic material. In various embodiments, the non-ferromagnetic tube is electrically insulating. In some embodiments, the ferromagnetic material is a metal and has a shape of a rod. An induction coil is wrapped about the tube. A fluid is passed through a space between the rod and tube, extending the length of the heating chamber, where thermal energy from the induction heating vaporizes the fluid. In various embodiments, the fluid is water, ionized water, non-ionized water, sterile water, or a solution of a metal salt and water. The coil is energized with an alternating current (AC) in the same way as a regular electromagnet. However, since the arrangement is optimized for heat generation, the frequency used is between 10-100 s of kHz, much higher than the 60 Hz line frequency. In essence, the induction coil acts as the primary of a transformer while the metal rod acts as the secondary. In various embodiments, the magnetic coupling of the heating chamber and coil arrangement is more than 90% efficient and the conversion of induced eddy current into Joule heat inside the metal rod is practically 100% efficient. Conversion efficiencies of the magnetic energy into heat energy within the heating chamber of 30% or higher, including 40, 50, 60, 70, 80, 90, and 100%, are within the scope of the invention. In various embodiments, a magnetic to heat energy conversion of 60% or higher is preferred to allow for a form factor for the induction coil/chamber that is hand held. In various embodiments, the ferromagnetic material comprises any one of, or alloys of, iron, nickel, stainless steel, manganese, silicon, carbon, copper, an electrically conducting material, an electrically insulating material, or a Curie material having a Curie temperature between 60 and 500° C. Since the rod is composed of metal, there are two distinct mechanisms of heat generation in the core: a first from eddy currents and a second from magnetic hysteresis.

FIG. 42 is an illustration of eddy currents induced by an alternating electromagnetic field. An applied high-frequency alternating current 4204 in an induction coil 4202 induces a rapidly-changing axial magnetic field 4214 of the same frequency in a metal core 4212. This axial magnetic field 4214 in turn induces rapidly-changing, circular currents, or eddy currents 4224, inside the conducting metal core 4212. The induced eddy currents 4224 readily generate Joule heat in the conductor with practically 100% efficiency.

There is a depth distribution of these induced eddy currents 4224 that depends on the frequency and strength of the applied alternating current 4204 and the material properties of the core material 4212. This depth distribution is readily controllable if all parameters are known and can be used advantageously to primarily heat the exterior of the core where the heat is transferred to the water for rapid evaporation. In one embodiment, the metal core is designed to be hollow so that no energy is used to heat a parasitic center, rather all energy is concentrated on the surface to be used for steam generation.

FIG. 43 is a graph illustrating the variation in magnetic hysteresis between different ferromagnetic and non-ferromagnetic materials. The three curves 4301, 4302, 4303 shown are hysteresis traces of an externally applied magnetic field $B_o$ 4305 and the resulting magnetization M 4310 of the ferromagnetic core material. The upper dash-dotted line 4307 and lower dash-dotted line 4309 indicate the positive and negative magnetic saturation of the material, respectively. Saturation means that an increasing external magnetic field will not result in a further increase in magnetization. The phenomenon of saturation occurs when all available magnetic domains have aligned themselves with the external magnetic field, at which point the maximum magnetization has been reached.

As the externally applied magnetic field $B_o$ 4305 is reduced toward zero, the magnetic domains tend to remain in their recently aligned orientation, and will only be partially "randomized" by thermal energy kT (always positive above the absolute temperature of 0K=−273° C.) if the aligning external field $B_o$ 4305 is reduced or eliminated. The retained magnetization M 4310 after removal of the $B_o$-field 4305 is called saturation remanence and is higher for magnetically soft materials as seen in curve 4301, lower for magnetically hard materials as seen in curve 4302, and zero for non-magnetic materials as seen in curve 4303.

As the externally applied magnetic field is reversed and increased in the reverse direction, the $B_o$-field 4305 exerts work on the magnetic domains and starts to re-align them in the opposite direction, resulting first in a decreased magnetization M 4310 and then in a reversal of the magnetization. Each flipping of a magnetic domain is lossy and causes friction, generating heat in the core material. As the $B_o$-field 4305 is further increased, saturation in the opposite direction is eventually reached. Repeating this process traces the hysteresis curves 4311, 4312, 4313. More Joule heat is generated as the domains are flipped more quickly.

The hysteresis curves 4311, 4312, 4313 each circumscribe a respective area 4321, 4322, 4323. The circumscribed area 4321 is larger in magnetically soft materials compared to the area 4322 in magnetically hard materials and to the area 4323 in non-magnetic materials. The area 4321, 4322, 4323 is an indication of how many magnetic domains aligned and re-aligned themselves with the externally applied magnetic field and is therefore a measure of how much heat was generated during the process. A larger circumscribed means more heat generated inside the ferromagnetic core material. Therefore, a soft ferromagnetic material will generate greater heat through magnetic hysteresis than a hard ferromagnetic material or non-magnetic material.

FIG. 44 is an illustration depicting a variety metal rods 4401, 4402, 4403, 4404, 4405 and a covering tube 4410 for an induction heating chamber in accordance with some embodiments of the present specification. Metal rods 4401, 4402, 4403, 4404 each include a threaded outer surface intended to force the water and steam along a spiral path to increase the time of contact between the rod and the water and steam. Increased contact time can result in better energy transfer to the water and steam. In various embodiments, the threaded outer surface can comprise grooves of circular, triangular, trapezoidal, or rectangular cross section. Metal rod 4405 includes a smooth outer surface. The inner diameter of tube 4410 is only slightly larger than the outer diameter of the metal rods 4401, 4402, 4403, 4404, 4405. When the tube 4410 is positioned coaxially over one of the metal rods, a small space is created between the tube 4410 and the metal rod. Water travels through this space, contacts the heated metal core, and is converted to steam. In a preferred embodiment, a heating chamber comprises metal rod 4405 and tube 4410.

FIG. 45 is an illustration of a metal rod 4502 having a threaded outer surface and a tube 4504 having a threaded inner surface for a heating chamber in accordance with one embodiment of the present specification. In one embodiment, the outer surface of the rod 4502 and inner surface of the tube 4504 include threads matching 5/16"-18 national coarse thread (NC). The tube 4504 fits over the rod 4502 and creates a spiral path for water and steam to travel.

FIG. 46A is an illustration of a smooth metal rod 4602 and a tube 4604 of a heating chamber in accordance with one embodiment of the present specification. The rod 4602 is placed beside the tube 4604 in the approximate axial position it occupies once inserted into the tube 4604 for operation. In various embodiments, the tube 4604 has a length ranging from 2¾ to 3¾ inches. In various embodiments, the tube 4604 has an inner diameter ranging from 7/32 inch to 11/32 inch and an outer diameter ranging from ⅜ inch to ½ inch. In one embodiment, the tube 4604 has a length of 3¼ inches, an inner diameter of 11/32 inch and an outer diameter of ½ inch. In various embodiments, the metal rod 4602 has a length ranging from 1½ to 2½ inches and a diameter ranging from 3/16 inch to 5/16 inch. In one embodiment, the metal rod 4602 has a length of 2 inches and a diameter of 5/16 inch. In one embodiment, the metal rod 4602 is composed of regular steel. In one embodiment, the metal rod 4602 has a surface area to volume ratio that is equal or greater than $2(D_1+L)/D_2 \times L$, where $D_1$ is the shortest cross-sectional dimension of the metal rod 4602, $D_2$ is the longest cross-sectional dimension of the metal rod, and L is the length of the metal rod. In various embodiments, the metal rod 4602 has a length less than 10 cm with a smallest cross-sectional dimension of greater than 1 mm. In other embodiments, the metal rod 4602 has a length greater than 1 mm and a largest cross-sectional dimension of less than 10 cm. In one embodiment, the metal rod 4602 has a length of 50.8 mm and a diameter of 7.94 mm. In various embodiments, the metal rod 4602 has a mass in a range between 1 g and 100 g. In one embodiment, the metal rod 4602 has a mass of 19.8 g.

FIG. 46C is a flow chart illustrating the steps involved in generating steam 4628 using an induction heated metal core 4624, in accordance with one embodiment of the present specification. Power 4622 is delivered to the system to cause an induction coil to heat the metal core 4624 as energy per unit time or joules per second [J/sec]. Water 4626 is input to the system having a flow rate F expressed in milliliters per minute [ml/min] at a room temperature $T_{room}$ [° C.]. The system outputs steam 4628 at a temperature $T_{steam}$ [° C.]. In various embodiments, if flash heating is used to rapidly generate steam at start-up, the metal core 4624, if pre-heated to more than 250° C., preferably possesses a thermal capacity greater than or equal to the heat needed to vaporize 1 ml of water but less than the heat needed to vaporize 100 ml of water from 25° C. to 125° C. The thermal capacity of the metal core 4624, expressed in cal/K, is a measure of how much energy the metal core 4624 can store in absolute terms for a given temperature increase. Since the thermal capacity is a measure of the absolute energy that can be stored in the metal core 4624, it scales approximately linearly with the mass of the metal core 4624 and the temperature of the metal core 4624 up to its melting point. Once the metal core 4624 has been pre-heated, for example, to 250° C., room temperature water 4626 is passed over the core 4624 and thermal energy is transferred from the core 4624 to the water 4626. Depending on the amount of energy stored in the metal core 4624, the transferred energy first heats the water 4626, then boils it, evaporates it, and then overheats the generated steam 4628 to a temperature greater than 100° C. The pre-heated metal core 4624 releases a certain amount of energy depending on how much it is allowed to cool as the stored thermal energy is transferred to the water 4626. The phase of the water 4626 depends on the volume of water 4626 and the amount of energy transferred. The water 4626 undergoes an abrupt phase transition but the metal core 4624 does not. The absolute thermal capacity in cal/K is for a given material and amount of said material and is different from the specific heat capacity, expressed in cal/g*K normalized to a unit mass. The specific heat capacity defines the properties of a material independent of the amount of said material.

In various embodiments, the metal core 4624 possesses a thermal capacity ranging from 0.05 cal/K to 1 Mcal/K and, more preferably, 640 cal/K to 64 kcal/K. The metal core 4624 possesses a minimum required thermal mass for effective and consistent rapid heating of vapor. A higher thermal mass allows for more stable temperatures in the metal core 4624. Too low of a thermal mass will result in fluctuating temperatures in the metal core 4624. In various embodiments, the metal core 4624 is composed of steel. Steel has a specific thermal capacity of 0.12 cal/g*K. In an embodiment, a 100 g steel core undergoes a 100 K temperature drop when its outer surface comes into contact with room temperature water. This releases approximately 1,200 cal of thermal energy (100 g*100 K*0.12 cal/g*K). Since water has a latent heat of vaporization of 543 cal/gm, approximately 2.2 ml of water can be vaporized using a 100 g steel core (1,200 cal/(543 cal/gm)) while its temperature drops 100K. This process uses a significant portion of the stored energy in the steel core and therefore, to continue the flow of vapor, the steel core needs to be re-supplied with thermal energy via induction heating. When pre-heated, the metal core 4624 uses a portion of its stored thermal energy to heat and vaporize water once the water touches its outer surface. In various embodiments, the metal core 4624 uses 1% to 100% of its stored thermal energy to vaporize a given volume of water. Using a smaller amount of the stored thermal energy, for example, 10%, during vaporization allows the metal core 4624 to maintain a more consistent temperature and improves system reliability.

In one embodiment, wherein the metal core 4624 comprises a steel rod having a length of 50.8 mm, a diameter of 7.94 mm, and a mass of 19.8 g, and water is supplied to the outer surface of the core 4624 at a rate of 5 ml/min (5 g/60 sec), the system is expected to exhibit a plurality of characteristics based on the following formulas.

The power ($P_{boil}$) needed to heat the water from room temperature (20° C.) to the boiling point (100° C.), a temperature difference of $\Delta T=80K$ is:

$$P_{boil} = \frac{M}{t} \cdot c_{water} \cdot \Delta T = \frac{5 \text{ g} \cdot 4.187 \text{ J} \cdot 80K}{60 \text{ sec} \cdot \text{g} \cdot K} = 27.9 \frac{J}{\text{sec}} = 27.9 \text{ W}$$

where M is the mass of water in grams, t is time in seconds, and $c_{water}$ is the specific heat capacity of water.

The power ($P_{vap}$) needed to vaporize the water at the boiling point (100° C.) into wet steam (100° C.) is:

$$P_{vap} = \frac{M}{t} \cdot \Delta H_{vap} = \frac{5 \text{ g} \cdot 2270 \text{ J}}{60 \text{ sec} \cdot \text{g}} = 189.2 \frac{J}{\text{sec}} = 189.2 \text{ W}$$

where M is the mass of water in grams, t is time in seconds, and $\Delta H_{vap}$ is the latent heat of vaporization of water.

The power ($P_{steam100 \rightarrow 250}$) needed to heat wet steam (100° C.) to overheated steam at 250° C., a temperature difference of $\Delta T=150K$ is:

$$P_{steam100 \rightarrow 250} = \frac{M}{t} \cdot c_{steam} \cdot \Delta T = \frac{5 \text{ g} \cdot 1.996 \text{ J} \cdot 150K}{60 \text{ sec} \cdot \text{g} \cdot K} = 25.0 \frac{J}{\text{sec}} = 25.0 \text{ W}$$

where M is the mass of water in grams, t is time in seconds, and $c_{steam}$ is the specific heat capacity of steam.

The power ($P_{water20 \rightarrow steam100}$) needed to generate steady state wet steam (100° C.) is:

$P_{water20 \rightarrow steam100} = P_{boil} + P_{vap} = 27.9 \text{ W} + 189.2 \text{ W} = 217.1 \text{ W}$ The power ($P_{water20 \rightarrow steam250}$) needed to generate steady state overheated steam at 250° C. is:

$P_{water20 \rightarrow steam250} = P_{boil} + P_{vap} + P_{steam100 \rightarrow steam250} = 27.9 \text{ W} + 189.2 \text{ W} + 25.0 \text{ W} = 242.1 \text{ W}$ In one embodiment, with no water flow and assuming no heat loss, the energy ($\Delta H_{20 \rightarrow 250}$) needed to heat the core 4624 from room temperature (20° C.) to 250° C. is:

$$\Delta H_{20 \rightarrow 250} = M \cdot c_{steel} \cdot \Delta T = \frac{19.8 \text{ g} \cdot 0.486 \text{ J} \cdot 230K}{\text{g} \cdot K} = 2213 \text{ J}$$

where M is the mass of the core in grams, and $c_{steel}$ is the specific heat capacity of steel.

The power needed to generate wet steam at a water flow rate of 5 ml/min from room temperature (20° C.) is calculated above to be 217.1 W. If this power level is used to preheat the core 4624 with no water flow, then the core 4624 will be heated from 20° C. to 250° C. in the time ($t_{preheat20 \rightarrow 250}$) of:

$$t_{preheat20 \rightarrow 250} = \frac{\Delta H_{20 \rightarrow 250}}{P_{water20 \rightarrow steam100}} = \frac{2213 \text{ J} \cdot \text{sec}}{217.1 \text{ J}} = 10.2 \text{ sec}$$

If the water flow rate is set to 5 ml/min and 242.1 W of power are provided, the system will output overheated steam at a temperature of 250° C. in a steady-state condition. If the overheated steam is directed toward a heat-absorbing surface (target tissue at 37° C.), then the following powers will be released to the surface.

Power ($P_{steam100 \rightarrow 250}$) release from 250° C. overheated steam to wet steam:

$P_{steam100 \rightarrow 250} = 25.0$ W, approximately 10.3% of the total power of 242.1 W.

Power ($P_{vap}$) release from release of latent heat of vaporization, wet steam to boiling water:

$P_{vap}$=189.2 W, approximately 78.2% of the total power of 242.1 W.

Remaining power ($P_{water100\rightarrow 37}$) released from boiling water as it cools to 37° C. in living tissue:

$P_{water100\rightarrow 37}$=22 W, approximately 9.1% of the total power of 242.1 W.

FIG. 46B is a top-down illustration of the metal rod 4602 positioned within the tube 4604 of the heating chamber 4600 of FIG. 46A. A space 4603 is created between the inner surface 4604a of the tube 4604 and the outer surface 4602a of the metal rod 4602. The space 4603 acts as a passage for the water as it travels between the tube 4604 and rod 4602 and is converted to steam by heat transfer from the rod 4602 to the water. In various embodiments, the width w of the space 4603 is no greater than 25 mm. In one embodiment, the width w of the space 4603 is 1 mm. In various embodiments, as water is pumped into the space 4603, the heating chamber is capable of creating steam and withstanding pressures between 1 and 100 PSI. In one embodiment, as water is pumped into the space 4603, the heating chamber is capable of creating steam and withstanding a pressure of at least 5 PSI. In various embodiments, water is pumped into the space 4603 at a flow rate of 0.1-100 ml/min.

During operation, the metal rod 4602 is heated via induction heating such that the temperature at its outer surface 4602a is at least 100° C. to convert water in the space 4603 to steam. The heat from the rod 4602 is also sufficient to heat the inner surface 4604a of the tube 4604 to at least 100° C. to allow for the vapor conversion to occur. In various embodiments, the tube 4604 provides sufficient thermal insulation such that its outer surface 4604b has a temperature less than 100° C., and preferably, less than 60, 50, 40, 30, and 25° C., to allow safe handling by an operator. In various embodiments, the temperature of the outer surface 4604b of the tube 4604 of the heating chamber does not increase by more than 500% of its pre-operation outer surface temperature during continuous operation time periods of 10, 9, 8, 7, 6, 5, 4, 3, 2, or 1 minute down to 5 seconds and any time period in between. In one embodiment, during continuous operation, a temperature of the ferromagnetic material of the heating chamber is maintained at a level greater than 100° C. In one embodiment, the temperature of the outer surface 4604b of the tube 4604 of the heating chamber does not increase by more than 500% of its pre-operation outer surface temperature during 5 minutes or less of continuous operation. In one embodiment, the heating chamber 4600 includes a valve at an outlet port that opens at pressures equal to or less than 5 atm. In one embodiment, the heating chamber 4600 includes a valve at an inlet port that allows backflow of the water at a pressure greater than 5 atm. In various embodiments, the ablation system further includes at least one cooling system to maintain the temperature of the outer surface 4604b of the tube 4604 at the temperature ranges listed above. In one embodiment, the heating chamber includes a mechanism positioned between the outer surface 4604b of the tube 4604 and an inner surface of the induction coil for cooling said outer surface 4604b. In one embodiment, the mechanism comprises a system for passing cooling fluid between said surface 4604b and said coil. In another embodiment, wherein said induction coil is an induction chamber having a three-dimensional body with a lumen within and comprising said coils in the body of said chamber, said induction chamber further comprises a cooling mechanism positioned along an inner surface of said body. In one embodiment, the cooling mechanism comprises a system for passing cooling fluid between said inner surface of said induction chamber body and said outer surface 4604b of said tube 4604. In one embodiment, a temperature of an outer surface 4604b of the tube 4604 does not exceed 120° C. during operation. In another embodiment, a temperature of an outer surface 4604b of the tube 4604 does not exceed 150° C. during operation.

In various embodiments, the tube 4604 is composed of a thermally insulating material. In one embodiment, the tube 4604 is composed of ceramic. In one embodiment, the ceramic is a machinable glass such as MACOR®. In another embodiment, the tube 4604 is composed of a thermoplastic. In one embodiment, the tube 4604 is composed of PEEK. Since PEEK has a melting temperature of 343° C., the temperature of the heating chamber, including the metal core, needs to be monitored so it does not approach high temperatures and melt the tube. In various embodiments, the temperature of the metal rod 4602 is continuously monitored during operation to create a metal rod 4602 temperature profile. The maximum temperature in the temperature profile is identified and the location of the maximum temperature in the metal rod 4602 is also identified. The temperature distribution and maximum temperature may change depending on the location of the boundary between water and steam (where vapor conversion occurs). In various embodiments, the temperature profile includes an axial temperature distribution and a radial temperature distribution which may be different in space and time. The radial temperature distribution is affected by volumetric heating and surface cooling of the rod 4602. In various embodiments, the metal rod 4602 is positioned in a vertical orientation and the maximum temperature location is along a vertical axis of the rod 4602. A temperature sensor, or thermocouple, is then positioned at the maximum temperature location in the metal rod 4602 to ensure that, during operation, the highest temperatures encountered in the heating chamber can be monitored. Feedback from this thermocouple is then used to regulate system operation and provide system stability. In one embodiment, a thermocouple is positioned within a central bore which is drilled into said metal rod 4602 from its distal end. In one embodiment, the bore is drilled into said distal end a distance approximately equal to ⅓ of the length of the metal rod 4602. In one embodiment, the metal rod 4602 has a length of approximately 5 cm and a central bore is drilled into the distal end of the rod 4602 to a distance of approximately 1.7 cm (approximately ⅓ of the total length of the rod 4602). A thermocouple is positioned within the bore. In various embodiments, the maximum temperature location in the metal rod 4602 is within 1 cm or more from the location of the thermocouple. In various embodiments, the thermocouple is positioned at a location having a temperature within 70% of the maximum temperature. In various embodiments, the thermocouple is positioned at a location that is approximately 1.7 cm from the location of the maximum temperature. FIG. 47 is an illustration of a distal end of a metal rod 4702 of a heating chamber with a thermocouple 4706 positioned therein. In one embodiment, the highest temperatures of the metal rod 4702 are encountered at its distal end and so the thermocouple 4706 is positioned at that location. A small bore 4703 has been drilled into the distal end of the metal rod 4702 to tightly fit the thermocouple 4706. In one embodiment, the end of the thermocouple 4706 is positioned ½ inch into the distal end of the metal rod 4702. Thermocouple 4706 is depicted as thermocouple 4034 in FIG. 40A and effectively regulates the temperature of the heating chamber core, thereby allowing proper and safe operation of the ablation system.

Monitoring the temperature of the induction coil, along with monitoring the temperature of the heating chamber core, is beneficial in providing a safe and properly functioning ablation system. In one embodiment, the highest temperatures experienced by the coil are located along its first layer of windings against the tube of the heating chamber. The outer layers of the coil are cooled by a fan, as described with reference to FIG. 40A. Cooling of the interior layers of the coil is inefficient, and therefore temperatures at these layers must be monitored to prevent damage to the coil. FIG. 48A is an illustration of a tube 4804 of a heating chamber and a thermocouple sheath 4807 in accordance with one embodiment of the present specification. The tube 4804 includes a cutout 4809 to accommodate the thermocouple sheath 4807. The sheath 4807 is partially inlaid into the outer surface of the tube 4804 such that it will not significantly increase the outer profile of the tube 4804 and push the coil inner diameter unnecessarily far from the heating chamber. In one embodiment, the sheath 4807 has a length that is sufficient to extend along the entire coil once the coil has been positioned about the tube 4804. The tip of a thermocouple can be repositioned anywhere along the length of the sheath 4807 to measure the axial temperature distribution of the interior of the induction coil. The thermocouple sheath 4807 is configured to house thermocouple 4036 depicted in FIG. 40A. FIG. 48B is an illustration of the tube 4804 of FIG. 48A with the thermocouple sheath 4807 positioned within the cutout 4809. In one embodiment, the temperature of the inner layers of the coil is monitored to remain below 155° C. and prevent damage to the coil. In one embodiment, the thermocouple sheath 4807 is composed of PEEK and has an outer diameter of 1/16 inch. In various embodiments, the sheath 4807 has a length ranging from 1 to 3 inches. In various embodiments, the cutout 4809 has a length equal to or greater than the length of the sheath 4807 to allow for repositioning of the sheath 4807. In one embodiment, a small infrared-transparent window insert into the PEEK heating chamber is created and an infrared sensor is used to measure the temperature of the core inside the PEEK heating chamber.

FIG. 48C is an illustration of the tube 4804 and thermocouple sheath 4807 of FIG. 48B with first and second flanges 4811, 4813 positioned over said tube 4804 and sheath 4807 in accordance with one embodiment of the present specification. The flanges 4811, 4813 serve to limit the proximal and distal placement of the coil on the tube and, together with the tube 4804, create a spool-like shape for the heating chamber. The sheath 4807 extends the entire length of the spool, allowing the tip of a thermocouple to probe the coil temperature at any axial position. In one embodiment, the metal rod inside the heating chamber extends slightly beyond the flanges 4811, 4813. FIG. 48D is an illustration of the tube 4804, sheath 4807, and flanges 4811, 4813 of FIG. 48C with a thermal compound 4815 applied to the components in accordance with one embodiment of the present specification. The thermal compound 4815 is applied liberally to the thermocouple sheath 4807, under the first layer of coil windings, to facilitate good thermal contact between the sheath 4807, tube 4804, and coil. In one embodiment, the thermal compound 4815 is silicone-based.

FIG. 48E is an illustration of the tube 4804, sheath 4807, flanges 4811, 4813, and thermal compound of FIG. 48D with an induction coil 4805 wrapped about said tube 4804 and sheath 4807. In one embodiment, the coil 4805 comprises 1,200-strand litz wire with each AWG-46 strand having a thickness of 42 µm. In one embodiment, each strand is coated with a thin insulating layer of polyester or polyurethane according to the NE-F1 Class F Electrical Insulation System and has a maximum working temperature of 155° C. In various embodiments, the coil 4805 is spaced apart from the outer surface of the tube 4804 by at least 0.1 mm. In one embodiment, during operation, the outer surface of the tube 4804 is configured to be heated to a temperature at least 20° C. below a temperature of the inner surface of the tube 4804. In one embodiment, a cooling agent is passed between the coil 4805 and the tube 4804 to maintain the temperature of the outer surface of the tube 4804 below 100° C. In another embodiment, a cooling agent is passed between the coil 4805 and the tube 4804 to maintain the temperature of the outer surface of the tube 4804 at a temperature which is at least 20° C. less than the temperature of an inner surface of the tube 4804. In one embodiment, during operation, the system is programmed to shut down heating when the outer surface of the tube 4804 is heated to a temperature greater than 100° C.

In one embodiment, an ablation system of the present specification includes a manifold configured to route the leads of the thermocouple fitted in the metal core to the system electronics. The manifold is configured to route the leads without causing a leak or a short circuit. FIG. 49A is an illustration of the distal end of a heating chamber 4900 depicting a lead 4917 of a thermocouple 4907 positioned within the metal core 4902 of the chamber in accordance with one embodiment of the present specification. The distal flange 4913 of the heating chamber 4900 is also shown. Another lead (not shown) extends distally from the thermocouple 4907. The leads of the thermocouple 4907 are in the fluid pathway and must be routed out of said pathway and to the system electronics. The lead 4917 depicted in FIG. 49 is insulated to avoid contacting and short circuiting with the other lead (not shown) of the thermocouple 4907. In one embodiment, the insulation is a fiberglass sheath. Contact and short circuit of the leads would in essence move the sensitive thermoelectric junction to the point of the short circuit. Therefore, one lead is insulated to prevent short circuiting.

FIG. 49B is an illustration of a manifold 4950 configured to route the leads of a heating core thermocouple in accordance with one embodiment of the present specification. In one embodiment, the manifold 4950 has a three-dimensional "cross" shape including a proximal section 4951, a distal section 4952, a left section 4953, and a right section (not shown), all extending outwardly from a center section 4955 of the cross. The interiors of the proximal section 4951 and distal section 4952 are in fluid communication with one another through the interior of the center section 4955. The interiors of the left section 4953 and right section (not shown) are configured to receive a compression seal and a compression screw as described below. In one embodiment, the manifold 4950 is composed of PEEK. The proximal section 4951 includes an opening fitted with a first connecting mechanism at its proximal end. The first connecting mechanism is configured to couple with an adapter 4925 which, in turn, in configured to couple to the distal end of the tube 4904 of the heating chamber 4900, fixedly securing the manifold 4950 to the heating chamber 4900. In one embodiment, the first connecting mechanism of the proximal section 4951 is a female 1/8"-27 NPT coupling and the adapter 4925 is a 1/8"-27 NPT male-male brass nipple.

The left section 4953 includes an opening 4963 at an end facing opposite to said center section. The opening 4953 enters into the interior of the left section 4953 which is in fluid communication with the interior of the center section 4955. The leads of a thermocouple fitted into the distal end of a metal heating core of the heating chamber 4900 are directed through the distal end of the tube 4904, through the adapter 4925, and into the interior of the proximal section 4951 of the manifold 4955 through the opening at the proximal end of said proximal section 4951. The leads pass through the interior of the center section 4955 and then one lead is directed through the interior of the left section 4953 while the other lead is passed through the interior of the right section (not shown). Referring to FIG. 49B, a lead 4927 is depicted extending out of the opening 4963 of the left section 4953. The other lead extends out of a similar opening on the right section of the manifold 4950. A compression seal 4965 and a compression screw 4967 are configured to fit securely into the interior of the left section 4953. The compression seal 4965 is inserted first and acts to seal the interior of the left section 4953 from the interior of the center section 4955 and thus the interiors of the proximal section 4951 and distal section 4952. The compression screw 4967 is screwed into the interior of the left section 4953 after the seal 4965 has been placed into position. An interior surface of the interior of the left section 4953 includes a thread for receiving the compression screw 4967. Small holes are bored through the center of the compression seal 4965 and compression screw 4967 for passage of the lead 4927. The lead 4927 fits snugly within said holes to prevent leaking. The lead 4927 then extends beyond the compression screw 4967 and to the system electronics. In one embodiment, compression seal 4965 is composed of high-temperature silicone rubber. In one embodiment, the compression seal 4965 has a thickness of 1/32 inch. In one embodiment, the compression screw 4967 is a drilled-out 1/4"-28 NF all-thread and the left section 4953 comprises a compression fitting feed-through with 1/4"-28 NF threads for receiving the compression screw 4967. The right section (not shown) functions in the same manner to the left section 4953 and includes another compression seal and compression screw for passage of the other lead.

FIG. 49C is an illustration of the manifold 4950 of FIG. 49B with a compression screw 4967 positioned in the left section 4953. One of the leads 4927 from the thermocouple fitted into the metal core of the heating chamber 4900 is depicted exiting the manifold 4950 through the compression screw 4967 in the left section 4953. Another lead 4917 is depicted extending from the right section 4954 on the opposite side of the manifold 4950. The manifold 4950 allows for safe routing of the leads 4917, 4927 from the heating chamber metal core thermocouple, out of the fluid pathway, and to the system electronics. FIG. 49D is a top-down illustration of the manifold 4950 of FIG. 49C depicting the routes taken by the thermocouple leads 4917, 4927 within the manifold 4950 as they exit the fluid pathway. The interior of the manifold 4950 is visible through an opening 4959 at the distal end of said manifold 4950. Lead 4917 is depicted with an insulating sheath within the manifold 4950 and extends upward from the interior of the proximal section of the manifold 4950, turns into the feed-through of the right section 4954, and exits the manifold 4950 through a compression screw 4957 fitted into said right section 4954. Lead 4927 is depicted within the manifold 4950 and extends upward from the interior of the proximal section of the manifold 4950, turns into the feed-through of the left section 4953, and exits the manifold 4950 through a compression screw 4967 fitted into said left section 4953.

FIG. 49E is an illustration of the manifold 4950 of FIG. 49D with a luer lock connector 4970 attached to the distal end of the manifold 4950. The luer lock connector 4970 functions as a steam port for the attachment of a catheter. The luer lock connector 4970 attaches to the distal section 4952 of the manifold at opening 4959 shown in FIG. 49D. The lumen of the heating chamber 4900 is in fluid communication with the interior of the manifold 4950, which in turn, is in fluid communication with the luer lock connector 4970. In one embodiment, the luer lock connector 4970 is composed of metal. In one embodiment, the metal luer lock 4970 and metal adapter 4925 draw heat away from the steam as they are better heat conductors than the PEEK of the manifold 4950. Therefore, in one embodiment, as depicted in FIG. 49F, the metal luer lock 4970 and metal adapter are wrapped in a thermally insulating material 4973, 4974, respectively. In one embodiment, the thermally insulating material 4973, 4974 is black thermal insulation tape. FIG. 49F also depicts the leads 4977 of an additional thermocouple positioned proximate the adapter connecting the heating chamber 4904 and the manifold 4950. This thermocouple measures the temperature just outside adapter which is closest to the temperature of the steam entering the proximal end of a catheter 4979 attached to the luer lock 4970. This thermocouple is depicted as thermocouple 4032 in FIG. 40A and effectively regulates the temperature of steam exiting the heating chamber, thereby providing the operator with sufficiently heated vapor for ablation. The adapter is not visible in FIG. 49F, as the adapter and said additional thermocouple are covered by insulating material 4974. In one embodiment, the entire manifold is then encapsulated in shrink tubing for additional insulation, as depicted with reference to manifold 4148 in FIG. 41C. In one embodiment, the shrink tubing is black polyolefin shrink tubing.

As discussed with reference to FIG. 40A, in one embodiment, an ablation system of the present specification includes three thermocouples. A first thermocouple is positioned distal to the heating chamber to sense the temperature of steam generated by said heating chamber. A second thermocouple is fitted into the distal end of the metal core of the heating chamber to monitor the hottest portion of said heating chamber. A third thermocouple is positioned between the tube of the heating chamber and the induction coil to ensure the coil is not damaged by high temperatures. FIG. 49G is a schematic diagram of a thermocouple analog front end in accordance with one embodiment of the present specification. The hot junction 4932 is placed at the point where temperature is to be measured and the cold junction 4934 is connected to terminal block 4147 of FIG. 41C. In one embodiment, the system includes a cold-junction compensation circuit. To minimize noise pickup by the thermocouples, the analog front end electronics of the thermocouples are designed with operational amplifiers in differential mode. Any noise coupled to the leads of the thermocouples is rejected as common-mode signal. Noise generated between the leads is mainly shorted out by the very low impedance of the thermocouple junction, assuring maximum noise rejection. To further reduce noise pickup, the analog front end electronics are located as close as possible to the thermocouple hot junctions. Referring again to FIG. 41C, in one embodiment, the system includes a steel shielding box 4145 containing the analog front end electronics of the thermocouples. The steel shielding box 4145 is positioned proximate the hot junctions which, as described above, are positioned just distal to the heating chamber 4104 under the thermally insulating material covering the manifold 4148, in the metal core of the heating chamber 4104, and under the induction coil 4105.

In various embodiments, one or more temperature sensors, or thermocouples, as described above, are used to regulate functionality of the vapor ablation system. Information sensed and relayed by the thermocouple(s) provides active and consistent temperature sensor readings to determine the stability of the system. Once a safe operating temperature, signifying system stability, has been sensed, the system then permits the user to proceed to the next step and generate steam for ablation. In various embodiments, the system allows for a higher maximum current to be provided to the induction coil, thereby increasing system responsiveness during steam delivery. In addition, in various embodiments, the treatment temperature, or steam temperature, is high (>100° C.) to improve steam generation efficiency. A microcontroller, comprising a portion of the data acquisition and control electronics 4024 of FIG. 40A, controls system temperatures based on sensed data from the thermocouple(s) and prevents temperature overshoot. In some embodiments, the microcontroller employs a proportional-integral-differential algorithm in a control loop feedback mechanism to control the core temperature. The microcontroller calculates an error value as the difference between the measured temperature and a pre-determined target treatment temperature and then minimizes the error by adjusting the process through the use of a manipulated variable. In some embodiments, steam temperature is also controlled by setting a taper temperature, as described with reference to FIG. 52 below. In one embodiment, setting a lower taper temperature provides increased control over steam temperature.

FIG. 49H is a flowchart listing the steps involved in regulating steam temperature and vapor ablation system stability, in accordance with one embodiment of the present specification. At step 4935, electrical energy is provided to an induction coil, resulting in induction heating of a heating chamber core and pre-heating of the core to a pre-determined temperature suitable for treatment. In various embodiments, the temperature suitable for treatment includes a range of stable temperatures sufficient for steam generation yet still low enough to prevent injury to the user or patient or damage to the system. In various embodiments, the temperature range is 100 to 300° C. In one embodiment, a sensed temperature is considered stable by the system, and steam generation is allowed to occur, when the sensed temperature is within +/−5% of a target temperature. At least one thermocouple continuously senses the temperature of the core at step 4936. Once the core temperature reaches the pre-determined temperature suitable for treatment at step 4937, the system permits the user to begin steam generation. In various embodiments, the system notifies that the desired core temperature has been reached, signifying the system is stable, by illuminating a "Core Ready" light on a graphical user interface (GUI) as described below with reference to FIG. 52. In various embodiments, the user can then generate steam and begin treatment by pressing a "Deliver Rx" button on the GUI as described below with reference to FIG. 55 or, optionally, press a foot switch to generate steam and begin treatment. Steam generation commences when water is introduced into the heating chamber by a pump at step 4938. Steam is then generated and delivered to target tissues for ablation treatment at step 4939. In various embodiments, energy delivery and thus steam generation ceases if the sensed core temperature rises above the pre-determined temperature suitable for treatment at step 4940. Once the core temperature falls below the pre-determined temperature suitable for treatment as sensed by the at least one thermocouple, steam generation and treatment may resume.

In another embodiment, the temperature of the chamber or the coil can be used to drive the therapeutic regimen.

FIG. 49I is a block diagram illustrating a vapor ablation kit 4980 comprising a handheld induction heating mechanism 4982 in accordance with one embodiment of the present specification. The kit comprises a closed water system which includes a water reservoir 4981 connected to a handheld induction heating chamber 4982 which is in turn connected to a catheter 4983. The kit is considered a closed water system as there are no parts of the system which touch the water and are not sterile. The catheter 4983, examples of which are presented above, is single use and disposable. The induction heating chamber 4982 and water reservoir 4982 are preferably disposable but, in another embodiment, could also be reused. This embodiment improves the efficacy of steam delivery by generating the steam closer to the target. In various embodiments, the kit 4980 includes at least one sensor for monitoring operational parameters of the kit 4980.

In another embodiment, the catheter includes a handle and the induction heating mechanism is not housed in the handle to improve operator safety. Since heating does not occur in the handle, the handle is safe for the operator to touch. In other embodiments, additional heating mechanisms can be deployed along the length of the catheter. These heating mechanisms could be used in various combinations for the ideal combination of safety, efficacy and reliability.

FIG. 49J is an illustration of a vapor ablation kit 4985 comprising a water reservoir 4986, heating chamber 4987, and catheter 4988, in accordance with another embodiment of the present specification. The kit 4985 also includes a handle 4989 for manipulating the catheter 4988. The kit is considered a closed water system as there are no parts of the system which touch the water and are not sterile. This embodiment also improves the efficacy of steam delivery by generating the steam closer to the target. In various embodiments, all components of the kit 4985 are single use and disposable. The heating chamber 4987 is positioned within a separate induction coil (not shown) controlled by a microprocessor. The water reservoir 4986, heating chamber 4987, catheter 4988, and handle 4989 are considered a 'catheter component' and the induction coil and microprocessor are considered a 'generator component'. In other embodiments, the catheter 4988 and handle 4989 are single use and disposable while the water reservoir 4986 and heating chamber 4987 can be reused. In some embodiments, the kit 4985 includes at least one sensor for monitoring operational parameters of the kit 4985.

System Software

As discussed with reference to FIG. 40A, the controller unit with graphical user interface (GUI) controls a plurality of subsystems and therefore key system parameters of the hardware of the ablation system. In one embodiment, the controller unit comprises a tablet PC and the GUI comprises the tablet touchscreen. The GUI functions as the central interacting point of the user with the steam generator. The GUI must be on and running properly to fully and safely control the operation of the ablation system. Therefore, in one embodiment, the GUI is powered on before the main power switch (switch 4114 of FIG. 41B) of the induction heater electronics is turned on at the front panel of the enclosure. In one embodiment, shutting the system down is accomplished by first disabling the heater and pump on the GUI, then switching off the main power switch, and finally shutting down the GUI.

The GUI controls the parameters of the ablation system and acquires data continuously at approximately 2 Hz or two samples per second. In various embodiments, the GUI displays these parameters in charts, on indicators, buttons, dials, and lights and sounds an acoustic alarm if triggered. In one embodiment, the GUI is configured to write all key system parameters to disk for later off-line data analysis. In one embodiment, the GUI offers the programming of three distinct programs for generating steam. These programs are saved to disk so they will be available after the GUI has been shut down. The programs can be loaded and automatically run the steam generator according to the program sequence.

FIG. 50 is a screenshot of a graphical user interface (GUI) home screen in accordance with one embodiment of the present specification. A tab labeled "Home" 5050 has been pressed to display said home screen. The GUI includes two distinct sections of common controls and indicators 5001 at the top and the tab control 5020 occupying the lower main section. The common controls 5001 are relevant to all tabs and can be seen at all times, regardless of which tab is pressed. Each tab has its own "theme" and is organized according to functional relation. Each tab is meant to convey the most pertinent information related to the descriptive topic of the tab label. In one embodiment, the tabs are arranged from left to right in the natural sequence of progression of the system data flow. To begin using the GUI and ablation system, a user starts the GUI loop by pressing the Pump/Heater Control button 5002. A light 5003 illuminates and/or flashes to notify the user that the GUI loop is running properly. The user then switches on the main power switch on the induction heater. The GUI will then begin to display system data and is ready to accept operator control. To shut down the GUI and ablation system, the user first pushes the Enable Pump button 5004 and Enable Heater button 5005 until each button reads "Disabled". The user then switches off the main power switch on the induction heater. The user then stops the GUI loop by pressing the Pump/Heater Control button 5002. The light 5003 will then go dark. Finally, the user presses the STOP button 5022 to stop the GUI and release device resources for the next launch of the GUI.

The common controls 5001 include up and down arrows for adjusting the pump flow rate 5007. The pump does not start until the Enable Pump button 5004 is pressed so that flow rate can be set before the pump is enabled. The common controls also includes up and down arrows for adjusting the heater current 5010. Adjusting the heater current sets the timing of the phase control electronics that controls the AC power delivered to the induction heater electronics. This current is not calibrated but is independently measured with the current-sensing circuitry. The heater does not start heating until the Enable Heater button 5005 is pressed so that the current can be set before the heater is enabled. The GUI is configured to log data of key parameters and write them to a file on the hard disk. The controls are available in a Data Logging section 5015 in the common controls 5001.

The GUI continuously checks critical parameters of the system, such as temperatures, pressure and water level. If any of these parameters exceed pre-set values, then an alarm will be audio-visually activated and the GUI will respond according to the particular alarm flag set. In one embodiment, the common controls 5001 include a Systems Alarms section 5030. If the core temperature exceeds 300° C. a "Temp.>300 C ?" button 5031 will change its text from "Temp. OK" to "Too High", its color will change to red, a warning message will be displayed, the heater will be turned off and the pump will be turned on for emergency cooling. In one embodiment, this emergency shutdown will not stop when the core temperature has dropped to safe levels, but rather the operator must check the system and take appropriate action. If the pressure exceeds 25 PSI the "Press.>25 PSI ?" button 5032 will change its text from "Pressure OK" to "Too High", its color will change to red, a warning message will be displayed and the heater and pump will both be turned off. In one embodiment, after a pressure shutdown, the operator must check the system and find out what caused the pressure to become excessive. Excessive pressure indicates a problem in the plumbing system, most likely a blockage that must be removed before normal operation can resume. If the water level in the water reservoir drops below approximately ⅓ the capacity of the reservoir, then the "Water Low?" button 5033 will change its text from "Level OK" to "Too Low" and its color will change to red. Because a low water level is not an acute emergency, the GUI will continue normal operation. However, the operator is advised to refill the water reservoir as soon as possible to assure normal operation and to prevent running the pump dry. Once a sufficient water level is reached the "Water Low?" button 5033 will change its text from "Too Low" to "Level OK" and its color will change to light gray. In one embodiment, the user can press and hold the "Alarm Check" button 5034 to check the proper functioning of the alarm indicators and the acoustic signals.

In one embodiment, the home screen includes at least one counter that serves as a diagnostic tool to monitor the loop characteristics of the GUI. The home screen depicted in FIG. 50 includes a Block Diagram Count 5052, a Master Loop Count 5054, a Loop 1 Count 5056, and a Loop 2 Count 5058. The GUI is programmed in multi-threaded architecture so that several tasks may be performed seemingly simultaneously in an apparent parallel fashion. This programming architecture has the advantage that no one loop forces another loop to wait for it to be finished. This offers great flexibility for the programmer and agility for the running GUI.

FIG. 51 is a screenshot of a graphical user interface (GUI) system status screen in accordance with one embodiment of the present specification. The GUI is programmed in an architecture that handles a number of threads and subroutines, each performing a dedicated task. The "System Status" screen (displayed by the user pressing the System Status tab 5150) contains a number of resource and error indicators which provide an overview of the entire system and ensure the proper functioning of all important software components. For example, the System Status screen displays the functional status for the microcontroller (Arduino) 5152, thermocouples 5154, file writing 5156, and read/write Rx config 5158. A green check mark 5155 indicates problem-free operation while a red cross 5159 is an error flag that must be addressed and its problem corrected before the GUI can properly function.

FIG. 52 is a screenshot of a graphical user interface (GUI) flow, heat, temps screen in accordance with one embodiment of the present specification. The "Flow, Heat, Temps" screen is accessed by pressing the Flow, Heat, Temps tab 5250 and displays charts 5252, 5254 of pump flow rate, heater current (set and actual) and thermocouple temperatures. These charts 5252, 5254 begin to progress as soon as the GUI loop is started by pressing the Pump/Heater Control button 5202. The screen also includes legends 5256, 5258 of the various charted parameters along with their displayed numeric values.

A Preheat Core button 5211 included in the common controls 5201 initiates a closed control loop that thermostatically regulates the temperature of the heater core and attempts to maintain its temperature at a selected core temperature. The selected core temperature can be set by using up and down arrows to adjust the Core Temp 5212. The closed control loop functions by considering a "Taper Temp. (° C.)" 5213 (also adjustable using up and down arrows) to prevent temperature overshoots when a high heater power is selected. When the actual core temperature, as indicated by "Temp. Core (° C.)" 5259 in the temperature chart, is below the taper temperature, then the full heater power is applied to rapidly heat the core and the "Heater Current (V)" 5210 is automatically set to its maximum value of 5.0 V. As the taper temperature is exceeded, the heater current will be set lower according to a linear relationship between the selected "Core Temp. (° C.)" 5212 and "Taper Temp. (° C.)" 5213. When the measured core temperature 5259 has reached the set "Core Temp. (° C.)" 5212, the "Heater Current (V)" 5210 is set to 2.0 V, the lowest programmed value in this tapering scheme. If the measured core temperature 5259 exceeds the set "Core Temp. (° C.)" 5212, then the Enable Heater button 5205 will be turned off and heating ceases. As the measured core temperature 5259 cools below the set "Core Temp. (° C.)" 5212, the regulating loop responds according to the actual core temperature. A light labeled "Core Ready" 5214 illuminates when the core has reached its set temperature. In one embodiment, a user can run trials to find the optimal setting for "Core Temp. (° C.)" 5212 and "Taper Temp. (° C.)" 5213 to produce the most steam with the smallest temperature overshoots for stable and continuous steam generation.

In one embodiment, the GUI includes chart controls 5222, 5224, 5226 to the right of the tab control section 5220. The chart controls 5222, 5224, 5226 are configured to affect all charts. The "Reset" button 5222 resets all charts and uses an auto-scale feature to set the Y-axis to the best range for visualization of the parameters. The "Chart History Size" 5224 is adjustable using up and down arrows and indicates how large a buffer the GUI will reserve to display data points of the charts and how far back in time scrolling is possible. "Time Span" 5226 is also adjustable using up and down arrows and controls how many data points will be displayed in the current charts. This number can be changed without loss of data in the buffer.

FIG. 53 is a screenshot of a graphical user interface (GUI) heat, pressure screen in accordance with one embodiment of the present specification. The "Heat, Pressure" screen is accessed by pressing the Heat, Pressure tab 5350 and is similar in layout and function as the "Flow, Heat, Temps" screen described above. The parameters charted and displayed are the "Set Heater Current", the "Actual Heater Power (W)" 5352 as calculated from the measured current and the "Chamber Inlet Pressure" 5354. The screen also includes legends 5356, 5358 of the various charted parameters along with their displayed numeric values.

FIG. 54 is a screenshot of a graphical user interface (GUI) program Rx screen in accordance with one embodiment of the present specification. The "Program Rx" screen is accessed by pressing the Program Rx tab 5450. On this screen, in one embodiment, the user can program three distinct treatments schemes (denoted by buttons Save Rx1 5452, Save Rx2 5454, and Save Rx3 5456) with varying Flow 5453, On-Time 5455, Off-Time 5457 and numbers of these Cycles 5459. To program a treatment, a user inputs the desired parameters 5453, 5455, 5457, 5459 and presses the corresponding Save Rx button 5452, 5454, 5456. When the Save Rx buttons 5452, 5454, 5456 are pressed, the GUI writes the selected parameter values to a dedicated file on the disk. Therefore, the programmed data is non-volatile and will be available at any time in the future until it is overwritten.

FIG. 55 is a screenshot of a graphical user interface (GUI) deliver Rx screen in accordance with one embodiment of the present specification. The "Deliver Rx" screen is accessed by pressing the Deliver Rx tab 5550 and is used to launch the programmatic delivery of steam for ablation. In one embodiment, the indicators of Flow 5553, On-Time 5555, Off-Time 5557 and Cycles 5559 are all set to zero by default to prevent accidental launching of a previously run program. To load a program that was previously programmed in the Program Rx screen, the user selects a treatment and presses the corresponding button 5552, 5554, 5556. In one embodiment, once pressed, the button latches and changes color to green while the parameter indicators populate with the values of the program. To start the treatment, the user presses the Deliver Rx button 5558 on the GUI or, in one embodiment, presses the optional foot switch (foot switch 4022 in FIG. 40A). Once treatment has started, the Deliver Rx button 5558 latches and changes color to green. The light labeled "Rx On" 5509 in the System Alarm section 5508 illuminates and steam generation commences. The Enable Pump button 5504 will be programmatically turned on and off according to the program. When the program has finished, the Deliver Rx button 5558 will unlatch and change color to gray. The light labeled "Rx On" 5509 will turn off and steam generation will stop. The light labeled "Rx On" 5509 is included so that the user may press other tabs to switch to other screens and still be able to confirm that the treatment program is running or has finished.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A vapor ablation system configured to ablate tissue in a duodenum of a patient, comprising:
   a pump configured to pump fluid from a source;
   a catheter, wherein the catheter comprises:
     an elongate catheter body having a lumen, a proximal end, and a distal end;
     a heating chamber positioned in-line with respect to the lumen of the catheter body and in fluid communication with the pump, wherein the heating chamber is configured to apply heat to the fluid to convert the fluid to a vapor ablative agent;
     a first expandable positioning element attached to the catheter body at a proximal end of the catheter body, wherein the first expandable positioning element is configured to position the catheter at a first fixed distance from the tissue to be ablated, wherein the first expandable positioning element is defined by a first conical shaped wire mesh structure and wherein the first conical shaped wire mesh structure is at least partially covered by a membrane;
     a second expandable positioning element attached to the catheter body at a distal end of the catheter body and separated from the first expandable positioning element by a length, wherein the second expandable positioning element is configured to position the catheter at a second fixed distance from the tissue to be ablated and wherein the second positioning element is defined by a second conical shaped wire mesh structure and wherein the second conical shaped wire mesh structure is at least partially covered by a membrane; and more than one port distributed along the length and circumferentially positioned around the catheter body, wherein the more than one port is configured to release the vapor ablative agent toward at least a portion of the duodenum; and a controller in operable communication with the pump and the heating chamber, wherein the controller is programmed to limit an amount of the vapor ablative agent delivered through the more than one port such that a pressure within the patient's duodenum does not exceed 5 atm.

2. The vapor ablation system of claim 1, further comprising a thermally insulated handle attached to the catheter body.

3. The vapor ablation system of claim 1, further comprising a thermally insulating material covering the catheter body.

4. The vapor ablation system of claim 1, wherein the heating chamber further comprises a plurality of channels that provide a contact surface area of the fluid with the chamber.

5. The vapor ablation system of claim 4, wherein the plurality of channels comprise metal.

6. The vapor ablation system of claim 1, wherein the heating chamber is configured to heat the fluid using resistive heating.

7. The vapor ablation system of claim 1, wherein the first expandable positioning element is separated from each of the more than one ports by a distance of 1 mm to 10 cm.

8. The vapor ablation system of claim 1, wherein the second expandable positioning element is separated from each of the more than one ports by a distance of 1 mm to 10 cm.

9. The vapor ablation system of claim 1, wherein the controller is programmed to determine an amount of the fluid needed to ablate the tissue.

10. The vapor ablation system of claim 1, wherein the controller is programmed to determine an amount of the vapor ablative agent needed to ablate the tissue.

11. The vapor ablation system of claim 1, wherein the controller is programmed to limit a maximum dose of the vapor ablative agent based on a type of disorder being treated.

12. The vapor ablation system of claim 1, further comprising a first filter disposed between, and in fluid communication with, the pump and the catheter.

13. The vapor ablation system of claim 1, wherein the controller is programmed to determine an amount of the fluid needed to ablate the tissue as a function of an amount of thermal energy required to ablate the tissue.

14. The vapor ablation system of claim 1, wherein the controller is programmed to determine an amount of the vapor ablative agent needed to ablate the tissue as a function of an amount of thermal energy required to ablate the tissue.

15. The vapor ablation system of claim 1, wherein the controller is programmed to adjust a flow rate of the fluid supplied to the catheter.

16. The vapor ablation system of claim 1, wherein the pump is a syringe pump.

17. The vapor ablation system of claim 16, wherein the syringe pump has a volume of at least 10 ml.

18. The vapor ablation system of claim 1, wherein the catheter is disposable and configured for a single use.

19. The vapor ablation system of claim 1, further comprising a shield attached to the catheter body and configured to cover a patient's ampulla of Vater to prevent the ablative agent from contacting the ampulla.

20. A vapor ablation system configured to ablate tissue in a duodenum of a patient, comprising:

a syringe pump comprising fluid in a reservoir;

a heating component in fluid communication with the syringe pump, wherein the heating component is configured to apply heat to the fluid to convert the fluid to a vapor ablative agent;

a catheter in fluid communication with the heating chamber, wherein the catheter further comprises:

an elongate catheter body having a lumen, a proximal end, and a distal end, wherein the lumen is positioned in-line with respect to the heating chamber;

a first expandable positioning element attached to the catheter body at a proximal end of the catheter body, wherein the first expandable positioning element is configured to position the catheter at a first fixed distance from the tissue to be ablated, wherein the first expandable positioning element is defined by a first conical shaped wire mesh structure and wherein the first conical shaped wire mesh structure is at least partially covered by a membrane;

a second expandable positioning element attached to the catheter body at a distal end of the catheter body and separated from the first expandable positioning element by a length, wherein the second expandable positioning element is configured to position the catheter at a second fixed distance from the tissue to be ablated and wherein the second positioning element is defined by a second conical shaped wire mesh structure and wherein the second conical shaped wire mesh structure is at least partially covered by a membrane; and more than one port distributed along the length and circumferentially positioned around the catheter body, wherein the more than one port is configured to release the vapor ablative agent toward at least a portion of the duodenum; and a controller programmed to limit an amount of the vapor ablative agent delivered through the more than one port such that a pressure within the patient's duodenum does not exceed 5 atm.

21. The vapor ablation system of claim 20, wherein the controller is further programmed to determine an amount of the vapor ablative agent needed to ablate the tissue based on a type of disorder being treated.

22. The vapor ablation system of claim 20, wherein the controller is further programmed to determine an amount of the fluid needed to ablate the tissue based on a type of disorder being treated.

23. The vapor ablation system of claim 20, further comprising a thermally insulated handle attached to the catheter body.

24. The vapor ablation system of claim 20, further comprising a thermally insulating material covering the catheter body.

25. The vapor ablation system of claim 20, wherein the heating component further comprises a plurality of channels that provide a contact surface area of the fluid with the heating component.

26. The vapor ablation system of claim 25, wherein the plurality of channels comprise metal.

27. The vapor ablation system of claim 20, wherein the heating component is configured to heat the fluid using resistive heating.

28. The vapor ablation system of claim 20, wherein the first expandable positioning element is separated from each of the more than one ports by a distance of 1 mm to 10 cm.

29. The vapor ablation system of claim 20, wherein the second expandable positioning element is separated from each of the more than one ports by a distance of 1 mm to 10 cm.

30. The vapor ablation system of claim 20, wherein the controller is programmed to limit a maximum dose of the vapor ablative agent based on a type of disorder being treated.

31. The vapor ablation system of claim 20, further comprising a first filter disposed between, and in fluid communication with, the pump and the catheter.

32. The vapor ablation system of claim 20, wherein the controller is programmed to determine an amount of the fluid needed to ablate the tissue as a function of an amount of thermal energy required to ablate the tissue.

33. The vapor ablation system of claim 20, wherein the controller is programmed to determine an amount of the vapor ablative agent needed to ablate the tissue as a function of an amount of thermal energy required to ablate the tissue.

34. The vapor ablation system of claim 20, wherein the controller is in operable communication with the pump and the heating component and programmed to adjust a flow rate of the fluid supplied to the catheter.

35. The vapor ablation system of claim 20, wherein the syringe pump has a volume of at least 10 ml.

36. The vapor ablation system of claim 20, wherein the catheter is disposable and configured for a single use.

37. The vapor ablation system of claim 20, further comprising a shield attached to the catheter body and configured to cover a patient's ampulla of Vater to prevent ablative agent from contacting the ampulla.

38. A vapor ablation system configured to ablate tissue in a duodenum of a patient, comprising:
  a syringe pump comprising fluid in a reservoir;
  a catheter comprising:
    an elongate catheter body having a lumen, a proximal end, and a distal end;
    a heating component in fluid communication with the catheter and positioned in-line with respect to the lumen and in fluid communication with the syringe pump, wherein the heating component is configured to apply heat to the fluid to convert the fluid to a vapor ablative agent;
    a first expandable positioning element attached to the catheter body at a proximal end of the catheter body, wherein the first expandable positioning element is configured to position the catheter at a first fixed distance from the tissue to be ablated, wherein the first expandable positioning element is defined by a first conical shaped wire mesh structure and wherein the first conical shaped wire mesh structure is at least partially covered by a membrane;
    a second expandable positioning element attached to the catheter body at a distal end of the catheter body and separated from the first expandable positioning element by a length, wherein the second expandable positioning element is configured to position the catheter at a second fixed distance from the tissue to be ablated and wherein the second positioning element is defined by a second conical shaped wire mesh structure and wherein the second conical shaped wire mesh structure is at least partially covered by a membrane; and
    more than one port distributed along the length and circumferentially positioned around the catheter body, wherein the more than one port is configured to release the vapor ablative agent toward at least a portion of the duodenum; and
  a controller programmed to limit an amount of the vapor ablative agent delivered through the more than one port such that a pressure within the patient's duodenum does not exceed 5 atm.

39. The vapor ablation system of claim 38, wherein the controller is further programmed to determine an amount of the vapor ablative agent needed to ablate the tissue based on a type of disorder being treated.

40. The vapor ablation system of claim 38, wherein the controller is further programmed to determine an amount of the fluid needed to ablate the tissue based on a type of disorder being treated.

41. The vapor ablation system of claim 38, further comprising a thermally insulated handle attached to the catheter body.

42. The vapor ablation system of claim 38, further comprising a thermally insulating material covering the catheter body.

43. The vapor ablation system of claim 38, wherein the heating component further comprises a plurality of channels that provide a contact surface area of the fluid with the heating component.

44. The vapor ablation system of claim 43, wherein the plurality of channels comprise metal.

45. The vapor ablation system of claim 38, wherein the heating component is configured to heat the fluid using resistive heating.

46. The vapor ablation system of claim 38, wherein the first expandable positioning element is separated from each of the more than one ports by a distance of 1 mm to 10 cm.

47. The vapor ablation system of claim 38, wherein the second expandable positioning element is separated from each of the more than one ports by a distance of 1 mm to 10 cm.

48. The vapor ablation system of claim 38, wherein the controller is programmed to limit a maximum dose of the vapor ablative agent based on a type of disorder being treated.

49. The vapor ablation system of claim 38, further comprising a first filter disposed between, and in fluid communication with, the pump and the catheter.

50. The vapor ablation system of claim 38, wherein the controller is programmed to determine an amount of the fluid needed to ablate the tissue as a function of an amount of thermal energy required to ablate the tissue.

51. The vapor ablation system of claim 38, wherein the controller is programmed to determine an amount of the vapor ablative agent needed to ablate the tissue as a function of an amount of thermal energy required to ablate the tissue.

52. The vapor ablation system of claim 38, wherein the controller is in operable communication with the pump and the heating component and programmed to adjust a flow rate of the fluid supplied to the catheter.

53. The vapor ablation system of claim 38, wherein the syringe pump has a volume of at least 10 ml.

54. The vapor ablation system of claim 38, wherein the catheter is disposable and configured for a single use.

55. The vapor ablation system of claim 38, further comprising a shield attached to the catheter body and configured to cover a patient's ampulla of Vater to prevent the ablative agent from contacting the ampulla.

* * * * *